US007332290B2

(12) United States Patent
Rubin et al.

(10) Patent No.: US 7,332,290 B2
(45) Date of Patent: Feb. 19, 2008

(54) DETECTION OF AMACR CANCER MARKERS IN URINE

(75) Inventors: Mark A. Rubin, Newton, MA (US); Arul M. Chinnaiyan, Plymouth, MI (US); Bharathi Laxman, Ann Arbor, MI (US); Arun Sreekumar, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 409 days.

(21) Appl. No.: 10/909,035

(22) Filed: Jul. 30, 2004

(65) Prior Publication Data

US 2005/0136493 A1 Jun. 23, 2005

Related U.S. Application Data

(63) Continuation-in-part of application No. 10/210,120, filed on Aug. 1, 2002, now Pat. No. 7,229,774.

(60) Provisional application No. 60/334,468, filed on Nov. 15, 2001, provisional application No. 60/309,581, filed on Aug. 2, 2001.

(51) Int. Cl.
*G01N 33/53* (2006.01)

(52) U.S. Cl. ............................ 435/7.1; 435/6; 435/7.4; 435/960; 436/501; 436/512; 436/536; 436/64; 436/813

(58) Field of Classification Search ..................... None
See application file for complete search history.

(56) References Cited

U.S. PATENT DOCUMENTS

| | | | | |
|---|---|---|---|---|
| 5,871,960 | A | 2/1999 | Smith et al. | |
| 5,871,961 | A | 2/1999 | Smith et al. | |
| 5,981,830 | A | 11/1999 | Wu et al. | |
| 6,335,170 | B1 | 1/2002 | Orntoft | |
| 6,465,611 | B1 | 10/2002 | Xu et al. | |
| 6,518,028 | B1 | 2/2003 | O'Brien | |
| 6,620,922 | B1 | 9/2003 | Xu et al. | |
| 6,630,305 | B1 | 10/2003 | Xu et al. | |
| 6,664,377 | B1 | 12/2003 | Xu | |
| 6,759,515 | B1 | 7/2004 | Xu et al. | |
| 6,800,746 | B2 | 10/2004 | Xu et al. | |
| 6,818,751 | B1 | 11/2004 | Xu et al. | |
| 2002/0123081 | A1* | 9/2002 | Richardson et al. | 435/7.23 |

FOREIGN PATENT DOCUMENTS

| | | |
|---|---|---|
| WO | WO 97/18825 | 5/1997 |
| WO | WO 01/25272 | 4/2001 |
| WO | WO 01/57194 | 8/2001 |
| WO | WO 01/62271 | 8/2001 |
| WO | WO 01/73032 | 10/2001 |
| WO | WO 01/77389 | 10/2001 |
| WO | WO 02/27324 | 4/2002 |
| WO | WO 02/059373 | 8/2002 |

OTHER PUBLICATIONS

Grover et al. Electrophoresis, vol. 18, pp. 814-818, 1997.*
Zielie, PJ The Journal of Urology, vol. 172, p. 1130-1133, Sep. 2004.*
rodgers, CG The Journal of Urology vol. 172, p. 1501-1503, Oct. 2004.*
Etzioni et al., "Cancer surveillance series: interpreting trends in prostate cancer—part III: Quantifying the link between population prostate-specific antigen testing and recent declines in prostate cancer mortality," J. Natl. Cancer Inst., 91:1033 [1999].
Maattanen et al., "European randomized study of prostate cancer screening: first-year results of the Finnish trial", Br. J. Cancer 79:1210 [1999].
Schroder et al., "Evaluation of the digital rectal examination as a screening test for prostate cancer. Rotterdam section of the European Randomized Study of Screening for Prostate Can," J. Natl. Cancer Inst., 90:1817 [1998].
Jacobsen et al., "Incidence of prostate cancer diagnosis in the eras before and after serum prostate-specific antigen testing," JAMA 274:1445 [1995].
Brown and Botstein, "Exploring the new world of the genome with DNA microarrays," Nat. Gent., 21:33 [1999].
Schmitz et al., "Purification and characterization of an alpha-methyacyl-CoA racemase from human liver," Eur J Biochem 231:815 [1995].
Tsao and Shibata, "Further evidence that one of the earliest alterations in colorectal carcinogenesis involves APC," Am J Pathol 145: 531 [1994].
McNeal and Bostwick, "Intraductal dysplasia: a premalignant lesion of the prostate," Hum Pathol 17:64 [1986].
McNeal et al., "Patterns of progression in prostate cancer," Lancet 1:60 [1986].
De Marzo et al., "Proliferative inflammatory atrophy of the prostate: implications for prostatic carcinogenesis," Am J Pathol 155:1985 [1999].
Shah et al., "Postatrophic hyperplasia of the prostate gland: neoplastic precursor or innocent bystander?," Am J Pathol 158:1767 [2001].
Saez et al., "Activators of the nuclear receptor PPARgamma enhance colon polyp formation,"Nat. Med. 4:1058 [1998].
Kubota et al., "Ligand for peroxisome proliferator-activated receptor gamma (troglitazone) has potent antitumor effect against human prostate cancer both in vitro and in vivo," Cancer Res. 58:3344 [1998].
Hisatake et al., "Down-Regulation of prostate-specific antigen expression by ligands for peroxisome proliferator-activated receptor gamma in human prostate cancer," Cancer Res. 60:5494 [2000].

(Continued)

*Primary Examiner*—Mary K. Zeman
(74) *Attorney, Agent, or Firm*—Casimir Jones, S.C.

(57) ABSTRACT

The present invention relates to compositions and methods for cancer diagnostics, including but not limited to, cancer markers. In particular, the present invention provides gene expression profiles associated with prostate cancers. The present invention also provides novel markers useful for the diagnosis, characterization, and treatment of prostate cancers. In particular, the present invention provides methods and compositions for the detection of α-methylacyl-CoA racemase (AMACR) in the urine as a marker for prostate cancer detection.

8 Claims, 145 Drawing Sheets

OTHER PUBLICATIONS

Smith et al., "Structural evolution of the annexin supergene family," Trends. Genet. 10:241 [1994].
Mailliard et al., "Calcium-dependent binding of S100C to the N-terminal domain of annexin I," J Biol. Chem. 271:719 [1996].
Pepinsky et al., "Epidermal growth factor-dependent phosphorylation of lipocortin," Nature 321:81 [1986].
Wallner et al., "Cloning and expression of human lipocortin, a phospholipase A2 inhibitor with potential anti-inflammatory activity," Nature 320:77 [1986].
Hubaishy et al., "Modulation of annexin II tetramer by tyrosine phosphorylation," Biochemistry 34:14527 [1995].
Chan et al., "Annexin IV inhibits calmodulin-dependent protein kinase II-activated chloride conductance. A novel mechanism for ion channel regulation," J. Biol. Chem. 269:32464 [1994].
Selbert et al., "Annexin VII relocalization as a result of dystrophin deficiency," Exp. Cell. Res. 222:199 [1996].
Eisen et al., "Cluster analysis and display of genome-wide expression patterns," PNAS 95:14863 [1998].
Shurbaji et al., "Immunohistochemical detection of a fatty acid synthase (OA-519) as a predictor of progression of prostate cancer," Hum. Pathol., 27:917 [1996].
Tsuji et al., "Hepsin, a cell membrane-associated protease. Characterization, tissue distribution, and gene localization," J. Biol. Chem., 266:16948 [1991].
Kurachi et al., "Hepsin," Methods Enzymol., 244:100 [1994].
Kazama et al., "Hepsin, a putative membrane-associated serine protease, activates human factor VII and initiates a pathway of blood coagulation on the cell surface leading to thrombin formation," J. Biol. Chem., 270:66 [1995].
Tanimoto et al., "Hepsin, a cell surface serine protease identified in hepatoma cells, is overexpressed in ovarian cancer," Cancer Res., 57:2884 [1997].
Shirogane, et al., "Synergistic roles for Pim-1 and c-Myc in STAT3-mediated cell cycle progression and antiapoptosis," Immunity 11:709 [1999].
Matikainen et al., "Interferon-alpha activates multiple STAT proteins and upregulates proliferation-associated IL-2Ralpha, c-myc, and pim-1 genes in human T cells," Blood 93:1980 [1999].
Torres Rosado et al., "Hepsin, a putative cell-surface serine protease, is required for mammalian cell growth," PNAS, 90:7181 [1993].
Cuypers et al., "Murine leukemia virus-induced T-cell lymphomagenesis: integration of proviruses in a distinct chromosomal region," Cell 37:141 [1984].
Breuer et al., "Very high frequency of lymphoma induction by a chemical carcinogen in pim-1 transgenic mice," Nature 340:61 [1989].
Sewalt et al., "Characterization of interactions between the mammalian polycomb-group proteins Enx1/EZH2 and EED suggests the existence of different mammalian polycomb-group protein complexes," Mol. Cell. Biol. 18:3586 [1998].
Webber et al., "Acinar differentiation by non-malignant immortalized human prostatic epithelial cells and its loss by malignant cells," Carcinogenesis 18:1225 [1997].
Yu et al., "Altered Hox expression and segmental identity in MII-mutant mice," Nature 378:505 [1995].
van Lohuizzen et al., "Identification of cooperating oncogenes in E mu-myc transgenic mice by provirus tagging," Cell 65:737 [1991].
Laible et al., "Mammalian homologues of the Polycomb-group gene Enhancer of zeste mediate gene silencing in Drosophila heterochomatin and at *S. cerevisiae* telomeres," Embo. J. 16:3219 [1997].
Jenuwein et al., "SET domain proteins modulate chromatin domains in eu- and heterochromatin," Cell. Mol. Life Sci. 54:80 [1998].
Satijn et al., "Polycomb group protein complexes: do different complexes regulate distinct target genes?," Biochim. Biophys. Acta. 1447:1 [1999].
Jacobs et al., "The oncogene and Polycomb-group gene bmi-1 regulates cell proliferation and senescence through the ink4a locus.," Nature 397:164 [1999].
Sinclair et al., "Enhancer of Polycomb is a suppressor of position-effect variegation in *Drosophila melanogaster*," Genetics 148:211 [1998].
Weigart et al., "CIBP/BARS induces fission of Golgi membranes by acylating tysophosphatidic acid," Nature 402:429 [1999].
Emmert Buck et al., "Molecular profiling of clinical tissue specimens: feasibility and applications," Am. J. Pathol., 156:1109 [2000].
Alizadeh et al., "Distinct types of diffuse large B-cell lymphoma identified by gene expression profiling," Nature 403:503 [2000].
Ferdinandusse et al., "Subcellular localization and physiological role of alpha-methylacyl-CoA racemase," J. Lipid Res., 41:1890 [2000].
Kotti et al., "In mouse alpha -methylacyl-CoA racemase, the same gene product is simultaneously located in mitochondria and peroxisomes," J. Biol.Chem., 275:20887 [2000].
Ferdinandusse et al., "Mutations in the gene encoding peroxisomal alpha-methylacyl-CoA racemase cause adult-onset sensory motor neuropathy," Nat. Genet., 24:188 [2000].
Ferdinandusse et al., Plasma analysis of di- and trihydroxycholestanoic acid diastereoisomers in peroxisomal alpha-methylacyl-CoA racemase deficienc J Lipid Res 42:137 [2001].
Moyad, "Fat reduction to prevent prostate cancer: waiting for more evidence?," Curr Opin Urol 11:457 [2001].
Willett, "Diet and cancer," Oncologist 5:393 [2000].
Zomer et al., "Pristanic acid and phytanic acid: naturally occurring ligands for the nuclear receptor peroxisome proliferator-activated receptor alpha," J. Lipid Res. 41:1801 [2000].
Yeldandi et al., "Hydrogen peroxide generation in peroxisome proliferator-induced oncogenesis," Mutat. Res. 448:159 [2000].
Shappell et al., "15S-Hydroxyeicostatetraenoic acid activates peroxisome proliferator-activated receptor gamma and inhibits proliferation in PC3 prostate carcinoma cells," Cancer Res. 61:497 [2001].
Mueller et al., "Effects of ligand activation of peroxisome proliferator-activated receptor gamma in human prostate cancer," PNAS 97:10990 [2000].
Paweletz et al., "Loss of annexin 1 correlates with early onset of tumorigenesis in esophageal and prostate carcinoma," Cancer Res. 60:6293 [2000].
Tomita et al., "Cadherin switching in human prostate cancer progression." Cancer Res., 60:3650 [2000].
Hammond et al., "An RNA-directed nuclease mediates post-transcriptional gene silencing in Drosophila cells," Nature 404:293 [2000].
Macejak et al., "Inhibition of hepatitis C virus (HCV)-RNA-dependent translation and replication of a chimeric HCV poliovirus using synthetic stabilized ribozymes," Hepatology 31:769 [2000].
Epstein and Potter, "The pathological interpretation and significance of prostate needle biopsy findings: implications and current controversies," J. Urol., 166:402 [2001].
Debril et al., "The pleiotropic functions of peroxisome proliferator-activated receptor gamma," J. Mol. Med. 79:30 [2001].
Kotti et al., "In mouse alpha -methylacyl-CoA racemase, the same gene product is simultaneously located in mitochondria and peroxisomes," J. Biol.Chem., 275:20887 [2000].
Clayton et al., "Clinical consequences of defects in peroxisomal beta-oxidation," Biochem. Soc. Trans. 29:298 [2001].
Dhanasekaran et al., "Delineation of prognostic biomarkers in prostate cancer," Nature 412: 822 [2001].
Hinoi et al., "Loss of CDX2 expression and microsatellite instability are prominent features of large cell minimally differentiated carcinomas of the colon," Am. J. Pathol. 159:2239 [2001 .
Kumar Smith et al., "Base excess and lactate as prognostic indicators for patients admitted to intensive care.," J. Biol. Chem. 276(24)21039-45 [2001].
Francis et al., "In vitro studies on L-771,688 (SNAP 6383), a new potent and selective alpha1A-adrenoceptor antagonist," Eur J Pharmacol 2:409 [2001].
Mahmoudi et al., "Chromatin silencing and activation by Polycomb and trithorax group proteins," Oncogene 20:3055 [2001].
O'Carroll et al., "The polycomb-group gene Ezh2 is required for early mouse development," Mol. Cell. Biol. 21:4330 [2001].

Visser et al., "The Polycomb group protein EZH2 is upregulated in proliferating, cultured human mantle cell lymphoma," Br. J. Hematol. 112:950 [2001].
Brock et al., "The Polycomb group—no longer an exclusive club?," Curr. Opin. Genet. Dev. 11:175 [2001].
Satijin et al., "The polycomb group protein EED interacts with YY1, and both proteins induce neural tissue in Xenopus embryos," Mol. Cell. Biol. 21:1360 [2001].
Welsh et al., "Analysis of gene expression identifies candidate markers and pharmacological targets in prostate cancer," Cancer Res. 61:5974 [2001].
Magee et al., "Expression profiling reveals hepsin overexpression in prostate cancer," Cancer Res. 61:5692 [2001].
Brichory et al., "An immune response manifested by the common occurrence of annexins I and II autoantibodies and high circulating levels of IL-6 in lung cancer," PNAS 98:9824-9829 (2001).
Riefier et al., "Binding of neuronal nitric-oxide synthase (nNOS) to carboxyl-terminal-binding protein (CtBP) changes the localization of CtBP from the nucleus to the cytosol: a novel function for targeting by the PDZ domain of nNOS," J. Biol. Chem. 276:48262 [2001].
Chinnadurai, "CtBP, an unconventional transcriptional corepressor in development and oncogenesis," Mol Cell. 9: 213 [2002].
Luo et al., "Human prostate cancer and benign prostatic hyperplasia: molecular dissection by gene expression pro," Cancer Res. 61:4683 [2001].
Chen et al., "Cloning of a human homolog of the Drosophila enhancer of zeste gene (EZH2) that maps to chromosome 21q22.2," Genomics 38:30 (1996).
Lou et al., "Human prostate cancer and benign prostatic hyperplasia: molecular dissection by gene expression profiling," Cancer Res. 61:4683 (2001).
Stamey et al., "Molecular genetic profiling of Gleason grade 4/5 prostate cancers compared to benign prostatic hyperplasia," J. Virology 166:2171 (2001).
An et al., Proceedings of the Annual Mtg. of An Assoc for Cancer Research 40:235 (1999).
Elek et al., "Microarray-based expression profiling in prostate tumors," Int. J. of In vivo Res 14:173 (2000).
Nelson et al., "Contemporary preoperative parameters predict cancer-free survival after radical prostatectomy: a tool to facilitate treatment decisions," Urol. Oncol. 21:213-8 [2003].
Nelson et al., "Preoperative parameters for predicting early prostate cancer recurrence after radical prostatectomy.," Urology 59:740-5; discussion 745-6 [2002].
Rubin et al., "alpha-Methylacyl coenzyme A racemase as a tissue biomarker for prostate cancer," JAMA 287(13):1662-70 [2002].
Scheurle et al., "HER-2/neu expression in archival non-small cell lung carcinomas using FDA-approved Hercep test," Anticancer Res. 20:2091 (2000).
Grande et al., "Prognostic value of serial tissue prostate-specific antigen measurements during different hormonal treatments in prostate cancer patients," Clin Cancer Res., 6:1790 (2000).
Gunster eta l., "Differential expression of human Polycomb group proteins in various tissues and cell types," J. Cell Biochem. Supl. 36:129 (2001).
Abel et al., "Characterization of EZH1, a human homolog of Drosophila Enhancer of zeste near BRCA1.," Genomics 37:161 (1996).

* cited by examiner

Figure 3
a
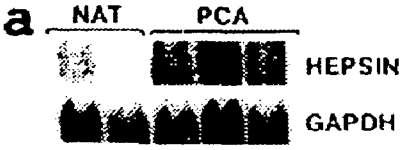
c
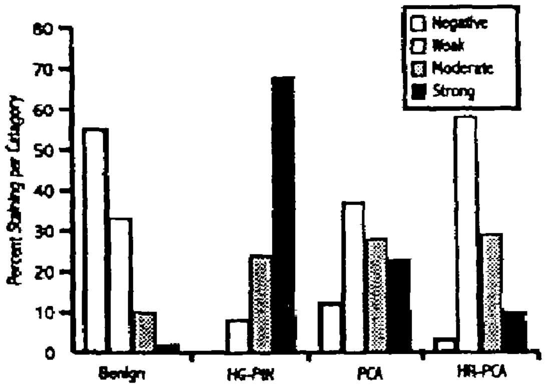
d
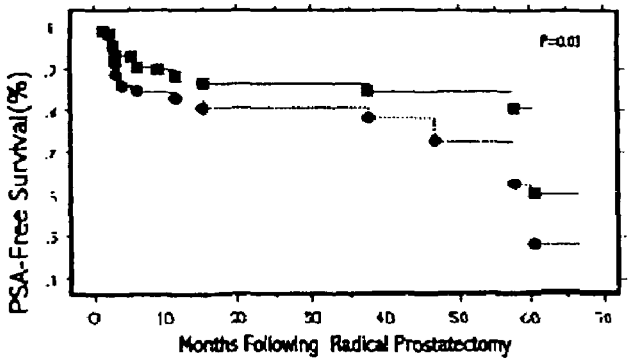

TMA

Figure 5
Normal Adjacent Pool
Commercial Pool
NAP-102
NAP-106
NAP-105
NAP-105
NAP-102
NAP-CPP
NAP-104
23431 T77023 KIAA0203 KIAA0203 gene product
23804 R38383 ZFP36 zinc finger protein homologous to Zfp-36 in mouse
358531 W96134 JUN v-jun avian sarcoma virus 17 oncogene homolog
79022 T62179 FOSB FBI murine osteosarcoma viral oncogene homolog
840944 AA486628 EGR1 early growth response
309776 N94588 CFLAR CASP8 and FADD-like apoptosis regulator
51448 H21041 ATF3 activating transcription factor
753104 AA478553 DCT dopachrome tautomerase dopachrome delta-isomerase, tyrosine-related protein2
898092 AA598794 CTGF connective tissue growth factor
278729 N62936 Homo sapiens mRNA; cDNA DKFZp586M1418 from clone DKFZp586M1418
244307 N75719 PAI1 plasminogen activator inhibitor, type
300103 W07099 NAGLU N-acetylglucosaminidase, alpha- Sanfilippo disease IIIB
470393 AA031513 MMP7 matrix metalloproteinase 7 matrilysin, uterine
50043 H17696 MBP myelin basic protein
470393 AA031513 MMP7 matrix metalloproteinase 7 matrilysin, uterine
134422 R31679 ESTs
788566 AA452966 PCP4 Purkinje cell protein4
840776 AA486082 SGK serum/glucocorticoid regulated kinase
813823 AA453712 LUM lumican
813823 AA453712 LUM lumican
501854 AA127965 sEST
503083 AA148641 MEIS2 Meis mouse homolog2
488434 AA047435 KIAA0203 KIAA0203 gene product
357970 W92594 DKFZP564B0769 DKFZP564B0769 protein
795323 AA454176 TPR translocated promoter region to activated MET oncogene
667598 AA228130 LEDGF lens epithelium derived growth factor
366966 AA026562 sEST
502396 AA156946 Homo sapiens mRNA; cDNA DKFZp564C2063 from clone DKFZp564C2063
188036 H44784 BPAG1 bullous pemphigoid antigen 1 230/240kD
203132 H54629 TNFSF10 tumor necrosis factor ligand superfamily, member 10
301309 NO DATA FOR THIS CLONE IN UNIGENE BUILD 106.
295140 N71647 ESTs, Weakly similar to similar to pre-mRNA splicing factor SRP20 [C.elegans]
40721 R55750 ESTs
85840 T72235 NNMT nicotinamide N-methyltransferase
365826 AA025819 GAS1 growth arrest-specific
324180 W47387 EVI5 ecotropic viral integration site5
416833 W86653 FKBP5 FK506-binding protein5
416833 W86653 FKBP5 FK506-binding protein5
243989 N45364 ESTs
838856 AA464880 CA3 carbonic anhydrase III, muscle specific
770066 AA430545 KIAA0056 KIAA0056 protein
132828 R27172 ESTs
810711 AA457700 CYB561 cytochrome b-561
34778 R19956 VEGF vascular endothelial growth factor
190732 H38650 SLC2A5 solute carrier family 2 facilitated glucose transporter, member5
258790 N40841 CCK cholecystokinin
241274 H91216 Homo sapiens mRNA; cDNA DKFZp586A0617 from clone DKFZp586A0617
179276 H50323 FASN fatty acid synthase
40887 NO DATA FOR THIS CLONE IN UNIGENE BUILD 106.
147414 H01340 MAP3K10 mitogen-activated protein kinase kinase kinase 10
347702 W81570 CTBP1 C-terminal binding protein
897781 AA598517 KRT8 keratin8
179276 H50323 FASN fatty acid synthase
485744 AA039932 TBXA2R thromboxane A2 receptor
70827 T46924 ABP1 amiloride binding protein 1 amine oxidase copper-containing
295889 N67017 LIFR leukemia inhibitory factor receptor
256895 N26311 PLAB prostate differentiation factor
NP -4 -3 -2 0 2 3 4
Expression fold change from pool

Figure 7
a
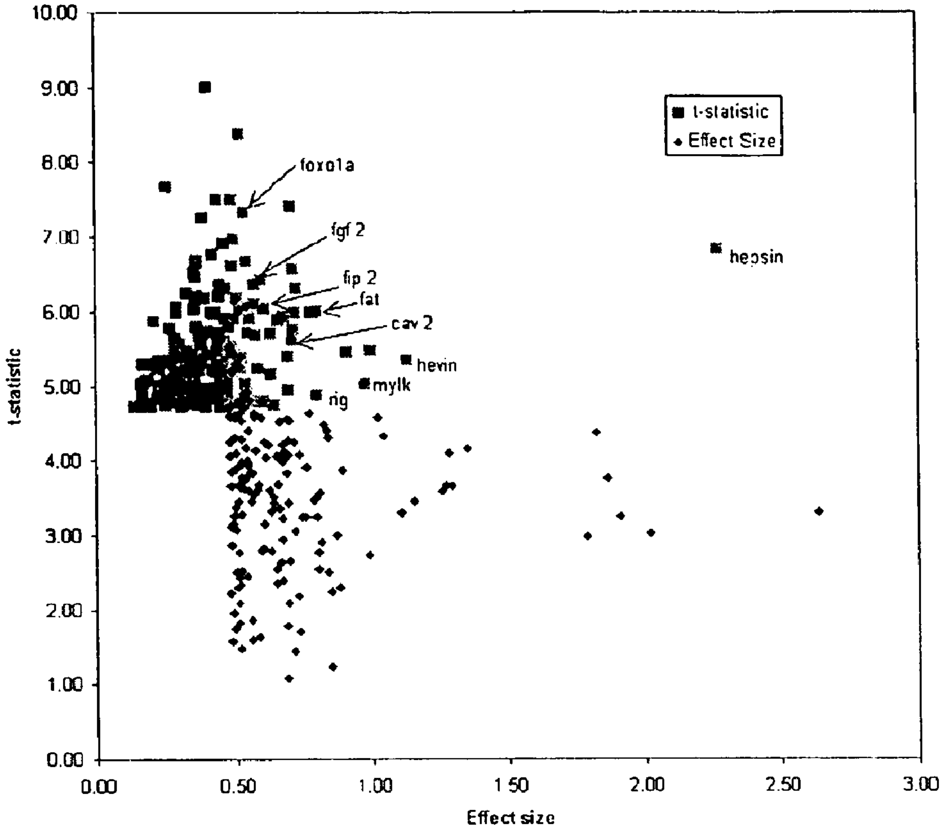
b
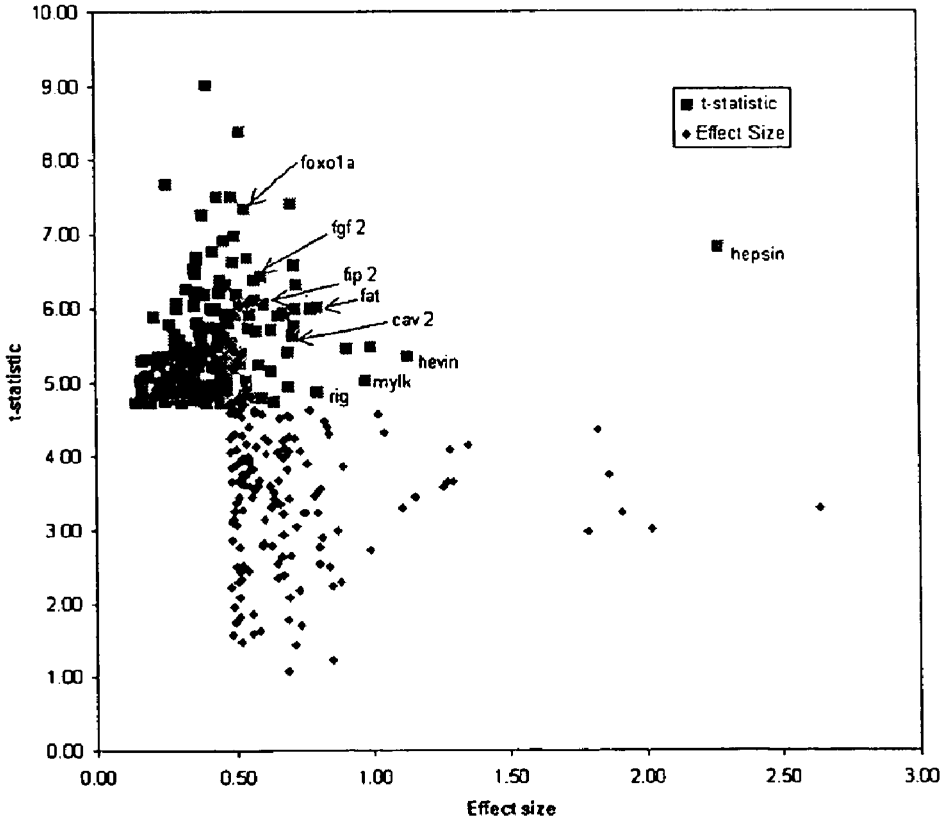

Figure 9 A

| SEQ ID NO | Name | Accession Number |
|---|---|---|
| 1 | Hepsin | M18930 |
| 2 | pim-1 | M54915 |
| 3 | FKBP5 | XM_004288 |
| 4 | FASN | NM_004104 |
| 5 | FOLH1 | M99487 |
| 6 | TNFSF10 | XM_045049 |
| 7 | PCM1 | XM_044711 |
| 8 | S100A11 | XM_047223 |
| 9 | IGFBP3 | XM_004689 |
| 10 | SLUG | XM_011634 |
| 11 | GSTM3 | J05459 |
| 12 | IL1R2 | X59770 |
| 13 | ITGB4 | X53587 |
| 14 | CCND2 | XM_034568 |
| 15 | EDNRB | S57283 |
| 16 | APP | X06989 |
| 17 | THROMBOSPONDIN 1 | X04665 |
| 18 | ANNEXIN A1 | XM_005665 |
| 19 | EPHA1 | M18391 |
| 20 | NCK1 | XM_051968 |
| 21 | MAPK6 | XM_017662 |
| 22 | SGK | XM_037045 |
| 23 | HEVIN | XM_011533 |
| 24 | MEIS2 | XM_012430 |
| 25 | MYLK | XM_042191 |
| 26 | FZD7 | NM_003507 |
| 27 | CAVEOLIN 2 | XM_004966 |
| 28 | TACC1 | XM_049505 |
| 29 | ARHB | XM_002689 |
| 30 | PSG9 | NM_002784 |
| 31 | GSTM1 | NM_000561 |
| 32 | Keratin 5 | XM_006847 |
| 33 | TIMP2 | XM_027036 |
| 34 | GELSOLIN | XM_016545 |
| 35 | ITM2C | AA034213 |
| 36 | GSTM5 | XM_002154 |
| 37 | VINCULIN | XM_011883 |
| 38 | FHL1 | XM_042931 |

Figure 9 B

| | | |
|---|---|---|
| 39 | GSTP1 | XM_040116 |
| 40 | MEIS1 | XM_010880 |
| 41 | ETS2 | XM_009766 |
| 42 | PPP2CB | XM_005121 |
| 43 | CATHEPSIN B | XM_005133 |
| 44 | COL1A2 | XM_029246 |
| 45 | RIG | XM_006029 |
| 46 | VIMENTIN | XM_042952 |
| 47 | MOESIN | XM_013042 |
| 48 | MCAM | XM_006077 |
| 49 | FIBRONECTIN 1 | XM_030549 |
| 50 | NBL1 | XM_001434 |
| 51 | ANNEXIN A4 | XM_031594 |
| 52 | ANNEXIN A11 | XM_035906 |
| 53 | IL1R1 | XM_002686 |
| 54 | IGFBP5 | XM_046731 |
| 55 | CYSTATIN C | XM_009599 |
| 56 | COL15A1 | XM_005592 |
| 57 | ADAMTS1 | XM_047796 |
| 58 | SKI | XM_001535 |
| 59 | EGR1 | XM_033546 |
| 60 | FOSB | NM_006732 |
| 61 | CFLAR | XM_027980 |
| 62 | JUN | XM_001472 |
| 63 | YWHAB | XM_009519 |
| 64 | NRAS | XM_001317 |
| 65 | C7 | J03507 |
| 66 | SCYA2 | XM_038982 |
| 67 | ITGA1 | XM_032902 |
| 68 | LUMICAN | XM_006900 |
| 69 | C1S | XM_032536 |
| 70 | C4BPA | XM_052053 |
| 71 | COL3A1 | XM_044878 |
| 72 | FAT | XM_003477 |
| 73 | MMECD10 | XM_030168 |
| 74 | CLUSTERIN | XM_005113 |
| 75 | PLA2G2A | XM_027887 |
| 76 | MADH4 | XM_030100 |
| 77 | SEPP1 | XM_011306 |
| 78 | RAB2 | XM_037653 |
| 79 | PP1CB | NM_002709 |
| 80 | MPDZ | XM_051281 |

Figure 9 C

| | | |
|---|---|---|
| 81 | PRKCL2 | XM_001880 |
| 82 | ATF2 | XM_027217 |
| 83 | RAB5A | NM_004162 |
| 84 | Cathepsin H | XM_007633 |
| 85 | CTBP1 | XM_003445 |
| 86 | MAP3K10 | XM_042665 |
| 87 | TBXA2R | XM_047633 |
| 88 | MTA1 | NM_004689 |
| 89 | RAP2 | NM_002886 |
| 90 | TRAP1 | XM_036666 |
| 91 | TFCP2 | XM_051171 |
| 92 | E2-EPF | XM_012615 |
| 93 | UBCH10 | XM_009488 |
| 94 | TASTIN | XM_006826 |
| 95 | EZH2 | XM_004774; NM004456 |
| 96 | FLS353 | AB024704 |
| 97 | MYBL2 | XM_009492 |
| 98 | LIMK1 | XM_051836 |
| 99 | TRAF4 | XM_031428 |
| 104 | AMACR | XM_043772; NM01324 |
| 114 | GP73 | AF236056 |
| 115 | CTBP2 | AF016507 |
| 116 | Annexin A2 | NM_004039 |
| 117 | Annexin A4 | XM_031596 |
| 118 | Annexin A11 | NM_001157 |
| 119 | ABCC5 (MDR5) | XM_002914 |
| 120 | ASNS | M27396 |
| 121 | TOP2A | NM_001067 |
| 122 | VaV2 | XM_005638 |

FIG. 10 A-1

SEQ ID NO:1

```
1     tcgagcccgc tttccaggga ccctacctga gggcccacag gtgaggcagc ctggcctagc
61    aggccccacg ccaccgcctc tgcctccagg ccgcccgctg ctgcggggcc accatgctcc
121   tgcccaggcc tggagactga cccgaccccg gcactacctc gaggctccgc cccacctgc
181   tggaccccag ggtcccaccc tggcccagga ggtcagccag ggaatcatta acaagaggca
241   gtgacatggc gcagaaggag ggtggccgga ctgtgccatg ctgctccaga cccaaggtgg
301   cagctctcac tgcggggacc ctgctacttc tgacagccat cggggcggca tcctgggcca
361   ttgtggctgt tctcctcagg agtgaccagg agccgctgta cccagtgcag gtcagctctg
421   cggacgctcg gctcatggtc tttgacaaga cggaagggac gtggcggctg ctgtgctcct
481   cgcgctccaa cgccagggta gccggactca gctgcgagga gatgggcttc ctcagggcac
541   tgacccactc cgagctggac gtgcgaacgg cgggcgccaa tggcacgtcg ggcttcttct
601   gtgtggacga ggggaggctg ccccacaccc agaggctgct ggaggtcatc tccgtgtgtg
661   attgccccag aggccgtttc ttggccgcca tctgccaaga ctgtggccgc aggaagctgc
721   ccgtggaccg catcgtggga ggccgggaca ccagcttggg ccggtggccg tggcaagtca
781   gccttcgcta tgatggagca cacctctgtg gggatccct gctctccggg gactgggtgc
841   tgacagccgc ccactgcttc ccggagcgga accgggtcct gtcccgatgg cgagtgtttg
901   ccggtgccgt ggcccaggcc tctccccacg gtctgcagct gggggtgcag gctgtggtct
961   accacgggggg ctatcttccc tttcgggacc ccaacagcga ggagaacagc aacgatattg
1021  ccctggtcca cctctccagt cccctgcccc tcacagaata catccagcct gtgtgcctcc
1081  cagctgccgg ccaggccctg gtggatggca agatctgtac cgtgacgggc tggggcaaca
1141  cgcagtacta tggccaacag gccggggtac tccaggaggc tcgagtcccc ataatcagca
1201  atgatgtctg caatggcgct gacttctatg gaaaccagat caagcccaag atgttctgtg
1261  ctggctaccc cgagggtggc attgatgcct gccagggcga cagcggtggt ccctttgtgt
1321  gtgaggacag catctctcgg acgccacgtt ggcggctgtg tggcattgtg agttggggca
1381  ctggctgtgc cctggcccag aagccaggcg tctacaccaa agtcagtgac ttccgggagt
1441  ggatcttcca ggccataaag actcactccg aagccagcgg catggtgacc cagctctgac
1501  cggtggcttc tcgctgcgca gcctccaggg cccgaggtga tcccggtggt gggatccacg
1561  ctgggccgag gatgggacgt tttcttcttt gggcccggtc cacaggtcca aggacaccct
1621  ccctccaggg tcctctcttc cacagtggcg ggcccactca gccccgagac cacccaacct
1681  caccctcctg acccccatgt aaatattgtt ctgctgtctg ggactcctgt ctaggtgccc
1741  ctgatgatgg gatgctcttt aaataataaa gatggttttg att
```

SEQ ID NO:2

```
1     gaggaggccc gagaggagtc ggtggcagcg gcggcggcgg gaccggcagc agcagcagca
61    gcagcagcag caaccactag cctcctgccc cgcggcgttg cgacgagccc cacgagccgc
121   tcaccccgcc gttctcagcg ctgcccgacc ccgctggcgc gcctcccgcc gcagtcccgg
181   cagcgcctca gttgtcctcc gactcgccct cggccttcgc gcagcgcagc acagccgcac
241   gcaccgcagc acagcacagc acagcccagg catagcttcg gcacagcccc ggctccggct
301   cctgcggcag ctcctctggc acgtccctgc gccgacattc tggaggttgg atgctcttgt
361   ccaaaatcaa ctcgcttgcc cacctgcgcg ccgcgccctg caacgacctg cacgccacca
421   agctggcgcc cggcaaggag aaggagcccc tggagtcgca gtaccaggtg ggcccgctac
481   tgggcagcgg cggcttcggc tcggtctact caggcatccg cgtctccgac aacttgccgg
541   tggccatcaa acacgtggag aaggaccgga tttccgactg gggagagctg cctaatggca
601   ctcgagtgcc catggaagtg gtcctgctga agaaggtgag ctcgggtttc tccggcgtca
661   ttaggctcct ggactggttc gagaggcccg acagtttcgt cctgatcctg gagaggcccg
721   agccggtgca agatctcttc gacttcatca cggaaagggg agccctgcaa gaggagctgg
781   cccgcagctt cttctggcag gtgctggagg ccgtgcggca ctgccacaac tgcggggtgc
```

FIG. 10 A-2

841 tacaccgcga catcaaggac gaaaacatcc ttatcgacct caatcgcggc gagctcaagc
901 tcatcgactt cgggtcgggg gcgctgctca aggacaccgt ctacacggac ttcgatggga
961 cccgagtgta tagccctcca gagtggatcc gctaccatcg ctaccatggc aggtcggcgg
1021 cagtctggtc cctggggatc ctgctgtatg atatggtgtg tggagatatt cctttcgagc
1081 atgacgaaga gatcatcagg ggccaggttt tcttcaggca gagggtctct tcagaatgtc
1141 agcatctcat tagatggtgc ttggccctga gaccatcaga taggccaacc ttcgaagaaa
1201 tccagaacca tccatggatg caagatgttc tcctgcccca ggaaactgct gagatccacc
1261 tccacagcct gtcgccgggg cccagcaaat agcagccttt ctggcaggtc ctcccctctc
1321 ttgtcagatg cccgagggag ggaagcttc tgtctccagc ttcccgagta ccagtgacac
1381 gtctcgccaa gcaggacagt gcttgataca ggaacaacat ttacaactca ttccagatcc
1441 caggcccctg gaggctgcct cccaacagtg gggaagagtg actctccagg ggtcctaggc
1501 ctcaactcct cccatagata ctctcttctt ctcataggtg tccagcattg ctggactctg
1561 aaatatcccg gggtggggg gtgggggtgg gcagaaccct gccaatggaa ctctttcttc
1621 atcatgagtt ctgctgaatg ccgcgatggg tcaggtaggg gggaaacagg ttgggatggg
1681 ataggactag cacattttaa gtccctgtca cctcttccga ctctttctga gtgccttctg
1741 tggggactcc ggctgtgctg ggagaaatac ttgaacttgc ctcttttacc tgctgcttct
1801 ccaaaaatct gcctgggttt tgttccctat ttttctctcc tgtcctccct cacccccctcc
1861 ttcatatgaa aggtgccatg gaagaggcta cagggccaaa cgctgagcca cctgcccttt
1921 tttctgcctc ctttagtaaa actccgagtg aactggtctt ccttttttggt ttttacttaa
1981 ctgtttcaaa gccaagacct cacacacaca aaaaaatgca caaaccaagc aatcaacaga
2041 aaagctgtaa atgtgtgtac agttggcatg gtagtataca aaaagattgt agtggatcta
2101 atttttaaga aattttgcct ttaagttatt ttacctgttt ttgtttcttg ttttgaaaga
2161 tgcgcattct aacctggagg tcaatgttat gtatttattt atttatttat ttggttccct
2221 tcctattcca agcttccata gctgctgccc tagttttctt tcctcctttc ctcctctgac
2281 ttggggacct tttgggggag ggctgcgacg cttgctctgt ttgtggggtg acgggactca
2341 ggcgggacag tgctgcagct ccctggcttc tgtggggccc ctcacctact tacccaggtg
2401 ggtcccggct ctgtgggtga tgggaggggc cattgctgac tgtgtatata ggataattat
2461 gaaacacagt tctggatggt gtgccttcca gatcctctct ggggctgtgt tttgagcagc
2521 aggtagcctg ctggttttat ctgagtgaaa tactgtacag ggaataaaa gagatcttat
2581 ttttttttta tacttgcgtt tggaataaaa accctttggc ttt SEQ ID NO:3
1 gaacaatgaa gaaagcccca cagccactgt tgctgagcag ggagaggata ttacctccaa
61 aaaagacagg ggagtattaa agattgtcaa aagagtgggg aatggtgagg aaacgccgat
121 gattggagac aaagtttatg tccattacaa aggaaaattg tcaaatggaa agaagtttga
181 ttccagtcat gatagaaatg aaccatttgt ctttagtctt ggcaaaggcc aagtcatcaa
241 ggcatgggac attggggtgg ctaccatgaa gaaaggagag atatgccatt tactgtgcaa
301 accagaatat gcatatggct cggctggcag tctccctaaa attccctcga atgcaactct
361 ctttttttgag attgagctcc ttgatttcaa aggagaggat ttatttgaag atggaggcat
421 tatccggaga accaaacgga aaggagaggg atattcaaat ccaaacgaag gagcaacagt
481 agaaatccac ctggaaggcc gctgtggtgg aaggatgttt gactgcagag atgtggcatt
541 cactgtgggc gaaggagaag accacgacat tccaattgga attgacaaag ctctggagaa
601 aatgcagcgg gaagaacaat gtattttata tcttggacca agatatggtt ttggagaggc
661 agggaagcct aaatttggca ttgaacctaa tgctgagctt atatatgaag ttacacttaa
721 gagcttcgaa aaggccaaag aatcctggga gatggatacc aaagaaaaat tggagcaggc
781 tgccattgtc aaagagaagg gaaccgtata cttcaaggga ggcaaataca tgcaggcggt
841 gattcagtat gggaagatag tgtcctggtt agagatggaa tatggtttat cagaaaagga
901 atcgaaagct tctgaatcat ttctccttgc tgcctttctg aacctggcca tgtgctacct
961 gaagcttaga gaatacacca aagctgttga atgctgtgac aaggcccttg gactggacag
1021 tgccaatgag aaaggcttgt ataggagggg tgaagcccag ctgctcatga acgagtttga
1081 gtcagccaag ggtgactttg agaaagtgct ggaagtaaac cccccagaata aggctgcaag

FIG. 10 A-3

```
1141  actgcagatc tccatgtgcc agaaaaaggc caaggagcac aacgagcggg accgcaggat
1201  atacgccaac atgttcaaga agtttgcaga gcaggatgcc aaggaagagg ccaataaagc
1261  aatgggcaag aagacttcag aaggggtcac taatgaaaaa ggaacagaca gtcaagcaat
1321  ggaagaagag aaacctgagg gccacgtatg acgccacgcc aaggagggaa gagtcccagt
1381  gaactcggcc cctcctcaat gggctttccc ccaactcagg acagaacagt gtttaatgta
1441  aagtttgtta tagtctatgt gattctggaa gcaaatggca aaaccagtag cttcccaaaa
1501  acagcccccc tgctgctgcc cggagggttc actgaggggt ggcacgggac cactccaggt
1561  ggaacaaaca gaaatgactg tggtgtggag ggagtgagcc agcagcttaa gtccagctca
1621  tttcagtttc tatcaacctt caagtatcca attcagggtc cctggagatc atcctaacaa
1681  tgtggggctg ttaggtttta cctttgaact ttcatagcac tgcagaaacc tttaaaaaaa
1741  aaatgcttca tgaatttctc ctttcctaca gttgggtagg gtaggggaag gaggataagc
1801  ttttgttttt taaatgactg aagtgctata aatgtagtct gttgcatttt taaccaacag
1861  aacccacagt agaggggtct catgtctccc cagttccaca gcagtgtcac agacgtgaaa
1921  gccagaacct cagaggccac ttgcttgctg acttagcctc ctcccaaagt ccccctcctc
1981  agccagcctc cttgtgagag tggctttcta ccacacacag cctgtccctg ggggagtaat
2041  tctgtcattc ctaaaacacc cttcagcaat gataatgagc agatgagagt ttctggatta
2101  gcttttccta ttttcgatga agttctgaga tactgaaatg tgaaaagagc aatcagaatt
2161  gtgctttttc tcccctcctc tattcctttt agggaataat attcaataca cagtacttcc
2221  tcccag
```

SEQ ID NO:4

```
1     atggaggagg tggtgattgc cggcatgttc gggaagctgc cagagtcgga gaacttgcag
61    gagttctggg acaacctcat cggcggtgtg gacatggtca cggacgatga ccgtcgctgg
121   aaggctgggc tctacggcct gccccggcgg tccggcaagc tgaaggacct gtctaggttt
181   gatgcctcct tcttcggagt ccaccccaag caggcacaca cgatggaccc tcagctgcgg
241   ctgctgctgg aagctaccta tgaagccatc gtggacggag gcatcaaccc agattcactc
301   cgaggaacac acactggcgt ctgggtgggc gtgagcggct ctgagacctc ggaggccctg
361   agccgagacc ccgagacact cgtgggctac agcatggtgg gctgccagcg agcgatgatg
421   gccaaccggc tctccttctt cttcgacttc agagggccca gcatcgcact ggacacagcc
481   tgctcctcca gcctgatggc cctgcagaac gcctaccagg ccatccacag cgggcagtgc
541   cctgccgcca tcgtgggggg catcaacgtc ctgctgaagc ccaacacctc cgtgcagttc
601   ttgaggctgg ggatgctcag ccccgagggc acctgcaagg ccttcgacac agcggggaat
661   gggtactgcc gctcggaggg tgtggtggct gtcctgctga ccaagaagtc cctggcccgg
721   aaggtctaca ccaccatcct gaacaaaggc accaatacag atggcttcaa ggagcaaggc
781   gtgaccttcc ctcaggatat ccaggagcag cctatccgct cgttgtacca gtcggccgga
841   gtggcccctg agtcatttga atacatcgaa gcccacggac caggcaccaa ggtgggcgac
901   ccccaggagc gtaatggcat cacccgagcc ctgtgcgcca cccgccagga gccgctgctc
961   atcggctcca ccaagtccaa catggggcac ccggagccag cctcggggct cgacgccctg
1021  gccaaggtgc tgctgtccct ggagcacggg ctctgggccc ccaacctgca cttccatagc
1081  cccaaccctg agatcccagc gctgttggat gggcggctgc aggtggtgga ccagcccctg
1141  cccgtccgtg gcggcaacgt gggcatcaac tcctttggct tcgggggctc caacatgcac
1201  atcatcctga ggcccaacac gcagtccgcc cccgcacccg ccccacatgc caccctgccc
1261  cgtctgctgc gggccagcgg acgcacccct gaggccgtgc agaagctgct ggagcagggc
1321  ctccggcaca gccagggcct ggctttcctg agcatgctga acgacatcgc ggctgtcccc
1381  gccaccgcca tgcccttccg tggctacgct gtgctgggtg gtgagacgcg gtggcccaga
1441  gtgcagcagg tgcccgctgg cgagcgcccg ctctggttca tctgctctgg gatgggcaca
1501  cagtggcgtg gaatggggct gagccttatg cgcctggacc gcttccgaga ttccatccta
1561  cgctccgatg aggctgtgaa ccgattcggc ctgaaggtgt cacagctgct gctgagcaca
1621  gacgagagca cctttgatga catcgtccat tcgtttgtga gcctgactgc catccagata
1681  ggcctcatag acctgctgag ctgcatggga cctgaggcag atggcatcgt cggccactcc
1741  ctgggggagt ggctgtcggt acgcgacggc tgcctgtccc aggaggaggc cgtcctcgct
```

FIG. 10 A-4

1801 gcctactgga ggggacagtg catcaaagaa gccccacttc ccgccggcgc catggcagcc
1861 gtgggcttgt cctgggagga gtgtaaacag cgctgccccc ctgcggtggt gcccgcctgc
1921 cacaactcca aggacacagt caccatctcg ggacctcagg ccccggtgtt tgagttcgtg
1981 gagcagctga ggaaggaggg tgtgtttgcc aaggaggtgc ggaccggcgg tatggccttc
2041 cactcctact tcatggaggc catcgcaccc ccactgctgc aggagctcaa gaaggtgatc
2101 cgggagccga agccacgttc agcccgctgg ctcagcacct ctatccccga ggcccagtgg
2161 cacagcagcc tggcacgcac gtcttccgcc gagtacaatg tcaacaacct ggtgagccct
2221 gtgctgttcc aggaggccct gtggcacgtg cctgagcacg cggtggtgct ggagatcgcc
2281 ccgaccccgt gccctcaggc tgtcctgaag cgggtccgta agccgagctg caccatcatc
2341 ccccgtatga agaaggatca cagggacaac ctggagttct tcctggccgg catcggcagg
2401 ctgcacctct caggcatcga cgccaacccc aatgccttgt tcccacctgt ggagtcccca
2461 gctccccgag gaactcccct catctcccca ctcatcaagt gggaccacag cctggcctgg
2521 gacgcgccgg ccgccgagga cttccccaac ggttcaggtt ccccctcagc caccatctac
2581 acatgcacac caagctccga gtctcctgac cgctacctgg tggaccacac catcgacggt
2641 cgcgtcctct tccccgccac tggctacctg agcatagtgt ggaagacgct ggcccgcgcc
2701 tgggctgggc tcgagcagct gcctgtggtg tttgaggatg tggtgcagca ccaggccacc
2761 atcctgccca agactgggac agtgtccttg gaggtacggc tcctggaggc caccggtgcc
2821 ttcgaggtgt cagagaacgg caacctggta gtgagtggga aggtgtacca gtgggatgac
2881 cctgacccca ggctcttcga ccacccggaa agtccccacc ccaattcccc acggagtccc
2941 ctcttcctgg cccaggcaga agtttacaag gagctgcgtc tgcgtggcta cgactacggc
3001 cctcatttcc agggcatcct ggaggccagc ctggaaggtg actcggggag gctgctgtgg
3061 aaggataact gggtgagctt catggacacc atgctgcaga tgtccatcct gggctcggcc
3121 aagcacggcc tgtacctacc cacccgtgtc accgccatcc acatcgaccc tgccacccac
3181 aggcagaagc tgtacacact gcaggacaag gcccaagtgg ctgacgtggt ggtgagcagg
3241 tggccgaggg tcacagtggc gggaggcgtc cacatctccg ggctccacac tgagtcggcc
3301 ccgcggcggc acgaggagca gcaggtgccc atcctggaga agttttgctt cactccccac
3361 acggaggagg ggtgcctgtc tgagcacgct gccctcgagg aggagctgca actgtgcaag
3421 gggctggtcg aggcactcga gaccaaggtg acccagcagg ggctgaagat ggtggtgccg
3481 gactggacgg ggcccagatc cccccgggac ccctcacagc aggaactgcc ccggctgttg
3541 tcggctgcct gcaggcttca gctcaacggg aacctgcagc tggagctggc gcaggtgctg
3601 gcccaggaga ggcccaagct gccagaggac cctctgctca gcggcctcct ggactccccg
3661 gcactcaagg cctgcctgga cactgccgtg gagaacatgc ccagcctgaa gatgaaggtg
3721 gtggaggtgc tggccggcca cggtcacctg tattcccgca tcccaggcct gctcagcccc
3781 catcccctgc tgcagctgag ctacacggcc accgaccgcc acccccaggc cctggaggct
3841 gcccaggccg agctgcagca gcacgacgtt gcccagggcc agtgggatcc cgcagaccct
3901 gcccccagcg ccctgggcag cgcggacctc ctggtgtgca actgtgctgt ggctgccctc
3961 ggggacccgg cctcagctct cagcaacatg gtggctgccc tgagagaagg gggctttctg
4021 ctcctgcaca cactgctccg gggcacccct cgggacatcg tggccttcct cacctccact
4081 gagccgcagt atggccaggg catcctgagc caggacgcgt gggagagcct cttctccagg
4141 gtgtcgctgc gcctggtggg cctgaagaag tccttctacg gcgccacgct cttcctgtgc
4201 cgccggccca ccccgcagga cagccccatc ttcctgccgg tggacgatac cagcttccgc
4261 tgggtggagt ctctgaaggg catcctggct gacgaagact cttcccggcc tgtgtggctg
4321 aaggccatca actgtgccac ctcgggcgtg gtgggcttgg tgaactgtct ccgccgagag
4381 cccggcggaa ccgtccggtg tgtgctgctc tccaacctca gcagcacctc ccacgtcccg
4441 gaggtggacc cgggctccgc agaactgcag aaggtgttgc agggagacct ggtgatgaac
4501 gtctaccgcg acggggcctg gggggttttc cgccacttcc tgctggagga caagcctgag
4561 gagccgacgg cacatgcctt tgtgagcacc ctcacccggg gggacctgtc ctccatccgc
4621 tgggtctgct cctcgctgcg ccatgcccag cccacctgcc ctggcgccca gctctgcacg
4681 gtctactacg cctccctcaa cttccgcgac atcatgctgg ccactggcaa gctgtcccct
4741 gatgccatcc cagggaagtg gacctcccag gacagcctgc taggtatgga gttctcgggc
4801 cgagacgcca gcggcaagcg tgtgatggga ctggtgcctg ccaagggcct ggccacctct

FIG. 10 A-5

```
4861  gtcctgctgt caccggactt cctctgggat gtgccttcca actggacgct ggaggaggcg
4921  gcctcggtgc ctgtcgtcta cagcacggcc tactacgcgc tggtggtgcg tgggcgggtg
4981  cgcccccgggg agacgctgct catccactcg ggctcgggcg gcgtgggcca ggccgccatc
5041  gccatcgccc tcagtctggg ctgccgcgtc ttcaccaccg tggggtcggc tgagaagcgg
5101  gcgtacctcc aggccaggtt cccccagctc gacagcacca gcttcgccaa ctcccgggac
5161  acatccttcg agcagcatgt gctgtggcac acgggcggga agggcgttga cctggtcttg
5221  aactccttgg cggaagagaa gctgcaggcc agcgtgaggt gcttcggtac gcacggtcgc
5281  ttcctggaaa ttggcaaatt cgacctttct cagaaccacc cgctcggcat ggctatcttc
5341  ctgaagaacg tgacattcca cggggtccta ctggatgcgt tcttcaacga gagcagtgct
5401  gactggcggg aggtgtgggc gcttgtcgag gccgccatcc gggatggggt ggtacggccc
5461  ctcaagtgca cggtgttcca tggggcccag gtggaggacg ccttccgcta catggcccaa
5521  gggaagcaca ttggcaaagt cgtcgtgcag gtgcttgcgg aggagccggc agtgctgaag
5581  ggggccaaac ccaagctgat gtcggccatc tccaagacct tctgcccggc ccacaagagc
5641  tacatcatcg ctggtggtct gggtggcttc ggcctggagt tggcgcagtg gctgatacag
5701  cgtggggtgc agaagctcgt gttgacttct cgctccggga tccggacagg ctaccaggcc
5761  aagcaggtcc gccggtggag gcgccagggg ctacaggtgc aggtgtccac cagcaacatc
5821  agctcactgg aggggggcccg gggcctcatt gccgaggcgg cgcagcttgg gcccgtgggg
5881  ggcgtcttca acctggccgt ggtcttgaga gatggcttgc tggagaacca gaccccagag
5941  ttcttccagg acgtctgcaa gcccaagtac agcggcaccc tgaacctgga cagggtgacc
6001  cgagaggcgt gccctgagct ggactacttt gtggtcttct cctctgtgag ctgcgggcgt
6061  ggcaatgcgg gacagagcaa ctacggcttt gccaattccg ccatggagcg tatctgtgag
6121  aaacgccggc acgaaggcct cccaggcctg gccgtgcagt ggggcgccat cggcaccgtg
6181  ggcattttgg tggagacgat gagcaccaac gacacgatcg tcagtggcac gctgcccacg
6241  cgcattggcg tccttggcct ggaggtgctg gacctcttcc tgaaccagcc ccacatggtc
6301  ctgagcagct ttgtgctggc tgagaaggct gcggcctata gggacaggga cagccagcgg
6361  gacctggtgg aggccgtggc acacatcctg ggcatccgcg acttggctgc tgtcaacctg
6421  ggcggctcac tggcggacct gggcctggac tcgctcatga gcgcgccggt gcgccagacg
6481  ctggagcgtg agctcaacct ggtgctgtcc gtgcgcgagg tgcggcaact cacgctccgg
6541  aaactgcagg agctgtcctc aaaggcggat gaagccagcg agctggcatg ccccacgccc
6601  aaggaggatg gtctggccca gcagcagact cagctgaacc tgcgctccct gctggtgaaa
6661  ccggagggcc ccaccctgat gcggctcaac tccgtgcaga gctcggagcg gcccctgttc
6721  ctggtgcacc caatcgaggc taccaccgtg ttccacagcc tcggtcccgg tctcagcatc
6781  cccacctatg gcctgcagtg caccccggct gcgccccttg acagcatcca cagcctggct
6841  gcctactaca tcgactgcat caggcaggtg cagcccgagg gcccctaccg cgtggccggc
6901  tactcctacg gggcctgcgt ggcctttgaa atgtgctccc agctgcaggc ccagcagagc
6961  ccagccccca cccacaacag cctcttcctg ttcgacggct cgcccaccta cgtactggcc
7021  tacacccaga gctaccgggc aaagctgacc ccaggctgta aggctgaggc tgagacggag
7081  gccatatgct tcttcgtgca gcagttcacg gacatggagc acaacagggt gctggaggcg
7141  ctgctgccgc tgaagggcct agaggagcgt gtggcagccg ccgtggacct gatcatcaag
7201  agccaccagg gcctggaccg ccaggagctg agctttgcgg cccggtcctt ctactacagg
7261  ctgcgtgccg ctgaccagta tacacccaag gccaagtaca gtggcaacgt gatgctactg
7321  cgggccaaga cgggtggccg ctacggcgag gacctgggcg cggactacaa cctctcccag
7381  gtatgcgacg ggaaagtatc cgtccatatc atcgagggtg accaccgcac gctgctggag
7441  ggcagcggcc tggagtccat catcagcatc atccacagct ccctggctga gccacgtgtg
7501  agtcgggagg gctag
```

SEQ ID NO:5

```
1     ctcaaaaggg gccggatttc cttctcctgg aggcagatgt tgcctctctc tctcgctcgg
61    attggttcag tgcactctag aaacactgct gtggtggaga aactggaccc caggtctgga
121   gcgaattcca gcctgcaggg ctgataagcg aggcattagt gagattgaga gagactttac
181   cccgccgtgg tggttggagg gcgcgcagta gagcagcagc acaggcgcgg gtcccgggag
```

FIG. 10 A-6

241 gccggctctg ctcgcgccga gatgtggaat ctccttcacg aaaccgactc ggctgtggcc
301 accgcgcgcc gcccgcgctg gctgtgcgct ggggcgctgg tgctggcggg tggcttcttt
361 ctcctcggct tcctcttcgg gtggtttata aaatcctcca atgaagctac taacattact
421 ccaaagcata atatgaaagc atttttggat gaattgaaag ctgagaacat caagaagttc
481 ttatataatt ttacacagat accacattta gcaggaacag aacaaaactt tcagcttgca
541 aagcaaattc aatcccagtg gaaagaattt ggcctggatt ctgttgagct agcacattat
601 gatgtcctgt tgtcctaccc aaataagact catcccaact acatctcaat aattaatgaa
661 gatggaaatg agattttcaa cacatcatta tttgaaccac ctcctccagg atatgaaaat
721 gtttcggata ttgtaccacc tttcagtgct ttctctcctc aaggaatgcc agagggcgat
781 ctagtgtatg ttaactatgc acgaactgaa gacttcttta aattggaacg ggacatgaaa
841 atcaattgct ctgggaaaat tgtaattgcc agatatggga aagttttcag aggaaataag
901 gttaaaaatg cccagctggc aggggccaaa ggagtcattc tctactccga ccctgctgac
961 tactttgctc ctggggtgaa gtcctatcca gatggttgga atcttcctgg aggtggtgtc
1021 cagcgtggaa atatcctaaa tctgaatggt gcaggagacc ctctcacacc aggttaccca
1081 gcaaatgaat atgcttatag gcgtggaatt gcagaggctg ttggtcttcc aagtattcct
1141 gttcatccaa ttggatacta tgatgcacag aagctcctag aaaaaatggg tggctcagca
1201 ccaccagata gcagctggag aggaagtctc aaagtgccct acaatgttgg acctggcttt
1261 actggaaact tttctacaca aaaagtcaag atgcacatcc actctaccaa tgaagtgaca
1321 agaatttaca atgtgatagg tactctcaga ggagcagtgg aaccagacag atatgtcatt
1381 ctgggaggtc accgggactc atgggtgttt ggtggtattg accctcagag tggagcagct
1441 gttgttcatg aaattgtgag gagctttgga acactgaaaa aggaagggtg gagacctaga
1501 agaacaattt tgtttgcaag ctgggatgca gaagaatttg gtcttcttgg ttctactgag
1561 tgggcagagg agaattcaag actccttcaa gagcgtggcg tggcttatat taatgctgac
1621 tcatctatag aaggaaacta cactctgaga gttgattgta caccgctgat gtacagcttg
1681 gtacacaacc taacaaaaga gctgaaaagc cctgatgaag gctttgaagg caaatctctt
1741 tatgaaagtt ggactaaaaa aagtccttcc ccagagttca gtggcatgcc caggataagc
1801 aaattgggat ctggaaatga ttttgaggtg ttcttccaac gacttggaat tgcttcaggc
1861 agagcacggt atactaaaaa ttgggaaaca aacaaattca gcggctatcc actgtatcac
1921 agtgtctatg aaacatatga gttggtggaa aagttttatg atccaatgtt taaatatcac
1981 ctcactgtgg cccaggttcg aggagggatg gtgtttgagc tagccaattc catagtgctc
2041 ccttttgatt gtcgagatta tgctgtagtt ttaagaaagt atgctgacaa aatctacagt
2101 atttctatga aacatccaca ggaaatgaag acatacagtg tatcatttga ttcacttttt
2161 tctgcagtaa agaattttac agaaattgct tccaagttca gtgagagact ccaggacttt
2221 gacaaaagca acccaatagt attaagaatg atgaatgatc aactcatgtt tctggaaaga
2281 gcatttattg atccattagg gttaccagac aggccttttt ataggcatgt catctatgct
2341 ccaagcagcc acaacaagta tgcaggggag tcattcccag gaatttatga tgctctgttt
2401 gatattgaaa gcaaagtgga cccttccaag gcctggggag aagtgaagag acagatttat
2461 gttgcagcct tcacagtgca ggcagctgca gagactttga gtgaagtagc ctaagaggat
2521 tctttagaga atccgtattg aatttgtgtg gtatgtcact cagaaagaat cgtaatgggt
2581 atattgataa attttaaaat tggtatattt gaaataaagt tgaatattat atataaaaaa
2641 aaaaaaaaaa aaa SEQ ID NO:6
1 cctcactgac tataaaagaa tagagaagga agggcttcag tgaccggctg cctggctgac
61 ttacagcagt cagactctga caggatcatg gctatgatgg aggtccaggg gggacccagc
121 ctgggacaga cctgcgtgct gatcgtgatc ttcacagtgc tcctgcagtc tctctgtgtg
181 gctgtaactt acgtgtactt taccaacgag ctgaagcaga tgcaggacaa gtactccaaa
241 agtggcattg cttgtttctt aaaagaagat gacagttatt gggaccccaa tgacgaagag
301 agtatgaaca gcccctgctg gcaagtcaag tggcaactcc gtcagctcgt tagaaagatg
361 attttgagaa cctctgagga aaccatttct acagttcaag aaaagcaaca aaatatttct
421 cccctagtga gagaaagagg tcctcagaga gtagcagctc acataactgg gaccagagga

FIG. 10 A-7

```
481 agaagcaaca cattgtcttc tccaaactcc aagaatgaaa aggctctggg ccgcaaaata
541 aactcctggg aatcatcaag gagtgggcat tcattcctga gcaacttgca cttgaggaat
601 ggtgaactgg tcatccatga aaaagggttt tactacatct attcccaaac atactttcga
661 tttcaggagg aaataaaaga aaacacaaag aacgacaaac aaatggtcca atatatttac
721 aaatacacaa gttatcctga ccctatattg ttgatgaaaa gtgctagaaa tagttgttgg
781 tctaaagatg cagaatatgg actctattcc atctatcaag gggaatatt tgagcttaag
841 gaaaatgaca gaatttttgt ttctgtaaca aatgagcact tgatagacat ggaccatgaa
901 gccagttttt ttggggcctt tttagttggc taactgacct ggaaagaaaa agcaataacc
961 tcaaagtgac tattcagttt tcaggatgat acactatgaa gatgtttcaa aaaatctgac
1021 caaaacaaac aaacagaaaa cagaaaacaa aaaaacctct atgcaatctg agtagagcag
1081 ccacaaccaa aaaattctac aacacacact gttctgaaag tgactcactt atcccaagag
1141 aatgaaattg ctgaaagatc tttcaggact ctacctcata tcagtttgct agcagaaatc
1201 tagaagactg tcagcttcca aacattaatg caatggttaa catcttctgt ctttataatc
1261 tactccttgt aaagactgta gaagaaagag caacaatcca tctctcaagt agtgtatcac
1321 agtagtagcc tccaggtttc cttaagggac aacatcctta agtcaaaaga gagaagaggc
1381 accactaaaa gatcgcagtt tgcctggtgc agtggctcac acctgtaatc ccaacatttt
1441 gggaacccaa ggtgggtaga tcacgagatc aagagatcaa gaccatagtg accaacatag
1501 tgaaacccca tctctactga aagtacaaaa attagctggg tgtgttggca catgcctgta
1561 gtcccagcta cttgagaggc tgaggcaaga gaattgtttg aacccgggag gcagaggttg
1621 cagtgtggtg agatcatgcc actacactcc agcctggcga cagagcgaga cttggtttca
1681 aaaaaaaaaa aaaaaaaaac ttcagtaagt acgtgttatt tttttcaata aaattctatt
1741 acagtatgtc
```

SEQ ID NO:7

```
   1 ggtcacatga ctccagtcta gctcgcattg cggctcccgc ccgggcgagt tctcgccccc
  61 gcgcggccgt tgccgaggag acggcgcatg tcccgccgcg cgttgccccc tctgcagtac
 121 ccccgcccct cttctcccac cacaatgaga tcctaagatg gcggtggctg cggcggttgg
 181 cgctgcgtag ctgaggtcga aaaggcggcc actggggccg aggcagccag gaaacgtgtg
 241 ggcctctctg ctgcggtctc cgagggccga ccgctgccgg cggcgggtcg tgggggctga
 301 ctgtcgctct gcctttgaca ggagaggctg cttcttgtag aggaaacagc tttgaagtgt
 361 ggagcgggaa aggagcagtt tctgagctgc aaaaactagt ttctaaacag agagttaatt
 421 gttaaatcca gtatggccac aggaggaggt ccctttgaag atggcatgaa tgatcaggat
 481 ttaccaaact ggagtaatga gaatgttgat gacaggctca acaatatgga ttggggtgcc
 541 caacagaaga aagcaaatag atcatcagaa aagaataaga aaaagtttgg tgtagaaagt
 601 gataaaagag taaccaatga tatttctccg gagtcgtcac caggagttgg aaggcgaaga
 661 acaaagactc cacatacgtt cccacacagt agatacatga gtcagatgtc tgtcccagag
 721 caggcagaat tagagaaact gaaacagcgg ataaacttca gtgatttaga tcagagaagc
 781 attggaagtg attcccaagg tagagcaaca gctgctaaca acaaacgtca gcttagtgaa
 841 aaccgaaagc ccttcaactt tttgcctatg cagattaata ctaacaagag caaagatgca
 901 tctacaagtc ccccaaacag agaaacgatt ggatcagcac agtgtaaaga gttgtttgct
 961 tctgctttaa gtaatgacct cttgcaaaac tgtcaggtgt ctgaagaaga tgggagggga
1021 gaacctgcaa tggagagcag ccagattgta agcaggcttg ttcaaattcg cgattatatt
1081 actaaagcta gttccatgcg ggaagatctt gtagagaaaa atgagagatc tgctaatgtt
1141 gagcgcctta ctcatctaat agatcacctt aaagaacaag agaagtcata tatgaaattt
1201 cttaaaaaaa tccttgccag agatcctcag caggagccta tggaagagat agaaaatttg
1261 aagaaacaac atgatttatt aaaaagaatg ttacaacagc aggagcaact aagagctcta
1321 cagggacggc aggctgcact tctagctctg caacataaag cagagcaagc tattgcagtg
1381 atggatgatt ctgttgttgc agaaactgca ggtagcttat ctggcgtcag tatcacatct
1441 gaactaaatg aagaattgaa tgacttaatt cagcgttttc ataatcagct tcgtgattct
1501 cagcctccag ctgttccaga caatagaaga caggcagaaa gtctttcatt aactagggag
1561 gtttcccaga gcaggaaacc atcagcttca gaacgtttac ctgatgagaa agtcgaactt
```

FIG. 10 A-8

```
1621 tttagcaaaa tgagagtgct acaggaaaag aaacaaaaaa tggacaaatt gcttggagaa
1681 cttcatacac ttcgagatca gcatcttaac aattcatcat cctctccaca aaggagtgtc
1741 gatcagagaa gtacttcagc tccctctgct tctgtaggct tggcaccggt tgtcaatgga
1801 gaatccaata gcctcacatc atctgttcct tatcctactg cttctctagt atctcagaat
1861 gagagtgaaa acgaaggcca cctcaatcca tctgaaaaac tccagaagtt aaatgaagtt
1921 cgaaagagat tgaatgagct aagagaatta gttcattatt atgaacaaac gtcagacatg
1981 atgacagatg ctgtgaatga aaacaggaaa gatgaagaaa ctgaagagtc agaatatgat
2041 tctgagcatg aaaattccga gcctgttact aacattcgaa atccacaagt agcttccact
2101 tggaatgaag taaatagtca tagtaatgca cagtgtgttt ctaataatag agatgggcga
2161 acagttaatt ctaattgtga aattaacaac agatctgctg ccaacataag ggctctaaac
2221 gtgcctcctt ctttagattg tcgatataat agagaagggg aacaggagat tcatgttgca
2281 caaggtgaag atgatgagga ggaggaggaa gaagcagaag aggagggagt cagtggagct
2341 tcattatcta gtcacaggag cagtctggtt gatgagcatc cagaagatgc tgaatttgaa
2401 cagaagatca accgacttat ggctgcaaaa cagaaactta gacagttaca agatcttgtt
2461 gctatggtac aggatgatga tgcagctcaa ggagttatct ctgccagtgc atcaaatttg
2521 gatgatttct acccagcaga agaagacacc aagcaaaatt caaataacac tagaggaaat
2581 gccaataaaa cacagaaaga tactggagta aatgaaaagg caagagagaa attttatgag
2641 gctaaactac agcagcaaca gagagagcta aaacaattgc aggaagaaag aaagaaactg
2701 attgacattc aggagaaaat tcaagcattg caaacggcat gccctgactt acagctgtca
2761 gctgctagtg tgggtaactg tcccaccaaa aaatatatgc cagctgttac ttcaacccca
2821 actgttaatc aacacgagac cagtacaagc aaatctgttt ttgagcctga agattcttca
2881 atagtagata atgagttgtg gtcagaaatg agaagacatg aaatgttgag ggaggagctg
2941 cgacagagaa gaaagcagct tgaagctctg atggctgaac atcagaggag gcaaggtcta
3001 gctgaaactg catctccagt ggctgtgtca ttgagaagtg atggatctga gaacctatgt
3061 actcctcagc aaagtagaac agaaaaaacg atggcaactt ggggagggtc tacccagtgt
3121 gcactagatg aagaaggaga tgaagacggt tacctttctg aaggaattgt tcggacagat
3181 gaagaggagg aagaagagca agatgccagt tccaatgata actttttctgt gtgtccttct
3241 racagtgtga atcataactc ctacaatgga aaggaaacta aaaataggtg gaagaacaat
3301 tgcccttttt cggcagatga aaattatcgt cctttagcca agacaaggca acagaatatc
3361 agcatgcaac ggcaagaaaa ccttcgttgg gtgtcagagc tctcttacgt agaagagaaa
3421 gaacaatggc aagaacaaat caatcagcta aagaaacagc ttgattttag tgtcagtatt
3481 tgtcagactt tgatgcaaga ccagcagact ctatcttgtc tgctacaaac tcttctcacg
3541 ggtccttaca gtgttatgcc cagcaatgtt gcatctcctc aagtacactt cataatgcac
3601 cagttgaacc agtgctatac tcagctaaca tggcaacaga ataatgttca gaggttgaaa
3661 caaatgctaa atgaacttat gcgccagcaa aatcagcatc cagaaaaacc tggaggcaag
3721 gaaagaggca gtagtgcatc gcaccctcct tctcccagtt tattttgtcc tttcagcttt
3781 ccaacacagc ctgtaaatct cttcaatata cctggattta ctaacttttc atcatttgca
3841 ccaggtatga atttcagccc tttatttcct tctaattttg gagatttttc tcagaatatc
3901 tctacaccca gtgaacagca gcaaccctta gcccagaatt cttcaggaaa aacagaatat
3961 atggcttttc caaaaccttt tgaaagcagt tcctctattg gagcagagaa accaaggaat
4021 aaaaaactgc ctgaagagga ggtggaaagc agtaggacac catggttata tgaacaagaa
4081 ggtgaagtag agaaaccatt tatcaagact ggattttcag tgtctgtaga aaaatctaca
4141 agtagtaacc gcaaaaatca attagataca aacggaagaa gacgccagtt tgatgaagaa
4201 tcactggaaa gctttagcag tatgcctgat ccagtagatc caacaacagt gactaaaaca
4261 ttcaagacaa gaaaagcgtc tgcacaggcc agcctggcat ctaaagataa aactcccaag
4321 tcaaaaagta agaagaggaa ttctactcag ctgaaaagca gagttaaaaa catcaggtat
4381 gaaagtgcca gtatgtctag cacatgtgaa ccttgcaaaa gtaggaacag acattcagcc
4441 cagactgaag agcctgttca agcaaaagta ttcagcagaa agaatcatga gcaactggaa
4501 aaaataataa aatgtaatag gtctacagaa atatcttcag aaactgggag tgatttttcc
4561 atgtttgaag ctttgcgaga tactatttat tctgaagtag ctacattaat ttctcaaaat
```

FIG. 10 A-9

4621 gaatctcgtc cacattttct tattgaactc ttccatgagc tgcagctactaaacacagac
4681 tacttgagac agagggcttt atatgcattg caggacatag tatccagaca tatttctgag
4741 agccatgaaa aaggagaaaa tgtaaagtca gtaaactctg gtacttggat agcatcaaac
4801 tcagaactta ctcctagtga gagccttgct actactgatg atgaaacttt tgagaagaac
4861 tttgaaagag aaacccataa aataagtgag caaaatgatg ctgataatgc tagtgtcctg
4921 tctgtatcat caaattttga gccttttgca acagatgatc taggtaacac cgtgattcac
4981 ttagatcaag cattagccag aatgagagaa tatgagcgta tgaagactga ggctgaaagt
5041 aactcaaata tgagatgcat ctgcaggatt attgaggatg gagatggtgc tggtgcaggt
5101 actacagtta ataatttaga agaaactccc gttattgaaa atcgtagttc acaacaacct
5161 gtaagtgaag tttctaccat cccatgtcct agaattgata ctcagcagct ggaccggcaa
5221 attaaagcaa ttatgaaaga agtcattcct tttttgaagg agcacatgga tgaagtatgc
5281 tcctcgcagc ttctaacttc agtaaggcgc atggttttga cccttaccca gcaaaatgat
5341 gagagcaaag agtttgtaaa gttctttcat aaacaacttg gaagtatatt acaggattca
5401 ctggcaaaat ttgctggcag aaaactgaaa gactgtggag aagatcttct tgtagagata
5461 tctgaagtgt tgttcaatga attggctttc tttaagctta tgcaagattt ggataataat
5521 agtataactg ttaaacagag atgcaaaagg aaaatagaag caactggagt gatacaatct
5581 tgtgccaaag agctaaaagg attcttgaag atcatggctc acctgctgga gagattgatg
5641 atgaagacaa agacaaggat gaaactgaaa cagttaagca gactcaaaca tctgaggtgt
5701 atgatggtcc caaaaatgta agatctgata tttctgatca agaggaagat gaagaaagtg
5761 aaggatgtcc agtgtctatt aatttgtcta aagctgaaac tcaggcttta actaattatg
5821 gaagtggaga agatgaaaat gaggatgaag aaatggaaga atttgaagaa ggccctgtgg
5881 atgtccagac ttccctccag gctaacactg aagctactga agaaaatgaa catgatgaac
5941 aggtcctaca acgtgacttt aaaaagacag cagaaagcaa aaatgtccca ttggaacgag
6001 aagccactag taaaaatgac caaaataact gtcctgtgaa accctgttac ctcaatatct
6061 tggaagatga gcaaccttta aatagtgctg cccataagga gtcacctcct actgttgatt
6121 caactcaaca gcctaaccct ttgccgttac gtttacctga aatggaaccc ttagtgccta
6181 gagtcaaaga agttaaatct gctcaggaaa ctcctgaaag ctctctggct ggaagtcctg
6241 atactgaatc tccagtgtta gtgaatgact atgaagcaga atctggtaat ataagtcaaa
6301 agtctgatga agaagatttt gtaaaagttg aagatttacc actgaaactg acaatatatt
6361 cagaggcaga tctaagaaag aaaatggtag aagaagaaca gaaaaaccat ttatctggtg
6421 aaatatgtga aatgcagacc gaagaattag ctggaaattc tgagacacta aaagaacctg
6481 aaacggtggg agcccagagt atatgagatg tcttcagagg ctcatctaac tctgtcctta
6541 catactcaat gcatatatga aaacaatact aaataaacat ctgatctgta taaaat SEQ ID NO:8
1 ctccaaaggc aaaaatctcc agccctacag agactgagcg gtgcatcgag tccctgattg
61 ctgtcttcca gaagtatgct ggaaaggatg gttataacta cactctctcc aagacagagt
121 tcgtaagctt catgaataca gaactagctg ccttcacaaa gaaccagaag gaccctggtg
181 tccttgaccg catgatgaag aaactggaca ccaacagtga tggtcagcta gatttctcag
241 aatttcttaa tctgattggt ggcctagcta tggcttgcca tgactccttc ctcaaggctg
301 tcccttccca gaagcggacc tgaggacccc ttggccctgg ccttcaaacc caccccctttt
361 ccttccagcc tttctgtcat catctccaca gcccacccat cccctgagca cactaaccac
421 ctcatgcagg ccccacctgc caatagtaat aaagcaatgt cactttttta aaacatgaa SEQ ID NO:9
1 gccgcttcct gcctggattc cacagcttcg cgccgtgtac tgtcgcccca tccctgcgcg
61 cccagcctgc caagcagcgt gccccggttg caggcgtcat gcagcgggcg cgacccacgc
121 tctgggccgc tgcgctgact ctgctggtgc tgctccgcgg gccgccggtg gcgcgggctg
181 gcgcgagctc ggcgggcttg ggtcccgtgg tgcgctgcga gccgtgcgac gcgcgtgcac
241 tggcccagtg cgcgcctccg cccgccgtgt gcgcggagct ggtgcgcgag ccgggctgcg
301 gctgctgcct gacgtgcgca ctgagcgagg gccagccgtg cggcatctac accgagcgct

FIG. 10 A-10

361 gtggctccgg ccttcgctgc cagccgtcgc ccgacgaggc gcgaccgctg caggcgctgc
421 tggacggccg cgggctctgc gtcaacgcta gtgccgtcag ccgcctgcgc gcctacctgc
481 tgccagcgcc gccagctcca ggaaatgcta gtgagtcgga ggaagaccgc agcgccggca
541 gtgtggagag cccgtccgtc tccagcacgc accgggtgtc tgatcccaag ttccaccccc
601 tccattcaaa gataatcatc atcaagaaag ggcatgctaa agacagccag cgctacaaag
661 ttgactacga gtctcagagc acagataccc agaacttctc ctccgagtcc aagcgggaga
721 cagaatatgg tccctgccgt agagaaatgg aagacacact gaatcacctg aagttcctca
781 atgtgctgag tcccaggggt gtacacattc ccaactgtga caagaaggga ttttataaga
841 aaaagcagtg tcgcccttcc aaaggcagga agcggggctt ctgctggtgt gtggataagt
901 atgggcagcc tctcccaggc tacaccacca aggggaagga ggacgtgcac tgctacagca
961 tgcagagcaa gtagacgcct gccgcaaggt taatgtggag ctcaaatatg ccttattttg
1021 cacaaaagac tgccaaggac atgaccagca gctggctaca gcctcgattt atatttctgt
1081 ttgtggtgaa ctgatttttt ttaaaccaaa gtttagaaag aggtttttga aatgcctatg
1141 gtttctttga atggtaaact tgagcatctt ttcactttcc agtagtcagc aaagagcagt
1201 ttgaattttc ttgtcgcttc ctatcaaaat attcagagac tcgagcacag cacccagact
1261 tcatgcgccc gtggaatgct caccacatgt tggtcgaagc ggccgaccac tgactttgtg
1321 acttaggcgg ctgtgttgcc tatgtagaga acacgcttca cccccactcc ccgtacagtg
1381 cgcacaggct ttatcgagaa taggaaaacc tttaaacccc ggtcatccgg acatcccaac
1441 gcatgctcct ggagctcaca gccttctgtg gtgtcatttc tgaaacaagg gcgtggatcc
1501 ctcaaccaag aagaatgttt atgtcttcaa gtgacctgta ctgcttgggg actattggag
1561 aaaataaggt ggagtcctac ttgtttaaaa aatatgtatc taagaatgtt ctagggcact
1621 ctgggaacct ataaaggcag gtatttcggg ccctcctctt caggaatctt cctgaagaca
1681 tggcccagtc gaaggcccag gatggctttt gctgcggccc cgtggggtag gagggacaga
1741 gagacaggga gagtcagcct ccacattcag aggcatcaca agtaatggca caattcttcg
1801 gatgactgca gaaaatagtg ttttgtagtt caacaactca agacgaagct tatttctgag
1861 gataagctct ttaaaggcaa agctttattt tcatctctca tcttttgtcc tccttagcac
1921 aatgtaaaaa agaatagtaa tatcagaaca ggaaggagga atggcttgct ggggagccca
1981 tccaggacac tgggagcaca tagagattca cccatgtttg ttgaacttag agtcattctc
2041 atgcttttct ttataattca cacatatatg cagagaagat atgttcttgt taacattgta
2101 tacaacatag ccccaaatat agtaagatct atactagata atcctagatg aaatgttaga
2161 gatgctattt gatacaactg tggccatgac tgaggaaagg agctcacgcc cagagactgg
2221 gctgctctcc cggaggccaa acccaagaag gtctggcaaa gtcaggctca gggagactct
2281 gccctgctgc agacctcggt gtggacacac gctgcataga gctctccttg aaaacagagg
2341 ggtctcaaga cattctgcct acctattagc ttttctttat tttttaact ttttgggggg
2401 aaaagtattt ttgagaagtt tgtcttgcaa tgtatttata aatagtaaat aaagttttta
2461 ccatt SEQ ID NO:10
1 atgccgcgct ccttcctggt caagaagcat ttcaacgcct ccaaaaagcc aaactacagc
61 gaactggaca cacatacagt gattatttcc ccgtatctct atgagagtta ctccatgcct
121 gtcataccac aaccagagat cctcagctca ggagcataca gccccatcac tgtgtggact
181 accgctgctc cattccacgc ccagctaccc aatggcctct ctcctctttc cggatactcc
241 tcatctttgg ggcgagtgag tccccctcct ccatctgaca cctcctccaa ggaccacagt
301 ggctcagaaa gccccattag tgatgaagag gaaagactac agtccaagct ttcagacccc
361 catgccattg aagctgaaaa gtttcagtgc aatttatgca ataagaccta ttcaactttt
421 tctgggctgg ccaaacataa gcagctgcac tgcgatgccc agtctagaaa atctttcagc
481 tgtaaatact gtgacaagga atatgtgagc ctgggcgccc tgaagatgca tattcggacc
541 cacacattac cttgtgtttg caagatctgc ggcaaggcgt tttccagacc ctggttgctt
601 caaggacaca ttagaactca cacgggggag aagccttttt cttgccctca ctgcaacaga
661 gcatttgcag acaggtcaaa tctgagggct catctgcaga cccattctga tgtaaagaaa
721 taccagtgca aaaactgctc caaaaccttc tccagaatgt ctctcctgca caaacatgag

FIG. 10 A-11

781 gaatctggct gctgtgtagc acactga

SEQ ID NO:11

```
   1 ctcggaagcc cgtcaccatg tcgtgcgagt cgtctatggt tctcgggtac tgggatattc
  61 gtgggctggc gcacgccatc cgcctgctcc tggagttcac ggatacctct tatgaggaga
 121 aacggtacac gtgcggggaa gctcctgact atgatcgaag ccaatggctg gatgtgaaat
 181 tcaagctaga cctggacttt cctaatctgc cctacctcct ggatgggaag aacaagatca
 241 cccagagcaa tgccatcttg cgctacatcg ctcgcaagca caacatgtgt ggtgagactg
 301 aagaagaaaa gattcgagtg gacatcatag agaaccaagt aatggatttc cgcacacaac
 361 tgataaggct ctgttacagc tctgaccacg aaaaactgaa gcctcagtac ttggaagagc
 421 tacctggaca actgaaacaa ttctccatgt ttctgtggaa attctcatgg tttgccgggg
 481 aaaagctcac ctttgtggat tttctcacct atgatatctt ggatcagaac cgtatatttg
 541 accccaagtg cctggatgag ttcccaaacc tgaaggcttt catgtgccgt tttgaggctt
 601 tggagaaaat cgctgcctac ttacagtctg atcagttctg caagatgccc atcaacaaca
 661 agatggccca gtggggcaac aagcctgtat gctgagcagg aggcagactt gcagagcttg
 721 ttttgtttca tcctgtccgt aaggggtcag cgctcttgct ttgctctttt caatgaatag
 781 cacttatgtt actggtgtcc agctgagttt ctcttgggta taaaggctaa aagggaaaaa
 841 ggatatgtgg agaatcatca agatatgaat tgaatcgctg cgatactgtg gcatttccct
 901 actccccaac tgagttcaag ggctgtaggt tcatgcccaa gccctgagag tgggtactag
 961 aaaaaacgag attgcacagt tggagagagc aggtgtgtta aatggactgg agtccctgtg
1021 aagactgggt gaggataaca caagtaaaac tgtggtactg atggacttaa ccggagttcg
1081 gaaaccgtcc tgtgtacaca tgggagttta gtgtgataaa ggcagtattt cagactggtg
1141 ggctagccaa tagagttggc aattgcttat tgaaactcat taaaaataat agagccccac
1201 ttgacactat tcactaaaat taatctggaa tttaaggccc aacattaaac acaaagctgt
1261 attgat
```

SEQ ID NO:12

```
   1 gccacgtgct gctgggtctc agtcctccac ttcccgtgtc ctctggaagt tgtcaggagc
  61 aatgttgcgc ttgtacgtgt tggtaatggg agtttctgcc ttcacccttc agcctgcggc
 121 acacacaggg gctgccagaa gctgccggtt tcgtgggagg cattacaagc gggagttcag
 181 gctggaaggg gagcctgtag ccctgaggtg cccccaggtg ccctactggt tgtgggcctc
 241 tgtcagcccc cgcatcaacc tgacatggca taaaaatgac tctgctagga cggtcccagg
 301 agaagaagag acacggatgt gggcccagga cggtgctctg tggcttctgc cagccttgca
 361 ggaggactct ggcacctacg tctgcactac tagaaatgct tcttactgtg acaaaatgtc
 421 cattgagctc agagtttttg agaatacaga tgctttcctg ccgttcatct catacccgca
 481 aattttaacc ttgtcaacct ctggggtatt agtatgccct gacctgagtg aattcacccg
 541 tgacaaaact gacgtgaaga ttcaatggta caaggattct cttcttttgg ataaagacaa
 601 tgagaaattt ctaagtgtga gggggaccac tcacttactc gtacacgatg tggccctgga
 661 agatgctggc tattaccgct gtgtcctgac atttgcccat gaaggccagc aatacaacat
 721 cactaggagt attgagctac gcatcaagaa aaaaaaagaa gagaccattc ctgtgatcat
 781 ttcccccctc aagaccatat cagcttctct ggggtcaaga ctgacaatcc cgtgtaaggt
 841 gtttctggga accggcacac ccttaaccac catgctgtgg tggacggcca atgacaccca
 901 catagagagc gcctacccgg gaggccgcgt gaccgagggg ccacgccagg aatattcaga
 961 aaataatgag aactacattg aagtgccatt gatttttgat cctgtcacaa gagaggattt
1021 gcacatggat tttaaatgtg ttgtccataa taccctgagt tttcagacac tacgcaccac
1081 agtcaaggaa gcctcctcca cgttctcctg ggcattgtg ctggccccac tttcactggc
1141 cttcttggtt ttggggggaa tatggatgca cagacggtgc aaacacagaa ctggaaaagc
1201 agatggtctg actgtgctat ggcctcatca tcaagacttt caatcctatc ccaagtgaaa
1261 taaatggaat gaaataattc aaacacaaaa aaaaaaaaaa aaaaaaa
```

SEQ ID NO:13

FIG. 10 A-12

1 gcgctgcccg cctcgtcccc accccccaac cccccgcgcc cgccctcgga cagtccctgc
61 tcgcccgcgc gctgcagccc catctcctag cggcagccca ggcgcggagg gagcgagtcc
121 gccccgaggt aggtccagga cgggcgcaca gcagcagccg aggctggccg ggagagggag
181 gaagaggatg gcagggccac gccccagccc atgggccagg ctgctcctgg cagccttgat
241 cagcgtcagc ctctctggga ccttggcaaa ccgctgcaag aaggccccag tgaagagctg
301 cacggagtgt gtccgtgtgg ataaggactg cgcctactgc acagacgaga tgttcaggga
361 ccggcgctgc aacacccagg cggagctgct ggccgcgggc tgccagcggg agagcatcgt
421 ggtcatggag agcagcttcc aaatcacaga ggagacccag attgacacca ccctgcggcg
481 cagccagatg tccccccaag gcctgcgggt ccgtctgcgg cccggtgagg agcggcattt
541 tgagctggag gtgtttgagc cactggagag ccccgtggac ctgtacatcc tcatggactt
601 ctccaactcc atgtccgatg atctggacaa cctcaagaag atggggcaga acctggctcg
661 ggtcctgagc cagctcacca gcgactacac tattggattt ggcaagtttg tggacaaagt
721 cagcgtcccg cagacggaca tgaggcctga gaagctgaag gagccctggc ccaacagtga
781 ccccccccttc tccttcaaga acgtcatcag cctgacagaa gatgtggatg agttccggaa
841 taaactgcag ggagagcgga tctcaggcaa cctggatgct cctgagggcg gcttcgatgc
901 catcctgcag acagctgtgt gcacgaggga cattggctgg cgcccggaca gcacccacct
961 gctggtcttc tccaccgagt cagccttcca ctatgaggct gatggcgcca acgtgctggc
1021 tggcatcatg agccgcaacg atgaacggtg ccacctggac accacgggca cctacaccca
1081 gtacaggaca caggactacc cgtcggtgcc caccctggtg cgcctgctcg ccaagcacaa
1141 catcatcccc atctttgctg tcaccaacta ctcctatagc tactacgaga agcttcacac
1201 ctatttccct gtctcctcac tgggggtgct gcaggaggac tcgtccaaca tcgtggagct
1261 gctggaggag gccttcaatc ggatccgctc caacctggac atccgggccc tagacagccc
1321 ccgaggcctt cggacagagg tcacctccaa gatgttccag aagacgagga ctgggtcctt
1381 tcacatccgg cggggggaag tgggtatata ccaggtgcag ctgcgggccc ttgagcacgt
1441 ggatgggacg cacgtgtgcc agctgccgga ggaccagaag ggcaacatcc atctgaaacc
1501 ttccttctcc gacggcctca agatggacgc gggcatcatc tgtgatgtgt gcacctgcga
1561 gctgcaaaaa gaggtgcggt cagctcgctg cagcttcaac ggagacttcg tgtgcggaca
1621 gtgtgtgtgc agcgagggct ggagtggcca gacctgcaac tgctccaccg gctctctgag
1681 tgacattcag ccctgcctgc gggagggcga ggacaagccg tgctccggcc gtggggagtg
1741 ccagtgcggg cactgtgtgt gctacggcga aggccgctac gagggtcagt tctgcgagta
1801 tgacaacttc cagtgtcccc gcacttccgg gttcctgtgc aatgaccgag gacgctgctc
1861 catgggccag tgtgtgtgtg agcctggttg gacaggccca agctgtgact gtcccctcag
1921 caatgccacc tgcatcgaca gcaatggggg catctgtaat ggacgtggcc actgtgagtg
1981 tggccgctgc cactgccacc agcagtcgct ctacacggac accatctgcg agatcaacta
2041 ctcggcgatc cacccgggcc tctgcgagga cctacgctcc tgcgtgcagt gccaggcgtg
2101 gggcaccggc gagaagaagg ggcgcacgtg tgaggaatgc aacttcaagg tcaagatggt
2161 ggacgagctt aagagagccg aggaggtggt ggtgcgctgc tccttccggg acgaggatga
2221 cgactgcacc tacagctaca ccatggaagg tgacggcgcc cctgggccca acagcactgt
2281 cctggtgcac aagaagaagg actgccctcc gggctccttc tggtggctca tcccccctgct
2341 cctcctcctc ctgccgctcc tggccctgct actgctgcta tgctggaagt actgtgcctg
2401 ctgcaaggcc tgcctggcac ttctcccgtg ctgcaaccga ggtcacatgg tgggctttaa
2461 ggaagaccac tacatgctgc gggagaacct gatggcctct gaccacttgg acacgcccat
2521 gctgcgcagc gggaacctca agggccgtga cgtggtccgc tggaaggtca ccaacaacat
2581 gcagcggcct ggctttgcca ctcatgccgc cagcatcaac cccacagagc tggtgcccta
2641 cgggctgtcc ttgcgcctgg cccgcctttg caccgagaac ctgctgaagc ctgacactcg
2701 ggagtgcgcc cagctgcgcc aggaggtgga ggagaacctg aacgaggtct acaggcagat
2761 ctccggtgta cacaagctcc agcagaccaa gttccggcag cagcccaatg ccgggaaaaa
2821 gcaagaccac accattgtgg acacagtgct gatggcgccc cgctcggcca agccggccct
2881 gctgaagctt acagagaagc aggtggaaca gagggccttc cacgacctca aggtggcccc
2941 cggctactac accctcactg cagaccagga cgcccggggc atggtggagt tccaggaggg
3001 cgtggagctg gtggacgtac gggtgcccct ctttatccgg cctgaggatg acgacgagaa

FIG. 10 A-13

```
3061 gcagctgctg gtggaggcca tcgacgtgcc cgcaggcact gccaccctcg gccgccgcct
3121 ggtaaacatc accatcatca aggagcaagc cagagacgtg gtgtcctttg agcagcctga
3181 gttctcggtc agccgcgggg accaggtggc ccgcatccct gtcatccggc gtgtcctgga
3241 cggcgggaag tcccaggtct cctaccgcac acaggatggc accgcgcagg gcaaccggga
3301 ctacatcccc gtggagggtg agctgctgtt ccagcctggg gaggcctgga aagagctgca
3361 ggtgaagctc ctggagctgc aagaagttga ctccctcctg cggggccgcc aggtccgccg
3421 tttccacgtc cagctcagca accctaagtt tggggcccac ctgggccagc cccactccac
3481 caccatcatc atcagggacc cagatgaact ggaccggagc ttcacgagtc agatgttgtc
3541 atcacagcca ccccctcacg gcgacctggg cgccccgcag aaccccaatg ctaaggccgc
3601 tgggtccagg aagatccatt tcaactggct gccccccttct ggcaagccaa tggggtacag
3661 ggtaaagtac tggattcagg gcgactccga atccgaagcc cacctgctcg acagcaaggt
3721 gccctcagtg gagctcacca acctgtaccc gtattgcgac tatgagatga aggtgtgcgc
3781 ctacggggct cagggcgagg gaccctacag ctccctggtg tcctgccgca cccaccagga
3841 agtgcccagc gagccagggc gtctggcctt caatgtcgtc tcctccacgg tgacccagct
3901 gagctgggct gagccggctg agaccaacgg tgagatcaca gcctacgagg tctgctatgg
3961 cctggtcaac gatgacaacc gacctattgg gcccatgaag aaagtgctgg ttgacaaccc
4021 taagaaccgg atgctgctta ttgagaacct tcgggagtcc cagccctacc gctacacggt
4081 gaaggcgcgc aacggggccg gctgggggcc tgagcgggag gccatcatca acctggccac
4141 ccagcccaag aggcccatgt ccatccccat catccctgac atccctatcg tggacgccca
4201 gagcggggag gactacgaca gcttccttat gtacagcgat gacgttctac gctctccatc
4261 gggcagccag aggcccagcg tctccgatga cactggctgc ggctggaagt tcgagcccct
4321 gctgggggag gagctggacc tgcggcgcgt cacgtggcgg ctgcccccgg agctcatccc
4381 gcgcctgtcg gccagcagcg ggcgctcctc cgacgccgag gcccccacgg ccccccggac
4441 gacggcggcg cgggcgggaa gggcggcagc cgtgccccgc agtgcgacac ccgggccccc
4501 cggagagcac ctggtgaatg gccggatgga ctttgccttc ccgggcagca ccaactccct
4561 gcacaggatg accacgacca gtgctgctgc ctatggcacc cacctgagcc cacacgtgcc
4621 ccaccgcgtg ctaagcacat cctccaccct cacacgggac tacaactcac tgacccgctc
4681 agaacactca cactcgacca cactgcccag ggactactcc accctcacct ccgtctcctc
4741 ccacgactct cgcctgactg ctggtgtgcc cgacacgccc acccgcctgg tgttctctgc
4801 cctggggccc acatctctca gagtgagctg gcaggagccg cggtgcgagc ggccgctgca
4861 gggctacagt gtggagtacc agctgctgaa cggcggtgag ctgcatcggc tcaacatccc
4921 caaccctgcc cagacctcgg tggtggtgga agacctcctg cccaaccact cctacgtgtt
4981 ccgcgtgcgg gcccagagcc aggaaggctg gggccgagag cgtgagggtg tcatcaccat
5041 tgaatcccag gtgcacccgc agagcccact gtgtcccctg ccaggctccg ccttcacttt
5101 gagcactccc agtgccccag gcccgctggt gttcactgcc ctgagcccag actcgctgca
5161 gctgagctgg gagcggccac ggaggcccaa tggggatatc gtcggctacc tggtgacctg
5221 tgagatggcc caaggaggag ggccagccac cgcattccgg gtggatggag acagccccga
5281 gagccggctg accgtgccgg gcctcagcga gaacgtgccc tacaagttca aggtgcaggc
5341 caggaccact gagggcttcg ggccagagcg cgagggcatc atcaccatag agtcccagga
5401 tggaggaccc ttcccgcagc tgggcagccg tgccgggctc ttccagcacc cgctgcaaag
5461 cgagtacagc agcatcacca ccacccacac cagcgccacc gagcccttcc tagtggatgg
5521 gctgaccctg ggggcccagc acctggaggc aggcggctcc ctcacccggc atgtgaccca
5581 ggagtttgtg agccggacac tgaccaccag cggaaccctt agcacccaca tggaccaaca
5641 gttcttccaa acttgaccgc accctgcccc acccccgcca tgtcccacta ggcgtcctcc
5701 cgactcctct cccggagcct cctcagctac tccatccttg cacccctggg ggcccagccc
5761 acccgcatgc acagagcagg ggctaggtgt ctcctgggag gcatgaaggg ggcaaggtcc
5821 gtcctctgtg ggcccaaacc tatttgtaac caaagagctg ggagcagcac aaggacccag
5881 cctttgttct gcacttaata aatggttttg ctactgctaa aaaaaaaaaa aaaaaaaaaa
5941 aaaaaaaaaa aaaaaaaaaa aaaaaaaaaa aaaaaaaaaa aaaaaaaaaa aaaa
```

SEQ ID NO:14

FIG. 10 A-14

1 ccgccgggct ggccatggag ctgctgtgcc acgaggtgga cccggtccgc agggccgtgc
61 gggaccgcaa cctgctccga gacgaccgcg tcctgcagaa cctgctcacc atcgaggagc
121 gctaccttcc gcagtgctcc tacttcaagt gcgtgcagaa ggacatccaa ccctacatgc
181 gcagaatggt ggccacctgg atgctggagg tctgtgagga acagaagtgc gaagaagagg
241 tcttccctct ggccatgaat tacctggacc gtttcttggc tggggtcccg actccgaagt
301 cccatctgca actcctgggt gctgtctgca tgttcctggc ctccaaactc aaagagacca
361 gcccgctgac cgcggagaag ctgtgcattt acaccgacaa ctccatcaag cctcaggagc
421 tgctggagtg ggaactggtg gtgctgggga agttgaagtg gaacctggca gctgtcactc
481 ctcatgactt cattgagcac atcttgcgca agctgcccca gcagcgggag aagctgtctc
541 tgatccgcaa gcatgctcag accttcattg ctctgtgtgc caccgacttt aagtttgcca
601 tgtacccacc gtcgatgatc gcaactggaa gtgtgggagc agccatctgt gggctccagc
661 aggatgagga agtgagctcg ctcacttgtg atgccctgac tgagctgctg gctaagatca
721 ccaacacaga cgtggattgt ctcaaagctt gccaggagca gattgaggcg gtgctcctca
781 atagcctgca gcagtaccgt caggaccaac gtgacggatc caagtcggag gatgaactgg
841 accaagccag caccccctaca gacgtgcggg atatcgacct gtgaggatgc cagttgggcc
901 gaaagagaga gacgcgtcca taatctggtc tcttcttctt tctggttgtt tttgttcttt
961 gtgttttagg gtgaaactta aaaaaaaaat tctgccccca cctagatcat atttaaagat
1021 cttttagaag tgagagaaaa aggtcctacg aaaacggaat aataaaaagc atttggtgcc
1081 tatttgaagt acagcataag ggaatccctt gtatatgcga acagttattg tttgattatg
1141 taaaagtaat agtaaaatgc ttacaggaaa acctgcagag tagttagaga atatgtatgc
1201 ctgcaatatg ggaacaaatt agaggagact tttttttttc atgttatgag ctagcacata
1261 cacccccttg tagtataatt tcaaggaact gtgtacgcca tttatggcat gattagattg
1321 caaagcaatg aactcaagaa ggaattgaaa taaggaggga catgatgggg aaggagtaca
1381 aaacaatctc tcaacatgat tgaaccattt gggatggaga agcacctttg ctctcagcca
1441 cctgttacta agtcaggagt gtagttggat ctctacatta atgtcctctt gctgtctaca
1501 gtagctgcta cctaaaaaaa gatgttttat tttgccagtt ggacacaggt gattggctcc
1561 tgggtttcat gttctgtgac atcctgcttc ttcttccaaa tgcagttcat tgcagacacc
1621 accatattgc tatctaatgg ggaaatgtag ctatgggcca taaccaaaac tcacatgaaa
1681 cggaggcaga tggagaccaa gggtgggatc cagaatggag tcttttctgt tattgtattt
1741 aaaagggtaa tgtggccttg gcatttcttc ttagaaaaaa actaattttt ggtgctgatt
1801 ggcatgtctg gttcacagtt tagcattgtt ataaaccatt ccattcgaaa agcactttga
1861 aaaattgttc ccgagcgata gatgggatgg tttatgca SEQ ID NO:15
1 gagacattcc ggtgggggac tctggccagc ccgagcaacg tggatcctga gagcactccc
61 aggtaggcat ttgccccggt gggacgcctt gccagagcag tgtgtggcag gcccccgtgg
121 aggatcaaca cagtggctga acactgggaa ggaactggta cttggagtct ggacatctga
181 aacttggctc tgaaactgcg cagcggccac cggacgcctt ctggagcagg tagcagcatg
241 cagccgcctc caagtctgtg cggacgcgcc ctggttgcgc tggttcttgc ctgcggcctg
301 tcgcggatct ggggagagga gagaggcttc ccgcctgaca gggccactcc gcttttgcaa
361 accgcagaga taatgacgcc acccactaag accttatggc ccaagggttc caacgccagt
421 ctggcgcggt cgttggcacc tgcggaggtg cctaaaggag acaggacggc aggatctccg
481 ccacgcacca tctcccctcc cccgtgccaa ggacccatcg agatcaagga gactttcaaa
541 tacatcaaca cggttgtgtc ctgccttgtg ttcgtgctgg ggatcatcgg gaactccaca
601 cttctgagaa ttatctacaa gaacaagtgc atgcgaaacg gtcccaatat cttgatcgcc
661 agcttggctc tgggagacct gctgcacatc gtcattgaca tccctatcaa tgtctacaag
721 ctgctggcag aggactggcc atttggagct gagatgtgta agctggtgcc tttcatacag
781 aaagcctccg tgggaatcac tgtgctgagt ctatgtgctc tgagtattga cagatatcga
841 gctgttgctt cttggagtag aattaaagga attggggttc caaaatggac agcagtagaa
901 attgttttga tttgggtggt ctctgtggtt ctggctgtcc ctgaagccat aggttttgat
961 ataattacga tggactacaa aggaagttat ctgcgaatct gcttgcttca tcccgttcag

FIG. 10 A-15

1021 aagacagctt tcatgcagtt ttacaagaca gcaaaagatt ggtggctgtt cagtttctat
1081 ttctgcttgc cattggccat cactgcattt ttttatacac taatgacctg tgaaatgttg
1141 agaaagaaaa gtggcatgca gattgcttta aatgatcacc taaagcagag acgggaagtg
1201 gccaaaaccg tcttttgcct ggtccttgtc tttgccctct gctggcttcc ccttcacctc
1261 agcaggattc tgaagctcac tctttataat cagaatgatc ccaatagatg tgaacttttg
1321 agctttctgt tggtattgga ctatattggt atcaacatgg cttcactgaa ttcctgcatt
1381 aacccaattg ctctgtattt ggtgagcaaa agattcaaaa actgctttaa gtcatgctta
1441 tgctgctggt gccagtcatt tgaagaaaaa cagtccttgg aggaaaagca gtcgtgctta
1501 aagttcaaag ctaatgatca cggatatgac aacttccgtt ccagtaataa atacagctca
1561 tcttgaaaga agaactattc actgtatttc attttcttta tattggaccg aagtcattaa
1621 aacaaaatga aacatttgcc aaaacaaaac aaaaaactat gtatttgcac agcacactat
1681 taaaatatta agtgtaatta ttttaacact cacagctaca tatgacattt tatgagctgt
1741 ttacggcatg gaaagaaaat cagtgggaat taagaaagcc tcgtcgtgaa agcacttaat
1801 tttttacagt tagcacttca acatagctct taacaacttc caggatattc acacaacact
1861 taggcttaaa aatgagctca ctcagaattt ctattctttc taaaaagaga tttattttta
1921 aatcaatggg actctgatat aaaggaagaa taagtcactg taaaacagaa cttttaaatg
1981 aagcttaaat tactcaattt aaaattttaa aatcctttaa aacaactttt caattaatat
2041 tatcacacta ttatcagatt gtaattagat gcaaatgaga gagcagttta gttgttgcat
2101 ttttcggaca ctggaaacat ttaaatgatc aggagggagt aacagaaaga gcaaggctgt
2161 ttttgaaaat cattacactt tcactagaag cccaaacctc agcattctgc aatatgtaac
2221 caacatgtca caaacaagca gcatgtaaca gactggcaca tgtgccagct gaatttaaaa
2281 tataatactt ttaaaaagaa aattattaca tcctttacat tcagttaaga tcaaacctca
2341 caaagagaaa tagaatgttt gaaaggctat cccaaaagac ttttttgaat ctgtcattca
2401 catacccctgt gaagacaata ctatctacaa ttttttcagg attattaaaa tcttcttttt
2461 tcactatcgt agcttaaact ctgtttggtt ttgtcatctg taaatactta cctacataca
2521 ctgcatgtag atgattaaat gagggcaggc cctgtgctca tagctttacg atggagagat
2581 gccagtgacc tcataataaa gactgtgaac tgcctggtgc agtgtccaca tgacaaaggg
2641 gcaggtagca ccctctctca cccatgctgt ggttaaaatg gtttctagca tatgtataat
2701 gctatagtta aaatactatt tttcaaaatc atacagatta gtacatttaa cagctacctg
2761 taaagcttat tactaatttt tgtattattt ttgtaaatag ccaatagaaa agtttgcttg
2821 acatggtgct ttctttcat ctagaggcaa aactgctttt tgagaccgta agaacctctt
2881 agctttgtgc gttcctgcct aatttttata tcttctaagc aaagtgcctt aggatagctt
2941 gggatgagat gtgtgtgaaa gtatgtacaa gagaaaacgg aagagagagg aaatgaggtg
3001 gggttggagg aaacccatgg ggacagattc ccattcttag cctaacgttc gtcattgcct
3061 cgtcacatca atgcaaaagg tcctgatttt gttccagcaa aacacagtgc aatgttctca
3121 gagtgacttt cgaaataaat tgggcccaag agctttaact cggtcttaaa atatgcccaa
3181 atttttactt tgtttttctt ttaataggct gggccacatg ttggaaataa gctagtaatg
3241 ttgttttctg tcaatattga atgtgatggt acagtaaacc aaaacccaac aatgtggcca
3301 gaaagaaaga gcaataataa ttaattcaca caccatatgg attctattta taaatcaccc
3361 acaaacttgt tctttaattt catcccaatc actttttcag aggcctgtta tcatagaagt
3421 cattttagac tctcaatttt aaattaattt tgaatcacta atattttcac agtttattaa
3481 tatatttaat ttctatttaa attttagatt atttttatta ccatgtactg aatttttaca
3541 tcctgatacc ctttccttct ccatgtcagt atcatgttct ctaattatct tgccaaattt
3601 tgaaactaca cacaaaaagc atacttgcat tatttataat aaaattgcat tcagtggctt
3661 tttaaaaaaa atgtttgatt caaaacttta acatactgat aagtaagaaa caattataat
3721 ttctttacat actcaaaacc aagatagaaa aaggtgctat cgttcaactt caaaacatgt
3781 ttcctagtat taaggacttt aatatagcaa cagacaaaat tattgttaac atggatgtta
3841 cagctcaaaa gatttataaa agattttaac ctattttctc ccttattatc cactgctaat
3901 gtggatgtat gttcaaacac cttttagtat tgatagctta catatggcca aaggaataca
3961 gtttatagca aaacatgggt atgctgtagc taactttata aaagtgtaat ataacaatgt
4021 aaaaaattat atatctggga ggatttttttg gttgcctaaa gtggctatag ttactgattt

FIG. 10 A-16

4081 tttattatgt aagcaaaacc aataaaaatt taagtttttt taacaactac cttatttttc
4141 actgtacaga cactaattca ttaaatacta attgattgtt taaaagaaat ataaatgtga
4201 caagtggaca ttatttatgt taaatataca attatcaagc aagtatgaag ttattcaatt
4261 aaaatgccac atttctggtc tctggg SEQ ID NO:16
1 gaattcccgc ggagcagcgt gcgcggggcc ccgggagacg gcggcggtag cggcgcgggc
61 agagcaagga cgcggcggat cccactcgca cagcagcgca ctcggtgccc cgcgcagggt
121 cgcgatgctg cccggtttgg cactgctcct gctggccgcc tggacggctc gggcgctgga
181 ggtacccact gatggtaatg ctggcctgct ggctgaaccc cagattgcca tgttctgtgg
241 cagactgaac atgcacatga atgtccagaa tgggaagtgg gattcagatc catcagggac
301 caaaacctgc attgatacca aggaaggcat cctgcagtat tgccaagaag tctaccctga
361 actgcagatc accaatgtgg tagaagccaa ccaaccagtg accatccaga actggtgcaa
421 gcggggccgc aagcagtgca agacccatcc ccactttgtg attccctacc gctgcttagt
481 tggtgagttt gtaagtgatg cccttctcgt tcctgacaag tgcaaattct tacaccagga
541 gaggatggat gtttgcgaaa ctcatcttca ctggcacacc gtcgccaaag agacatgcag
601 tgagaagagt accaacttgc atgactacgg catgttgctg ccctgcggaa ttgacaagtt
661 ccgaggggta gagtttgtgt gttgcccact ggctgaagaa agtgacaatg tggattctgc
721 tgatgcggag gaggatgact cggatgtctg gtggggcgga gcagacacag actatgcaga
781 tgggagtgaa gacaaagtag tagaagtagc agaggaggaa gaagtggctg aggtggaaga
841 agaagaagcc gatgatgacg aggacgatga ggatggtgat gaggtagagg aagaggctga
901 ggaaccctac gaagaagcca cagagagaac caccagcatt gccaccacca ccaccaccac
961 cacagagtct gtggaagagg tggttcgaga ggtgtgctct gaacaagccg agacggggcc
1021 gtgccgagca atgatctccc gctggtactt tgatgtgact gaagggaagt gtgccccatt
1081 cttttacggc ggatgtggcg gcaaccggaa caactttgac acagaagagt actgcatggc
1141 cgtgtgtggc agcgccattc ctacaacagc agccagtacc cctgatgccg ttgacaagta
1201 tctcgagaca cctggggatg agaatgaaca tgcccatttc cagaaagcca aagagaggct
1261 tgaggccaag caccgagaga gaatgtccca ggtcatgaga gaatgggaag aggcagaacg
1321 tcaagcaaag aacttgccta aagctgataa gaaggcagtt atccagcatt tccaggagaa
1381 agtggaatct ttggaacagg aagcagccaa cgagagacag cagctggtgg agacacacat
1441 ggccagagtg gaagccatgc tcaatgaccg ccgccgcctg gccctggaga actacatcac
1501 cgctctgcag gctgttcctc ctcggcctcg tcacgtgttc aatatgctaa agaagtatgt
1561 ccgcgcagaa cagaaggaca gacagcacac cctaaagcat ttcgagcatg tgcgcatggt
1621 ggatcccaag aaagccgctc agatccggtc ccaggttatg acacacctcc gtgtgattta
1681 tgagcgcatg aatcagtctc tctccctgct ctacaacgtg cctgcagtgg ccgaggagat
1741 tcaggatgaa gttgatgagc tgcttcagaa agagcaaaac tattcagatg acgtcttggc
1801 caacatgatt agtgaaccaa ggatcagtta cggaaacgat gctctcatgc catctttgac
1861 cgaaacgaaa accaccgtgg agctccttcc cgtgaatgga gagttcagcc tggacgatct
1921 ccagccgtgg cattcttttg ggcctgactc tgtgccagcc aacacagaaa acgaagttga
1981 gcctgttgat gcccgccctg ctgccgaccg aggactgacc actcgaccag gttctgggtt
2041 gacaaatatc aagacggagg agatctctga agtgaagatg gatgcagaat tccgacatga
2101 ctcaggatat gaagttcatc atcaaaaatt ggtgttcttt gcagaagatg tgggttcaaa
2161 caaaggtgca atcattggac tcatggtggg cggtgttgtc atagcgacag tgatcgtcat
2221 caccttggtg atgctgaaga agaaacagta cacatccatt catcatggtg tggtggaggt
2281 tgacgccgct gtcaccccag aggagcgcca cctgtccaag atgcagcaga acggctacga
2341 aaatccaacc tacaagttct ttgagcagat gcagaactag acccccgcca cagcagcctc
2401 tgaagttgga cagcaaaacc attgcttcac tacccatcgg tgtccattta tagaataatg
2461 tgggaagaaa caaacccgtt ttatgattta ctcattatcg ccttttgaca gctgtgctgt
2521 aacacaagta gatgcctgaa cttgaattaa tccacacatc agtaatgtat tctatctctc
2581 tttacatttt ggtctctata ctacattatt aatgggtttt gtgtactgta aagaatttag
2641 ctgtatcaaa ctagtgcatg aatagattct ctcctgatta tttatcacat agccccttag

FIG. 10 A-17

2701 ccagttgtat attattcttg tggtttgtga cccaattaag tcctacttta catatgcttt
2761 aagaatcgat gggggatgct tcatgtgaac gtgggagttc agctgcttct cttgcctaag
2821 tattcctttc ctgatcacta tgcattttaa agttaaacat ttttaagtat ttcagatgct
2881 ttagagagat tttttttcca tgactgcatt ttactgtaca gattgctgct tctgctatat
2941 ttgtgatata ggaattaaga ggatacacac gtttgtttct tcgtgcctgt tttatgtgca
3001 cacattaggc attgagactt caagcttttc tttttttgtc cacgtatctt tgggtctttg
3061 ataaagaaaa gaatccctgt tcattgtaag cacttttacg gggcgggtgg ggaggggtgc
3121 tctgctggtc ttcaattacc aagaattc SEQ ID NO:17
1 gccgccctcg ccaccgctcc cggccgccgc gctccggtac acacaggatc cctgctgggc
61 accaacagct ccaccatggg gctggcctgg ggactaggcg tcctgttcct gatgcatgtg
121 tgtggcacca accgcattcc agagtctggc ggagacaaca gcgtgtttga catctttgaa
181 ctcaccgggg ccgcccgcaa ggggtctggg cgccgactgg tgaagggccc cgacccttcc
241 agcccagctt tccgcatcga ggatgccaac ctgatccccc ctgtgcctga tgacaagttc
301 caagacctgg tggatgctgt gcggacagaa aagggtttcc tccttctggc atccctgagg
361 cagatgaaga agacccgggg cacgctgctg gccctggagc ggaaagacca ctctggccag
421 gtcttcagcg tggtgtccaa tggcaaggcg ggcaccctgg acctcagcct gaccgtccaa
481 ggaaagcagc acgtggtgtc tgtggaagaa gctctcctgg caaccggcca gtggaagagc
541 atcaccctgt ttgtgcagga agacagggcc cagctgtaca tcgactgtga aaagatggag
601 aatgctgagt tggacgtccc catccaaagc gtcttcacca gagacctggc cagcatcgcc
661 agactccgca tcgcaaaggg gggcgtcaat gacaatttcc aggggggtgct gcagaatgtg
721 aggtttgtct ttggaaccac accagaagac atcctcagga acaaaggctg ctccagctct
781 accagtgtcc tcctcaccct tgacaacaac gtggtgaatg gttccagccc tgccatccgc
841 actaactaca ttggccacaa gacaaaggac ttgcaagcca tctgcggcat ctcctgtgat
901 gagctgtcca gcatggtcct ggaactcagg ggcctgcgca ccattgtgac cacgctgcag
961 gacagcatcc gcaaagtgac tgaagagaac aaagagttgg ccaatgagct gaggcggcct
1021 cccctatgct atcacaacgg agttcagtac agaaataacg aggaatggac tgttgatagc
1081 tgcactgagt gtcactgtca gaactcagtt accatctgca aaaaggtgtc ctgccccatc
1141 atgccctgct ccaatgccac agttcctgat ggagaatgct gtcctcgctg ttggcccagc
1201 gactctgcgg acgatggctg gtctccatgg tccgagtgga cctcctgttc tacgagctgt
1261 ggcaatggaa ttcagcagcg cggccgctcc tgcgatagcc tcaacaaccg atgtgagggc
1321 tcctcggtcc agacacggac ctgccacatt caggagtgtg acaagagatt taaacaggat
1381 ggtggctgga gccactggtc cccgtggtca tcttgttctg tgacatgtgg tgatggtgtg
1441 atcacaagga tccggctctg caactctccc agcccccaga tgaacgggaa accctgtgaa
1501 ggcgaagcgc gggagaccaa agcctgcaag aaagacgcct gccccatcaa tggaggctgg
1561 ggtccttggt caccatggga catctgttct gtcacctgtg gaggaggggt acagaaacgt
1621 agtcgtctct gcaacaaccc cacaccccag tttggaggca aggactgcgt tggtgatgta
1681 acagaaaacc agatctgcaa caagcaggac tgtccaattg atggatgcct gtccaatccc
1741 tgctttgccg gcgtgaagtg tactagctac cctgatggca gctggaaatg tggtgcttgt
1801 ccccctggtt acagtggaaa tggcatccag tgcacagatg ttgatgagtg caaagaagtg
1861 cctgatgcct gcttcaacca caatggagag caccggtgtg agaacacgga ccccggctac
1921 aactgcctgc cctgcccccc acgcttcacc ggctcacagc ccttcggcca gggtgtcgaa
1981 catgccacgg ccaacaaaca ggtgtgcaag ccccgtaacc cctgcacgga tgggacccac
2041 gactgcaaca agaacgccaa gtgcaactac ctgggccact atagcgaccc catgtaccgc
2101 tgcgagtgca agcctggcta cgctggcaat ggcatcatct gcggggagga cacagacctg
2161 gatggctggc ccaatgagaa cctggtgtgc gtggccaatg cgacttacca ctgcaaaaag
2221 gataattgcc ccaaccttcc caactcaggg caggaagact atgacaagga tggaattggt
2281 gatgcctgtg atgatgacga tgacaatgat aaaattccag atgacaggga caactgtcca
2341 ttccattaca acccagctca gtatgactat gacagagatg atgtgggaga ccgctgtgac

FIG. 10 A-18

```
2401 aactgtccct acaaccacaa cccagatcag gcagacacag acaacaatgg ggaaggagac
2461 gcctgtgctg cagacattga tggagacggt atcctcaatg aacgggacaa ctgccagtac
2521 gtctacaatg tggaccagag agacactgat atggatgggg ttggagatca gtgtgacaat
2581 tgcccccttgg aacacaatcc ggatcagctg gactctgact cagaccgcat tggagatacc
2641 tgtgacaaca atcaggatat tgatgaagat ggccaccaga acaatctgga caactgtccc
2701 tatgtgccca atgccaacca ggctgaccat gacaaagatg gcaagggaga tgcctgtgac
2761 cacgatgatg acaacgatgg cattcctgat gacaaggaca actgcagact cgtgcccaat
2821 cccgaccaga aggactctga cggcgatggt cgaggtgatg cctgcaaaga tgattttgac
2881 catgacagtg tgccagacat cgatgacatc tgtcctgaga atgttgacat cagtgagacc
2941 gatttccgcc gattccagat gattcctctg gaccccaaag ggacatccca aaatgaccct
3001 aactgggttg tacgccatca gggtaaagaa ctcgtccaga ctgtcaactg tgatcctgga
3061 ctcgctgtag gttatgatga gtttaatgct gtggacttca gtggcacctt cttcatcaac
3121 accgaaaggg acgatgacta tgctggattt gtctttggct accagtccag cagccgcttt
3181 tatgttgtga tgtggaagca agtcacccag tcctactggg acaccaaccc cacgagggct
3241 cagggatact cgggcctttc tgtgaaagtt gtaaactcca ccacagggcc tggcgagcac
3301 ctgcggaacg ccctgtggca cacaggaaac acccctggcc aggtgcgcac cctgtggcat
3361 gaccctcgtc acataggctg gaaagatttc accgcctaca gatggcgtct cagccacagg
3421 ccaaagacgg gtttcattag agtggtgatg tatgaaggga agaaaatcat ggctgactca
3481 ggacccatct atgataaaac ctatgctggt ggtagactag ggttgtttgt cttctctcaa
3541 gaaatggtgt tcttctctga cctgaaatac gaatgtagag atccctaatc atcaaattgt
3601 tgattgaaag actgatcata aaccaatgct ggtattgcac cttctggaac tatgggcttg
3661 agaaaacccc caggatcact tctccttggc ttccttcttt tctgtgcttg catcagtgtg
3721 gactcctaga acgtgcgacc tgcctcaaga aaatgcagtt ttcaaaaaca gactcagcat
3781 tcagcctcca atgaataaga catcttccaa gcatataaac aattgctttg gtttcctttt
3841 gaaaaagcat ctacttgctt cagttgggaa ggtgcccatt ccactctgcc tttgtcacag
3901 agcagggtgc tattgtgagg ccatctctga gcagtggact caaaagcatt ttcaggcatg
3961 tcagagaagg gaggactcac tagaattagc aaacaaaacc accctgacat cctccttcag
4021 gaacacgggg agcagaggcc aaagcactaa ggggagggcg catacccgag acgattgtat
4081 gaagaaaata tggaggaact gttacatgtt cggtactaag tcattttcag gggattgaaa
4141 gactattgct ggatttcatg atgctgactg gcgttagctg attaacccat gtaaataggc
4201 acttaaatag aagcaggaaa gggagacaaa gactggcttc tggacttcct ccctgatccc
4261 caccccttact catcacctgc agtggccaga attagggaat cagaatcgaa accagtgtaa
4321 ggcagtgctg gctgccattg cctggtcaca ttgaaattgg tggcttcatt ctagatgtag
4381 cttgtgcaga tgtagcagga aaataggaaa acctaccatc tcagtgagca ccag
```

SEQ ID NO:18

```
  1 atttctcttt agttctttgc aagaaggtag agataaagac actttttcaa aaatggcaat
 61 ggtatcagaa ttcctcaagc aggcctggtt tattgaaaat gaagagcagg aatatgttca
121 aactgtgaag tcatccaaag gtggtcccgg atcagcggtg agcccctatc ctaccttcaa
181 tccatcctcg gatgtcgctg ccttgcataa ggccataatg gttaaaggtg tggatgaagc
241 aaccatcatt gacattctaa ctaagcgaaa caatgcacag cgtcaacaga tcaaagcagc
301 atatctccag gaaacaggaa agcccctgga tgaaacactg aagaaagccc ttacaggtca
361 ccttgaggag gttgttttag ctctgctaaa aactccagcg caatttgatg ctgatgaact
421 tcgtgctgcc atgaagggcc ttggaactga tgaagatact ctaattgaga ttttggcatc
481 aagaactaac aaagaaatca gagacattaa cagggtctac agagaggaac tgaagagaga
541 tctggccaaa gacataacct cagacacatc tggagatttt cggaacgctt tgctttctct
601 tgctaagggt gaccgatctg aggactttgg tgtgaatgaa gacttggctg attcagatgc
661 cagggccttg tatgaagcag gagaaaggag aaaggggaca gacgtaaacg tgttcaatac
721 catcccttacc accagaagct atccacaact tcgcagagtg tttcagaaat acaccaagta
781 cagtaagcat gacatgaaca aagttctgga cctggagttg aaaggtgaca ttgagaaatg
```

FIG. 10 A-19

```
 841 cctcacagct atcgtgaagt gcgccacaag caaaccagct ttctttgcag gaagcttca
 901 tcaagccatg aaaggtgttg gaactcgcca taaggcattg atcaggatta tggtttcccg
 961 ttctgaaatt gacatgaatg atatcaaagc attctatcag aagatgtatg gtatctccct
1021 ttgccaagcc atcctggatg aaaccaaagg agattatgag aaaatcctgg tggctctttg
1081 tggaggaaac taaacattcc cttgatggtc tcaagctatg atcagaagac tttaattata
1141 tattttcatc ctataagctt aaataggaaa gtttcttcaa caggattaca gtgtagctac
1201 ctacatgctg aaaaatatag cctttaaatc atttttatat tataactctg tataatagag
1261 ataagtccat tttttaaaaa tgttttcccc aaaccataaa accctataca agttgttcta
1321 gtaacaatac atgagaaaga tgtctatgta gctgaaaata aaatgacgtc acaagac
```

SEQ ID NO:19

```
   1 gcccccgccc ggcccgcccc gctctcctag tcccttgcaa cctggcgctg catccgggcc
  61 actgtcccag gtcccaggtc ccggcccgga gctatggagc ggcgctggcc cctggggcta
 121 gggctggtgc tgctgctctg cgccccgctg cccccggggg cgcgcgccaa ggaagttact
 181 ctgatggaca caagcaaggc acagggagag ctgggctggc tgctggatcc cccaaaagat
 241 gggtggagtg aacagcaaca gatactgaat gggacacccc tctacatgta ccaggactgc
 301 ccaatgcaag gacgcagaga cactgaccac tggcttcgct ccaattggat ctaccgcggg
 361 gaggaggctt cccgcgtcca cgtggagctg cagttcaccg tgcgggactg caagagtttc
 421 cctgggggag ccgggcctct gggctgcaag gagaccttca accttctgta catggagagt
 481 gaccaggatg tgggcattca gctccgacgg cccttgttcc agaaggtaac cacggtggct
 541 gcagaccaga gcttcaccat tcgagacctt gcgtctggct ccgtgaagct gaatgtggag
 601 cgctgctctc tgggccgcct gacccgccgt ggcctctacc tcgctttcca caacccgggt
 661 gcctgtgtgg ccctggtgtc tgtccgggtc ttctaccagc gctgtcctga gaccctgaat
 721 ggcttggccc aattcccaga cactctgcct ggccccgctg ggttggtgga agtggcgggc
 781 acctgcttgc cccacgcgcg ggccagcccc aggccctcag gtgcaccccg catgcactgc
 841 agccctgatg gcgagtggct ggtgcctgta ggacggtgcc actgtgagcc tggctatgag
 901 gaaggtggca gtggcgaagc atgtgttgcc tgccctagcg gctcctaccg gatggacatg
 961 gacacacccc attgtctcac gtgcccccag cagagcactg ctgagtctga gggggccacc
1021 atctgtacct gtgagagcgg ccattacaga gctcccgggg agggccccca ggtggcatgc
1081 acaggtcccc cctcggcccc ccgaaacctg agcttctctg cctcagggac tcagctctcc
1141 ctgcgttggg aacccccagc agatacgggg ggacgccagg atgtcagata cagtgtgagg
1201 tgttcccagt gtcagggcac agcacaggac gggggggccct gccagccctg tggggtgggc
1261 gtgcacttct cgccgggggc ccgggcgctc accacacctg cagtgcatgt caatggcctt
1321 gaaccttatg ccaactacac ctttaatgtg gaagcccaaa atggagtgtc agggctgggc
1381 agctctggcc atgccagcac ctcagtcagc atcagcatgg ggcatgcaga gtcactgtca
1441 ggcctgtctc tgagactggt gaagaaagaa ccgaggcaac tagagctgac ctgggcgggg
1501 tcccggcccc gaagccctgg ggcgaacctg acctatgagc tgcacgtgct gaaccaggat
1561 gaagaacggt accagatggt tctagaaccc agggtcttgc tgacagagct gcagcctgac
1621 accacataca tcgtcagagt ccgaatgctg accccactgg gtcctggccc tttctcccct
1681 gatcatgagt ttcggaccag cccaccagtg tccaggggcc tgactggagg agagattgta
1741 gccgtcatct ttgggctgct gcttggtgca gccttgctgc ttgggattct cgttttccgg
1801 tccaggagag cccagcggca gaggcagcag aggcacgtga ccgcgccacc gatgtggatc
1861 gagaggacaa gctgtgctga agccttatgt ggtacctcca ggcatacgag gaccctgcac
1921 agggagcctt ggactttacc cggaggctgg tctaatttc cttcccggga gcttgatcca
1981 gcgtggctga tggtggacac tgtcatagga gaaggagagt ttggggaagt gtatcgaggg
2041 accctcaggc tccccagcca ggactgcaag actgtggcca ttaagacctt aaaagacaca
2101 tccccaggtg gccagtggtg gaacttcctt cgagaggcaa ctatcatggg ccagtttagc
2161 cacccgcata ttctgcatct ggaaggcgtc gtcacaaagc gaaagccgat catgatcatc
2221 acagaattta tggagaatgc agccctggat gccttcctga gggagcggga ggaccagctg
2281 gtccctgggc agctagtggc catgctgcag ggcatagcat ctggcatgaa ctacctcagt
2341 aatcacaatt atgtccaccg ggacctggct gccagaaaca tcttggtgaa tcaaaacctg
```

FIG. 10 A-20

```
2401 tgctgcaagg tgtctgactt tggcctgact cgcctcctgg atgactttga ggcacatac
2461 gaaacccagg gaggaaagat ccctatccgt tggacagccc ctgaagccat tgcccatcgg
2521 atcttcacca cagccagcga tgtgtggagc tttgggattg tgatgtggga ggtgctgagc
2581 tttggggaca agccttatgg ggagatgagc aatcaggagg ttatgaagag cattgaggat
2641 gggtaccggt tgccccctcc tgtggactgc cctgcccctc tgtatgagct catgaagaac
2701 tgctgggcat atgaccgtgc ccgccggcca cacttccaga agcttcaggc acatctggag
2761 caactgcttg ccaaccccca ctccctgcgg accattgcca actttgaccc cagggtgact
2821 cttcgcctgc ccagcctgag tggctcagat gggatcccgt atcgaaccgt ctctgagtgg
2881 ctcgagtcca tacgcatgaa acgctacatc ctgcacttcc actcggctgg gctggacacc
2941 atggagtgtg tgctggagct gaccgctgag gacctgacgc agatgggaat cacactgccc
3001 gggcaccaga agcgcattct ttgcagtatt cagggattca aggactgatc cctcctctca
3061 ccccatgccc aatcagggtg caaggagcaa ggacggggcc aaggtcgctc atggtcactc
3121 cctgcgcccc ttcccacaac ctgccagact aggctatcgg tgctgcttct gcccgcttta
3181 aggagaaccc tgctctgcac cccagaaaac ctctttgttt taaaagggag gtgggggtag
3241 aagtaaaagg atgatcatgg gagggagctc aggggttaat atatatacat acatacacat
3301 atatatattg ttgtaaataa acaggaaatg attttctgcc tccatcccac ccatcagggc
3361 tgcaggcact
```

SEQ ID NO:20

```
   1 ccaagagcta cgcggcggcg gcggagcgca ggcctcgtgc cgttacggcc atcacggcgg
  61 ccgcagtggc gtcctggagc cctcctcagt gctgaagctg ctgaaagatg gcagaagaag
 121 tggtggtagt agccaaattt gattatgtgg cccaacaaga acaagagttg gacatcaaga
 181 agaatgagag attatggctt ctggatgatt ctaagtcctg gtggcgagtt cgaaattcca
 241 tgaataaaac aggttttgtg ccttctaact atgtggaaag gaaaaacagt gctcggaaag
 301 catctattgt gaaaaaccta aaggatacct taggcattgg aaaagtgaaa agaaaaccta
 361 gtgtgccaga ttctgcatct cctgctgatg atagttttgt tgacccaggg gaacgtctct
 421 atgacctcaa catgcccgct tatgtgaaat ttaactacat ggctgagaga gaggatgaat
 481 tatcattgat aaaggggaca aaggtgatcg tcatggagaa atgcagtgat gggtggtggc
 541 gtggtagcta caatggacaa gttggatggt tcccttcaaa ctatgtaact gaagaaggtg
 601 acagtccttt gggtgaccat gtgggttctc tgtcagagaa attagcagca gtcgtcaata
 661 acctaaatac tgggcaagtg ttgcatgtgg tacaggctct ttacccattc agctcatcta
 721 atgatgaaga acttaatttc gagaaaggag atgtaatgga tgttattgaa aaacctgaaa
 781 atgacccaga gtggtggaaa tgcaggaaga tcaatggtat ggttggtcta gtaccaaaaa
 841 actatgttac cgttatgcag aataatccat taacttcagg tttggaacca tcacctccac
 901 agtgtgatta cattaggcct tcactcactg gaaagtttgc tggcaatcct tggtattatg
 961 gcaaagtcac caggcatcaa gcagaaatgg cattaaatga aagaggacat gaaggggatt
1021 tcctcattcg tgatagtgaa tcttcgccaa atgatttctc agtatcacta aaagcacaag
1081 ggaaaaacaa gcattttaaa gtccaactaa aagagactgt ctactgcatt gggcagcgta
1141 aattcagcac catggaagaa cttgtagaac attacaaaaa ggcaccaatt tttacaagtg
1201 aacaaggaga aaaattatat cttgtcaagc atttatcatg atactgctga ccagaagtga
1261 ctgctgtgta gctgtaattt gtcatgtaat tgaagactga gaaaatgttg ggtccagtcg
1321 tgcttgattg gaaattgttg tttctaaatc tatatgagaa ttgacaataa gtatttttat
1381 tataactcag cccatacata tatactatgt atgcagtgca tctgcataga acagttcctt
1441 atccttggcc ttctgtttta ttgttttttt ctttgctgtt ttccctttgc ttctaatatt
1501 acagttttgt attttgtaaa caaaaatcaa ataatgcata tcagaatctt tatatggaag
1561 aaatccttta ttgcctttcc tttgtttcct tgtaaaggca ccctgttctg ttatggtttt
1621 tcattatata aaattattat atctatatat gacatatgct aaaatttctt ggagagtgtt
1681 aatcttttct gtgactaaat agcaataata agtggaaaat tagaaattat ttccaggtat
1741 tatatttgtc acaggccatt gtaaatacca agtatattgt gtctgccata atttttaaaa
1801 atacattcat tgtcttcagt catacagcaa gacacatgag acatagatta gaaaacatgt
```

FIG. 10 A-21

1861 tgtacaattt taatttacaa ctgttggaaa taaaaatcac ttaatttttt tcc

SEQ ID NO:21
1 catggcggcg actgcggcaa agcgagagcc tcggagacgc cgctgccgcc agcacagccg
61 gagacctgag ccgacactgg gggcagtccg cgagccccgc actctctcga tgagtcggag
121 aagtcccgtt gtatcagagt aagatggacg gtagctttga ttgtgattgt ggtgagctgg
181 agccacctga tcactaacaa aagacatctt ctgttaacca acagccgcca gggcttcctg
241 ttgaaataaa tatatagcaa caaaggaaaa aaagaagcaa aacggaaata gtgcttacca
301 gcaccttaga atgatgctgc tcaggaccag tccaacactg aatgtatctg cactgtgagg
361 agaatgttca tagaagcctg ttgtgtgcat atttattcac atttttgtta aatgttaaat
421 cgtttagcac ggtaatctga gtgcacagta tgtcatttca ttccgtttga gtttcttgtt
481 ttcgttaaat gtctgcagag ttgctgcccc tttcttgaac tatgagtact gcaatctttt
541 taattctcaa tatgaataga gctttttgag ctttaaatct aaggggaact cgacaggcct
601 gtttggcata tgcaatgaac atcaagaaac catcttgctg tggaagcata attatttttc
661 ttctcccttt ttgaaagatc tttccttttg atgccagttt tcttccttgt ttacacaagt
721 tcaatttgaa aggaaaaggc aatagtaagg gtttcaaaat ggcagagaaa tttgaaagtc
781 tcatgaacat tcatggtttt gatctgggtt ctaggtatat ggacttaaaa ccattgggtt
841 gtggaggcaa tggcttggtt ttttctgctg tagacaatga ctgtgacaaa agagtagcca
901 tcaagaaaat tgtccttact gatccccaga gtgtcaaaca tgctctacgt gaaatcaaaa
961 ttattagaag acttgaccat gataacattg tgaaagtgtt tgagattctt ggtcccagtg
1021 gaagccaatt aacagacgat gtgggctctc ttacggaact gaacagtgtt tacattgttc
1081 aggagtacat ggagacagac ttggctaatg tgctggagca gggcccttta ctggaagagc
1141 atgccaggct tttcatgtat cagctgctac gggggctcaa gtatattcac tctgcaaatg
1201 tactgcacag agatctcaaa ccagctaatc ttttcattaa tacggaagac ttggtgctga
1261 agataggtga ctttggtctt gcacggatca tggatcctca ttattcccat aagggtcatc
1321 tttctgaagg attggttact aaatggtaca gatctccacg tcttttactt tctcctaata
1381 attatactaa agccattgac atgtgggctg caggctgcat ctttgctgaa atgctgactg
1441 gtaaaacccct ttttgcaggt gcacatgaac ttgaacagat gcagctgatt ttagaatcta
1501 ttcctgttgt acatgaggaa gatcgtcagg agcttctcag cgtaattcca gtttacatta
1561 gaaatgacat gactgagcca cacaaacctt taactcagct gcttccagga attagtcgag
1621 aagcactgga tttcctggaa caaattttga catttagccc catggatcgg ttaacagcag
1681 aagaagcact ctcccatcct tacatgagca tatattcttt tccaatggat gagccaattt
1741 caagccatcc ttttcatatt gaagatgaag ttgatgatat tttgcttatg gatgaaactc
1801 acagtcacat ttataactgg gaaaggtatc atgattgtca gttttcagag catgattggc
1861 ctgtacataa caactttgat attgatgaag ttcagcttga tccaagagct ctgtccgatg
1921 tcactgatga agaagaagta caagttgatc cccgaaaata tttggatgga gatcgggaaa
1981 agtatctgga ggatcctgct tttgatacca attactctac tgagccttgt tggcaatact
2041 cagatcatca tgaaaacaaa tattgtgatc tggagtgtag ccatacttgt aactacaaaa
2101 cgaggtcatc atcatattta gataacttag tttggagaga gagtgaagtt aaccattact
2161 atgaacccaa gcttattata gatctttcca attggaaaga acaaagcaaa gaaaaatctg
2221 ataagaaagg caaatcaaaa tgtgaaagga atggattggt taaagcccag atagcgctag
2281 aggaagcatc acagcaactg gctggaaaag aaagggaaaa gaatcaggga tttgattttg
2341 attcctttat tgcaggaact attcagctta gttcccagca tgagcctact gatgttgttg
2401 ataaattaaa tgacttgaat agctcagtgt cccaactaga attgaaaagt ttgatatcaa
2461 agtcagtaag ccaagaaaaa caggaaaaag gaatggcaaa tctggctcaa ttagaagcct
2521 tgtaccagtc ttcttgggac agccagtttg tgagtggtgg ggaggactgt tttttcataa
2581 atcagttttg tgaggtaagg aaggatgaac aagttgagaa ggaaaacact tacactagtt
2641 acttggacaa gttctttagc aggaaagaag atactgaaat gctagaaact gagccagtag
2701 aggatgggaa gcttggggag agaggacatg aggaaggatt tctgaacaac agtggggagt
2761 tcctctttaa caagcagctc gagtccatag gcatcccaca gtttcacagt ccagttgggt
2821 caccacttaa gtcaatacag gccacattaa caccttctgc tatgaaatct tcccctcaaa

FIG. 10 A-22

```
2881 ttcctcatca aacatacagc agcattctga aacatctgaa ctaaaacact cagcagacat
2941 ttatctttgt attcttcatg aaatgtgttt tgtctttttt tattactagt gtttaagtca
3001 tttttttactt gaatcagatg gtgtcattta gtaaggattt tatgagttct tgttttttaa
3061 aatccagact ttctttttct acatgtgaga tagttttcat tttaactggc atgtcatttg
3121 cacacaaaaa taaagactag agcaaaataa tgcaacgcag gaggagaaaa gaaatgcact
3181 aagacaagaa cattctctca tagaacattg atctgtttta caggaaacaa accttgcctt
3241 gaaatttaca cagtgag

SEQ ID NO:22
   1 ggtctttgag cgctaacgtc tttctgtctc cccgcggtgg tgatgacggt gaaaactgag
  61 gctgctaagg gcaccctcac ttactccagg atgaggggca tggtggcaat tctcatcgct
 121 ttcatgaagc agaggaggat gggtctgaac gactttattc agaagattgc caataactcc
 181 tatgcatgca aacaccctga agttcagtcc atcttgaaga tctcccaacc tcaggagcct
 241 gagcttatga atgccaaccc ttctcctcca ccaagtcctt ctcagcaaat caaccttggc
 301 ccgtcgtcca atcctcatgc taaaccatct gactttcact tcttgaaagt gatcggaaag
 361 ggcagttttg gaaaggttct tctagcaaga cacaaggcag aagaagtgtt ctatgcagtc
 421 aaagttttac agaagaaagc aatcctgaaa aagaaagagg agaagcatat tatgtcggag
 481 cggaatgttc tgttgaagaa tgtgaagcac cctttcctgg tgggccttca cttctctttc
 541 cagactgctg acaaattgta ctttgtccta gactacatta atggtggaga gttgttctac
 601 catctccaga gggaacgctg cttcctggaa ccacgggctc gtttctatgc tgctgaaata
 661 gccagtgcct tgggctacct gcattcactg aacatcgttt atagagactt aaaaccagag
 721 aatattttgc tagattcaca gggacacatt gtccttactg acttcggact ctgcaaggag
 781 aacattgaac acaacagcac aacatccacc ttctgtggca cgccggagta tctcgcacct
 841 gaggtgcttc ataagcagcc ttatgacagg actgtggact ggtggtgcct gggagctgtc
 901 ttgtatgaga tgctgtatgg cctgccgcct ttttatagcc gaaacacagc tgaaatgtac
 961 gacaacattc tgaacaagcc tctccagctg aaaccaaata ttacaaattc cgcaagacac
1021 ctcctggagg gcctcctgca gaaggacagg acaaagcggc tcggggccaa ggatgacttc
1081 atggagatta agagtcatgt cttcttctcc ttaattaact gggatgatct cattaataag
1141 aagattactc ccccttttaa cccaaatgtg agtgggccca acgacctacg gcactttgac
1201 cccgagttta ccgaagagcc tgtccccaac tccattggca agtcccctga cagcgtcctc
1261 gtcacagcca gcgtcaagga agctgccgag gctttcctag gcttttccta tgcgcctccc
1321 acggactctt tcctctgaac cctgttaggg cttggtttta aaggatttta tgtgtgtttc
1381 cgaatgtttt agttagcctt ttggtggagc cgccagctga caggacatct tacaagagaa
1441 tttgcacatc tctggaagct tagcaatctt attgcacact gttcgctgga agctttttga
1501 agagcacatt ctcctcagtg agctcatgag gttttcattt ttattcttcc ttccaacgtg
1561 gtgctatctc tgaaacgagc gttagagtgc cgccttagac ggaggcagga gtttcgttag
1621 aaagcggacg ctgttctaaa aaaggtctcc tgcagatctg tctgggctgt gatgacgaat
1681 attatgaaat gtgccttttc tgaagagatt gtgttagctc caaagctttt cctatcgcag
1741 tgtttcagtt ctttattttc ccttgtggat atgctgtgtg aaccgtcgtg tgagtgtggt
1801 atgcctgatc acagatggat tttgttataa gcatcaatgt gacacttgca ggacactaca
1861 acgtgggaca ttgtttgttt cttccatatt tggaagataa atttatgtgt agactttttt
1921 gtaagatacg gttaataact aaaatttatt gaaatggtct tgcaatgact cgtattcaga
1981 tgcttaaaga aagcattgct gctacaaata tttctatttt tagaaagggt ttttatggac
2041 caatgcccca gttgtcagtc agagccgttg gtgtttttca ttgtttaaaa tgtcacctgt
2101 aaaatgggca ttatttatgt tttttttttt gcattcctga taattgtatg tattgtataa
2161 agaacgtctg tacattgggt tataacacta gtatatttaa acttacaggc ttatttgtaa
2221 tgtaaaccac cattttaatg tactgtaatt aacatggtta taatacgtac aatccttccc
2281 tcatcccatc acacaacttt ttttgtgtgt gataaactga ttttggtttg caataaaacc
2341 ttgaaaaata ttta
```

FIG. 10 A-23

SEQ ID NO:23

```
   1 gagcagcaga atttcaactc cagtagactt gaatatgcct ctgggcaaag aagcagagct
  61 aacgaggaaa gggatttaaa gagtttttct tgggtgtttg tcaaactttt attccctgtc
 121 tgtgtgcaga ggggattcaa cttcaatttt tctgcagtgg ctctgggtcc agccccttac
 181 ttaaagatct ggaaagcatg aagactgggc tttttttcct atgtctcttg ggaactgcag
 241 ctgcaatccc gacaaatgca agattattat ctgatcattc caaaccaact gctgaaacgg
 301 tagcacctga caacactgca atccccagtt taagggctga agctgaagaa aatgaaaaag
 361 aaacagcagt atccacagaa gacgattccc accataaggc tgaaaaatca tcagtactaa
 421 agtcaaaaga ggaaagccat gaacagtcag cagaacaggg caagagttct agccaagagc
 481 tgggattgaa ggatcaagag gacagtgatg gtcacttaag tgtgaatttg gagtatgcac
 541 caactgaagg tacattggac ataaaagaag atatgagtga gcctcaggag aaaaaactct
 601 cagagaacac tgattttttg gctcctggtg ttagttcctt cacagattct aaccaacaag
 661 aaagtatcac aaagagagag gaaaaccaag aacaacctag aaattattca catcatcagt
 721 tgaacaggag cagtaaacat agccaaggcc taaggatca aggaaaccaa gagcaggatc
 781 caaatatttc caatggagaa gaggaagaag aaaaagagcc aggtgaagtt ggtacccaca
 841 atgataacca agaaagaaag acagaattgc ccagggagca tgctaacagc aagcaggagg
 901 aagacaatac ccaatctgat gatattttgg aagagtctga tcaaccaact caagtaagca
 961 agatgcagga ggatgaattt gatcagggta accaagaaca agaagataac tccaatgcag
1021 aaatggaaga ggaaaatgca tcgaacgtca ataagcacat tcaagaaact gaatggcaga
1081 gtcaagaggg taaaactggc ctagaagcta tcagcaacca caaagagaca gaagaaaaga
1141 ctgtttctga ggctctgctc atggaaccta ctgatgatgg taataccacg cccagaaatc
1201 atggagttga tgatgatggc gatgatgatg gcgatgatgg cggcactgat ggccccaggc
1261 acagtgcaag tgatgactac ttcatcccaa gccaggcctt tctggaggcc gagagagctc
1321 aatccattgc ctatcacctc aaaattgagg agcaaagaga aaaagtacat gaaaatgaaa
1381 atataggtac cactgagcct ggagagcacc aagaggccaa gaaagcagag aactcatcaa
1441 atgaggagga aacgtcaagt gaaggcaaca tgagggtgca tgctgtggat tcttgcatga
1501 gcttccagtg taaaagaggc cacatctgta aggcagacca acagggaaaa cctcactgtg
1561 tctgccagga tccagtgact tgtcctccaa caaaacccct tgatcaagtt tgtggcactg
1621 acaatcagac ctatgctagt tcctgtcatc tattcgctac taaatgcaga ctggagggga
1681 ccaaaaaggg gcatcaactc cagctggatt attttggagc ctgcaaat
```

SEQ ID NO:24

```
   1 cggataagga caaaaaacgc cagaagaaaa gaggcatttt ccccaaagta gcaacaaata
  61 tcatgagagc atggctcttc cagcatctca cacatccgta cccttccgaa gagcagaaga
 121 aacagttagc gcaagacaca ggacttacaa ttctccaagt aaacaactgg tttattaatg
 181 ccagaagaag aatagtacag cccatgattg accagtcaaa tcgagcagtg agccaaggag
 241 cagcatatag tccagagggt cagcccatgg ggagctttgt gttggatggt cagcaacaca
 301 tggggatccg gcctgcagga cctatgagtg gaatgggcat gaatatgggc atggatgggc
 361 aatggcacta catgtaacct tcatcatgta aagcaatcgc aaagcaaggg ggaagtttgc
 421 agagcatgcc aggggactac gtttctcagg gtggtcctat gggaatgagt atggcacagc
 481 caagttacac tcctccccag atgaccccac accctactca attaagacat ggaccccccaa
 541 tgcattcata tttgccaagc catccccacc acccagccat gatgatgcac ggaggacccc
 601 ctacccaccc tggaatgact atgtcagcac agagccccac aatgttaaat tctgtagatc
 661 ccaatgttgg cggacaggtt atggacattc atgcccaata gtataaggga actcaaggga
 721 aaaggaaaca cacgcaaaaa ctattttaag actttctgaa ctttgaccag atgttgacac
 781 ttaatatgaa attccagaca gctgtgatta tttttttactt ttgtcatttt tcatcaagca
 841 acagaggacc aatgcaacaa gaacacaaat gtgaaatcat gggctgactg agacaattct
 901 gtccatgtaa agatcctctg gaaaaagact ccgagagtta taactactgt agtataaata
 961 taggaactaa gttaaacttg tacatttctg ttgatcacgc cgttatgttg cctcaaatag
1021 ttttagaaga gaaaaaaaaa tatatccttg ttttccacac tatgtgtgtt gttcccaaaa
1081 gaatgactgt tttggttcat cagtgaattc accatccagg agagactgtg gtatatattt
```

FIG. 10 A-24

1141 taaacctgtt gggccaatga gaaaagaacc acactggaga tcatgatgaa cttttggctg
1201 aacctcatca ctcgaactcc agcttcaaga atgtgttttc atgcccggcc tttgttcctc
1261 cataaatgtg tcctttagtt tcaaacagat ctttatagtt cgtgcttcat aagccaattc
1321 ttattattat ttttggggga ctcttcttca aagagcttgc caatgaagat ttaaagacag
1381 agcaggagct tcttccagga gttctgagcc ttggttgtgg acaaaacaat cttaagttgg
1441 gcagctttcc tcaacacaaa aaaaagttat taatggtcat tgaaccataa ctaggacttt
1501 atcagaaact caaagcttgg gggataaaaa ggagcaagag aatactgtaa caaacttcgt
1561 acagagttcg gtctattaat tgtttcatgt tagatattct atgtgtttac ctcaattgaa
1621 aaaaaaaaga atgtttttgc tagtatcaga tctgctgtgg aattggtatt gtatgtccat
1681 gaattcttct tttctcagca cgtgttcctc actagaagaa aatgctgtta cctttaagct
1741 ttgtcaaatt tacattaaaa tacttgtatg aggactgtga cgttatgtta aaaaaaaaaa
1801 ggtgttaagt cacaaaaagc ggtaataaat atttcatttt tgattttt SEQ ID NO:25
1 agcacactga ggaggcgatc cgccagcagg aggtggagca gctggacttc cgagacctcc
61 tggggaagaa ggtgagtaca aagaccctat cggaagacga cctgaaggag atcccagccg
121 agcagatgga tttccgtgcc aacctgcagc ggcaagtgaa gccaaagact gtgtctgagg
181 aagagaggaa ggtgcacagc ccccagcagg tcgattttcg ctctgtcctg gccaagaagg
241 ggacttccaa gacccccgtg cctgagaagg tgccaccgcc aaaacctgcc accccggatt
301 ttcgctcagt gctgggtggc aagaagaaat taccagcaga gaatggcagc agcagtgccg
361 agaccctgaa tgccaaggca gtggagagtt ccaagcccct gagcaatgca cagccttcag
421 ggcccttgaa acccgtgggc aacgccaagc ctgctgagac cctgaagcca atgggcaacg
481 ccaagcctgc cgagaccctg aagcccatgg gcaatgccaa gcctgatgag aacctgaaat
541 ccgctagcaa agaagaactc aagaaagacg ttaagaatga tgtgaactgc aagagaggcc
601 atgcagggac cacagataat gaaaagagat cagagagcca ggggacagcc ccagccttca
661 agcagaagct gcaagatgtt catgtggcag agggcaagaa gctgctgctc cagtgccagg
721 tgtcttctga ccccccagcc accatcatct ggacgctgaa cggaaagacc atcaagacca
781 ccaagttcat catcctctcc caggaaggct cactctgctc cgtctccatc gagaaggcac
841 tgcctgagga cagaggctta tacaagtgtg tagccaagaa tgacgctggc caggcggagt
901 gctcctgcca agtcaccgtg gatgatgctc cagccagtga gaacaccaag gccccagaga
961 tgaaatcccg gaggcccaag agctctcttc ctcccgtgct aggaactgag agtgatgcga
1021 ctgtgaaaaa gaaacctgcc cccaagacac ctccgaaggc agcaatgccc cctcagatca
1081 tccagttccc tgaggaccag aaggtacgcg caggagagtc agtggagctg tttggcaaag
1141 tgacaggcac tcagcccatc acctgtacct ggatgaagtt ccgaaagcag atccaggaaa
1201 gcgagcacat gaaggtggag aacagcgaga atggcagcaa gctcaccatc ctggccgcgc
1261 gccaggagca ctgcggctgc tacacactgc tggtggagaa caagctgggc agcaggcagg
1321 cccaggtcaa cctcactgtc gtggataagc cagaccccc agctggcaca ccttgtgcct
1381 ctgacattcg gagctcctca ctgaccctgt cctggtatgg ctcctcatat gatgggggca
1441 gtgctgtaca gtcctacagc atcgagatct gggactcagc caacaagacg tggaaggaac
1501 tagccacatg ccgcagcacc tctttcaacg tccaggacct gctgcctgac cacgaatata
1561 agttccgtgt acgtgcaatc aacgtgtatg gaaccagtga gccaagccag gagtctgaac
1621 tcacaacggt aggagagaaa cctgaagagc cgaaggatga agtggaggtg tcagacgatg
1681 atgagaagga gcccgaggtt gattaccgga cagtgacaat caatactgaa caaaaagtat
1741 ctgacttcta cgacattgag gagagattag gatctgggaa atttggacag gtctttcgac
1801 ttgtagaaaa gaaaactcga aaagtctggg cagggaagtt cttcaaggca tattcagcaa
1861 aagagaaaga gaatatccgg caggagatta gcatcatgaa ctgcctccac caccctaagc
1921 tggtccagtg tgtggatgcc tttgaagaaa aggccaacat cgtcatggtc ctggagatcg
1981 tgtcaggagg ggagctgttt gagcgcatca ttgacgagga ctttgagctg acggagcgtg
2041 agtgcatcaa gtacatgcgg cagatctcgg agggagtgga gtacatccac aagcagggca
2101 tcgtgcacct ggacctcaag ccggagaaca tcatgtgtgt caacaagacg ggcaccagga

FIG. 10 A-25

```
2161 tcaagctcat cgactttggt ctggccagga ggctggagaa cgcggggtct ctgaaggtcc
2221 tctttggcac cccagaattt gtggctcctg aagtgatcaa ctatgagccc atcggctacg
2281 ccacagacat gtggagcatc ggggtcatct gctacatcct agtcagtggc ctttcccccct
2341 tcatgggaga caacgataac gaaaccttgg ccaacgttac ctcagccacc tgggacttcg
2401 acgacgaggc attcgatgag atctccgacg atgccaagga tttcatcagc aatctgctga
2461 agaaagatat gaaaaaccgc ctggactgca cgcagtgcct tcagcatcca tggctaatga
2521 aagataccaa gaacatggag gccaagaaac tctccaagga ccggatgaag aagtacatgg
2581 caagaaggaa atggcagaaa acgggcaatg ctgtgagagc cattggaaga ctgtcctcta
2641 tggcaatgat ctcagggctc agtggcagga aatcctcaac agggtcacca accagcccgc
2701 tcaatgcaga aaaactagaa tctgaagaag atgtgtccca agctttcctt gaggctgttg
2761 ctgaggaaaa gcctcatgta aaaccctatt tctctaagac cattcgcgat ttagaagttg
2821 tggagggaag tgctgctaga tttgactgca agattgaagg atacccagac cccgaggttg
2881 tctggttcaa agatgaccag tcaatcaggg agtcccgcca cttccagata gactacgatg
2941 aggacgggaa ctgctcttta attattagtg atgtttgcgg ggatgacgat gccaagtaca
3001 cctgcaaggc tgtcaacagt cttggagaag ccacctgcac agcagagctc attgtggaaa
3061 cgatggagga aggtgaaggg gaaggggaag aggaagaaga gtgaaacaaa gccagagaaa
3121 agcagtttct aagtcatatt aaaaggacta tttctctaaa actc
```

SEQ ID NO:26

```
   1 ctctcccaac cgcctcgtcg cactcctcag gctgagagca ccgctgcact cgcggccggc
  61 gatgcgggac cccggcgcgg ccgctccgct ttcgtccctg ggcctctgtg ccctggtgct
 121 ggcgctgctg ggcgcactgt ccgcgggcgc cggggcgcag ccgtaccacg gagagaaggg
 181 catctccgtg ccggaccacg gcttctgcca gcccatctcc atcccgctgt gcacggacat
 241 cgcctacaac cagaccatcc tgcccaacct gctgggccac acgaaccaag aggacgcggg
 301 cctcgaggtg caccagttct acccgctggt gaaggtgcag tgttctcccg aactccgctt
 361 tttcttatgc tccatgtatg cgcccgtgtg caccgtgctc gatcaggcca tcccgccgtg
 421 tcgttctctg tgcgagcgcg cccgccaggg ctgcgaggcg ctcatgaaca agttcggctt
 481 ccagtggccc gagcggctgc gctgcgagaa cttcccggtg cacggtgcgg gcgagatctg
 541 cgtgggccag aacacgtcgg acggctccgg gggcccaggc ggcggcccca ctgcctaccc
 601 taccgcgccc tacctgccgg acctgccctt caccgcgctg cccccggggg cctcagatgg
 661 caggggggcgt cccgccttcc ccttctcatg cccccgtcag ctcaaggtgc ccccgtacct
 721 gggctaccgc ttcctgggtg agcgcgattg tggcgccccg tgcgaaccgg gccgtgccaa
 781 cggcctgatg tactttaagg aggaggagag gcgcttcgcc cgcctctggg tgggcgtgtg
 841 gtccgtgctg tgctgcgcct cgacgctctt taccgttctc acctacctgg tggacatgcg
 901 gcgcttcagc tacccagagc ggcccatcat cttcctgtcg ggctgctact tcatggtggc
 961 cgtggcgcac gtggccggct tccttctaga ggaccgcgcc gtgtgcgtgg agcgcttctc
1021 ggacgatggc taccgcacgg tggcgcaggg caccaagaag gagggctgca ccatcctctt
1081 catggtgctc tacttcttcg gcatggccag ctccatctgg tgggtcattc tgtctctcac
1141 ttggttcctg gcggccggca tgaagtgggg ccacgaggcc atcgaggcca actcgcagta
1201 cttccacctg gccgcgtggg ccgtgcccgc cgtcaagacc atcactatcc tggccatggg
1261 ccaggtagac ggggacctgc tgagcggggt gtgctacgtt ggcctctcca gtgtggacgc
1321 gctgcggggc ttcgtgctgg cgcctctgtt cgtctacctc ttcataggca cgtccttctt
1381 gctggccggc ttcgtgtccc tcttccgtat ccgcaccatc atgaaacacg acggcaccaa
1441 gaccgagaag ctggagaagc tcatggtgcg catcggcgtc ttcagcgtgc tctacacagt
1501 gcccgccacc atcgtcctgg cctgctactt ctacgagcag gccttccgcg agcactggga
1561 gcgcacctgg ctcctgcaga cgtgcaagag ctatgccgtg ccctgcccgc ccggccactt
1621 cccgcccatg agccccgact tcaccgtctt catgatcaag tacctgatga ccatgatcgt
1681 cggcatcacc actggcttct ggatctggtc gggcaagacc ctgcagtcgt ggcgccgctt
1741 ctaccacaga cttagccaca gcagcaaggg ggagactgcg gtatgagccc cggcccctcc
1801 ccacctttcc caccccagcc ctcttgcaag aggagaggca cggtagggaa aagaactgct
```

FIG. 10 A-26

```
1861 gggtgggggc ctgtttctgt aactttctcc ccctctactg agaagtgacc tggaagtgag
1921 aagttctttg cagatttggg gcgaggggtg atttggaaaa gaagacctgg gtggaaagcg
1981 gtttggatga aaagatttca ggcaaagact tgcaggaaga tgatgataac ggcgatgtga
2041 atcgtcaaag gtacgggcca gcttgtgcct aatagaaggt tgagaccagc agagactgct
2101 gtgagtttct cccggctccg aggctgaacg gggactgtga gcgatccccc tgctgcaggg
2161 cgagtggcct gtccagaccc ctgtgaggcc ccgggaaagg tacagccctg tctgcggtgg
2221 ctgctttgtt ggaaagaggg agggcctcct gcggtgtgct tgtcaagcag tggtcaaacc
2281 ataatctctt ttcactgggg ccaaactgga gcccagatgg gttaatttcc agggtcagac
2341 attacggtct ctcctcccct gccccctccc gcctgttttt cctcccgtac tgctttcagg
2401 tcttgtaaaa taagcatttg gaagtcttgg gaggcctgcc tgctagaatc ctaatgtgag
2461 gatgcaaaag aaatgatgat aacattttga gataaggcca aggagacgtg gagtaggtat
2521 ttttgctact ttttcatttt ctggggaagg caggaggcag aaagacgggt gttttatttg
2581 gtctaatacc ctgaaaagaa gtgatgactt gttgcttttc aaaacaggaa tgcatttttc
2641 cccttgtctt tgttgtaaga gacaaaagag gaaacaaaag tgtctccctg tggaaaggca
2701 taactgtgac gaaagcaact tttataggca aagcagcgca aatctgaggt ttcccgttgg
2761 ttgttaattt ggttgagata aacattcctt tttaaggaaa agtgaagagc agtgtgctgt
2821 cacacaccgt taagccagag gttctgactt cgctaaagga aatgtaagag gttttgttgt
2881 ctgttttaaa taaatttaat tcggaacaca tgatccaaca gactatgtta aaatattcag
2941 ggaaatctct cccttcattt actttttctt gctataagcc tatatttagg tttcttttct
3001 atttttttct cccatttgga tcctttgagg taaaaaaaca taatgtcttc agcctcataa
3061 taaaggaaag ttaattaaaa aaaaaaagca aagagccatt ttgtcctgtt ttcttggttc
3121 catcaatctg tttattaaac atcatccata tgctgaccct gtctctgtgt ggttgggttg
3181 ggaggcgatc agcagatacc atagtgaacg aagaggaagg tttgaaccat gggccccatc
3241 tttaaagaaa gtcattaaaa gaaggtaaac ttcaaagtga ttctggagtt ctttgaaatg
3301 tgctggaaga cttaaattta ttaatcttaa atcatgtact ttttttctgt aatagaactc
3361 ggattctttt gcatgatggg gtaaagctta gcagagaatc atgggagcta acctttatcc
3421 cacctttgac actaccctcc aatcttgcaa cactatcctg tttctcagaa cagtttttaa
3481 atgccaatca tagagggtac tgtaaagtgt acaagttact ttatatatgt aatgttcact
3541 tgagtggaac tgctttttac attaaagtta aaatcgatct tgtgtttctt caaccttcaa
3601 aactatctca tctgtcagat ttttaaaact ccaacacagg ttttggcatc ttttgtgctg
3661 tatcttttaa gtgcatgtga aatttgtaaa atagagataa gtacagtatg tatattttgt
3721 aaatctccca tttttgtaag aaaatatata ttgtatttat acatttttac tttggatttt
3781 tgttttgttg gctttaaagg tctaccccac tttatcacat gtacagatca caaataaatt
3841 tttttaaata c
```

SEQ ID NO:27

```
  1 ggggctcggg acggccgggc tgggagctgg agcccacagc gggaagcggc cgccgcccgg
 61 gcctcgcagg gctaggcgag gcgagggggg gcggggccgg gcgctacggg aaggggaggc
121 cgcgcggacc gggagccgca ccgcgccagc cgggctgcag cggccgcgca ccaaggctgc
181 gatggggctg gagacggaga aggcggacgt acagctcttc atggacgacg actcctacag
241 ccaccacagc ggcctcgagt acgccgaccc cgagaagttc gcggactcgg accaggaccg
301 ggatccccac cggctcaact cgcatctcaa gctgggcttc gaggatgtga tcgcagagcc
361 ggtgactacg cactcctttg acaaagtgtg gatctgcagc catgccctct ttgaaatcag
421 caaatacgta atgtacaagt tcctgacggt gttcctggcc attcccctgg ccttcattgc
481 gggaattctc tttgccaccc tcagctgtct gcacatctgg attttaatgc cttttgtaaa
541 gacctgccta atggttctgc cttcagtgca gacaatatgg aagagtgtga cagatgttat
601 cattgctcca ttgtgtacga gcgtaggacg atgcttctct tctgtcagcc tgcaactgag
661 ccaggattga atacttggac cccaggtctg gagattggga tactgtaata cttctttgtt
721 attataacat aaaagcacca ctgttctgtt catttcctag ctgttctaat taagaaaact
781 attaagatga gcaaccacat ttagaaatgt ttattgacag gtcttttcaa ataatgcttt
```

FIG. 10 A-27

```
 841 tctaattaat agccaaagat ttcatatcta actttgtaac cagaattata cagtaagttg
 901 acaccactta gatttaaagg cagacagttt tgctttagta caatagtata cattttataa
 961 tgatgaactt ataatgatta agggacattt ctataaaaat actacaatag ttttatgcac
1021 aacttcccat taaaaatgag atttcttatt tgtttgtctg tttttactct gggagtaata
1081 ctttttaaat tacctttaca tatatagtca ctggcatact gagaatatac aatgatcctg
1141 gaaattgcag taacaaaagc acacaacgat tatagtaact ataagataca ataaaacaaa
1201 taaatatgaa agtagattca tgaaaatgta ttcctttaaa atattgtttt cctacaggcc
1261 tatttaacaa gatgtttcat tttactgtat attttgtagt taatataaat gttgctctaa
1321 tcagattgct taaaagcatt tttattatat ttatgttgtt gaactaatat atgaaataag
1381 taaatgtagc tcccacaagg taaacttcat tggtaagatt gcactgttct gattatgtaa
1441 gcatttgtac atcttctttg gaaataaaag ataaaa
```

SEQ ID NO:28

```
   1 gtttagaaca gcctacagac ccagtggcac gagacgggcc tctctcccaa acatcttcca
  61 agccagatcc tagtcagtgg gaaagcccca gcttcaaccc ctttgggagc cactctgttc
 121 tgcagaactc cccacccctc tcttctgagg gctcctacca ctttgaccca gataactttg
 181 acgaatccat ggatcccttt aaaccaacta cgaccttaac aagcagtgac ttttgttctc
 241 ccactggtaa tcacgttaat gaaatcttag aatcacccaa gaaggcaaag tcgcgtttaa
 301 taacgactac tgaacaagtg aaatttctct gttttctgtt gagtggctgt aaggtgaaga
 361 agcatgaaac tcagtctctc gccctggatg catgttctcg ggatgaaggg gcagtgatct
 421 cccagatttc agacatttct aatagggatg gccatgctac tgatgaggag aaactggcat
 481 ccacgtcatg tggtcagaaa tcagctggtg ccgaggtgaa aggtgagcca gaggaagacc
 541 tggagtactt tgaatgttcc aatgttcctg tgtctaccat aaatcatgcg ttttcatcct
 601 cagaagcagg catagagaag gagacgtgcc agaagatgga agaagacggg tccactgtgc
 661 ttgggctgct ggagtcctct gcagagaagg cccctgtgtc ggtgtcctgt ggaggtgaga
 721 gccccctgga tgggatctgc ctcagcgaat cagacaagac agccgtgctc accttaataa
 781 gagaagagat aattactaaa gagattgaag caaatgaatg gaagaagaaa tacgaagaga
 841 cccggcaaga agttttggag atgaggaaaa ttgtagctga atatgaaaag actattgctc
 901 aaatgattga tgaacaaagg acaagtatga cctctcagaa gagcttccag caactgacca
 961 tggagaagga acaggccctg gctgacctta actctgtgga aaggtccctt tctgatctct
1021 tcaggagata tgagaacctg aaaggtgttc tggaagggtt caagaagaat gaagaagcct
1081 tgaagaaatg tgctcaggat tacttagcca gagttaaaca agaggagcag cgataccagg
1141 ccctgaaaat ccacgcagaa gagaaactgg acaaagccaa tgaagagatt gctcaggttc
1201 gaacaaaagc aaaggctgag agtgcagctc tccatgctgg actccgcaaa gagcagatga
1261 aggtggagtc cctggaaagg gccctgcagc agaagaacca agaaattgaa gaactgacaa
1321 aaatctgtga tgagctgatt gcaaagctgg gaaagactga ctgagacact ccccctgtta
1381 gctcaacaga tctgcatttg gctgcttctc ttgtgaccac aattatcttg ccttatccag
1441 gaataattgc ccctttgcag agaaaaaaaa aaacttaaaa aaagcacatg cctactgctg
1501 cctgtcccgc tttgctgcca atgcaacagc cctggaagaa accctagagg gttgcatagt
1561 ctagaaagga gtgtgacctg acagtgctgg agcctcctag tttcccccta tgaaggttcc
1621 cttaggctgc tgagtttggg tttgtgattt atctttagtt tgttttaaag tcatctttac
1681 tttcccaaat gtgttaaatt tgtaactcct ctttggggtc ttctccacca cctgtctgat
1741 tttttgtga tctgtttaat cttttaattt tttagtatca gtggttttat ttaaggagac
1801 agtttggcct attgttactt ccaatttata atcaagaagg ggctctggat ccccttttaa
1861 attacacaca ctctcacaca catacatgta tgtttataga tgctgctgct cttttccctg
1921 aagcatagtc aagtaagaac tgctctacag aaggacatat ttccttggat gtgagaccct
1981 attttgaaat agagtcctga ctcagaacac caacttaaga atttggggga ttaaagatgt
2041 gaagaccaca gtcttgggtt ttcatatctg gagaagacta tttgccatga cgttttgttg
2101 ccctggtatt tggacactcc tcagctttaa tgggtgtggc ccctttaggg ttagtcctca
2161 gactaatgat agtgtctgct ttctgcatga acggcaatat gggactccct ccaagctagg
2221 gtttggcaag tctgccctag agtcatttac tctcctctgc ctccatttgt taatacagaa
```

FIG. 10 A-28

2281 tcaacattta gtcttcatta tcttttttt tttttttgag acagagtttc gatctatttt
2341 aagtatgtga agaaaatcta cttgtaaaag gctcagatct taattaaaag gtaattgtag
2401 cacattacca attataaggt gaagaaatgt tttttccca agtgtgatgc attgttcttc
2461 agatgttgaa aagaaagcaa aaaatacctt ctaacttaag acagaatttt taacaaaatg
2521 agcagtaaaa gtcacatgaa ccactccaaa aatcagtgca ttttgcatat ttttaaacaa
2581 agacagcttg ttgaatactg agaagaggag tgcaaggaga aggtctgtac taacaaagcc
2641 aaattcctca agctcttact ggactcagtt cagagtggtg ggccattaac cccaacatgg
2701 aatttttcca tataaatctc aatgaattcc ctttcatttg aataggcaaa cccaaatcca
2761 tgcaagtgtt ttaaagcact gtcctgtctt aatcttacat gctgaaagtc ttcatggtga
2821 tatgcactat attcagtata cgtatgtttt cctacttctc ttgtaaaact gttgcatgat
2881 ccaacttcag caatgaattg tgcctagtgg agaacctcta tagatcttaa aaaatgaatt
2941 attctttagc agtgtattac tcacatgggt gcaatcttta gccccaggga ggtcaataat
3001 gtcttttaaa gccagaagtc acattttacc aatatgcatt tatcataatt ggtgcttagg
3061 ctgtatattc aagcctgttg tcttaacatt ttgtataaaa aagaacaaca gaaattatct
3121 gtcatttgag aagtggcttg acaatcattt gagctttgaa agcagtcact gtggtgtaat
3181 atgaatgctg tcctagtggt catagtacca agggcacgtg tctccccttg gtataactga
3241 tttccttttt agtcctctac tgctaaataa gttaattttg cattttgcag aaagaaacat
3301 tgattgctaa atctttttgc tgctgtgttt tggtgttttc atgtttactt gttttatatt
3361 gatctgtttt aagtatgaga ggcttatagt gccctccatt gtaaatccat agtcatcttt
3421 ttaagcttat tgtgtttaag aaagtagcta tgtgttaaac agaggtgatg gcagcccttc
3481 cctagcacac tggtggaaga gaccccttaa gaacctgacc ccagtgaatg aagctgatgc
3541 acagggagca ccaaaggacc ttcgttaagt gataattgtc ctggcctctc agccatgacc
3601 gttatgagga aatatccccc attcgaactt aacagatgcc tcctctccaa agagaattaa
3661 aatcgtagct tgtacagatc aagagaatat actgggcaga atgaagtatg tttgtttatt
3721 tttctttaaa aataaaggat tttggaactc tggagagtaa gaatatagta tagagtttgc
3781 ctcaacacat gtgagggcca aataacctgc tagctaggca gtaataaact ctgttacaga
3841 agagaaaaag ggccgggcac agtggcttat tcctgtaatc ccaacactgt ggaaggccga
3901 ggcaggagga tcacttgagt ccaggagttt gaaacctacc taggcaacat ggtgaaacct
3961 tgtctctacc aaaataaaaa ttagctgggc atggtggcac gtgcctgtgg tcccagctac
4021 ttgggaggct gaggtgggag cctgggaggt caaggctgca gtgagccatg atcatgccac
4081 tgcactccat cctgggtgac agcaagatct tgtctc

SEQ ID NO:29

1 cgagttcccc gaggtgtacg tgcccaccgt cttcgagaac tatgtggccg acattgaggt
61 ggacggcaag caggtggagc tggcgctgtg ggacacggcg ggccaggagg actacgaccg
121 cctgcggccg ctctcctacc cggacaccga cgtcattctc atgtgcttct cggtggacag
181 cccggactcg ctggagaaca tccccgagaa gtgggtcccc gaggtgaagc acttctgtcc
241 caatgtgccc atcatcctgg tggccaacaa aaaagacctg cgcagcgacg agcatgtccg
301 cacagagctg gcccgcatga agcaggaacc cgtgcgcacg gatgacggcc gcgccatggc
361 cgtgcgcatc caagcctacg actacctcga gtgctctgcc aagaccaagg aaggcgtgcg
421 cgaggtcttc gagacggcca cgcgcgccgc gctgcagaag cgctacggct cccagaacgg
481 ctgcatcaac tgctgcaagg tgctatgagg gccgcgcccg tcgcgcctgc ccctgccggc

SEQ ID NO:30

1 cggggagacc atggggcccc tctcagcccc ttcctgcaca cacctcatca cttggaaggg
61 ggtcctgctc acagcatcac ttttaaactt ctggaatccg cccaccactg ccgaagtcac
121 gattgaagcc cagccaccca aagtttctga ggggaaggat gttcttctac ttgttcacaa
181 tttgccccag aatcttcctg gctacttctg gtacaaaggg gaaatgacgg acctctacca
241 ttacattata tcgtatatag ttgatggtaa aataattata tatgggcctg catacagtgg
301 aagagaaaca gtatattcca acgcatccct gctgatccag aatgtcaccc ggaaggatgc

FIG. 10 A-29

```
 361 aggaacctac accttacaca tcataaagcg aggtgatgag actagagaag aaattcgaca
 421 tttcaccttc accttatact atggtccaga cctccccaga atttaccctt cattcaccta
 481 ttacggttca ggagaaaacc tcgacttgtc ctgcttcacg gaatctaacc caccggcaga
 541 gtatttttgg acaattaatg ggaagtttca gcaatcagga caaaagctct ttatccccca
 601 aattactaga aatcatagcg ggctctatgt ttgctctgtt cataactcag ccactggcaa
 661 ggaaatctcc aaatccatga cagtcaaagt ctctggtccc tgccatggag acctgacaga
 721 gtttcagtca tgactgcaac aactgagaca ctgagaaaaa gaacaggctg ataccttcat
 781 gaaattcaag acaaagaaga aaaaaactca atgttattgg actaaataat caaaaggata
 841 atgttttcat aattttttat tggaaaatgt gctgattctt tgaatgtttt attctccaga
 901 tttatgaact ttttttcttc agcaattggt aaagtatact tttgtaaaca aaaattgaaa
 961 tatttgcttt tgctgtctat ctgaatgccc cagaattgtg aaactactca tgagtactca
1021 taggtttatg gtaataaagt tatttgcaca tgttccgtag ttt
```

SEQ ID NO:31

```
   1 gcaccaacca gcaccatgcc catgatactg gggtactggg acatccgcgg gctggcccac
  61 gccatccgcc tgctcctgga atacacagac tcaagctatg aggaaaagaa gtacacgatg
 121 ggggacgctc ctgattatga cagaagccag tggctgaatg aaaaattcaa gctgggcctg
 181 gactttccca atctgcccta cttgattgat ggggctcaca agatcaccca gagcaacgcc
 241 atcttgtgct acattgcccg caagcacaac ctgtgtgggg agacagaaga ggagaagatt
 301 cgtgtggaca ttttggagaa ccagaccatg gacaaccata tgcagctggg catgatctgc
 361 tacaatccag aatttgagaa actgaagcca aagtacttgg aggaactccc tgaaaagcta
 421 aagctctact cagagtttct ggggaagcgg ccatggtttg caggaaacaa gatcactttt
 481 gtagattttc tcgtctatga tgtccttgac ctccaccgta tatttgagcc caactgcttg
 541 gacgccttcc caaatctgaa ggacttcatc tcccgctttg agggcttgga gaagatctct
 601 gcctacatga agtccagccg cttcctccca agacctgtgt tctcaaagat ggctgtctgg
 661 ggcaacaagt agggccttga aggcaggagg tgggagtgag gagcccatac tcagcctgct
 721 gcccaggctg tgcagcgcag ctggactctg catcccagca cctgcctcct cgttcctttc
 781 tcctgtttat tcccatcttt actcccaaga cttcattgtc cctcttcact ccccctaaac
 841 ccctgtccca tgcaggccct ttgaagcctc agctacccac tatccttcgt gaacatcccc
 901 tcccatcatt acccttccct gcactaaagc cagcctgacc ttccttcctg ttagtggttg
 961 tgtctgcttt aaagcctgcc tggcccctcg cctgtggagc tcagccccga gctgtccccg
1021 tgttgcatga aggagcagca ttgactggtt tacaggccct gctcctgcag catggtccct
1081 gcctaggcct acctgatgga agtaaagcct caaccac
```

SEQ ID NO:32

```
   1 ttcaggaacc ggtttggtgc tggtgctgga ggcggctatg gctttggagg tggtgccggt
  61 agtggatttg gtttcggcgg tggagctggt ggtggctttg ggctcggtgg cggagctggc
 121 tttggaggtg gcttcggtgg ccctggcttt cctgtctgcc ctcctggagg tatccaagag
 181 gtcactgtca accagagtct cctgactccc ctcaacctgc aaatcgaccc cagcatccag
 241 agggtgagga ccgaggagcg cgagcagatc aagaccctca acaataagtt tgcctccttc
 301 atcgacaagg tgcggttcct ggagcagcag aacaaggttc tggacaccaa gtggaccctg
 361 ctgcaggagc agggcaccaa gactgtgagg cagaacctgg agccgttgtt cgagcagtac
 421 atcaacaacc tcaggaggca gctggacagc atcgtggggg aacggggccg cctggactca
 481 gagctgagaa acatgcagga cctggtggaa gacttcaaga acaagtatga ggatgaaatc
 541 aacaagcgta ccactgctga gaatgagttt gtgatgctga agaaggatgt agatgctgcc
 601 tacatgaaca aggtggagct ggaggccaag gttgatgcac tgatggatga gattaacttc
 661 atgaagatgt tctttgatgc ggagctgtcc cagatgcaga cgcatgtctc tgacacctca
 721 gtggtcctct ccatggacaa caaccgcaac ctggacctgg atagcatcat cgctgaggtc
 781 aaggcccagt atgaggagat tgccaaccgc agccggacag aagccgagtc ctggtatcag
 841 accaagtatg aggagctgca gcagacagct ggccggcatg gcgatgacct ccgcaacacc
 901 aagcatgaga tctctgagat gaaccggatg atccagaggc tgagagccga gattgacaat
```

FIG. 10 A-30

```
 961 gtcaagaaac agtgcgccaa tctgcagaac gccattgcgg atgccgagca gcgtggggag
1021 ctggccctca aggatgccag gaacaagctg gccgagctgg aggaggccct gcagaaggcc
1081 aagcaggaca tggcccggct gctgcgtgag taccaggagc tcatgaacac caagctggcc
1141 ctggacgtgg agatcgccac ttaccgcaag ctgctggagg gcgaggaatg cagactcagt
1201 ggagaaggag ttggaccagt caacatctct gttgtcacaa gcagtgtttc ctctggatat
1261 ggcagtggca gtggctatgg cggtggcctc ggtggaggtc ttggcggcgg cctcggtgga
1321 ggtcttgccg gaggtagcag tggaagctac tactccagca gcagtggggg tgtcggccta
1381 ggtggtgggc tcagtgtggg gggctctggc ttcagtgcaa gcagtggccg agggctgggg
1441 gtgggctttg gcagtggcgg gggtagcagc tccagcgtca aatttgtctc caccacctcc
1501 tcctcccgga agagcttcaa gagctaagaa cctgctgcaa gtcactgcct tccaagtgca
1561 gcaacccagc ccatggagat tgcctcttct aggcagttgc tcaagccatg ttttatcctt
1621 ttctggagag tagtctagac caagccaatt gcagaaccac attctttggt tcccaggaga
1681 gccccattcc cagcccctgg tctcccgtgc cgcagttcta tattctgctt caaatcagcc
1741 ttcaggtttc ccacagcatg gcccctgctg acacgagaac ccaaagtttt cccaaatcta
1801 aatcatcaaa acagaatccc caccccaatc ccaaattttg ttttggttct aactacctcc
1861 agaatgtgt

SEQ ID NO:33
   1 agtgatcagg gccaaagcgg tcagtgagaa ggaagtggac tctggaaacg acatttatgg
  61 caaccctatc aagaggatcc agtatgagat caagcagata aagatgttca aagggcctga
 121 gaaggatata gagtttatct acacggcccc ctcctcggca gtgtgtgggg tctcgctgga
 181 cgttggagga aagaaggaat atctcattgc aggaaaggcc gagggggacg gcaagatgca
 241 catcaccctc tgtgacttca tcgtgccctg ggacaccctg agcaccaccc agaagaagag
 301 cctgaaccac aggtaccaga tgggctgcga gtgcaagatc acgcgctgcc ccatgatccc
 361 gtgctacatc tcctccccgg acgagtgcct ctggatggac tgggtcacag agaagaacat
 421 caacgggcac caggccaagt tcttcgcctg catcaagaga agtgacggct cctgtgcgtg
 481 gtaccgcggc gcggcgcccc ccaagcagga gtttctcgac atcgaggacc cataagcagg
 541 cctccaacgc ccctgtggcc aactgcaaaa aaagcctcca agggtttcga ctggtccagc
 601 tctgacatcc cttcctggaa acagcatgaa taaaacactc atcccatggg tccaaattaa
 661 tatg

SEQ ID NO:34
   1 tgtcgccacc atggctccgc accgccccgc gcccgcgctg ctttgcgcgc tgtccctggc
  61 gctgtgcgcg ctgtcgctgc ccgtccgcgc ggccactgcg tcgcgggggg cgtcccaggc
 121 gggggcgccc caggggcggg tgcccgaggc gcggcccaac agcatggtgg tggaacaccc
 181 cgagttcctc aaggcaggga aggagcctgg cctgcagatc tggcgtgtgg agaagttcga
 241 tctggtgccc gtgcccacca acctttatgg agacttcttc acgggcgacg cctacgtcat
 301 cctgaagaca gtgcagctga ggaacggaaa tctgcagtat gacctccact actggctggg
 361 caatgagtgc agccaggatg agagcggggc ggccgccatc tttaccgtgc agctggatga
 421 ctacctgaac ggccgggccg tgcagcaccg tgaggtccag ggcttcgagt cggccacctt
 481 cctaggctac ttcaagtctg gcctgaagta caagaaagga ggtgtggcat caggattcaa
 541 gcacgtggta cccaacgagg tggtggtgca gagactcttc caggtcaaag ggcggcgtgt
 601 ggtccgtgcc accgaggtac ctgtgtcctg ggagagcttc aacaatggcg actgcttcat
 661 cctggacctg ggcaacaaca tccaccagtg gtgtggttcc aacagcaatc ggtatgaaag
 721 actgaaggcc acacaggtgt ccaagggcat ccgggacaac gagcggagtg gccgggcccg
 781 agtgcacgtg tctgaggagg gcactgagcc cgaggcgatg ctccaggtgc tgggccccaa
 841 gccggctctg cctgcaggta ccgaggacac cgccaaggag gatgcggcca accgcaagct
 901 ggccaagctc tacaaggtct ccaatggtgc agggaccatg tccgtctccc tcgtggctga
 961 tgagaacccc ttcgcccagg gggccctgaa gtcagaggac tgcttcatcc tggaccacgg
1021 caaagatggg aaaatctttg tctggaaagg caagcaggca aacacggagg agaggaaggc
1081 tgccctcaaa acagcctctg acttcatcac caagatggac taccccaagc agactcaggt
```

FIG. 10 A-31

```
1141 ctcggtcctt cctgagggcg gtgagacccc actgttcaag cagttcttca agaactggcg
1201 ggacccagac cagacagatg gcctgggctt gtcctacctt tccagccata tcgccaacgt
1261 ggagcgggtg cccttcgacg ccgccaccct gcacacctcc actgccatgg ccgcccagca
1321 cggcatggat gacgatggca caggccagaa acagatctgg agaatcgaag gttccaacaa
1381 ggtgcccgtg gaccctgcca catatggaca gttctatgga ggcgacagct acatcattct
1441 gtacaactac cgccatggtg gccgccaggg gcagataatc tataactggc agggtgccca
1501 gtctacccag gatgaggtcg ctgcatctgc catcctgact gctcagctgg atgaggagct
1561 gggaggtacc cctgtccaga gccgtgtggt ccaaggcaag gagcccgccc acctcatgag
1621 cctgtttggt gggaagccca tgatcatcta caagggcggc acctcccgcg agggcgggca
1681 gacagcccct gccagcaccc gcctcttcca ggtccgcgcc aacagcgctg gagccacccg
1741 ggctgttgag gtattgccta aggctggtgc actgaactcc aacgatgcct ttgttctgaa
1801 aaccccctca gccgcctacc tgtgggtggg tacaggagcc agcgaggcag agaagacggg
1861 ggcccaggag ctgctcaggg tgctgcgggc ccaacctgtg caggtggcag aaggcagcga
1921 gccagatggc ttctgggagg ccctgggcgg gaaggctgcc taccgcacat ccccacggct
1981 gaaggacaag aagatggatg cccatcctcc tcgcctcttt gcctgctcca acaagattgg
2041 acgttttgtg atcgaagagg ttcctggtga gctcatgcag gaagacctgg caacggatga
2101 cgtcatgctt ctggacacct gggaccaggt ctttgtctgg gttggaaagg attctcaaga
2161 agaagaaaag acagaagcct tgacttctgc taagcggtac atcgagacgg acccagccaa
2221 tcgggatcgg cggacgccca tcaccgtggt gaagcaaggc tttgagcctc cctcctttgt
2281 gggctggttc cttggctggg atgatgatta ctggtctgtg gaccccttgg acagggccat
2341 ggctgagctg gctgcctgag gaggggcagg gcccacccat gtcaccggtc agtgcctttt
2401 ggaactgtcc ttccctcaaa gaggccttag agcgagcaga gcagctctgc tatgagtgtg
2461 tgtgtgtgtg tgtgttgttt cttttttttt tttttacagt atccaaaaat agccctgcaa
2521 aaattcagag tccttgcaaa attgtctaaa atgtcagtgt ttgggaaatt aaatccaata
2581 aaaacatttt gaagtgtg
```

SEQ ID NO:35

```
gaagtaaaagattttattgttctatagacacttctgaaaagagatctaattgagaaaat
atacaaagcatttaagagtttcatccccagagactgactgaaggcgttacagccctcctc
tccaaggctcagggctgagaacggttagcatatcgaatgatcagtaaaaacatgcaaaag
tgagaaggaaagggaaaaaggtgcattcccctaagctgagggggatggaatttcagaaca
gaggangcagggtggacaagtaccaaggtggctctccctttccctctgtgtnatctttca
aaaccanttccaagcntggatnaaagcaa
```

SEQ ID NO:36

```
  1 caaagtctga gccccgctcc gctgatgcct gtctgcagaa tccgcaccaa ccagcaccat
 61 gcccatgact ctggggtact gggacatccg tgggctggcc cacgccatcc gcttgctcct
121 ggaatacaca gactcaagct atgtggaaaa gaagtacacg ctgggggacg ctcctgacta
181 tgacagaagc cagtggctga atgaaaaatt caagctgggc ctggactttc ccaatctgcc
241 ctacttgatt gatggggctc acaagatcac ccagagcaat gccatcctgc gctacattgc
301 ccgcaagcac aacctgtgtg gggagacaga agaggagaag attcgtgtgg acattttgga
361 gaaccaggtt atggataacc acatggagct ggtcagactg tgctatgacc cagattttga
421 gaaactgaag ccaaaatact tggaggaact ccctgaaaag ctaaagctct actcagagtt
481 tctggggaag cggccatggt ttgcaggaga caagatcacc tttgtggatt tccttgccta
541 tgatgtcctt gacatgaagc gtatatttga gcccaagtgc ttggacgcct tcctaaactt
601 gaaggacttc atctcccgct ttgagggttt gaagaagatc tctgcctaca tgaagtccag
661 ccaattcctc cgaggtcttt tgtttggaaa gtcagctaca tggaacagca aatagggccc
721 agtgatgcca gaagatggga gggaggagcc aaccttgctg cctgcgaccc tggaggacag
781 cctgactccc tggacctgcc ttcttccttt ttccttcttt ctactctctt ctcttcccca
841 aggcctcatt ggcttccttt cttctaacat catccctccc cgcatcgagg ctctttaaag
```

FIG. 10 A-32

```
 901 cttcagctcc ccactgtcct ccatcaaagt ccccctccta acgtcttcct ttccctgcac
 961 taacgccaac ctgactgctt ttcctgtcag tgcttttctc ttctttgaga agccagactg
1021 atctctgagc tccctagcac tgtcctcaaa gaccatctgt atgccctgct ccctttgctg
1081 ggtccctacc ccagctccgt gtgatgccca gtaaagcctg aaccatgcct gccatgtctt
1141 gtcttattcc ctgaggctcc cttgactcag gactgtgctc gaattgtggg tggtttttg
1201 tcttctgttg tccacagcca gagcttagtg gatgggtgtg tgtgtgtgtg tgttggggt
1261 ggtgatcagg caggttcata aatttccttg gtcatttctg ccctctagcc acatccctct
1321 gttcctcact gtggggatta ctacagaaag gtgctctgtg ccaagttcct cactcattcg
1381 cgctcctgta ggccgtctag aactggcatg gttcaaagag gggctaggct gatggggaag
1441 ggggctgagc agctcccagg cagactgcct tctttcaccc tgtcctgata gacttccctg
1501 atctagatat ccttcgtcat gacacttctc aataaaacgt atcccaccgt attgt
```

```
SEQ ID NO:37
   1 ggttgagaat gcttgcacca agcttgtcca ggcagctcag atgcttcagt cagaccctta
  61 ctcagtgcct gctcgagatt atctaattga tgggtcaagg ggcatcctct ctggaacatc
 121 agacctgctc cttaccttcg atgaggctga ggtccgtaaa attattagag tttgcaaagg
 181 aattttggaa tatcttacag tggcagaggt ggtggagact atggaagatt tggtcactta
 241 cacaaagaat cttgggccag gaatgactaa gatggccaag atgattgacg agagacagca
 301 ggagctcact caccaggagc accgagtgat gttggtgaac tcgatgaaca ccgtgaaaga
 361 gttgctgcca gttctcattt cagctatgaa gatttttgta acaactaaaa actcaaaaaa
 421 ccaaggcata gaggaagctt taaaaaatcg caattttact gtagaaaaaa tgagtgctga
 481 aattaatgag ataattcgtg tgttacaact cacctcttgg gatgaagatg cctgggccag
 541 caaggacact gaagccatga agagagcatt ggcctccata gactccaaac tgaaccaggc
 601 caaaggttgg ctccgtgacc ctagtgcctc cccaggggat gctggtgagc aggccatcag
 661 acagatctta gatgaagctg gaaaagttgg tgaactctgt gcaggcaaag aacgcaggga
 721 gattctggga acttgcaaaa tgctagggca gatgactgat caagtggctg acctccgtgc
 781 cagnnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnnnnnn nnnnnnnnnn nnnaggctcg
1141 agccttggcc aaacaggtgg ccacggccct gcagaacctg cagaccaaaa ccaaccgggc
1201 tgtggccaac agcagaccgg ccaaagcagc tgtacacctt gagggcaaga ttgagcaagc
1261 acagcggtgg attgataatc ccacagtgga tgaccgtgga gtcggtcagg ctgccatccg
1321 ggggcttgtg gccgaagggc atcgtctggc taatgttatg atggggcctt atcggcaaga
1381 tcttctcgcc aagtgtgacc gagtggacca gctgacagcc cagctggctg acctggctgc
1441 cagaggggaa ggggagagtc ctcaggcacg agcacttgca tctcagctcc aagactcctt
1501 aaaggatcta aaagctcgga tgcaggaggc catgactcag gaagtgtcag atgttttcag
1561 cgataccaca actcccatca agctgttggc agtggcagcc acggcgcctc ctgatgcgcc
1621 taacagggaa gaggtatttg atgagagggc agctaacttt gaaaaccatt caggaaagct
1681 tggtgctacg gccgagaagg cggctgcggt tggtactgct aataaatcaa cagtggaagg
1741 cattcaggcc tcagtgaaga cggcccgaga actcacaccc caggtggtct cggctgctcg
1801 tatcttactt aggaaccctg gaaatcaagc tgcttatgaa cattttgaga ccatgaagaa
1861 ccagtggatc gataatgttg aaaaaatgac agggctggtg gacgaagcca ttgataccaa
1921 atctctgttg gatgcttcag aagaagcaat taaaaaagac ctggacaagt gcaaggtagc
1981 tatggccaac attcagcctc agatgctggt tgctggggca accagtattg ctcgtcgggc
2041 caaccggatc ctgctggtgg ctaagaggga ggtggagaat tccgaggatc ccaagttccg
2101 tgaggctgtg aaagctgcct ctgatgaatt gagcaaaacc atctccccga tggtgatgga
2161 tgcaaaagct gtggctggaa acatttccga ccctggactg caaaagagct tcctggactc
```

FIG. 10 A-33

2221 aggatatcgg atcctgggag ctgtggccaa ggtcagagaa gccttccaac ctcaggagcc
2281 tgacttcccg ccgcctccac cagaccttga acaactccga ctaacagatg agcttgctcc
2341 tcccaaacca cctctgcctg aaggtgaggt ccctccacct aggcctccac caccagagga
2401 aaaggatgaa gagttccctg agcagaaggc cggggaggtg attaaccagc caatgatgat
2461 ggctgccaga cagctccatg atgaagctcg caaatggtcc agcaagggca atgacatcat
2521 tgcagcagcc aagcgcatgg ctctgctgat ggctgagatg tctcggctgg taagaggggg
2581 cagtggtacc aagcgggcac tcattcagtg tgccaaggac atcgccaagg cctcagatga
2641 ggtgactcgg ttggccaagg aggttgccaa gcagtgcaca gataaacgga ttagaaccaa
2701 cctcttacag gtatgtgagc gaatcccaac cataagcacc cagctcaaaa tcctgtccac
2761 agtgaaggcc accatgctgg gccggaccaa catcagtgat gaggagtctg agcaggccac
2821 agagatgctg gttcacaatg cccagaacct catgcagtct gtgaaggaga ctgtgcggga
2881 agctgaagct gcttcaatca aaattcgaac agatgctgga tttacactgc gctgggttag
2941 aaagactccc tggtaccagt aggcacctgg ctgagcctgg ctggcacaga aacctctact
3001 aaaaagaagg aaaatgatct gagtcccagg agctgcccag agttgctggg agctgaaaaa
3061 tcacatcctg gcctggcaca tcagaaagga atgggggcct cttcaaatta gaagacattt
3121 atactctttt ttcatggaca ctttgaaatg tgtttctgta taaagcctgt attctcaaac
3181 acagttacac ttgtgcaccc tctatcccaa taggcagact gggtttctag cccatggact
3241 tcacataagc tcagaatcca agtgaacact agccagacac tctgctctgc ccttgttccc
3301 taggggacac ttccctctgt ttctctttcc ttggctccca ttcactcttc cagaatccca
3361 agacccaggg cccaggcaaa tcagttacta agaagaaaat tgctgtgcct cccaaaattg
3421 ttttgagctt tccatgttgc tgccaaccat accttccttc cctgggctgt gctacctggg
3481 tccttttcag aagtgagctt tgctgctaca ggggaaggtg gcctctgtgg agccccagca
3541 tatgggggcc tggattcatt tcctgccctt cctcagttta atccttctag tttcccacaa
3601 tataaaactg tacttcactg tcaggaagaa atcacagaat catatgattc tgcttttacc
3661 atgcccctga gcaatgtctg tgctagggaa acttcccgtc ccatatcctg cctcagcccg
3721 ccaaggtagc catcccatga acacactgtg tcctggtgct ctctgccact ggaagggcag
3781 agtagccagg gtgtggccct gccatcttcc cagcagggcc actcccggca ctccatgctt
3841 agtcactgcc tgcagaggtc tgtgctgagg ccttatcatt cattcttagc tcttaattgt
3901 tcattttgag ctgaaatgct gcattttaat tttaaccaaa acatgtctcc tatcctggtt
3961 tttgtagcct tcctccacat cctttctaaa caagatttta aagacatgta ggtgtttgtt
4021 catctgtaac tctaaaagat ccttttttaaa ttcagtccta agaaagagga gtgcttgtcc
4081 cctaagagtg tttaatggca aggcagccct gtctgaagga cacttcctgc ctaagggaga
4141 gtggtatttg cagactagaa ttctagtgct gctgaagatg aatcaatggg aaatactact
4201 cctgtaattc ctacctccct gcaaccaact acaaccaagc tctctgcatc tactcccaag
4261 tatggggttc aagagagtaa tgggtttcat atttcttatc accacagtaa gttcctacta
4321 ggcaaaatga gagggcagtg tttccttttt ggtacttatt actgctaagt atttcccagc
4381 acatgaaacc ttattttttc ccaaagccag aaccagatga gtaaaggagt aagaaccttg
4441 cctgaacatc cttccttccc acccatcgct gtgtgttagt tcccaacatc gaatgtgtac
4501 aacttaagtt ggtcctttac actcaggctt tcactatttc ctttataatg aggatgatta
4561 ttttcaaggc cctcagcata tttgtatagt tgcttgcctg atataaatgc aatattaatg
4621 cctttaaagt atgaatctat gccaaagatc acttgttgtt ttactaaaga aagattactt
4681 agaggaaata agaaaaatca tgtttgctct cccggttctt ccagtggttt gagacactgg
4741 tttacacttt atgccggatg tgcttttctc caatatcagt gctcgagaca cagtgaagca
4801 aattaaaaaa aa SEQ ID NO:38
1 atatccagcc tttgccgaat acatcctatc tgccacacat ccagcgtgag gtccctccag
61 ctacaaggtg ggcaccatgg cggagaagtt tgactgccac tactgcaggg atcccttgca
121 ggggaagaag tatgtgcaaa aggatggcca ccactgctgc ctgaaatgct ttgacaagtt
181 ctgtgccaac acctgtgtgg aatgccgcaa gcccatcggt gcggactcca aggaggtgca

FIG. 10 A-34

```
 241 ctataagaac cgcttctggc atgacacctg cttccgctgt gccaagtgcc ttcacccctt
 301 ggccaatgag acctttgtgg ccaaggacaa caagatcctg tgcaacaagt gcaccactcg
 361 ggaggactcc cccaagtgca aggggtgctt caaggccatt gtggcaggag atcaaaacgt
 421 ggagtacaag ggaccgtct ggcacaaaga ctgcttcacc tgtagtaact gcaagcaagt
 481 catcgggact ggaagcttct tccctaaagg ggaggacttc tactgcgtga cttgccatga
 541 gaccaagttt gccaagcatt gcgtgaagtg caacaaggcc atcacatctg gaggaatcac
 601 ttaccaggat cagccctggc atgccgattg ctttgtgtgt gttacctgct ctaagaagct
 661 ggctgggcag cgtttcaccg ctgtggagga ccagtattac tgcgtggatt gctacaagaa
 721 ctttgtggcc aagaagtgtg ctggatgcaa gaaccccatc actgggaaaa ggactgtgtc
 781 aagagtgagc cacccagtct ctaaagctag gaagccccca gtgtgccacg ggaaacgctt
 841 gcctctcacc ctgtttccca gcgccaacct ccggggcagg catccgggtg gagagaggac
 901 ttgtccctcg tgggtggtgg ttctttatag aaaaaatcga agcttagcag ctcctcgagg
 961 cccgggtttg gtaaaggctc cagtgtggtg gcctatgaag gacaatcctg gcacgactac
1021 tgcttccact gcaaaaaatg ctccgtgaat ctggccaaca agcgctttgt tttccaccag
1081 gagcaagtgt attgtcccga ctgtgccaaa aagctgtaaa ctgacagggg ctcctgtcct
1141 gtaaaatggc atttgaatct cgttctttgt gtccttactt tctgccctat accatcaata
1201 ggggaagagt ggtccttccc ttctttaaag ttctccttcc gtcttttctc ccattttaca
1261 gtattactca aataagggca cacagtgatc atattagcat ttagcaaaaa gcaaccctgc
1321 agcaaagtga atttctgtcc ggctgcaatt taaaaatgaa aacttaggta gattgactct
1381 tctgcatgtt tctcatagag cagaaaagtg ctaatcattt agccacttag tgatgtaagc
1441 aagaagcata ggagataaaa cccccactga gatgcctctc atgcctcagc tgggacccac
1501 cgtgtagaca cacgacatgc aagagttgca gcggctgctc caactcactg ctcaccctct
1561 tctgtgagca ggaaaagaac cctactgaca tgcatggttt aacttcctca tcagaactct
1621 gcccttcctt ctgttctttt gtgctttcaa ataactaaca cgaacttcca gaaaattaac
1681 atttgaactt agctgtaatt ctaaactgac ctttccccgt actaacgttt ggtttccccg
1741 tgtggcatgt tttctgagcg ttcctacttt aaagcatgga acatgcaggt gatttgggaa
1801 gtgtagaaag acctgagaaa acgagcctgt ttcagaggaa catcgtcaca acgaatactt
1861 ctggaagctt aacaaaacta accctgctgt ccttttttatt gtttttaatt aatatttttg
1921 ttttaattga tagcaaaata gtttatgggt ttggaaactt gcatgaaaat attttagccc
1981 cctcagatgt tcctgcagtg ctgaaattca tcctacggaa gtaaccgcaa aactctag
```

SEQ ID NO:39

```
   1 tgccgcccta caccgtggtc tatttcccag ttcgagnnnn nnnnnnnnnn nnnnnnnnnn
  61 nnnnnnnnnn nnnnnnnngc tgctggcaga tcagggccag agctggaagg aggaggtggt
 121 gaccgtggag acgtggcagg agggctcact caaagcctcc tgcctatacg ggcagctccc
 181 caagttccag gacggagacc tcaccctgta ccagtccaat accatcctgc gtcacctggn
 241 nnnnnnnnnn nnnnnnnnnn nnnnnnnngg ctctatggga aggaccagca ggaggcagcc
 301 ctggtggaca tggtgaatga cggcgtggag gacctccgct gcaaatacat ctccctcatc
 361 tacaccaact atgaggcggg caaggatgac tatgtgaagg cactgcccgg gcaactgaag
 421 ccttttgaga ccctgctgtc ccagaaccag ggaggcaaga ccttcattgt gggagaccag
 481 atctccttcg ctgactacaa cctgctggac ttgctgctga tccatgaggt cctagcccct
 541 ggctgcctgg atgcgttccc cctgctctca gcatatgtgg ggcgcctcag tgcccggccc
 601 aagctcaagg ccttcctggc ctcccctgag tacgtgaacc tccccatcaa tggcaacggg
 661 aaacagtgag ggttgggggg actctgagcg g
```

SEQ ID NO:40

```
   1 cttttcacac tggccttaaa gaggatatat tagaagttga agtaggaagg gagccagaga
  61 ggccgatggc gcaaaggtac gacgatctac cccattacgg gggcatggat ggagtaggca
 121 tcccctccac gatgtatggg gacccgcatg cagccaggtc catgcagccg gtccaccacc
 181 tgaaccacgg gcctcctctg cactcgcatc agtacccgca cacagctcat accaacgcca
```

FIG. 10 A-35

```
 241 tggcccccag catgggctcc tctgtcaatg acgctttaaa gagagataaa gatgccattt
 301 atggacaccc cctcttccct ctcttagcac tgatttttga gaaatgtgaa ttagctactt
 361 gtaccccccg cgagccgggg gtggcgggcg gggacgtctg ctcgtcagag tcattcaatg
 421 aagatatagc cgtgttcgcc aaacagattc gcgcagaaaa acctctattt tcttctaatc
 481 cagaactgga taacttgatg attcaagcca tacaagtatt aaggtttcat ctattggaat
 541 tagagaaggt acacgaatta tgtgacaatt tctgccaccg gtatattagc tgtttgaaag
 601 ggaaaatgcc tatcgatttg gtgatagacg atagagaagg aggatcaaaa tcagacagtg
 661 aagatataac aagatcagca aatctaactg accagccctc ttggaacaga gatcatgatg
 721 acacggcatc tactcgttca ggaggaaccc caggcccttc cagcggtggc cacacgtcac
 781 acagtgggga caacagcann nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnncacccctt
 961 acccttctga agaacagaaa aagcagttgg cacaagacac gggactcacc atccttcaag
1021 tgaacaattg gtttattaat gcccggagaa gaatagtgca gcccatgata gaccagtcca
1081 accgagcagt aagtcaagga acaccttata atcctgatgg acagcccatg ggaggtttcg
1141 taatggacgg tcagcaacat atgggaatta gagcaccagg acctatgagt ggaatgggca
1201 tgaatatggg catggagggg cagtggcact acatgtaacc ttcatctagt taaccaatcg
1261 caaagcaagg gggaaggctg caaagtatgc caggggagta tgtagcccgg ggtggtccaa
1321 tgggtgtgag tatgggacag ccaagttata cccaacccca gatgcccccc catcctgctc
1381 agctgcgtca tgggcccccc atgcatacgt acattcctgg acaccctcac cacccaacag
1441 tgatgatgca tggaggaccg ccccaccctg gaatgccaat gtcagcatca agccccacag
1501 ttcttaatac aggagaccca acaatgagtg gacaagtcat ggacattcat gctcagtagc
1561 ttaagggaat atgcattgtc tgcaatggtg actgatttca aatcatgttt tttctgcaat
1621 gactgtggag ttccattctt ggcatctact ctggaccaag gagcatccct aattcttcat
1681 agggaccttt aaaaagcagg aaataccaac tgaagtcaat ttgggggaca tgctaaataa
1741 ctatataaga cattaagaga acaaagagtg aaatattgta aatgctatta tactgttatc
1801 catattacgt tgtttcttat agatttttta aaaaaaatgt gaaatttttc cacactatgt
1861 gtgttgtttc catagctctt cacttcctcc agaagcctcc ttacattaaa aagccttaca
1921 gttatcctgc aagggacagg aaggtctgat ttgcaggatt tttagagcat taaaataact
1981 atcaggcaga agaatctttc ttctcgccta ggatttcagc catgcgcgcg ctctctctct
2041 ttctctctct tttcctctct ctccctcttt ctagcctggg gcttgaattt gcatgtctaa
2101 ttcatttact caccatattt gaattggcct gaacagatgt aaatcgggaa ggatgggaaa
2161 aactgcagtc atcaacaatg attaatcagc tgttgcaggc agtgtcttaa ggagactggt
2221 aggaggaggc atggaaacca aaaggccgtg tgtttagaag cctaattgtc acatcaagca
2281 tcattgtccc catgcaacaa ccaccacctt atacatcact tcctgtttta agcagctcta
2341 aaacatagac tgaagattta tttttaatat gttgacttta tttctgagca aagcatcggt
2401 catgtgtgta ttttttcata gtcccacctt ggagcattta tgtagacatt gtaaataaat
2461 tttgtgcaaa aaggactgga aaaatgaact gtattattgc aatttttttt t
```

SEQ ID NO:41

```
   1 ctcaataagc caaccatgtc tttcaaggat tacatccaag agaggagtga cccagtggag
  61 caaggcaaac cagttatacc tgcagctgtg ctggccggct tcacaggaag tggacctatt
 121 cagctgtggc agtttctcct ggagctgcta tcagacaaat cctgccagtc attcatcagc
 181 tggactggag acggatggga gtttaagctc gccgaccccg atgaggtggc ccgccggtgg
 241 ggaaagagga aaaataagcc caagatgaac tacgagaagc tgagccgggg cttacgctac
 301 tattacgaca agaacatcat ccacaagacg tcggggaagc gctacgtgta ccgcttcgtg
 361 tgcgacctcc agaacttgct ggggttcacg cccgaggaac tgcacgccat cctgggcgtc
 421 cagcccgaca cggaggactg a
```

SEQ ID NO:42

```
   1 ggacgacaag gcgttcacca aggagctgga ccagtgggtc gagcagctga acgagtgtaa
```

FIG. 10 A-36

```
  61 gcagctgaac gagaaccaag tgcggacgct gtgcgagaag gcaaaggaaa ttttaacaaa
 121 agaatcaaat gtgcaagagg ttcgttgccc tgttactgtc tgtggagatg tgcatggtca
 181 atttcatgat cttatggaac tctttagaat tggtggaaaa tcaccggata caaactactt
 241 attcatgggt gactatgtag acagaggata ttattcagtg gagactgtga ctcttcttgt
 301 agcattaaag gtgcgttatc cagaacgcat tacaatattg agaggaaatc acgaaagccg
 361 acaaattacc caagtatatg gcttttatga tgaatgtctg cgaaagtatg ggaatgccaa
 421 cgtttggaaa tattttacag atctctttga ttatcttcca cttacagctt tagtagatgg
 481 acagatattc tgcctccatg gtggcctctc tccatccata gacacactgg atcatataag
 541 agccctggat cgtttacagg aagttccaca tgagggccca atgtgtgatc tgttatggtc
 601 agatccagat gatcgtggtg gatggggtat ttcaccacgt ggtgctggct acacatttgg
 661 acaagacatt tctgaaacct ttaaccatgc caatggtctc acactggttt ctcgtgccca
 721 ccagcttgta atggagggat acaattggtg tcatgatcgg aatgtggtta ccattttcag
 781 tgcacccaat tactgttatc gttgtgggaa ccaggctgct atcatggaat tagatgacac
 841 tttaaaatat tccttccttc aatttgaccc agcgcctcgt cgtggtgagc ctcatgttac
 901 acggcgcacc ccagactact tcctataaat ttctcctggg aaacctgcct ttgtatgtgg
 961 aagtatacct ggctttttaa aatatatgta tttaaaaaca aaaagcaaca gtaatctatg
1021 tgtttctgta acaaattggg atctgtcttg gcattaaacc acatcatgga ccaaatgtgc
1081 catactaatg atgagcattt agcacaattt gagactgaaa tttagtacac tatgttctag
1141 gtcagtctaa cagtttgcct gctgtattta tagtaaccat tttcctttgg actgttcaag
1201 caaaaaaggt aactaactgc ttcatctcct tttgcgctta tttggaaatt ttagttatag
1261 tgtttaactg gcatggatta atagagttgg agttttattt ttaagaaaaa ttcacaagct
1321 aacttccact aatccattat cctttatttt attgaaatgt ataattaact taactgaaga
1381 aaaggttctt cttgggagta tgttgtcata acatttaaag agatttccct tcatttaaac
1441 taaattactg ttttatgttg atctgcatat ttctgtatat ttgtcatgac agtgcttgca
1501 tcctatttgg tgtactcagc aaataaactt t
```

SEQ ID NO:43

```
   1 cctgtgagca ccacgtcaac ggctcccggc ccccatgcac gggggaggga gatacccccca
  61 agtgtagcaa gatctgtgag cctggctaca gcccgaccta caaacaggac aagcactacg
 121 gatacaattc ctacagcgtc tccaatagcg agaaggacat catggccgag atctacaaaa
 181 acggccccgt ggagggagct ttctctgtgt attcggactt cctgctctac aagtcaggag
 241 tgtaccaaca cgtcaccgga gagatgatgg gtggccatgc catccgcatc ctgggctggg
 301 gagtggagaa tggcacaccc tactggctgg ttgccaactc ctggaacact gactggggtg
 361 acaatggctt ctttaaaata ctcagaggac aggatcactg tggaatcgaa tcagaagtgg
 421 tggctggaat tccacgcacc gatcagtact gggaaaagat ctaatctgcc gtgggcctgt
 481 cgtgccagtc ctgggggcga gatgggggta gaaatgcatt ttattcttta agttcacgta
 541 agatacaagt ttcagacagg gtctgaagga ctggattggc caaacatcag acctgtcttc
 601 caaggagacc aagtcctggc tacatcccag cctgtggtta cagtgcagac aggccatgtg
 661 agccaccgct gccagcacag agcgtccttc cccctgtaga ctagtgccgt agggagtacc
 721 tgttgcccca gctgactgtg gccccctccg tgatccatcc atctccaggg agcaagacag
 781 agacccagga atggaaagcg gagttcctaa caggatgaaa gttcccccat cagttccccc
 841 agtacctcca agcaagtagc tttccacatt tgtcacagaa atcagaggag agatggtgtt
 901 gggagccctt tggagaacgc cagtctccca ggccccctgc atctatcgag tttgcaatgt
 961 cacaacctct ctgatcttgt gctcagcatg attctttaat agaagtttta ttttttcgtg
1021 cactctgcta atcatgtggg tgagccagtg gaacagcggg agacctgtgc tagttttaca
1081 gattgcctcc ttatgacgcg gctcaaaagg aaaccaagtg gtcaggagtt gtttctgacc
1141 cactgatctc tactaccaca aggagaatag tttaggagaa accagctttt actgtttttg
1201 aaaaattaca gcttcaccct gtcaagttaa caaggaatgc ctgtgccaat aaaaggtttc
```

SEQ ID NO:44

```
   1 gtgtcccata gtgtttccaa acttggaaag ggcgggggag ggcgggagga tgcggagggc
```

FIG. 10 A-37

61 ggaggtatgc agacaacgag tcagagtttc cccttgaaag cctcaaaagt gtccacgtcc
121 tcaaaaagaa tggaaccaat ttaagaagcc agccccgtgg ccacgtccct tcccccattc
181 gctccctcct ctgcgccccc gcaggctcct cccagctgtg gctgcccggg cccccagccc
241 cagccctccc attggtggag gccctttgg aggcacccta gggccaggga aacttttgcc
301 gtataaatag ggcagatccg ggctttatta ttttagcacc acggcagcag gaggtttcgg
361 ctaagttgga ggtactggcc acgactgcat gcccgcgccc gccaggtgat acctccgccg
421 gtgacccagg ggctctgcga cacaaggagt ctgcatgtct aagtgctaga catgctcagc
481 tttgtggata cgcggacttt gttgctgctt gcagtaacct tatgcctagc aacatgccaa
541 tctttacaag aggaaactgt aagaaagggc ccagccggag atagaggacc acgtggagaa
601 aggggtccac caggcccccc aggcagagat ggtgaagatg gtcccacagg ccctcctggt
661 ccacctggtc ctcctggccc ccctggtctc ggtgggaact ttgctgctca gtatgatgga
721 aaaggagttg gacttggccc tggaccaatg ggcttaatgg gacctagagg cccacctggt
781 gcagctggag ccccaggccc tcaaggtttc caaggacctg ctggtgagcc tggtgaacct
841 ggtcaaactg gtcctgcagg tgctcgtggt ccagctggcc ctcctggcaa ggctggtgaa
901 gatggtcacc ctggaaaacc cggacgacct ggtgagagag gagttgttgg accacagggt
961 gctcgtggtt tccctggaac tcctggactt cctggcttca aaggcattag gggacacaat
1021 ggtctggatg gattgaaggg acagcccggt gctcctggtg tgaagggtga acctggtgcc
1081 cctggtgaaa atggaactcc aggtcaaaca ggagcccgtg ggcttcctgg tgagagagga
1141 cgtgttggtg cccctggccc agctggtgcc cgtggcagtg atggaagtgt gggtcccgtg
1201 ggtcctgctn nnnnnnnnng gtctgctggc cctccaggct tcccaggtgc ccctggcccc
1261 aagggtgaaa ttggagctat tggtaacgct ggtcctgctg gtcccgccgg tccccgtggt
1321 gaagtgggtc ttccaggcct ctccggcccc gttggacctc ctggtaatcc tggagcaaac
1381 ggccttactg gtgccaaggg tgctgctggc cttcccggcg ttgctggggc tcccggcctc
1441 cctggacccc gcggtattcc tggccctgtt ggtgctgccg gtgctactgg tgccagagga
1501 cttgttggtg agcctggtcc agctggctcc aaaggagaga gcggtaacaa gggtgagccc
1561 ggctctgctg ggccccaagg tcctcctggt cccagtggtg aagaaggaaa gagaggccct
1621 aatggggaag ctggatctgc cggccctcca ggacctcctg ggctgagagg tagtcctggt
1681 tctcgtggtc ttcctggagc tgatggcaga gctggcgtca tgggccctcc tggtagtcgt
1741 ggtgcaagtg gccctgctgg agtccgagga cctaatggag atgctggtcg ccctggggag
1801 cctggtctca tgggacccag aggtcttcct ggttcccctg gaaatatcgg ccccgctgga
1861 aaagaaggtc ctgtcggcct ccctggcatc gacggcaggc ctggcccaat tggccccgtt
1921 ggagcaagag gagagcctgg caacattgga ttccctggac ccaaaggccc cactggtgac
1981 cctggcaaaa acggtgataa aggtcatgct ggtcttgctg gtgctcgggg tgctccaggt
2041 cctgatggaa acaatggtgc tcagggacct cctggaccac agggtgttca aggtggaaaa
2101 ggtgaacagg gtcccgctgg tcctccaggc ttccagggtc tgcctggccc ctcaggtccc
2161 gctggtgaag ttggcaaacc aggagaaagg ggtctccatg gtgagtttgg tctccctggt
2221 cctgctggtc caagagggga acgcggtccc ccaggtgaga gtggtgctgc cggtcctact
2281 ggtcctattg gaagccgagg tccttctgga cccccagggc ctgatggaaa caagggtgaa
2341 cctggtgtgg ttggtgctgt gggcactgct ggtccatctg gtcctagtgg actcccagga
2401 gagaggggtg ctgctggcat acctggaggc aagggagaaa agggtgaacc tggtctcaga
2461 ggtgaaattg gtaaccctgg cagagatggt gctcgtggtg ctcatggtgc tgtaggtgcc
2521 cctggtcctg ctggagccac aggtgaccgg ggcgaagctg gggctgctgg tcctgctggt
2581 cctgctggtc ctcggggaag ccctggtgaa cgtggcgagg tcggtcctgc tggccccaac
2641 ggatttgctg gtccggctgg tgctgctggt caaccgggtg ctaaaggaga aagaggaggc
2701 aaagggccta agggtgaaaa cggtgttgtt ggtcccacag gccccgttgg agctgctggc
2761 ccagctggtc caaatggtcc ccccggtcct gctggaagtc gtggtgatgg aggcccccct
2821 ggtatgactg gtttccctgg tgctgctgga cggactggtc ccccaggacc ctctggtatt
2881 tctggccctc ctggtccccc tggtcctgct gggaaagaag ggcttcgtgg tcctcgtggt
2941 gaccaaggtc cagttggccg aactggagaa gtaggtgcag ttggtccccc tggcttcgct
3001 ggtgagaagg gtccctctgg agaggctggt actgctggac ctcctggcac tccaggtcct
3061 cagggtcttc ttggtgctcc tggtattctg ggtctccctg gctcgagagg tgaacgtggt

FIG. 10 A-38

```
3121 ctacctggtg ttgctggtgc tgtgggtgaa cctggtcctc ttggcattgc cggccctcct
3181 ggggcccgtg gtcctcctgg tgctgtgggt agtcctggag tcaacggtgc tcctggtgaa
3241 gctggtcgtg atggcaaccc tgggaacgat ggtcccccag gtcgcgatgg tcaacccgga
3301 cacaagggag agcgcggtta ccctggcaat attggtcccg ttggtgctgc aggtgcacct
3361 ggtcctcatg gccccgtggg tcctgctggc aaacatggaa accgtggtga aactggtcct
3421 tctggtcctg ttggtcctgc tggtgctgtt ggcccaagag gtcctagtgg cccacaaggc
3481 attcgtggcg ataagggaga gcccggtgaa aaggggccca gaggtcttcc tggcttcaag
3541 ggacacaatg gattgcaagg tctgcctggt atcgctggtc accatggtga tcaaggtgct
3601 cctggctccg tgggtcctgc tggtcctagg ggccctgctg gtccttctgg ccctgctgga
3661 aaagatggtc gcactggaca tcctggtacg gttggacctg ctggcattcg aggccctcag
3721 ggtcaccaag gccctgctgg ccccccctggt ccccctggcc ctcctggacc tccaggtgta
3781 agcggtggtg gttatgactt tggttacgat ggagacttct acagggctga ccagcctcgc
3841 tcagcacctt ctctcagacc caaggactat gaagttgatg ctactctgaa gtctctcaac
3901 aaccagattg agacccttct tactcctgaa ggctctagaa agaacccagc tcgcacatgc
3961 cgtgacttga gactcagcca cccagagtgg agcagtggtt actactggat tgaccccaac
4021 caaggatgca ctatggaagc catcaaagta tactgtgatt tccctaccgg cgaaacctgt
4081 atccgggccc aacctgaaaa catcccagcc aagaactggt ataggagctc caaggacaag
4141 aaacacgtct ggctaggaga aactatcaat gctggcagcc agtttgaata taatgttgaa
4201 ggagtgactt ccaaggaaat ggctacccaa cttgccttca tgcgcctgct ggccaactat
4261 gcctctcaga acatcaccta ccactgcaag aacagcattg catacatgga tgaggagact
4321 ggcaacctga aaaaggctgt cattctacag ggctctaatg atgttgaact tgttgctgag
4381 ggcaacagca ggttcactta cactgttctt gtagatggct gctctaaaaa gacaaatgaa
4441 tggggaaaga caatcattga atacaaaaca aataagccat cacgcctgcc cttccttgat
4501 attgcacctt tggacatcgg tggtgctgac catgaattct ttgtggacat tggcccagtc
4561 tgtttcaaat aaatgaactc aatctaaatt aaaaaagaaa gaaatttgaa aaaactttct
4621 ctttgccatt tcttcttctt cttttttaac tgaaagctga atccttccat ttcttctgca
4681 catctacttg cttaaattgt gggcaaaaga gaaaaagaag gattgatcag agcattgtgc
4741 aatacagttt cattaactcc ttcccccgct cccccaaaaa tttgaatttt tttttcaaca
4801 ctcttacacc tgttatggaa aatgtcaacc tttgtaagaa aaccaaaata aaaattgaaa
4861 aataaaaacc ataaacattt gcaccacttg tggcttttga atatcttcca cagagggaag
4921 tttaaaaccc aaacttccaa aggtttaaac tacctcaaaa cactttccca tgagtgtgat
4981 ccacattgtt aggtgctgac ctagacagag atgaactgag gtccttgttt tgttttgttc
5041 ataatacaaa ggtgctaatt aatagtattt cagatacttg aagaatgttg atggtgctag
5101 aagaatttga gaagaaatac tcctgtattg agttgtatcg tgtggtgtat tttttaaaaa
5161 atttgattta gcattcatat tttccatctt attcccaatt aaaagtatgc agattatttg
5221 cccaaagttg tcctcttctt cagattcagc atttgttctt tgccagtctc attttcatct
5281 tcttccatgg ttccacagaa gctttgtttc ttgggcaagc agaaaaatta aattgtacct
5341 attttgtata tgtgagatgt ttaaataaat tgtgaaaaaa atgaaataaa gcatgtttgg
5401 ttttccaaaa gaacatat
```

SEQ Id NO:45

```
  1 cagaccacag gaatacctaa tgcctttttt ctcttcctgt ctttgtccct cacactacag
 61 caggcccctc ccttccctct tcaacctcat cctccctccc cacaggccca gagaaccagt
121 tgggctttgt tctcctgcag gctatggttc atcatgcaaa tagctcctgt gtcagaaatg
181 ctttttggct tcaaataaca gaaaagctaa caccagcttt atcaataata atatcggtgg
241 tttacttaag gtgtccagag atggtggaga acaggattgg tttcctcctc aatgtcaagg
301 actcaaagac tctttctgtg gtagggccac atcctaaacc ctgtatcctg tgattattta
361 cctgacaggg caaaagagat tttgcagatg caattaaggt taaggacctt gacgtgggaa
421 gattgtgatt atttacctga cagggcaaaa gagattttgc agatgcaatt aaggttaagg
481 accttgacgt gggaagatta ttctggatta tctaggtggg cgcaatttga tcacatgggt
```

FIG. 10 A-39

```
 541 ccccagaagt ggagaacctt tcccacctgt agaaagccag agagctggca cctgagaagg
 601 acagaactgt cactgcagga tttgaagatg aaggggccca tgagccaagg aatgccagtg
 661 acctatagag gctaaaaaac agcaaggaaa tggactctcc ccagagcctc cagaggaatg
 721 cagccctgtt gatcacatga tcaccagatg gctgccccag agccaaatgt cgcttcctga
 781 gcaccatact caaaggcagg ggaagtggat ggagggcagg agctccattc ttgtttgcca
 841 ctctcctttt gtcaattggg aaaaaattcc agaaactctg ggagccctcc ccttacattt
 901 cctgggtcat ggggccagcc ctagctgctg gagggactga gaactgctgt tgagcagttt
 961 acctgacggc atctgccatg gcttggcagg aactctggct ttgggagaga gcagcagcaa
1021 ggtattcaag caccacctcc acccagcccc tcccacattt cactcaggac tgagtaaagg
1081 agacactcag atgctactca gatgctggct tcagctaagt attttgcaaa gcctctcgtg
1141 ttcttacaag tttgtggcta tcatgacaaa atggagcagc ctactatatc tacatataca
1201 actatggggg acctagtttt atctcattta ccacaatgtt ttcaatcatt ttttggatga
1261 cataatttt agcctcttct ctaaatgctt cctcaagctt tccttgcctt ccagccactg
1321 caaatgactt gcagtttccc ctacatggca cctgaccctt gtgcctccct ccctctgccc
1381 atggcccaga aagccctttc ctgtgccctc tggcttcctg ataaactcct atcatcttca
1441 agagccagtt cccatgccag ctctccccaa gtgctccact gaggcttccg taacacctct
1501 gttcccacat cgggttgact gtctttgttt tgtcattgct tgctctggct gtgtctccct
1561 cattagactg ggatgccttc aaggtaggga ccctatctgg gtcagcttgg caccccaaag
1621 cgtaccacag cacctgattc tgaggaggct ctcagtagat atctgttgag taaccagaat
1681 gtagggtggt cctgatggtt tctgacattg aatagaaaac agctccctat ttgatcttaa
1741 aataatcact ataacctgga catactgtac tagatgctgt ttttgtctga cttctactct
1801 gtcaatctct ttgcacctcc atttgttcat ctgtgaaatg aagaaaatgc tcatggagtt
1861 cagtgaagat taaatgaatg aatataggta gactgcctaa tctggcactt gccacgcagc
1921 tgacttcaat atagtagctc taatattatg gtccttgagg atcttactgt cttatggccc
1981 agaactgcat ttgattaaag aaggctcccc taaaaaaaga gtcatacata ttccatttgt
2041 cctttcagaa ggccgtgaag catttacact ctttaagaca aattcccatc caaaaatagt
2101 taagatttct aaaatatttt gatgctgaaa gaggtgtgct tcagttgggt ggcaaatttg
2161 cttctatgga agatttttaa tacaggttgt ttctatttta ctttttctgg ctgaaaggat
2221 tttacattta ttcaaagtca aaagggaaaa gaaatccaag aactacagaa gagcagttga
2281 agtgatttat gcttgatttc taaatgcaac ttatgtttat acataattta aaactcaaag
2341 aaagcatgct tatacaatca tgtgcaactt taaactttaa gaactctgga tgaatacatg
2401 gtggcaacag tccatgacac ctgaaaacat catttgtgga gtggcgtaga gttcagtgtt
2461 cgcagtcgca tattacaacc atgtttcaca cagccctgct cggtttgatt ttctccacgt
2521 ggttgataat tgtcttcagt tgctgctaag tgattttgca aatttc
```

SEQ ID NO:46

```
   1 gtccccgcgc cagagacgca gccgcgctcc caccacccac acccaccgcg ccctcgttcg
  61 cctcttctcc gggagccagt ccgcgccacc gccgccgccc aggccatcgc caccctccgc
 121 agccatgtcc accaggtccg tgtcctcgtc ctcctaccgc aggatgttcg gcggcccggg
 181 caccgcgagc cggccgagct ccagccggag ctacgtgact acgtccaccc gcacctacag
 241 cctgggcagc gcgctgcgcc ccagcaccag ccgcagcctc tacgcctcgt ccccgggcgg
 301 cgtgtatgcc acgcgctcct ctgccgtgcg cctgcggagc agcgtgcccg gggtgcggct
 361 cctgcaggac tcggtggact tctcgctggc cgacgccatc aacaccgagt tcaagaacac
 421 ccgcaccaac gagaaggtgg agctgcagga gctgaatgac cgcttcgcca actacatcga
 481 caaggtgcgc ttcctggagc agcagaataa gatcctgctg gccgagctcg agcagctcaa
 541 gggccaaggc aagtcgcgcc tgggggacct ctacgaggag gagatgcggg agctgcgccg
 601 gcaggtggac cagctaacca acgacaaagc ccgcgtcgag gtggagcgcg acaacctggc
 661 cgaggacatc atgcgcctcc gggagaaatt gcaggaggag atgcttcaga gagaggaagc
 721 cgaaaacacc ctgcaatctt tcagacagga tgttgacaat gcgtctctgg cacgtcttga
 781 ccttgaacgc aaagtggaat ctttgcaaga agagattgcc tttttgaaga aactccacga
 841 agaggaaatc caggagctgc aggctcagat tcaggaacag catgtccaaa tcgatgtgga
```

FIG. 10 A-40

```
 901 tgtttccaag cctgacctca cggctgccct gcgtgacgta cgtcagcaat atgaaagtgt
 961 ggctgccaag aacctgcagg aggcagaaga atggtacaaa tccaagtttg ctgacctctc
1021 tgaggctgcc aaccggaaca atgacgccct gcgccaggca aagcaggagt ccactgagta
1081 ccggagacag gtgcagtccc tcacctgtga agtggatgcc cttaaaggaa ccaatgagtc
1141 cctggaacgc cagatgcgtg aaatggaaga gaactttgcc gttgaagctg ctaactacca
1201 agacactatt ggccgcctgc aggatgagat tcagaatatg aaggaggaaa tggctcgtca
1261 ccttcgtgaa taccaagacc tgctcaatgt taagatggcc cttgacattg agattgccac
1321 ctacaggaag ctgctggaag gcgaggagag caggatttct ctgcctcttc caaacttttc
1381 ctccctgaac ctgagggaaa ctaatctgga ttcactccct ctggttgata cccactcaaa
1441 aaggacactt ctgattaaga cggttgaaac tagagatgga caggttatca acgaaacttc
1501 tcagcatcac gatgaccttg aataaaaatt gcacacactc agtgcagcaa tatattacca
1561 gcaagaataa aaaagaaatc catatcttaa agaaacagct ttcaagtgcc tttctgcagt
1621 ttttcaggag cgcaagatag atttggaata ggaataagct ctagttctta acaaccgaca
1681 ctcctacaag atttagaaaa aagtttacaa cataatctag tttacagaaa aatcttgtgc
1741 tagaatactt tttaaaaggt attttgaata ccattaaaac tgcttttttt tttccagcaa
1801 gtatccaacc aacttggttc tgcttcaata aatctttgga aaaactc
```

SEQ ID NO:47

```
   1 ggccagccga atccaagccg tgtgtactgc gtgctcagca ctgcccgaca gtcctagcta
  61 aacttcgcca actccgctgc ctttgccgcc accatgccca aaacgatcag tgtgcgtgtg
 121 accaccatgg atgcagagct ggagtttgcc atccagccca acaccaccgg gaagcagcta
 181 tttgaccagg tggtgaaaac tattggcttg agggaagttt ggttctttgg tctgcagtac
 241 caggacacta aaggtttctc cacctggctg aaactcaata agaaggtgac tgcccaggat
 301 gtgcggaagg aaagcccccct gctctttaag ttccgtgcca agttctaccc tgaggatgtg
 361 tccgaggaat tgattcagga catcactcag cgcctgttct ttctgcaagt gaaagagggc
 421 attctcaatg atgatattta ctgcccgcct gagaccgctg tgctgctggc ctcgtatgct
 481 gtccagtcta agtatggcga cttcaataag gaagtgcata agtctggcta cctggccgga
 541 gacaagttgc tcccgcagag agtcctggaa cagcacaaac tcaacaagga ccagtgggag
 601 gagcggatcc aggtgtggca tgaggaacac cgtggcatgc tcagggagga tgctgtcctg
 661 gaatatctga agattgctca agatctggag atgtatggtg tgaactactt cagcatcaag
 721 aacaagaaag gctcagagct gtggctgggg gtggatgccc tgggtctcaa catctatgag
 781 cagaatgaca gactaactcc caagataggc ttcccctgga gtgaaatcag gaacatctct
 841 ttcaatgata agaaatttgt catcaagccc attgacaaaa aagccccgga cttcgtcttc
 901 tatgctcccc ggctgcggat taacaagcgg atcttggcct tgtgcatggg gaaccatgaa
 961 ctatacatgc gccgtcgcaa gcctgatacc attgaggtgc agcagatgaa ggcacaggcc
1021 cgggaggaga agcaccagaa gcagatggag cgtgctatgc tggaaaatga gaagaagaag
1081 cgtgaaatgg cagagaagga gaaagagaag attgaacggg agaaggagga gctgatggag
1141 aggctgaagc agatcgagga acagactaag aaggctcagc aagaactgga agaacagacc
1201 cgtagggctc tggaacttga gcaggaacgg aagcgtgccc agagcgaggc tgaaaagctg
1261 gccaaggagc gtcaagaagc tgaagaggcc aaggaggcct tgctgcaggc ctcccgggac
1321 cagaaaaaga ctcaggaaca gctggccttg gaaatggcag agctgacagc tcgaatctcc
1381 cagctggaga tggcccgaca gaagaaggag agtgaggctg tggagtggca gcagaaggcc
1441 cagatggtac aggaagactt ggagaagacc cgtgctgagc tgaagactgc catgagtaca
1501 cctcatgtgg cagagcctgc tgagaatgag caggatgagc aggatgagaa tggggcagag
1561 gctagtgctg acctacgggc tgatgctatg gccaaggacc gcagtgagga ggaacgtacc
1621 actgaggcag agaagaatga gcgtgtgcag aagcacctga aggccctcac ttcggagctg
1681 gccaatgcca gagatgagtc caagaagact gccaatgaca tgatccatgc tgagaacatg
1741 cgactgggcc gagacaaata caagaccctg cgccagatcc ggcagggcaa caccaagcag
1801 cgcattgacg aatttgagtc tatgtaatgg gcacccagcc tctagggacc cctcctccct
1861 ttttccttgt ccccacactc ctacacctaa ctcacctaac tcatactgtg ctggagccac
1921 taactagagc agccctggag tcatgccaag catttaatgt agccatggga ccaaacctag
```

FIG. 10 A-41

```
1981 ccccttagcc cccacccact tccctgggca aatgaatggc tcactatggt gccaatggaa
2041 cctcctttct cttctctgtt ccattgaatc tgtatggcta gaatatccta cttctccagc
2101 ctagaggtac tttccacttg attttgcaaa tgcccttaca cttactgttg tcctatggga
2161 gtcaagtgtg gagtaggttg gaagctagct cccctcctct cccctaccac tgtcttcttc
2221 agggtcctga gatttacacg gttggagtgt tatgcggtct agggaatgag acaggaccta
2281 ggatatcttc tccaggatgt caactgacct aaaatttgcc ctcccatccc gtttagagtt
2341 atttaggctt tgtaacgatt gggggataaa aagatgttca gtcatttttg tttctacctc
2401 ccagatcgga tctgttgcaa actcagcctc aataagcctt gtcgttgact ttagggactc
2461 aatttctccc cagggtggat gggggaaatg gtgccttcaa gaccttcacc aaacatacta
2521 gaagggcatt ggccattcta ttgtggcaag gctgagtaga agatcctacc ccaattcctt
2581 gtaggagtat aggccggtct aaagtgagct ctatgggcag atctacccct tacttattat
2641 tccagatctg cagtcacttc gtgggatctg cccctccctg cttcaatacc caaatcctct
2701 ccagctataa cagtagggat gagtacccaa aagctcagcc agccccatca ggactcttgt
2761 gaaaagagag gatatgttca cacctagcgt cagtattttc cctgctaggg gttttaggtc
2821 tcttcccctc tcagagctac ttgggccata gctcctgctc cacagccatc ccagccttgg
2881 catctagagc ttgatgccag taggctcaac tagggagtga gtgcaaaaag ctgagtatgg
2941 tgagagaagc ctgtgccctg atccaagttt actcaaccct ctcaggtgac caaaatcccc
3001 ttctcatcac tcccctccaa agaggtgact gggccctgcc tctgtttgac aaacctctaa
3061 cccaggtctt gacaccagct gttctgtccc ttggagctgt aaaccagaga gctgctgggg
3121 attctggcct agtcccttcc acacccccac cccttgctct caacccagga gcatccacct
3181 ccttctctgt ctcatgtgtg ctcttcttct ttctacagta ttatgtactc tactgatatc
3241 taaatattga tttctgcctt ccttgctaat gcaccattag aagatattag tcttggggca
3301 ggatgatttt ggcctcatta ctttaccacc cccacacctg gaaagcatat actatattac
3361 aaaatgacat tttgccaaaa ttattaatat aagaagcttt cagtattagt gatgtcatct
3421 gtcactatag gtcatacaat ccattcttaa agtacttgtt atttgttttt attattactg
3481 tttgtcttct ccccagggtt cagtcctcaa ggggccatcc tgtcccacca tgcagtgccc
3541 ctagcttaga gcctccctca attccccctg gccaccaccc cccactctgt gcctgacctt
3601 gaggagtctt gtgtgcattg ctgtgaatta gctcacttgg tgatatgtcc tatattggct
3661 aaattgaaac ctggaattgt ggggcaatct attaatagct gccttaaagt cagtaactta
3721 cccttaggga ggctgggggga aaaggttaga ttttgtattc aggggttttt tgtgtacttt
3781 ttgggttttt taaaaattgt ttttggaggg gtttatgctc aatccatgtt ctatttcagt
3841 gccaataaaa tttaggaaga cttc
```

SEQ ID NO:48

```
  1 ggtgtgcccg gagaggctga gcagcctgcg cctgagctgg tggaggtgga agtgggcagc
 61 acagcccttc tgaagtgcgg cctctcccag tcccaaggca acctcagcca tgtcgactgg
121 ttttctgtcc acaaggagaa gcggacgctc atcttccgtg tgcgccaggg ccagggccag
181 agcgaacctg ggagtacgga gcagcggctc agcctccagg acagaggggc tactctggcc
241 ctgactcaag tcaccccccca agacgagcgc atcttcttgt gccagggcaa gcgccctcgg
301 tcccaggagt accgcatcca gctccgcgtc tacaaagctc cggaggagcc aaacatccag
361 gtcaaccccc tgggcatccc tgtgaacagt aaggagcctg aggaggtcgc tacctgtgta
421 gggaggaacg ggtaccccat tcctcaagtc atctggtaca agaatggccg gcctctgaag
481 gaggagaaga accgggtcca cattcagtcg tcccagactg tggagtcgag tggtttgtac
541 accttgcaga gtattctgaa ggcacagctg gttaaagaag acaaagatgc ccagttttac
601 tgtgagctca actaccggct gcccagtggg aaccacatga aggagtccag ggaagtcacc
661 gtccctgttt tctacccgac agaaaaagtg tggctggaag tggagcccgt gggaatgctg
721 aaggaagggg accgcgtgga aatcaggtgt ttggctgatg gcaaccctcc accacacttc
781 agcatcagca agcagaaccc cagcaccagg gaggcagagg aagagacaac caacgacaac
841 ggggtcctgg tgctggagcc tgcccggaag gaacacagtg ggcgctatga atgtcagggc
901 ctggacttgg acaccatgat atcgctgctg agtgaaccac aggaactact ggtgaactat
```

FIG. 10 A-42

```
 961 gtgtctgacg tccgagtgag tcccgcagca cactgagaga caggaaggca gcagcctcac
1021 cctgacctgt gaggcagaga gtagccagga cctcgagttc cagtggctga gagaagagac
1081 aggccaggtg ctggaaaggg ggcctgtgct tcagttgcat gacctgaaac gggaggcagg
1141 aggcggctat cgctgcgtgg cgtctgtgcc cagcataccc ggcctgaacc gcacacagct
1201 ggtcaacgtg gccattttg gcccccttg gatggcattc aaggagagga aggtgtgggt
1261 gaaagagaat atggtgttga atctgtcttg tgaagcgtca gggcaccccc ggcccaccat
1321 ctcctggaac gtcaacggca cggcaagtga acaagaccaa gatccacagc gagtcctgag
1381 caccctgaat gtcctcgtga ccccggagct gttggagaca ggtgttgaat gcacggcctc
1441 caacgacctg ggcaaaaaca ccagcatcct cttcctggag ctggtcaatt taaccaccct
1501 cacaccagac tccaacacaa ccactggcct cagcacttcc actgccagtc ctcataccag
1561 agccaacagc acctccacag agagaaagct gccggagccg gagagccggg gcgtggtcat
1621 cgtggctgtg attgtgtgca tcctggtcct ggcggtgctg ggcgctgtcc tctatttcct
1681 ctataagaag ggcaagctgc cgtgcaggcg ctcagggaag caggagatca cgctgccccc
1741 gtctcgtaag agcgaacttg tagttgaagt taagtcagat aagctcccag aagagatggg
1801 cctcctgcag ggcagcagcg gtgacaagag ggctccggga gaccagggag agaaatacat
1861 cgatctgagg cattagcccc gaatcacttc agctcccttc cctgcctgga ccattcccag
1921 ctccctgctc actcttctct cagccaaagc ctccaaaggg actagagaga agcctcctgc
1981 tcccctcgcc tgcacacccc ctttcagagg gccactgggt taggacctga ggacctcact
2041 tggccctgca aggcccgctt ttcagggacc agtccaccac catctccacg ttgagtgaag
2101 ctcatcccaa gcaaggagcc ccagtctccc gagcgggtag gagagtttct tgtagaacgt
2161 gtttttttctt tacacacatt atggctgtaa atacctggct cctgccagca gctgagctgg
2221 gtagcctctc tgagctggga ttacaggtgt gagccactgc gcccagccaa
```

SEQ ID NO:49

```
   1 caaacttggt ggcaacttgc ctcccggtgc gggcgtctct cccccaccgt ctcaacatgc
  61 ttaggggtcc ggggcccggg ctgctgctgc tggccgtcct gtgcctgggg acagcggtgc
 121 cctccacggg agcctcgaag agcaagaggc aggctcagca aatggttcag ccccagtccc
 181 cggtggctgt cagtcaaagc aagcccggtt gttatgacaa tggaaaacac tatcagataa
 241 atcaacagtg ggagcggacc tacctaggca atgcgttggt ttgtacttgt tatggaggaa
 301 gccgaggttt taactgcgag agtaaacctg aagctgaaga gacttgcttt gacaagtaca
 361 ctgggaacac ttaccgagtg ggtgacactt atgagcgtcc taaagactcc atgatctggg
 421 actgtacctg catcggggct gggcgaggga gaataagctg taccatcgca aaccgctgcc
 481 atgaaggggg tcagtcctac aagattggtg acacctggag gagaccacat gagactggtg
 541 gttacatgtt agagtgtgtg tgtcttggta atggaaaagg agaatggacc tgcaagccca
 601 tagctgagaa gtgttttgat catgctgctg ggacttccta tgtggtcgga gaaacgtggg
 661 agaagcccta ccaaggctgg atgatggtag attgtacttg cctgggagaa ggcagcggac
 721 gcatcacttg cacttctaga aatagatgca acgatcagga cacaaggaca tcctatagaa
 781 ttggagacac ctggagcaag aaggataatc gaggaaacct gctccagtgc atctgcacag
 841 gcaacggccg aggagagtgg aagtgtgaga ggcacacctc tgtgcagacc acatcgagcg
 901 gatctggccc cttcaccgat gttcgtgcag ctgtttacca accgcagcct cacccccagc
 961 ctcctcccta tggccactgt gtcacagaca gtggtgtggt ctactctgtg gggatgcagt
1021 ggctgaagac acaaggaaat aagcaaatgc tttgcacgtg cctgggcaac ggagtcagct
1081 gccaagagac agctgtaacc cagacttacg gtggcaactc aaatggagag ccatgtgtct
1141 taccattcac ctacaatggc aggacgtgca gcacaacttc gaattatgag caggaccaga
1201 aatactcttt ctgcacagac cacactgttt tggttcagac tcgaggagga aattccaatg
1261 gtgccttgtg ccacttcccc ttcctataca acaaccacaa ttacactgat tgcacttctg
1321 agggcagaag agacaacatg aagtggtgtg ggaccacaca gaactatgat gccgaccaga
1381 agtttgggtt ctgccccatg gctgcccacg aggaaatctg cacaaccaat gaaggggtca
1441 tgtaccgcat tggagatcag tgggataagc agcatgacat gggtcacatg atgaggtgca
1501 cgtgtgttgg gaatggtcgt ggggaatgga catgcattgc ctactcgcag cttcgagatc
1561 agtgcattgt tgatgacatc acttacaatg tgaacgacac attccacaag cgtcatgaag
```

FIG. 10 A-43

```
1621 aggggcacat gctgaactgt acatgcttcg gtcagggtcg gggcaggtgg aagtgtgatc
1681 ccgtcgacca atgccaggat tcagagactg ggacgtttta tcaaattgga gattcatggg
1741 agaagtatgt gcatggtgtc agataccagt gctactgcta tggccgtggc attggggagt
1801 ggcattgcca acctttacag acctatccaa gctcaagtgg tcctgtcgaa gtatttatca
1861 ctgagactcc gagtcagccc aactcccacc ccatccagtg gaatgcacca cagccatctc
1921 acatttccaa gtacattctc aggtggagac ctgtgagtat cccacccaga aaccttggat
1981 actgagtctc ctaatcttat caattctgat ggtttctttt tttcccagct tttgagccaa
2041 caactctgat taactattcc tatagcattt actatatttg tttagtgaac aaacaatatg
2101 tggtcaatta aattgacttg tagactg
```

SEQ ID NO:50

```
   1 acccccgcac ccagctccgc aggaccggcg ggcgcgcgcg ggctctggag gccacgggca
  61 tgatgcttcg ggtcctggtg gggctgtcc tccctgccat gctactggct gccccaccac
 121 ccatcaacaa gctggcactg ttcccagata agagtgcctg gtgcgaagcc aagaacatca
 181 cccagatcgt gggccacagc ggctgtgagg ccaagtccat ccagaacagg gcgtgcctag
 241 gacagtgctt cagctacagc gtccccaaca ccttcccaca gtccacagag tccctggttc
 301 actgtgactc ctgcatgcca gcccagtcca tgtgggagat tgtgacgctg gagtgcccgg
 361 gccacgagga ggtgcccagg gtggacaagc tggtggagaa gatcctgcac tgtagctgcc
 421 aggcctgcgg caaggagcct agtcacgagg ggctgagcgt ctatgtgcag ggcgaggacg
 481 ggccgggatc ccagcccggc acccaccctc acccccatcc ccaccccat cctggcgggc
 541 agacccctga gcccgaggac ccccctgggg ccccccacac agaggaagag gggctgagg
 601 actgaggccc ccccaactct tcctcccctc tcatccccct gtggaatgtt gggtctcact
 661 ctctggggaa gtcaggggag aagctgaagc ccccctttgg cactggatgg acttggcttc
 721 agactcggac ttgaatgctg cccggttgcc atggagatct gaaggggcgg ggttagagcc
 781 aagctgcaca atttaatata ttcaagagtg gggggaggaa gcagaggtct tcagggctct
 841 ttttttgggg ggggtggtct cttcctgtct ggcttctaga gatgtgcctg tgggaggggg
 901 aggaagttgg ctgagccatt gagtgctggg ggaggccatc caagatggca tgaatcgggc
 961 taaggtccct gggggtgcag atggtactgc tgaggtcccg ggcttagtgt gagcatcttg
1021 ccagcctcag gcttgaggga gggctgggct agaaagacca ctggcagaaa caggaggctc
1081 cggcccacag gtttccccaa ggcctctcac cccacttccc atctccaggg aagcgtcgcc
1141 ccagtggcac tgaagtggcc ctccctcagc ggaggggttt gggagtcagg cctgggcagg
1201 accctgctga ctcgtggcgc gggagctggg agccaggctc tccgggcctt tctctggctt
1261 ccttggcttg cctggtgggg gaaggggagg aggggaagaa ggaaagggaa gagtcttcca
1321 aggccagaag gagggggaca accccccaag accatccctg aagacgagca tccccctcct
1381 ctccctgtta gaaatgttag tgccccgcac tgtgccccaa gttctaggcc ccccagaaag
1441 ctgccagagc cggccgcctt ctcccctctc ccagggatgc tctttgtaaa tatcggatgg
1501 gtgtgggagt gaggggttac ctccctcgcc ccaaggttcc agaggcccta ggcgggatgg
1561 gctcgctgaa cctcgaggaa ctccaggacg aggaggacat gggacttgcg tggacagtca
1621 gggttcactt gggctctctc tagctcccca attctgcctg cctcctccct cccagctgca
1681 ctttaaccct agaaggtggg gacctggggg gagggacagg gcaggcgggc ccatgaagaa
1741 agcccctcgt tgcccagcac tgtctgcgtc tgctcttctg tgcccagggt ggctgccagc
1801 ccactgcctc ctgcctgggg tggcctggcc ctcctggctg ttgcgacgcg ggcttctgga
1861 gcttgtcacc attggacagt ctccctgatg gaccctcagt cttctcatga ataaattc
```

SEQ ID NO:51

```
   1 atccgtcccg gataagaccc gctgtctggc cctgagtagg gtgtgacctc cgcagccgca
  61 gaggaggagc gcagcccggc ctcgaagaac ttctgcttgg gtggctgaac tctgatcttg
 121 acctagagtc atggccatgg caaccaaagg aggtactgtc aaagctgctt caggattcaa
 181 tgccatggaa gatgcccaga ccctgaggaa ggccatgaaa gggctcggca ccgatgaaga
 241 cgccattatt agcgtccttg cctaccgcaa caccgcccag cgccaggaga tcaggacagc
```

FIG. 10 A-44

```
 301 ctacaagagc accatcggca gggacttgat agacgacctg aagtcagaac tgagtggcaa
 361 cttcgagcag gtgattgtgg ggatgatgac gcccacggtg ctgtatgacg tgcaagagct
 421 gcgaagggcc atgaagggag ccggcactga tgagggctgc ctaattgaga tcctggcctc
 481 ccggacccct gaggagatcc ggcgcataag ccaaacctac cagcagcaat atggacggag
 541 ccttgaagat gacattcgct ctgacacatc gttcatgttc cagcgagtgc tggtgtctct
 601 gtcagctggt gggagggatg aaggaaatta tctggacgat gctctcgtga gacaggatgc
 661 ccaggacctg tatgaggctg gagagaagaa atgggggaca gatgaggtga aatttctaac
 721 tgttctctgt tcccggaacc gaaatcacct gttgcatggt ttgatgaata caaaaggata
 781 tcacagaagg atattgaaca gagtattaaa tctgaaacat ctggtagctt tgaagatgct
 841 ctgctggcta tagtaaagtg catgaggaac aaatctgcat attttgctga aaagctctat
 901 aaatcgatga agggcttggg caccgatgat aacaccctca tcagagtgat ggtttctcga
 961 gcagaaattg acatgttgga tatccgggca cacttcaaga gactctatgg aaagtctctg
1021 tactcgttca tcaagggtga cacatctgga gactacagga aagtactgct tgttctctgt
1081 ggaggagatg attaaaataa aaatcccaga aggacaggag gattctcaac actttgaatt
1141 tttttaactt catttttcta cactgctatt atcattatct cagaatgctt atttccaatt
1201 aaaacgccta cagctgcctc ct
```

SEQ ID NO:52

```
   1 tggggcagcc gcgcccgcgg tgttttccgc ccggcgctgg cggctgctgc gcccgcggct
  61 ccccagtgcc ccgagtgccc cgcgggcccc gcgagcggga gtgggaccca gcccctaggc
 121 agaacccagg cgccgcgccc gggacgcccg cggagagagc cactcccgcc cacgtcccat
 181 ttcgcccctc gcgtccggag tcctcgtggc cagatctaac catgagctac cctggctatc
 241 ccccgccccc aggtggctac ccaccagctg caccaggtgg tggtccctgg ggaggtgctg
 301 cctaccctcc tccgcccagc atgcccccca tcgggctgga taacgtggcc acctatgcgg
 361 ggcagttcaa ccaggactat ctctcgggaa tggcggccaa catgtctggg acatttggag
 421 gagccaacat gcccaacctg taccctgggg cccctggggc tggctaccca ccagtgcccc
 481 ctggcggctt tgggcagccc ccctctgccc agcagcctgt tcctccctat gggatgtatc
 541 caccccccagg aggaaaccca ccctccagga tgccctcata tccgccatac ccaggggccc
 601 ctgtgccggg ccagcccatg ccaccccccg gacagcagcc cccaggggcc taccctgggc
 661 agccaccagt gacctaccct ggtcagcctc cagtgccact ccctgggcag cagcagccag
 721 tgccgagcta cccaggatac ccggggtctg ggactgtcac ccccgctgtg cccccaaccc
 781 agtttggaag ccgaggcacc atcactgatg ctcccggctt tgaccccctg cgagatgccg
 841 aggtcctgcg gaaggccatg aaaggcttcg ggacggatga gcaggccatc attgactgcc
 901 tggggagtcg ctccaacaag cagcggcagc agatcctact ttccttcaag acggcttacg
 961 gcaaggattt gatcaaagat ctgaaatctg aactgtcagg aaactttgag aagacaatct
1021 tggctctgat gaagacccca gtcctctttg acatttatga gataaaggaa gccatcaagg
1081 gggttggcac tgatgaagcc tgcctgattg agatcctcgc ttcccgcagc aatgagcaca
1141 tccgagaatt aaacagagcc tacaaagcag aattcaaaaa gaccctggaa gaggccattc
1201 gaagcgacac atcagggcac ttccagcggc tcctcatctc tctctctcag ggaaaccgtg
1261 atgaaagcac aaacgtggac atgtcactcg cccagagaga tgcccaggag ctgtatgcgg
1321 ccggggagaa ccgcctggga acagacgagt ccaagttcaa tgcggttctg tgctcccgga
1381 gccgggccca cctggtagca gttttcaatg agtaccagag aatgacaggc cgggacattg
1441 agaagagcat ctgccgggag atgtccgggg acctggagga gggcatgctg gccgtggtga
1501 aatgtctcaa gaataccccca gccttctttg cggagaggct caacaaggcc atgagggggg
1561 caggaacaaa ggaccggacc ctgattcgca tcatggtgtc tcgcagcgag accgacctcc
1621 tggacatcag atcagagtat aagcggatgt acggcaagtc gctgtaccac gacatctcgg
1681 gagatacttc aggggattac cggaagattc tgctgaagat ctgtggtggc aatgactgaa
1741 cagtgactgg tggctcactt ctgcccacct gccggcaaca ccagtgccag gaaaaggcca
1801 aaagaatgtc tgtttctaac aaatccacaa atagccccga gattcaccgt cctagagctt
1861 aggcctgtct tccacccctc ctgacccgta tagtgtgcca caggacctgg gtcggtctag
1921 aactctctca ggatgccttt tctaccccat ccctcacagc ctcttgctgc taaaatagat
```

FIG. 10 A-45

```
1981 gtttcatttt tctgactcat gcaatcattc ccctttgcct gtggctaaga cttggcttca
2041 tttcgtcatg taattgtata tttttatttg gaggcatatt ttcttttctt acagtcattg
2101 ccagacagag gcatacaagt ctgtttgctg catacacatt tctggtgagg gcgactgggt
2161 gggtgaagca ccgtgtcctc gctgaggaga gaaagggagg cgtgcctgag aaggtagcct
2221 gtgcatctgg tgagtgtgtc acgagctttg ttactgccaa actcactcct ttttagaaaa
2281 aacaaaaaaa aagggccaga aagtcattcc ttccatcttc cttgcagaaa ccacgagaac
2341 aaagccagtt ccctgtcagt gacagggctt cttgtaattt gtggtatgtg ccttaaacct
2401 gaatgtctgt agccaaaact tgtttccaca ttaagagtca gccagctctg gaatggtctg
2461 gaaatgtc
```

SEQ ID NO:53

```
   1 tagacgcacc ctctgaagat ggtgactccc tcctgagaag ctggacccct tggtaaaaga
  61 caaggccttc tccaagaaga atatgaaagt gttactcaga cttatttgtt tcatagctct
 121 actgatttct tctctggagg ctgataaatg caaggaacgt gaagaaaaaa taattttagt
 181 gtcatctgca aatgaaattg atgttcgtcc ctgtcctctt aacccaaatg aacacaaagg
 241 cactataact tggtataaag atgacagcaa gacacctgta tctacagaac aagcctccag
 301 gattcatcaa cacaaagaga aactttggtt tgttcctgct aaggtggagg attcaggaca
 361 ttactattgc gtggtaagaa attcatctta ctgcctcaga attaaaataa gtgcaaaatt
 421 tgtggagaat gagcctaact tatgttataa tgcacaagcc atatttaagc agaaactacc
 481 cgttgcagga gacggaggac ttgtgtgccc ttatatggag ttttttaaaa atgaaaataa
 541 tgagttacct aaattacagt ggtataagga ttgcaaacct ctacttcttg acaatataca
 601 ctttagtgga gtcaaagata ggctcatcgt gatgaatgtg gctgaaaagc atagagggaa
 661 ctatacttgt catgcatcct acacatactt gggcaagcaa tatcctatta cccgggtaat
 721 agaatttatt actctagagg aaaacaaacc cacaaggcct gtgattgtga gcccagctaa
 781 tgagacaatg gaagtagact tgggatccca gatacaattg atctgtaatg tcaccggcca
 841 gttgagtgac attgcttact ggaagtggaa tgggtcagta attgatgaag atgacccagt
 901 gctaggggaa gactattaca gtgtggaaaa tcctgcaaac aaaagaagga gtaccctcat
 961 cacagtgctt aatatatcgg aaattgaaag tagattttat aaacatccat ttacctgttt
1021 tgccaagaat acacatggta tagatgcagc atatatccag ttaatatatc cagtcactaa
1081 tttccagaag cacatgattg gtatatgtgt cacgttgaca gtcataattg tgtgttctgt
1141 tttcatctat aaaatcttca agattgacat tgtgctttgg tacagggatt cctgctatga
1201 ttttctccca ataaaagctt cagatggaaa gacctatgac gcatatatac tgtatccaaa
1261 gactgttggg gaagggtcta cctctgactg tgatattttt gtgtttaaag tcttgcctga
1321 ggtcttggaa aaacagtgtg gatataagct gttcatttat ggaagggatg actacgttgg
1381 ggaagacatt gttgaggtca ttaatgaaaa cgtaaagaaa agcagaagac tgattatcat
1441 tttagtcaga gaaacatcag gcttcagctg gctgggtggt tcatctgaag agcaaatagc
1501 catgtataat gctcttgttc aggatggaat taaagttgtc ctgcttgagc tggagaaaat
1561 ccaagactat gagaaaatgc cagaatcgat taaattcatt aagcagaaac atggggctat
1621 ccgctggtca ggggacttta cacagggacc acagtctgca aagacaaggt tctggaagaa
1681 tgtcaggtac cacatgccag tccagcgacg gtcaccttca tctaaacacc agttactgtc
1741 accagccact aaggagaaac tgcaaagaga ggctcacgtg cctctcgggt agcatggaga
1801 agttgccaag agttctttag gtgcctcctg tcttatggcg ttgcaggcca ggttatgcct
1861 catgctgact tgcagagttc atggaatgta actatatcat cctttatccc tgaggtcacc
1921 tggaatcaga ttattaaggg aataagccat gacgtcaata gcagcccagg gcacttcaga
1981 gtagagggct tgggaagatc ttttaaaaag gcagtaggcc cggtgtggtg gctcacgcct
2041 ataatcccag cactttggga ggctgaagtg ggtggatcac cagaggtcag gagttcgaga
2101 ccagcccagc caacatggca aaaccccatc tctactaaaa atacaaaaat gagctaggca
2161 tggtggcaca cgcctgtaat cccagctaca cctgaggctg aggcaggaga attgcttgaa
2221 ccggggagac ggaggttgca gtgagccgag tttgggccac tgcactctag cctggcaaca
```

FIG. 10 A-46

```
2281 gagcaagact ccgtctcaaa aaaagggcaa taaatgccct ctctgaatgt ttgaactgcc
2341 aagaaaaggc atggagacag cgaactagaa gaaagggcaa gaaggaaata gccaccgtct
2401 acagatggct tagttaagtc atccacagcc caagggcggg gctatgcctt gtctggggac
2461 cctgtagagt cactgaccct ggagcggctc tcctgagagg tgctgcaggc aaagtgagac
2521 tgacacctca ctgaggaagg gagacatatt cttggagaac tttccatctg cttgtatttt
2581 ccatacacat ccccagccag aagttagtgt ccgaagaccg aattttattt tacagagctt
2641 gaaaactcac ttcaatgaac aaagggattc tccaggattc caaagttttg aagtcatctt
2701 agctttccac aggagggaga gaacttaaaa aagcaacagt agcagggaat tgatccactt
2761 cttaatgctt tcctccctgg catgaccatc ctgtcctttg ttattatcct gcattttacg
2821 tctttggagg aacagctccc tagtggcttc ctccgtctgc aatgtccctt gcacagccca
2881 cacatgaacc atccttccca tgatgccgct cttctgtcat cccgctcctg ctgaaacacc
2941 tcccaggggc tccacctgtt caggagctga agcccatgct ttcccaccag catgtcactc
3001 ccagaccacc tccctgccct gtcctccagc ttcccctcgc tgtcctgctg tgtgaattcc
3061 caggttggcc tggtggccat gtcgcctgcc cccagcactc ctctgtctct gctcttgcct
3121 gcacccttcc tcctcctttg cctaggaggc cttctcgcat tttctctagc tgatcagaat
3181 tttaccaaaa ttcagaacat cctccaattc cacagtctct gggagacttt ccctaagagg
3241 cgacttcctc tccagccttc tctctctggt caggcccact gcagagatgg tggtgagcac
3301 atctgggagg ctggtctccc tccagctgga attgctgctc tctgagggag aggctgtggt
3361 ggctgtctct gtccctcact gccttccagg agcaatttgc acatgtaaca tagatttatg
3421 taatgcttta tgtttaaaaa cattccccaa ttatcttatt taatttttgc aattattcta
3481 attttatata tagagaaagt gacctatttt ttaaaaaaat cacactctaa gttctattga
3541 acctaggact tgagcctcca tttctggctt ctagtctggt gttctgagta cttgatttca
3601 ggtcaataac ggtccccccct cactccacac tggcacgttt gtgagaagaa atgacatttt
3661 gctaggaagt gaccgagtct aggaatgctt ttattcaaga caccaaattc caaacttcta
3721 aatgttggaa ttttcaaaaa ttgtgtttag attttatgaa aaactcttct actttcatct
3781 attctttccc tagaggcaaa catttcttaa aatgtttcat tttcattaaa aatgaaagcc
3841 aaatttatat gccaccgatt gcaggacaca agcacagttt taagagttgt atgaacatgg
3901 agaggacttt tggtttttat atttctcgta tttaatatgg gtgaacacca acttttattt
3961 ggaataataa ttttcctcct aaacaaaaac acattgagtt taagtctctg actcttgcct
4021 ttccacctgc tttctcctgg gcccgctttg cctgcttgaa ggaacagtgc tgttctggag
4081 ctgctgttcc aacagacagg gcctagcttt catttgacac acagactaca gccagaagcc
4141 catggagcag ggatgtcacg tcttgaaaag cctattagat gttttacaaa tttaattttg
4201 cagattattt tagtctgtca tccagaaaat gtgtcagcat gcatagtgct aagaaagcaa
4261 gccaatttgg aaacttaggt tagtgacaaa attggccaga gagtgggggt gatgatgacc
4321 aagaattaca agtagaatgg cagctggaat ttaaggaggg acaagaatca atggataagc
4381 gtgggtggag gaagatccaa acagaaaagt gcaaagttat tccccatctt ccaagggttg
4441 aattctggag gaagaagaca cattcctagt tccccgtgaa cttcctttga cttattgtcc
4501 ccactaaaac aaaacaaaaa acttttaatg ccttccacat taattagatt ttcttgcagt
4561 tttttatgg catttttttta aagatgccct aagtgttgaa gaagagtttg caaatgcaac
4621 aaaatattta attaccggtt gttaaaactg gtttagcaca atttatattt tccctctctt
4681 gcctttctta tttgcaataa aaggtattga gccatttttt aaatgacatt tttgataaat
4741 tatgtttgta ctagttgatg aaggagtttt ttttaacctg tttatataat tttgcagcag
4801 aagccaaatt ttttgtatat taaagcacca aattcatgta cagcatgcat cacggatcaa
4861 tagactgtac ttattttcca ataaaatttt caaactttgt actgtta
```

SEQ ID NO:54

```
   1 ccctgcactc tcgctctcct gccccacccc gaggtaaagg gggcgactaa gagaagatgg
  61 tgttgctcac cgcggtcctc ctgctgctgg ccgcctatgc ggggccggcc cagagcctgg
 121 gctccttcgt gcactgcgag ccctgcgacg agaaagccct ctccatgtgc ccccccagcc
 181 ccctgggctg cgagctggtc aaggagccgg gctgcggctg ctgcatgacc tgcgccctgg
```

FIG. 10 A-47

```
241 ccgaggggca gtcgtgcggc gtctacaccg agcgctgcgc ccaggggctg cgctgcctcc
301 cccggcagga cgaggagaag ccgctgcacg ccctgctgca cggccgcggg gtttgcctca
361 acgaaaagag ctaccgcgag caagtcaaga tcgagagaga ctcccgtgag cacgaggagc
421 ccaccacctc tgagatggcc gaggagacct actcccccaa gatcttccgg cccaaacaca
481 cccgcatctc cgagctgaag gctgaagcag tgaagaagga ccgcagaaag aagctgaccc
541 agtccaagtt tgtcggggga gccgagaaca ctgcccaccc ccggatcatc tctgcacctg
601 agatgagaca ggagtctgag cagggcccct gccgcagaca catggaggct tccctgcagg
661 agctcaaagc cagcccacgc atggtgcccc gtgctgtgta cctgcccaat tgtgaccgca
721 aaggattcta caagagaaag cagtgcaaac cttcccgtgg ccgcaaacgt ggcatctgct
781 ggtgcgtgga caagtacggg atgaagctgc caggcatgga gtacgttgac ggggactttc
841 agtgccacac cttcgacagc agcaacgttg agtgatgcgt cccccccaa cctttccctc
901 accccctccc acccccagcc ccgactccag ccagcgcctc cctccacccc aggacgccac
961 tcatttcatc tcatttaagg gaaaaatata tatctatcta tttg
```

SEQ ID NO:55

```
  1 cgcagcgggt cctctctatc tagctccagc ctctcgcctg cgccccactc cccgcgtccc
 61 gcgtcctagc cgaccatggc cgggcccctg cgcgccccgc tgctcctgct ggccatcctg
121 gccgtggccc tggccgtgag ccccgcggcc ggctccagtc ccggcaagcc gccgcgccta
181 gtgggaggcc ccatggacgc cagcgtggag gaggagggtg tgcggcgtgc actggacttt
241 gccgtcggcg agtacaacaa agccagcaac gacatgtacc acagccgcgc gctgcaggtg
301 gtgcgcgccc gcaagcagat cgtagctggg gtgaactact tcttggacgt ggagctgggc
361 cgaaccacgt gtaccaagac ccagcccaac ttggacaact gcccttcca tgaccagcca
421 catctgaaaa ggaaagcatt ctgctctttc cagatctacg ctgtgccttg gcagggcaca
481 atgaccttgt cgaaatccac ctgtcaggac gcctaggggt ctgtaccggg ctggcctgtg
541 cctatcacct cttatgcaca cctcccaccc cctgtattcc cacccctgga ctggtggccc
601 ctgccttggg gaaggtctcc ccatgtgcct gcaccaggag acagacagag aaggcagcag
661 gcggcctttg ttgctcagca aggggctctg ccctccctcc ttccttcttg cttctcatag
721 ccccggtgtg cggtgcatac acccccacct cctgcaataa aatagtagca tc
```

SEQ ID NO:56

```
   1 gaaagatgga tcactccagc tcaaagagaa catgtgggaa tgaaaggaca ggctgggccc
  61 aaaggagaaa agggtgatgc tggggaggag cttcctggcc ctcctgaacc ttctgggcct
 121 gttggaccca cggcaggagc agaagcagag ggctctggcc taggctgggg ctcggacgtc
 181 ggctctggct ctggtgacct ggtgggcagt gagcagctgc tgagaggtcc tccaggaccc
 241 ccagggccac ctggcttacc tgggattcca ggaaaaccag gaactgatgt tttcatggga
 301 ccccctggat ctcctggaga ggatggacct gctggtgaac ctgggccccc gggccctgag
 361 ggacagcctg gagttgatgg agccaccggc cttcccggga tgaaaggggga gaagggagca
 421 agagggccta atggctcagt tggtgaaaag ggtgaccctg gcaacagagg cttacctgga
 481 cccccgggga aaaagggaca agctggccct cctggggtca tgggaccccc agggcctcct
 541 ggacccccctg ggcccccagg ccctggatgc acaatgggac ttggattcga ggataccgaa
 601 ggctctggaa gcacccagct attgaatgaa cccaaactct ccagaccaac ggctgcaatt
 661 ggtctcaaag gagagaaagg agaccgggga cccaagggag aaagggggat ggatggagcc
 721 agtattgtgg gacccccctgg gccgagaggg ccacctgggc acatcaaggt cttgtctaat
 781 tccttgatca atatcaccca tggattcatg aatttctcgg acattcctga gctggtgggg
 841 cctccggggc cggacgggtt gcctgggctg ccaggatttc cagggtccta gaggaccaaa
 901 aggtgacact ggtttacctg gctttccagg actaaaagga gaacagggcg agaagggaga
 961 gccgggtgcc atcctgacag aggacattcc tctggaaagg ctgatgggga aaaagggtga
1021 acctggaatg catggagccc caggaccaat ggggcccaaa ggaccaccag gacataaagg
1081 agaatttggc cttcccgggc gacctggtcg cccaggactg aatggcctca agggtaccaa
```

FIG. 10 A-48

1141 aggagatcca ggggtcatta tgcagggccc acctggctta cctggccctc caggcccccc
1201 tgggccacct ggagctgtga ttaacatcaa aggagccatt ttcccaatac ccgtccgacc
1261 acactgcaaa atgccagttg atactgctca tcctgggagt ccagagctca tcacttttca
1321 cggtgttaaa ggagagaaag gatcctgggg tcttcctggc tcaaagggag aaaaaggcga
1381 ccagggagcc cagggaccac caggtcctcc acttgatcta gcttacctga gacactttct
1441 gaacaacttg aagggggaga atggagacaa ggggttcaaa ggtgaaaaag gagaaaaagg
1501 agacattaat ggcagcttcc ttatgtctgg gcctccaggc ctgcccggaa atccaggccc
1561 ggctggccaa aaagggggaga cagtcgttgg gccccaagga cccccaggtg ctcctggtct
1621 gcctgggcca cctggctttg gaagacctgg tgatcctggg ccaccggggc ccccggggcc
1681 accaggacct ccagctatcc tgggagcagc tgtggccctt ccaggtcccc ctggccctcc
1741 aggacagcca gggcttcccg gatccagaaa cctggtcaca gcattcagca acatggatga
1801 catgctgcag aaagcgcatt tggttataga aggaacattc atctacctga gggacagcac
1861 tgagtttttc attcgtgtta gagatggctg gaaaaaatta cagctgggag aactgatccc
1921 cattcctgcc gacagccctc cacccccctgc gctttccagc aacccacatc agcttctgcc
1981 tccaccaaac cctatttcaa gtgccaatta tgagaagcct gctctgcatt tggctgctct
2041 gaacatgcca ttttctgggg acattcgagc tgattttcag tgcttcaagc aggccagagc
2101 tgcaggactg ttgtccacct accgagca SEQ ID NO:57
1 tagaaattgt taattttaac aatccagagc aggccaacga ggctttgctc tcccgacccg
61 aactaaaggt ccctcgctcc gtgcgctgct acgagcggtg tctcctgggg ctccaatgca
121 gcgagctgtg cccgaggggt tcggaaggcg caagctgggc agcgacatgg ggaacgcgga
181 gcgggctccg ggtctcgga gctttgggcc agtacccacg ctgctgctgc tcgccgcggc
241 gctactggcc gtgtcggacg cactcgggcg cccctccgag gaggacgagg agctagtggt
301 gccggagctg gagcgcgccc cgggacacgg gaccacgcgc ctccgcctgc acgcctttga
361 ccagcagctg gatctggagc tgcggcccga cagcagcttt ttggcgcccg gcttcacgct
421 ccagaacgtg gggcgcaaat ccgggtccga gacgccgctt ccggaaaccg acctggcgca
481 ctgcttctac tccggcaccg tgaatggcga tcccagctcg gctgccgccc tcagcctctg
541 cgagggcgtg cgcggcgcct tctacctgct gggggaggcg tatttcatcc agccgctgcc
601 cgccgccagc gagcgcctcg ccaccgccgc cccaggggag aagccgccgg caccactaca
661 gttccacctc ctgcggcgga atcggcaggg cgacgtcggc ggcacgtgcg gggtcgtgga
721 cgacgagccc cggccgactg ggaaagcgga gaccgaagac gaggacgaag ggactgaggg
781 cgaggacgaa ggggctcagt ggtcgccgca ggacccggca ctgcaaggcg taggacagcc
841 cacaggaact ggaagcataa gaaagaagcg atttgtgtcc agtcaccgct atgtggaaac
901 catgcttgtg gcagaccagt cgatggcaga attccacggc agtggtctaa agcattacct
961 tctcacgttg ttttcggtgg cagccagatt gtacaaacac cccagcattc gtaattcagt
1021 tagcctggtg gtggtgaaga tcttggtcat ccacgatgaa cagaaggggc cggaagtgac
1081 ctccaatgct gccctcactc tgcggaactt ttgcaactgg cagaagcagc acaacccacc
1141 cagtgaccgg gatgcagagc actatgacac agcaattctt ttcaccagac aggacttgtg
1201 tgggtcccag acatgtgata ctcttgggat ggctgatgtt ggaactgtgt gtgatccgag
1261 cagaagctgc tccgtcatag aagatgatgg tttacaagct gccttcacca cagcccatga
1321 attaggccac gtgtttaaca tgccacatga tgatgcaaag cagtgtgcca gccttaatgg
1381 tgtgaaccag gattcccaca tgatggcgtc aatgctttcc aacctggacc acagccagcc
1441 ttggtctcct tgcagtgcct acatgattac atcatttctg gataatggtc atggggaatg
1501 tttgatggac aagcctcaga atcccataca gctcccaggc gatctccctg gcacctcgta
1561 cgatgccaac cggcagtgcc agtttacatt tggggaggac tccaaacact gccccgatgc
1621 agccagcaca tgtagcacct tgtggtgtac cggcacctct ggtggggtgc tggtgtgtca
1681 aaccaaacac ttcccgtggg cggatggcac cagctgtgga gaagggaaat ggtgtatcaa
1741 cggcaagtgt gtgaacaaaa ccgacagaaa gcattttgat acgccttttc atggaagctg
1801 gggaatgtgg gggccttggg gagactgttc gagaacgtgc ggtggaggag tccagtacac
1861 gatgagggaa tgtgacaacc cagtcccaaa gaatggaggg aagtactgtg aaggcaaacg

FIG. 10 A-49

```
1921 agtgcgctac agatcctgta accttgagga ctgtccagac aataatggaa aaacctttag
1981 agaggaacaa tgtgaagcac acaacgagtt ttcaaaagct tcctttggga gtgggcctgc
2041 ggtggaatgg attcccaagt acgctggcgt ctcaccaaag gacaggtgca agctcatctg
2101 ccaagccaaa ggcattggct acttcttcgt tttgcagccc aaggttgtag atggtactcc
2161 atgtagccca gattccacct ctgtctgtgt gcaaggacag tgtgtaaaag ctggttgtga
2221 tcgcatcata gactccaaaa agaagtttga taaatgtggt gtttgcgggg gaaatggatc
2281 tacttgtaaa aaaatatcag gatcagttac tagtgcaaaa cctggatatc atgatatcat
2341 cacaattcca actggagcca ccaacatcga agtgaaacag cggaaccaga ggggatccag
2401 gaacaatggc agctttcttg ccatcaaagc tgctgatggc acatatattc ttaatggtga
2461 ctacactttg tccaccttag agcaagacat tatgtacaaa ggtgttgtct tgaggtacag
2521 cggctcctct gcggcattgg aaagaattcg cagctttagc cctctcaaag agcccttgac
2581 catccaggtt cttactgtgg gcaatgccct tcgacctaaa attaaataca cctacttcgt
2641 aaagaagaag aaggaatctt tcaatgctat ccccactttt tcagcatggg tcattgaaga
2701 gtggggcgaa tgttctaagt catgtgaatt gggttggcag agaagactgg tagaatgccg
2761 agacattaat ggacagcctg cttccgagtg tgcaaaggaa gtgaagccag ccagcaccag
2821 accttgtgca gaccatccct gcccccagtg gcagctgggg gagtggtcat catgttctaa
2881 gacctgtggg aagggttaca aaaaaagaag cttgaagtgt ctgtcccatg atggaggggt
2941 gttatctcat gagagctgtg atcctttaaa gaaacctaaa catttcatag acttttgcac
3001 aatggcagaa tgcagttaag tggtttaagt ggtgttagct ttgagggcaa ggcaaagtga
3061 ggaagggctg gtgcagggaa agcaagaagg ctggagggat ccagcgtatc ttgccagtaa
3121 ccagtgaggt gtatcagtaa ggtgggatta tgggggtaga tagaaaagga gttgaatcat
3181 cagagtaaac tgccagttgc aaatttgata ggatagttag tgaggattat taacctctga
3241 gcagtgatat agcataataa agccccgggc attattatta ttatttcttt tgttacatct
3301 attacaagtt tagaaaaaac aaagcaattg tcaaaaaaag ttagaactat tacaacccct
3361 gtttcctggt acttatcaaa tacttagtat catgggggtt gggaaatgaa aagtaggaga
3421 aaagtgagat tttactaaga cctgttttac tttacctcac taacaatggg gggagaaagg
3481 agtacaaata ggatctttga ccagcactgt ttatggctgc tatggtttca gagaatgttt
3541 atacattatt tctaccgaga attaaaactt cagattgttc aacatgagag aaaggctcag
3601 caacgtgaaa taacgcaaat ggcttcctct ttcctttttt ggaccatctc agtctttatt
3661 tgtgtaattc attttgagga aaaaacaact ccatgtattt attcaagtgc attaaagtct
3721 acaatggaaa aaaagcagtg aagcattaga tgctggtaaa agctagagga gacacaatga
3781 gcttagtacc tccaacttcc tttctttcct accatgtaac cctgctttgg gaatatggat
3841 gtaaagaagt aacttgtgtc tcatgaaaat cagtacaatc acacaaggag gatgaaacgc
3901 cggaacaaaa atgaggtgtg tagaacaggg tcccacaggt ttggggacat tgagatcact
3961 tgtcttgtgg tggggaggct gctgaggggt agcaggtcca tctccagcag ctggtccaac
4021 agtcgtatcc tggtgaatgt ctgttcagct cttctgtgag aatatgattt tttccatatg
4081 tatatagtaa aatatgttac tataaattac atgtacttta taagtattgg tttgggtgtt
4141 ccttccaaga aggactatag ttagtaataa atgcctataa taacatattt atttttatac
4201 atttatttct aatgaaaaaa acttttaaat tatatcgctt ttgtggaagt gcatataaaa
4261 tagagtattt atacaatata tgttactaga aataaaagaa cacttttgg
```

SEQ ID NO:58

```
  1 gggcccgggc gcgcgggagc gggagcggcc gggggagccg gagcgcacca tggaggcggc
 61 ggcaggcggc cgcggctgtt tccagccgca cccggggctg cagaagacgc tggagcagtt
121 ccacctgagc tccatgagct cgctgggcgg cccggccgct ttctcggcgc gctgggcgca
181 ggaggcctac aagaaggaga gcgccaagga ggcgggcgcg gccgcggtgc cggcgccggt
241 gcccgcagcc accgagccgc cgcccgtgct gcacctgccc gccatccagc cgccgccgcc
301 cgtgctgccc gggcccttct tcatgccgtc cgaccgctcc accgagcgct gcgagaccgt
361 actggaaggc gagaccatct cgtgcttcgt ggtgggaggc gagaagcgcc tgtgtctgcc
421 gcagattctc aactcggtgc tgcgcgactt ctcgctgcag cagatcaacg cggtgtgcga
481 cgagctccac atctactgct cgcgctgcac ggccgaccag ctggagatcc tcaaagtcat
```

FIG. 10 A-50

```
 541 gggcatcctg cccttctcgg cgccctcgtg cgggctcatc accaagacgg acgccgagcg
 601 cctgtgcaac gcgctgctct acggcggcgc ctacccgccg ccctgcaaga aggagctggc
 661 cgccagcctg gcgctgggcc tggagctcag cgagcgcagc gtccgcgtgt accacgagtg
 721 cttcggcaag tgtaaggggc tgctggtgcc cgagctctac agcagcccga gcgccgcctg
 781 catccagtgc ctggactgcc gcctcatgta cccgccgcac aagttcgtgg tgcactcgca
 841 caaggccctg gagaaccgga cctgccactg gggcttcgac tcggccaact ggcgggccta
 901 catcctgctg agccaggatt acacgggcaa ggaggagcag gcgcgcctcg gccgctgcct
 961 ggacgacgtg aaggagaaat tcgactatgg caacaagtac aagcggcggg tgccccgggt
1021 ctcctctgag cctccggcct ccataagacc caaaacagat gacacctctt cccagtcccc
1081 cgcgccttcc gaaaaggaca agccgtccag ctggctgcgg accttggccg gctcttccaa
1141 taagagcctg ggctgtgttc accctcgcca gcgcctctct gctttccgac cctggtcccc
1201 cgcagtgtca gcgagtgaga aagagctctc cccacacctc ccggccctca tccgagacag
1261 cttctactcc tacaagagct ttgagacagc cgtggcgccc aacgtggccc tcgcaccgcc
1321 ggcccagcag aaggttgtga gcagccctcc gtgtgccgcc gccgtctccc gggcccccga
1381 gcctctcgcc acttgcaccc agcctcggaa gcggaagctg actgtggaca ccccaggagc
1441 cccagagacg ctggcgcccg tggctgcccc agaggaggac aaggactcgg aggcggaggt
1501 ggaagttgaa agcagggagg aattcacctc ctccttgtcc tcgctctctt ccccgtcctt
1561 tacctcatcc agctccgcca aggacctggg ctccccgggt gcgcgtgccc tgccctcggc
1621 cgtccctgat gctgcggccc ctgccgacgc cccagtggg ctggaggcgg agctggagca
1681 cctgcggcag gcactggagg gcggcctgga caccaaggaa gccaaagaga agttcctgca
1741 tgaggtggtc aagatgcgcg tgaagcagga ggagaagctc agcgcagccc tgcaggccaa
1801 gcgcagcctc caccaggagc tggagttcct acgcgtggcc aagaaggaga agctgcggga
1861 ggccacggag gccaagcgta acctgcggaa ggagatcgag cgtctccgcg ccgagaacga
1921 gaagaagatg aaagaggcca acgagtcacg gctgcgcctg aagcgggagc tggagcaggc
1981 gcggcaggcc cgggtgtgcg acaagggctg cgaggcgggc cgcctgcgcg ccaagtactc
2041 ggcccagatc gaagacctgc aggtgaagct gcagcacgcg gaggcggacc gggagcagct
2101 gcgggccgac ctgctgcggg agcgcgaggc ccgggagcac ctggagaagg tggtgaagga
2161 gctgcaggaa cagctgtggc cgcgggcccg ccccgaggct gcgggcagcg agggcgctgc
2221 ggagctggag ccgtagattc cgtgcctgcc gccgcagcgc cgccgacaac gcgggtgcag
2281 gggggcgcgg ctgggcggtg cagctccgcc cggctccgcc cctgcagccc acacagcaca
2341 acgtcttacc gtgcctatta ccaagcgagt gtttgtaacc atgtagtttt ggaacccact
2401 gcaaaatttt ctactggcca agttcaagtg agtaagccgc gtcccccaac tacagctgga
2461 gacggggcca gctcggcggc ctgctggtcc tctgcttgct ggaacattct aacatttaca
2521 cttttgttat aagctattta aaaccagtaa ggagacttga aattcagaaa atcaacacat
2581 ttttaaatga ctaacttcta aaagccccaa cacatgacgc catctgaaga cccgcaacgg
2641 agtgggggtg gcggccgccc caccctcccc acccggggaa gccatcacag ctcatctgcc
2701 cgcggctgcg tgaggacagc aggggttttt cttcagagtc tattttttca gcgacaagga
2761 cccaggtctt cctgctgctg ccagggagag cagggacagt gccgcgtgcg agatgagctc
2821 gaacactgcc cgccttactg ccgcctaccc cgcccgccac gccgccgtcg atgccagcgc
2881 tgtccccacg ggtaccagga agtgcagagc cgcacaggag ctgccccgga gctgagggga
2941 cggtcttcgg ctcctctgca ccccgtgatt ctgcccacgc tcctccacca cgaggcactg
3001 acctgcgtcg ggtggtgacc gtggctggcg gtcacgccct cagcccctcc gggcacacgt
3061 gccgcctgac cgggcgaccc ttttcagttc ggcaaacgtc gctcccttca ttttgggact
3121 gaggctgcag cattggaaca aaagagcatt atttcaattt ttctttcttt tttttgttc
3181 gttcatttaa acgtatattt agaactgcac tttgtccaca accttccctt ctctttctat
3241 tccccagtga actgaggttt ttaccgattt atagagcagt caaatccgaa gtgctcgagt
3301 gcttagaaac cccctctggt gcttggttga acaagggaat cacaagaaaa cgaaaatgca
3361 aaaactgaac ttcgggggtc gttctgtgcc ttccagcatc ttgtacagca aatcctgact
3421 cgtgtctttt taccccaag atatctgtct tcagtagcga ctgaatctgc cactctcaga
3481 ataagttc
```

FIG. 10 A-51

SEQ Id NO:59

```
   1 gccgccgccg ccatccgccg ccgcagccag cttccgccgc cgcaggaccg gcccctgccc
  61 cagcctccgc agccgcggcg cgtccacgcc cgcccgcgcc cagggcgagt cggggtcgcc
 121 gcctgcacgc ttctcagtgt tccccgcgcc ccgcatgtaa cccggccagg cccccgcaac
 181 tgtgtcccct gcagctccag ccccgggctg catccccccg ccccgacacc agctctccag
 241 cctgctcgtc caggatggcc gcggccaagg ccgagatgca gctgatgtcc ccgctgcaga
 301 tctctgaccc gttcggatcc tttcctcact cgcccaccat ggacaactac cctaagctgg
 361 aggagatgat gctgctgagc aacggggctc cccagttcct cggcgccgcc ggggccccag
 421 agggcagcgg cagcaacagc agcagcagca gcagcggggg cggtggaggc ggcgggggcg
 481 gcagcaacag cagcagcagc agcagcacct tcaaccctca ggcggacacg ggcgagcagc
 541 cctacgagca cctgaccgca gagtcttttc ctgacatctc tctgaacaac gagaaggtgc
 601 tggtggagac cagttacccc agccaaacca ctcgactgcc ccccatcacc tatactggcc
 661 gcttttccct ggagcctgca cccaacagtg gcaacacctt gtggcccgag cccctcttca
 721 gcttggtcag tggcctagtg agcatgacca acccaccggc ctcctcgtcc tcagcaccat
 781 ctccagcggc ctcctccgcc tccgcctccc agagcccacc cctgagctgc gcagtgccat
 841 ccaacgacag cagtcccatt tactcagcgg cacccacctt ccccacgccg aacactgaca
 901 ttttccctga gccacaaagc caggccttcc cgggctcggc agggacagcg ctccagtacc
 961 cgcctcctgc ctaccctgcc gccaagggtg gcttccaggt tcccatgatc cccgactacc
1021 tgtttccaca gcagcagggg gatctgggcc tgggcacccc agaccagaag cccttccagg
1081 gcctggagag ccgcacccag cagccttcgc taacccctct gtctactatt aaggcctttg
1141 ccactcagtc gggctcccag gacctgaagg ccctcaatac cagctaccag tcccagctca
1201 tcaaacccag ccgcatgcgc aagtacccca accggcccag caagacgccc ccccacgaac
1261 gcccttacgc ttgcccagtg gagtcctgtg atcgccgctt ctcccgctcc gacgagctca
1321 cccgccacat ccgcatccac acaggccaga agcccttcca gtgccgcatc tgcatgcgca
1381 acttcagccg cagcgaccac ctcaccaccc acatccgcac ccacacaggc gaaaagccct
1441 tcgcctgcga catctgtgga agaaagtttg ccaggagcga tgaacgcaag aggcatacca
1501 agatccactt gcggcagaag gacaagaaag cagacaaaag tgttgtggcc tcttcggcca
1561 cctcctctct ctcttcctac ccgtccccgg ttgctacctc ttacccgtcc ccggttacta
1621 cctcttatcc atccccggcc accacctcat acccatcccc tgtgcccacc tccttctcct
1681 ctcccggctc ctcgacctac ccatcccctg tgcacagtgg cttcccctcc ccgtcggtgg
1741 ccaccacgta ctcctctgtt ccccctgctt tcccggccca ggtcagcagc ttcccttcct
1801 cagctgtcac caactccttc agcgcctcca cagggctttc ggacatgaca gcaacctttt
1861 ctcccaggac aattgaaatt tgctaaaggg aaaggggaaa gaaagggaaa agggagaaaa
1921 agaaacacaa gagacttaaa ggacaggagg aggagatggc cataggagag gagggttcct
1981 cttaggtcag atggaggttc tcagagccaa gtcctccctc tctactggag tggaaggtct
2041 attggccaac aatcctttct gcccacttcc ccttccccaa ttactattcc ctttgacttc
2101 agctgcctga aacagccatg tccaagttct tcacctctat ccaaagaact tgatttgcat
2161 ggattttgga taaatcattt cagtatcatc tccatcatat gcctgacccc ttgctccctt
2221 caatgctaga aaatcgagtt ggcaaaatgg ggtttgggcc cctcagagcc ctgccctgca
2281 cccttgtaca gtgtctgtgc catggatttc gtttttcttg ggtactcttt gatgtgaaga
2341 taatttgcat attctattgt attatttgga gttaggtcct cacttggggg aaaaaaaaaa
2401 aagaaaagcc aagcaaacca atggtgatcc tctattttgt gatgatgctg tgacaataag
2461 tttgaacctt ttttttgaa acagcagtcc cagtattctc agagcatgtg tcagagtgtt
2521 gttccgttaa ccttttttgta aatactgctt gaccgtactc tcacatgtgg caaaatatgg
2581 tttggttttt cttttttttt ttttttgaaa gtgtttttttc ttcgtccttt tggtttaaaa
2641 agtttcacgt cttggtgcct tttgtgtgat gcgccttgct gatggcttga catgtgcaat
2701 tgtgagggac atgctcacct ctagccttaa gggggggcagg gagtgatgat ttgggggagg
2761 ctttgggagc aaaataagga agagggctga gctgagcttc ggttctccag aatgtaagaa
2821 aacaaaatct aaaacaaaat ctgaactctc aaaagtctat ttttttaact gaaaatgtaa
2881 atttataaat atattcagga gttggaatgt tgtagttacc tactgagtag gcggcgattt
2941 ttgtatgtta tgaacatgca gttcattatt ttgtggttct attttacttt gtacttgtgt
```

FIG. 10 A-52

3001 ttgcttaaac aaagtgactg tttggcttat aaacacattg aatgcgcttt attgcccatg
3061 ggatatgtgg tgtatatcct tccaaaaaat taaaacgaaa ataaagta SEQ ID NO:60
1 cattcataag actcagagct acggccacgg cagggacacg cggaaccaag acttggaaac
61 ttgattgttg tggttcttct tggggttat gaaatttcat taatcttttt tttttccggg
121 gagaaagttt ttggaaagat tcttccagat atttcttcat tttcttttgg aggaccgact
181 tacttttttt ggtcttcttt attactcccc tccccccgtg ggacccgccg gacgcgtgga
241 ggagaccgta gctgaagctg attctgtaca gcgggacagc gctttctgcc cctgggggag
301 caacccctcc ctcgcccctg ggtcctacgg agcctgcact ttcaagaggt acagcggcat
361 cctgtggggg cctgggcacc gcaggaagac tgcacagaaa ctttgccatt gttggaacgg
421 gacgttgctc cttccccgag cttccccgga cagcgtactt tgaggactcg ctcagctcac
481 cggggactcc cacggctcac cccggacttg caccttactt ccccaacccg gccatagcct
541 tggcttcccg gcgacctcag cgtggtcaca ggggcccccc tgtgcccagg gaaatgtttc
601 aggctttccc cggagactac gactccggct cccggtgcag ctcctcaccc tctgccgagt
661 ctcaatatct gtcttcggtg gactccttcg gcagtccacc caccgccgcg gcctcccagg
721 agtgcgccgg tctcggggaa atgcccggtt ccttcgtgcc cacggtcacc gcgatcacaa
781 ccagccagga cctccagtgg cttgtgcaac ccaccctcat ctcttccatg gcccagtccc
841 aggggcagcc actggcctcc cagccccccgg tcgtcgaccc ctacgacatg ccgggaacca
901 gctactccac accaggcatg agtggctaca gcagtggcgg agcgagtggc agtggtgggc
961 cttccaccag cggaactacc agtgggcctg ggcctgcccg cccagcccga gcccggccta
1021 ggagaccccg agaggagacg ctcaccccag aggaagagga gaagcgaagg gtgcgccggg
1081 aacgaaataa actagcagca gctaaatgca ggaaccggcg gagggagctg accgaccgac
1141 tccaggcgga gacagatcag ttggaggaag aaaaagcaga gctggagtcg gagatcgccg
1201 agctccaaaa ggagaaggaa cgtctggagt ttgtgctggt ggcccacaaa ccgggctgca
1261 agatccccta cgaagagggg cccgggccgg gcccgctggc ggaggtgaga gatttgccgg
1321 gctcagcacc ggctaaggaa gatggcttca gctggctgct gccgcccccg ccaccaccgc
1381 ccctgcccctt ccagaccagc caagacgcac cccccaacct gacggcttct ctctttacac
1441 acagtgaagt tcaagtcctc ggcgacccct tccccgttgt taacccttcg tacacttctt
1501 cgtttgtcct cacctgcccg gaggtctccg cgttcgccgg cgcccaacgc accagcggca
1561 gtgaccagcc ttccgatccc ctgaactcgc cctccctcct cgctcggtga actctttaga
1621 cacacaaaac aaacaaacac atgggggaga gagacttgga agaggaggag gaggaggaga
1681 aggaggagag agaggggaag agacaaagtg ggtgtgtggc ctccctggct cctccgtctg
1741 accctctgcg gccactgcgc cactgccatc ggacaggagg attccttgtg ttttgtcctg
1801 cctcttgttt ctgtgccccg gcgaggccgg agagctggtg actttgggga caggggggtgg
1861 gaaggggatg gacaccccca gctgactgtt ggctctctga cgtcaaccca agctctgggg
1921 atgggtgggg agggggggcgg gtgacgccca ccttcgggca gtcctgtgtg aggatgaagg
1981 gacgggggtg ggaggtaggc tgtggggtgg gctggagtcc tctccagaga ggctcaacaa
2041 ggaaaaatgc cactccctac ccaatgtctc ccacacccac cctttttttg gggtgcccag
2101 gttggtttcc cctgcactcc cgaccttagc ttattgatcc cacatttcca tggtgtgaga
2161 tcctctttac tctgggcaga agtgagcccc cccttaaagg gaattcgatg ccccccctaga
2221 ataatctcat ccccccaccc gacttctttt gaaatgtgaa cgtccttcct tgactgtcta
2281 gccactccct cccagaaaaa ctggctctga ttggaatttc tggcctccta aggctcccca
2341 ccccgaaatc agcccccagc cttgtttctg atgacagtgt tatcccaaga ccctgccccc
2401 tgccagccga ccctcctggc cttcctcgtt gggccgctct gatttcaggc agcaggggct
2461 gctgtgatgc cgtcctgctg gagtgattta tactgtgaaa tgagttggcc agattgtggg
2521 gtgcagctgg gtggggcagc acacctctgg ggggataatg tccccactcc cgaaagcctt
2581 tcctcggtct cccttccgtc catccccctt cttcctcccc tcaacagtga gttagactca
2641 agggggtgac agaaccgaga agggggtgac agtcctccat ccacgtggcc tctctctctc
2701 tcctcaggac cctcagccct ggcctttttc tttaaggtcc cccgaccaat ccccagccta

FIG. 10 A-53

```
2761 ggacgccaac ttctcccacc ccttggcccc tcacatcctc tccaggaagg cagtgagggg
2821 ctgtgacatt tttccggaga agatttcaga gctgaggctt tggtaccccc aaacccccaa
2881 tatttttgga ctggcagact caaggggctg gaatctcatg attccatgcc cgagtccgcc
2941 catccctgac catggttttg gctctcccac cccgccgttc cctgcgcttc atctcatgag
3001 gatttcttta tgaggcaaat ttatattttt taatatcggg gggtggacca cgccgccctc
3061 catccgtgct gcatgaaaaa cattccacgt gccccttgtc gcgcgtctcc catcctgatc
3121 ccagacccat tccttagcta tttatccctt tcctggtttc cgaaaggcaa ttatatctat
3181 tatgtataag taaatatatt atatatggat gtgtgtgtgt gcgtgcgcgt gagtgtgtga
3241 gcgcttctgc agcctcggcc taggtcacgt tggccctcaa agcgagccgt tgaattggaa
3301 actgcttcta gaaactctgg ctcagcctgt ctcgggctga cccttttctg atcgtctcgg
3361 cccctctgat tgttcccgat ggtctctctc cctctgtctt ttctcctccg cctgtgtcca
3421 tctgaccgtt ttcacttgtc tcctttctga ctgtccctgc caatgctcca gctgtcgtct
3481 gactctgggt tcgttgggga catgagattt tattttttgt gagtgagact gagggatcgt
3541 agatttttac aatctgtatc tttgacaatt ctgggtgcga gtgtgagagt gtgagcaggg
3601 cttgctcctg ccaaccacaa ttcaatgaat ccccgacccc cctaccccat gctgtacttg
3661 tggttctctt tttgtatttt gcatctgacc ccggggggct gggacagatt ggcaatgggc
3721 cgtcccctct ccccttggtt ctgcactgtt gccaataaaa agctcttaaa aacgc

SEQ ID NO:61
   1 agcgagcttg cagcctcacc gacgagtctc aactaaaagg gactcccgga gctaggggtg
  61 gggactcggc ctcacacagt gagtgccggc tattggactt ttgtccagtg acagctgaga
 121 caacaaggac cacgggagga ggtgtaggag agaagcgccg cgaacagcga tcgcccagca
 181 ccaagtccgc ttccaggctt tcggtttctt tgcctccatc ttgggtgcgc cttcccggcg
 241 tctaggggag cgaaggctga ggtggcagcg gcaggagagt ccggccgcga caggacgaac
 301 tcccccactg gaaaggattc tgaaagaaat gaagtcagcc ctcagaaatg aagttgactg
 361 cctgctggct ttctgttgac tggcccggag ctgtactgca agacccttgt gagcttccct
 421 agtctaagag taggatgtct gctgaagtca tccatcaggt tgaagaagca cttgatacag
 481 atgagaagga gatgctgctc tttttgtgcc gggatgttgc tatagatgtg gttccaccta
 541 atgtcaggga ccttctggat attttacggg aaagaggtaa gctgtctgtc ggggacttgg
 601 ctgaactgct ctacagagtg aggcgatttg acctgctcaa acgtatcttg aagatggaca
 661 gaaaagctgt ggagacccac ctgctcagga accctcacct tgtttcggac tatagagtgc
 721 tgatggcaga gattggtgag gatttggata aatctgatgt gtcctcatta attttcctca
 781 tgaaggatta catgggccga ggcaagataa gcaaggagaa ggtttcttgg accttgtggt
 841 tgagttggag aaactaaatc tggttgcccc agatcaactg gatttattag aaaaatgcct
 901 aaagaacatc cacagaatag acctgaagac aaaaatccag aagtacaagc agtctgttca
 961 aggagcaggg acaagttaca ggaatgttct ccaagcagca atccaaaaga gtctcaagga
1021 tccttcaaat aacttcaggc tccataatgg gagaagtaaa gaacaaagac ttaaggaaca
1081 gcttggcgct caacaagaac cagtgaagaa atccattcag gaatcagaag ctttttttgcc
1141 tcagagcata cctgaagaga gatacaagat gaagagcaag cccctaggaa tctgcctgat
1201 aatcgattgc attggcaatg agacagagct tcttcgagac accttcactt ccctgggcta
1261 tgaagtccag aaattcttgc atctcagtat gcatggtata tcccagattc ttggccaatt
1321 tgcctgtatg cccgagcacc gagactacga cagctttgtg tgtgtcctgg tgagccgagg
1381 aggctcccag agtgtgtatg gtgtggatca gactcactca gggctccccc tgcatcacat
1441 caggaggatg ttcatgggag attcatgccc ttatctagca gggaagccaa agatgttttt
1501 tattcagaac tatgtggtgt cagagggcca gctggaggac agcagcctct tggaggtgga
1561 tgggccagcg atgaagaatg tggaattcaa ggctcagaag cgagggctgt gcacagttca
1621 ccgagaagct gacttcttct ggagcctgtg tactgcggac atgtccctgc tggagcagtc
1681 tcacagctca ccatccctgt acctgcagtg cctctcccag aaactgagac aagaaagaaa
1741 acgcccactc ctggatcttc acattgaact caatggctac atgtatgatt ggaacagcag
1801 agtttctgcc aaggagaaat attatgtctg gctgcagcac actctgagaa agaaacttat
```

FIG. 10 A-54

```
1861 cctctcctac acataagaaa ccaaaaggct gggcgtagtg gctcacacct gtaatcccag
1921 cactttggga ggccaaggag ggcagatcac ttcaggtcag gagttcgaga ccagcctggc
1981 caacatggta aacgctgtcc ctagtaaaaa tacaaaaatt a

SEQ ID NO:62
   1 agagttgcac tgagtgtggc tgaagcagcg aggcgggagt ggaggtgcgc ggagtcaggc
  61 agacagacag acacagccag ccagccaggt cggcagtata gtccgaactg caaatcttat
 121 tttcttttca ccttctctct aactgcccag agctagcgcc tgtggctccc gggctggtgt
 181 ttcgggagtg tccagagagc ctggtctcca gccgccccccg ggaggagagc cctgctgccc
 241 aggcgctgtt gacagcggcg gaaagcagcg gtacccacgc gcccgccggg ggaagtcggc
 301 gagcggctgc agcagcaaag aactttcccg gctgggagga ccggagacaa gtggcagagt
 361 cccggagcca acttttgcaa gcctttcctg cgtcttaggc ttctccacgg cggtaaagac
 421 cagaaggcgg cggagagcca cgcaagagaa gaaggacgtg cgctcagctt cgctcgcacc
 481 ggttgttgaa cttgggcgag cgcgagccgc ggctgccggg cgccccctcc ccctagcagc
 541 ggaggagggg acaagtcgtc ggagtccggg cggccaagac ccgccgccgg ccggccactg
 601 cagggtccgc actgatccgc tccgcgggga gagccgctgc tctgggaagt gagttcgcct
 661 gcggactccg aggaaccgct gcgcacgaag agcgctcagt gagtgaccgc gacttttcaa
 721 agccgggtag cgcgcgcgag tcgacaagta agagtgcggg aggcatctta attaaccctg
 781 cgctccctgg agcgagctgg tgaggagggc gcagcgggga cgacagccag cgggtgcgtg
 841 cgctcttaga gaaactttcc ctgtcaaagg ctccgggggg cgcgggtgtc ccccgcttgc
 901 cacagccctg ttgcggcccc gaaacttgtg cgcgcagccc aaactaacct cacgtgaagt
 961 gacggactgt tctatgactg caaagatgga aacgaccttc tatgacgatg ccctcaacgc
1021 ctcgttcctc ccgtccgaga gcggacctta tggctacagt aaccccaaga tcctgaaaca
1081 gagcatgacc ctgaacctgg ccgacccagt ggggagcctg aagccgcacc tccgcgccaa
1141 gaactcggac ctcctcacct cgcccgacgt ggggctgctc aagctggcgt cgcccgagct
1201 ggagcgcctg ataatccagt ccagcaacgg gcacatcacc accacgccga cccccaccca
1261 gttcctgtgc cccaagaacg tgacagatga gcaggagggc ttcgccgagg gcttcgtgcg
1321 cgccctggcc gaactgcaca gccagaacac gctgcccagc gtcacgtcgg cggcgcagcc
1381 ggtcaacggg gcaggcatgg tggctcccgc ggtagcctcg gtggcagggg gcagcggcag
1441 cggcggcttc agcgccagcc tgcacagcga gccgccggtc tacgcaaacc tcagcaactt
1501 caacccaggc gcgctgagca gcggcggcgg ggcgccctcc tacggcgcgg ccggcctggc
1561 ctttcccgcg caaccccagc agcagcagca gccgccgcac cacctgcccc agcagatgcc
1621 cgtgcagcac ccgcggctgc aggccctgaa ggaggagcct cagacagtgc ccgagatgcc
1681 cggcgagaca ccgcccctgt cccccatcga catggagtcc caggagcgga tcaaggcgga
1741 gaggaagcgc atgaggaacc gcatcgctgc ctccaagtgc cgaaaaagga agctggagag
1801 aatcgcccgg ctggaggaaa aagtgaaaac cttgaaagct cagaactcgg agctggcgtc
1861 cacggccaac atgctcaggg aacaggtggc acagcttaaa cagaaagtca tgaaccacgt
1921 taacagtggg tgccaactca tgctaacgca gcagttgcaa acattttgaa gagagaccgt
1981 cgggggctga ggggcaacga agaaaaaaaa taacacagag agacagactt gagaacttga
2041 caagttgcga cggagagaaa aaagaagtgt ccgagaacta aagccaaggg tatccaagtt
2101 ggactgggtt gcgtcctgac ggcgccccca gtgtgcacga gtgggaagga cttggcgcgc
2161 cctcccttgg cgtggagcca gggagcggcc gcctgcgggc tgccccgctt tgcggacggg
2221 ctgtccccgc gcgaacggaa cgttggactt ttcgttaaca ttgaccaaga actgcatgga
2281 cctaacattc gatctcattc agtattaaag gggggagggg gagggggtta caaactgcaa
2341 tagagactgt agattgcttc tgtagtactc cttaagaaca caaagcgggg ggagggttgg
2401 ggaggggcgg caggagggag gtttgtgaga gcgaggctga gcctacagat gaactctttc
2461 tggcctgcct tcgttaactg tgtatgtaca tatatatatt ttttaatttg atgaaagctg
2521 attactgtca ataaacagct tcatgccttt gtaagttatt tcttgtttgt ttgtttgggt
2581 atcctgccca gtgttgtttg taaataagag atttggagca ctctgagttt accatttgta
2641 ataaagtata taattttttt atgttttgtt tctgaaaatt ccagaaagga tatttaagaa
```

FIG. 10 A-55

2701 aatacaataa actattggaa agtactcccc taacctcttt tctgcatcat ctgtagatac
2761 tagctatcta ggtggagttg aaagagttaa gaatgtcgat taaaatcact ctcagtgctt
2821 cttactatta agcagtaaaa actgttctct attagacttt agaaataaat gtacctgatg
2881 tacctgatgc tatggtcagg ttatactcct cctcccccag ctatctatat ggaattgctt
2941 accaaaggat agtgcgatgt ttcaggaggc tggaggaagg ggggttgcag tggagaggga
3001 cagcccactg agaagtcaaa catttcaaag tttggattgt atcaagtggc atgtgctgtg
3061 accatttata atgttagtag aaattttaca ataggtgctt attctcaaag caggaattgg
3121 tggcagattt tacaaaagat gtatccttcc aatttggaat cttctctttg acaattccta
3181 gataaaaaga tggcctttgc ttatgaatat ttataacagc attcttgtca caataaatgt
3241 attcaaatac caat SEQ ID NO:63
1 gtggagctac cgccaccgcc gccgccgatt ccggagccgg ggtagtcgcc gccgccgccg
61 ccgctgcagc cactgcaggc accgctgccg ccgcctgagt agtgggctta ggaaggaaga
121 ggtcatctcg ctcggagctt cgctcggaag ggtctttgtt ccctgcagcc ctcccacggg
181 aatgacaatg gataaaagtg agctggtaca gaaagccaaa ctcgctgagc aggctgagcg
241 atatgatgat atggctgcag ccatgaaggc agtcacagaa caggggcatg aactctccaa
301 cgaagagaga aatctgctct ctgttgccta caagaatgtg gtaggcgccc gccgctcttc
361 ctggcgtgtc atctccagca ttgagcagaa aacagagagg aatgagaaga agcagcagat
421 gggcaaagag taccgtgaga agatagaggc agaactgcag gacatctgca atgatgttct
481 ggagctgttg gacaaatatc ttattcccaa tgctacacaa ccagaaagta aggtgttcta
541 cttgaaaatg aaaggagatt attttaggta tctttctgaa gtggcatctg gagacaacaa
601 acaaaccact gtgtcgaact cccagcaggc ttaccaggaa gcatttgaaa ttagtaagaa
661 agaaatgcag cctacacacc caattcgtct tggtctggca ctaaatttct cagtctttta
721 ctatgagatt ctaaactctc ctgaaaaggc ctgtagcctg gcaaaaacgg catttgatga
781 agcaattgct gaattggata cgctgaatga agagtcttat aaagacagca ctctgatcat
841 gcagttactt agggacaatc tcactctgtg gacatcggaa aaccagggag acgaaggaga
901 cgctggggag ggagagaact aatgtttctc gtgctttgtg atctgttcag tgtcactctg
961 taccctcaac atatatccct tgtgcgat SEQ ID NO:64
1 gtgccgctcc ttggtggggg ctgttcatgg cggttccggg gtctccaaca tttttcccgg
61 ctgtggtcct aaatctgtcc aaagcagagg cagtggagct tgaggttctt gctggtgtga
121 aatgactgag tacaaactgg tggtggttgg agcaggtggt gttgggaaaa gcgcactgac
181 aatccagcta atccagaacc actttgtaga tgaatatgat cccaccatag aggattctta
241 cagaaaacaa gtggttatag atggtgaaac ctgtttgttg gacatactgg atacagctgg
301 acaagaagag tacagtgcca tgagagacca atacatgagg acaggcgaag gcttcctctg
361 tgtatttgcc atcaataata gcaagtcatt tgcggatatt aacctctaca gggagcagat
421 taagcgagta aaagactcgg atgatgtacc tatggtgcta gtgggaaaca agtgtgattt
481 gccaacaagg acagttgata caaaacaagc ccacgaactg gccaagagtt acgggattcc
541 attcattgaa acctcagcca agaccagaca gggtgttgaa gatgcttttt acacactggt
601 aagagaaata cgccagtacc gaatgaaaaa actcaacagc agtgatgatg ggactcaggg
661 ttgtatggga ttgccatgtg tggtgatgta acaagatact tttaaagttt tgtcagaaaa
721 gagccacttt caagctgcac tgacaccctg gtcctgactt ccctggagga gaagtattcc
781 tgttgctgtc ttcagtctca cagagaagct cctgctactt ccccagctct cagtagttta
841 gtacaataat ctctatttga gaagttctca gaataactac ctcctcactt ggctgtctga
901 ccagagaatg cacctcttgt tactccctgt tatttttctg ccctgggttc ttccacagca
961 caaacacacc tctgccaccc caggtttttc atctgaaaag cagttcatgt ctgaaacaga
1021 gaaccaaacc gcaaacgtga aattctattg aaaacagtgt cttgagctct aaagtagcaa
1081 ctgctggtga tttttttttt ctttttactg ttgaacttag aactatgcta atttttggag

FIG. 10 A-56

```
1141 aaatgtcata aattactgtt ttgccaagaa tatagttatt attgctgttt ggtttgttta
1201 taatgttatc ggctctattc tctaaactgg catctgctct agattcataa atacaaaaat
1261 gaatactgaa ttttgagtct atcctagtct tcacaacttt gacgtaatta aatccaactt
1321 tcacagtgaa gtgccttttt cctagaagtg gtttgtagac ttcctttata atatttcagt
1381 ggaatagatg tctcaaaaat ccttatgcat gaaatgaatg tctgagatac gtctgtgact
1441 tatctaccat tgaaggaaag ctatatctat ttgagagcag atgccatttt gtacatgtat
1501 gaaattggtt ttccagaggc ctgttttggg gctttcccag gagaaagatg aaactgaaag
1561 cacatgaata atttcactta ataattttta cctaatctcc actttttca taggttacta
1621 cctatacaat gtatgtaatt tgtttcccct agcttactga taaacctaat attcaatgaa
1681 cttccatttg tattcaaatt tgtgtcatac cagaaagctc tacatttgca gatgttcaaa
1741 tattgtaaaa ctttggtgca ttgttattta atagctgtga tcagtgattt tcaaacctca
1801 aatatagtat attaacaaat tacattttca ct
```

SEQ ID NO:65

```
   1 atgaaggtga taagcttatt cattttggtg ggatttatag gagagttcca aagtttttca
  61 agtgcctcct ctccagtcaa ctgccagtgg gacttctatg ccccttggtc agaatgcaat
 121 ggctgtacca agactcagac tcgcaggcgg tcagttgctg tgtatgggca gtatggaggc
 181 cagccttgtg ttggaaatgc ttttgaaaca cagtcctgtg aacctacaag aggatgtcca
 241 acagaggagg gatgtggaga gcgtttcagg tgcttttcag gtcagtgcat cagcaaatca
 301 ttggtttgca atggggattc tgactgtgat gaagacagtg ctgatgaaga cagatgtgag
 361 gactcagaaa ggagaccttc ctgtgatatc gataaacctc ctcctaacat agaacttact
 421 ggaaatggtt acaatgaact cactggccag tttaggaaca gagtcatcaa taccaaaagt
 481 tttggtggtc aatgtagaaa ggtgtttagt ggggatggaa aagatttcta caggctgagt
 541 ggaaatgtcc tgtcctatac attccaggtg aaaataaata atgattttaa ttatgaattt
 601 tacaatagta cttggtctta tgtaaaacat acgtcgacag aacacacatc atctagtcgg
 661 aagcgctcct tttttagatc ttcatcatct tcttcacgca gttatacttc acataccaat
 721 gaaatccata aaggaaagag ttaccaactg ctggttgttg agaacactgt tgaagtggct
 781 cagttcatta ataacaatcc agaattttta caacttgctg agccattctg gaaggagctt
 841 tcccacctcc cctctctgta tgactacagt gcctaccgaa gattaatcga ccagtacggg
 901 acacattatc tgcaatctgg gtcgttagga ggagaataca gagttctatt ttatgtggac
 961 tcagaaaaat taaaacaaaa tgattttaat tcagtcgaag aaaagaaatg taaatcctca
1021 ggttggcatt ttgtcgttaa atttcaagt catggatgca aggaactgga aaacgcttta
1081 aaagctgctt caggaaccca gaacaatgta ttgcgaggag aaccgttcat cagaggggga
1141 ggtgcaggct tcatatctgg ccttagttac ctagagctgg acaatcctgc tggaaacaaa
1201 aggcgatatt ctgcctgggc agaatctgtg actaatcttc ctcaagtcat aaaacaaaag
1261 ctgacacctt tatatgagct ggtaaaggaa gtaccttgtg cctctgtgaa aaaactatac
1321 ctgaaatggg ctcttgaaga gtatctggat gaatttgacc cctgtcattg ccggccttgt
1381 caaaatggtg gtttggctac tgttgagggg acccattgtc tgtgccattg caaaccgtac
1441 acatttggtg cggcgtgtga gcaaggagtc ctcgtaggga atcaagcagg aggggttgat
1501 ggaggttgga gttgctggtc ctcttggagc ccctgtgtcc aagggaagaa aacaagaagc
1561 cgtgaatgca ataacccacc tcccagtggg ggtgggagat cctgcgttgg agaaacgaca
1621 gaaagcacac aatgcgaaga tgaggagctg gagcacttga ggttgcttga accacattgc
1681 tttcctttgt ctttggttcc aacagaattc tgtccatcac ctcctgcctt gaaagatgga
1741 tttgttcaag atgaaggtcc aatgtttcct gtggggaaaa atgtagtgta cacttgcaat
1801 gaaggatact ctcttattgg aaacccagtg gccagatgtg gagaagattt acggtggctt
1861 gttggggaaa tgcattgtca gaaaattgcc tgtgttctac ctgtactgat ggatggcata
1921 cagagtcacc cccaaaaacc tttctacaca gttggtgaga aggtgactgt ttcctgttca
1981 ggtggcatgt ccttagaagg tccttcagca tttctctgtg gctccagcct taagtggagt
2041 cctgagatga agaatgcccg ctgtgtacaa aaagaaaatc cgttaacaca ggcagtgcct
2101 aaatgtcagc gctgggagaa actgcagaat tcaagatgtg tttgtaaaat gccctacgaa
```

FIG. 10 A-57

```
2161 tgtggacctt ccttggatgt atgtgctcaa gatgagagaa gcaaaaggat actgcctctg
2221 acagtttgca agatgcatgt tctccactgt cagggtagaa attacaccct tactggtagg
2281 gacagctgta ctctgcctgc ctcagctgag aaagcttgtg gtgcctgccc actgtgggga
2341 aaatgtgatg ctgagagcag caaatgtgtc tgccgagaag catcggagtg cgaggaagaa
2401 gggtttagca tttgtgtgga agtgaacggc aaggagcaga cgatgtctga gtgtgaggcg
2461 ggcgctctga gatgcagagg gcagagcatc tctgtcacca gcataaggcc ttgtgctgcg
2521 gaaacccagt aggctcctgg aggccatggt cagcttgctt ggaatccagc aggcagctgg
2581 ggctgagtga aaacatctgc acaactgggc actggacagc ttttccttct tctccagtgt
2641 ctaccttcct cctcaactcc cagccatctg tataaacaca atcctttgtt ctcccaaatc
2701 tgaatcgaat tactcttttg cctccttttt aatgtcagta aggatatgag cctttgcaca
2761 ggctggctgc gtgttcttga aataggtgtt accttctctg ggccttggtt ttttaaaatc
2821 tgtaaaatta gaggattgca ctagagaaac ttgaatgctc cattcaggcc tatcatttta
2881 ttaagtatga ttgacacagc ccatgggcca gaacacactc tacaaaatga ctaggataac
2941 agaaagaacg tgatctcctg attagagagg gtggttttcc tcaatggaac caaatataaa
3001 gaggacttga acaaaaatga cagatacaaa ctatttctat cctgagtagt aatctcacac
3061 ttcatcctat agagtcaacc accacagata ggaattcctt attctttttt taattttttt
3121 aagacagagt ctcactttgt tgcccaggct ggagcgcagt ggggtgatct catctccctg
3181 caacctccgc ctcctgggtt gaagcgattc ttgtgcctca gcttcccaag cagctgggat
3241 tacaggtgcc cgccaccacg cccagctaat ttttgcattt ttagtagaga tgggtttcac
3301 catgttggcc atgctcgtct ccaactcctg acctcaggta atccgtctgc cttggcctcc
3361 caaatgctgg gattacagac atgaaccacc acgcctggct ggaatactta ctcttgtcgg
3421 gagattgaac cactaaaatg ttagagcaga attcattatg ctgtggtcac aggggtgtct
3481 tgtctgagaa caaatacaat tcagtcttct ctttggggtt ttagtatgtg tcaaacatag
3541 gactggaagt ttgcccctgt tctttttctt tttgaaagaa catcagttca tgcctgaggc
3601 atgagtgact gtgcatttga gatagttttc cctattctgt ggatacagtc ccagagtttt
3661 cagggagtac acaggtagat tagtttgaag cattgacctt ttatttattc cttatttctc
3721 tttcatcaaa acaaaacagc agctgtggga ggagaaatga gagggcttaa atgaaattta
3781 aaataagcta tattatacaa atactatctc tgtattgttc tgaccctggt aaatatattt
3841 caaaacttca gatgacaagg attagaacac tcattaagat gctattcttc
```

SEQ ID NO:66

```
  1 ctaacccaga aacatccaat tctcaaactg aagctcgcac tctcgcctcc agcatgaaag
 61 tctctgccgc ccttctgtgc ctgctgctca tagcagccac cttcattccc caagggctcg
121 ctcagccaga tgcaatcaat gccccagtca cctgctgtta taacttcacc aataggaaga
181 tctcagtgca gaggctcgcg agctatagaa gaatcaccag cagcaagtgt cccaaagaag
241 ctgtgatctt caagaccatt gtggccaagg agatctgtgc tgaccccaag cagaagtggg
301 ttcaggattc catggaccac ctggacaagc aaacccaaac tccgaagact tgaacactca
361 ctccacaacc caagaatctg cagctaactt attttcccct agctttcccc agacaccctg
421 ttttatttta ttataatgaa ttttgtttgt tgatgtgaaa cattatgcct taagtaatgt
481 taattcttat ttaagttatt gatgttttaa gtttatcttt catggtacta gtgtttttta
541 gatacagaga cttggggaaa ttgcttttcc tcttgaacca cagttctacc cctgggatgt
601 tttgagggtc tttgcaagaa tcattaatac aaagaatttt ttttaacatt ccaatgcatt
661 gctaaaatat tattgtggaa atgaatattt tgtaactatt acaccaaata aatatatttt
721 tgtac
```

SEQ ID NO:67

```
  1 ttcaatgttg atgtgaaaaa ttcaatgact ttcagcggcc cggtggaaga catgtttgga
 61 tatactgttc aacaatatga aaatgaagaa ggaaaatggg tgcttattgg ttctccgtta
121 gttggccaac ccaaaaacag aactggagat gtctataagt gtccagttgg gagaggtgaa
181 tcattacctt gcgtaaagtt ggatctacca gttaatacat caattcccaa tgtcacagaa
```

FIG. 10 A-58

```
 241 gtaaaggaga acatgacatt tggatcaact ttagtcacca acccaaatgg aggatttctg
 301 gcttgtgggc ccttatatgc ctatagatgt ggacatttgc attacacaac tggaatctgt
 361 tctgacgtca gccccacatt tcaagtcgtg aattccattg cccctgtaca agaatgcagc
 421 actcaactgg acatagtcat agtgctggat ggttccaaca gtatttaccc atgggacagt
 481 gttacagctt ttttaaatga ccttcttgaa agaatggata ttggtcctaa acagacacag
 541 gttggaattg tacagtatgg agaaaacgtg acccatgagt tcaacctcaa taagtattct
 601 tccaccgaag aggtacttgt tgcagcaaag aaaatagtcc agagaggtgg ccgccagact
 661 atgacagctc ttggaataga cacagcaaga aaggaggcat tcacggaagc ccggggtgcc
 721 cgaagaggag ttaaaaaagt catggttatt gtgacagatg gagagtctca tgacaatcat
 781 cgactgaaga aggtcatcca agactgtgaa gatgaaaaca ttcaacggtt ttccatagct
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnctt catatgaaat ggaaatgtct cagactggct tcagtgctca ttattcacag
1081 nnnnnnnnnn nnnnnnnnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnnnnn
1201 nnnnnnnnnn nnnnnnnnnn nnnnngttac actgtaaact ctgctactgc ttcttctgga
1261 gatgtgctct atattgctgg acagcctcgg tacaatcata caggccaggt cattatctac
1321 aggatggaag atggaaacat caaaattctc cagacgctca gtggagaaca gattggttcc
1381 tactttggca gtattttaac aacaactgac attgacaagg attctaatac tgacattctt
1441 ctagtcggag cccctatgta catgggaaca gagaaggagg agcaaggaaa agtgtatgtg
1501 tatgctctca atcagacaag gtttgaatat caaatgagcc tggaacctat taagcagacg
1561 tgctgttcat ctcggcagca caattcatgc acaacagaaa acaaaaatga gccatgcggg
1621 gctcgttttg gaactgcaat tgctgctgta aaagacctca atcttgatgg atttaatgac
1681 atcgtgatag gagctccgct ggagatgatc acgggggagc tgtgtacatt tatcatggaa
1741 gtggcaagac tataaggaaa gagtatgcac aacgtattcc atcaggtggg gatggtaaga
1801 cactgaaatt ttttggccag tctatccacg gagaaatgga tttaaatggt gacggtctga
1861 cagatgtgac tattgggggc cttggtggtg ctgccctctt ctggtcccga gatgtggccg
1921 tagttaaagt gaccatgaat tttgagccaa ataaagtgaa tattcaaaag aaaaactgcc
1981 atatggaggg aaaggaaaca gtatgcataa atgctacagt gtgttttgat gtgaaattaa
2041 agtctaaaga agacacgatt tatgaagctg atttgcagta ccgtgtcacc ctagattcac
2101 taagacaaat atcacgaagt tttttctctg gaactcaaga gagaaaggtt caaaggaaca
2161 tcacagttcg aaaatcagaa tgcactaagc actccttcta catgttgaca agcatgactt
2221 tcaggactct gtgagaataa cgttggactt taatcttacc gatccagaaa atgggcctgt
2281 tcttgatgat tctctaccaa actcagtaca tgaatatatt ccctttgcca aagattgtgg
2341 aaataaggaa aaatgtatct cagacctcag cctgcatgtc gccaccactg aaaaggacct
2401 gctgattgtc cgatcccaga atgataagtt caacgttagc ctcacagtca aaaatacaaa
2461 ggacagtgcc tataacacca ggacaatagt gcattattct ccaaatctag tttttttcagg
2521 aattgaggct atccaaaaag acagttgtga atctaatcat aatatcacat gtaaagttgg
2581 atatcccttc ctgagaagag gagagatggt aactttcaaa atattgtttc agtttaacac
2641 atcctatctc atggaaaatg tgaccattta tttaagtgca acaagtgaca gcgaagaacc
2701 tcctgaaacc ctttctgata atgtagtaaa catttctatc ccggtaaaat atgaagttgg
2761 actacagttt tacagctctg caagtgaata ccacatttca attgctgcca atgagacagt
2821 ccctgaagtt attaattcta ctgaggacat tggaaatgaa attaatatct tctacttgat
2881 tagaaaaagt ggatcttttc caatgccaga gcttaagctg tcaatttcat tccccaatat
2941 gacatcaaat ggttaccctg tgctgtaccc aactggattg tcatcttctg agaatgcaaa
3001 ctgcagaccc catatctttg aggatccttt cagtatcaac tctggaaaga aaatgactac
3061 atcaactgac catctcaaac gaggcacaat tctggactgc aatacatgta aatttgctac
3121 catcacatgt aatctcactt cttctgacat cagccaagtc aatgtttcgc ttatcttgtg
3181 gaaaccaact tttataaaat catatttttc cagcttaaat cttactataa ggggagaact
3241 tcggagtgaa aatgcatctc tggttttaag tagcagcaat caaaaaagag agcttgctat
```

FIG. 10 A-59

```
3301 tcaaatatcc aaagatgggc taccgggcag agtgccatta tgggtcatcc tgctgagtgc
3361 ttttgccgga ttgttgctgt taatgctgct cattttagca ctgtggaaga ttggattctt
3421 caaaagacca ctgaaaaaga aaatggagaa a
```

SEQ ID NO:68

```
   1 gtatcactca gaatctggca gccagttccg tcctgacaga gttcacagca tatattggtg
  61 gattcttgtc catagtgcat ctgctttaag aattaacgaa agcagtgtca agacagtaag
 121 gattcaaacc atttgccaaa aatgagtcta agtgcattta ctctcttcct ggcattgatt
 181 ggtggtacca gtggccagta ctatgattat gattttcccc tatcaattta tgggcaatca
 241 tcaccaaact gtgcaccaga atgtaactgc cctgaaagct acccaagtgc catgtactgt
 301 gatgagctga aattgaaaag tgtaccaatg gtgcctcctg gaatcaagta tctttacctt
 361 aggaataacc agattgacca tattgatgaa aaggcctttg agaatgtaac tgatctgcag
 421 tggctcattc tagatcacaa ccttctagaa aactccaaga taaaagggag agttttctct
 481 aaattgaaac aactgaagaa gctgcatata aaccacaaca acctgacaga gtctgtgggc
 541 ccacttccca aatctctgga ggatctgcag cttactcata acaagatcac aaagctgggc
 601 tcttttgaag gattggtaaa cctgaccttc atccatctcc agcacaatcg gctgaaagag
 661 gatgctgttt cagctgcttt taaaggtctt aaatcactcg aataccttga cttgagcttc
 721 aatcagatag ccagactgcc ttctggtctc cctgtctctc ttctaactct ctacttagac
 781 aacaataaga tcagcaacat ccctgatgag tatttcaagc gttttaatgc attgcagtat
 841 ctgcgtttat ctcacaacga actggctgat agtggaatac ctggaaattc tttcaatgtg
 901 tcatccctgg ttgagctgga tctgtcctat aacaagctta aaaacatacc aactgtcaat
 961 gaaaaccttg aaaactatta cctggaggtc aatcaacttg agaagtttga cataaagagc
1021 ttctgcaaga tcctggggcc attatcctac tccaagatca agcatttgcg tttggatggc
1081 aatcgcatct cagaaaccag tcttccaccg gatatgtatg aatgtctacg tgttgctaac
1141 gaagtcactc ttaattaata tctgtatcct ggaacaatat tttatggtta tgtttttctg
1201 tgtgtcagtt ttcatagtat ccatatttta ttactgttta ttacttccat gaattttaaa
1261 atctgaggga aatgttttgt aaacatttat ttttttaaa gaaaagatga aaggcaggcc
1321 tatttcatca caagaacaca cacatataca cgaatagaca tcaaactcaa tgctttattt
1381 gtaaatttag tgttttttta tttctactgt caaatgatgt gcaaaacctt ttactggttg
1441 catggaaatc agccaagttt tataatcctt aaatcttaat gttcctcaaa gcttggatta
1501 aatacatatg gatgttactc tcttgcacca aattatcttg atacattcaa atttgtctgg
1561 ttaaaaaata ggtggtagat attgaggcca agaatattgc aaaatacatg aagcttcatg
1621 cacttaaaga agtattttta gaataagaat ttgcatactt acctagtgaa acttttctag
1681 aattattttt cactctaagt catgtatgtt tctctttgat tatttgcatg ttatgtttaa
1741 taagctacta gcaaaataaa acatagcaaa tg
```

SEQ ID NO:69

```
   1 tggacagagg agcagtaaca atccccactc tccaattgtg gaagagttcc aagtcccata
  61 caacaaactc caggtgatct ttaagtcaga cttttccaat gaagagcgtt ttacggggtt
 121 tgctgcatac tatgttgcca cagacataaa tgaatgcaca gattttgtag atgtcccttg
 181 tagccacttc tgcaacaatt tcattggtgg ttacttctgc tcctgccccc cggaatattt
 241 cctccatgat gacatgaaga attgcggagt taattgcagt ggggatgtat tcactgcact
 301 gattggggag attgcaagtc ccaattatcc caaaccatat ccagagaact caaggtgtga
 361 ataccagatc cggttggaga aagggttcca agtggtggtg accttgcgga gagaagattt
 421 tgatgtggaa gcagctgact cagcgggaaa ctgccttgac agtttagttt ttgttgcagg
 481 agatcggcaa tttggtcctt actgtggtca tggattccct gggcctctaa atattgaaac
 541 caagagtaat gctcttgata tcatcttcca aactgatcta acagggcaaa aaaagggctg
 601 gaaacttcgc tatcatggag atccaatgcc ctgccctaag gaagacactc ccaattctgt
 661 ttgggagcct gcgaaggcaa aatatgtctt tagagatgtg gtgcagataa cctgtctgga
 721 tgggtttgaa gttgtggagg gacgtgttgg tgcaacatct ttctattcga cttgtcaaag
```

FIG. 10 A-60

```
 781 caatggaaag tggagtaatt ccaaactgaa atgtcaacct gtggactgtg gcattcctga
 841 atccattgag aatggtaaag ttgaagaccc agagagcact ttgtttggtt ctgtcatccg
 901 ctacacttgt gaggagccat attactacat ggaaaatgga ggaggtgggg agtatcactg
 961 tgctggtaac gggagctggg tgaatgaggt gctgggcccg gagctgccga aatgtgttcc
1021 aggtctgtgg agtccccaga gaaccctttg aagaaaaaca gaggataatt ggaggatccg
1081 atgcagatat taaaaacttc ccctggcaag tcttctttga caacccatgg gctggtggag
1141 cgctcattaa tgagtactgg gtgctgacgg ctgctcatgt tgtggaggga aacagggagc
1201 caacaatgta tgttgggtcc acctcagtgc agacctcacg gctggcaaaa tccaagatgc
1261 tcactcctga gcatgtgttt attcatccgg gatggaagct gctggaagtc ccagaaggac
1321 gaaccaattt tgataatgac attgcactgg tgcggctgaa agacccagtg aaaatgggac
1381 ccaccgtctc tcccatctgc ctaccaggca cctcttccga ctacaacctc atggatgggg
1441 acctgggact gatctcaggc tggggccgaa cagagaagag agatcgtgct gttcgcctca
1501 aggcggcaag gttacctgta gctcctttaa gaaaatgcaa agaagtgaaa gtggagaaac
1561 ccacagcaga tgcagaggcc tatgttttca ctcctaacat gatctgtgct ggaggagaga
1621 agggcatgga tagctgtaaa ggggacagtg gtggggcctt tgctgtacag gatcccaatg
1681 acaagaccaa attctacgca gctggcctgg tgtcctgggg gccccagtgt gggacctatg
1741 ggctctacac acgggtaaag aactatgttg actggataat gaagactatg caggaaaata
1801 gcaccccccg tgaggactaa tccagataca tcccaccagc ctctccaagg gtggtgacca
1861 atgcattacc ttctgttcct tatgatattc tcattatttc atcatgactg aaagaagaca
1921 cgagcgaatg atttaaatag aacttgattg ttgagacgcc ttgctagagg tagagtttga
1981 tcatagaatt gtgctggtca tacatttgtg gtctgactcc ttggggtcct ttccccggag
2041 tacctattgt agataacact atgggtgggg cactcctttc ttgcactatt ccacagggat
2101 accttaattc tttgtttcct ctttacctgt tcaaaattcc atttacttga tcattctcag
2161 tatccactgt ctatgtacaa taaaggatgt ttataagc
```

SEQ ID NO:70

```
   1 aaactctgat ctggggagga accaggacta catagatcaa ggcagttttc ttctttgaga
  61 aactatccca gatatcatca tagagtcttc tgctcttcct caactaccaa agaaaaacat
 121 cagcgaagca gcaggccatg caccccccaa aaactccatc tggggctctt catagaaaaa
 181 ggaaaatggc agcctggccc ttctccaggc tgtggaaagt ctctgatcca attctcttcc
 241 aaatgacctt gatcgctgct ctgttgcctg ctgttcttgg caattgtggt cctccaccca
 301 ctttatcatt tgctgccccg atggatatta cgttgactga gacacgcttc aaaactggaa
 361 ctactctgaa atacacctgc ctccctggct acgtcagatc ccattcaact cagacgctta
 421 cctgtaattc tgatggcgaa tgggtgtata acaccttctg tatctacaaa cgatgcagac
 481 acccaggaga gttacgtaat gggcaagtag agattaagac agatttatct tttggatcac
 541 aaatagaatt cagctgttca gaaggatttt tcttaattgg ctcaaccact agtcgttgtg
 601 aagtccaaga tagaggagtt ggctggagtc atcctctccc acaatgtgaa attgtcaagt
 661 gtaagcctcc tccagacatc aggaatggaa ggcacagcgg tgaagaaaat ttctacgcat
 721 acggcttttc tgtcacctac agctgtgacc cccgcttctc actcttgggc catgcctcca
 781 tttcttgcac tgtggagaat gaaacaatag gtgtttggag accaagccct cctacctgtg
 841 aaaaaatcac ctgtcgcaag ccagatgttt cacatgggga aatggtctct ggatttggac
 901 ccatctataa ttacaaagac actattgtgt ttaagtgcca aaaaggtttt gttctcagag
 961 gcagcagtgt aattcattgt gatgctgata gcaaatggaa tccttctcct cctgcttgtg
1021 agcccaatag ttgtattaat ttaccagaca ttccacatgc ttcctgggaa acatatccta
1081 ggccgacaaa agaggatgtg tatgttgttg ggactgtgtt aaggtaccgc tgtcatcctg
1141 gctacaaacc cactacagat gagcctacga ctgtgatttg tcagaaaaat ttgagatgga
1201 ccccatacca aggatgtgag gcgttatgtt gccctgaacc aaagctaaat aatggtgaaa
1261 tcactcaaca caggaaaagt cgtcctgcca atcactgtgt ttatttctat ggagatgaga
1321 tttcattttc atgtcatgag accagtaggt tttcagctat atgccaagga gatggcacgt
1381 ggagtccccg aacaccatca tgtggagaca tttgcaattt tcctcctaaa attgcccatg
1441 ggcattataa acaatctagt tcatacagct tttcaaaga agagattata tatgaatgtg
```

FIG. 10 A-61

```
1501 ataaaggcta cattctggtc ggacaggcga aactctcctg cagttattca cactggtcag
1561 ctccagcccc tcaatgtaaa gctctgtgtc ggaaaccaga attagtgaat ggaaggttgt
1621 ctgtggataa ggatcagtat gttgagcctg aaaatgtcac catccaatgt gattctggct
1681 atggtgtggt tggtccccaa agtatcactt gctctgggaa cagaacctgg tacccagagg
1741 tgcccaagtg tgagtgggag acccccgaag gctgtgaaca agtgctcaca ggcaaaagac
1801 tcatgcagtg tctcccaaac ccagaggatg tgaaaatggc cctggaggta tataagctgt
1861 ctctggaaat tgaacaactg gaactacaga gagacagcgc aagacaatcc actttggata
1921 aagaactata atttttctca aaagaaggag gaaaaggtgt cttgctggct tgcctcttgc
1981 aattcaatac agatcagttt agcaaatcta ctgtcaattt ggcagtgata ttcatcataa
2041 taaatatcta gaaatgataa tttgctaaag tttagtgctt tgagattgtg aaattattaa
2101 tcatcctctg tgtggctcat gtttttgctt ttcaacacac aaagcacaaa ttttttttcg
2161 attaaaaatg tatgtat
```

SEQ Id NO:71

```
  1 gccctgctgg ccctgctggt gctcccnnnn nnnnnnnnnn nnnnnnnnnn nnnggtcctc
 61 aaggcccacg tggtgacaaa ggtgaaacag gtgaacgtgg agctgctggc atcaaaggac
121 atcgaggatt ccctggtaat ccaggtgccc caggttctcc agggccctgc tggtcagcag
181 ggtgcaatcg gcagtccagg acctgcaggc cccagaggac ctgttggacc cagtggacct
241 cctggcaaag atggaaccag tggacatcca ggtcccattg gaccaccagg gcctcgaggt
301 aacagaggtg aaagaggatc tgagggctcc ccaggccacc cagggcaacc aggccctcct
361 ggacctcctg gtgcccctgg tccttgc
```

SEQ Id NO:72

```
   1 gggcgcgggg agagggcgcg ggagcggctc gcgcggcagg taccatgcgg acgcgcgagc
  61 ccggcgaggg ccccggcagg cccggtccct gctcgggggc gcgctgagac ggcgggtgag
 121 ctccacgaga gcgccgtcgc cacttcgggc caactttgcg attcccgaca gttaagcaat
 181 ggggagacat ttggctttgc tcctgcttct gctccttctc ttccaacatt ttggagacag
 241 tgatggcagc caacgacttg aacagactcc tctgcagttt acacacctcg agtacaacgt
 301 caccgtgcag gagaactctg cagctaagac ttatgtgggg catcctgtca agatgggtgt
 361 ttacattaca catccagcgt gggaagtaag gtacaaaatt gtttccggag acagtgaaaa
 421 cctgttcaaa gctgaagagt acattctcgg agacttttgc tttctaagaa taaggaccaa
 481 aggaggaaat acagctattc ttaatagaga agtgaaggat cactacacat tgatagtgaa
 541 agcacttgaa aaaaatacta atgtggaggc gcgaacaaag gtcagggtgc aggtgctgga
 601 tacaaatgac ttgagaccgt tattctcacc cacctcatac agcgtttctt tacctgaaaa
 661 cacagctata aggaccagta tcgcaagagt cagcgccacg gatgcagaca taggaaccaa
 721 cggggaattt tactacagtt ttaaagatcg aacagatatg tttgctattc acccaaccag
 781 tggtgtgata gtgttaactg gtagacttga ttacctagag accaagctct atgagatgga
 841 aatcctcgct gcggaccgtg gcatgaagtt gtatgggagc agtggcatca gcagcatggc
 901 caagctaacg gtgcacatcg aacaggccaa tgaatgtgct ccggtgataa cagcagtgac
 961 attgtcacca tcagaactgg acagggaccc agcatatgca attgtgacag tggatgactg
1021 cgatcagggt gccaatggtg acatagcatc tttaagcatc gtggcaggtg accttctcca
1081 gcagtttaga acagtgaggt cctttccagg gagtaaggag tataaagtca aagccatcgg
1141 tggcattgat tgggacagtc atcctttcgg ctacaatctc acactacagg ctaaagataa
1201 aggaactccg ccccagttct cttctgttaa agtcattcac gtgacttctc cacagttcaa
1261 agccgggcca gtcaagtttg aaaaggatgt ttacagagca gaaataagtg aatttgctcc
1321 tcccaacaca cctgtggtca tggtaaaggc cattcctgct tattcccatt tgaggtatgt
1381 ttttaaaagt acacctggaa aagctaaatt cagtttaaat tacaacactg gtctcatttc
1441 tattttagaa ccagttaaaa gacagcaggc agcccatttt gaacttgaag taacaacaag
1501 tgacagaaaa gcgtccacca aggtcttggt gaaagtctta ggtgcaaata gcaatccccc
1561 tgaatttacc cagacagcgt acaaagctgc ttttgatgag aacgtgccca ttggtactac
```

FIG. 10 A-62

```
1621 tgtcatgagc ctgagtgccg tagaccctga tgagggtgag aacgggtacg tgacatacag
1681 tatcgcaaat ttaaatcatg tgccgtttgc gattgaccat ttcactggtg ccgtgagtac
1741 gtcagaaaac ctggactacg aactgatgcc tcgggtttat actctgagga ttcgtgcatc
1801 agactggggc ttgccgtacc gccgggaagt cgaagtcctt gctacaatta ctctcaataa
1861 cttgaatgac aacacacctt tgtttgagaa aataaattgt gaagggacaa ttcccagaga
1921 tctaggcgtg ggagagcaaa taaccactgt ttctgctatt gatgcagatg aacttcagtt
1981 ggtacagtat cagattgaag ctggaaatga actggatttc tttagtttaa accccaactc
2041 gggggtattg tcattaaagc gatcgctaat ggatggctta ggtgcaaagg tgtctttcac
2101 agtctgagaa tcacagctac agatggagaa aattttgcca caccattata tatcaacata
2161 acagtggctg ccagtcacaa gctggtaaac ttgcagtgtg aagagactgg tgttgccaaa
2221 atgctggcag agaagctcct gcaggcaaat aaattacaca accagggaga ggtggaggat
2281 attttcttcg attctcactc tgtcaatgct cacataccgc agtttagaag cactcttccg
2341 actggtattc aggtaaagga aaaccagcct gtgggttcca gtgtaatttt catgaactcc
2401 actgaccttg acactggctt caatggaaaa ctggtctatg ctgtttctgg aggaaatgag
2461 gatagttgct tcatgattga tatggaaaca ggaatgctga aaattttatc tcctcttgac
2521 cgtgaaacaa cagacaaata caccctgaat attaccgtct atgaccttgg gataccccag
2581 aaggctgcgt ggcgtcttct acatgtcgtg gttgtcgatg ccaatgataa tccacccgag
2641 tttttacagg agagctattt tgtggaagtg agtgaagaca aggaggtaca tagtgaaatc
2701 atccaggttg aagccacaga taaagacctg gggcccaacg gacacgtgac gtactcaatt
2761 gttacagaca cagacacatt ttcaattgac agcgtgacgg gtgttgttaa catcgcacgc
2821 cctctggatc gagagctgca gcatgagcac tccttaaaga ttgaggccag ggaccaagcc
2881 agagaagagc ctcagctgtt ctccactgtc gttgtgaaag tatcactaga agatgttaat
2941 gacaacccac ctacatttat tccacctaat tatcgtgtga aagtccgaga ggatcttcca
3001 gaaggaaccg tcatcatgtg gttagaagcc cacgatcctg atttaggtca gtctggtcag
3061 gtcagcacac agccttctgg accacggaga aggaaacttc gatgtggata aactcagtgg
3121 agcagttagg atcgtccagc agttggactt tgagaagaag caagtgtata atctcactgt
3181 gagggccaaa gacaagggaa agccagtttc tctgtcttct acttgctatg ttgaagttga
3241 ggtggttgat gtgaatgaga acctgcaccc acccgtgttt tccagctttg tggaaaaggg
3301 gacagtgaaa gaagatgcac ctgttggttc attggtaatg acggtgtcgg ctcatgatga
3361 ggacgccaga agagatgggg agatccgata ctccattaga gatggctctg gcgttggtgt
3421 tttcaaaata ggtgaagaga caggtgtcat agagacgtca gatcgactgg accgtgaatc
3481 gacctcccat tattggctaa cagtctttgc aaccgatcag ggtgtcgtgc ctctttcatc
3541 gttcatagag atctacatag aggttgagga tgtcaatgac aatgcaccac agacatcaga
3601 gcctgtttat tacccagaaa tcatggaaaa ttctcctaaa gatgtatctg tggtccagat
3661 cgaggcattt gatccagatt cgagctctaa tgacaagctc atgtacaaaa ttacaagtgg
3721 aaatccacaa ggattctttt caatacatcc taaaacaggt ctcatcacaa ctacgtcaag
3781 gaagctagac cgagaacagc aagatgaaca catattagag gttactgtga cagacaatgg
3841 tagtcccccc aaatcaacca ttgcaagagt cattgtgaaa atccttgatg aaaatgacaa
3901 caaacctcag tttctgcaaa agttctacaa aatcagactc cctgagcggg aaaagccaga
3961 ccgagaaaga aatgccagac gggagccgct ctatcgcgtc atagccaccg acaaggatga
4021 gggccccaat gcagaaatct cctacagcat cgaagacggg aatgagcatg gcaaattttt
4081 catcgaaccg aaaactggag tggtttcgtc caagaggttt tcagcagctg gagaatatga
4141 tattctttca attaaggcag ttgacaatgg tcgccctcaa aagtcatcaa ccaccagact
4201 ccatattgaa tggatctcca agcccaaacc gtccctggag cccatttcat ttgaagaatc
4261 atttttacc tttactgtga tggaaagtga ccccgttgct cacatgattg gagtaatatc
4321 tgtggagcct cctggcatac ccctttggtt tgacatcact ggtggcaact acgacagtca
4381 cttcgatgtg gacaagggaa ctggaaccat cattgttgcc aaacctcttg atgcagaaca
4441 gaagtcaaac tacaacctca cagtcgaggc tacagatgga accaccacta tcctcactca
4501 ggtattcatc aaagtaatag acacaaatga ccatcgtcct cagttttcta catcaaagta
4561 tgaagttgtt attcctgaag atacagcgcc agaaacagaa attttgcaaa tcagtgctgt
```

FIG. 10 A-63

```
4621 ggatcaggat gagaaaaaca aactaatcta cactctgcag agcagtagag atccactgag
4681 tctcaagaaa tttcgtcttg atcctgcaac cggctctctc tatacttctg agaaactgga
4741 tcatgaagct gttcaccagc acaccctcac ggtcatggta cgagatcaag atgtgcctgt
4801 aaaacgcaac tttgcaagga ttgtggtcaa tgtcagcgac acgaatgacc acgccccgtg
4861 gttcaccgct tcctcctaca aagggcgggt ttatgaatcg gcagccgttg gctcagttgt
4921 gttgcaggtg acggctctgg acaaggacaa agggaaaaat gctgaagtgc tgtactcgat
4981 cgagtcagnn nnnnnnngaa atattggaaa ttcttttatg attgatcctg tcttgggctc
5041 tattaaaact gccaaagaat tagatcgaag taaccaagcg gagtatgatt taatggtaaa
5101 agctacagat aagggcagtc caccaatgag tgaaataact tctgtgcgta tctttgtcac
5161 aattgctgac aacgcctctc cgaagtttac atcaaaagaa tattctgttg aacttagtga
5221 aactgtcagc attgggagtt tcgttgggat ggttacagcc catagtcaat catcagtggt
5281 gtatgaaata aaagatggaa atacaggtga tgcttttgat attaatccac attctggaac
5341 tatcatcact cagaaagccc tggactttga aactttgccc atttacacat tgataataca
5401 aggaactaac atggctggtt tgtccactaa tacaacggtt ctagttcact tgcaggatga
5461 gaatgacaac gcgccagttt ttatgcaggc agaatataca ggactcatta gtgaatcagc
5521 ctcaattaac agcgtggtcc taacagacag gaatgtccca ctggtgattc gagcagctga
5581 tgctgataaa gactcaaatg ctttgcttgt atatcacatt gttgaaccat ctgtacacac
5641 atattttgct attgattcta gcactggtgc tattcataca gtactaagtc tggactatga
5701 agaaacaagt atttttcact ttaccgtcca agtgcatgac atgggaaccc cacgtttatt
5761 tgctgagtat gcagcgaatg taacagtaca tgtaattgac attaatgact gccccctgt
5821 gtttgccaag ccattatatg aagcatctct tttgttacca acatacaaag gagtaaaagt
5881 catcacagta aatgctacag atgctgattc aagtgcattc tcacagttga tttactccat
5941 caccgaaggc aacatcgggg agaagttttc tatggactac aagactggtg ctctcactgt
6001 ccaaaacaca actcagttaa gaagccgcta cgagctaacc gttagagctt ccgatggcag
6061 atttgccggc cttacctctg tcaaaattaa tgtgaaagaa agcaaagaaa gtcacctaaa
6121 gtttacccag gatgtctact ctgcggtagt gaaagagaat tccaccgagg ccgaaacatt
6181 agctgtcatt actgctattg ggaatccaat caatgagcct ttgttttatc acatcctcaa
6241 cccagatcgc agatttaaaa taagccgcac ttcaggagtt ctgtcaacca ctggcacgcc
6301 cttcgatcgt gagcagcagg aggcgtttga tgtggttgta gaagtgacag aggaacataa
6361 gccttctgca gtggcccacg ttgtcgtgaa ggtcattgta gaagaccaaa atgataatgc
6421 gccggtgttt gtcaaccttc cctactacgc cgttgttaaa gtggacactg aggtgggcca
6481 tgtcattcgc tatgtcactg ctgtagacag agacagtggc agaaacgggg aagtgcatta
6541 ctacctcaag gaacatcatg aacactttca aattggaccc ttgggtgaaa tttcactgaa
6601 aaagcaattt gagcttgaca ccttaaataa agaatatctt gttacagtgg ttgcaaaaga
6661 tggagggaac ccggcctttt cagcggaagt tatcgttccg atcactgtca tgaataaagc
6721 catgcctgtg tttgaaaaac ctttctacag tgcagagatt gcagagagca tccaggtgca
6781 cagccctgtg gtccacgtgc aggctaacag cccggaaggc ctgaaagtgt tctacagcat
6841 cacagacgga gaccctttca gccagttcac tattaacttc aatactggag ttatcaatgt
6901 catagctcct ctggactttg aggcccaccc ggcatataag ctgagcatac gcgcaactga
6961 ctccttgacg ggcgctcatg ctgaagtatt tgtggacatc atagtagacg acatcaatga
7021 taaccctcct gtgtttgctc agcagtctta tgcggtgacc ctgtctgagg catctgtaat
7081 tggaacgtct gttgttcaag ttagagccac cgattctgat tcagaaccaa atagaggaat
7141 ctcataccag atgtttggga atcacagcaa gagtcatgat cattttcatg tagacagcag
7201 cactggcctc atctcactac tcagaaccct ggattacgag cagtcccggc agcacacgat
7261 tttgtgagg gcagttgatg gtggtatgcc cacgctgagc agtgatgtga ttgtcacggt
7321 ggacgttacc gacctcaatg ataatccacc actctttgaa caacagattt atgaagccag
7381 aattagcgag cacgcccctc atgggcattt cgtgacctgt gtaaaagcct atgatgcaga
7441 cagttcagac atagacaagt tgcagtattc cattctgtct ggcaatgatc ataaacattt
7501 tgtcattgac agtgcaacag ggattatcac cctctcaaac ctgcaccggc acgccctgaa
7561 gccattttac agtcttaacc tgtcagtgtc tgatggagtt tttagaagtt ccacccaggt
```

FIG. 10 A-64

```
 7621 tcatgtaact gtaattggag gcaatttgca cagtcctgct ttccttcaga acgaatatga
 7681 agtggaacta gctgaaaacg ctcccctaca taccctggtg atggaggtga aaactacgga
 7741 tggggattct ggtatttatg gtcacgttac ttaccatatt gtaaatgact ttgccaaaga
 7801 cagattttac ataaatgaga gaggacagat atttactttg gaaaaacttg atcgagaaac
 7861 cccggcggag aaagtgatct cagtccgttt aatggctaag gatgctggag gaaaagttgc
 7921 tttctgcacc gtgaatgtca tccttacaga tgacaatgac aatgcaccac aatttcgagc
 7981 aaccaaatac gaagtgaata tcgggtccag tgctgctaaa gggacttcag tcgttaaagt
 8041 tcttgcaagt gatgccgatg agggctccaa tgccgacatc acctatgcca ttgaagcaga
 8101 ctctgaaagt gtaaaagaga atttggaaat taacaaactg tccggcgtaa tcactacaaa
 8161 ggagagcctc attggcttgg aaaatgaatt cttcactttc tttgttagag ctgtggataa
 8221 tgggtctcca tcaaaagaat ctgttgttct tgtctatgtt aaaatccttc caccggaaat
 8281 gcagcttcca aaattttcag aacctttcta tacctttaca gtgtcagagg acgtgcctat
 8341 tggaacagag atagatctca tccgagcaga acatagtggg actgttcttt acagcctggt
 8401 caaagggaat actccagaaa gcaataggga tgagtccttt gtgattgaca gacagagcgg
 8461 gagactgaag ttggagaaga gtcttgatca tgagacaact aagtggtatc agttttccat
 8521 actggccagg tgcactcaag atgaccatga gatggtggct tctgtagatg ttagtatcca
 8581 agtgaaagat gcaaatgaca acagcccggt ctttgaatct agtccatatg aggcattcat
 8641 tgttgaaaac ctgccagggg gaagtagagt aattcagatc agggcatctg atgctgactc
 8701 aggaaccaac ggccaagtta tgtatagcct ggatcagtca caaagtgtgg aagtcattga
 8761 atcctttgcc attaacatgg aaacaggctg gattacaact ttaaaggaac ttgaccatga
 8821 aaagagagac aattaccaga ttaaagtggt tgcatcagat catggtgaaa agatccagct
 8881 atcctccaca gccattgtgg atgttaccgt caccgatgtc aacgatagtc caccacgatt
 8941 cacggccgag atctataaag ggactgtgag tgaggatgac ccccaaggtg gggtgattgc
 9001 catcttaagt accacggatg ctgattctga agagatcaac agacaagtta catatttcat
 9061 aacaggaggg gatcctttag gacagtttgc cgttgaaact atacagaatg aatggaaggt
 9121 atatgtgaag aaacctctag acagggaaaa aagggacaat taccttctta ctatcacggc
 9181 aactgatggc accttctcat caaaagcgat agttgaagtg aaagttctgg atgcaaatga
 9241 caacagtcca gtttgtgaaa agactttata ttcagacact attcctgaag acgtccttcc
 9301 tggaaaattg atcatgcaga tctctgctac agacgcagac atccgctcta acgctgaaat
 9361 tacttacacg ttattgggtt caggtgcaga aaaattcaaa ctaaatccag acacaggtga
 9421 actgaaaacg tcaacccccc ttgatcgtga ggagcaagct gtttatcatc ttctcgtcag
 9481 ggccacagat ggaggaggaa gattctgcca agccagtatt gtgctcacgc tagaagatgt
 9541 gaacgataac gcccccgaat tctctgccga tccttatgcc atcaccgtgt ttgaaaacac
 9601 agagccggga acgctgctga caagagtgca ggccacagat gccgacgcag gattaaatcg
 9661 gaagatttta tactcactga ttgactctgc tgatgggcag ttctccatta acgaattatc
 9721 tggaattatt cagttagaaa aacctttgga cagagaactc caggcagtat acaccctctc
 9781 tttgaaagct gtggatcaag gcttgccaag gaggctgact gccactggca ctgtgattgt
 9841 atcagttctt gacataaatg acaacccccc tgtgtttgag taccgtgaat atggtgccac
 9901 cgtgtctgag gacattcttg ttggaactga agttcttcaa gtgtatgcag caagtcggga
 9961 tattgaagca aatgcagaaa tcacctactc aataataagt ggaaatgaac atgggaaatt
10021 cagcatagat tctaaaacag nnnnnnnnnn nnnnnnnnnn nnnnnnnnnn nnnnnnnnnn
10081 nnnnnnnnnn nnnnnnnnnn nnnnnnnnnn nnnnnnnnnn nnnnnnnnnn nnnnnnnnnn
10141 nnnnnnnnnn nnnnnnnnnn nnnnnnnnnn nnnnnnnnnn nnnnnnnnnn nnnnnnnnnn
10201 nnnnnnnnnn nnnnnnnnnn nnnnnnnnnn nnnnnnnnnn nnnnnnnnnn nnnnnnnnnn
10261 nnnnnnnnnn nnnnnnnnnn nnnnnnnnnn nnnnnnnnnn nnnnnnnnnn nnnnnnnnnn
10321 nnnnnnnnnn nnnnnnnnnn nnnnnnnnnn nnnnnnnnnn nnnnnnnnnn nnnnnnnnnn
10381 nnnnnnnnnn nnnnnnnnnn nnnnnnnnnn nnnnnnnnnn nnnnnnnnnn nnnnnnnnnn
10441 nnnnnnnnnn nnnnnnnnnn nnnnnnnnnn nnnnnnnnnn nnnnnnnnnn nnnnnnnnnn
10501 nnnnnnnnnn nnnnnnnnnn nnnnnnnnnn nnnnnnngaa aataagccag tgggcttcag
10561 cgtgctgcag ctggtagtaa cagatgagga ttcttcccat aacggtccac ccttcttctt
```

FIG. 10 A-65

```
10621 tactattgta actggaaatg atgagaaggc ttttgaagtt aacccgcaag gagtcctcct
10681 gacatcatct gccatcaaga ggaaggagaa agatcattac ttactgcagg tgaaggtggc
10741 agataatgga aagcctcagt tgtcatcttt gacatacatt gacattaggg taattgagga
10801 gagcatctat ccgcctgcga ttttgcccct ggagattttc atcacctctt ctggagaaga
10861 atactcaggt ggcgtcattg ggaagatcca tgccacagac caggacgtgt atgatactct
10921 aacctacagt ctcgaccctc agatggacaa cctgttctct gtttccagca caggggggcaa
10981 gctgatagca cacaaaaagc tagacatagg gcaatacctt ctcaatgtca gcgtaacaga
11041 tgggaagttc acgacggtgg ccgacatcac agtgcatatc agacaagtca cacaggagat
11101 gttgaaccac accatcgcga tccgctttgc caacctcact ccggaagaat tcgttggtga
11161 ctactggcgc aacttccagc gagctttacg gaacatcctg ggtgtgagga ggaacgacat
11221 acagattgtt agtttgcagt cctctgaacc tcacccacat ctggacgtct tactttttgt
11281 agagaaacca ggtagtgctc agatctcaac aaaacaactt ctgcacaaga ttaactcttc
11341 cgtgactgac attgaggaaa tcattggagt taggatactg aatgtattcc agaaactctg
11401 cgcgggactg gactgcccct ggaagttctg cgatgaaaag gtgtctgtgg atgaaagtgt
11461 gatgtcaaca cacagcacag ccagactgag ttttgtgact ccccgccacc acagggcagc
11521 ggtgtgtctc tgcaaagagg gaaggtgccc acctgtccac catggctgtg aagatgatcc
11581 gtgccctgag ggatccgaat gtgtgtctga tccctgggag gagaaacaca cctgtgtctg
11641 tcccagcggc aggtttggtc agtgcccagg gagttcatct atgacactga ctggaaacag
11701 ctacgtgaaa taccgtctga cggaaaatga aaacaaatta gagatgaaac tgaccatgag
11761 gctcagaaca tattccacgc atgcggttgt catgtatgct cgaggaactg actatagcat
11821 cttggagatt catcatggaa ggtgcagtca annnnnnnnn nnnnnnnnnn nnnnnnnnnn
11881 nnnnnnnnnn nnncattcag gtcaatgatg ggcagtggca cgcagtggcc ctggaagtga
11941 atggaaacta tgctcgcttg gttctagacc aagttcatac tgcatcgggc acagccccag
12001 ggactctgaa aaccctgaac ctggataact atgtgttttt tggtggccac atccgtcagc
12061 agggaacaag gcatggaaga agtcctcaag ttggtaatgg tttcaggggt tgtatggact
12121 ccatttattt gaatgggcag gagctcccct taaacagcaa acccagaagc tatgcacaca
12181 tcgaagagtc ggtggatgta tctccaggct gcttcctgac ggccacggaa gactgcgcca
12241 gcaacccttg ccagaatgga ggcgtttgca atccgtcacc tgctggaggt tattactgca
12301 aatgcagtgc cttgtacata gggacccact gtgagataag cgtcaatccg tgttcctcca
12361 agccatgcct ctatgggggc acgtgtgttg tcgacaacgg aggctttgtt tgccagtgta
12421 gaggattata tactggtcag aggtgtcagc ttagtccata ctgcaaagat gaaccctgta
12481 agaatggcgg aacatgcttt gacagtttgg atggcgccgt ttgtcagtgt gattcgggtt
12541 ttaggggaga aaggtgtcag agtgatatcg acgagtgctc tggaaaccct tgcctgcacg
12601 gggccctctg tgagaacacg cacggctcct atcactgcaa ctgcagccac gagtacaggg
12661 gacgtcactg cgaggatgct gcgcccaacc agtatgtgtc cacgccgtgg aacattgggt
12721 tggcggaagg aattggaatc gttgtgtttg ttgcagggat atttttactg gtggtggtgt
12781 ttgttctctg ccgtaagatg attagtcgga aaaagaagca tcaggctgaa cctaaagaca
12841 agcacctggg acccgctacg gctttcttgc aaagaccgta ttttgattcc aagctaaata
12901 agaacattta ctcagacata ccaccccagg tgcctgtccg gcctatttcc tacaccccga
12961 gtattccaag tgactcaaga aacaatctgg accgaaattc cttcgaagga tctgctatcc
13021 cagagcatcc cgaattcagc acttttaacc ccgagtctgt gcacgggcac cgaaaagcag
13081 tggcggtctg cagcgtggcg ccaaacctgc ctcccccacc cccttcaaac tcccccttctg
13141 acagcgactc catccagaag cctagctggg actttgacta tgacacaaaa gtggtggatc
13201 ttgatccctg tctttccaag aagcctctag aggaaaagcc ttcccagcca tacagtgccc
13261 gggaaagcct gtctgaagtg cagtctctga gctccttcca gtccgaatcg tgcgatgaca
13321 atgggtatca ctgggataca tcagattgga tgccaagcgt tcctctgccg gacatacaag
13381 agttccccaa ctatgaggtg attgatgagc agacacccct gtactcagca gatccaaacg
13441 ccatcgatac ggactattac cctggaggct acgacatcga aagtgatttt cctccacccc
13501 cagaagactt ccccgcagct gatgagctac caccgttacc gcccgaattc agcaatcagt
13561 ttgaatccat ccaccctcct agagacatgc ctgccgcggg tagcttgggt tcttcatcaa
```

FIG. 10 A-66

13621 gaaaccggca gaggttcaac ttgaatcagt atttgcccaa tttttatccc ctcgatatgt
13681 ctgaacctca aacaaaaggc actggtgaga atagtacttg tagagaaccc catgcccctt
13741 acccgccagg gtatcaaaga cacttcgagg cgcccgctgt cgagagcatg cccatgtctg
13801 tgtacgcctc caccgcctcc tgctctgacg tgtcagcctg ctgcgaagtg gagtccgagg
13861 tcatgatgag tgactatgag agcggggacg acggccactt cgaagaggtg acgatcccgc
13921 ccctggattc ccagcagcac acggaagtct gactctcaac tccccccaaa gtgcctgact
13981 ttagtgaacc tagaggtgat gtgagtaatc cgcgctgttc tttgcagcag tgcttccaag
14041 ctttttttgg tgagccgaat gggcatggct gcgctggatc ctgcgcctct ggacgtgcta
14101 gccatttcca gtgtcccaac tactgtcatc gtgaggtttt catcggctgt gccatttccc
14161 aacgtctttt gggatttaca tctgtctgtg ttaaaataat caaacgaaaa atcagtcctg
14221 tgttgtcagc atgattcatg tatttatata gatttgatta ttttaatttt cctgtctctt
14281 tttttgtaa atttatgta cagatttgat ttttcatagt tttaactaga tttccaagat
14341 attttgtgca tttgtttcaa ctgaattttg gtggtgtcag tgccattatc tagcaccctg
14401 attttttttt ttttactata accagggttt cattctgtct ttttccactg aagtgtgaca
14461 ttttgttagt acatttcagt gtagtcattc atttctagct gtacatagga tgaaggagag
14521 atcagataca tgaacatgtc ttacatgggt tgctgtattt agaattataa acatttttca
14581 ttattggaaa gtgtaacggg gaccttctgc atacctgttt agaaccaaaa ccaccatgac
14641 acagttttta tagtgtctgt atatttgtga tgcaatggtc ttgtaaaggt ttttaatgaa
14701 aactaccatt agccagtctt tcttactgac aataaattat taataaaat SEQ Id NO:73
1 gattttaggt gatgggcaag tcagaaagtc agatggatat aactgatatc aacactccaa
61 agccaaagaa gaaacagcga tggactccac tggagatcag cctctcggtc cttgtcctgc
121 tcctcaccat catagctgtg acaatgatcg cactctatgc aacctacgat gatggtattt
181 gcaagtcatc agactgcata aaatcagctg ctcgactgat ccaaaacatg gatgccacca
241 ctgagccttg tacagacttt ttcaaatatg cttgcggagg ctggttgaaa cgtaatgtca
301 ttcccgagac cagctcccgt tacggcaact ttgacatttt aagagatgaa ctagaagtcg
361 ttttgaaaga tgtccttcaa gaacccaaaa ctgaagatat agtagcagtg cagaaagcaa
421 aagcattgta caggtcttgt ataaatgaat ctgctattga tagcagaggt ggagaacctc
481 tactcaaact gttaccagac atatatgggt ggccagtagc aacagaaaac tgggagcaaa
541 aatatggtgc ttcttggaca gctgaaaaag ctattgcaca actgaattct aaatatggga
601 aaaaagtcct tattaatttg tttgttggca ctgatgataa gaattctgtg aatcatgtaa
661 ttcatattga ccaacctcga cttggcctcc cttctagaga ttactatgaa tgcactggaa
721 tctataaaga ggcttgtaca gcatatgtgg attttatgat ttctgtggcc agattgattc
781 gtcaggaaga aagattgccc atcgatgaaa accagcttgc tttggaaatg aataaagtta
841 tggaattgga aaaagaaatt gccaatgcta cggctaaacc tgaagatcga aatgatccaa
901 tgcttctgta taacaagatg acattggccc agatccaaaa taacttttca ctagagatca
961 atgggaagcc attcagctgg ttgaatttca caaatgaaat catgtcaact gtgaatatta
1021 gtattacaaa tgaggaagat gtggttgttt atgctccaga atatttaacc aaacttaagc
1081 ccattcttac caaatattct gccagagatc ttcaaaattt aatgtcctgg agattcataa
1141 tggatcttgt aagcagcctc agccgaacct acaaggagtc cagaaatgct ttccgcaagg
1201 ccctttatgg tacaacctca gaaacagcaa cttggagacg ttgtgcaaac tatgtcaatg
1261 ggaatatgga aaatgctgtg gggaggcttt atgtggaagc agcatttgct ggagagagta
1321 aacatgtggt cgaggatttg attgcacaga tccgagaagt ttttattcag actttagatg
1381 acctcacttg gatggatgcc gagacaaaaa agagagctga agaaaaggcc ttagcaatta
1441 aagaaaggat cggctatcct gatgacattg tttcaaatga taacaaactg aataatgagt
1501 acctcgagtt gaactacaaa gaagatgaat acttcgagaa cataattcaa aatttgaaat
1561 tcagccaaag taaacaactg aagaagctcc gagaaaaggt ggacaaagat gagtggataa
1621 gtggagcagc tgtagtcaat gcattttact cttcaggaag aaatcagata gtcttcccag
1681 ccggcattct gcagcccccc ttctttagtg cccagcagtc caactcattg aactatgggg

FIG. 10 A-67

1741 gcatcggcat ggtcatagga cacgaaatca cccatggctt cgatgacaat ggcagaaact
1801 ttaacaaaga tggagacctc gttgactggt ggactcaaca gtctgcaagt aactttaagg
1861 agcaatccca gtgcatggtg tatcagtatg gaaacttttc ctgggacctg gcaggtggac
1921 agcaccttaa tggaattaat acactgggag aaaacattgc tgataatgga ggtcttggtc
1981 aagcatacag agcctatcag aattatatta aaaagaatgg cgaagaaaaa ttacttcctg
2041 gacttgacct aaatcacaaa caactatttt tcttgaactt tgcacaggtg tggtgtggaa
2101 cctataggcc agagtatgcg gttaactcca ttaaaacaga tgtgcacagt ccaggcaatt
2161 tcaggattat tgggactttg cagaactctg cagagttttc agaagccttt cactgccgca
2221 agaattcata catgaatcca gaaaagaagt.gccgggtttg gtgatcttca aaagaagcat
2281 tgcagccctt ggctagactt gccaacacca cagaaatggg gaattctcta atcgaaagaa
2341 aatgggccct aggggtcact gtactgactt gagggtgatt aacagagagg gcaccatcac
2401 aatacagata acattaggtt gtcctagaaa gggtgtggag ggaggaaggg ggtctaaggt
2461 ctatcaagtc aatcatttct cactgtgtac ataatgctta atttctaaag ataatattac
2521 tgtttatttc tgtttctcat atggtctacc agtttgctga tgtccctaga aaacaatgca
2581 aaacctttga ggtagaccag gatttctaat caaaagggaa aagaagatgt tgaagaatac
2641 agttaggcac cagaagaaca gtaggtgaca ctatagttta aaacacattg cctaactact
2701 agtttttact tttatttgca acatttacag tccttcaaaa tccttccaaa gaattcttat
2761 acacattggg gccttggagc ttacatagtt ttaaactcat ttttgccata catcagttat
2821 tcattctgtg atcatttatt ttaagcactc ttaaagcaaa aaatgaatgt ctaaaattgt
2881 tttttgttgt acctgctttg actgatgctg agattcttca ggcttcctgc aattttctaa
2941 gcaatttctt gctctatctc tcaaaacttg gtatttttca gagatttata taaatgtaaa
3001 aataataatt tttatattta attattaact acatttatga gtaactatta ttataggtaa
3061 tcaatgaata ttgaagtttc agcttaaaat aaacagttgt gaaccaagat ctataaagcg
3121 atatacagat gaaaatttga gactatttaa acttataaat catattgatg aaaagattta
3181 agcacaaact ttagggtaaa aattgccatt ggacagttgt ctagagatat atatacttgt
3241 ggtttcaaa ttggactttc aaaattaaat ctgtccctga gagtgtctct gataaaaggg
3301 caaatctgca cctatgtagc tctgcatctc ctgtcttttc aggtttgtca tcagatggaa
3361 atattttgat aataaattga aattgtgaac tcattgctcc ctaagactgt gacaactgtc
3421 taactttaga agtgcatttc tgaatagaaa tgggaggcct ctgatggacc ttctagaatt
3481 ataagtcaca aagagttctg gaaaagaact gtttactgct tgataggaat tcatcttttg
3541 aggcttctgt tcctctcttt tcctgttgta ttgactattt tcgttcatta cttgattaag
3601 attttacaaa agaggagcac ttccaaaatt cttatttttc ctaacaaaag atgaaagcag
3661 ggaatttcta tctaaatgat gagtattagt tccctgtctc ttgaaaaatg cccatttgcc
3721 tttaaaaaaa aaagttacag aaatactata acatatgtac ataaattgca taaagcataa
3781 gtatacagtt caataaactt aactttaact gaacaatggc cctgtagcca gcacctgtaa
3841 gaaacagagc agtaccagcg ctctaaaagc acctccttgt cactttatta ctcccagaac
3901 aacaactatc ctgacttcta atatcattca ctagctttgc ctggttttgt cttttatgca
3961 gatagaatca atcagtatgt attcttttgt gcctggcttc tttctctcag ccttacattt
4021 gtgagattcc tctgtattgt gctgattgtg gatcttttca ttctcattgc agaataatgt
4081 tctattgtgg gacttattac aatttgttca tcctattgtt gatgggcact tgagaacttt
4141 ccattttggc gctattacaa atagtgcaac tatgaatgta ctgcatgtta ccatcttact
4201 tgagccttta atggacttat ttcttcaaat ccttccaaaa attattataa gcattgaaat
4261 tatagtttca agccaactgt ggataccctt accctttcct cctttatcac aaccaccgtt
4321 acaagtatac ttatatttcc ctaaaataca tttaaaactt acctaagtga catttgtagt
4381 tggagtaata ggagcttcca gctctaataa aacagctgtc tctaacttat tttatttcca
4441 tcatgtcaga gcaggtgaag agccagaagt gaagagtgac tagtacaaat tataaaaagc
4501 cactagactc ttcactgtta gctttttaaa acattaggct cccatcccta tggaggaaca
4561 actctccagt gcctggatcc cctctgtcta caaatataag attttctggg cctaaaggat
4621 agatcaaagt caaaaatagc aatgcctccc tatccctcac acatccagac atcatgaatt
4681 ttacatggta ctcttgttga gttctgtaga gccttctgat gtctctaaag cactaccgat

FIG. 10 A-68

```
4741 tctttggagt tgtcacatca gataagacat atctctaatt ccatccataa atccagttct
4801 actatggctg agttctggtc aaagaaagaa agtttagaag ctgagacaca aagggttggg
4861 agctgatgaa actcacaaat gatggtagga agaagctctc gacaataccc gttggcaagg
4921 agtctgcctc catgctgcag tgttcgagtg gattgtaggt gcaagatgga aaggattgta
4981 ggtgcaagct gtccagagaa aagagtcctt gttccagccc tattctgcca ctcctgacag
5041 ggtgaccttg ggtatttgca atattccttt gggcctctgc ttctctcacc taaaaaaaga
5101 gaattagatt atattggtgg ttctcagcaa gagaaggagt atgtgtccaa tgctgccttc
5161 ccatgaatct gtctcccagt tatgaatcag tgggcaggat aaactgaaaa ctcccattta
5221 cgtgtctgaa tcgagtgaga caaaatttta gtccaaataa caagtaccaa agttttatca
5281 agtttgggtc tgtgctgctg ttactgttaa ccatttaagt ggggcaaaac cttgctaatt
5341 ttctcaaaag catttatcat tcttgttgcc acagctggag ctctcaaact aaaagacatt
5401 tgttattttg gaaagaagaa agactctatt ctcaaagttt cctaatcaga aatttttatc
5461 agtttccagt ctcaaaaata caaaataaaa acaaacgttt ttaatact
```

SEQ ID NO:74

```
   1 atgtccaatc agggaagtaa gtacgtcaat aaggaaattc aaaatgctgt caacggggtg
  61 aaacagataa agactctcat agaaaaaaca aacgaagagc gcaagacact gctcagcaac
 121 ctagaagaag ccaagaagaa gaaagaggat gccctaaatg agaccaggga atcagagaca
 181 aagctgaagg agctcccagg agtgtgcaat gagaccatga tggccctctg ggaagagtgt
 241 aagccctgcc tgaaacagac ctgcatgaag ttctacgcac gcgtctgcag aagtggctca
 301 ggcctggttg gccgccagct tgaggagttc ctgaaccaga gctcgccctt ctacttctgg
 361 atgaatggtg accgcatcga ctccctgctg gagaacgacc ggcagcagac gcacatgctg
 421 gatgtcatgc aggaccactt cagccgcgcg tccagcatca tagacgagct cttccaggac
 481 aggttcttca cccgggagcc ccaggatacc taccactacc tgcccttcag cctgccccac
 541 cggaggcctc acttcttctt tcccaagtcc cgcatcgtcc gcagcttgat gcccttctct
 601 ccgtacgagc ccctgaactt ccacgccatg ttccagccct tccttgagat gatacacgag
 661 gctcagcagg ccatggacat ccacttccat agcccggcct tccagcaccc gccaacagaa
 721 ttcatacgag aaggcgacga tgaccggact gtgtgccggg agatccgcca caactccacg
 781 ggctgcctgc ggatgaagga ccagtgtgac aagtgccggg agatcttgtc tgtggactgt
 841 tccaccaaca acccctccca ggctaagctg cggcgggagc tcgacgaatc cctccaggtc
 901 gctgagaggt tgaccaggaa atacaacgag ctgctaaagt cctaccagtg gaagatgctc
 961 aacacctcct ccttgctgga gcagctgaac gagcagttta actgggtgtc ccggctggca
1021 aacctcacgc aaggcgaaga ccagtactat ctgcgggtca ccacggtggc ttcccacact
1081 tctgactcgg acgttccttc cggtgtcact gaggtggtcg tgaagctctt tgactctgat
1141 cccatcactg tgacggtccc tgtagaagtc tccaggaaga accctaaatt tatggagacc
1201 gtggcggaga aagcgctgca ggaataccgc aaaaagcacc gggaggagtg agatgtggat
1261 gttgcttttg cacctacggg ggcatctgag tccagctccc cccaagatga gctgcagccc
1321 cccagagaga gctctgcacg tcaccaagta accaggcccc agcctccagg cccccaactc
1381 cgcccagcct ctccccgctc tggatcctgc actctaacac tcgactctgc tgctcatggg
1441 aagaacagaa ttgctcctgc atgcaactaa ttcaataaaa ctgtcttgtg agctg
```

SEQ ID NO:75

```
   1 gaaggaaaaa gagcaacaga tccagggagc attcacctgc cctgtctcca aacagccttg
  61 tgcctcacct acccccaacc tcccagaggg agcagctatt taaggggagc aggagtgcag
 121 aacaaacaag acggcctggg gatacaactc tggagtcctc tgagagagcc accaaggagg
 181 agcaggggag cgacggccgg ggcagaagtt gagaccaccc agcagaggag ctaggccagt
 241 ccatctgcat ttgtcaccca agaactctta ccatgaagac cctcctactg ttggcagtga
 301 tcatgatctt tggcctactg caggcccatg ggaatttggt gaatttccac agaatgatca
 361 agttgacgac aggaaaggaa gccgcactca gttatggctt ctacggctgc cactgtggcg
```

FIG. 10 A-69

```
421 tgggtggcag aggatccccc aaggatgcaa cggatcgctg ctgtgtcact catgactgtt
481 gctacaaacg tctggagaaa cgtggatgtg gcaccaaatt tctgagctac aagtttagca
541 actcggggag cagaatcacc tgtgcaaaac aggactcctg cagaagtcaa ctgtgtgagt
601 gtgataaggc tgctgccacc tgttttgcta gaaacaagac gacctacaat aaaaagtacc
661 agtactattc caataaacac tgcagaggga gcacccctcg ttgctgagtc ccctcttccc
721 tggaaacctt ccacccagtg ctgaatttcc ctctctcata ccctccctcc ctaccctaac
781 caagttcctt ggccatgcag aaagcatccc tcacccatcc tagaggccag gcaggagccc
841 ttctataccc acccagaatg agacatccag cagatttcca gccttctact gctctcctcc
901 acctcaactc cgtgcttaac caaagaagct gtactccggg gggtctcttc tgaataaagc
961 aattagc
```

SEQ ID NO:76

```
   1 gctccatcaa gtatgatggt gaaggatgaa tatgtgcatg actttgaggg acagccatcg
  61 ttgtccactg aaggacattc aattcaaacc atccagcatc caccaagtaa tcgtgcatcg
 121 acagagacat acagcacccc agctctgtta gccccatctg agtctaatgc taccagcact
 181 gccaactttc ccaacattcc tgtggcttcc acaagtcagc ctgccagtat actgggggc
 241 agccatagtg aaggactgtt gcagatagca tcagggcctc agccaggaca gcagcagaat
 301 ggatttactg gtcagccagc tacttaccat cataacagca ctaccacctg gactggaagt
 361 aggactgcac catacacacc taatttgcct caccaccaaa acggccatct tcagcaccac
 421 ccgcctatgc cgccccatcc cggacattac tggcctgttc acaatgagct tgcattccag
 481 cctcccattt ccaatcatcc tgctcctgag tattggtgtt ccattgctta ctttgaaatg
 541 gatgttcagg taggagagac atttaaggtt ccttcaagct gccctattgt tactgttgat
 601 ggatacgtgg acccttctgg aggagatcgc ttttgtttgg gtcaactctc caatgtccac
 661 aggacagaag ccattgagag agcaaggttg cacataggca aaggtgtgca gttggaatgt
 721 aaaggtgaag gtgatgtttg ggtcaggtgc cttagtgacc acgcggtctt tgtacagagt
 781 tactacttag acagagaagc tgggcgtgca cctggagatg ctgttcataa gatctaccca
 841 agtgcatata taaaggtctt tgatttgcgt cagtgtcatc gacagatgca gcagcaggcg
 901 gctactgcac aagctgcagc agctgcccag gcagcagccg tggcaggaaa catccctggc
 961 ccaggatcag taggtggaat agctccagct atcagtctgt cagctgctgc tggaattggt
1021 gttgatgacc ttcgtcgctt atgcatactc aggatgagtt ttgtgaaagg ctggggaccg
1081 gattacccaa gacagagcat caaagaaaca ccttgctgga ttgaaattca cttacaccgg
1141 gccctccagc tcctagacga agtacttcat accatgccga ttgcagaccc acaaccttta
1201 gactgaggtc ttttaccgtt ggggccctta accttatcag gatggtggac tacaaaatac
1261 aatcctgttt ataatctgaa gatatatttc acttttgttc tgctttatct tttcataaag
1321 ggttgaaaat gtgtttgctg ccttgctcct agcagacaga aactggatta aaacaatttt
1381 ttttttcctc ttcagaactt gtcaggcatg gctcagagct tgaagattag gagaaacaca
1441 ttcttattaa ttcttcacct gttatgtatg aaggaatcat tccagtgcta gaaaatttag
1501 ccctttaaaa cgtcttagag ccttttatct gcagaacatc gatatgtata tcattctaca
1561 gaataatcca gtattgctga ttttaaaggc agagaagttc tcaaagttaa ttcacctatg
1621 ttatttgtg tacaagttgt tattgttgaa catacttcaa aaataatgtg ccatgtgggt
1681 gagttaattt taccaagagt aactttactc tgtgtttaaa aagtaagtta ataatgtatt
1741 gtaatctttc atccaaaata ttttttgcaa gttatattag tgaagatggt ttcaattcag
1801 attgtcttgc aacttcagtt ttatttttgc caaggcaaaa aactcttaat ctgtgtgtat
1861 attgagaatc ccttaaaatt accagacaaa aaaatttaaa attacgtttg ttattcctag
1921 tggatgactg ttgatgaagt atacttttcc cctgttaaac agtagttgta ttcttctgta
1981 tttctaggca caaggttggt tgctaagaag cctataagag gaatttcttt tccttcattc
2041 atagggaaag gttttgtatt ttttaaaaca ctaaaagcag cgtcactcta cctaatgtct
2101 cactgttctg caaaggtggc aatgcttaaa ctaaataatg aataaactga atattttgga
2161 aactgctaaa ttctatgtta aatactgtgc agaataatgg aaacattaca gttcataata
2221 ggtagtttgg atatttttgt acttgatttg atgtgacttt ttttggtata atgtttaaat
```

FIG. 10 A-70

2281 catgtatgtt atgatattgt ttaaaattca gtttttgtat cttggggcaa gactgcaaac
2341 ttttttatat cttttggtta ttctaagccc tttgccatca atgatcatat caattggcag
2401 tgactttgta tagagaattt aagtagaaaa gttgcagatg tattgactgt accacagaca
2461 caatatgtat gctttttacc tagctggtag cataaataaa actgaatctc aacat SEQ ID NO:77
1 gcaggcccgt tggaagtggt tgtgacaacc ccagcaatgt ggagaagcct ggggcttgcc
61 ctggctctct gtctcctccc atcgggagga acagagagcc aggaccaaag ctccttatgt
121 aagcaacccc cagcctggag cataagagat caagatccaa tgctaaactc caatggttca
181 gtgactgtgg ttgctcttct tcaagccagc tgatacctgt gcatactgca ggcatctaaa
241 ttagaagacc tgcgagtaaa actgaagaaa gaaggatatt ctaatatttc ttatattgtt
301 gttaatcatc aaggaatctc ttctcgatta aaatacacac atcttaagaa taaggtttca
361 gagcatattc ctgtttatca acaagaagaa aaccaaacag atgtctggac tcttttaaat
421 ggaagcaaag atgacttcct catatatgat agatgtggcc gtcttgtata tcatcttggt
481 ttgccttttt ccttcctaac tttcccatat gtagaagaag ccattaagat tgcttactgt
541 gaaaagaaat gtggaaactg ctctctcacg actctcaaag atgaagactt ttgtaaacgt
601 gtatctttgg ctactgtgga taaaacagtt gaaactccat cgcctcatta ccatcatgag
661 catcatcaca atcatggaca tcagcacctt ggcagcagtg agctttcaga gaatcagcaa
721 ccaggagcac caaatgctcc tactcatcct gctcctccag gccttcatca ccaccataag
781 cacaagggtc agcataggca gggtcaccca gagaaccgag atatgccagc aagtgaagat
841 ttacaagatt tacaaaagaa gctctgtcga aagagatgta taaatcaatt actctgtaaa
901 ttgcccacag attcagagtt ggctcctagg agctgatgct gccattgtcg acatctgata
961 tttgaaaaaa cagggtctgc aatcacctga cagtgtaaag aaaacctccc atctttatgt
1021 agctgacagg gacttcgggc agaggagaac ataactgaat cttgtcagtg acgtttgcct
1081 ccagctgcct gacaaataag tcagcagctt atacccacag aagccagtgc cagttgacgc
1141 tgaaagaatc aggcaaaaaa gtgagaatga ccttcaaact aaatatttaa aataggacat
1201 actccccaat ttagtctaga cacaatttca tttccagcat ttttataaac taccaaatta
1261 gtgaaccaaa aatagaaatt agatttgtgc aaacatggag aaatctactg aattggcttc
1321 cagattttaa attttatgtc atagaaatat tgactcaaac catatttttt atgatggagc
1381 aactgaaagg tgattgcagc ttttggttaa tatgtctttt tttttctttt tccagtgttc
1441 tatttgcttt aatgagaata gaaacgtaaa ctatgaccta ggggtttctg ttggataatt
1501 agcagtttag aatggaggaa gaacaacaaa gacatgcttt ccattttttt ctttacttat
1561 ctctcaaaac aatattactt tgtcttttca atcttctact tttaactaat aaaataagtg
1621 gattttgtat tttaagatcc agaaatactt aacacgtgaa tattttgcta aaaaagcata
1681 tataactatt ttaaatatcc atttatcttt tgtatatcta agactcatcc tgatttttac
1741 tatcacacat gaataaagcc tttgtatctt tctttctcta atgttgtatc atactcttct
1801 aaaacttgag tggctgtctt aaaagatata aggggaaaga taatattgtc tgtctctata
1861 ttgcttagta agtatttcca tagtcaatga tggtttaata ggtaaaccaa accctataaa
1921 cctgacctcc tttatggtta atactattaa gcaagaatgc agtacagaat tggatacagt
1981 acggatttgt ccaaataaat tcaataaaaa ccttaaa SEQ ID NO:78
1 caaccacttg acaacctggt tagaagatgc ccgccagcat tccaattcca acatggtcat
61 tatgcttatt ggaaataaaa gtgatttaga atctagaaga gaagtaaaaa aagaagaagg
121 tgaagctttt gcacgagaac atggactcat cttcatggaa acgtctgcta agactgcttc
181 caatgtagaa gaggcattta ttaatacagc aaaagaaatt tatgaaaaaa ttcaagaagg
241 agtctttgac attaataatg aggcaaatgg cattaaaatt ggccctcagc atgctgctac
301 caatgcaaca catgcaggca atcagggagg acagcaggct gggggcggct gctgttgagt
361 ctgtttttac tgtctagctg cccaacgggg cctactcact tattctttca ccccctctcc

FIG. 10 A-71

```
 421 tcctgctcag ctgagacatg aaactatttg aaatggcttt atgtcacaga agactttaat
 481 ccgtcaaatt cttgtataac tttgaataaa tggttaatgt tcacttaaaa gacagatttt
 541 ggagattgta ttcatatcta tttgcatttg atttctaggt caattgatgt gattattttt
 601 gttaaatgtt gtcttgtgcc cttaactacg aactgaattg tattaaacac tacaaagtca
 661 tcttgagtat tttaaatcgg tttgtgtagt taggtttccc aacatctgtg gttacctaat
 721 gtttaatatt atagaactgt cctcagaaac tttgtcaatt ttcacggcta taaggaaaca
 781 gaaggactct tttaattctg tatttatcat ttactttctg tatatatagt ttaataacct
 841 gcttgggtgt aatttgccaa gcttgaattc tttaatgcat ttgcataaat tctatactgt
 901 ttagagctta aagctacaga agcattgtta ggaattgctt ggacactgaa ttttaaactt
 961 tttgacattg ttaacaagca tgttcatctt ttcttgtcac tagtccaaga aaaatatgct
1021 taatgtatat tacaaaggct ttgtatatgt taacctgttt taatgccaaa agtttgcttt
1081 gtccacaatt tccttaagac ctcttcagaa agggatttgt ttgccttaat gaatactgtt
1141 gggaaaaaac acagtataat gagtgaaaag ggcagaagca agaaatttct acatcttagc
1201 gactccaaga agaatgagta tccacattta gatggcacat tatgaggact ttaatctttc
1261 cttaaacaca ataatgtttt ctttttttctt ttattcacat gatttctaag tatatttttc
1321 atgcaggaca gtttttcaac cttgatgtac agtgactgtg taaaattttt ctttcagtgg
1381 caacctctat aatctttaaa atatggtgag catcttgtct gttttgaagg ggatatgaca
1441 ataaatctat cagatggaaa atcctgtt

SEQ ID NO:79
   1 cctgggtctg acgcggccct gttcgagggg gcctctcttg tttatttatt tattttccgt
  61 gggtgcctcc gagtgtgcgc gcgctctcgc tacccggcgg ggaggggggtg gggggagggc
 121 ccgggaaaag ggggagttgg agccggggtc gaaacgccgc gtgacttgta ggtgagagaa
 181 cgccgagccg tcgccgcagc ctccgccgcc gagaagccct tgttcccgct gctgggaagg
 241 agagtctgtg ccgacaagat ggcggacggg gagctgaacg tggacagcct catcacccgg
 301 ctgctggagg tacgaggatg tcgtccagga aagattgtgc agatgactga agcagaagtt
 361 cgaggcttat gtatcaagtc tcgggagatc tttctcagcc agcctattct tttggaattg
 421 gaagcaccgc tgaaaatttg tggagatatt catggacaat atacagattt actgagatta
 481 tttgaatatg gaggtttccc accagaagcc aactatcttt tcttaggaga ttatgtggac
 541 agaggaaagc agtctttgga aaccatttgt ttgctattgg cttataaaat caaatatcca
 601 gagaacttct ttctcttaag aggaaaccat gagtgtgcta gcatcaatcg catttatgga
 661 ttctatgatg aatgcaaacg aagatttaat attaaattgt ggaagacctt cactgattgt
 721 tttaactgtc tgcctatagc agccattgtg gatgagaaga tcttctgttg tcatggagga
 781 ttgtcaccag acctgcaatc tatggagcag attcggagaa ttatgagacc tactgatgtc
 841 cctgatacag gtttgctctg tgatttgcta tggtctgatc cagataagga tgtgcaaggc
 901 tggggagaaa atgatcgtgg tgtttccttt acttttggag ctgatgtagt cagtaaattt
 961 ctgaatcgtc atgatttaga tttgatttgt cgagctcatc aggtggtgga agatggatat
1021 gaatttttttg ctaaacgaca gttggtaacc ttattttcag ccccaaatta ctgtggcgag
1081 tttgataatg ctggtggaat gatgagtgtg gatgaaactt tgatgtgttc atttcagata
1141 ttgaaaccat ctgaaaagaa agctaaatac cagtatggtg gactgaattc tggacgtcct
1201 gtcactccac ctcgaacagc taatccgccg aagaaaaggt gaagaaagga attctgtaaa
1261 gaaaccatca gatttgttaa ggacatactt cataatatat aagtgtgcac tgtaaaacca
1321 tccagccatt tgacacccctt tatgatgtca cacctttaac ttaaggagac gggtaaagga
1381 tcttaaattt ttttctaata gaaagatgtg ctacactgta ttgtaataag tatactctgt
1441 tatagtcaac aaagttaaat ccaaattcaa aattatccat taaagttaca tcttcatgta
1501 tcacaatttt taaagttgaa aagcatccca gttaaactag atgtgatagt taaaccagat
1561 gaaagcatga tgatccatct gtgtaatgtg gttttagtgt tgcttggttg tttaattatt
1621 ttgagcttgt tttgtttttg tttgttttca ctagaataat ggcaaatact tctaattttt
1681 ttccctaaac atttttaaaa gtgaaatatg ggaagagctt tacagacatt caccaactat
1741 tattttccct tgtttatcta cttagatatc tgtttaatct tactaagaaa actttcgcct
1801 cattacatta aaaaggaatt ttagagattg attgttttaa aaaaaaatac gcacattgtc
```

FIG. 10 A-72

```
1861 caatccagtg attttaatca tacagtttga ctgggcaaac tttacagctg atagtgaata
1921 ttttgcttta tacaggaatt gacactgatt tggatttgtg cactctaatt tttaacttat
1981 tgatgctcta ttgtgcagta gcatttcatt taagataagg ctcatatagt attacccaac
2041 tagttggtaa tgtgattatg tggtaccttg gctttaggtt ttcattcgca cggaacacct
2101 tttggcatgc ttaacttcct ggtaacacct tcacctgcat tggttttctt tttctttttt
2161 ctttcttttt tttttttttt tttttttga gttgttgttt gtttttagat ccacagtaca
2221 tgagaatcct tttttgacaa gccttggaaa gctgacactg tctcttttc ctccctctat
2281 acgaaggatg tatttaaatg aatgctggtc agtgggacat tttgtcaact atgggtattg
2341 ggtgcttaac tgtctaatat tgccatgtga atgttgtata cgattgtaag gcttatgtca
2401 ctaaagattt ttattctgat tttttcataa tcaaaggtca tatgatactg tatagacaag
2461 ctttgtagtg aagtatagta gcaataattt ctgtacctga tcaagtttat tgcagccttt
2521 cttttcctat ttcttttttt taagggttag tattaacaaa tggcaatgag tagaaaagtt
2581 aacatgaaga ttttagaagg agagaactta caggacacag atttgtgatt ctttgactgt
2641 gacactattg gatgtgattc taaaagcttt tattgagcat tgtcaaattt gtaagcttca
2701 tagggatgga catcatatct ataatgccct tctatatgtg ctaccataga tgtgacattt
2761 ttgaccttaa tatcgtcttt gaaaatgtta aattgagaaa cctgttaact tacattttat
2821 gaattggcac attgtattac ttactgcaag agatatttca ttttcagcac agtgcaaaag
2881 ttctttaaaa tgcatatgtc tttttttcta attccgtttt gttttaaagc acattttaaa
2941 tgtagttttc tcatttagta aaagttgtct aattgatatg aagcctgact gatttttttt
3001 ttccttacag tgagacattt aagcacacat tttattcaca tagatactat gtccttgaca
3061 tattgaaatg attcttttct gaaagtattc atgatctgca tatgatgtat taggttaggt
3121 cacaaaggtt ttatctgagg tgatttaaat aacttcctga ttggagtgtg taagctgagc
3181 gatttctaat aaaattttag ttgtacactt ttagtagtca tagtgaagca ggtctagaaa
3241 ataagccttt ggcagggaaa aagggcaatg ttgattaatc tcagtattaa accacattaa
3301 tctgtatccc attgtctggc ttttgtaaat tcatccaggt caagactaag tatgttggtt
3361 aataggaatc cttttttttt tttaaagact aaatgtgaaa aaataatcac tacttaagct
3421 aattaatatt ggtcattaaa tttaaaggat ggaaatttat catgtttaaa aattattcaa
3481 gcactcttaa aaccacttaa acagcctcca gtcataaaaa tgtgttcttt acaaatattt
3541 gcttggcaac acgacttgaa ataaataaaa ctttgtttct taggagaaaa
```

SEQ ID NO:80

```
   1 gcaacctgcc ccattatccc tggctgcgaa acaaccatcg agatttccaa agggcgaaca
  61 gggctgggcc tgagcatcgt tgggggttca gacacgctgc tgggtgccat tattatccat
 121 gaagtttatg aagaaggagc agcatgtaaa gatggaagac tctgggctgg agatcagatc
 181 ttagaggtga atggaattga cttgagaaag gccacacatg atgaagcaat caatgtcctg
 241 agacagacgc cacagagagt gcgcctgaca ctctacagag atgaggcccc atacaaagag
 301 gaggaagtgt gtgacaccct cactattgag ctgcagaaga agccgggaaa aggcctagga
 361 ttaagtattg ttggtaaaag aaacgatact ggagtatttg tgtcagacat tgtcaaagga
 421 ggaattgcag atgccgatgg aagactgatg cagggagacc agatattaat ggtgaatggg
 481 gaagacgttc gtaatgccac ccaagaagcg gttgccgctt tgctaaagtg ttccctaggc
 541 acagtaacct tggaagttgg aagaatcaaa gctggtccat tccattcaga gaggaggcca
 601 tctcaaagca gccaggtgag tgaaggcagc ctgtcatctt tcacttttcc actctctgga
 661 tccagtacat ctgagtcact ggaaagtagc tcaaagaaga atgcattggc atctgaaata
 721 cagggattaa gaacagtcga aatgaaaaag ggccctactg actcactggg aatcagcatt
 781 gctggaggag taggcagccc acttggtgat gtgcctatat ttattgcaat gatgcaccca
 841 actggagttg cagcacagac ccaaaaactc agagttgggg ataggattgt caccatctgt
 901 ggcacatcca ctgagggcat gactcacacc caagcagtta acctactgaa aaatgcatct
 961 ggctccattg aaatgcaggt ggttgctgga ggagacgtga gtgtggtcac aggtcatcag
1021 caggagcctg caagttccag tctttctttc actgggctga cgtcaagcag tatatttcag
1081 gatgatttag gacctcctca atgtaagtct attacactag agcgaggacc agatggctta
```

FIG. 10 A-73

```
1141 ggcttcagta tagttggagg atatggcagc cctcatggag acttacccat ttatgttaaa
1201 acagtgtttg caaagggagc agcctctgaa gacggacgtc tgaaaagggg cgatcagatc
1261 attgctgtca atgggcagag tctagaagga gtcacccatg aagaagctgt tgccatcctt
1321 aaacggacaa aaggcactgt cactttgatg gttctctctt gaattggctg ccagaattga
1381 accaacccaa cccctagctc acctcctact gtaaagagaa tgcactggtc ctgacaattt
1441 ttatgctgtg ttcagccggg tcttcaaaac tgtagggggg aaataacact taagtttctt
1501 tttctcatct agaaatgctt tccttactga caacctaaca tcatttttct tttcttcttg
1561 cattttgtga acttaaagag aaggaatatt tgtgtaggtg aatctcgttt ttatttgtgg
1621 agatatctaa tgttttgtag tcacatgggc aagaattatt acatgctaag ctggttagta
1681 taaagaaaga taattctaaa gctaaccaaa gaaaatggct tcagtaaatt aggatgaaaa
1741 atgaaaatat

SEQ ID NO:81
   1 ggagcgcaat ggcgtccaac cccgaacggg gggagattct gctcacggaa ctgcaggggg
  61 attcccgaag tcttccgttt tctgagaatg tgagtgctgt tcaaaaatta gacttttcag
 121 atacaatggt gcagcagaaa ttggatgata tcaaggatcg aattaagaga gaaataagga
 181 aagaactgaa aatcaaagaa ggagctgaaa atctgaggaa agtcacaaca gataaaaaaa
 241 gtttggctta tgtagacaac attttgaaaa aatcaaataa aaaattagaa gaactacatc
 301 acaagctgca ggaattaaat gcacatattg ttgtatcaga tccagaagat attacagatt
 361 gcccaaggac tccagatact ccaaataatg accctcgttg ttctactagc aacaatagat
 421 tgaaggcctt acaaaaacaa ttggatatag aacttaaagt aaaacaaggt gcagagaata
 481 tgatacagat gtattcaaat ggatcttcaa aggatcggaa actccatggt acagctcagc
 541 aactgctcca ggacagcaag acaaaaatag aagtcatacg aatgcagatt cttcaggcag
 601 tccagactaa tgaattggct tttgataatg caaaacctgt gataagtcct cttgaacttc
 661 ggatggaaga attaaggcat cattttagga tagagtttgc agtagcagaa ggtgcaaaga
 721 atgtaatgaa attacttggc tcaggaaaag taacagacag aaaagcactt tcagaagctc
 781 aagcaagatt taatgaatca agtcagaagt tggacctttt aaagtattca ttagagcaaa
 841 gattaaacga agtccccaag aatcatccca aaagcaggat tattattgaa gaactttcac
 901 ttgttgctgc atcaccaaca ctaagtccac gtcaaagtat gatatctacg caaaatcaat
 961 atagtacact atccaaacca gcagcactaa caggtacttt ggaagttcgt cttatgggct
1021 gccaagatat cctagagaat gtccctggac ggtcaaaagc aacatcagtt gcactgcctg
1081 gttggagtcc aagtgaaacc agatcatctt tcatgagcag aacgagtaaa agtaaaagcg
1141 gaagtagtcg aaatcttcta aaaaccgatg acttgtccaa tgatgtctgt gctgttttga
1201 agctcgataa tactgtggtt ggccaaacta gctggaaacc catttccaat cagtcatggg
1261 accagaagtt tacactggaa ctggacaggt cacgtgaact ggaaatttca gtttattggc
1321 gtgattggcg gtctctgtgt gctgtaaaat ttctgaggtt agaagatttt ttagacaacc
1381 aacggcatgg catgtgtctc tatttggaac cacagggtac tttatttgca gaggttacct
1441 tttttaatcc agttattgaa agaagaccaa aacttcaaag acaaaagaaa attttttcaa
1501 agcaacaagg caaaacattt ctcagagctc ctcaaatgaa tattaatatt gccacttggg
1561 gaaggctagt aagaagagct attcctacag taaatcattc tggcaccttc agccctcaag
1621 ctcctgtgcc tactacagtg ccagtggttg atgtacgcat ccctcaacta gcacctccag
1681 ctagtgattc tacagtaacc aaattggact ttgatcttga gcctgaacct cctccagccc
1741 caccacgagc ttcttctctt ggagaaatag atgaatcttc tgaattaaga gttttggata
1801 taccaggaca ggattcagag actgtttttg atattcagaa tgacagaaat agtatacttc
1861 caaaatctca atctgaatac aagcctgata ctcctcagtc aggcctagaa tatagtggta
1921 ttcaagaact tgaggacaga agatctcagc aaaggtttca gtttaatcta caagatttca
1981 ggtgttgtgc tgtcttggga agaggacatt ttggaaaggt gcttttagct gaatataaaa
2041 acacaaatga gatgtttgct ataaaagcct taaagaaagg agatattgtg gctcgagatg
2101 aagtagacag cctgatgtgt gaaaaaagaa tttttgaaac tgtgaatagt gtaaggcatc
2161 ccttttggt gaaccttttt gcatgtttcc aaaccaaaga gcatgtttgc tttgtaatgg
```

FIG. 10 A-74

```
2221 aatatgctgc cggtggggac ctaatgatgc acattcatac tgatgtcttt tctgaaccaa
2281 gagctgtatt ttatgctgct tgtgtagttc ttgggttgca gtatttacat gaacacaaaa
2341 ttgtttatag agatttgaaa ttggataact tattgctaga tacagagggc tttgtgaaaa
2401 ttgctgattt tggtctttgc aaagaaggaa tgggatatgg agatagaaca agcacatttt
2461 gtggcactcc tgaatttctt gccccagaag tattaacaga aacttcttat acaagggctg
2521 tagattggtg gggccttggc gtgcttatat atgaaatgct tgttggtgag tctccctttc
2581 ctggtgatga tgaagaggaa gtttttgaca gtattgtaaa tgatgaagta aggtatccaa
2641 ggttcttatc tacagaagcc atttctataa tgagaaggct gttaagaaga aatcctgaac
2701 ggcgccttgg ggctagcgag aaagatgcag aggatgtaaa aaagcaccca tttttccggc
2761 taattgattg gagcgctctg atggacaaaa aagtaaagcc accatttata cctaccataa
2821 gaggacgaga agatgttagt aattttgatg atgaatttac ctcagaagca cctattctga
2881 ctccacctcg agaaccaagg atactttcgg aagaggagca ggaaatgttc agagattttg
2941 actacattgc tgattggtgt taagttgcta gacactgcga aaccaagctg actcacaaga
3001 agacctctta aaaatagcaa cccttcattt gctctctgtg ccaccaatag cttctgagtt
3061 ttttgttgtt gttgttttta ttgaaacacg tgaagatttg tttaaaagta ccattctaat
3121 acttcttcaa aagtggctcc tcattgtact tcagcgtaaa tatgagcact ggaaacagtt
3181 tcatggagtt taagttgagt gaacatcggc catgaaaatc catcacgaat acttttggat
3241 caatagtcta tttt
```

SEQ ID NO:82

```
  1 atgaaattca agttacatgt gaattctgcc aggcaataca aggacctgtg gaatatgagt
 61 gatgacaaac cctttctatg tactgcgcct ggatgtggcc agagtgaagt caccctgctg
121 agaaatgaag tggcacagct gaaacagctt cttctggctc ataaagattg ccctgtaacc
181 gccatgcaga agaaatctgg ctatcatact gctgataaag atgatagttc agaagacatt
241 tcagtgccga gtagtccaca tacagaagct atacagcata gttcggtcag cacatccaat
301 ggagtcagtt caacctccaa ggcagaagct gtagccactt cagtcctcac ccagatggcg
361 gaccagagta cagagcctgc tctttcacag atcgttatgg ctccttcctc ccagtcacag
421 ccctcaggaa gttgattaaa aacctgcagt acaacagttt tagatactca ttagtgactt
481 caaagggaaa tcaaggaaag accagtttc
```

SEQ ID NO:83

```
  1 gaattctgga agttcattga agagtctgaa attagggact tatttcaaat ttggacatgg
 61 ctagtcgagg cgcaacaaga cccaacggcc caaatactgg aaataaaata tgccagttca
121 aactagtact tctgggagag tccgctgttg gcaaatcaag cctagtgctt cgttttgtga
181 aaggccaatt tcatgaattt caagagagta ccattggggc tgcttttcta acccaaactg
241 tatgtcttga tgacactaca gtaaagtttg aaatctggga tacagctggt caagaaggat
301 accatagcct agcaccaatg tactacagag gagcacaagc agccatagtt gtatatgata
361 tcacaaatga ggagtccttt gcaagagcaa aaaattgggt taaagaactt cagaggcaag
421 caagtcctaa cattgtaata gctttatcgg gaaacaaggc cgacctagca aataaaagag
481 cagtagattt ccaggaagca cagtcctatg cagatgacaa tagtttatta ttcatggaga
541 catccgctaa aacatcaatg aatgtaaatg aaatattcat ggcaatagct aaaaaattgc
601 caaagaatga accacaaaat ccaggagcaa attctgccag aggaggagga gtagacctta
661 ccgaacccac acaaccaacc aggaatcagt gttgtagtaa ctaaacctct agtttgaac
```

SEQ Id NO:84

```
  1 gacgctctgg gccgccacct ccgcggaccc tgagcgcaag agccaagccg ccagcgctgc
 61 gatgtgggcc acgctgccgc tgctctgcgc cggggcctgg ctcctgggag tccccgtctg
121 cggtgccgcc gaactgtgcg tgaactcctt agagaagttt cacttcaagt catggatgtc
181 taagcaccgt aagacctaca gtacggagga gtaccaccac aggctgcaga cgtttgccag
241 caactggagg aagataaacg cccacaacaa tgggaaccac acatttaaaa tggcactgaa
```

FIG. 10 A-75

```
 301 ccaattttca gacatgagct ttgctgaaat aaaacacaag tatctctggt cagagcctca
 361 gaattgctca gccaccaaaa gtaactacct tcgaggtact ggtccctacc caccttccgt
 421 ggactggcgg aaaaaaggaa attttgtctc acctgtgaaa aatcagggtg cctgcggcag
 481 ttgctggact ttctccacca ctggggccct ggagtctgcg atcgccatcg caaccggaaa
 541 gatgctgtcc ttggcggaac agcagctggt ggactgcgcc caggacttca ataatcacgg
 601 ctgccaaggg ggtctcccca gccaggcttt cgagtatatc ctgtacaaca aggggatcat
 661 gggtgaagac acctacccct accagggcaa ggatggttat tgcaagttcc aacctggaaa
 721 ggccatcggc tttgtcaagg atgtagccaa catcacaatc tatgacgagg aagcgatggt
 781 ggaggctgtg gccctctaca accctgtgag ctttgccttt gaggtgactc aggacttcat
 841 gatgtataga accggcatct actccagtac ttcctgccat aaaactccag ataaagtaaa
 901 ccatgcagta ctggctgttg ggtatggaga aaaaaatggg atcccttact ggatcgtgaa
 961 aaactcttgg ggtccccagt ggggaatgaa cgggtacttc ctcatcgagc gcggaaagaa
1021 catgtgtggc ctggctgcct gcgcctccta ccccatccct ctggtgtgag ccgtggcagc
1081 cgcagcgcag actggcggag aaggagagga acgggcagcc tgggcctggg tggaaatcct
1141 gccctggagg aagttgtggg gagatccact gggaccccca acattctgcc ctcacctctg
1201 tgcccagcct ggaaacctac agacaaggag gagttccacc atgagctcac ccgtgtctat
1261 gacgcaaaga tcaccagcca tgtgccttag tgtccttctt aacagactca aaccacatgg
1321 accacgaata ttctttctgt ccagaagggc tactttccac atatagagct ccagggactg
1381 tcttttctgt attcgctgtt caataaacat tgagtgagca cctccccaga tgg
```

SEQ ID NO:85

```
   1 ggtcggggcc cgcggccgct cgcgcctctc gatgggcagc tcgcacttgc tcaacaaggg
  61 cctgccgctt ggcgtccgac ctccgatcat gaacgggccc ctgcacccgc ggcccctggt
 121 ggcattgctg gatggccggg actgcacagt ggagatgccc atcctgaagg acgtggccac
 181 tgtggccttc tgcgacgcgc agtccacgca ggagatccat gagaaggtcc tgaacgaggc
 241 tgtgggggcc ctgatgtacc acaccatcac tctcaccagg gaggacctgg agaagttcaa
 301 agccctccgc atcatcgtcc ggattggcag tggttttgac aacatcgaca tcaagtcggc
 361 cggggattta ggcattgccg tctgcaacgt gcccgcggcg tctgtggagg agacggccga
 421 ctcgacgctg tgccacatcc tgaacctgta ccggcgggcc acctggctgc accaggcgct
 481 gcgggagggc acacgagtcc agagcgtcga gcagatccgc gaggtggcgt ccggcgctgc
 541 caggatccgc ggggagacct tgggcatcat cggacttgtc gcgtggggca ggcagtggcg
 601 ctgcgggcca aggccttcgg cttcaacgtg ctcttctacg acccttactt gtcggatggc
 661 gtggagcggg cgctggggct gcagcgtgtc agcaccctgc aggacctgct cttccacagc
 721 gactgcgtga ccctgcactg cggcctcaac gagcacaacc accacctcat caacgacttc
 781 accgtcaagc agatgagaca aggggccttc ctggtgaaca cagcccgggg tggcctggtg
 841 gatgagaagg cgctggccca ggccctgaag gagggccgga tccgcggcgc ggccctggat
 901 gtgcacgagt cggaaccctt cagctttagc cagggccctc tgaaggatgc acccaacctc
 961 atctgcaccc cccatgctgc atggtacagc gagcaggcat ccatcgagat gcgagaggag
1021 gcggcacggg agatccgcag agccatcaca ggccggatcc cagacagcct gaagaactgt
1081 gtcaacaagg accatctgac agccgccacc cactgggcca gcatggaccc cgccgtcgtg
1141 caccctgagc tcaatggggc tgcctatagg taccctccgg gcgtggtggg cgtggccccc
1201 actggcatcc cagctgctgt ggaaggtatc gtccccagcg ccatgtccct gtcccacggc
1261 ctgccccctg tggcccaccc gccccacgcc ccttctcctg gccaaaccgt caagcccgag
1321 gcggatagag accacgccag tgaccagttg tagcccggga ggagctctcc agcctcggcg
1381 cctgggcaga gggcccggaa accctcggac cagagtgtgt ggaggaggca tctgtgtggt
1441 ggccctggca ctgcagagac tggtccgggc tgtcaggagg cgggaggggg cagcgctggg
1501 cctcgtgtcg cttgtcgtcg tccgtcctgt gggcgctctg ccctgtgtcc ttcgcgttcc
1561 tcgttaagca gaagaagtca gtagttattc tcccatgaac gttcttgtct gtgtacagtt
1621 tttagaacat tacaaaggat ctgtttgctt agctgtcaac aaaaagaaaa cctgaaggag
1681 catttggaag tcaatttgag gttttttttt ttgttttttt tttttttgta tgttggaacg
1741 tgccccagaa tgaggcagtt ggcaaacttc tcaggacaat gaatccttcc cgtttttctt
```

FIG. 10 A-76

```
1801 tttatgccac acagtgcatt gtttttttcta cctgcttgtc ttatttttag aataatttag
1861 aaaaacaaaa caaaggctgt ttttcctaat tttggcatga acccccccctt gttccaaatg
1921 aagacggcat cacgaagcag ctccaaaagg aaaagcttgg gcggtgccca gcgtgcccgc
1981 tgcccatcga cgtctgtcct ggggacgtgg agggtggcag cgtccccgcc tgcaccagtg
2041 ccgtcctgct gatgtggtag gctagcaata ttttggttaa aatcatgttt gtg

SEQ ID NO:86
   1 cgcgcggcca ggccctctta gccctctgcc gtttgggggg cacgggtgaa cctgccgccc
  61 cactcccacc ccgccccgcc ccgcccgtac agccaaatcg gaagggacga gcctgccctt
 121 tgaaagggtt tttttcttg ctcctgcgga gggcgcccca gccatggccc tcaggagctc
 181 cctagacccc gcagggactg ccctccatcc cggccgccgg ggcccgccct ctgcatcccg
 241 cgggcagcct gtgtgaagcg gcctcccgca gcccccggcc cctcccccat ggaggaggag
 301 gaggggggcgg tggccaagga gtggggcacg acccccgcgg ggcccgtctg gaccgcggtg
 361 ttcgactacg aggcggcggg cgacgaggag ctgaccctgc ggaggggcga tcgcgtccag
 421 gtgctttccc aagactgtgc ggtgtccggc gacgagggct ggtggaccgg gcagctcccc
 481 agcggccgcg tgggcgtctt ccccagcaac tacgtggccc ccggcgcccc cgctgcaccc
 541 gcgggcctcc agctgcccca ggagatcccc ttccacgagc tgcagctaga ggagatcatc
 601 ggtgtggggg gctttggcaa ggtctatcgg gccctgtggc gtggcgagga ggtggcagtc
 661 aaggccgccc ggctggaccc tgagaaggac ccggcagtga cagcggagca ggtgtgccag
 721 gaagcccggc tctttggagc cctgcagcac cccaacataa ttgcccttag ggcgcctgc
 781 ctcaaccccc cacacctctg cctagtgatg gagtatgccc ggggtggtgc actgagcagg
 841 gtgctggcag gtcgccgggt gccacctcac gtgctggtca actgggctgt gcaggtggcc
 901 cggggcatga actacctaca caatgatgcc cctgtgccca tcatccaccg ggacctcaag
 961 tccatcaaca tcctgatcct ggaggccatc gagaaccaca acctcgcaga cacggtgctc
1021 aagatcacgg acttcggcct cgcccgcgag tggcacaaga ccaccaagat gagcgctgcg
1081 gggacctacg cctggatggc gccggaggtt atccgtctct ccctcttctc caaaagcagt
1141 gatgtctgga gcttcggggt gctgctgtgg gagctgctga cgggggaggt cccctaccgt
1201 gagatcgacg ccttggccgt ggcgtatggc gtggctatga ataagctgac gctgcccatt
1261 ccctccacgt gccccgagcc ctttgcccgc ctcctggagg aatgctggga cccagacccc
1321 cacgggcggc cagatttcgg tagcatcttg aagcggcttg aagtcatcga acagtcagcc
1381 ctgttccaga tgccactgga gtccttccac tcgctgcagg aagactggaa gctggagatt
1441 cagcacatgt ttgatgacct tcggaccaag gagaaggagc ttcggagccg tgaggaggag
1501 ctgctgcggg cggcacagga gcagcgcttc caggaggagc agctgcggcg gcgggagcag
1561 gagctggcag aacgtgagat ggacatcgtg gaacgggagc tgcacctgct catgtgccag
1621 ctgagccagg agaagccccg ggtccgcaag cgcaagggca acttcaagcg cagccgcctg
1681 ctcaagctgc gggaaggcgg cagccacatc agcctgccct ctggctttga gcataagatc
1741 acagtccagg cctctccaac tctggataag cggaaaggat ccgatggggc cagccccccct
1801 gcaagcccca gcatcatccc ccggctgagg gccattcgcc tgactcccgt ggactgtggt
1861 ggcagcagca gtggcagcag cagtggagga agtgggacat ggagccgcgg tgggccccca
1921 aagaaggaag aactggtcgg gggcaagaag aagggacgaa cgtgggggcc cagctccacc
1981 ctgcagaagg agcgggtggg aggagaggag aggctgaagg ggctgggggga aggaagcaaa
2041 cagtggtcat caagtgcccc caacctgggc aagtccccca aacacacacc cagtcgccgc
2101 tggcttcgcc agcctcaatg agatggagga gttcgcggag gcagaggatg gaggcagcag
2161 cgtgcccccct tcccccctact cgaccccgtc ctacctctca gtgccactgc ctgccgagcc
2221 ctccccgggg gcgcgggcgc cgtgggagcc gacgccgtcc gcgcccccccg ctcggtgggg
2281 acacggcgcc cggcggcgct gcgacctggc gctgctaggc tgcgccacgc tgctgggggc
2341 tgtgggcctg ggcgccgacg tggccgaggc gcgcgcggcc gacggtgagg agcagcggcg
2401 ctggctcgac ggcctcttct ttccccgcgc cggccgcttc ccgcggggcc tcagcccacc
2461 cgcgcgtccc cacggccgcc gcgaagacgt gggccccggc ctgggcctgg cgccctcggc
2521 caccctcgtg tcgctgtcgt ccgtgtccga ctgcaactcc acgcgttcac tgctgcgctc
```

FIG. 10 A-77

2581 tgacagtgac gaggccgcac cggccgcgcc ctccccacca ccctccccgc ccgcgcccac
2641 acccacgccc tcgcccagca ccaaccccct ggtggacctg gagctggaga gcttcaagaa
2701 ggacccccgc cagtcgctca cgcccaccca cgtcacggct gcatgcgctg tgagccgcgg
2761 gcaccggcgg acgccatcgg atggggcgct ggggcagcgg gggccgcccg agcccgcggg
2821 ccatggccct ggccctcgtg accttctgga cttcccccgc ctgcccgacc cccaggccct
2881 gttcccagcc cgccgccggc cccctgagtt cccaggccgc cccaccaccc tgacctttgc
2941 cccgagacct cggccggctg ccagtcgccc ccgcttggac ccctggaaac tggtctcctt
3001 cggccggaca ctcaccatct cgcctcccag caggccagac actccggaga gccctgggcc
3061 ccccagcgtg cagcccacac tgctggacat ggacatggag gggcagaacc aagacagcac
3121 agtgcccctg tgcggggccc acggctccca ctaaggcctg cccaccaccg cccgcctggg
3181 cagccatgaa tgtagcgccc caggccctgc cccagcccgc catgccacaa ggtgggggag
3241 gccctgggca ggatgttcac tctatttatt ggggaaggag ggaggggggg gacacttaac
3301 ttattccttt gtaccccagg gggtggagcc ctgtgcccac cctgcactgg ggggagggtg
3361 ggcagggata ctcagggaca gggcatcatg ggggatttgg cacaaaatgg agcattaaag
3421 gtaacccctg ccccc SEQ ID NO:87
1 gggcccgccc ctggtcacag ccagactgac tcagtttccc tgggaggtcc cgctcgagcc
61 cgtccttccc ctccctctgc ccgcccccag ccctcgcccc accctcggcg cccgcacatc
121 tgcctgctca gctccagacg gcgcccggac ccccgggcgc gggatccagc caggtgggag
181 ccccgcagat gaggtctctg aaggtgtgcc tgaaccagtg ccagcctgcc ctgtctgcag
241 catcggcctg atggggtggt gactgatccc tcagggctcc ggagccatgt ggcccaacgg
301 cagttccctg ggccctgtt tccggcccac aaacattacc ctggaggaga gacggctgat
361 cgcctcgccc tggttcgccg cctccttctg cgtggtgggc ctggcctcca acctgctggc
421 cctgagcgtg ctggcgggcg cgcggcaggg gggttcgcac acgcgctcct ccttcctcac
481 cttcctctgc ggcctcgtcc tcaccgactt cctggggctg ctggtgaccg gtaccatcgt
541 ggtgtcccag cacgccgcgc tcttcgagtg gcacgccgtg gaccctggct gccgtctctg
601 tcgcttcatg ggcgtcgtca tgatcttctt cggcctgtcc ccgctgctgc tgggggccgc
661 catggcctca gagcgctacc tgggtatcac ccggcccttc tcgcgcccgg cggtcgcctc
721 gcagcgccgc gcctgggcca ccgtggggct ggtgtgggcg gccgcgctgg cgctgggcct
781 gctgcccctg ctgggcgtgg gtcgctacac cgtgcaatac ccggggtcct ggtgcttcct
841 gacgctgggc gccgagtccg gggacgtggc cttcgggctg ctcttctcca tgctgggcgg
901 cctctcggtc gggctgtcct tcctgctgaa cacggtcagc gtggccaccc tgtgccacgt
961 ctaccacggg caggaggcgg cccagcagcg tccccgggac tccgaggtgg agatgatggc
1021 tcagctcctg ggatcatgg tggtggccag cgtgtgttgg ctgccccttc tggtcttcat
1081 cgcccagaca gtgctgcgaa acccgcctgc catgagcccc gccgggcagc tgtcccgcac
1141 cacggagaag gagctgctca tctacttgcg cgtggccacc tggaaccaga tcctggaccc
1201 ctgggtgtat atcctgttcc gccgcgccgt gctccggcgt ctccagcctc gcctcagcac
1261 ccggcccagg tcgctgtccc tccagcccca gctcacgcag cgctccgggc tgcagtagga
1321 agtggacaga gcgcccctcc cgcgcctttc cgcggagccc ttggcccctc ggacagccca
1381 tctgcctgtt ctgaggattc aggggctggg ggtgctggat ggacagtggg catcagcagc
1441 agggttttgg gttgacccca atccaacccg gggaccccca actcctccct gatcctttta
1501 ccaagcactc tcccttcctc ggcccctttt tcccatccag agctcccacc ccttctctgc
1561 gtccctccca accccaggaa gggcatgcag acattggaag agggtcttgc attgctattt
1621 tttttttag acggagtctt gctctgtccc ccaggctgga gtgcagtggc gcaatctcag
1681 ctcactgcaa cctccacctc ccgggttcaa gcgattctcc tgcctcagcc tcctgagtag
1741 ctgggactat aggcgcgcgc caccacgccc ggctaatttt tgtattttta gtagagacgg
1801 ggtttcaccg tgttggccag gctggtcttg aactcctgac ctcaggtgat tcaccagcct
1861 cagcctccca aagtgctggg atcacaggca tgaaccacca cacctggcca ttttttttt
1921 ttttttaga cggagtctca ctctgtggcc cagcctggag tacagtggca cgatctcggc

FIG. 10 A-78

```
1981 tcactgcaac ctccgcctcc cgggttcaag cgattctcgt gcctcagcct cccgagcagc
2041 tgggattaca ggcgtaagcc actgcgcccg gccttgcatg ctctttgacc ctgaatttga
2101 cctacttgct ggggtacagt tgcttccttt tgaacctcca acagggaagg ctctgtccag
2161 aaaggattga atgtgaacgg gggcaccccc ttttcttgcc aaaatatatc tctgcctttg
2221 gttttat

SEQ ID NO:88
   1 cccggacatg gccgccaaca tgtacagggt cggagactac gtctactttg agaactcctc
  61 cagcaaccca tacctgatcc ggagaatcga ggagctcaac aagacggcca atgggaacgt
 121 ggaggccaaa gtggtgtgct tctaccggag gcgggacatc tccagcaccc tcatcgccct
 181 ggccgacaag cacgcaaccc tgtcagtctg ctataaggcc ggaccggggg cggacaacgg
 241 cgaggaaggg gaaatagaag aggaaatgga gaatccggaa atggtggacc tgcccgagaa
 301 actaaagcac cagctgcggc atcgggagct gttcctctcc cggcagctgg agtctctgcc
 361 cgccacgcac atcaggggca agtgcagcgt caccctgctc aacgagaccg agtcgctcaa
 421 gtcctacctg gagcgggagg atttcttctt ctattctcta gtctacgacc cacagcagaa
 481 gaccctgctg gcagataaag gagagattcg agtaggaaac cggtaccagg cagacatcac
 541 cgacttgtta aaagaaggcg aggaggatgg ccgagaccag tccaggttgg agacccaggt
 601 gtgggaggcg cacaacccac tcacagacaa gcagatcgac cagttcctgg tggtggcccg
 661 ctctgtgggc accttcgcac gggccctgga ctgcagcagc tccgtccgac agcccagcct
 721 gcacatgagc gccgcagctg cctcccgaga catcaccctg ttccacgcca tggatactct
 781 ccacaagaac atctacgaca tctccaaggc catctcggcg ctggtgccgc agggcgggcc
 841 cgtgctctgc agggacgaga tggaggagtg gtctgcatca gaggccaacc ttttcgagga
 901 agccctggaa aaatatggga aggatttcac ggacattcag caagattttc tcccgtggaa
 961 gtcgctgacc agcatcattg agtactacta catgtggaag accaccgaca gatacgtgca
1021 gcagaaacgc ttgaaagcag ctgaagctga gagcaagtta aagcaagttt atattcccaa
1081 ctataacaag ccaaatccga accaaatcag cgtcaacaac gtcaaggccg gtgtggtgaa
1141 cggcacgggg gcgccgggcc agagccctgg ggctggccgg gcctgcgaga gctgttacac
1201 cacacagtct taccagtggt attcttgggg tccccctaac atgcagtgtc gtctctgcgc
1261 atcttgttgg acatattgga agaaatatgg tggcttgaaa atgccaaccc ggttagatgg
1321 agagaggcca ggaccaaacc gcagtaacat gagtccccac ggcctcccag cccggagcag
1381 cgggagcccc aagtttgcca tgaagaccag gcaggctttc tatctgcaca cgacgaagct
1441 gacgcggatc gcccggcgcc tgtgccgtga gatcctgcgc ccgtggcacg ctgcgcggaa
1501 cccctacctg cccatcaaca gcgcggccat caaggccgag tgcacggcgc ggctgcccga
1561 agcctcccag agcccgctgg tgctgaagca ggcggtacgc aagccgctgg aagccgtgct
1621 tcggtatctt gagacccacc cccgcccccc caagcctgac cccgtgaaaa gcgtgtccag
1681 cgtgctcagc agcctgacgc ccgccaaggt ggcccccgtc atcaacaacg gctcccccac
1741 catcctgggc aagcgcagct acgagcagca caacggggtg gacggcaaca tgaagaagcg
1801 cctcttgatg cccagtaggg gtctggcaaa ccacggacag accaggcaca tgggaccaag
1861 ccggaacctc ctgctcaacg ggaagtccta ccccaccaaa gtgcgcctga tccggggggg
1921 ctccctgccc ccagtcaagc ggcggcggat gaactggatc gacgccccgg gtgacgtgtt
1981 ctacatgccc aaagaggaga ccaggaagat ccgcaagctg ctctcatcct cggaaaccaa
2041 gcgtgctgcc cgccggccct acaagcccat cgccctgcgc cagagccagg ccctgccgcc
2101 gcggccaccg ccacctgcgc ccgtcaacga cgagcccatc gtcatcgagg actaggggcc
2161 gcccccacct gcggccgccc cccgcccctc gcccgcccac acggcccctt cccagccagc
2221 ccgccgcccg cccctcagtt tggtagtgcc ccacctcccg ccctcacctg aagagaaacg
2281 cgctccttgg cggacactgg gggaggagag gaagaagcgc ggctaactta ttccgagaat
2341 gccgaggagt tgtcgttttt agctttgtgt ttactttttg gctggagcgg agatgagggg
2401 ccaccccgtg cccctgtgct gcggggcctt ttgcccggag gccgggccct aaggttttgt
2461 tgtgttctgt tgaaggtgcc attttaaatt ttatttttat tacttttttt gtagatgaac
2521 ttgagctctg taacttacac ctggaatgtt aggatcgtgc ggccgcggcc ggccgagctg
```

FIG. 10 A-79

```
2581 cctggcgggg ttggcccttg tcttttcaag taattttcat attaaacaaa aacaaagaaa
2641 aaaaatctta taaaaaggaa aa
```

SEQ ID NO:89

```
   1 atgagagagt acaaagtggt ggtgctgggc tcgggcggcg tgggcaagtc cgcgctcacc
  61 gtgcagttcg tgacgggctc cttcatcgag aagtacgacc cgaccatcga agacttttac
 121 cgcaaggaga ttgaggtgga ctcgtcgccg tcggtgctgg agatcctgga tacggcgggc
 181 accgagcagt tcgcgtccat gcgggacctg tacatcaaga acggccaggg cttcatcctg
 241 gtctacagcc tcgtcaacca gcagagcttc caggacatca agcccatgcg ggaccagatc
 301 atccgcgtga agcggtacga gcgcgtgccc atgatcctgg tgggcaacaa ggtggacctg
 361 gagggtgagc gcgaggtctc gtacggggag ggcaaggccc tggctgagga gtggagctgc
 421 cccttcatgg agacgtcggc caaaaacaaa gcctcggtag acgagctatt tgccgagatc
 481 gtgcggcaga tgaactacgc ggcgcagtcc aacggcgatg agggctgctg ctcggcctgc
 541 gtgatcctct ga
```

SEQ ID NO:90

```
   1 gagctgcggg cgctgctgct gtggggccgc cgcctgcggc ctttgctgcg ggcgccggcg
  61 ctggcggccg tgccgggagg aaaaccaatt ctgtgtcctc ggaggaccac agcccagttg
 121 ggcccccaggc gaaacccagc ctggagcttg caggcaggac gactgttcag cacgcagacc
 181 gccgaggaca aggaggaacc cctgcactcg attatcagca gcacagagag cgtgcagggt
 241 tccacttcca aacatgagtt ccaggccgag acaaagaagc ttttggacat tgttgcccgg
 301 tccctgtact cagaaaaaga ggtgtttata cgggagctga tctccaatgc cagcgatgcc
 361 ttggaaaaac tgcgtcacaa actggtgtct gacggccaag cactgccaga aatggagatt
 421 cacttgcaga ccaatgccga gaaaggcacc atcaccatcc aggatactgg tatcgggatg
 481 acacaggaag agctggtgtc caacctgggg acgattgcca gatcggggtc aaaggccttc
 541 ctggatgctc tgcagaacca ggctgaggcc agcagcaaga tcatcggcca gtttggagtg
 601 ggtttctact cagctttcat ggtggctgac agagtggagg tctattcccg ctcggcagcc
 661 ccggggagcc tgggttacca gtggctttca gatggttctg gagtgtttga aatcgccgaa
 721 gcttcgggag ttagaaccgg gacaaaaatc atcatccacc tgaaatccga ctgcaaggag
 781 ttttccagcg aggcccgggt gcgagatgtg gtaacgaagt acagcaactt cgtcagcttc
 841 cccttgtact tgaatggaag gcggatgaac accttgcagg ccatctggat gatggacccc
 901 aaggatgtcc gtgagtggca acatgaggag ttctaccgct acgtcgcgca ggctcacgac
 961 aagccccgct acaccctgca ctataagacg gacgcaccgc tcaacatccg cagcatcttc
1021 tacgtgcccg acatgaaacc gtccatgttt gatgtgagcc gggagctggg ctccagcgtt
1081 gcactgtaca gccgcaaagt cctcatccag accaaggcca cggacatcct gcccaagtgg
1141 ctgcgcttca tccgaggtgt ggtggacagt gaggacattc ccctgaacct cagccgggag
1201 ctgctgcagg agagcgcact catcaggaaa ctccgggacg ttttacagca gaggctgatc
1261 aaattcttca ttgaccagag taaaaaagat gctgagaagt atgcaaagtt' ttttgaagat
1321 tacggcctgt tcatgcggga gggcattgtg accgccaccg agcaggaggt caaggaggac
1381 atagcaaagc tgctgcgcta cgagtcctcg gcgctgccct ccgggcagct aaccagcctc
1441 tcagaatacg ccagccgcat gcgggccggc acccgcaaca tctactacct gtgcgccccc
1501 aaccgtcacc tggcagagca ctcaccctac tatgaggcca tgaagaagaa agacacagag
1561 gttctcttct gctttgagca gtttgatgag ctcaccctgc tgcaccttcg tgagtttgac
1621 aagaagaagc tgatctctgt ggagacggac atagtcgtgg atcactacaa ggaggagaag
1681 tttgaggaca ggtccccagc cgccgagtgc ctatcagaga aggagacgga ggagctcatg
1741 gcctggatga gaaatgtgct ggggtcgcgt gtcaccaacg tgaaggtgac cctccgactg
1801 gacacccacc ctgccatggt caccgtgctg gagatggggg ctgcccgcca cttcctgcgc
1861 atgcagcagc tggccaagac ccaggaggag cgcgcacagc tcctgcagcc cacgctggag
1921 atcaacccca ggcacgcgct catcaagaag ctgaatcagc tgcgcgcaag cgagcctggc
```

FIG. 10 A-80

```
1981 ctggctcagc tgctggtgga tcagatatac gagaacgcca tgattgctgc tggacttgtt
2041 gacgacccta gggccatggt gggccgcttg aatgagctgc ttgtcaaggc cctggagcga
2101 cactgacagc cagggggcca gaaggactga caccacagat gacagcccca cctccttgag
2161 ctttatttac ctaaatttaa aggtatttct taacccga
```

SEQ ID NO:91

```
   1 agtgatgtcc ttgcattgcc catttttaag caagaagagt cgagtttgcc tcctgataat
  61 gagaataaaa tcctgccttt tcaatatgtg ctttgtgctg ctacctctcc agcagtgaaa
 121 ctccatgatg aaaccctaac gtatctcaat caaggacagt cttatgaaat tcgaatgcta
 181 gacaatagga aacttggaga acttccagaa attaatggca aattggtgaa gagtatattc
 241 cgtgtggtgt tccatgacag aaggcttcag tacactgagc atcagcagct agagggctgg
 301 aggtggaacc gacctggaga cagaattctt gacatagata tcccgatgtc tgtgggtata
 361 atcgatccta gggctaatcc aactcaacta aatacagtgg agttcctgtg ggaccctgca
 421 aagaggacat ctgtgtttat tcaggtgcac tgtattagca cagagttcac tatgaggaaa
 481 catggtggag aaaagggggt gccattccga gtacaaatag ataccttcaa ggagaatgaa
 541 aacggggaat atactgagca cttacactcg gccagctgcc agatcaaagt tttcaagcca
 601 aaggtgcaga cagaaagcaa aaaacggata gggaaaaaat ggagaaacga acacctcatg
 661 aaaaggagaa atatcagcct tcctatgaga caaccatact cacagagtgt tctccatggc
 721 ccgagatcac gtatgtcaat aactccccat cacctggctt caacagttcc catagcagtt
 781 tttctcttgg ggaaggaaat ggttcaccaa accaccagcc agagccaccc cctccagtca
 841 cagataacct cttaccaaca accacacctc aggaagctca gcagtggttg catcgaaatc
 901 gtttttctac attcacaagg cttttcacaa acttctcagg ggcagattta ttgaaattaa
 961 ctagagatga tgtgatccaa atctgtggcc ctgcagatgg aatcagactt tttaatgcat
1021 taaaaggccg gatggtgcgt ccaaggttaa ccatttatgt ttgtcaggaa tcactgcagt
1081 tgagggagca gcaacaacag cagcagcaac agcagcagaa gcatgaggat ggagactcaa
1141 atggtacttt cttcgtttac catgctatct atctagaaga actaacagct gttgaattga
1201 cagaaaaaat tgctcagctt ttcagcattt ccccttgcca gatcagccag atttacaagc
1261 aggggccaac aggaattcat gtgctcatca gtgatgagat gatacagaac tttcaggaag
1321 aagcatgttt tattctggac acaatgaaag cagaaaccaa tgatagctat catatcatac
1381 tgaagtagga gtgcggcgtt tcgtgcccag tggctgctcc ttccttcacc tctgaaaacg
1441 gccctcttga agggggatat gaatggagat ttgaaggtct gcaagaacct gactcgtctg
1501 actgtgtgtg gaggagtcca ggccatggag gcagaatcct ggccctctgt gttggcccaa
1561 gctcttgtgg tacacacaga ttactgccca atatgcagtt ctgcagctgt tttagttaaa
1621 tttctggacc ttgttgttgt taaatatcag tagaaactct acataattta gagtgtatgt
1681 agggcataat gatgatggga attgtgtgat gtttaacagg aagatcttaa attttgtgat
1741 atggagccct gtaatttttt tcttatataa aaatgggtat ctatattcat
```

SEQ ID NO:92

```
   1 aggtctgttc cgcatgaaac tcctgctggg gaaggacttc cctgcctccc cacccaaggg
  61 ctacttcctg accaagatct tccacccgaa cttgggcgcc aatggcgaga tgtgcgtcaa
 121 cgtgctcaag agggactgga cggctgagct gggcatccga cacgtactgc tgaccatcaa
 181 gtgcctgctg atccacccta accccgagtc tgcactcaac gaggaggcgg gccgcctgct
 241 cttggagaac tacgaggagt atgcggctcg ggcccgtctg ctcacagaga tccacggggg
 301 cgccggcggg cccagcggca gggccaaagc cgggcgggcc ctggccagtg gcactgcagc
 361 ttcctccacc gactctgggg ccccaggggg cttgggaggg gctgagggtc ccatggccaa
 421 gaagcatgct ggcgagcgcg ataagaagct ggcggccaag aaaaagacgg acaagaagcg
 481 ggcgctacgg cggctgtagt gggctctctt cctccttcca ccgtgacccc aacctctcct
 541 gtcccctccc tccaactctg tctctaagtt atttaaatta tggctggggt cggggagggt
 601 acagggggca ctgagacctg gatttgtttt tttaaataaa gttggaaaag ca
```

FIG. 10 A-81

SEQ ID NO:93

```
  1 gtcgtgttct ccgagttcct gtctctctgc caacgccgcc cggatggctt cccaaaaccg
 61 cgacccagcc gccactagcg tcgccgccgc ccgtaaagga gctgagccga gcgggggcgc
121 cgcccggggt ccggtgggca aaaggctaca gcaggagctg atgaccctca tgatgtctgg
181 cgataaaggg atttctgcct tccctgaatc agacaacctt ttcaaatggg tagggaccat
241 ccatggagca gctggaacag tatatgaaga cctgaggtat aagctctcgc tagagttccc
301 cagtggctac ccttacaatg cgcccacagt gaagttcctc acgccctgct atcaccccaa
361 cgtggacacc cagggtaaca tatgcctgga catcctgaag gaaaagtggt ctgccctgta
421 tgatgtcagg accattctgc tctccatcca gagccttcta ggagaaccca acattgatag
481 tcccttgaac acacatgctg ccgagctctg gaaaaacccc acagctttta agaagtacct
541 gcaagaaacc tactcaaagc aggtcaccag ccaggagccc tgacccaggc tgcccagcct
601 gtccttgtgt cgtcttttta atttttcctt agatggtctg tcctttttgt gatttctgta
661 taggactctt tatcttgagc tgtggtattt ttgttttgtt tttgtctttt aaattaagcc
721 tcggttgagc ccttgtatat taaataaatg catttttgtc ctttttttaga c
```

SEQ ID NO:94

```
   1 ctccagcagc acccgagagg gtcaggagaa aagcggagga agctgggtag gccctgaggg
  61 gcctcggtaa gccatcatga ccacccggca agccacgaag gatcccctcc tccggggtgt
 121 atctcctacc cctagcaaga ttccggtacg ctctcagaaa cgcacgcctt tccccactgt
 181 tacatcgtgc gccgtggacc aggagaacca agatccaagg agatgggtgc agaaaccacc
 241 gctcaatatt caacgccccc tcgttgattc agcaggcccc aggccgaaag ccaggcacca
 301 ggcagagaca tcacaaagat tggtggggat cagtcagcct cggaacccct tggaagagct
 361 caggcctagc cctaggggtc aaaatgtggg gcctgggccc cctgcccaga cagaggctcc
 421 agggaccata gagtttgtgg ctgaccctgc agccctggcc accatcctgt caggtgaggg
 481 tgtgaagagc tgtcacctgg ggcgccagcc tagtctggct aaaagagtac tggttcgagg
 541 aagtcaggga ggcaccaccc agagggtcca gggtgttcgg gcctctgcat atttggcccc
 601 cagaaccccc acccaccgac tggaccctgc cagggcttcc tgcttctcta ggctggaggg
 661 accaggacct cgaggccgga cattgtgtcc ccagaggcta caggctctga tttcaccttc
 721 aggaccttcc tttcaccctt ccactcgccc cagtttccag gagctaagaa gggagacagc
 781 tggcagcagc cggacttcag tgagccaggc ctcaggattg ctcctggaga ccccagtcca
 841 gcctgctttc tctcttccta aaggagaacg cgaggttgtc actcactcag atgaaggagg
 901 tgtggcctct cttggtctgg cccagcgagt accattaaga gaaaaccgag aaatgtcaca
 961 taccagggac agccatgact cccacctgat gccctcccct gcccctgtgg cccagcccctt
1021 gcctggccat gtggtgccat gtccatcacc ctttggacgg gctcagcgtg taccctcccc
1081 aggccctcca actctgacct catattcagt gttgcggcgt ctcaccgttc aacctaaaac
1141 ccggttcaca cccatgccat caaccccccag agttcagcag gcccagtggc tgcgtggtgt
1201 ctcccctcag tcctgctctg aagatcctgc cctgccctgg gagcaggttg ccgtccggtt
1261 gtttgaccag gagagttgta taaggtcact ggagggttct gggaaaccac cggtggccac
1321 tccttctgga ccccactcta acagaacccc cagcctccag gaggtgaaga ttcaacgcat
1381 cggtatcctg caacagctgt tgagacagga agtagagggg ctggtagggg gccagtgtgt
1441 ccctcttaat ggaggctctt ctctggatat ggttgaactt cagcccctgc tgactgagat
1501 ttctagaact ctgaatgcca cagagcataa ctctgggact tcccaccttc ctggactgtt
1561 aaaacactca gggctgccaa agccctgtct tccagaggag tgcggggaac cacagccctg
1621 ccctccggca gagcctgggc ccccagaggc cttctgtagg agtgagcctg agataccaga
1681 gccctccctc caggaacagc ttgaagtacc agagccctac cctccagcag aacccaggcc
1741 cctagagtcc tgctgtagga gtgagcctga gataccggag tcctctcgcc aggaacagct
1801 tgaggtacct gagccctgcc ctccagcaga acccaggccc ctagagtcct actgtaggat
1861 tgagcctgag ataccggagt cctctcgcca ggaacagctt gaggtacctg agccctgccc
1921 tccagcagaa cccgggcccc ttcagcccag cacccagggg cagtctggac ccccagggcc
1981 ctgccctagg gtagagctgg gggcatcaga gccctgcacc ctggaacata gaagtctaga
```

FIG. 10 A-82

```
2041 gtccagtcta ccaccctgct gcagtcagtg ggctccagca accaccagcc tgatcttctc
2101 ttcccaacac ccgctttgtg ccagcccccc tatctgctca ctccagtctt tgagaccccc
2161 agcaggccag gcaggcctca gcaatctggc ccctcgaacc ctagccctga gggagcgcct
2221 caaatcgtgt ttaaccgcca tccactgctt ccacgaggct cgtctggacg atgagtgtgc
2281 cttttacacc agccgagccc ctccctcagg ccccacccgg gtctgcacca accctgtggc
2341 tacattactc gaatggcagg atgccctgtg tttcattcca gttggttctg ctgcccccca
2401 gggctctcca tgatgagaca accactcctg ccctgccgta cttcttcctt ttagccctta
2461 tttattgtcg gtctgcccat gggactggga gccgcccact tttgtcctca ataaagtttc
2521 taaagta

SEQ ID NO:95
   1 agaataatca tgggccagac tgggaagaaa tctgagaagg gaccagtttg ttggcggaag
  61 cgtgtaaaat cagagtacat gcgactgaga cagctcaaga ggttcagacg agctgatgaa
 121 gtaaaggtat gtttagttcc aatcgtcaga aaattttgga aagaacggaa atcttaaacc
 181 aagaatggaa acagcgaagg atacagcctg tgcacatcct gacttctgtg agctcattgc
 241 gcgggactag ggagtgttcg gtgaccagtg acttggattt tccaacacaa gtcatcccat
 301 taaagactct gaatgcagtt gcttcagtac ccataatgta ttcttggtct cccctacagc
 361 agaattttat ggtggaagat gaaactgttt tacataacat tccttatatg ggagatgaag
 421 ttttagatca ggatggtact ttcattgaag aactaataaa aaattatgat gggaaagtac
 481 acggggatag agaatgtggg tttataaatg atgaaatttt tgtggagttg gtgaatgccc
 541 ttggtcaata taatgatgat gacgatgatg atgatggaga cgatcctgaa gaaagagaag
 601 aaaagcagaa agatctggag gatcaccgag atgataaaga aagccgccca cctcggaaat
 661 ttccttctga taaaattttt gaagccattt cctcaatgtt tccagataag ggcacagcag
 721 aagaactaaa ggaaaaatat aaagaactca ccgaacagca gctcccaggc gcacttcctc
 781 ctgaatgtac ccccaacata gatggaccaa atgctaaatc tgttcagaga gagcaaagct
 841 tacactcctt tcatacgctt ttctgtaggc gatgttttaa atatgactgc ttcctacatc
 901 cttttcatgc aacacccaac acttataagc ggaagaacac agaaacagct ctagacaaca
 961 aaccttgtgg accacagtgt taccagcatt tggagggagc aaaggagttt gctgctgctc
1021 tcaccgctga gcggataaag accccaccaa aacgtccagg aggccgcaga agaggacggc
1081 ttcccaataa cagtagcagg cccagcaccc ccaccattaa tgtgctggaa tcaaaggata
1141 cagacagtga tagggaagca gggactgaaa cgggggggaga gaacaatgat aaagaagaag
1201 aagagaagaa agatgaaact tcgagctcct ctgaagcaaa ttctcggtgt caaacaccaa
1261 taaagatgaa gccaaatatt gaacctcctg agaatgtgga gtggagtggt gctgaagcct
1321 caatgtttag agtcctcatt ggcacttact atgacaattt ctgtgccatt gctaggttaa
1381 ttgggaccaa aacatgtaga caggtgtatg agtttagagt caaagaatct agcatcatag
1441 ctccagctcc cgctgaggat gtggatactc ctccaaggaa aaagaagagg aaacaccggt
1501 tgtgggctgc acactgcaga aagatacagc tgaaaaagga cggctcctct aaccatgttt
1561 acaactatca accctgtgat catccacggc agccttgtga cagttcgtgc ccttgtgtga
1621 tagcacaaaa tttttgtgaa aagttttgtc aatgtagttc agagtgtcaa aaccgctttc
1681 cgggatgccg ctgcaaagca cagtgcaaca ccaagcagtg cccgtgctac ctggctgtcc
1741 gagagtgtga ccctgacctc tgtcttactt gtggagccgc tgaccattgg gacagtaaaa
1801 atgtgtcctg caagaactgc agtattcagc ggggctccaa aaagcatcta ttgctggcac
1861 catctgacgt ggcaggctgg gggattttta tcaaagatcc tgtgcagaaa aatgaattca
1921 tctcagaata ctgtggagag attatttctc aagatgaagc tgacagaaga gggaaagtgt
1981 atgataaata catgtgcagc tttctgttca acttgaacaa tgattttgtg gtggatgcaa
2041 cccgcaaggg taacaaaatt cgttttgcaa atcattcggt aaatccaaac tgctatgcaa
2101 aagttatgat ggttaacggt gatcacagga taggtatttt tgccaagaga gccatccaga
2161 ctggcgaaga gctgtttttt gattacagat acagccaggc tgatgccctg aagtatgtcg
2221 gcatcgaaag agaaatggaa atcccttgac atctgctacc tcctcccccc tcctctgaaa
2281 cagctgcctt agcttcagga acctcgagta ctgtgggcaa tttagaaaaa gaacatgcag
```

FIG. 10 A-83

```
2341 tttgaaattc tgaatttgca aagtactgta agaataattt atagtaatga gtttaaaaat
2401 caacttttta ttgccttctc accagctgca aagtgttttg taccagtgaa tttttgcaat
2461 aatgcagtat ggtacatttt tcaactttga ataaagaata cttgaacttg tc
```

SEQ ID NO: 96

```
   1 caggtctgag gcgaagctag gtgagccgtg ggaagaaaag agggagcagc tagggcgcgg
  61 gtctccctcc tcccggagtt tggaacggct gaagttcacc ttccagcccc tagcgccgtt
 121 cgcgccgcta ggcctggctt ctgaggcggt tgcggtgctc ggtcgccgcc taagcggggc
 181 agggtgcgaa caggggcttc gggccacgct tctcttggcg acaggatttt gctgtgaagt
 241 ccgtccggga aacggaggaa aaaaagagtt gcgggaggct gtctgctaat aacggttctt
 301 gatacatatt tgccagactt caagatttca gaaaaggggt gaaagagaag attgcaactt
 361 tgagtcagac ctgtaggcct gatagactga ttaaaccaca gaaggtgacc tgctgagaaa
 421 agtggtacaa atactgggaa aaacctgctc ttctgcgtta agtgggagac aatgtcacaa
 481 gttaaaagct cttattccta tgatgccccc tcggatttca tcaatttttc atccttggat
 541 gatgaaggag atactcaaaa catagattca tggtttgagg agaaggccaa tttggagaat
 601 aagttactgg ggaagaatgg aactggaggg ctttttcagg gcaaaactcc tttgagaaag
 661 gctaatcttc agcaagctat tgtcacacct ttgaaaccag ttgacaacac ttactacaaa
 721 gaggcagaaa aagaaaatct tgtggaacaa tccattccgt caaatgcttg ttcttccctg
 781 gaagttgagg cagccatatc aagaaaaact ccagcccagc ctcagagaag atctcttagg
 841 ctttctgctc agaaggattt ggaacagaaa gaaaagcatc atgtaaaaat gaaagccaag
 901 agatgtgcca ctcctgtaat catcgatgaa attctaccct ctaagaaaat gaaagtttct
 961 aacaacaaaa agaagccaga ggaagaaggc agtgctcatc aagatactgc tgaaaacaat
1021 gcatcttccc cagagaaagc caagggtaga catactgtgc cttgtatgcc acctgcaaag
1081 cagaagtttc taaaaagtac tgaggagcaa gagctggaga agagtatgaa aatgcagcaa
1141 gaggtggtgg agatgcggaa aaagaatgaa gaattcaaga aacttgctct ggctggaata
1201 gggcaacctg tgaagaaatc agtgagccag gtcaccaaat cagttgactt ccacttccgc
1261 acagatgagc gaatcaaaca acatcctaag aaccaggagg aatataagga agtgaacttt
1321 acatctgaac tacgaaagca tccttcatct cctgcccgag tgactaaggg atgtaccatt
1381 gttaagcctt tcaacctgtc ccaaggaaag aaaagaacat ttgatgaaac agtttctaca
1441 tatgtgcccc ttgcacagca agttgaagac ttccataaac gaacccctaa cagatatcat
1501 ttgaggagca agaaggatga tattaacctg ttaccctcca aatcttctgt gaccaagatt
1561 tgcagagacc cacagactcc tgtactgcaa accaaacacc gtgcacgggc tgtgacctgc
1621 aaaagtacag cagagctgga ggctgaggag ctcgagaaat tgcaacaata caaattcaaa
1681 gcacgtgaac ttgatcccag aatacttgaa ggtgggccca tcttgcccaa gaaaccacct
1741 gtgaaaccac ccaccgagcc tattggcttt gatttggaaa ttgagaaaag aatccaggag
1801 cgagaatcaa agaagaaaac agaggatgaa cactttgaat ttcattccag accttgccct
1861 actaagattt tggaagatgt tgtgggtgtt cctgaaaaga aggtacttcc aatcaccgtc
1921 cccaagtcac cagcctttgc attgaagaac agaattcgaa tgcccaccaa agaagatgag
1981 gaagaggacg aaccggtagt gataaaagct caacctgtgc cacattatgg ggtgcctttt
2041 aagccccaaa tcccagaggc aagaactgtg gaaatatgcc ctttctcgtt tgattctcga
2101 gacaaagaac gtcagttaca gaaggagaag aaaataaaag aactgcagaa aggggaggtg
2161 cccaagttca aggcacttcc cttgcctcat tttgacacca ttaacctgcc agagaagaag
2221 gtaaagaatg tgacccagat tgaacctttc tgcttggaga ctgacagaag aggtgctctg
2281 aaggcacaga cttggaagca ccagctggaa gaagaactga gacagcagaa agaagcagct
2341 tgtttcaagg ctcgtccaaa caccgtcatc tctcaggagc cctttgttcc caagaaagag
2401 aagaaatcag ttgctgaggg cctttctggt tctctagttc aggaaccttt tcagctggct
2461 actgagaaga gagccaaaga gcggcaggag ctggagaaga gaatggctga ggtagaagcc
2521 cagaaagccc agcagttgga ggaggccaga ctacaggagg aagagcagaa aaaagaggag
2581 ctggccaggc tacggagaga actggtgcat aaggcaaatc caatacgcaa gtaccagggt
2641 ctggagataa agtcaagtga ccagcctctg actgtgcctg tatctcccaa attctccact
```

FIG. 10 A-84

2701 cgattccact gctaaactca gctgtgagct gcggataccg cccggcaatg ggacctgctc
2761 ttaacctcaa acctaggacc gtcttgcttt gtcattgggc atggagagaa cccatttctc
2821 cagactttta cctacccgtg cctgagaaag catacttgac aactgtggac tccagttttg
2881 ttgagaattg ttttcttaca ttactaaggc taataatgag atgtaactca tgaatgtctc
2941 gattagactc catgtagtta cttcctttaa accatcagcc ggccttttat atgggtcttc
3001 actctgacta gaatttagtc tctgtgtcag cacagtgtaa tctctattgc tattgcccct
3061 tacgactctc accctctccc cacttttttt aaaaatttta accagaaaat aaagatagtt
3121 aaatcctaag atagagatta agtcatggtt taaatgagga acaatcagta aatcagattc
3181 tgtcctcttc tctgcatacc gtgaatttat agttaaggat ccctttgctg tgagggtaga
3241 aaacctcacc aactgcacca gtgaggaaga agactgcgtg gattcatggg gagcctcaca
3301 gcagccacgc agcaggctct gggtggggct gccgttaagg cacagttctt tccttactgg
3361 tgctgataac aacagggaac cgtgcagtgt gcattttaag acc SEQ ID NO:97
1 cttcaacccg cgccggcggc gactgcagtt cctgcgagcg aggagcgcgg gacctgctga
61 cacgctgacg ccttcgagcg cggcccgggg cccggagcgg ccggagcagc ccgggtcctg
121 accccggccc ggctcccgct ccgggctctg ccggcgggcg ggcgagcgcg gcgcggtccg
181 ggccgggggg atgtctcggc ggacgcgctg cgaggatctg gatgagctgc actaccagga
241 cacagattca gatgtgccgg agcagaggga tagcaagtgc aaggtcaaat ggacccatga
301 ggaggacgag cagctgaggg ccctggtgag gcagtttgga cagcaggact ggaagttcct
361 ggccagccac ttccctaacc gcactgacca gcaatgccag tacaggtggc tgagagtttt
421 gaatccagac cttgtcaagg ggccatggac caaagaggaa gaccaaaaag tcatcgagct
481 ggttaagaag tatggcacaa agcagtggac actgattgcc aagcacctga agggccggct
541 ggggaagcag tgccgtgaac gctggcacaa ccacctcaac cctgaggtga agaagtcttg
601 ctggaccgag gaggaggacc gcatcatctg cgaggcccac aaggtgctgg gcaaccgctg
661 ggccgagatc gccaagatgt tgccagggag gacagacaat gctgtgaaga atcactggaa
721 ctctaccatc aaaaggaagg tggacacagg aggcttcttg agcgagtcca aagactgcaa
781 gcccccagtg tacttgctgc tggagctcga ggacaaggac ggcctccaga gtgcccagcc
841 cacggaaggc cagggaagtc ttctgaccaa ctggccctcc gtccctccta ccataaagga
901 ggaggaaaac agtgaggagg aacttgcagc agccaccaca tcgaaggaac aggagcccat
961 cggtacagat ctggacgcag tgcgaacacc agagcccttg gaggaattcc cgaagcgtga
1021 ggaccaggaa ggctccccac cagaaacgag cctgccttac aagtgggtgg tggaggcagc
1081 taacctcctc atccctgctg tgggttctag cctctctgaa gccctggact tgatcgagtc
1141 ggaccctgat gcttggtgtg acctgagtaa atttgacctc cctgaggaac catctgcaga
1201 ggacagtatc aacaacagcc tagtgcagct gcaagcgtca catcagcagc aagtcctgcc
1261 accccgccag ccttccgccc tggtgcccag tgtgaccgag taccgcctgg atggccacac
1321 catctcagac ctgagccgga gcagccgggg cgagctgatc cccatctccc ccagcactga
1381 agtcgggggc tctggcattg gcacaccgcc ctctgtgctc aagcggcaga ggaagaggcg
1441 tgtggctctg tcccctgtca ctgagaatag caccagtctg tccttcctgg attcctgtaa
1501 cagcctcacg cccaagagca cacctgttaa gaccctgccc ttctcgccct cccagtttct
1561 gaacttctgg aacaaacagg acacattgga gctggagagc ccctcgctga catccacccc
1621 agtgtgcagc cagaaggtgg tggtcaccac accactgcac cgggacaaga cacccctgca
1681 ccagaaacat gctgcgtttg taaccccaga tcagaagtac tccatggaca acactcccca
1741 cacgccaacc ccgttcaaga acgccctgga gaagtacgga cccctgaagc ccctgccaca
1801 gaccccgcac ctggaggagg acttgaagga ggtgctgcgt tctgaggctg gcatcgaact
1861 catcatcgag gacgacatca ggcccgagaa gcagaagagg aagcctgggc tgcggcggag
1921 ccccatcaag aaagtccgga agtctctggc tcttgacatt gtggatgagg atgtgaagct
1981 gatgatgtcc acactgccca agtctctatc cttgccgaca actgcccctt caaactcttc
2041 cagcctcacc ctgtcaggta tcaaagaaga caacagcttg ctcaaccagg gcttcttgca
2101 ggccaagccc gagaaggcag cagtggccca gaagccccga agccacttca cgacacctgc

FIG. 10 A-85

2161 ccctatgtcc agtgcctgga agacggtggc ctgcgggggg accagggacc agcttttcat
2221 gcaggagaaa gcccggcagc tcctgggccg cctgaagccc agccacacat ctcggaccct
2281 catcttgtcc tgaggtgttg agggtgtcac gagcccattc tcatgtttac aggggttgtg
2341 ggggcagagg gggtctgtga atctgagagt cattcaggtg acctcctgca gggagccttc
2401 tgccaccagc ccctccccag actctcaggt ggaggcaaca gggccatgtg ctgccctgtt
2461 gccgagccca gctgtgggcg gctcctggtg ctaacaacaa agttccactt ccaggtctgc
2521 ctggttccct ccccaaggcc acagggagct ccgtcagctt ctcccaagcc cacgtcaggc
2581 ctggcctcat ctcagaccct gcttaggatg gggatgtgg ccaggggtgc tcctgtgctc
2641 accctctctt ggtgcatttt tttggaagaa taaaattgcc tctctctt SEQ ID NO:98
1 atgaggttga cgctactttg ttgcacctgg agggaagaac gtatgggaga ggaaggaagc
61 gagttgcccg tgtgtgcaag ctgcggccag aggatctatg atggccagta cctccaggcc
121 ctgaacgcgg actggcacgc agactgcttc aggtgttgtg actgcagtgc ctccctgtcg
181 caccagtact atgagaagga tgggcagctc ttctgcaaga aggactactg ggcccgctat
241 ggcgagtcct gccatgggtg ctctgagcaa atcaccaagg gactggttat ggtggctggg
301 gagctgaagt accaccccga gtgtttcatc tgcctcacgt gtgggacctt tatcggtgac
361 ggggacacct acacgctggt ggagcactcc aagctgtact gcgggcactg ctactaccag
421 actgtggtga cccccgtcat cgagcagatc ctgcctgact cccctggctc ccacctgccc
481 cacaccgtca ccctggtgtc catcccagcc tcatctcatg gcaagcgtgg actttcagtc
541 tccattgacc ccccgcacgg cccaccgggc tgtggcaccg agcactcaca caccgtccgc
601 gtccagggag tggatccggg ctgcatgagc ccagatgtga agaattccat ccacgtcgga
661 gaccggatct tggaaatcaa tggcacgccc atccgaaatg tgcccctgga cgagattgac
721 ctgctgattc aggaaaccag ccgcctgctc cagctgaccc tcgagcatga ccctcacgat
781 acactgggcc acgggctggg gcctgagacc agccccctga gctctccggc ttatactccc
841 agcggggagg cgggcagctc tgcccggcag aaacctgtct tcgcaaggac ctgggtcgct
901 ctgagtccct ccgcgtagtc tgccggccac accgcatctt ccggccgtcg gacctcatcc
961 acggggaggt gctgggcaag ggctgcttcg gccaggctat caaggtgaca caccgtgaga
1021 caggtgaggt gatggtgatg aaggagctga tccggttcga cgaggagacc cagaggacgt
1081 tcctcaagga ggtgaaggtc atgcgatgcc tggaacaccc caacgtgctc aagttcatcg
1141 gggtgctcta caaggacaag aggctcaact tcatcactga gtacatcaag ggcggcacgc
1201 tccggggcat catcaagagc atggacagcc agtacccatg gagccagaga gtgagctttg
1261 ccaaggacat cgcatcaggg atggcctacc tccactccat gaacatcatc caccgagacc
1321 tcaactccca caactgcctg gtccgcgaga acaagaatgt ggtggtggct gacttcgggc
1381 tggcgcgtct catggtggac gagaagactc agcctgaggg cctgcggagc ctcaagaagc
1441 cagaccgcaa gaagcgctac accgtggtgg gcaaccccta ctggatggca cctgagatga
1501 tcaacggccg cagctatgat gagaaggtgg atgtgttctc ctttgggatc gtcctgtgcg
1561 agatcatcgg gcgggtgaac gcagaccctg actacctgcc ccgcaccatg gactttggcc
1621 tcaacgtgcg aggattcctg gaccgctact gccccccaaa ctgccccccg agcttcttcc
1681 ccatcaccgt gcgctgttgc gatctggacc ccgagaagag gccatccttt gtgaagctgg
1741 aacactggct ggagaccctc cgcatgcacc tggccggcca cctgccactg ggcccacagc
1801 tggagcagct ggacagaggt ttctgggaga cctaccggcg cggcgagagc ggactgcctg
1861 cccaccctga ggtccccgac tga SEQ ID NO:99
1 atgcctggct tcgactacaa gttcctggag aagcccaagc gacggctgct gtgcccactg
61 tgcgggaagc ccatgcgcga gcctgtgcag gtttccacct gcggccaccg tttctgcgat
121 acctgcctgc aggagttcct cagtgaagga gtcttcaagt gccctgagga ccagcttcct
181 ctggactatg ccaagatcta cccagacccg gagctggaag tacaagtatt gggcctgcct
241 atccgctgca tccacagtga ggagggctgc cgctggagtg ggccactacg tcatctacag

FIG. 10 A-86

301 ggccacctga atacctgcag cttcaatgtc attccctgcc ctaatcgctg ccccatgaag
361 ctgagccgcc gtgatctacc tgcacacttg cagcatgact gccccaagcg gcgcctcaag
421 tgcgagtttt gtggctgtga cttcagtggg gaggcctatg aggtggatga gagttctctg
481 ggctttggtt atcccaagtt catctcccac caggacattc gaaagcgaaa ctatgtgcgg
541 gatgatgcag tcttcatccg tgctgctgtt gaactgcccc ggaagatcct cagctga SEQ ID NO:104
1 ttgcaggctg ctgggctggg gctaagggct gctcagtttc cttcagcggg gcactgggaa
61 gcgccatggc actgcagggc atctcggtcg tggagctgtc cggcctggcc ccgggcccgt
121 tctgtgctat ggtcctggct gacttcgggg cgcgtgtggt acgcgtggac cggcccggct
181 cccgctacga cgtgagccgc ttgggccggg gcaagcgctc gctagtgctg gacctgaagc
241 agccgcgggg agccgccgtg ctgcggcgtc tgtgcaagcg gtcggatgtg ctgctggagc
301 ccttccgccg cggtgtcatg gagaaactcc agctgggccc agagattctg cagcgggaaa
361 atccaaggct tatttatgcc aggctgagtg gatttggcca gtcaggaagc ttctgccggt
421 tagctggcca cgatatcaac tatttggctt tgtcaggtgt tctctcaaaa attggcagaa
481 gtggtgagaa tccgtatgcc ccgctgaatc tcctggctga ctttgctggt ggtggcctta
541 tgtgtgcact gggcattata atggctcttt ttgaccgcac acgcactggc aagggtcagg
601 tcattgatgc aaatatggtg gaaggaacag catatttaag ttcttttctg tggaaaactc
661 agaaatcgag tctgtgggaa gcacctcgag gacagaacat gttggatggt ggagcacctt
721 tctatacgac ttacaggaca gcagatgggg aattcatggc tgttggagca atagaacccc
781 agttctacga gctgctgatc aaaggacttg gactaaagtc tgatgaactt cccaatcaga
841 tgagcatgga tgattggcca gaaatgaaga agaagtttgc agatgtattt gcaaagaaga
901 cgaaggcaga gtggtgtcaa atctttgacg gcacagatgc ctgtgtgact ccggttctga
961 cttttgagga ggttgttcat catgatcaca acaaggaacg ggctcgtttt atcaccagtg
1021 aggagcagga cgtgagcccc cgccctgcac ctctgctgtt aaacacccca gccatccctt
1081 ctttcaaaag ggatcctttc ataggagaac acactgagga gatacttgaa gaatttggat
1141 tcagccgcga agagatttat cagcttaact cagataaaat cattgaaagt aataaggtaa
1201 aagctagtct ctaacttcca ggcccacggc tcaagtgaat ttgaatactg catttacagt
1261 gtagagtaac acataacatt gtatgcatgg aaacatggag gaacagtatt acagtgtcct
1321 accactctaa tcaagaaaag aattacagac tctgattcta cagtgatgat tgaattctaa
1381 aaatggttat cattagggct tttgatttat aaaactttgg gtacttatac taaattatgg
1441 tagttattct gccttccagt ttgcttgata tatttgttga tattaagatt cttgacttat
1501 attttgaatg ggttctagtg aaaaaggaat gatatattct tgaagacatc gatatacatt
1561 tatttacact cttgattcta caatgtagaa aatgaggaaa tgccacaaat tgtatggtga
1621 taaaagtcac gtgaaacaga gtgattggtt gcatccaggc cttttgtctt ggtgttcatg
1681 atctccctct aagcacattc caaactttag caacagttat cacactttgt aatttgcaaa
1741 gaaaagtttc acctgtattg aatcagaatg ccttcaactg aaaaaaacat atccaaaata
1801 atgaggaaat gtgttggctc actacgtaga gtccagaggg acagtcagtt ttagggttgc
1861 ctgtatccag taactcgggg cctgtttccc cgtgggtctc tgggctgtca gctttccttt
1921 ctccatgtgt ttgatttctc ctcaggctgg tagcaagttc tggatcttat acccaacaca
1981 cagcaacatc cagaaataaa gatct SEQ ID NO:114
1 cggaggcgct gggcgcacgg cgcggagccg gccggagctc gaggccggcg gcggcgggag
61 agcgacccgg gcggcctcgt agcggggccc cggatccccg agtggcggcc ggagcctcga
121 aaagagattc tcagcgctga ttttgagatg atgggcttgg gaaacgggcg tcgcagcatg
181 aagtcgccgc ccctcgtgct ggccgccctg gtggcctgca tcatcgtctt gggcttcaac
241 tactggattg cgagctcccg gagcgtggac ctccagacac ggatcatgga gctggaaggc
301 agggtccgca gggcggctgc agagagaggc gccgtggagc tgaagaagaa cgagttccag
361 ggagagctgg agaagcagcg ggagcagctt gacaaaatcc agtccagcca caacttccag
421 ctggagagcg tcaacaagct gtaccaggac gaaaaggcgg ttttggtgaa taacatcacc

FIG. 10 A-87

```
 481 acaggtgaga ggctcatccg agtgctgcaa gaccagttaa agaccctgca gaggaattac
 541 ggcaggctgc agcaggatgt cctccagttt cagaagaacc agaccaacct ggagaggaag
 601 ttctcctacg acctgagcca gtgcatcaat cagatgaagg aggtgaagga acagtgtgag
 661 gagcgaatag aagaggtcac caaaaagggg aatgaagctg tagcttccag agacctgagt
 721 gaaaacaacg accagagaca gcagctccaa gccctcagtg agcctcagcc caggctgcag
 781 gcagcaggcc tgccacacac agaggtgcca caagggaagg gaaacgtgct tggtaacagc
 841 aagtcccaga caccagcccc cagttccgaa gtggttttgg attcaaagag acaagttgag
 901 aaagaggaaa ccaatgagat ccaggtggtg aatgaggagc ctcagaggga caggctgccg
 961 caggagccag gccgggagca ggtggtggaa gacagacctg taggtggaag aggcttcggg
1021 ggagccggag aactgggcca gaccccacag gtgcaggctg ccctgtcagt gagccaggaa
1081 aatccagaga tggagggccc tgagcgagac cagcttgtca tccccgacgg acaggaggag
1141 gagcaggaag ctgccgggga agggagaaac cagcagaaac tgagaggaga agatgactac
1201 aacatggatg aaaatgaagc agaatctgag acagacaagc aagcagccct ggcagggaat
1261 gacagaaaca tagatgtttt taatgttgaa gatcagaaaa gagacaccat aaatttactt
1321 gatcagcgtg aaaagcggaa tcatacactc tgaattgaac tggaatcaca tatttcacaa
1381 cagggccgaa gagatgacta taaaatgttc atgagggact gaatactgaa aactgtgaaa
1441 tgtactaaat aaaatgtaca tctgaagatg attattgtga aattttagta tgcactttgt
1501 gtaggaaaaa atggaatggt cttttaaaca gcttttgggg gggtactttg gaagtgtcta
1561 ataaggtgtc acaatttttg gtagtaggta tttcgtgaga agttcaacac caaaactgga
1621 acatagttct ccttcaagtg ttggcgacag cggggcttcc tgattctgga atataacttt
1681 gtgtaaatta acagccacct atagaagagt ccatctgctg tgaaggagag acagagaact
1741 ctgggttccg tcgtcctgtc cacgtgctgt accaagtgct ggtgccagcc tgttacctgt
1801 tctcactgaa aagtctggct aatgctcttg tgtagtcact tctgattctg acaatcaatc
1861 aatcaatggc ctagagcact gactgttaac acaaacgtca ctagcaaagt agcaacagct
1921 ttaagtctaa atacaaagct gttctgtgtg agaatttttt aaaaggctac ttgtataata
1981 acccttgtca tttttaatgt acaaaacgct attaagtggc ttagaatttg aacatttgtg
2041 gtctttattt actttgcttc gtgtgtgggc aaagcaacat cttccctaaa tatatattac
2101 caagaaaagc aagaagcaga ttaggttttt gacaaaacaa acaggccaaa agggggctga
2161 cctggagcag agcatggtga gaggcaaggc atgagagggc aagtttgttg tggacagatc
2221 tgtgcctact ttattactgg agtaaaagaa aacaaagttc attgatgtcg aaggatatat
2281 acagtgttag aaattaggac tgtttagaaa aacaggaata caatggttgt ttttatcata
2341 gtgtacacat ttagcttgtg gtaaatgact cacaaaactg attttaaaat caagttaatg
2401 tgaattttga aaattactac ttaatcctaa ttcacaataa caatggcatt aaggtttgac
2461 ttgagttggt tcttagtatt atttatggta aataggctct taccacttgc aaataactgg
2521 ccacatcatt aatgactgac ttcccagtaa ggctctctaa ggggtaagta ggaggatcca
2581 caggatttga gatgctaagg ccccagagat cgtttgatcc aaccctctta ttttcagagg
2641 ggaaaatggg gcctagaagt tacagagcat ctagctggtg cgctggcacc cctggcctca
2701 cacagactcc cgagtagctg ggactacagg cacacagtca ctgaagcagg ccctgtttgc
2761 aattcacgtt gccacctcca acttaaacat tcttcatatg tgatgtcctt agtcactaag
2821 gttaaacttt cccacccaga aaaggcaact tagataaaat cttagagtac tttcatactc
2881 ttctaagtcc tcttccagcc tcactttgag tcctccttgg ggttgatagg aattttctct
2941 tgctttctca ataaagtctc tattcatctc atgtttaatt tgtacgcata gaattgctga
3001 gaaataaaat gttctgttca acttaaaaaa aaaaaaaaaa aa
```

SEQ ID NO:115

```
  1 cgggcgatgc cgcgctgcgg gggggccgca cagccgccgc caccgccacc gccgccgggt
 61 ggggtgggag gggcgggaac gcgcgccgcc gcctccaggg tgggcgcctt tcgccgtgga
121 cgccgaccgt ccgggacgag ggtttcatca ccttaaatgg ttttgaacca atgaaggtgt
```

FIG. 10 A-88

```
 181 attcccttaa aaagacggac agcccatcgt gtgaactata gagtttgtgg acagatttat
 241 attgggttca tagtggcgtc atgcacgcag actcctgcaa gttcccctaa gttcttagag
 301 gactgctttg ccttttgatc tgagagttgc aaagttccat aaagaatggc ccttgtggat
 361 aagcacaaag tcaagagaca gcgattggac agaatttgtg aaggtatccg cccccagatc
 421 atgaacggcc ccctgcaccc ccgccccctg gtggcgctgc tggacggccg cgactgcact
 481 gtggagatgc ccatcctgaa ggacctggcc actgtggcct tctgtgacgc gcagtcgacg
 541 caggaaatcc acgagaaggt tctaaacgaa gccgtgggcg ccatgatgta ccacaccatc
 601 accctcacca gggaggacct ggagaagttc aaggccctga gagtgatcgt gcggataggc
 661 agtggctatg acaacgtgga catcaaggct gccggcgagc tcggaattgc cgtgtgcaac
 721 atcccgtctg cagccgtgga agagacagcg gactctacca tctgccacat cctcaacctg
 781 taccggagga acacgtggct gtaccaggca ctgcgggaag gcacgcgggt tcagagcgtg
 841 gagcagatcc gcgaggtggc ctcgggagcg gcccgcatcc gtggggagac gctgggcctc
 901 attggctttg gtcgcacggg gcaggcggtt gcagttcgag ccaaggcctt tggattcagc
 961 gtcatatttt atgaccccta cttgcaggat gggatcgagc ggtccctggg cgtgcagagg
1021 gtctacaccc tgcaggattt gctgtatcag agcgactgcg tctccttgca ctgcaatctc
1081 aacgaacata accaccacct catcaatgac tttaccataa agcagatgag gcagggagca
1141 ttccttgtga acgcagcccg tggcggcctg gtggacgaga aagccttagc acaagccctc
1201 aaggagggca ggatacgagg ggcagccctc gacgtgcatg agtcagagcc cttcagcttt
1261 gctcagggtc cgttgaaaga tgccccgaat ctcatctgca ctcctcacac tgcctggtac
1321 agtgagcagg cgtcactgga gatgagggag gcagctgcca ccgagatccg ccgagccatc
1381 acaggtcgca tcccagaaag cttaagaaat tgtgtgaaca aggaattctt tgtcacatca
1441 gcgccttggt cagtaataga ccagcaagca attcatcctg agctcaatgg tgccacatac
1501 agatatccgc caggcatcgt gggtgtggct ccaggaggac ttcctgcagc catggaaggg
1561 atcatccctg gaggcatccc agtgactcac aacctcccga cagtggcaca tccttcccaa
1621 gcgccctctc ccaaccagcc cacaaaacac ggggacaatc gagagcaccc caacgagcaa
1681 tagcagagaa tgccagaagg taatcactca gatacacttg ggaccaagag acagtgaaaa
1741 atagatgaac taagagaaaa agaatcggat ggtctttgta actgattctg gacatatgca
1801 tcattgatgt tgcagtgttg aaactacaag agctagaaaa ctgaagatgt cgtctgctta
1861 cggaagcgct gaaagactag gatgtgattt attaacgacc aacttctgtt attgtgtgtt
1921 aagtttttca tctgtgcatc aaatcacaaa aagaataaat agagcttttt cctttatcag
1981 tcccttgggc acagcaggtc ctgaacaccc tgctctacaa tgttgcatca agagttcaaa
2041 caacaaaata aaaaatatta agaggaaatc cccatcctgt gacttgagtc ccttaagtct
2101 acaggggctg gtgacctctt tttgctaata ggaaaatcac attactacaa aatgggggaga
2161 aaactgtttg cctgtggtag acacctgcac gcataggatt gaagacagta caggctgctg
2221 tacagagaag cgcctctcac atctgaactg catactgagc gggcaagtcg gttgtaagtt
2281 cagtaaaacc ctctgatgat gcaaaaaaaa aaaaaaagta ttaagtttca caagctgttt
2341 gtactcaaat atattttctc agtttcag
```

SEQ ID NO:116

```
   1 catttgggga cgctctcagc tctcggcgca cggcccagct tccttcaaaa tgtctactgt
  61 tcacgaaatc ctgtgcaagc tcagcttgga gggtgatcac tctacacccc caagtgcata
 121 tgggtctgtc aaagcctata ctaactttga tgctgagcgg gatgctttga acattgaaac
 181 agccatcaag accaaaggtg tggatgaggt caccattgtc aacattttga ccaaccgcag
 241 caatgcacag agacaggata ttgccttcgc ctaccagaga aggaccaaaa aggaacttgc
 301 atcagcactg aagtcagcct tatctggcca cctggagacg gtgattttgg gcctattgaa
 361 gacacctgct cagtatgacg cttctgagct aaaagcttcc atgaaggggc tgggaaccga
 421 cgaggactct ctcattgaga tcatctgctc cagaaccaac caggagctgc aggaaattaa
 481 cagagtctac aaggaaatgt acaagactga tctggagaag gacattattt cggacacatc
 541 tggtgacttc cgcaagctga tggttgccct ggcaaagggt agaagagcag aggatggctc
```

FIG. 10 A-89

```
 601 tgtcattgat tatgaactga ttgaccaaga tgctcgggat ctctatgacg ctggagtgaa
 661 gaggaaagga actgatgttc ccaagtggat cagcatcatg accgagcgga gcgtgcccca
 721 cctccagaaa gtatttgata ggtacaagag ttacagccct tatgacatgt tggaaagcat
 781 caggaaagag gttaaaggag acctggaaaa tgctttcctg aacctggttc agtgcattca
 841 gaacaagccc ctgtattttg ctgatcggct gtatgactcc atgaagggca aggggacgcg
 901 agataaggtc ctgatcagaa tcatggtctc ccgcagtgaa gtggacatgt tgaaaattag
 961 gtctgaattc aagagaaagt acggcaagtc cctgtactat tatatccagc aagacactaa
1021 gggcgactac cagaaagcgc tgctgtacct gtgtggtgga gatgactgaa gcccgacacg
1081 gcctgagcgt ccagaaatgg tgctcaccat gcttccagct aacaggtcta gaaaaccagc
1141 ttgcgaataa cagtccccgt ggccatccct gtgagggtga cgttagcatt acccccaacc
1201 tcattttagt tgcctaagca ttgcctggcc ttcctgtcta gtctctcctg taagccaaag
1261 aaatgaacat tccaaggagt tggaagtgaa gtctatgatg tgaaacactt tgcctcctgt
1321 gtactgtgtc ataaacagat gaataaactg aatttgtact tt
```

SEQ ID NO:117

```
   1 gccccaggtg cgcttcccct agagagggat tttccggtct cgtgggcaga ggaacaacca
  61 ggaacttggg ctcagtctcc accccacagt ggggcggatc cgtcccggat aagacccgct
 121 gtctggccct gagtagggtg tgacctccgc agccgcagag gaggagcgca gcccggcctc
 181 gaagaacttc tgcttgggtg gctgaactct gatcttgacc tagagtcatg gccatggcaa
 241 ccaaaggagg tactgtcaaa gctgcttcag gattcaatgc catggaagat gcccagaccc
 301 tgaggaaggc catgaaaggg ctcggcaccg atgaagacgc cattattagc gtccttgcct
 361 accgcaacac cgcccagcgc caggagatca ggacagccta caagagcacc atcggcaggg
 421 acttgataga cgacctgaag tcagaactga gtggcaactt cgagcaggtg attgtgggga
 481 tgatgacgcc cacggtgctg tatgacgtgc aagagctgcg aagggccatg aagggagccg
 541 gcactgatga gggctgccta attgagatcc tggcctcccg gaccccctgag gagatccggc
 601 gcataagcca aacctaccag cagcaatatg gacggagcct tgaagatgac attcgctctg
 661 acacatcgtt catgttccag cgagtgctgg tgtctctgtc agctggtggg agggatgaag
 721 gaaattatct ggacgatgct ctcgtgagac aggatgccca ggacctgtat gaggctggag
 781 agaagaaatg gggacagat gaggtgaaat ttctaactgt tctctgttcc cggaaccgaa
 841 atcacctgtt gcatgtgttt gatgaataca aaaggatatc acagaaggat attgaacaga
 901 gtattaaatc tgaaacatct ggtagctttg aagatgctct gctggctata gtaaagtgca
 961 tgaggaacaa atctgcatat tttgctgaaa agctctataa atcgatgaag ggcttgggca
1021 ccgatgataa caccctcatc agagtgatgg tttctcgagc agaaattgac atgttggata
1081 tccgggcaca cttcaagaga ctctatggaa agtctctgta ctcgttcatc aagggtgaca
1141 catctggaga ctacaggaaa gtactgcttg ttctctgtgg aggagatgat taaaataaaa
1201 atcccagaag gacaggagga ttctcaacac tttgaatttt tttaacttca tttttctaca
1261 ctgctattat cattatctca gaatgcttat ttccaattaa aacgcctaca gctgcctcct
1321 agaatataga ctgtctgtat tattattcac ctataattag tcattatgat gctttaaagc
1381 tgtacttgca tttcaaagct tataagatat aaatggagat tttaaagtag aaataaatat
1441 gtattccatg tttttaaaag attactttct actttgtgtt tcacagacat tgaatatatt
1501 aaattattcc atattttctt ttcagtgaaa aattttttaa atggaagact gttctaaaat
1561 cactttttc cctaatccaa tttttagagt ggctagtagt ttcttcattt gaaattgtaa
1621 gcatccggtc agtaagaatg cccatccagt tttctatatt tcatagtcaa agccttgaaa
1681 gcatctacaa atctcttttt ttaggttttg tccatagcat cagttgatcc ttactaagtt
1741 tttcatggga gacttccttc atcacatctt atgttgaaat cactttctgt agtcaaagta
1801 taccaaaacc aatttatctg aactaaattc taaagtatgg ttatacaaac catatacatc
1861 tggttaccaa acataaatgc tgaacattcc atattattat agttaatgtc ttaatccagc
```

FIG. 10 A-90

1921 ttgcaagtga atggaaaaaa aaataagctt caaactaggt attctgggaa tgatgtaatg
1981 ctctgaattt agtatgatat aaagaaaact tttttgtgct aaaaatactt tttaaaatca
2041 attttgttga ttgtagtaat ttctatttgc actgtgcctt tcaactccag aaacattctg
2101 aagatgtact tggatttaat taaaaagttc actttgt

SEQ ID NO:118

1 gctgctgcgc ccgcggctcc ccagtgcccc gagtgccccg cgggccccgc gagcgggagt
61 gggacccagc cctaggcaga acccaggcgc cgcgcccggg acgcccgcgg agagagccac
121 tcccgcccac gtcccatttc gcccctcgcg tccggagtcc ccgtggccag atctaaccat
181 gagctaccct ggctatcccc cgcccccagg tggctaccca ccagctgcac caggtggtgg
241 tccctgggga ggtgctgcct accctcctcc gcccagcatg ccccccatcg ggctggataa
301 cgtggccacc tatgcggggc agttcaacca ggactatctc tcgggaatgg cggccaacat
361 gtctgggaca tttggaggag ccaacatgcc caacctgtac cctggggccc ctggggctgg
421 ctacccacca gtgcccccctg gcggctttgg gcagcccccc tctgcccagc agcctgttcc
481 tccctatggg atgtatccac ccccaggagg aaacccaccc tccaggatgc cctcatatcc
541 gccataccca ggggcccctg tgccgggcca gcccatgcca ccccccggac agcagccccc
601 aggggcctac cctgggcagc caccagtgac ctaccctggt cagcctccag tgccactccc
661 tgggcagcag cagccagtgc cgagctaccc aggataccccg gggtctggga ctgtcacccc
721 cgctgtgccc ccaacccagt ttggaagccg aggcaccatc actgatgctc ccggctttga
781 ccccctgcga gatgccgagg tcctgcggaa ggccatgaaa ggcttcggga cggatgagca
841 ggccatcatt gactgcctgg ggagtcgctc caacaagcag cggcagcaga tcctactttc
901 cttcaagacg gcttacggca aggatttgat caaagatctg aaatctgaac tgtcaggaaa
961 ctttgagaag acaatcttgg ctctgatgaa gaccccagtc ctctttgaca tttatgagat
1021 aaaggaagcc atcaaggggg ttggcactga tgaagcctgc ctgattgaga tcctcgcttc
1081 ccgcagcaat gagcacatcc gagaattaaa cagagcctac aaagcagaat tcaaaaagac
1141 cctggaagag gccattcgaa gcgacacatc agggcacttc cagcggctcc tcatctctct
1201 ctctcaggga aaccgtgatg aaagcacaaa cgtggacatg tcactcgccc agagagatgc
1261 ccaggagctg tatgcggccg gggagaaccg cctgggaaca gacgagtcca agttcaatgc
1321 ggttctgtgc tcccggagcc gggcccacct ggtagcagtt ttcaatgagt accagagaat
1381 gacaggccgg gacattgaga agagcatctg ccgggagatg tccggggacc tggaggaggg
1441 catgctggcc gtggtgaaat gtctcaagaa taccccagcc ttctttgcgg agaggctcaa
1501 caaggccatg agggggcag gaacaaagga ccggaccctg attcgcatca tggtgtctcg
1561 cagcgagacc gacctcctgg acatcagatc agagtataag cggatgtacg gcaagtcgct
1621 gtaccacgac atctcgggag atacttcagg ggattaccgg aagattctgc tgaagatctg
1681 tggtggcaat gactgaacag tgactggtgg ctcacttctg cccacctgcc ggcaacacca
1741 gtgccaggaa aaggccaaaa gaatgtctgt ttctaacaaa tccacaaata gccccgagat
1801 tcaccgtcct agagcttagg cctgtcttcc acccctcctg acccgtatag tgtgccacag
1861 gacctgggtc ggtctagaac tctctcagga tgccttttct accccatccc tcacagcctc
1921 ttgctgctaa aatagatgtt tcatttttct gaaaaaaa

SEQ ID NO:119

1 ggctcatgct cgggagcgtg gttgagcggc tggcgcggtt gtcctggagc aggggcgcag
61 gaattctgat gtgaaactaa cagtctgtga gccctggaac ctccactcag agaagatgaa
121 ggatatcgac ataggaaaag agtatatcat ccccagtcct gggtatagaa gtgtgaggga
181 gagaaccagc acttctggga cgcacagaga ccgtgaagat tccaagttca ggagaactcg
241 accgttggaa tgccaagatg ccttggaaac agcagcccga gccgagggcc tctctcttga
301 tgcctccatg cattctcagc tcagaatcct ggatgaggag catcccaagg gaaagtacca
361 tcatggcttg agtgctctga agcccatccg gactacttcc aaacaccagc acccagtgga

FIG. 10 A-91

```
 421 caatgctggg cttttttcct gtatgacttt ttcgtggctt tcttctctgg cccgtgtggc
 481 ccacaagaag ggggagctct caatggaaga cgtgtggtct ctgtccaagc acgagtcttc
 541 tgacgtgaac tgcagaagac tagagagact gtggcaagaa gagctgaatg aagttgggcc
 601 agacgctgct tccctgcgaa gggttgtgtg gatcttctgc cgcaccaggc tcatcctgtc
 661 catcgtgtgc ctgatgatca cgcagctggc tggcttcagt ggaccagcct tcatggtgaa
 721 acacctcttg gagtataccc aggcaacaga gtctaacctg cagtacagct tgttgttagt
 781 gctgggcctc ctcctgacgg aaatcgtgcg gtcttggtcg cttgcactga cttgggcatt
 841 gaattaccga accggtgtcc gcttgcgggg ggccatccta accatggcat ttaagaagat
 901 ccttaagtta aagaacatta aagagaaatc cctgggtgag ctcatcaaca tttgctccaa
 961 cgatgggcag agaatgtttg aggcagcagc cgttggcagc ctgctggctg gaggacccgt
1021 tgttgccatc ttaggcatga tttataatgt aattattctg ggaccaacag gcttcctggg
1081 atcagctgtt tttatcctct tttacccagc aatgatgttt gcatcacggc tcacagcata
1141 tttcaggaga aaatgcgtgg ccgccacgga tgaacgtgtc cagaagatga atgaagttct
1201 tacttacatt aaatttatca aaatgtatgc ctgggtcaaa gcattttctc agagtgttca
1261 aaaaatccgc gaggaggagc gtcggatatt ggaaaaagct gggtacttcc agagcatcac
1321 tgtgggtgtg gctcccattg tggtggtgat tgccagcgtg gtgaccttct ctgttcatat
1381 gaccctgggc ttcgatctga cagcagcaca ggctttcaca gtggtgacag tcttcaattc
1441 catgactttt gctttgaaag taacaccgtt ttcagtaaag tccctctcag aagcctcagt
1501 ggctgttgac agatttaaga gtttgtttct aatggaagag gttcacatga taaagaacaa
1561 accagccagt cctcacatca agatagagat gaaaaatgcc accttggcat gggactcctc
1621 ccactccagt atccagaact cgcccaagct gacccccaaa atgaaaaaag acaagagggc
1681 ttccaggggc aagaaagaga aggtgaggca gctgcagcgc actgagcatc aggcggtgct
1741 ggcagagcag aaaggccacc tcctcctgga cagtgacgag cggcccagtc ccgaagagga
1801 agaaggcaag cacatccacc tgggccacct gcgcttacag aggacactgc acagcatcga
1861 tctggagatc caagagggta aactggttgg aatctgtggc agtgtgggaa gtggaaaaac
1921 ctctctcatt tcagccattt taggccagat gacgcttcta gagggcagca ttgcaatcag
1981 tggaaccttc gcttatgtgg cccagcaggc ctggatcctc aatgctactc tgagagacaa
2041 catcctgttt gggaaggaat atgatgaaga aagatacaac tctgtgctga acagctgctg
2101 cctgaggcct gacctggcca ttcttcccag cagcgacctg acggagattg gagagcgagg
2161 agccaacctg agcggtgggc agcgccagag gatcagcctt gcccgggcct tgtatagtga
2221 caggagcatc tacatcctgg acgacccccct cagtgcctta gatgcccatg tgggcaacca
2281 catcttcaat agtgctatcc ggaaacatct caagtccaag acagttctgt ttgttaccca
2341 ccagttacag tacctggttg actgtgatga agtgatcttc atgaaagagg gctgtattac
2401 ggaaagaggc acccatgagg aactgatgaa tttaaatggt gactatgcta ccatttttaa
2461 taacctgttg ctgggagaga caccgccagt tgagatcaat tcaaaaaagg aaaccagtgg
2521 ttcacagaag aagtcacaag acaagggtcc taaaacagga tcagtaaaga aggaaaaagc
2581 agtaaagcca gaggaagggc agcttgtgca gctggaagag aaagggcagg gttcagtgcc
2641 ctggtcagta tatggtgtct acatccaggc tgctgggggc cccttggcat tcctggttat
2701 tatggccctt ttcatgctga atgtaggcag caccgccttc agcacctggt ggttgagtta
2761 ctggatcaag caaggaagcg ggaacaccac tgtgactcga gggaacgaga cctcggtgag
2821 tgacagcatg aaggacaatc ctcatatgca gtactatgcc agcatctacg ccctctccat
2881 ggcagtcatg ctgatcctga aagccattcg aggagttgtc tttgtcaagg gcacgctgcg
2941 agcttcctcc cggctgcatg acgagctttt ccgaaggatc cttcgaagcc ctatgaagtt
3001 ttttgacacg accccccacag ggaggattct caacaggttt tccaaagaca tggatgaagt
3061 tgacgtgcgg ctgccgttcc aggccgagat gttcatccag aacgttatcc tggtgttctt
3121 ctgtgtggga atgatcgcag gagtcttccc gtggttcctt gtggcagtgg ggccccttgt
3181 catcctcttt tcagtcctgc acattgtctc cagggtcctg attcgggagc tgaagcgtct
3241 ggacaatatc acgcagtcac ctttcctctc ccacatcacg tccagcatac agggccttgc
3301 caccatccac gcctacaata aagggcagga gtttctgcac agataccagg agctgctgga
3361 tgacaaccaa gctccttttt ttttgtttac gtgtgcgatg cggtggctgg ctgtgcggct
```

FIG. 10 A-92

```
3421 ggacctcatc agcatcgccc tcatcaccac cacggggctg atgatcgttc ttatgcacgg
3481 gcagattccc ccagcctatg cgggtctcgc catctcttat gctgtccagt taacggggct
3541 gttccagttt acggtcagac tggcatctga gacagaagct cgattcacct cggtggagag
3601 gatcaatcac tacattaaga ctctgtcctt ggaagcacct gccagaatta agaacaaggc
3661 tccctcccct gactggcccc aggagggaga ggtgaccttt gagaacgcag agatgaggta
3721 ccgagaaaac ctccctctcg tcctaaagaa agtatccttc acgatcaaac ctaaagagaa
3781 gattggcatt gtggggcgga caggatcagg gaagtcctcg ctggggatgg ccctcttccg
3841 tctggtggag ttatctggag gctgcatcaa gattgatgga gtgagaatca gtgatattgg
3901 ccttgccgac ctccgaagca aactctctat cattcctcaa gagccggtgc tgttcagtgg
3961 cactgtcaga tcaaatttgg accccttcaa ccagtacact gaagaccaga tttgggatgc
4021 cctggagagg acacacatga aagaatgtat tgctcagcta cctctgaaac ttgaatctga
4081 agtgatggag aatggggata acttctcagt gggggaacgg cagctcttgt gcatagctag
4141 agccctgctc cgccactgta agattctgat tttagatgaa gccacagctg ccatggacac
4201 agagacagac ttattgattc aagagaccat ccgagaagca tttgcagact gtaccatgct
4261 gaccattgcc catcgcctgc acacggttct aggctccgat aggattatgg tgctggccca
4321 gggacaggtg gtggagtttg acaccccatc ggtccttctg tccaacgaca gttcccgatt
4381 ctatgccatg tttgctgctg cagagaacaa ggtcgctgtc aagggctgac tcctccctgt
4441 tgacgaagtc tcttttcttt agagcattgc cattccctgc ctggggcggg cccctcatcg
4501 cgtcctccta ccgaaacctt gcctttctcg attttatctt tcgcacagca gttccggatt
4561 ggcttgtgtg tttcactttt agggagagtc atattttgat tattgtattt attccatatt
4621 catgtaaaca aaatttagtt tttgttctta attgcactct aaaaggttca gggaaccgtt
4681 attataattg tatcagaggc ctataatgaa gctttatacg tgtagctata tctatatata
4741 attctgtaca tagcctatat ttacagtgaa aatgtaagct gtttatttta tattaaaata
4801 agcactgtgc taataacagt gcatattcct ttctatcatt tttgtacagt ttgctgtact
4861 agagatctgg ttttgctatt agactgtagg aagagtagca tttcattctt ctctagctgg
4921 tggtttcacg gtgccaggtt ttctgggtgt ccaaaggaag acgtgtggca atagtgggcc
4981 ctccgacagc cccctctgcc gcctccccac ggccgctcca ggggtggctg gagacgggtg
5041 ggcggctgga gaccatgcag agcgccgtga gttctcaggg ctcctgcctt ctgtcctggt
5101 gtcacttact gtttctgtca ggagagcagc ggggcgaagc ccaggcccct tttcactccc
5161 tccatcaaga atggggatca cagagacatt cctccgagcc ggggagtttc tttcctgcct
5221 tcttcttttt gctgttgttt ctaaacaaga atcagtctat ccacagagag tcccactgcc
5281 tcaggttcct atggctggcc actgcacaga gctctccagc tccaagacct gttggttcca
5341 agccctggag ccaactgctg ctttttgagg tggcactttt tcatttgcct attcccacac
5401 ctccacagtt cagtggcagg gctcaggatt tcgtgggtct gttttccttt ctcaccgcag
5461 tcgtcgcaca gtctctctct ctctctcccc tcaaagtctg caactttaag cagctcttgc
5521 taatcagtgt ctcacactgg cgtagaagtt tttgtactgt aaagagacct acctcaggtt
5581 gctggttgct gtgtggtttg gtgtgttccc gcaaaccccc tttgtgctgt ggggctggta
5641 gctcaggtgg gcgtggtcac tgctgtcatc aattgaatgg tcagcgttgc atgtcgtgac
5701 caactagaca ttctgtcgcc ttagcatgtt tgctgaacac cttgtggaag caaaaatctg
5761 aaaatgtgaa taaaattatt ttggattttg t
```

SEQ ID NO:120

```
  1 aaacttcccg cacgcgttac aggagccagg tcggtataag cgccacgcct cgccgcccgt
 61 caagctgtcc acatccctgg cctcagcccg ccacatcacc ctgacctgct tacgcccaga
121 ttttcttcaa tcacatctga ataaatcact tgaagaaagc ttatagcttc attgcaccat
181 gtgtggcatt tgggcgctgt ttggcagtga tgattgcctt tctgttcagt gtctgagtgc
241 tatgaagatt gcacacagag gtccagatgc attccgtttt gagaatgtca atggatacac
301 caactgctgc tttggatttc accggttggc ggtagttgac ccgctgtttg gaatgcagcc
361 aattcgagtg aagaaatatc cgtatttgtg gctctgttac aatggtgaaa tctacaacca
421 taagaagatg caacagcatt ttgaatttga ataccagacc aaagtggatg gtgagataat
```

FIG. 10 A-93

```
 481 ccttcatctt tatgacaaag gaggaattga gcaaacaatt tgtatgttgg atggtgtgtt
 541 tgcatttgtt ttactggata ctgccaataa gaaagtgttc ctgggtagag atacatatgg
 601 agtcagacct ttgtttaaag caatgacaga agatggattt ttggctgtat gttcagaagc
 661 taaaggtctt gttacattga agcactccgc gactcccttt ttaaaagtgg agccttttct
 721 tcctggacac tatgaagttt tggatttaaa gccaaatggc aaagttgcat ccgtggaaat
 781 ggttaaatat catcactgtc gggatgtacc cctgcacgcc ctctatgaca atgtggagaa
 841 actctttcca ggttttgaga tagaaactgt gaagaacaac ctcaggatcc tttttaataa
 901 tgctgtaaag aaacgtttga tgacagacag aaggattggc tgccttttat caggggggctt
 961 ggactccagc ttggttgctg ccactctgtt gaagcagctg aaagaagccc aagtacagta
1021 tcctctccag acatttgcaa ttggcatgga agacagcccc gatttactgg ctgctagaaa
1081 ggtggcagat catattggaa gtgaacatta tgaagtcctt tttaactctg aggaaggcat
1141 tcaggctctg gatgaagtca tattttcctt ggaaacttat gacattacaa cagttcgtgc
1201 ttcagtaggt atgtatttaa tttccaagta tattcggaag aacacagata gcgtggtgat
1261 cttctctgga gaaggatcag atgaacttac gcagggttac atatattttc acaaggctcc
1321 ttctcctgaa aaagccgagg aggagagtga gaggcttctg agggaactct atttgtttga
1381 tgttctccgc gcagatcgaa ctactgctgc ccatggtctt gaactgagag tcccatttct
1441 agatcatcga tttttttcct attacttgtc tctgccacca gaaatgagaa ttccaaagaa
1501 tgggatagaa aaacatctcc tgagagagac gtttgaggat tccaatctga tacccaaaga
1561 gattctctgg cgaccaaaag aagccttcag tgatggaata acttcagtta agaattcctg
1621 gtttaagatt ttacaggaat acgttgaaca tcaggttgat gatgcaatga tggcaaatgc
1681 agcccagaaa tttcccttca atactcctaa aaccaaagaa ggatattact accgtcaagt
1741 ctttgaacgc cattacccag gccgggctga ctggctgagc cattactgga tgcccaagtg
1801 gatcaatgcc actgaccctt ctgcccgcac gctgacccac tacaagtcag ctgtcaaagc
1861 ttaggtggtc tttatgctgt aatgtgaaag caaatatttc ttcgtgttgg atggggactg
1921 tgggtagata ggggaacaat gagagtcaac tcaggctaac ttgggtttga aaaaaataaa
1981 attcctaaat tt
```

SEQ ID NO:121

```
   1 aggttcaagt ggagctctcc taaccgacgc gcgtctgtgg agaagcggct tggtcggggg
  61 tggtctcgtg gggtcctgcc tgtttagtcg ctttcagggt tcttgagccc cttcacgacc
 121 gtcaccatgg aagtgtcacc attgcagcct gtaaatgaaa atatgcaagt caacaaaata
 181 aagaaaaatg aagatgctaa gaaaagactg tctgttgaaa gaatctatca aaagaaaaca
 241 caattggaac atattttgct ccgcccagac acctacattg gttctgtgga attagtgacc
 301 cagcaaatgt gggtttacga tgaagatgtt ggcattaact atagggaagt cacttttgtt
 361 cctggtttgt acaaaatctt tgatgagatt ctagttaatg ctgcggacaa caaacaaagg
 421 gacccaaaaa tgtcttgtat tagagtcaca attgatccgg aaaacaattt aattagtata
 481 tggaataatg gaaaaggtat tcctgttgtt gaacacaaag ttgaaaagat gtatgtccca
 541 gctctcatat ttggacagct cctaacttct agtaactatg atgatgatga aaagaaagtg
 601 acaggtggtc gaaatggcta tggagccaaa ttgtgtaaca tattcagtac caaatttact
 661 gtggaaacag ccagtagaga atacaagaaa atgttcaaac agacatggat ggataatatg
 721 ggaagagctg gtgagatgga actcaagccc ttcaatggag aagattatac atgtatcacc
 781 tttcagcctg atttgtctaa gtttaaaatg caaagcctgg acaaagatat tgttgcacta
 841 atggtcagaa gagcatatga tattgctgga tccaccaaag atgtcaaagt ctttcttaat
 901 ggaaataaac tgccagtaaa aggatttcgt agttatgtgg acatgtattt gaaggacaag
 961 ttggatgaaa ctggtaactc cttgaaagta atacatgaac aagtaaacca caggtgggaa
1021 gtgtgtttaa ctatgagtga aaaaggcttt cagcaaatta gctttgtcaa cagcattgct
1081 acatccaagg gtggcagaca tgttgattat gtagctgatc agattgtgac taaacttgtt
1141 gatgttgtga agaagaagaa caagggtggt gttgcagtaa aagcacatca ggtgaaaaat
```

FIG. 10 A-94

1201 cacatgtgga tttttgtaaa tgccttaatt gaaaacccaa cctttgactc tcagacaaaa
1261 gaaaacatga ctttacaacc caagagcttt ggatcaacat gccaattgag tgaaaaattt
1321 atcaaagctg ccattggctg tggtattgta gaaagcatac taaactgggt gaagtttaag
1381 gcccaagtcc agttaaacaa gaagtgttca gctgtaaaac ataatagaat caagggaatt
1441 cccaaactcg atgatgccaa tgatgcaggg ggccgaaact ccactgagtg tacgcttatc
1501 ctgactgagg gagattcagc caaaactttg gctgtttcag gccttggtgt ggttgggaga
1561 gacaaatatg ggggttttccc tcttagagga aaaatactca atgttcgaga agcttctcat
1621 aagcagatca tggaaaatgc tgagattaac aatatcatca agattgtggg tcttcagtac
1681 aagaaaaact atgaagatga agattcattg aagacgcttc gttatgggaa gataatgatt
1741 atgacagatc aggaccaaga tggttcccac atcaaaggct tgctgattaa ttttatccat
1801 cacaactggc cctctcttct gcgacatcgt tttctggagg aatttatcac tcccattgta
1861 aaggtatcta aaaacaagca agaaatggca ttttacagcc ttcctgaatt tgaagagtgg
1921 aagagttcta ctccaaatca taaaaaatgg aaagtcaaat attacaaagg tttgggcacc
1981 agcacatcaa aggaagctaa agaatacttt gcagatatga aaagacatcg tatccagttc
2041 aaatattctg gtcctgaaga tgatgctgct atcagcctgg cctttagcaa aaaacagata
2101 gatgatcgaa aggaatggtt aactaatttc atggaggata gaagacaacg aaagttactt
2161 gggcttcctg aggattactt gtatggacaa actaccacat atctgacata taatgacttc
2221 atcaacaagg aacttatctt gttctcaaat tctgataacg agagatctat cccttctatg
2281 gtggatggtt tgaaaccagg tcagagaaag gttttgttta cttgcttcaa acggaatgac
2341 aagcgagaag taaaggttgc ccaattagct ggatcagtgg ctgaaatgtc ttcttatcat
2401 catggtgaga tgtcactaat gatgaccatt atcaatttgg ctcagaattt tgtgggtagc
2461 aataatctaa acctcttgca gcccattggt cagtttggta ccaggctaca tggtggcaag
2521 gattctgcta gtccacgata catctttaca atgctcagct ctttggctcg attgttattt
2581 ccaccaaaag atgatcacac gttgaagttt ttatatgatg acaaccagcg tgttgagcct
2641 gaatggtaca ttcctattat tcccatggtg ctgataaatg gtgctgaagg aatcggtact
2701 gggtggtcct gcaaaatccc caactttgat gtgcgtgaaa ttgtaaataa catcaggcgt
2761 ttgatggatg gagaagaacc tttgccaatg cttccaagtt acaagaactt caagggtact
2821 attgaagaac tggctccaaa tcaatatgtg attagtggtg aagtagctat tcttaattct
2881 acaaccattg aaatctcaga gcttcccgtc agaacatgga cccagacata caaagaacaa
2941 gttctagaac ccatgttgaa tggcaccgag aagacacctc ctctcataac agactatagg
3001 gaataccata cagataccac tgtgaaattt gttgtgaaga tgactgaaga aaaactggca
3061 gaggcagaga gagttggact acacaaagtc ttcaaactcc aaactagtct cacatgcaac
3121 tctatggtgc tttttgacca cgtaggctgt ttaaagaaat atgacacggt gttggatatt
3181 ctaagagact tttttgaact cagacttaaa tattatggat taagaaaaga atggctccta
3241 ggaatgcttg gtgctgaatc tgctaaactg aataatcagg ctcgctttat cttagagaaa
3301 atagatggca aaataatcat tgaaaataag cctaagaaag aattaattaa agttctgatt
3361 cagaggggat atgattcgga tcctgtgaag gcctggaaag aagcccagca aaaggttcca
3421 gatgaagaag aaaatgaaga gagtgacaac gaaaaggaaa ctgaaaagag tgactccgta
3481 acagattctg gaccaacctt caactatctt cttgatatgc ccctttggta tttaaccaag
3541 gaaaagaaag atgaactctg caggctaaga aatgaaaaag aacaagagct ggacacatta
3601 aaaagaaaga gtccatcaga tttgtggaaa gaagacttgg ctacatttat tgaagaattg
3661 gaggctgttg aagccaagga aaaacaagat gaacaagtcg gacttcctgg gaaagggggg
3721 aaggccaagg ggaaaaaaac acaaatggct gaagttttgc cttctccgcg tggtcaaaga
3781 gtcattccac gaataaccat agaaatgaaa gcagaggcag aaaagaaaaa taaaaagaaa
3841 attaagaatg aaaatactga aggaagccct caagaagatg gtgtggaact agaaggccta
3901 aaacaaagat tagaaaagaa acagaaaaga gaaccaggta caaagacaaa gaaacaaact
3961 acattggcat ttaagccaat caaaaaagga aagaagagaa atccctggtc tgattcagaa
4021 tcagatagga gcagtgacga aagtaatttt gatgtccctc cacgagaaac agagccacgg
4081 agagcagcaa caaaaacaaa attcacaatg gatttggatt cagatgaaga tttctcagat
4141 tttgatgaaa aaactgatga tgaagatttt gtcccatcag atgctagtcc acctaagacc

FIG. 10 A-95

```
4201 aaaacttccc caaaacttag taacaaagaa ctgaaaccac agaaaagtgt cgtgtcagac
4261 cttgaagctg atgatgttaa gggcagtgta ccactgtctt caagccctcc tgctacacat
4321 ttcccagatg aaactgaaat tacaaaccca gttcctaaaa agaatgtgac agtgaagaag
4381 acagcagcaa aaagtcagtc ttccacctcc actaccggtg ccaaaaaaag ggctgcccca
4441 aaaggaacta aaagggatcc agctttgaat tctggtgtct ctcaaaagcc tgatcctgcc
4501 aaaaccaaga atcgccgcaa aaggaagcca tccacttctg atgattctga ctctaatttt
4561 gagaaaattg tttcgaaagc agtcacaagc aagaaatcca aggggagag tgatgacttc
4621 catatggact ttgactcagc tgtggctcct cgggcaaaat ctgtacgggc aaagaaacct
4681 ataaagtacc tggaagagtc agatgaagat gatctgtttt aaaatgtgag gcgattattt
4741 taagtaatta tcttaccaag cccaagactg gttttaaagt tacctgaagc tcttaacttc
4801 ctcccctctg aatttagttt ggggaaggtg tttttagtac aagacatcaa agtgaagtaa
4861 agcccaagtg ttctttagct ttttataata ctgtctaaat agtgaccatc tcatgggcat
4921 tgttttcttc tctgctttgt ctgtgttttg agtctgcttt cttttgtctt taaaacctga
4981 tttttaagtt cttctgaact gtagaaatag ctatctgatc acttcagcgt aaagcagtgt
5041 gtttattaac catccactaa gctaaaacta gagcagtttg atttaaaagt gtcactcttc
5101 ctccttttct actttcagta gatatgagat agagcataat tatctgtttt atcttagttt
5161 tatacataat ttaccatcag atagaacttt atggttctag tacagatact ctactacact
5221 cagcctctta tgtgccaagt ttttctttaa gcaatgagaa attgctcatg ttcttcatct
5281 tctcaaatca tcagaggcca aagaaaaaca ctttggctgt gtctataact tgacacagtc
5341 aatagaatga agaaaattag agtagttatg tgattatttc agctcttgac ctgtcccctc
5401 tggctgcctc tgagtctgaa tctcccaaag agagaaacca atttctaaga ggactggatt
5461 gcagaagact cggggacaac atttgatcca agatcttaaa tgttatattg ataaccatgc
5521 tcagcaatga gctattagat tcattttggg aaatctccat aatttcaatt tgtaaacttt
5581 gttaagacct gtctacattg ttatatgtgt gtgacttgag taatgttatc aacgtttttg
5641 taaatattta ctatgttttt ctattagcta aattccaaca attttgtact ttaataaa
```

SEQ ID NO:122

```
   1 gcgccatgga gcagtggcgg cagtgcggcc gctggctcat cgattgcaag gtcctgccgc
  61 ccaaccaccg ggtggtgtgg ccctcggccg tggtcttcga cctggcgcag gcgctgcgcg
 121 acggggtcct tctgtgccag ctgctgcaca acctctcccc cggctccatc gacctcaagg
 181 acatcaactt ccggccgcag atgtcccagt ttctgtgttt gaagaacata cgcaccttcc
 241 tgaaagtctg ccacgataaa tttggattaa ggaacagcga gctgtttgac ccctttgacc
 301 tcttcgatgt gcgagacttt ggaaaggtca tctccgcggt gtcgaggctc tccctgcaca
 361 gcatcgcgca gaacaaaggg atcaggcctt ttccctcaga ggagaccaca gagaatgacg
 421 atgacgtcta ccgcagcctg gaggagctgg ccgacgagca tgacctgggg gaggacatct
 481 acgactgcgt cccgtgtgag gatggagggg acgacatcta cgaggacatc atcaaggtgg
 541 aggtgcagca gcccatgatt agatacatgc agaaaatggg catgactgaa gatgacaaga
 601 ggaactgctg cctgctggag atccaggaga ccgaggccaa gtactaccgc accctggagg
 661 acattgagaa gaactacatg agccccctgc ggctggtgct gagcccggcg gacatggcag
 721 ctgtcttcat taacctggag gacctgatca aggtgcatca cagcttcctg agggccatcg
 781 acgtgtccgt gatggtgggg ggcagcacgc tggccaaggt cttcctcgat ttcaaggaaa
 841 ggcttctgat ctacggggag tactgcagcc acatggagca cgcccagaac acactgaacc
 901 agctcctggc cagccgggag gacttcaggc agaaagtcga ggagtgcaca ctgaaggtcc
 961 aggatggaaa atttaagctg caagacctgc tggtggtccc catgcagagg gtgctcaaat
1021 accacctgct cttgaaggag cttctgagcc attctgcgga acggcctgag aggcagcagc
1081 tcaaagaagc actggaagcc atgcaggact tggcgatgta catcaatgaa gttaaacggg
1141 acaaggagac cttgaggaaa atcagcgaat ttcagagttc tatagaaaat ttgcaagtga
1201 aactggagga atttggaaga ccaaagattg acggggaact gaaagtccgg tccatagtca
1261 accacaccaa gcaggacagg tacttgttcc tgtttgacaa ggtggtcatc gtctgcaagc
1321 ggaagggcta cagctacgag ctcaaggaga tcatcgagct gctgttccac aagatgaccg
```

FIG. 10 A-96

1381 acgaccccat gaacaacaag gacgtcaaga agtctcacgg gaaaatgtgg tcctacggct 1441 tctacctaat tcaccttcaa ggaaagcagg gcttccagtt tttctgcaaa acagaagata 1501 tgaagaggaa gtggatggag cagtttgaga tggccatgtc aaacatcaag ccagacaaag 1561 ccaatgccaa ccaccacagt ttccagatgt acacgtttga caagaccacc aactgcaaag 1621 cctgcaaaat gttcctcagg ggcaccttct accagggata catgtgtacc aagtgtggcg 1681 tcggggcaca caaggagtgc ctggaagtga tacctccctg caagttcact tctcctgcag 1741 atctggacgc ctccggagcg ggaccaggtc ccaagatggt ggccatgcag aattaccatg 1801 gcaacccagc ccctcccggg aagcctgtgc tgaccttcca gacgggcgac gtgcttgagc 1861 tgctgagggg cgaccctgag tctccgtggt gggagggtcg tctggtacaa accaggaagt 1921 cagggtattt ccccagctca tctgtgaagc cctgccctgt ggatggaagg ccgcccatca 1981 gccggccgcc atcccgggag atcgactaca ctgcataccc ctggtttgca ggtaacatgg 2041 agaggcagca gacggacaac ctgctcaagt cccacgccag cgggacctac ctgatcaggg 2101 agcggcctgc cgaggctgag cgctttgcaa taagcatcaa gttcaatgat gaggtgaagc 2161 acatcaaggt ggtggagaag gacaactgga tccacatcac agaggccaag aaattcgaca 2221 gcctcctgga gttggtggag tactaccagt gccactcact gaaggagagc ttcaagcagc 2281 tggacaccac actcaagtac ccctacaagt cccgggaacg ttcggcctcc agggcctcca 2341 gccggtcccc agcttcctgt gcttcctaca acttttcttt tctcagtcct cagggcctca 2401 gctttgcttc tcagggcccc tccgctccct tctggtcagt gttcacgccc cgcgtcatcg 2461 gcacagctgt ggccaggtat aactttgccg cccgagatat gagggagctt tcgctgcggg 2521 agggtgacgt ggtgaggatc tacagccgca tcggcggaga ccagggctgg tggaagggcg 2581 agaccaacgg acggattggc tggtttcctt caacgtacgt agaagaggag ggcatccagt 2641 gacggcagga acgtggacaa gactcgcaga ttttcttggg agagtcactc cagccctgaa 2701 gtctgtctct agctcctctg tgactcagag gggaaatacc aacctcccag tct

AMACR IN PCA SERA

FIGURE 13
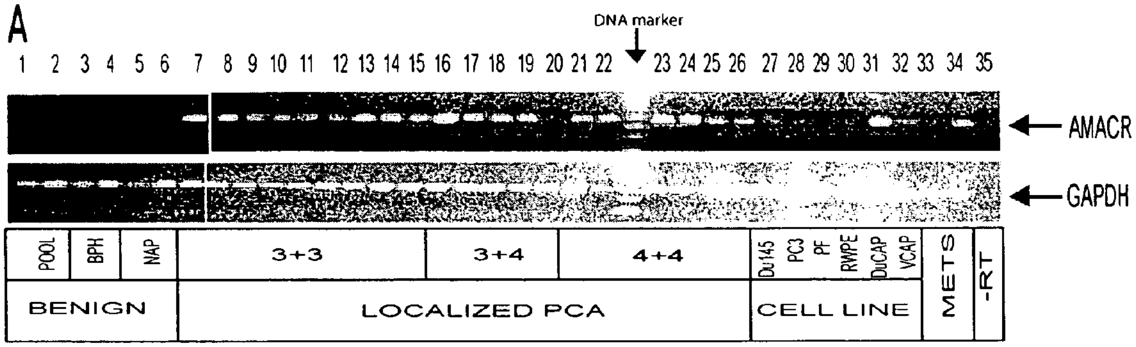
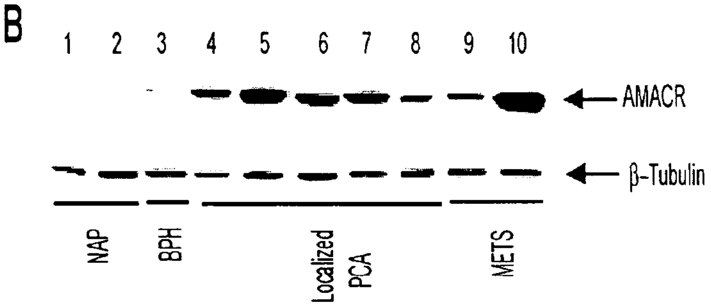

AMACR IN PCA CELL LINES

AMACR IN PCA SERA

Immunoblot Analysis for AMACR in Prostate Cancer and Normal Sera

| Sample | PSA |
| --- | --- |
| 2-10 | Positive |
| 61-65 | Negative |

IMMUNOBLOT ANALYSIS OF URINE SAMPLES FOR AMACR

U1-U10 : FEMALES WITH BLADDER CANCER
U11-U20 : MALES WITH BLADDER CANCER AND INC PROSTATE

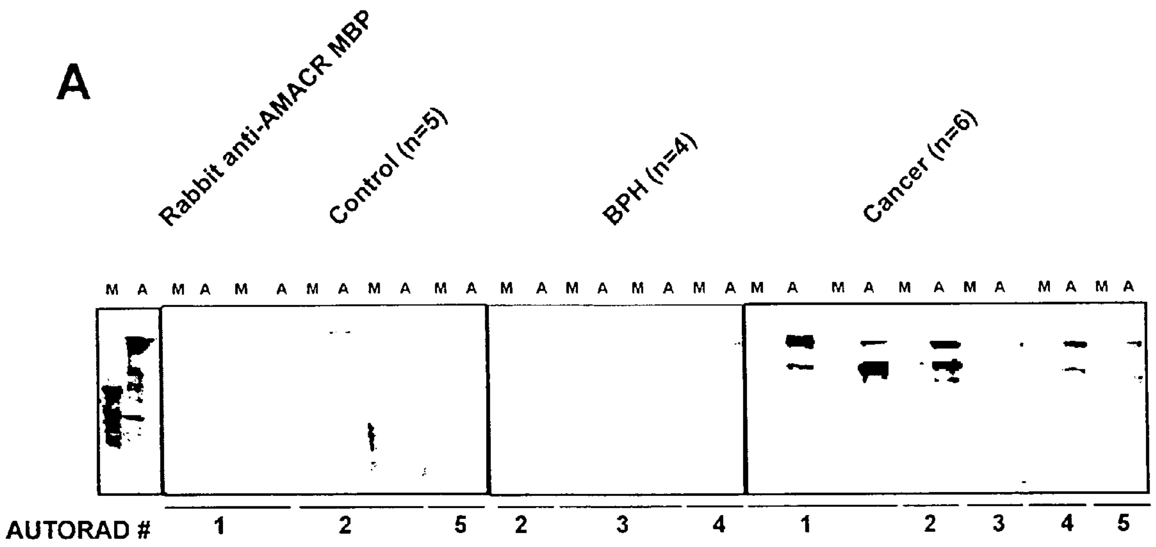
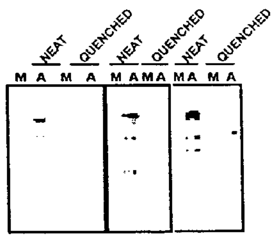
Figure 29

Figure 39

| Characteristic | Value |
|---|---|
| Mean age (yr) ± SEM * | 58.1 ± 0.7 |
| Mean gland weight (g) ± SEM # | 44.3 ± 1.6 |
| Mean gland size (cm) ± SEM ! | 1.4 ± 0.1 |
| **PSA @** | |
| Mean (ng/ml) ± SEM | 7.8 ± 0.9 |
| 0-2.5 ng/ml (%) | 13.3 |
| 2.6 –10 ng/ml (%) | 72.2 |
| 4- 10 ng/ml (%) | 66.7 |
| > 10 ng/ml (%) | 14.4 |
| **Gleason grade •** | |
| =< 6 (%) | 29.3 |
| >=7 (%) | 70.4 |
| **Primary tumor identification †** | |
| T1 (%) | 84.4 |
| T2 (%) | 11.7 |
| T3 (%) | 2.6 |
| **Ethinicity ‡** | |
| White (Not Hispanic origin) (%) | 78.3 |
| Hispanic (%) | 0 |
| Asian or Pacific Islander (%) | 0 |
| Black (Not Hispanic origin) (%) | 10.9 |
| Unknown (%) | 10.9 |

* Data were available for 94 patients only.
\# Data were available for 77 patients only.
! Data were available for 76 patients only.
@ Data were available for 90 patients only.
• Data were available for 92 patients only
† Data were available for 77 patients only.
‡ Data were available for 46 patients only.

| All (n=204) | | |
|---|---|---|
| | Recurred | censored |
| AMACR- | 30 | 50 |
| AMACR+ | 18 | 106 |

a.

C.

DECTECTION OF AMACR CANCER MARKERS IN URINE

This application is a Continuation in Part of U.S. patent application Ser. No. 10/210,120 filed Aug. 01, 2002, now U.S. Pat. No. 7,229,774 which claims priority to U.S. Provisional Application Ser. No. 60/309,581 filed Aug, 02, 2001 and U.S. Provisional Application Ser. No. 60/334,468 filed Nov. 15, 2001; each of which is herein incorporated by reference in its entirety.

This invention was made with government support under National Cancer Institute Grant nos. P50CA69568, P50CA90381, and CA97063; Grant No. R01AG21404 awarded by the N. I. H, Grant no. RSG-02-179-MGO awarded by the American Cancer Society, and Grant No. DAMD17-03-1-0105 from ARMY/MRMC. The Government has certain rights in the invention.

FIELD OF THE INVENTION

The present invention relates to compositions and methods for cancer diagnostics, including but not limited to, cancer markers. In particular, the present invention provides gene expression profiles associated with prostate cancers. The present invention also provides novel markers useful for the diagnosis, characterization, and treatment of prostate cancers. In particular, the present invention provides methods and compositions for the use of α-methylacyl-CoA racemase (AMACR) as a marker for prostate cancer detection and prognosis.

BACKGROUND OF THE INVENTION

Afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer and 39,200 will die in 2001.

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals.

The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., J. Natl. Cancer Inst., 91:1033 [1999]; Maattanen et al., Br. J. Cancer 79:1210 [1999]; Schroder et al., J. Natl. Cancer Inst., 90:1817 [1998]). A major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., JAMA 274:1445 [1995]). This has resulted in a surge of equivocal prostate needle biopsies (Epstein and Potter J. Urol., 166: 402 [2001]). Thus, development of additional serum and tissue biomarkers to supplement PSA screening is needed.

SUMMARY OF THE INVENTION

The present invention relates to compositions and methods for cancer diagnostics, including but not limited to, cancer markers. In particular, the present invention provides gene expression profiles associated with prostate cancers. The present invention also provides novel markers useful for the diagnosis, characterization, and treatment of prostate cancers.

Accordingly, in some embodiments, the present invention provides a method for detecting the presence or absence of α-methylacyl-CoA racemase (AMACR) in urine, comprising providing urine from a subject and a reagent for detecting AMACR in the urine; and contacting the urine with the reagent under conditions such that the reagent detects the presence or absence of AMACR in the urine. In some embodiments, the level of AMACR in the urine is determined and assigned a score between 0 (absence of AMACR) and 4 (highest level AMACR expression) and a minimum threshold level is set to 1. In some embodiments, the presence of AMACR in the urine at a level above the minimum threshold level is indicative of a diagnosis of cancer in the subject. In some embodiments, the cancer is prostate cancer. In some embodiments, the reagent is an antibody (e.g., including, but not limited to, a single chain antibody, an Fab, and an epitope-binding fragment of an antibody). In some embodiments, the reagent comprises a label (e.g., including, but not limited to, a radioactive label, a fluorescent label, a chemiluminescent label, or a bioluminescent label).

The present invention additionally provides a kit for detecting the presence or absence of prostate cancer in a subject, comprising a reagent capable of specifically detecting the presence or absence of AMACR in urine and instructions for using the kit. In some embodiments, the reagent comprises an antibody that specifically binds to an AMACR polypeptide. In some embodiments, the reagent comprises a label (e.g., including, but not limited to, a radioactive label, a fluorescent label, a chemiluminescent label, or a bioluminescent label). In other embodiments, the kit instructions comprise instructions for determining whether the levels of AMACR in the urine are above a minimum threshold value.

The present invention further provides a method for determining risk of prostate cancer progression in a subject, comprising providing a prostate cancer tissue sample from the subject, detecting the presence or absence of AMACR in the sample, and determining that the subject is at increased risk for prostate cancer progression if the AMACR levels are below a maximum threshold value. In some embodiments, the prostate cancer tissue sample is obtained by surgical resection from the subject. In some embodiments, prostate cancer progression comprises prostate specific antigen failure. In other embodiments, prostate cancer progression comprises prostate cancer-specific death. In some embodiments, detection of AMACR comprises detecting an AMACR polypeptide. In some embodiments, detection of AMACR polypeptide comprises exposing the prostate cancer tissue sample to an antibody specific to AMACR polypeptide and detecting the binding of the antibody to the polypeptide. In some embodiments, the antibody is detectably labeled (e.g., including, but not limited to, a radioactive label, a fluorescent label, a chemiluminescent label, or a bioluminescent label). In certain embodiments, the AMACR polypeptide is detected and quantified by a semi-automated image analysis system. In some embodiments, the subject comprises a human subject.

DESCRIPTION OF THE FIGURES

FIG. 1*a* shows a dendrogram describing the relatedness of the samples. FIG. 1*b* shows a cluster diagram of the samples groups compared against normal adjacent prostate pool as a reference. FIG. 1*c* shows a cluster diagram of the samples groups compared against commercial prostate pool reference.

FIG. 3 shows the expression of hepsin in prostate cancer samples as determined by Northern blot analysis and immunohistochemistry. FIG. 3*a* shows Northern blot analysis of human hepsin (top) and normalization with GAPDH (bottom). NAT indicates normal adjacent prostate tissue and PCA indicates prostate cancer. FIG. 3*c* shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET). FIG. 3*d* shows Kaplan Meier Analysis.

FIG. 4*a* shows a histogram of pim-1 protein expression by tissue type as assessed from 810 tissue microarray elements. High-grade intraepithelial neoplasia (HG-PIN). Localized prostate cancer (PCA). FIG. 4*b* shows a Kaplan-Meier analysis. The tope line represents patients with strong Pim-1 staining. The bottom line represents patients with absent/weak Pim-1 expression.

FIG. 7 shows data for gene selection based on computed t-statistics for the NAP and CP pools.

FIG. 9 describes exemplary accession numbers and sequence ID Numbers for exemplary genes of the present invention.

FIG. 10 provides exemplary sequences of some genes of the present invention.

FIG. 13 describes an analysis of AMACR transcript and protein levels in prostate cancer.

FIG. 19A shows AMACR protein expression in localized hormone naive PCA. FIG. 19B shows strong AMACR expression in a naive lymph node metastasis. Error bars represent the 95% CI of the mean expression of the primary naive prostate cancer and corresponding lymph node metastases.

FIG. 17A shows PCA demonstrating strong hormonal effect due to anti-androgen treatment. FIG. 17B shows Western Blot analysis representing the baseline AMACR expression in different prostate cell lines (Left) and Western Blot analysis of LNCaP cells for AMACR and PSA expression after treatment with an androgen or an anti-androgen for 24 h and 48 hours (right).

FIG. 20*a* shows a cluster diagram depicting genes that molecularly distinguish metastatic prostate cancer (MET) from clinically localized prostate cancer (PCA). FIG. 20*b* shows a DNA microarray analysis of prostate cancer that reveals upregulation of EZH2 in metastatic prostate cancer. FIG. 20*c* shows RT-PCR analysis of the EZH2 transcript in prostate tissue and cell lines. FIG. 20*d* shows increased expression of EZH2 protein in prostate cancer.

FIG. 21*a* shows tissue microarray analysis of EZH2 expression. The mean EZH2 protein expression for the indicated prostate tissues is summarized using error bars with 95% confidence intervals. FIG. 21*b* shows a Kaplan-Meier analysis demonstrating that patients with clinically localized prostate cancers that have high EZH2 expression (Moderate/Strong staining) have a greater risk for prostate cancer recurrence after prostatectomy (log rank test, p=0.03).

FIG. 22*a* shows an immunoblot analysis of RNA interference using siRNA duplexes targeting the EZH2 sequence in prostate cells. FIG. 22*b* shows that RNA interference of EZH2 decreases cell proliferation as assessed by cell counting assay. FIG. 22*c* shows that RNA interference of EZH2 inhibits cell proliferation as assessed by WST assay. FIG. 22*d* shows that RNA interference of EZH2 induces G2/M arrest of prostate cells.

FIG. 23*a* shows a schematic diagram of EZH2 constructs used in transfection/transcriptome analysis. ER, modified ligand binding domain of estrogen receptor. H-1 and H-2, homology domains 1 and 2 which share similarity between EZH2 and E(z). CYS, cysteine-rich domain. SET, SET domain. TAG, myc-epitope tag. NLS, nuclear localization signal. FIG. 23*b* shows confirmation of expression of EZH2 constructs used in a. An anti-myc antibody was used. FIG. 23*c* shows a cluster diagram of genes that are significantly repressed by EZH2 overexpression. FIG. 23*d* shows SAM analysis of gene expression profiles of EZH2 transfected cells compared against EZH2 SET transfected cells. FIG. 23*e* shows a model for potential functional interactions of EZH2 as elucidated by transcriptome analysis and placed in the context of previously reported interactions. +, induction. −, repression.

FIG. 29 shows immunoblot analysis of the humoral response of AMACR. FIG. 29*a* shows an immunoblot analysis of the humoral response to AMACR. FIG. 29*b* shows a control experiment where the humoral response was blocked.

FIG. 30*a* shows the level of GP73 in individual samples after microarray analysis. FIG. 30*b* shows the result of GP73 transcripts determined by DNA microarray analysis from 76 prostate samples grouped according to sample type and averaged.

FIG. 31*a* shows Western blot analysis of GP73 protein in prostate cancer. FIG. 31*b* shows an immunoblot analysis of the Golgi resident protein Golgin 97.

FIG. 39 shows clinical and pathology data from patients with biopsy-proven clinically localized prostate cancer.

FIG. 40A shows Western blot analysis of sera from control subjects and prostate cancer patients probed with anti-AMACR antibody. FIG. 40B shows immunoblot analysis of plasma from prostate cancer patients and a control subject (CON). FIG. 40C shows immunoblot analysis of prostatic excretions from prostate cancer patients.

FIG. 41A shows concentrated urine samples from control subjects and prostate cancer patients immunoblotted with anti-AMACR antibody. FIG. 41B shows specificity of the AMACR immunoreactive band. FIG. 41C shows categorization of urine samples based on AMACR reactivity scores with 4 being the strongest reactivity and 0 being no reactivity. FIG. 41D shows a receiver operating characteristic (ROC) curve for detection of AMACR in urine as assessed by immunoblot analysis (n=110 sera from clinically localized prostate cancer patients and n=116 control subjects).

FIG. 42 shows AMACR expression analysis and correlation of low AMACR expression with higher risk of PSA biochemical recurrence.

GENERAL DESCRIPTION

Figure 1:
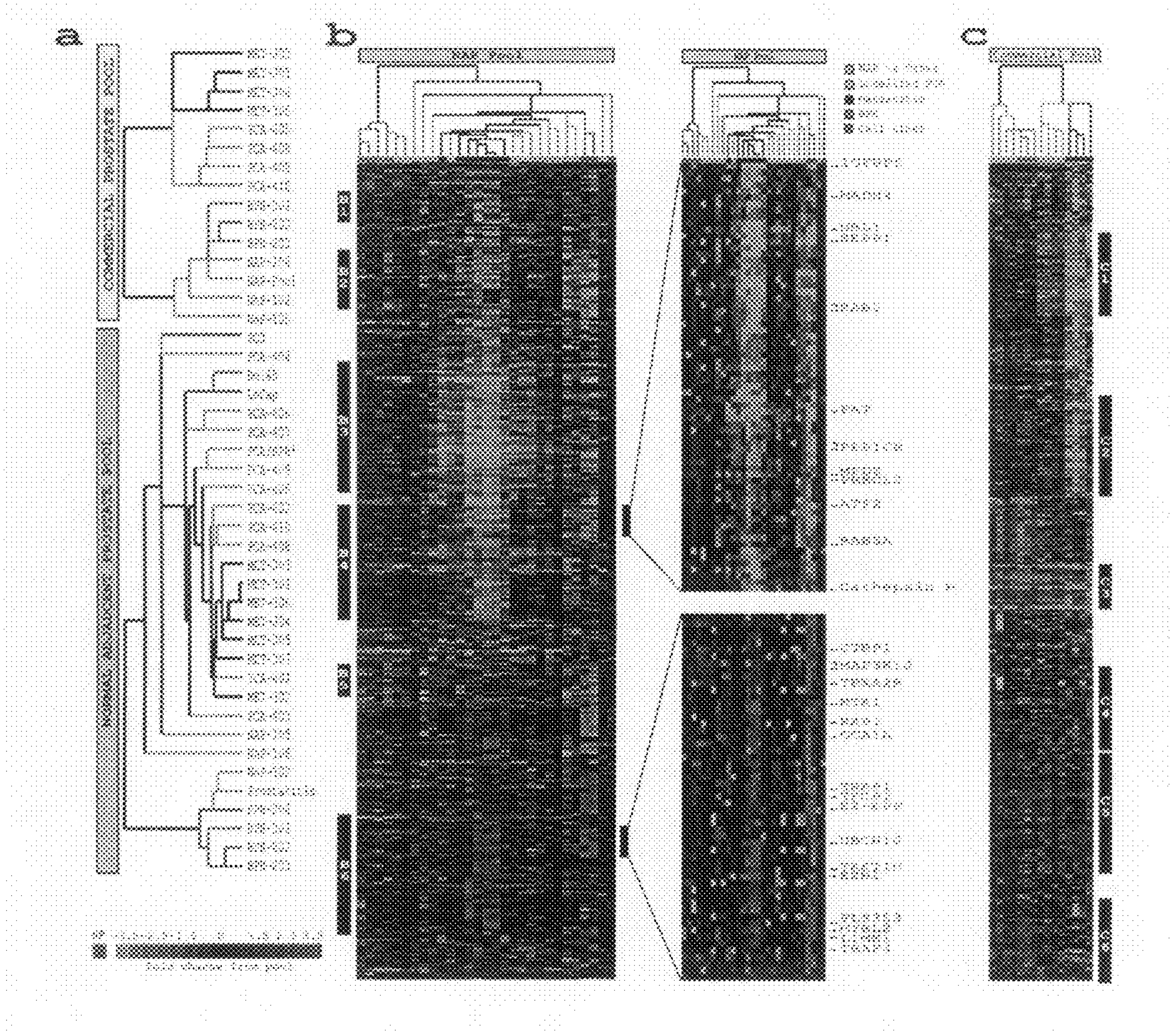
FIG. 1 shows a gene expression profile of prostate cancer samples.

Exploring the molecular circuitry that differentiates indolent PCA from aggressive PCA has the potential to lead to the discovery of prognostic markers and novel therapeutic targets. Insight into the mechanisms of prostate carcinogenesis is also gleaned by such a global molecular approach.

Similar to breast cancer (Lopez-Otin and Diamandis, Endor. Rev., 19:365 [1998]), PCA develops in a complex milieu of genetic and environmental factors in which steroid hormone signaling plays a central role. The primary precursor lesion of PCA, high-grade prostatic intraepithelial neoplasia (HG-PIN), has several characteristics similar to other early invasive carcinomas (i.e., chromosomal abnormalities and cytologic features). Loss of specific chromosomal regions (e.g., 8p21, 10q, 13q, 17p) along with losses and mutations of tumor suppressor genes such as Nkx3.1, PTEN, Rb, and p53 have been implicated in the initiation and progression of prostate cancer (Abate-Shen and Shen, supra). With the emergence of global profiling strategies, a systematic analysis of genes involved in PCA is now possible. DNA microarray technology is revolutionizing the way fundamental biological questions are addressed in the post-genomic era. Rather than the traditional approach of focusing on one gene at a time, genomic-scale methodologies allow for a global perspective to be achieved. The power of this approach lies in its ability to comparatively analyze genome-wide patterns of mRNA expression (Brown and Botstein, Nat. Gent., 21:33 [1999]). Obtaining large-scale gene expression profiles of tumors allows for the identification of subsets of genes that function as prognostic disease markers or biologic predictors of therapeutic response (Emmert-Buck et al., Am. J. Pathol., 156:1109 [2000]). Golub et al. used DNA arrays in the molecular classification of acute leukemias (Golub et al., Science 286:531 [1999], demonstrating the feasibility of using microarrays for identifying new cancer classes (class discovery) and for assigning tumors to known classes (class prediction). Using a similar approach, Alizadeh et al. showed that diffuse large B-cell lymphoma could be dissected into two prognostic categories by gene expression profiling (Alizadeh et al., Nature 403:503 [2000]). They provided evidence that lymphomas possessing a gene expression signature characteristic of germinal center B cells had a more favorable prognosis than those expressing genes characteristic of activated peripheral B-cells. Similar large-scale classifications of breast cancer and melanoma have been undertaken, and as with the other studies, molecular classification was the primary focus (Alizadeh et al., supra).

Accordingly, the present invention provides an analysis of gene expression profiles in benign and malignant prostate tissue. Three candidate genes, AMACR, hepsin and pim-1, identified by DNA microarray analysis of PCA, were characterized at the protein level using PCA tissue microarrays. Analysis of the differential gene expression profiles of normal and neoplastic prostate has led to the identification of a select set of genes that define a molecular signature for PCA. The expression profiling experiments of the present invention demonstrate a role for multiple, collaborative gene expression alterations which ultimately manifest as the neoplastic phenotype. By making direct comparative hybridizations of normal and neoplastic tissues, genes that molecularly distinguish benign tissue from malignant are identified.

α-Methylacyl-CoA Racemase (AMACR) is an enzyme that plays an important role in bile acid biosynthesis and β-oxidation of branched-chain fatty acids (Ferdinandusse et al., J. Lipid Res., 41:1890 [2000]; Kotti et al., J. Biol. Chem., 275:20887 [2000]). Mutations of the AMACR gene have been shown to cause adult-onset sensory motor neuropathy (Ferdinandusse et al., Nat. Genet., 24:188 [2000]). In diagnostically challenging prostate biopsy cases, pathologists often employ the basal cell markers 34βE12 or p63, which stain the basal cell layer of benign glands that is not present in malignant glands. Thus, in many biopsy specimens, the pathologist must rely on absence of staining to make the final diagnosis of prostate cancer. Experiments conducted during the development of the present invention identified AMACR as a marker expressed in cancerous biopsy tissue. Thus, the clinical utility of AMACR in prostate needle biopsies is large. For example, at the University of Michigan Medical Center, approximately 400 prostate needle biopsies are performed per year and approximately 20% require the use of a basal-cell specific marker to evaluate difficult lesions, characterized by a small amount of atypical glands. Accordingly, it is contemplated that in combination with basal cell specific markers, such as 34βE12 or p63, screening for AMACR expression by the methods of the present invention results in fewer cases diagnosed as "atypical without a definitive diagnosis."

Identification of the over-expression of AMACR in prostate cancer has clinical utility beyond diagnostic uses. Experiments conducted during the development of the present invention revealed that the only non-cancerous tissue to expresses significant levels of AMACR protein is the human liver. The present invention is not limited to a particular mechanism. Indeed, an understanding of the mechanism in not necessary to practice the present invention. Nonetheless, it is contemplated that AMACR activity is required for prostate cancer growth and by virtue of its specificity serves as a therapeutic target and a diagnostic marker.

Experiments conducted during the course of development of the present invention demonstrated that AMACR is present in the serum of prostate cancer patients. In addition, a humoral response to AMACR was identified based on the presence of antibodies to AMACR in the serum of prostate cancer patients.

The presence of AMACR was detected in very few prostate cancer patients' serum when compared to prostatic excretions obtained ex vivo from prostate cancer patients. Urine samples from prostate cancer patients were thus analyzed for the presence of AMACR (see Example 16). AMACR was detectable with high specificity and sensitivity in a large percentage of urine samples from prostate cancer patients, and the AMACR reactivity in the urine was not associated with PSA levels at time of diagnosis, Gleason score, pathologic stage, or prostate weight. Therefore, the present invention has utility for the non-invasive diagnosis or screening of prostate cancer.

Additional experiments conducted during the course of development of the present invention investigated AMACR expression in different groups of prostate cancer, including the aspect of neo-adjuvant hormonal withdrawal in localized disease. AMACR expression was found to be hormone independent in cell culture experiments. PSA, a gene known to be regulated by androgens, demonstrated hormone related alterations in expression under the same conditions. The present invention is not limited to a particular mechanism. Indeed, an understanding of the mechanism is not necessary to practice the present invention. Nonetheless, it is contemplated that these findings provide evidence that AMACR is not regulated by the androgen pathway. It is further contemplated that the decreased AMACR expression in hormone refractory tissue allows the use of AMACR as a biomarker for hormone resistance. It is also contemplated that, given the fact that hormone treatment in the mean of hormonal withdrawal did not affect AMACR expression in the cell culture, that some other mechanism than the androgen pathway is responsible for AMACR downregulation in the integrity of cancer tissue.

The present invention is not limited to a particular mechanism. Indeed, an understanding of the mechanism is not necessary to practice the present invention. Nonetheless, it is contemplated that, alternatively, AMACR is over expressed in the development of cancer, perhaps playing an important role in providing energy for the neoplastic cells. However, as the tumors become de-differentiated, they no longer require these sources of energy. It is contemplated that poorly differentiated tumors may take over other pathways to accomplish this same activity of branched fatty acid oxidation. There is no association with the proliferative rate of the tumor cells and AMACR expression.

Further experiments conducted during the course of development of the present invention showed that decreased AMACR expression in localized prostate cancer is associated with biochemical recurrence and cancer specific death. Example 17 describes the analysis in detail. Briefly, a quantitative AMACR protein expression test was developed to determine prostate cancer risk progression for patients with clinically localized prostate cancer treated by radical prostatectomy. The cohort of men was followed long-term after prostatectomy, with cancer specific death or biochemical failure as the study endpoint. Therefore, the present invention has utility for the stratification of patients into risk groups for biochemical failure or prostate cancer specific death.

AMACR expression was also examined in other cancers. Examination of other tumors demonstrated that colon cancer has the highest AMACR expression. As colorectal cancers are not known to be hormonally regulated, the fact that de-differentiation and decreased AMACR expression were correlated in PCA further supports the hypothesis that de-differentiation leads to decreased AMACR expression in the hormone refractory metastatic PCA. Hormone treatment is also a front line therapy in metastatic prostate cancer but is known to loose efficacy, selecting out hormone insensitive clones. The present invention is not limited to a particular mechanism. Indeed, an understanding of the mechanism is not necessary to practice the present invention. Nonetheless, it is contemplated that this phenomenon explains the observation that strong hormone treatment effect is consistent with decreased AMACR expression due to selection of potentially more de-differentiated cells.

The AMACR gene product is an enzyme, which plays an important role in bile acid biosynthesis and beta-oxidation of branched-chain fatty acids (Kotti et al., J. Biol. Chem. 275:20887 [2000]; Ferdinandusse et al., J Lipid Res 42:137 [2001]). AMACR over expression occurs in tumors with a high percentage of lipids such as PCA and colorectal cancer. The relationship between fatty acid consumption and cancer is a controversial subject in the development of PCA and colorectal cancer (Moyad, Curr Opin Urol 11:457 [2001]; Willett, Oncologist 5:393 [2000]). An essential role for AMACR in the oxidation of bile acid intermediates has been demonstrated. AMACR encodes an enzyme which catalyzes the racemization of alpha-methyl branched carboxylic coenzyme A thioesters and is localized in peroxisomes and mitochondria (Schmitz et al., Eur. J. Biochem. 231:815 [1995]). The present invention is not limited to a particular mechanism. Indeed, an understanding of the mechanism is not necessary to practice the present invention. Nonetheless, it is contemplated that, as AMACR is involved in the metabolism of lipids, that this leads to alterations in the oxidant balance of a cell. It is further contemplated that these changes are associated with DNA damage, malignant transformation, and other parameters of cell disturbance.

Additional experiments conducted during the course of development of the present invention demonstrated that AMACR mRNA and protein product are over expressed in a number of adenocarcinomas, including colorectal, prostate, breast, and ovarian and melanoma. Adenocarcinoma from the colorectum and prostate demonstrated consistent AMACR over expression (92% and 83% of tumor, respectively). Thus, AMACR is of use in the diagnosis of colonic neoplasia. For example, in some embodiments of the present invention, AMACR is used in the diagnosis of dysplasia. Specifically, in the setting of inflammatory bowel disease (IBD), where the identification of dysplasia may be diagnostically challenging, one evaluates putative lesions for their AMACR protein expression intensity. In some embodiments, this is performed in conjunction with the analysis of the adenomatous polyposis coli gene, since mutations in this gene are also believed to occur early in the development of colorectal neoplasia (Kinzler and Vogelstein, Cell 87:159 [1996]; Tsao and Shibata, Am J Pathol 145:531 [1994]).

Colonic adenomas (Kinzler and Vogelstein, supra; Tsao and Shibata, supra) and high-grade PIN (McNeal and Bostwick, Hum Pathol 17:64 [1986]; McNeal et al., Lancet 1:60 [1986]) are well known precursors of invasive colonic and prostate cancer, respectively. Experiments conducted during the course of development of the present invention demonstrated that AMACR is over expressed in colorectal adenomas (75%) and high-grade PIN (64%). Further supporting AMACR expression in early neoplastic lesions was the presence of focal AMACR expression in some atrophic prostate lesions. Some atrophic lesions (i.e., proliferative inflammatory atrophy and postatrophic hyperplasia) have recently been recognized as proliferative in nature with molecular alterations suggestive of early neoplastic changes (De Marzo et al., Am. J. Pathol. 155:1985 [1999]; Shah et al., Am. J. Pathol. 158:1767 [2001]). Some morphologically benign prostate glands were also observed to have focal moderate AMACR staining. The present invention is not limited to a particular mechanism. Indeed, an understanding of the mechanism is not necessary to practice the present invention. Nonetheless, it is contemplated that AMACR may have a role in the early steps of cancer development.

Several cancers that are associated with AMACR over expression, including colorectal, prostate and breast cancer, have been linked to high-fat diet. The exact mechanism how high-fat diet contributes to tumorigenesis in these organ systems is unknown, but emerging evidence suggest that peroxisome proliferator activated receptor (PPAR) mediated pathway plays a critical role (Debril et al., J. Mol. Med. 79:30 [2001]). Diet fatty acids have been shown to function as peroxisome proliferators and bind to and activate PPARs (Zomer et al., J. Lipid Res. 41:1801 [2000]), a family of nuclear receptor transcriptional factors. Activation of PPAR mediated pathways in turn control cell proliferation and differentiation. In addition, it can also alter the cellular oxidant balance (Yeldandi et al., Mutat. Res. 448:159 [2000]). The present invention is not limited to a particular mechanism. Indeed, an understanding of the mechanism is not necessary to practice the present invention. Nonetheless, it is contemplated that these effects act in concert to contribute to the tumorigenesis of several cancers. This hypothesis is supported by the findings that peroxisome proliferators, when given to mice, enhance the development colon adenomatous polyps in mice (Saez et al., Nat. Med. 4:1058 [1998]). In addition, PPARs are expressed in several prostate cancer cell lines and their ligands, and peroxisome proliferators, when added to culture, affect the growth of these cell lines (Shappell et al., Cancer Res. 61:497 [2001]; Mueller et al., PNAS 97:10990 [2000]). A phase II clinical trial also showed that troglitazone, a PPARγ activator, could stabilize PSA level in patients with prostate cancer (Kubota et al., Cancer Res. 58:3344 [1998]; Hisatake et al., Cancer Res. 60:5494 [2000]).

AMACR is an involved in the β-oxidation of pristanic acid (Ferdinandusse et al., J. Lipid. Res. 41:1890 [2000]). Pristanic acid can function as a PPAR α activator and promote cell growth (Zomer et al., J. Lipid Res. 41:1801 [2000]). The present invention is not limited to a particular mechanism. Indeed, an understanding of the mechanism is not necessary to practice the present invention. Nonetheless, it is contemplated that hyperfunctioning of β-oxidation pathway leads to exhaustion of reducing molecules and alters the cellular oxidant status (Yeldandi et al., Mutat. Res. 448:159 [2000]).

The present invention further provides methods of targeting AMACR as a therapeutic target in cancer treatment. Over expressed in high percentage of colorectal, prostate, breast and melanoma, but not in adjacent normal tissues, AMACR is targeted using antibody or enzyme inhibitors. Toxicity is expected not to be a major concern because individuals with congenital absence of this enzyme have no or insignificant clinical manifestations (Clayton et al., Biochem. Soc. Trans. 29:298 [2001]).

Annexins are a group of structurally related calcium-binding proteins, which have a domain that binds to phospholipids and an amino terminal domain that determines specificity (Smith et al., Trends. Genet. 10:241 [1994]; Mailliard et al., J. Biol. Chem. 271:719 [1996]). The annexins are involved in regulation of membrane trafficking, cellular adhesion and possible tumorigenesis. Experiments conducted during the course of development of the present invention used cDNA microarrays to study the expression patterns of multiple annexin family members in a wide range of prostate tissue samples in order to determine their role in PCA progression. Meta-analysis of gene expression data was employed to help further validate the cDNA expression array findings. Finally, high-density tissue microarrays were used to assess annexin protein expression levels by immunohistochemistry.

Eight annexins were evaluated for their mRNA expression levels in benign prostatic tissue, localized hormone naïve PCA and metastatic hormone refractory PCA samples. Five annexins (1,2,4,7, and 11) demonstrated a progressive down regulation at the transcript level going from benign prostatic tissue to localized PCA to hormone refractory PCA. In order to validate the cDNA expression array finding of these 5 annexin family members, a meta-analysis was performed, which confirmed that when looking across 4 studies where at least two studies reported results, annexin 1,2,4, and 6 were significantly down regulated in localized PCA samples when compared to benign prostatic tissue. Therefore the meta-analysis confirmed results on annexin 1, 2, and 4. In these examples, summary statistics across all datasets found these annexins to be significantly down regulated at the cDNA level. However, not all of the 4 studies had significant down-regulation. Annexin 4, for example, was significantly down regulated in two of four studies but the resultant summary statistic, which also takes into account the number of samples evaluated, was statistically significant. Annexins 7,8, and 13 were not found to be significantly under expressed. As demonstrated in FIG. 1, annexin 7 does decrease significantly when comparing localized PCA and metastatic PCA.

The protein expression levels of all above five annexins tested were statistically significantly decreased in hormone refractory PCA samples when compared to either localized PCA or benign prostate tissue. Four of 5 annexins also demonstrated a decrease in protein expression in clinically localized PCA as compared to benign prostate tissue. However, in none of these cases was the protein expression found to be significantly decreased. This second validation method at the protein level confirmed the cDNA expression array data for annexin 1,2,4, 7, and 11.

Based on gene expression array data described herein, localized PCA cells down regulate their mRNA levels of annexins but maintained the corresponding protein expression levels. The present invention is not limited to a particular mechanism. Indeed, an understanding of the mechanism is not necessary to practice the present invention. Nonetheless, it is contemplated that post-translational alteration may compensate for decrease mRNA, producing enough protein to maintain levels seen with benign samples. Since annexins play an important role in maintaining cellular adhesion, once the cells eventually lose this ability, tumor progression may occur. Therefore, as one might anticipate, annexin expression levels decreased significantly in the advanced hormone refractory PCA samples. This was confirmed at the protein level by significant decreases as demonstrated by immunohistochemistry.

A sequential down-regulation of annexins in both transcriptional and translational levels in metastatic PCA samples was observed. Annexin I, also called lipocortin, has been described as a phospholipase A2 inhibitor, and served as a substrate of epidermal growth factor receptor (Pepinsky et al., Nature 321:81 [1986]; Wallner et al., Nature 320:77 [1986]). The significant reduction of protein level has been shown in esophageal and prostate tumor cells (Paweletz et al., Cancer Res. 60:6293 [2000]). Annexin 2, also called p36, appears an efficient substrate of protein kinase C and Src pp60 (Hubaishy et al., Biochemistry 34:14527 [1995]). Annexin 4, called endonexin, regulates C1-flux by mediating calmodulin kinase II (CaMKII) activity (Chan et al., J. Biol. Chem. 269:32464 [1994]). Annexin 7, synexin, is involved in Duchenne's muscular dystrophy (Selbert et al. Exp. Cell. Res. 222:199 [1996]). Its gene is located on human chromosome 10q21, and its protein expression was decreased in hormone refractory tumor cells. In conclusion, the results of experiments conducted during the course of development of the present invention suggest that down regulation of several annexin family members may play a role in the development of the lethal PCA phenotype.

Additional experiments conducted during the course of development of the present invention identified additional markers that exhibited altered (e.g., increased or decreased) expression in prostate cancer. Additional markers include, but are not limited to, EZH2, Annexins 1, 2, 4, 7, and 11, CTBP 1 and 2, GP73, ABCC5 (MDR5), ASNS, TOP2A, and Vav2. In particular, EZH2 was identified as a marker that was overexpressed in prostate cancer, and in particular, in metastatic prostate cancer. EZH2 was further identified as being correlated with clinical failure (e.g., increased PSA levels). In addition, siRNA inhibition of EZH2 resulted in a decrease in cell proliferation of a prostate cancer cell line.

The present invention thus identifies markers and targets for diagnostic and therapeutic agents in a variety of cancers.

Definitions

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "characterizing prostate tissue in a subject" refers to the identification of one or more properties of a prostate tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "prostate cancer tissue sample" refers to a sample consisting substantially (e.g., greater than 80%, preferably greater than 90%, and even more preferably greater than 99%) of prostate cells (e.g., that have been classified as cancerous by a pathologist or other qualified individual or instrument). Generally, the prostate is removed from a subject by surgery (e.g., radical prostatectomy) and a section of the prostate suspected of comprising cancerous cells is analyzed. Example 17 illustrates the detection of AMACR in prostate cancer tissue samples.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. Cancer marker expression may be characterized using any suitable method, including but not limited to, those described in illustrative Examples 1-15 below.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous prostate control" refers to measuring the level of expression of a gene (e.g., the level of mRNA or protein) relative to the level in a non-cancerous prostate control sample. Gene expression can be measured using any suitable method, including but not limited to, those described herein.

As used herein, the term "threshold level" refers to a cutoff point or level of gene (e.g., AMACR) expression that has been established based on experimental or clinical data. In some embodiments, "threshold level" refers to the amount of a gene product (e.g., mRNA or protein) in a sample or a calculated numerical value based on multiple variables. The threshold level is a cutoff point above or below which certain characteristics or outcomes (e.g., cancer diagnosis, progression or death) are likely to occur. Generally, values above or below a defined threshold level correlate with some other characteristic or outcome, such as increased risk of death. Example 17 describes in detail the establishment of threshold levels of AMACR expression in prostate cancer tissue that correlate with risk of prostate cancer progression. Two end points of cancer progression, prostate specific antigen failure and prostate cancer-specific death, were correlated with threshold levels of normalized AMACR from multiple samples. This correlation allows distinct threshold values of AMACR in the prostate cancer samples to be used in predicting risk of prostate cancer progression. Threshold levels can be determined using any suitable method (e.g., statistical analysis of a group of samples with a known outcome). In some embodiments, threshold values are used by clinicians in the diagnosis and characterization of prostate cancer in a subject.

As used herein, the term "detecting a change in gene expression (e.g., hepsin, pim-1, EZH2, or AMACR) in said prostate cell sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in Examples 1-17 below.

As used herein, the term "reactivity score" refers to a value (e.g., numerical value) representing the amount of a given substance in a sample. In some embodiments, the sample of interest (e.g., urine) is contacted ("reacted") with a reagent that allows for determination of the quantity of the substance of interest (e.g., the level of mRNA or protein) present in the sample. The amount of the given substance in the sample is compared to amounts of the substance in positive and negative control samples (e.g., samples with high reactivity and non-reactivity to the reagent), and a score is assigned to the sample based on that comparison. The reactivity score of the substance (e.g., protein) can be determined by quantitation with an instrument or by visual inspection; for example, an individual can visually examine band intensities on a gel or blot that contains the substance of interest that has been hybridized with labeled DNA, RNA, antibody or other detectable marker. The more substance of interest in the sample, the higher the reactivity score.

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the term "prostate cancer expression profile map" refers to a presentation of expression levels of genes in a particular type of prostate tissue (e.g., primary, metastatic, and pre-cancerous prostate tissues). The map may be presented as a graphical representation (e.g., on paper or on a computer screen), a physical representation (e.g., a gel or array) or a digital representation stored in computer memory. Each map corresponds to a particular type of prostate tissue (e.g., primary, metastatic, and pre-cancerous) and thus provides a template for comparison to a patient sample. In preferred embodiments, maps are generated from pooled samples comprising tissue samples from a plurality of patients with the same type of tissue.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the terms "prostate specific antigen failure" and "biochemical failure" refer to the development of high prostate specific antigen levels in a patient following prostate cancer therapy (e.g., surgery). See Examples 3 and 4 for examples of how prostate specific antigen failure is determined. As used herein, the term "risk of developing prostate specific antigen failure" refers to a subject's relative risk (e.g., the percent chance or a relative score) of developing prostate specific antigen failure following prostate cancer therapy.

As used herein, the term "post surgical tumor tissue" refers to cancerous tissue (e.g., prostate tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g. the presence or absence of cancerous cells). An initial diagnosis does not include information about the stage of the cancer of the risk of prostate specific antigen failure.

As used herein, the term "biopsy tissue" refers to a sample of tissue (e.g., prostate tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "inconclusive biopsy tissue" refers to biopsy tissue for which histological examination has not determined the presence or absence of cancer.

As used herein, the term "basal cell marker" refers to a marker (e.g., an antibody) that binds to proteins present in the basal cell layer of benign prostate glands. Exemplary basal cell markers include, but are not limited to, 34βE12 and p63 (See e.g., O'Malley et al., Virchows Arch. Pathol. Anat. Histopathol., 417:191 [1990]; Wojno et al., Am. J. Surg. Pathol., 19:251 [1995]; Googe et al., Am. J. Clin. Pathol., 107:219 [1997]; Parsons et al., Urology 58:619; and Signoretti et al., Am. J. Pathol., 157:1769 [2000]).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Upregulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of fommamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with $tk^-$ cell lines, the CAD gene that is used in conjunction with CAD-deficient cells and the mammalian hypoxanthine-guanine phosphoribosyl transferase (hprt) gene that is used in conjunction with $hprt^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnostics, including but not limited to, cancer markers. In particular, the present invention provides gene expression profiles associated with prostate cancers. Accordingly, the present invention provides method of characterizing prostate tissues, kits for the detection of markers, as well as drug screening and therapeutic applications.

I. Markers for Prostate Cancer

The present invention provides markers whose expression is specifically altered in cancerous prostate tissues. Such markers find use in the diagnosis and characterization of prostate cancer.

A. Identification of Markers

Experiments conducted during the development of the present invention resulted in the identification of genes whose expression level was altered (e.g., increased or decreased) in PCA. The methods utilized glass slide cDNA microarrays that included approximately 5000 known, named genes, 4400 ESTs, and 500 control elements, as well as normal and cancerous prostate tissue. Differentially expressed genes were divided into functional clusters. The expression of relevant genes was confirmed using Western blot analysis. Protein expression in prostate tissues was measured for several genes of interest.

The methods of the present invention (See e.g., Example 2) were used to identify clusters of genes that were up or down regulated in PCA, benign prostate tissue, pre-cancerous tissue, and normal prostate. From these clusters, two genes, hepsin and pim-1 were identified as genes that were of particular relevance. Immunohistochemistry (See e.g., Example 4) was used to characterize the presence of hepsin and pim-1 proteins in prostate tissue. Hepsin was found to stain strongly in pre-cancerous tissue (HG-PIN). In addition, hepsin was found to stain less strongly in PCA tissues of men found to have an increased risk of metastasis as measured by PSA failure (increased PSA following surgery), thus confirming the diagnostic utility of hepsin. In addition, deceased expression of pim-1 in PCA tissue was also found to be associated with increased risk of PSA failure. Accordingly, in some embodiments, the present invention provides methods of detecting and characterizing prostate tissues.

The methods of the present invention identified a further gene, alpha-methyl-CoA racemase (AMACR), that was found to be expressed in PCA, but not benign prostate tissue (See e.g., Example 5). AMACR was found to be present in the serum and urine of prostate or bladder cancer patients (See e.g., Example 16). In addition, a humoral response to AMACR was identified. Further, an association between AMACR expression and disease prognosis was identified (See e.g. Example 17).

In still further embodiments, the methods of the present invention were used to characterize the EZH2 gene. EZH2 was found to be up-regulated in metastatic prostate cancer. The inhibition of EZH2 expression in prostate cells inhibited cell proliferation in vitro, as well as inducing transcriptional repression of a variety of genes. The methods of the present invention further identified CtBP1 and CTBP2, as well as that GP73 as being over-expressed in metastatic prostate cancer relative to localized prostate cancer and benign tissue.

In still further embodiments, the methods of the present invention identified annexins 1, 2, 4, 7 and 11 as being significantly decreased in hormone refractory PCA when compared to localized hormone naïve Pca. Tissue microarray analysis revealed a significant decrease in protein expression for annexins 1, 2, 4, 7 and 11 in hormone refractory PCA as compared to localized Pca. No significant differences were detected between the clinically localized PCA and non-cancerous prostate tissues.

B. Detection of Markers

In some embodiments, the present invention provides methods for detection of expression of cancer markers (e.g., prostate cancer markers). In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, prostatic secretions, and urine). The present invention further provides panels and kits for the detection of markers. In preferred embodiments, the presence of a cancer marker is used to provide a prognosis to a subject. For example, the detection of hepsin or pim-1 in prostate tissues is indicative of a cancer that is likely to metastasize and the expression of hepsin is indicative of a pre-cancerous tissue that is likely to become cancerous. In addition, the expression of AMACR is indicative of cancerous tissue. The information provided is also used to direct the course of treatment. For example, if a subject is found to have a marker indicative of a highly metastasizing tumor, additional therapies (e.g., hormonal or radiation therapies) can be started at a earlier point when they are more likely to be effective (e.g., before metastasis). In addition, if a subject is found to have a tumor that is not responsive to hormonal therapy, the expense and inconvenience of such therapies can be avoided.

The present invention is not limited to the markers described above. Any suitable marker that correlates with cancer or the progression of cancer may be utilized, including but not limited to, those described in the illustrative examples below (e.g., FKBP5, FASN, FOLH1, TNFSF10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1MAPK6, SGK, HEVIN, MEIS2, MYLK, FZD7, CAVEOLIN 2, TACC1, ARHB, PSG9, GSTM1KERATIN 5, TIMP2, GELSOLIN, ITM2C, GSTM5, VINCULIN, FHL1, GSTP1, MEIS1, ETS2, PPP2CB, CATHEPSIN B, CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1LUMICAN, C1S, C4BPA, COL3A1, FAT, MMECD10, CLUSTERIN, PLA2G2A, MADh4, SEPP1RAB2, PP1CB, MPDZ, PRKCL2, CTBP1CTBP2, MAP3K10, TBXA2F, MTA1RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4. Additional markers are also contemplated to be within the scope of the present invention. Any suitable method may be utilized to identify and characterize cancer markers suitable for use in the methods of the present invention, including but not limited to, those described in illustrative Examples 1-17 below. For example, in some embodiments, markers identified as being up or down-regulated in PCA using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. For example, a panel may include markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides an expression profile map comprising expression profiles of cancers of various stages or prognoses (e.g., likelihood of future metastasis). Such maps can be used for comparison with patient samples. In some embodiments comparisons are made using the method described in Example 2. However, the present invention is not limited to the method described in Example 2. Any suitable method may be utilized, including but not limited to, by computer comparison of digitized data. The comparison data is used to provide diagnoses and/or prognoses to patients.

1. Detection of RNA

In some preferred embodiments, detection of prostate cancer markers (e.g., including but not limited to, those disclosed herein) is detected by measuring the expression of corresponding mRNA in a tissue sample (e.g., prostate tissue). mRNA expression may be measured by any suitable method, including but not limited to, those disclosed below.

In some embodiments, RNA is detection by Northern blot analysis. Northern blot analysis involves the separation of RNA and hybridization of a complementary labeled probe. An exemplary method for Northern blot analysis is provided in Example 3.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or “cDNA” using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of cancer markers is detected by measuring the expression of the corresponding protein or polypeptide. Protein expression may be detected by any suitable method. In some embodiments, proteins are detected by the immunohistochemistry method of Example 4. In other embodiments, proteins are detected by their binding to an antibody raised against the protein. The generation of antibodies is described below.

In some preferred embodiments, urine or prostate cancer samples are tested for levels of AMACR using AMACR-specific antibodies (Examples 16 and 17). Amounts of AMACR are normalized and compared to other samples, allowing for the determination of threshold AMACR levels that correlate with presence of prostate cancer or risk of cancer progression.

In some embodiments, AMACR levels in urine are scored by visual inspection of band intensity on Western blots, with 0 being no band and 4 being the highest band intensity. Associations are made between AMACR levels and presence of prostate cancer, and a minimum threshold level set to 1 allows for discrimination between presence (values greater than 1) and absence (values below 1) of prostate cancer (see Example 16).

Experiments conducted during the development of the present invention resulted in the discovery that AMACR expression decreases in metastatic prostate cancer, in contrast to increased AMACR expression in clinically localized prostate cancer. Thus, in some embodiments, AMACR levels are examined in prostate cancer tissue samples to determine risk of cancer progression and poor prognosis (Example 17). In some embodiments, the samples are scored by semi-automated quantitation of tissue hybridized with anti-AMACR antibodies. The values are normalized to background counterstain and AMACR levels in other prostate cancer samples. In one embodiment, a threshold level is established below which a correlation between AMACR levels and risk of prostate specific antigen failure exists. In another embodiment, a threshold level is established below which a correlation between AMACR levels and prostate cancer-specific death exists.

In some embodiments, levels of AMACR in new urine or prostate cancer samples are compared to the threshold levels established during the course of development of the present invention. In other embodiments, individual laboratories or clinics use urine or prostate cancer samples on site to define threshold levels of AMACR expression that correlate with presence of cancer or prognosis; in other embodiments, panels of data from urine or prostate cancer samples are available in an electronic format for use by researchers and clinicians in multiple locations. In other embodiments, a centralized database exists where data from samples are entered on an ongoing basis by clinicians and researchers, thereby reinforcing and refining AMACR threshold levels that correlate with prostate cancer or prognosis over time.

Antibody binding is detected by techniques known in the art (e.g., radioimmunoassay, ELISA (enzyme-linked immunosorbant assay), “sandwich” immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of metastasis or PSA failure) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

4. Kits

In yet other embodiments, the present invention provides kits for the detection and characterization of prostate cancer. In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

5. In vivo Imaging

In some embodiments, in vivo imaging techniques are used to visualize the expression of cancer markers in an animal (e.g., a human or non-human mammal). For example, in some embodiments, cancer marker mRNA or protein is labeled using an labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

II. Antibodies

The present invention provides isolated antibodies. In preferred embodiments, the present invention provides monoclonal antibodies that specifically bind to an isolated polypeptide comprised of at least five amino acid residues of the cancer markers described herein (e.g., hepsin, pim-1, AMACR, EZH2, CTBP). These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for anticancer drugs). The screening methods of the present invention utilize cancer markers identified using the methods of the present invention (e.g., including but not limited to, hepsin, pim-1, AMACR, EZH2, and CTBP). For example, in some embodiments, the present invention provides methods of screening for compound that alter (e.g., increase or decrease) the expression of cancer marker genes. In some embodiments, candidate compounds are antisense agents (e.g., oligonucleotides) directed against cancer markers. See Section IV below for a discussion of antisense therapy. In other embodiments, candidate compounds are antibodies that specifically bind to a cancer marker of the present invention.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer markers activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic (e.g., androgen independent) prostate cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound'library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a cancer marker protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity. The cell, for example, can be of mammalian origin.

The ability of the test compound to modulate cancer marker binding to a compound, e.g., a cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer markers substrate in a complex. For example, compounds (e.g., substrates) can be labeled with $^{125}I$, $^{35}S$$^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiorneter can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein or biologically active portion thereof is evaluated. Preferred biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of the cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

IV. Cancer Therapies

In some embodiments, the present invention provides therapies for cancer (e.g., prostate cancer). In some embodiments, therapies target cancer markers (e.g., including but not limited to, hepsin, pim-1, AMACR, EZH2, and CTBP).

A. Antisense Therapies

In some embodiments, the present invention targets the expression of cancer markers. For example, in some embodiments, the present invention employs compositions comprising oligomeric antisense compounds, particularly oligonucleotides (e.g. those identified in the drug screening methods described above), for use in modulating the function of nucleic acid molecules encoding cancer markers of the present invention, ultimately modulating the amount of cancer marker expressed. This is accomplished by providing antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular $—CH_2$, $—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$, and $—O—N(CH_3)—CH_2—CH_2—$ [wherein the phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a $O(CH_2)_2ON(CH_3)_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$.

Other preferred modifications include 2'-methoxy(2'-O—$CH_3$), 2'-aminopropoxy(2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisensce oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of cancer markers of the present invention. Examples of genetic manipulation include, but are not limited to, gene knockout (e.g., removing the cancer marker gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like.

Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target prostate tumors that express a cancer marker of the present invention (e.g., hepsin, pim-1, EZH2, Annexin, CTBP, GP73, and AMACR). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker of the present invention (e.g., hepsin, pim-1, EZH2, Annexin, CTBP, GP73, and AMACR), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a cancer marker of the present invention (e.g., hepsin, pim-1, EZH2, Annexin, CTBP, GP73, and AMACR). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising the antisense or antibody compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

V. Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); 1 or L (liters); ml (milliliters); μl (microliters); cm (centimeters); mm (millimeters); μm (micrometers); nm (nanometers); and ° C. (degrees Centigrade).

EXAMPLE 1

Preparation of Total RNA and Reference Pools

The prostate surgical specimens were obtained from The University of Michigan Specialized Research Program in Prostate Cancer (S.P.O.R.E.) Tumor Bank with Institutional Review Board approval. Tumors samples were derived from patients with clinically localized and advanced hormone refractory prostate cancer. Table 1 shows the samples used in the present studies. All patients were operated on between 1993 and 1998 for clinically localized prostate cancer as determined by preoperative PSA, digital-rectal examination, and prostate needle biopsy. In addition, a subset of patients received bone and CAT scans to evaluate the possibility of metastatic spread. All patients received radical prostatectomy as a monotherapy (i.e., no hormonal or radiation therapy). The advanced prostate tumors were collected from a series of 12 rapid autopsies performed at the University of Michigan on men who died of hormone refractory prostate cancer. In brief, the majority of these patients had either widely metastatic prostate cancer which was treated with hormonal therapy followed by chemotherapy, or patients who presented with clinically localized disease which progressed and were then treated with both hormonal and chemotherapy. The majority of cases had multiple metastatic lesions to numerous sites. All autopsies were performed within 4-6 hours after death. The clinical and pathologic findings of these cases have recently been reported (Rubin et al., Clin. Cancer Res., 6:1038 [2000]). All samples used for the tissue microarray study were fixed in 10% formalin.

Tissues were homogenized using a polytron homogenizer (Brinkman Instruments) in Trizol (Gibco BRL) and the total RNA was isolated according to the standard Trizol protocol. The total RNA obtained was further subjected to an additional round of phenol chloroform extraction, precipitated and resuspended in RNAse free water. Total RNA was quantitated by spectrophotmetric (260/280 nm) absorbance and integrity judged by denaturing-formaldehyde agarose gel electrophoresis. Total RNA from four normal tissues was combined in equal concentrations to obtain the reference pool. The human prostate total RNA used in the commercial reference pool was obtained from Clontech, Inc.

TABLE 1

| Prostate Samples | | | |
|---|---|---|---|
| ID | PSA level | Tissue | Gleason Score |
| BPH-201 | 6.2 | Prostate | NA |
| BPH-202 | 3.9 | Prostate | NA |
| BPH-203 | 3.9 | Prostate | NA |
| BPH-204 | 4.6 | Prostate | NA |
| BPH-205 | 4.6 | Prostate | NA |
| BPH-206 | 4.6 | Prostate | NA |
| BPH-207 | 4.8 | Prostate | NA |
| BPH-208 | 13.6 | Prostate | NA |
| BPH-209 | 9.8 | Prostate | NA |
| BPH-210 | 4.6 | Prostate | NA |
| BPH-211 | 2.6 | Prostate | NA |
| BPH-212 | 7.1 | Prostate | NA |
| BPH-214 | | Prostate | NA |
| BPH-215 | 5.4 | Prostate | NA |
| Prostatitis | 9.8 | Prostate | NA |
| NAP-101 | 4.6 | Prostate | NA |
| NAP-102 | 9.8 | Prostate | NA |
| NAP-104 | 7 | Prostate | NA |
| NAP-105 | 0.09 | Prostate | NA |
| NAP-107 | 4.7 | Prostate | NA |
| PCA-401 | 5.2 | Prostate | 4 + 4 |
| PCA-402 | 22 | Prostate | 4 + 3 |
| PCA-403 | 4.7 | Prostate | 3 + 3 |
| PCA-404 | 8.5 | Prostate | 3 + 3 |
| PCA-405 | 4.6 | Prostate | 3 + 3 |
| PCA-406 | 7.8 | Prostate | 3 + 3 |
| PCA-407 | 7.8 | Prostate | 3 + 3 |
| PCA-408 | 5.4 | Prostate | 3 + 3 |
| PCA-409 | 7 | Prostate | 3 + 3 |
| PCA-410 | 44.6 | Prostate | 4 + 4 |
| PCA-414 | | Prostate | 3 + 4 |
| PCA-416 | 24.1 | Prostate | 4 + 4 |
| PCA-417 | 12.4 | Prostate | 4 + 4 |
| PCA-420 | | Prostate | 3 + 3 |
| PCA-421 | 13.6 | Prostate | 3 + 4 |
| MET-301 | | Lung | NA |
| MET-302 | | Liver | NA |
| MET-303 | | Liver | NA |
| MET-304 | | Stomach | NA |
| MET-305 | | Adrenal | NA |
| MET-306 | | Prostate | NA |
| MET-307 | | Lymph Node | NA |
| MET-308 | | Lymph Node | NA |
| MET-309 | | Lymph Node | NA |
| MET-310 | | Liver | NA |
| MET-311 | | Soft tissue | NA |
| MET-312 | | Liver | NA |
| MET-313 | | Soft tissue | NA |
| MET-314 | | Soft tissue | NA |
| MET-315 | | Soft tissue | NA |
| MET-316 | | Soft tissue | NA |
| MET-317 | | Liver | NA |
| MET-318 | | bone | NA |
| MET-319 | | bone | NA |
| MET-320 | | bone | NA |

Table 1. Samples employed in the study. Designating PSA level in ng/mL, Organ sources and Gleason scores. Normal adjacent prostate (NAP), Benign prostatic hyperplasia (BPH), Localized prostate cancer (PCA) and Hormone refractory metastatic prostate cancer (MET). NA refers to "not applicable".

EXAMPLE 2

Microarray Analysis

This example describes the use of microarray analysis to identify genes that demonstrate an altered level of expression in cancerous or benign prostate tissues.

A. Experimental Methods

Microarray analysis of gene expression was conducted essentially as described by the Brown and Derisi Labs. The sequence-verified cDNA clones on the human cDNA microarray are available from the web site of Research Genetics. Based on the latest Unigene build, the 10K human cDNA microarray used covers approximately 5520 known, named genes and 4464 ESTs. All chips have various control elements that include human, rat, and yeast genomic DNAs, SSC, yeast genes and "housekeeping genes," among others. In addition, 500 cancer- and apoptosis-related cDNAs from Research Genetics were used to serve as independent controls for clone tracking and function as duplicates for quality control. Three metastatic prostate cancer cell lines: DU-145, LnCAP, and PC3 were also profiled for gene expression.

Fluorescently labeled (Cy5) cDNA was prepared from total RNA from each experimental sample. The two reference samples used in this study were labeled using a second distinguishable fluorescent dye (Cy3) and included a pool of normal adjacent prostate tissue (NAP) from four patients (distinct from those used in the experimental samples) and a commercial pool of normal prostate tissues (CP). In addition to minimizing patient-to-patient variation, comparisons against pools of normal prostate tissue facilitate the discovery of genes that molecularly distinguish prostate neoplasms. The two reference pools are different in that one is comprised of normal adjacent prostate tissue, which may be influenced by paracrine effects mediated by PCA, and furthermore is exposed to the same environmental and genetic factors as the adjacent PCA. By contrast, the CP pool is derived from 19 individuals with no known prostate pathology and also represents a renewable commercially available reference resource.

Purified PCR products, generated using the clone inserts as template, were spotted onto poly-L-lysine coated microscope slides using an Omnigrid robotic arrayer (GeneMachines, CA) equipped with quill-type pins (Majer Scientific, AZ). One full print run generated approximately 100 DNA microarrays. Protocols for printing and post-processing of arrays are well known in the art.

B. Data analysis

Primary analysis was done using the Genepix software package. Images of scanned microarrays were gridded and linked to a gene print list. Initially, data was viewed as a scatter plot of Cy3 versus Cy5 intensities. Cy3 to Cy5 ratios were determined for the individual genes along with various other quality control parameters (e.g., intensity over local background). The Genepix software analysis package flags spots as absent based on spot characteristics (refer to the web site of Axon Instruments, Inc.). Bad spots or areas of the array with obvious defects were manually flagged. Spots with small diameters (<50 microns) and spots with low signal strengths<350 fluorescence intensity units over local background in the more intense channel were discarded. Flagged spots were not included in subsequent analyses. Data were scaled such that the average median ratio value for all spots was normalized to 1.0 per array.

These files were then imported into a MICROSOFT ACCESS database. The data for the required experiments were extracted from the database in a single table format with each row representing an array element, each column a hybridization and each cell the observed normalized median of ratios for the array element of the appropriate hybridization. Prior to clustering, the normalized median of ratio values of the genes were log base 2 transformed and filtered for presence across arrays and selected for expression levels and patterns depending on the experimental set as stated. Average linkage hierarchial clustering of an uncentered Pearson correlation similarity matrix was applied using the program Cluster (Eisen et al., PNAS 95:14863 [1998]), and the results were analyzed and figures generated with the program TreeView. TreeView and Cluster are available from Michael Eisen's lab at the Lawrence Berkeley National Lab.

C. Results

Over forty 10K human cDNA microarrays were used to assess gene expression in four clinical states of prostate-derived tissues in relation to two distinct reference pools of normal specimens. FIG. 1 provides an overview of the variation in gene expression across the different tissue specimens analyzed. A hierarchical clustering algorithm was employed to group genes and experimental samples based on similarities of gene expression patterns over all the genes and samples tested, respectively.

1. Expression Dendrograms

Relationships between the experimental samples are summarized as dendrograms (FIG. 1*a*), in which the pattern and length of the branches reflect the relatedness of the samples. FIG. 1*a* shows dendrograms that reveal the variation in gene expression pattern between experimental samples with the two references employed. Individual samples in each group are indicated by the branches of the same color whereby METs are in dark blue, localized PCAs in orange, NAPs in light blue, BPHs in gray, and cell lines in pink. Asterisk (*) indicates a sample that was initially documented as BPH, but was later confirmed to have 5% cancer tissue. The details of metastatic samples used in this study are as follows: MET 301, from Lung; MET 302 and 303 from liver; MET 304, from stomach; MET 305 from adrenal gland; MET 306 from prostate; and MET 307 was from lymph node. Hierarchical clustering of the data identified distinct patterns of gene expression between the various groups analyzed. Each row represents a single gene with 1520 genes depicted in b, and 1006 genes depicted in c. The results represent the ratio of hybridization of fluorescent cDNA probes prepared from each experimental mRNA to the respective reference pools. These ratios are a measure of relative gene expression in each experimental sample and are depicted according to the color scale at the bottom left. Red and green colors in the matrix represent genes that are up- and down-regulated, respectively, relative to the reference pool employed. Black lines in the matrix represent transcript levels that are unchanged, while gray lines signify technically inadequate or missing data (NP, not present). Color saturation reflects the magnitude of the ratio relative to the median for each set of samples.

FIG. 1*b* shows a cluster diagram of the various sample groups compared against normal adjacent prostate pool as reference. Prior to hierarchical average-linkage clustering, the data was filtered for at least a 2-fold change in expression ratio and ratio measurements present in 50% of the samples. By this method, 1520 genes were selected from the NAP reference data set. Indicated by vertical bars on the left (b1 to b6) of FIG. 1*b* are regions identified with characteristic gene expression signatures. Clusters b1 and b5 show genes up-regulated in localized PCA but not in metastatic PCA. Clusters b2 and b4 highlight genes down-regulated in metastatic PCA and the cell lines DU145 and LnCAP. Cluster b3 identifies genes down-regulated in both localized PCA and metastatic PCA. Cluster b6 highlights genes that are primarily up-regulated in metastatic PCA alone. Portions of Clusters b4 and b6 are shown enlarged with selected genes shown using Human genome organization (HUGO) gene nomenclature.

FIG. 1*c* shows a cluster diagram of the various sample groups compared against the commercial prostate pool reference. Prior to hierarchical average-linkage clustering, the data was filtered for at least a 3-fold change in expression ratio and ratio measurements present in 75% of the samples resulting in a total of 1006 genes. Regions with distinct patterns (c1-c6) are indicated by vertical bars to the right of FIG. 1*c*. Cluster c1 depicts genes down-regulated in both localized PCA and metastatic PCA. Cluster c2 represents genes down-regulated only in metastatic PCA. Cluster c3 shows genes that are highly represented in the commercial pool. Cluster c4 highlights genes that are up-regulated in localized PCA and in metastatic PCA. Cluster c5 represent genes with a low representation in the commercial pool. Cluster c6, represents genes that are down-regulated in metastatic PCA but are up-regulated in all other samples used.

Benign conditions of the prostate such as BPH and NAP cluster separately from malignant PCA cell lines or tissues, regardless of the reference pool used. Within the PCA cluster, it is also evident that metastatic PCA and clinically localized PCA formed distinct subgroups. Similarly, in the "benign" grouping, BPH tended to distinguish itself from NAP. Interestingly, one of the "BPH" samples initially clustered with the localized PCA group. Upon further histopathologic review, however, it was discovered that this sample contained a small focus of neoplastic tissue (~5%), thus accounting for its initial misclassification (now designated PCA+BPH in FIG. 1*a*).

Eisen matrix formats (Eisen et al., supra) of the variation in gene expression are also presented (FIG. 1*b* and 1*c*). With a global perspective of the data, it is apparent that metastatic PCA dominates the analysis and has the greatest variation in gene expression of the samples tested. Bars on the left or right of each matrix represent clusters of coordinately expressed genes highlighting interrelationships between specimens. For example, Clusters b3 and c1 represent genes down-regulated in both localized and metastatic PCA (FIGS. 1*b* and 1*c*). By contrast, Clusters b6 and b4 highlight genes that are specifically up- and down-regulated in metastatic PCA, respectively (FIG. 1*b*). IGFBP-5, DANI, FAT tumor suppressor and RAB5A are examples of genes that are down-regulated specifically in metastatic PCA and also have a proposed role in oncogenesis ("magnified" regions, FIG. 1*b*). Similarly, cancer-related genes that are up-regulated in metastatic PCA include MTA-1 (metastasis-associated 1), MYBL2, and FLS353 (preferentially expressed in colorectal cancer). Many genes in this "met-specific" cluster are shared by both the metastatic PCA tissue and the two PCA cell lines DU145 and LnCAP.

A total of 53 prostate specimens were profiled against the commercial pool. They include 4 normal adjacent prostate tissue (NAP), 14 benign prostatic hyperplasia (BPH), 1 prostatitis, 14 localized prostate cancer (PCA) and 20 hormone refractory metastatic PCA (MET). Prior to hierarchial average-linkage clustering, the data was filtered for at least 3-fold change in Cy5/Cy3 ratios and measurements present in 75% of the samples. By this method 1325 genes were selected. The data expands on FIG. 1*c* with an additional 40 samples, which include all from FIG. 1*b*, and also includes 28 additional prostate specimens.

2. Focused Clusters

Figure 6:
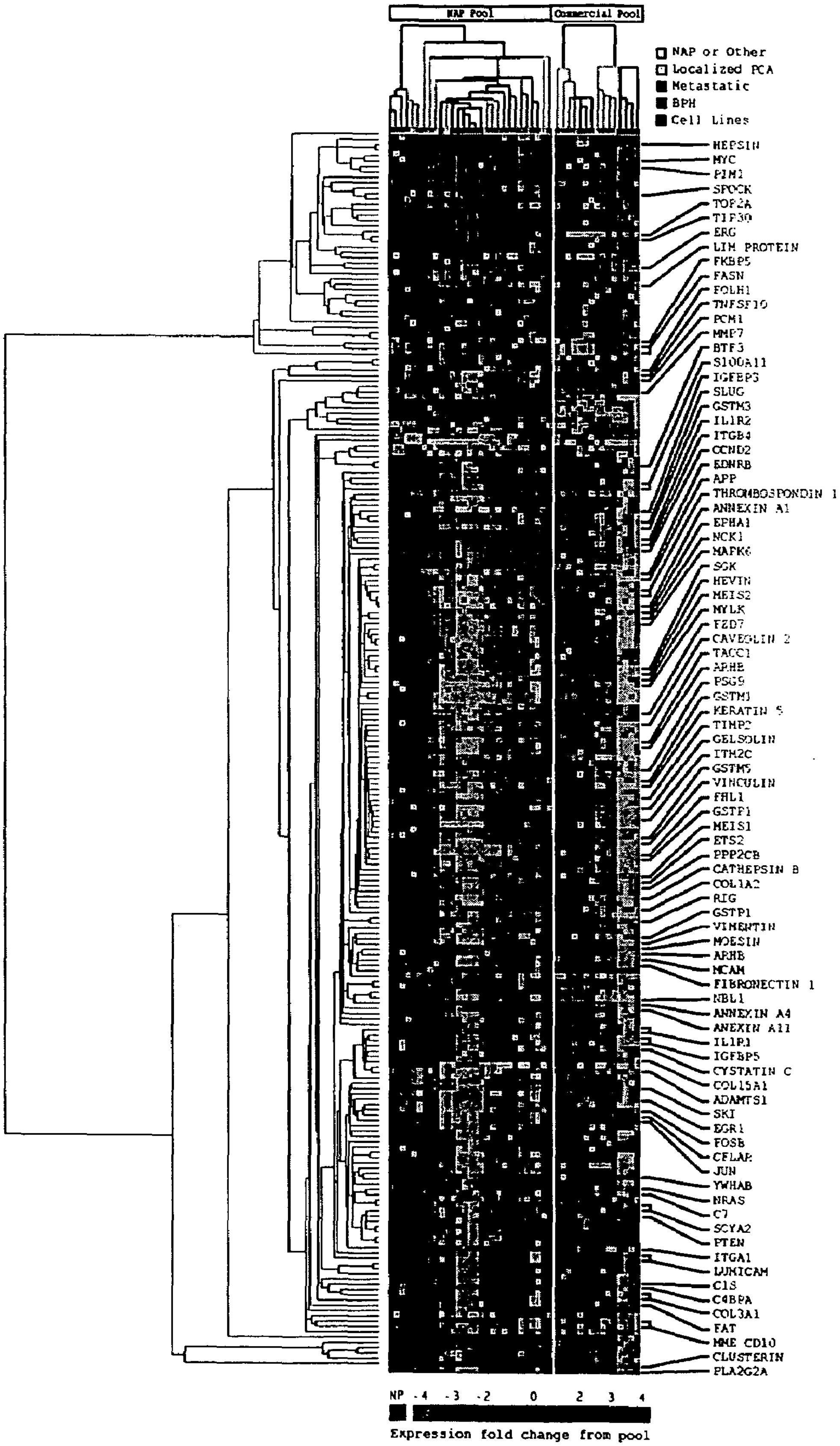
FIG. 6 shows a focused cluster of prostate cancer related genes.

Data was next assessed by examining functional groups of known, named genes. Cancer-related functional clusters were arbitrarily defined including cell growth/cell death, cell adhesion, anti-protease/protease, free radical scavengers, inflammation/immunity, phosphatase/kinase, transcription, and miscellaneous (FIGS. 2 and 6).

One of several available methods of gene selection was used to create a more limited set of genes for future exploration. In one method, t-statistics (based on MET/PCA vs. benign) were computed for each gene. The cell line samples were excluded from the analysis. Also, genes and ESTs that had data missing from 20% of samples were excluded from analysis. The t-statistics were ranked in two ways. First, they were ranked by absolute magnitude, which takes into account the inter-sample variability in expression ratios. Second, they were ranked by the magnitude of the numerator of the test statistic, which is based on the biological difference in expression ratios and designated as "effect size" (for MET/PCA vs. benign). A scatterplot of the genes with the 200 largest effect sizes and 200 largest t-statistics was then plotted (See FIG. 7). FIG. 7 shows gene selection based on computed t-statistics for each gene. Two groups were used in the analysis: PCA/MET and benign (NAP/BPH). FIG. 7*a* shows analysis of NAP pool data. FIG. 7*b* shows analysis of CP pool data. Selected genes are named and 200 genes for each data set are shown. Gene selection based on each method is shown. Selected gene names or symbols (as specified by Human genome organization (HUGO) gene nomenclature) are shown.

Genes that made both lists were also looked at separately in order to identify potential candidate genes. Implementing this methodology on both reference pool data sets (NAP and CP) yielded genes that included hepsin, pim-1, IM/ENIGMA, TIMP2, hevin, rig, and thrombospondin-1, among others. Several genes identified using gene selection methods are described in more detail in the context of "functional" clusters described in FIG. 2.

Figure 2:
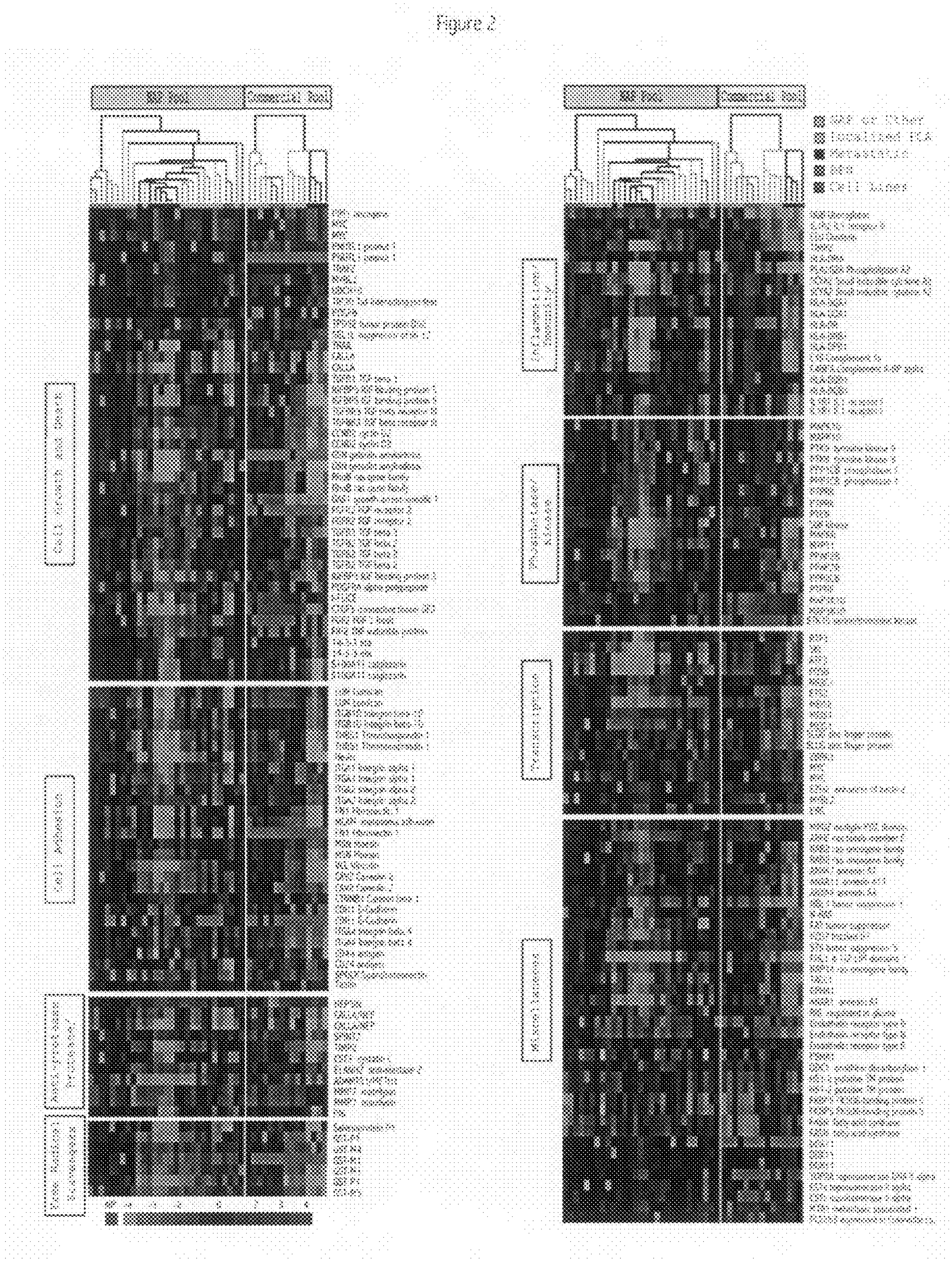
FIG. 2 shows functional clusters of genes differentially expressed in prostate cancer.

FIG. 2 shows the differential expression of functional clusters of select genes in prostate cancer. Gene names or symbols (as specified by Human genome organization (HUGO) gene nomenclature) are shown. The same convention for representing changes in transcript levels was used as in FIG. 1. The sample order from FIG. 1 was preserved for clarity.

Figure 8:
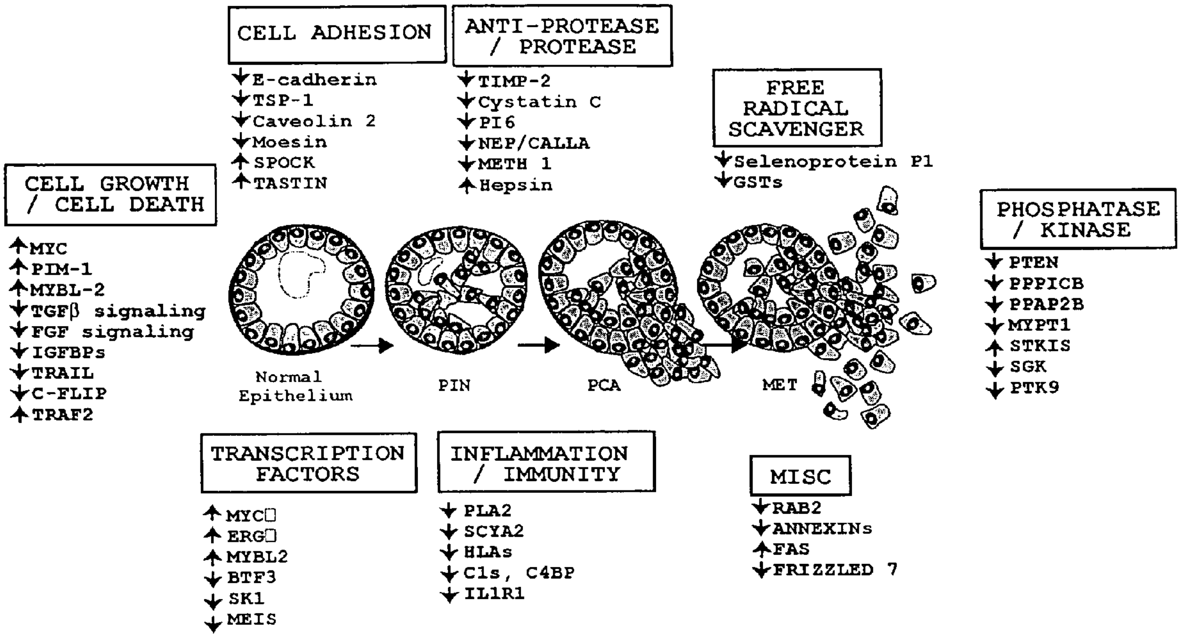
FIG. 8 shows an overview of genes differentially expressed in prostate cancer.

FIG. 8 shows a focused cluster of PCA-related genes. The same convention for representing changes in transcript levels was used as in FIG. 1. This cluster of 231 genes was generated by selecting for a 3.5-fold variation in at least 2 of any class, and ratio measurements present in 75% of the samples. Classes included: PCA vs. NAP, MET vs. NAP, PCA vs. CP and MET vs. CP.

The reliability of the hierarchical clustering results was assessed using three separate methods: that of Calinski and Harabasz (1974), Hartigan (1975) and Krzanowski and Lai (1985). The number of "stable" clusters estimated by all these methods is two. In the CP pool data set, that would elicit a valid benign cluster (NAP and BPH) and a malignant cluster (PCA and MET).

Many of the genes identified in these "focused" clusters have been implicated directly or indirectly as cancer biomarkers or mediators of carcinogenesis. Several have been shown to be dysregulated in PCA. For example, the tumor suppressor gene PTEN was down-regulated, while the proto-oncogene myc was up-regulated in the microarray analysis of PCA (FIG. 2) (Abate-Shen and Shen, supra). Likewise, decreased expression of E-cadherin and increased expression of fatty acid synthase, both of which have been shown to be dysregulated in PCA were observed (Tomita et al., Cancer Res., 60:3650 [2000] and Shurbaji et al., Hum. Pathol., 27:917 [1996]). In addition to uncharacterized expressed sequence tags (ESTs), there are numerous genes that were identified by the screen but not previously known to be associated with PCA. It is contemplated that they find use as cancer markers.

Exemplary nucleic acid sequences for some of the genes identified in focused clusters are shown in FIGS. 9 and 10. The present invention is not limited to the particular nucleic acid sequences described in FIGS. 9 and 10. One skilled in the art recognizes that additional variants, homologs, and mutants of the described sequences find use in the practice of the present invention.

3. Comparison Between NAP and CP Pools

Figure 5:
FIG. 5 shows a comparison of gene expression profiles for normal adjacent prostate tissue and normal prostate tissue reference.

A direct comparison between the NAP and CP pool was also made and notable gene expression differences were readily apparent. FIG. 5 shows a comparison between the NAP and CP pools. The same convention for representing changes in transcript levels was used as in FIG. 1. The cluster was obtained by selecting for genes with at least a 2.5-fold variation in any two of the samples of each class, namely the normal tissues versus the NAP pool and normal tissue versus the CP pool at a 50% filter. Of the genes analyzed 59 were selected with this criteria. Genes that were found to be up-regulated in the NAP pool in comparison with CP pool included connective tissue growth factor, EGR-1 (Early Growth Response 1), matrilysin (MMP7), CFLAR/I-FLICE (caspase 8 and FADD-like apoptosis regulator), lumican, serum glucocorticoid regulated kinase, lens epithelium derived growth factor, PAI1 (plasminogen activator inhibitor type I), JUN and FOS B, among others. Vascular endothelial growth factor (VEGF), growth arrest specific (GAS1), cholecystokinin (CCK), amiloride binding protein (ABP1) were among the down-regulated genes in the normal adjacent prostate pool when compared to the commercial pool. The present invention is not limited to a particular mechanism. Indeed, an understanding of the mechanism is not necessary to practice the present invention. Nonetheless, it is contemplated that the gene expression differences between normal prostate adjacent to PCA (NAP) and normal prostate tissue from individuals without prostate pathology (CP) may be attributable to a "field effect" induced by PCA itself.

EXAMPLE 3

Northern Blot Analysis

Thirty micrograms of total RNA was resolved by denaturing formaldehyde agarose gel and transferred onto Hybond membrane (Amersham) by a capillary transfer set up. Hybridizations were performed by the method described by Church and Gilbert, 1984. Signal was visualized and quantitated by phosphorimager. For relative fold estimation, the ratio between the signals obtained from hepsin and GAPDH probes was calculated.

Selected genes identified by microarray analysis were corroborated by Northern analysis. For example, hevin, 4½ LIM domain protein and gelsolin were shown to be 3.2-, 3.2- and 1.9-fold down-regulated, respectively by microarray and 8.8-, 4.5-, and 3.5-fold down-regulated by Northern analysis. Similarly, hepsin was 4.3-fold up-regulated by microarray and 11.3-fold up-regulated by Northern analysis (FIG. 3*a*). As hepsin is a cell-surface serine protease with transcript expression precisely restricted to localized and metastatic PCA, its expression was examined in more detail at the protein level (See Example 4 below).

EXAMPLE 4

Tissue Analysis

This example describes the analysis of protein expression in normal and cancerous prostate tissues.

A. Tissue microarray construction.

Kononen et al. have described a method for evaluating tumor tissues in large numbers on a single glass slide (Kononen et al., Nat. Med., 4:844 [1998]). These high-density tissue microarrays allow for analysis of up to 1,000 tissue samples on a single slide. These slides can be evaluated by routine light microscopy on hematoxylin and eosin (H&E) prepared and immunohistochemically stained slides. Thus, candidate cancer biomarkers, identified by gene expression methodologies, can be evaluated at the protein level over a large number of clinically stratified tumor specimens.

Prostate tissues used in microarray analysis included 4 BPH, 8 NAP, 1 commercial pool of normal prostate tissue (from 19 individuals), 1 prostatitis, 11 localized PCA, and 7 metastatic PCA specimens. High-density tissue microarrays (TMA) were assembled using a manual tissue puncher/array (Beecher Instruments, Silver Springs, Md.) as previously described (Kononen et al., Nat. Med., 4:844 [1998]; Perrone et al., J. Natl. Cancer Inst., 92:937 [2000]). The instrument consists of thin-walled stainless steel needles with an inner diameter of approximately 600 μm and stylet used to transfer and empty the needle contents. The assembly is held in an X-Y position guide that is manually adjusted by digital micrometers. Small biopsies are retrieved from selected regions of donor tissue and are precisely arrayed in a new paraffin block. Tissue cores were 0.6 mm in diameter and ranged in length from 1.0 mm to 3.0 mm depending on the depth of tissue in the donor block. Multiple replicate core samples of normal, HGPIN, and PCA were acquired from each tissue block of each case. Cores were inserted into a 45×20×12 mm recipient bock and spaced at a distance of 0.8 mm apart. Prostate tumor grading was performed using the system described by Gleason (Gleason, Cancer Chemother Rep., 50:125 [1966]). Pathologic stages for the radical prostatectomies were determined using the TNM staging system (Schroder et al., Prostate Suppl., 4:129 [1992]). Surgical margins were assessed separately and are not included in tumor staging.

B. Immunohistochemistry

TMA sections were cut at five-micron thick intervals for immunohistochemistry. Initial sections were stained for hematoxylin and eosin to verify histology. TMA slides prepared from formalin-fixed paraffin embedded tissue were heated for 0.5-1 hours at 60° centigrade. All slides were placed in 10 millimolar citrate buffer (pH 6.0) and microwaved for 5 minutes. Standard biotin-avidin complex immunohistochemistry was performed. The affinity purified polyclonal Rabbit antibody against hHepsin was used at a 1:40 dilution (original concentration 0.2 mg/ml) for this study. Immunostaining intensity was scored by a dedicated genitourinary pathologist as absent, weak, moderate, or strong. Scoring was performed using a telepathology system in a blinded fashion without knowledge of overall Gleason score (e.g., tumor grade), tumor size, or clinical outcome (Perrone et al., supra). A total of 738 tissue samples from benign (n=205), high-grade PIN (n=38), localized prostate cancer (n=335) and hormone refractory prostate cancer (n=160) were examined.

Similarly, pim-1 was analyzed using two TMA blocks from a total of 810 PCA samples from 135 patients. Six PCA samples were evaluated from each case and a median score was calculated. In addition, a small number of samples with benign prostatic tissues (e.g., benign epithelium and atrophy) and HG-PIN were examined. Immunohistochemistry was performed as above, using a rabbit polyclonal antibody against the N-terminus of pim-1 (Santa Cruz Biotechnology) at a 1:100 dilution. Pim-1 demonstrated cytoplasmic staining and was graded as either negative, weak, moderate, or strong. All samples were reviewed blinded with respect to all related pathology and clinical data.

C. Statistical methods

A nonparametric ANOVA test (Mann-Whitney [two categories]) was employed to evaluate whether the prostate samples expressed hepsin and pim-1 at different levels based on various parameters (tissue type, Gleason score, and tumor size). Kaplan-Meier analysis was used to estimate the cumulative percentage of PSA free progression ("survival"). The log-rank test was employed to assess the differences in disease free progression hepsin immunostaining. Cox proportional-hazard regression was used for multivariate analysis. Commercial software from SPSS (Chicago, Ill.) was used for this study.

D. Results

1. Hepsin

Figure 3B:
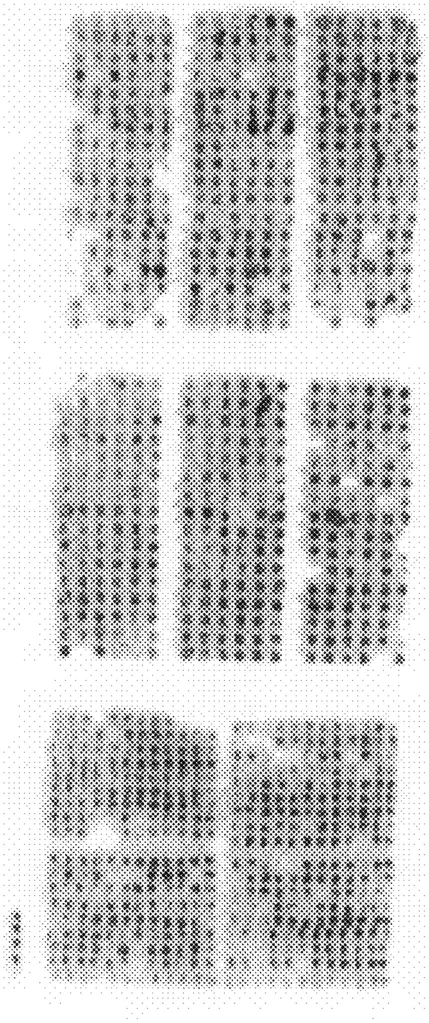
FIG. 3*b* shows tissue microarrays used for hepsin analysis.

Microarrays used in this study are shown in FIG. 3*b*. Over 700 benign and malignant prostate tissues were immunohistochemically profiled on tissue microarrays (FIG. 3*c*-*e*) using an affinity-purified hepsin-peptide antibody (Tsuji et al., J. Biol. Chem., 266:16948 [1991]). FIG. 3 shows the overexpression of Hepsin, a transmembrane serine protease, in prostate cancer. FIG. 3*a* shows a Northern blot analysis of human hepsin (top) and normalization with GAPDH (bottom). NAT indicates normal adjacent prostate tissue and PCA indicates prostate cancer. FIG. 3*b* shows tissue microarrays used for hepsin analysis. Staining was done with hemotoxylin and eosin to verify histology.

Immunohistochemical stains demonstrated absent or weak staining of benign prostate (c1), strong staining in localized prostate cancer (c2-6), and strong staining in a high-grade prostate tumor (magnification 100× was used for all images, samples measure 0.6 mm in diameter). Benign prostate glands demonstrate weak expression in the secretory, luminal cells and strong basal cell staining. In areas where prostate cancer and benign prostate glands are seen, significant hepsin staining differences are observed. Infiltrating prostate cancers (d3-4) demonstrate strong hepsin protein expression. Magnification for all images was 400×. FIG. 3*c* shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET). Relative strength of hepsin staining was qualitatively assessed and categorized. Percentage of hepsin staining per category is shown on the y-axis. FIG. 3*d* shows Kaplan Meier Analysis. PSA-free survival was stratified by level of hepsin protein expression into two categories absent/low expression (circles) versus moderate/strong expression (squares).

Internal controls showed that liver tissue, as previously described, stained strongly for hepsin. Overall, hepsin exhibited predominantly membrane staining and was preferentially expressed in neoplastic prostate over benign prostate (Mann-Whitney test, p<0.0001). Importantly, the precursor lesion of PCA, HG-PIN, had the strongest expression of hepsin, and almost never had absent staining (Mann-Whitney, p<0.0001). Most cases of low or absent hepsin staining were seen in benign prostate specimens. In addition, hormone refractory metastatic cancers were intermediate in staining intensity between localized prostate tumors and benign prostate.

Men who develop elevated PSA levels following radical prostatectomy are at a high risk to develop distant metastases and die due to prostate cancer (Pound et al., JAMA, 281:1591 [1999]. Therefore, to assess the usefulness of hepsin as a potential PCA biomarker, PSA failure was defined as a PSA elevation of greater than 0.2 ng/ml following radical prostatectomy. Analysis was performed on 334 localized prostate cancer samples treating each as an independent sample. PSA elevation following radical prostatectomy was significantly associated with absent and low hepsin immunostaining with a 28% (46/119 samples) PSA failure rate, in contrast to 17% (28/141 samples) PSA failure rate for tumors with moderate to strong hepsin expression (FIG. 3*d*, Log Rank test P=0.03). Multivariate analysis was performed to examine if these results were independent of Gleason score, a well-established histologic grading system for PCA (Gleason, Hum. Pathol., 23:273 [1992]). Based on the results from fitting a Cox proportional hazards model, there is an association of weak or absent hepsin protein expression in PCA with increased risk of PSA elevation following prostatectomy, similar to high Gleason score (corresponding risk ratios were 2.9 (p=0.0004) and 1.65 (p=0.037), respectively). Weak or absent hepsin expression was also associated with large prostate cancers; the median tumor dimension for prostate tumors with moderate to strong expression was 1.3 cm but 1.5 cm for tumors with absent or weak staining (Mann-Whitney Rank test, P=0.043). Taken together, hepsin protein expression in PCA correlated inversely with measures of patient prognosis.

Hepsin is a 51 kDa transmembrane protein with highest expression in the liver, and like PSA, is a serine protease (Kurachi et al., Methods Enzymol., 244:100 [1994]). The protease domain of hepsin has access to the extracellular space and can potentially activate other proteases or degrade components of extracellular matrix. The function of hepsin is poorly understood. It has been proposed to have a role in controlling cell growth (Torres-Rosado et al., PNAS, 90:7181 [1993], cell morphology, and activating the extrinsic coagulation pathway on the cell surface, leading to thrombin formation (Kazama et al., J. Biol. Chem., 270:66 [1995]). Additionally, hepsin mRNA levels have been shown to be elevated in ovarian carcinomas (Tanimoto et al., Cancer Res., 57:2884 [1997]). The present invention is not limited to a particular mechanism. Indeed, an understanding of the mechanism is not necessary to practice the present invention. Nonetheless, it is contemplated that the high expression of hepsin in HG-PIN, and not benign prostate, suggests that hepsin plays a role in the establishment of PIN or in the transition from HG-PIN to carcinoma. Subsequent decreases in hepsin expression seen in large localized cancers and hormone-refractory cancers suggest a decreased requirement of this protease in later stages of PCA. Alternatively, patients with advanced PCA often develop disseminated intravascular coagulation (DIC) (Riddell et al., J. Nucl. Med., 37:401 [1996]) whereby hepsin may play an important role.

2. pim-1

Tumorigenic growth of the prostate depends on the evasion of normal homeostatic control mechanisms, where cell proliferation exceeds cell death (Bruckheimer and Kyprianou, Cell Tissue Res., 301: 153 [2000]). While it is well known that the oncogene myc is overexpressed in many PCAs (Buttyan et al., prostate 11:327-37 [1987]; Abate-Shen and Shen, supra), the present invention demonstrates that the proto-oncogene pim-1 kinase is similarly up-regulated (cell growth/cell death cluster, FIG. 2). Previous studies suggest that the cooperative interaction between pim-1 and myc may induce lymphoid cell transformation by promoting cell cycle progression and blocking apoptosis (Shirogane, et al., Immunity 11:709 [1999]). The present analysis supports a similar co-transcriptional regulation (or gene amplification) of pim-1 and myc possibly mediating a synergistic oncogenic effect in PCA.

Figure 4:
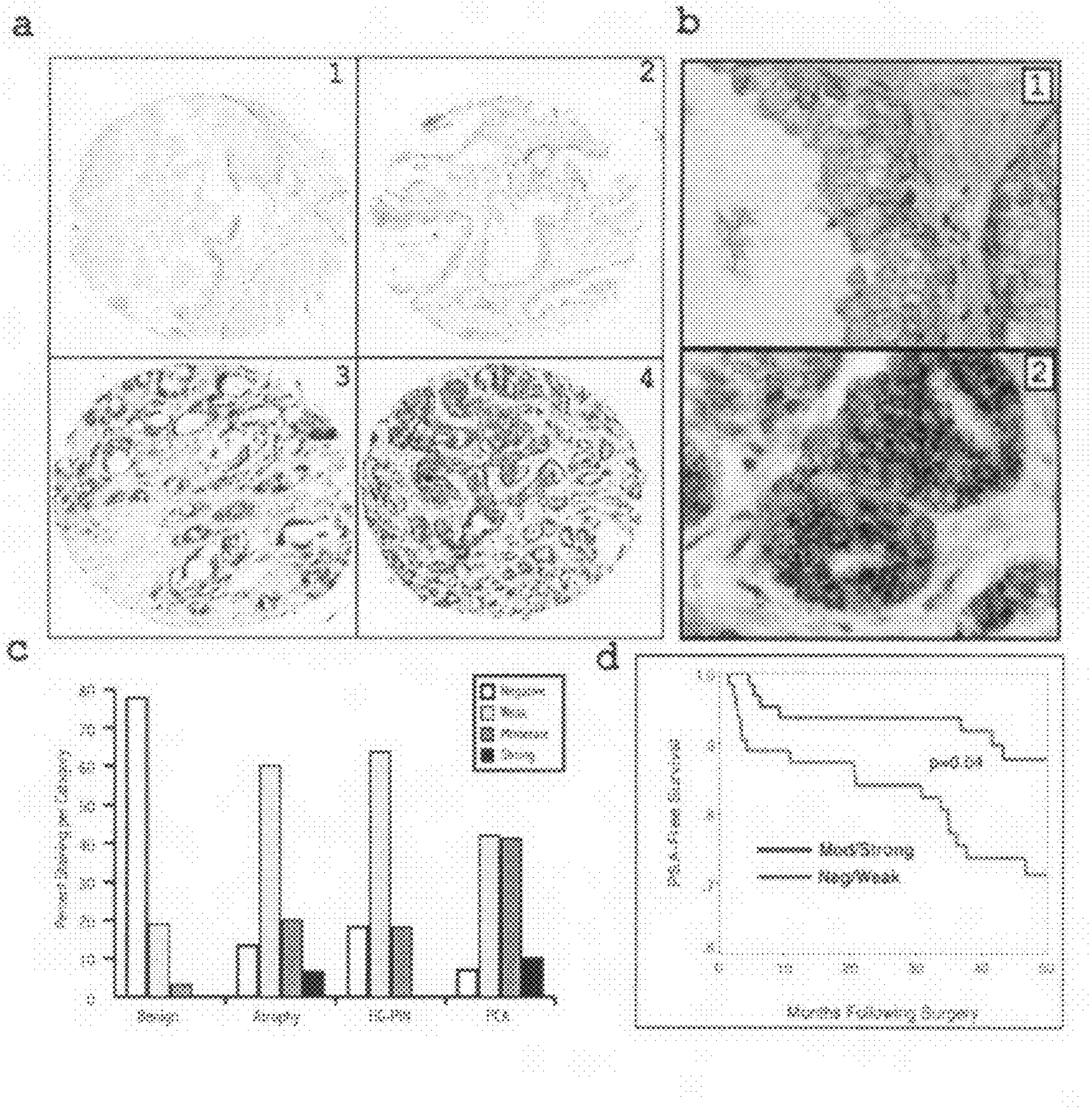
FIG. 4 shows the expression of pim-1 in prostate cancer samples as determined by Northern blot analysis and immunohistochemistry.

Pim-1 kinase protein expression in PCA was also explored using high-denisty TMAs. FIG. 4 shows the overexpression of pim-1 in prostate cancer. Immunohistochemical stains demonstrated absent or weak staining of benign prostate, and strong cytoplasmic staining in localized prostate cancer. Benign prostate glands demonstrated absent or weak expression in the secretory, luminal cells. Infiltrating prostate cancers demonstrated strong pim-1 protein expression. Magnification for all images 1000×. FIG. 4*a* shows a histogram of pim-1 protein expression by tissue type as assessed from 810 tissue microarray elements. High-grade intraepithelial neoplasia (HG-PIN). Localized prostate cancer (PCA). Relative strength of pim-1 staining is represented in the included legend. The percentage of pim-1 staining per category shown on y-axis. FIG. 4*b* shows Kaplan-Meier analysis demonstrating that patients with PCA that have negative to weak pim-1 expression (bottom line) are at a greater risk of developing PSA-failure following prostatectomy (log rank p=0.04). PSA-free survival was stratified by level of pim-1 protein expression into two categories absent/weak expression (bottom line) versus moderate/strong expression (top line).

Pim-1 protein was found to be markedly overexpressed in PCA (FIG. 4). Negative to weak pim-1 protein expression was observed in the majority of benign prostatic epithelial (97%), prostatic atrophy (73%), and high-grade PIN (82%) samples (FIG. 4*a*). In contrast, moderate to strong pim-1 expression was observed in approximately half of the PCA samples (51%) (FIG. 4*a*). Kaplan-Meier analysis for PSA-free survival demonstrated positive extraprostatic extension, seminal vesicle invasion, Gleason score greater than 7 and decreased pim-1 expression to be associated with a higher cumulative rate of PSA failure (FIG. 4*b*). By univariate Cox models, it was found that Pim-1 expression is a strong predictor of PSA recurrence (hazard ratio (HR)=2.1 (95% CI 1.2-3.8, p=0.01)).

Among the variables examined, significant predictors of PSA recurrence were Gleason score (HR=1.8 (95% CI. 1.1-3.0), p=0.03), Gleason pattern 4/5 PCA (HR=3.9(95% CI 1.8-8.3), p<0.001), extraprostatic extension status (HR=2.6 (95% CI 1.6-4.2), p<0.0001), surgical margin status (HR=2.6 (95% CI 1.2-5.6), p=0.01), seminal vesicle status (HR=3.5 (95% CI 2.0-6.2), p<0.0001), the natural log of pre-operative PSA level (HR=2.5 (95% CI 1.6-3.8), p<0.001), HR=2.4, p<0.001), and maximum tumor dimension (HR=2.7 (95% CI 1.6-4.7), p<0.0001). Presence of Gleason pattern 4/5 PCA (HR=3.8 (95% CI 1.4-10.0), p<0.01), Ln(PSA) (HR=2.1 (95% CI 1.1-3.9), p=0.02), and decreased pim-1 protein expression (HR=4.5 (95% CI 1.6-15.2), p=0.01) were both found to be significant predictors of PSA recurrence by a multivariate Cox model. Thus, even more so than hepsin, decreased expression of pim-1 kinase in PCA correlated significantly with measures of poor patient outcome.

Pim-1 kinase is a proto-oncogene that is regulated by cytokine receptors (Matikainen et al., Blood 93:1980 [1999]). It was first described as a common site of proviral integration in murine retrovirus-induced T cell lymphomas (Cuypers et al., Cell 37:141 [1984]), and was previously thought to be involved exclusively in hematopoietic malignancies (Breuer et al., Nature 340:61 [1989]). Co-transcriptional regulation of pim-1 and myc was observed in the experiments described herein (FIG. 2 cell growth/cell death cluster). Chronic overexpression of myc in the ventral prostate of transgenic mice induced epithelial abnormalities similar to low-grade PIN, but progression to adenocarcinoma in this model was never observed (Zhang et al., Prostate 43:278 [2000]). The present invention is not limited to any one mechanism. Indeed, an understanding of the mechanism is not necessary to practice the present invention. Nonetheless, it is contemplated that pim-1 overexpression may potentiate myc-induced prostate carcinogenesis.

FIG. 8 provides a schematic overview of representative genes differentially expressed in PCA identified by DNA microarray analysis. Genes are grouped functionally and arrows represent up- or down-regulation in metastatic hormone-refractory PCA (MET) and/or localized PCA (PCA) relative to normal prostate epithelium. See FIG. 2 for gene expression levels.

EXAMPLE 5

AMACR Expression Analysis

The Example describes the analysis of the gene expression data described in Examples 1-4 above to identify AMACR as being consistently over-expressed in prostate cancer.

A. Tissue Samples

In order to examine the widest range of prostate cancer specimens, clinical samples were taken from the radical prostatectomy series at the University of Michigan and from the Rapid Autopsy Program. Both programs are part of the University of Michigan Prostate Cancer Specialized Program of Research Excellence (S.P.O.R.E.) Tissue Core.

Prostatectomy cases for the tissue microarray (TMA) outcomes array were selected from a cohort of 632 patients, who underwent radical retropubic prostatectomy at the University of Michigan as a monotherapy (i.e., no hormonal or radiation therapy) for clinically localized prostate cancer between the years of 1994 and 1998. Clinical and pathology data for all patients was acquired with approval from the Institutional Review Board at the University of Michigan. Detailed clinical, pathology, and TMA data is maintained on a secure relational database (Manley et al., Am. J. Pathol., 159:837 [2001]).

Processing of the prostate specimens began within approximately 15-20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol., 164:1583 [2000]). Briefly, alternate sections of the prostate gland were submitted for histologic review. The remaining sections were frozen and stored in the SPORE Tissue Core. These samples were collected only from patients who had signed an IRB-approved informed consent. The samples were snap-frozen in OCT embedding media at −80° C. and stored in a holding area until the pathology report was finalized. These frozen samples were not available to researchers until adequate diagnosis and staging had been performed. The samples used for cDNA expression array analysis and RT-PCR were all evaluated by the study pathologists. All samples were grossly trimmed such that greater than 95% of the sample represented the desired lesion (e.g., prostate cancer, BPH, or benign prostate). Samples with prostate cancer were also assigned a Gleason score based on the sample used for molecular analysis.

In order to study hormone refractory prostate cancer, a Rapid Autopsy Protocol was used, which represents a valuable source of metastatic prostate tumors. Modeled after protocols developed at the University of Washington (Seattle, Wash.) and Johns Hopkins University (Baltimore, Md.), this program allows men with advanced prostate cancer to consent to an autopsy immediately after death. To date, 23 complete autopsies have been performed with a median time of 2 hours from death to autopsy. This procedure has previously been described in detail (Rubin et al., Clin. Cancer Res., 6:1038 [2000]). In brief, patients diagnosed with hormone refractory prostate cancer were asked to take part in a posthumous tissue donor program. The objectives and procedures for tissue donation were explained to the patient. Having agreed to participate in this IRB-approved tumor donor program, permission for autopsy is obtained before the death, with consent provided by the patient, or by next of kin. Hormone refractory primary and metastatic prostate cancer samples were collected using liquid nitrogen. Mirrored samples from the same lesion were placed in 10% buffered formalin. The fixed samples were embedded in paraffin and used for the development of TMAs. As with the prostatectomy samples, the study pathologist reviewed the glass slides, circled areas of viable prostate cancer, while avoiding areas of necrosis, and used these slides as a template for TMA construction.

B. Pathology and Evaluation

Prostates were inked before the assessment of surgical margins. Surgical margins from the apex and base were cut perpendicular to the prostatic urethral axis. The seminal vesicles were cut perpendicular to their entry into the prostate gland and submitted as the seminal vesicle margin. The prostates for this study were all partially embedded, taking alternate full sections from the apex, mid, and base. Detailed prostatectomy pathology reports included the presence or absence of surgical margin involvement by tumor (surgical margin status), the presence of extraprostatic extension, and seminal vesicle invasion. Tumors were staged using the TNM system, which includes extraprostatic extension and seminal vesicle invasion but does not take into account surgical margin status (Bostwick et al., Simin. Urol. Oncol., 17:222 [1999]). Tumors were graded using the Gleason grading system (Gleason, Cancer Chemother. Rep., 50:125 [1966]; Gleason, The Veterans Administration Cooperative Urological Research Group. Histologic Grading and Clinical Staging of Prostate Carcinoma. In: Tannenbaum M, editor. Urologic Pathology: The Prostate. Philadelphia: Lea & Febiger; 1977. p. 171-98).

As preparation for the construction of the TMAs, all glass slides were re-reviewed to identify areas of benign prostate, prostatic atrophy, high-grade prostatic intraepithelial neoplasia, and prostate cancer. To optimize the transfer of these designated tissues to the arrays, area of tumor involvement was encircled on the glass slide template as tightly around each lesion as possible. Areas with infiltrating tumor adjacent to benign glands were avoided.

C. RT-PCR

Total RNA integrity was judged by denaturing-formaldehyde agarose gel electrophoresis. cDNA was prepared using 1 μg of total RNA isolated from prostate tissue specimens. Primers used to amplify specific gene products were: AMACR sense, 5'CGTATGCCCCGCTGAATCTCGTG-3' (SEQ ID NO:100); AMACR antisense, 5'-TGGCCAATCATCCGTGCTCATCTG-3' (SEQ ID NO:101); GAPDH sense, 5'-CGGAGTCAACGGATTTGGTCGTAT-3' (SEQ ID NO:102); and GAPDH antisense, 5'-AGCCTTCTCCATGGTGGTGAAGAC-3' (SEQ ID NO: 103). PCR conditions for AMACR and GAPDH comprised 94° C. for 5 min, 28 cycles of 95° C. for 1 min, 60° C. for 1 min (annealing), and 72° C. for 1 min, and a final elongation step of 72° C. for 7 min. PCR reactions used a volume of 50 μl, with 1 unit of Taq DNA polymerase (Gibco BRL). Amplification products (5 μl) were separated by 2% agarose gel electrophoresis and visualized by ultraviolet light.

D. Immunoblot Analysis

Representative prostate tissue specimens were used for Western blot analysis. Tissues were homogenized in NP-40 lysis buffer containing 50 mmol/L Tris-HCl, pH 7.4, 1% Nonidet P-40 (Sigma, St. Louis. MO) and complete proteinase inhibitor cocktail (Roche, Ind., USA). Fifteen μg of protein extracts were mixed with SDS sample buffer and electrophoresed onto a 10% SDS-polyacrylamide gel under reducing conditions. The separated proteins were transferred onto nitrocellulose membranes (Amersham Pharmacia Biotech, Piscataway, N.J.). The membrane was incubated for 1 hour in blocking buffer (Tris-buffered saline with 0.1% Tween (TBS-T) and 5% nonfat dry milk). The AMACR antibody (Obtained from Dr. R Wanders, University of Amsterdam) was applied at 1:10,000 diluted in blocking buffer overnight at 4° C. After washing three times with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.) and autoradiography.

For β-tubulin western blots, the AMACR antibody probed membrane was stripped with Western Re-Probe buffer (Geno-tech, St. Louis, Mo.) and blocked in Tris-buffered saline with 0.1% Tween (TBS-T) with 5% nonfat dry milk and incubated with rabbit anti β-tubulin antibodies (Santa Cruz Biotechnologies, Santa Cruz, Calif.) at 1:500 for two hours. The western blot was then processed as described above.

E. Immunohistochemistry

Standard indirect immunohistochemistry (IHC) was performed to evaluate AMACR protein expression using a polyclonal anti-AMACR antibody. Protein expression was scored as negative (score=1), weak (score 2), moderate (3) and strong (4). In order to evaluate whether AMACR protein expression was associated with prostate cancer proliferation, a subset of samples were evaluated using the monoclonal mouse IgG Mib-1 antibody for Ki-67 (1:150 dilution, Coulter-Immunotech, Miami, Fla.). Microwave pretreatment (30 minutes at 100 C. in Tris EDTA Buffer) for antigen retrieval was performed using 3,3' diaminobenzidine tetrahydrocloride as a chromogen. Lymph node tissue with known high Ki-67 positivity was used as a control.

F. Tissue Microarray Construction, Digital Image Capture, and Analysis

Five TMAs were used for this study. Three contained tissue from the prostatectomy series and two contained hormone refractory prostate cancer from the Rapid Autopsy Program. The TMAs were assembled using the manual tissue arrayer (Beecher Instruments, Silver Spring, Md.) as previously described (Kononen et al., Nat. Med., 4:844 [1998]; Perrone et al., J. Natl. Cancer Inst., 92:937 [2000]). Tissue cores from the circled areas (as described above) were targeted for transfer to the recipient array blocks. Five replicate tissue cores were sampled from each of the selected tissue types. The 0.6 mm diameter TMA cores were each spaced at 0.8 mm from core-center to core-center. After construction, 4 μm sections were cut and H&E staining was performed on the initial slide to verify the histology.

TMA H&E images were acquired using the BLISS Imaging System (Bacus Labs, Lombard, Ill.). AMACR protein expression was evaluated in a blinded manner. All images were scored for AMACR protein expression intensity. In addition, all TMA samples were assigned a diagnosis (i.e., benign, atrophy, high-grade prostatic intraepithelial neoplasia, and prostate cancer). This is recommended because the targeted tissues may not be what were actually transferred. Therefore, verification was performed at each step. TMA slides were evaluated for proliferation index using a CAS200 Cell Analysis System (Bacus Labs). Selected areas were evaluated under the 40× objective. Measurements were recorded as the percentage of total nuclear area that was positively stained. All positive nuclear staining, regardless of the intensity, was measured. Sites for analysis were selected to minimize the presence of stromal and basal cells; only tumor epithelium was evaluated. Specimens were evaluated for Ki-67 expression as previously described (Perrone et al., J. Natl. Cancer Inst. 92:937 [2000]). Each measurement was based on approximately 50-100 epithelial nuclei. Due to the fixed size of TMA samples, repeat non-overlapping measurement was the maximum attainable.

G. Analysis of Prostate Needle Biopsies

In order to evaluate the usefulness of AMACR expression in diagnostic 18 gauge needle biopsies, 100 consecutive biopsies with prostate cancer or atypia that required further work-up were tested for AMACR expression. All cases were immunostained using two basal cell specific markers (34βE12 and p63) and AMACR. Cases were evaluated for cancer sensitivity and specificity. Twenty-six of these cases were seen in consultation with a pathologist and were considered diagnostically difficult, requiring expert review and additional characterization.

H. Results

Figure 11:
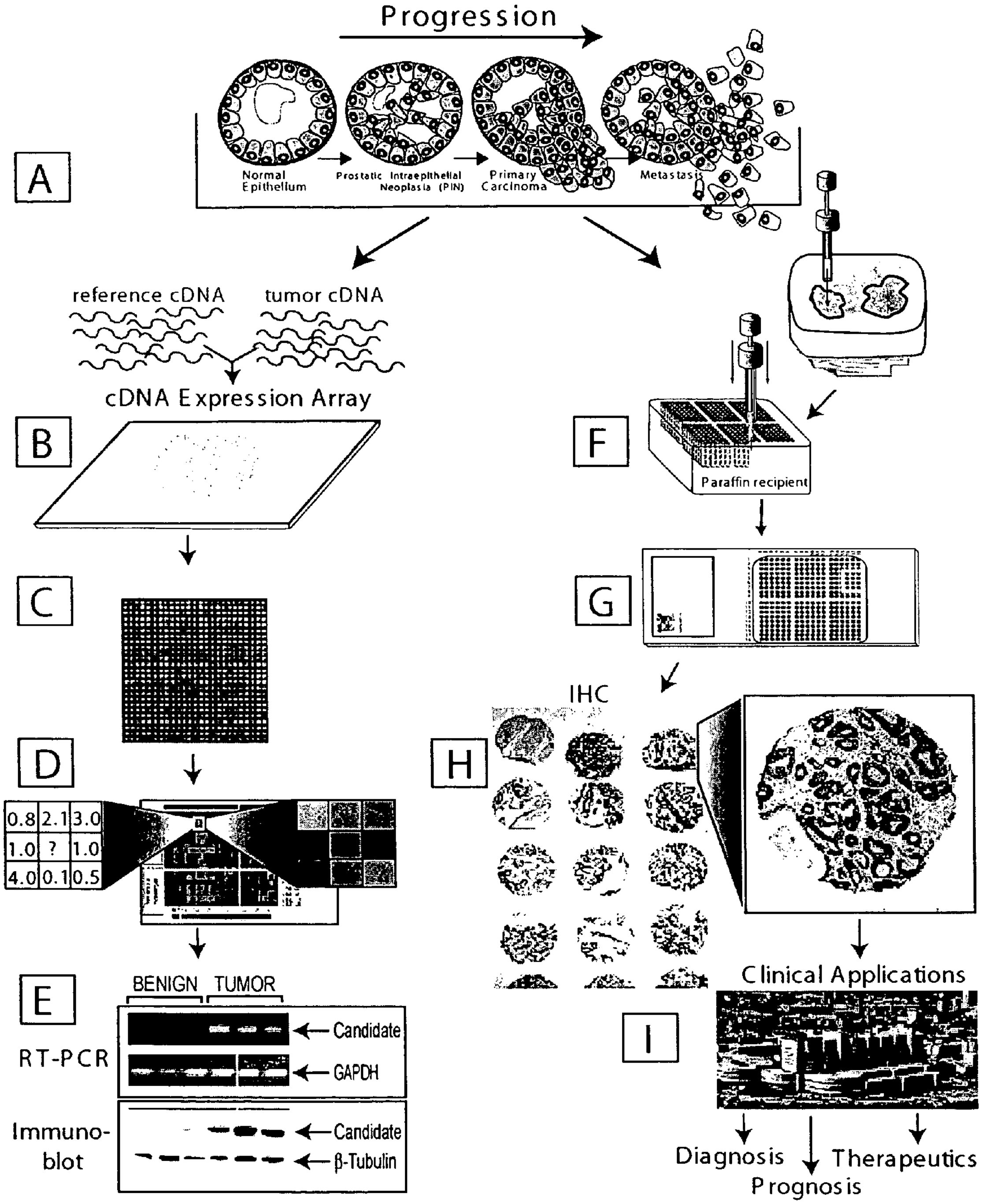
FIG. 11 an overview of the discovery and characterization of AMACR in prostate cancer utilized in some embodiments of the present invention.

FIG. 11 shows a schematic of the DNA and tissue microarray paradigm that lead to the discovery and characterization of AMACR in prostate cancer. A) Prostate cancer progression as adapted from Abate-Shen and Shen, (Genes Dev., 14:2410 [2000]). Distinct molecular changes occur at each stage of prostate cancer progression that can be studied using DNA microarray or "chip" technology. B) cDNA generated from tumor (prostate cancer) and reference (benign prostate tissue) samples is labeled with distinguishable fluorescent dyes and interrogated with a DNA microarray that can monitor thousands of genes in one experiment. C) After hybridization, the DNA microarray is analyzed using a scanner and fluorescence ratios determined for each gene (in this case prostate cancer/benign tissue). D) The ratios are deposited into a computer database and subsequently analyzed using various statistical algorithms. One exemplary method of surveying the data (Eisen et al., PNAS 95:14863 [1998]) assigns color intensity to the ratios of gene expression. In this case, shades of red represent genes that are up-regulated in prostate cancer (e.g., a ratio of 4.0) and shades of green represent genes that a down-regulated (e.g., ratio of 0.1). Genes that are unchanged between tumor and benign tissues are represented by a black color and missing elements by a gray color. E) Genes that are identified by DNA microarray can then be validated at the transcript level (e.g., Northern blot, RT-PCR) or at the protein level (e.g., immunoblot). F) Construction of prostate cancer tissue microarrays facilitates the study of hundreds of patients (rather than hundreds of genes). G) Each tissue microarray slide contains hundreds of clinically stratified prostate cancer specimens linked to clinical and pathology databases (not shown). H) Tissue microarray slides can then be analyzed using various molecular or biochemical methods (in this case immunohistochemistry). I) Both DNA and tissue microarray data have clinical applications. Examples include, but are not limited to: 1. using gene expression profiles to predict patient prognosis, 2. identification of clinical markers and 3. development of novel therapeutic targets.

Figure 12:
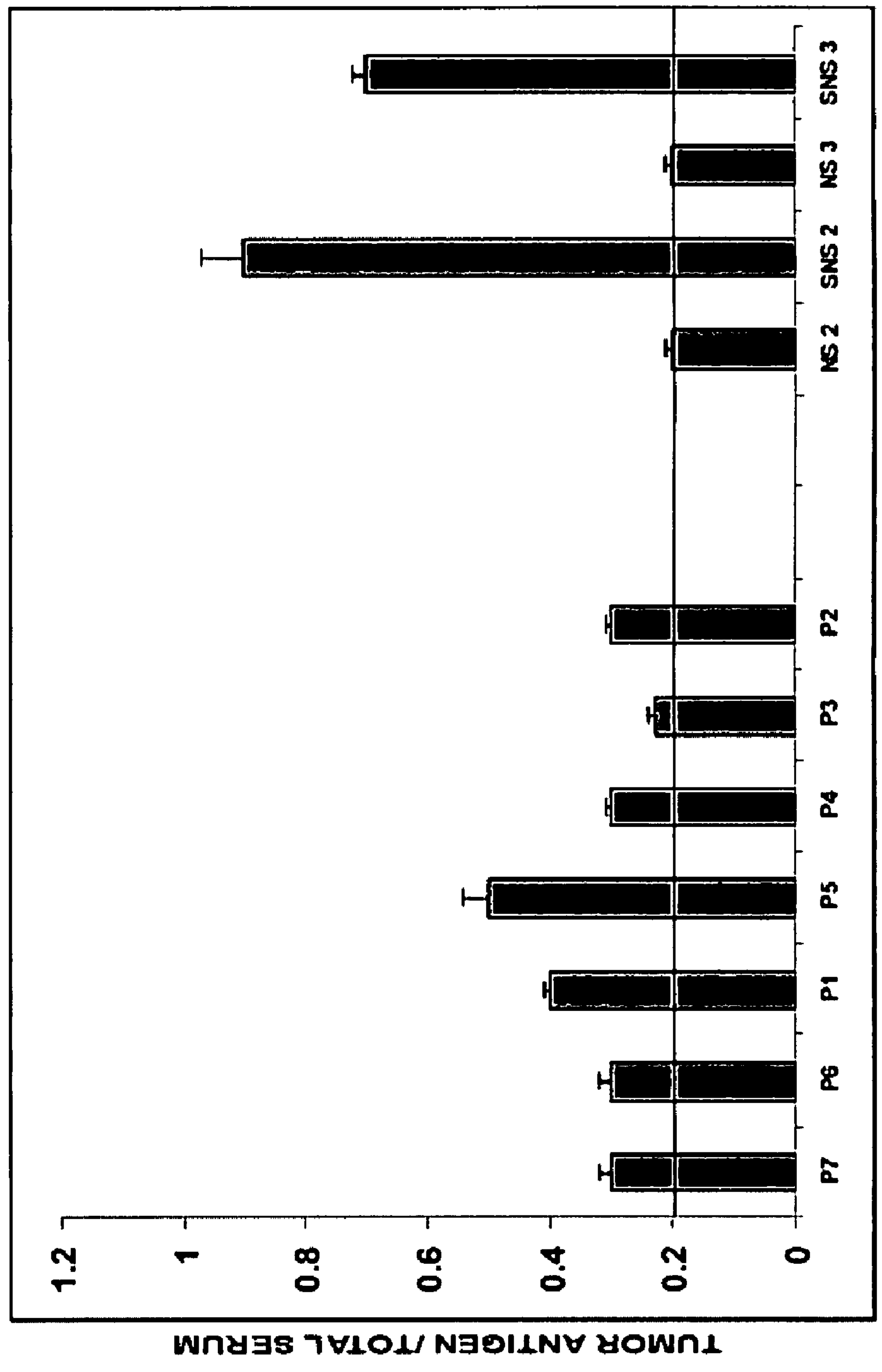
FIG. 12 describes a DNA microanalysis of AMACR expression in prostate cancer.

FIG. 12 summarizes AMACR transcript levels as determined by DNA microarray analysis over 57 prostate cancer specimens. Samples (Dhanasekaran et al., Nature 412: 822 [2001]) were grouped according to tissue type and averaged. The experimental sample was labeled in the Cy5 channel while the reference sample (pool of benign prostate tissue) was labeled in the Cy3 channel. The box-plot demonstrates the range of AMACR expression within each group. Tissues were grouped into the following classes benign (normal adjacent prostate tissue), benign prostatic hyperplasia (BPH), clinically localized prostate cancer, and metastatic prostate cancer. In relation to benign prostate tissues, localized prostate cancer and metastatic prostate cancer were 3.1 (Mann-Whitney test, $p<0.0001$) and 1.67 (Mann-Whitney test, $p<0.004$) fold up-regulated, respectively (represented as Cy5/Cy3 ratios).

DNA microarray results of AMACR mRNA levels were validated using an independent experimental methodology. AMACR-specific primers were generated and RT-PCR performed on the various RNA samples from 28 prostate tissue specimens and 6 prostate cell lines (FIG. 13A). GAPDH served as the loading control. Pool, refers to RNA from normal prostate tissues obtained from a commercial source. NAP, normal adjacent prostate tissue from a patient who has prostate cancer. 3+3, 3+4, 4+4, refers to the major and minor Gleason patterns of the clinically localized prostate cancer (PCA) examined. MET, metastatic prostate cancer. Various prostate cell lines are also examined. RT-PCR without enzyme served as a negative control. An RT-PCR product was clearly observed in the 20 localized prostate cancer samples but not in the benign samples examined. Metastatic prostate cancer and prostate cell lines displayed varying levels of AMACR transcript as compared to localized prostate cancer.

In order to gauge AMACR protein levels, immunoblot analysis was performed on selected prostate tissue extracts (FIG. 13B). β-tubulin served as a control for sample loading. Similar to AMACR transcript, over-expression of AMACR protein was observed in malignant prostate tissue relative to benign prostate tissue.

In order to validate protein expression of AMACR in situ, a separate cohort of prostate samples from those used in the cDNA expression array analysis was used. These prostate samples were taken from the University of Michigan Prostate SPORE Tissue Core and were assembled onto high-density tissue microarrays (schematically illustrated in FIG. 11F-H). Moderate to strong AMACR protein expression was seen in clinically localized prostate cancer samples with predominately cytoplasmic localization. A large contrast in levels of AMACR in malignant epithelia relative to adjacent benign epithelia was seen. Prostatic intraepithelial neoplasia (PIN) and some atrophic lesions, which are thought to be potentially pre-cancerous lesions (Putzi et al., Urology 56:828 [2000]; Shah et al., Am. J. Pathol., 158:1767 [2001]), demonstrated cytoplasmic staining of AMACR. High-grade prostate cancer also demonstrated strong cytoplasmic staining. However, no association was identified with AMACR staining intensity and Gleason (tumor) score. Many of the metastatic prostate cancer samples demonstrated only weak AMACR expression. The metastatic samples showed uniform PSA immunostaining, confirming the immunogenicity of these autopsy samples.

Figure 14:
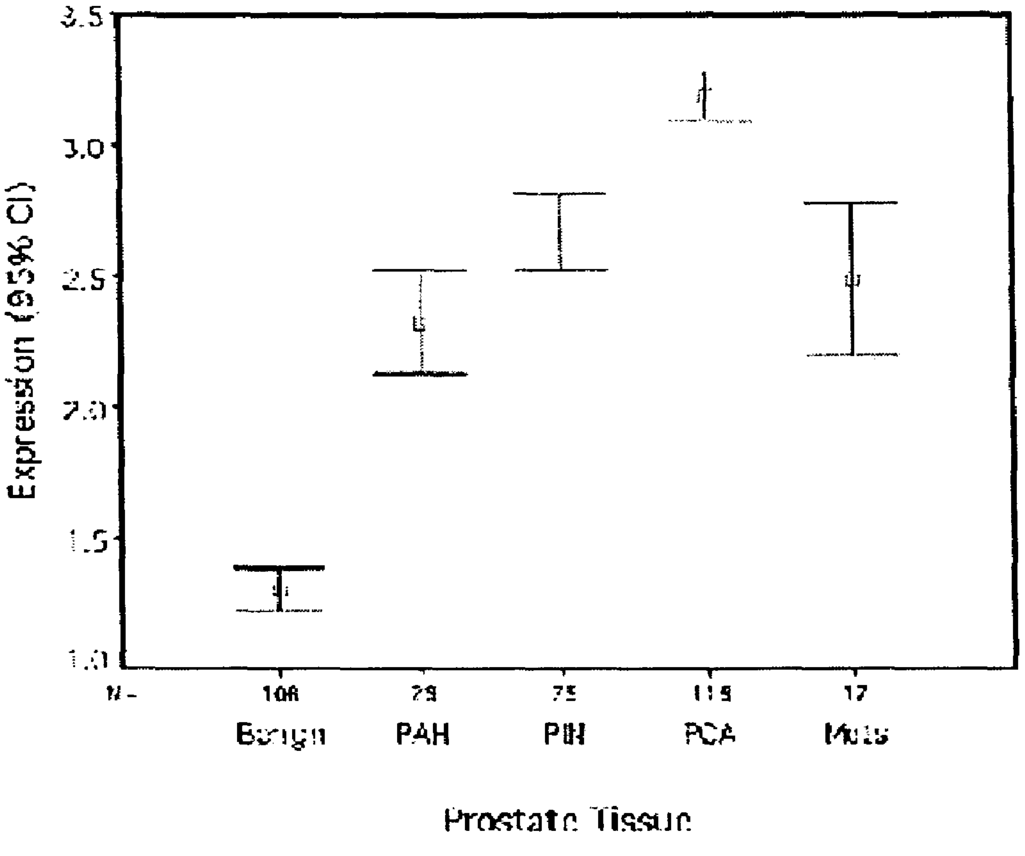
FIG. 14 describes an analysis of AMACR protein expression using prostate cancer tissue microarrays.

In order to assess AMACR protein expression over hundreds of prostate specimens, the tissue microarray data was quantitated. Benign prostate, atrophic prostate, PIN, localized prostate cancer, and metastatic prostate cancer demonstrated mean AMACR protein staining intensity of 1.0 (SE 0), 2.0 (SE 0.1), 2.5 (SE 0.1), 3.0 (SE 0), and 2.5 (SE 0.1), respectively (ANOVA p-value<0.0001). This data is graphically summarized using error bars representing the 95% confidence interval for each tissue category (FIG. 14).

The correlation of AMACR levels with tumor proliferation was next investigated using Ki-67 (Pyrrone et al., supra). There was no significant association between AMACR expression and Ki-67 expression with a correlation coefficient of 0.13 (p-value=0.22). In addition, no significant associations were identified between AMACR protein expression and pathology parameters such as radical prostatectomy, Gleason score, tumor stage, tumor size (cm), or surgical margin status. AMACR protein levels were next evaluated for association with PSA recurrence following surgery in 120 prostatectomy cases with a median follow-up time of 3 years. No statistically significant association was identified. AMACR demonstrated uniform moderate to strong expression in clinically localized prostate cancer with a high sensitivity for tumor and an equally high specificity. In addition, a preliminary survey of normal tissues including ovary, liver, lymph nodes, spleen, testis, stomach, thyroid, colon, pancreas, cerebrum, and striated muscle revealed significant AMACR protein expression in only normal liver.

The large difference in AMACR protein levels between normal secretory epithelial cells and malignant cells provides a clinical use for testing AMACR expression in prostate needle biopsy specimens. In diagnostically challenging cases, pathologists often employ the basal cell markers 34βE12 (O'Malley et al., Virchows Arch A Patho. Anat. Histopathol., 417:191 [1990]; Wojno et al., Am. J. Surg. Pathol., 19:251 [1995]; Googe et al., Am. J. Clin. Pathol., 107:219 [1997] or p63 (Parson et al., Urology 58:619 [2001]; Signoretti et al., Am. J. Pathol., 157:1769 [2000]), which stain the basal cell layer of benign glands. This second basal cell layer is absent in malignant glands. In many equivocal biopsy specimens, the surgical pathologist must rely on absence of staining to make the final diagnosis of prostate cancer. The clinical utility of AMACR immunostaining on 94 prostate needle biopsies was evaluated. The results are shown in Table 2. The sensitivity and specificity were calculated as 97% and 100%, respectively. These results included 26 cases where the final diagnosis required the use of a basal cell specific immunohistochemical marker (i.e., 34βE12 or p63).

This example demonstrated that AMACR is associated with PCA and that AMACR expression in prostate biopsies is useful for the diagnosis of cancer in inconclusive biopsy samples.

TABLE 2

Clinical utility of Assessing AMACR Protein in Prostate Needle Biopsies (n = 94)

| Sensitivity (TP/ (TP + FN)) | Specificity (TN/ (TN + FP)) | Positive Predictive Value (TP/ (TP + FP)) | Negative Predictive Value (TN/ (TN + FN)) |
|---|---|---|---|
| 97% ((68/(2 + 68)) | 100% ((24/(24 + 0)) | 100% ((68/(68 + 0)) | 92% ((24/24 + 2)) |

EXAMPLE 6

Hormone Regulation of AMACR

This example describes studies that indicate that AMACR expression is hormone independent.

A. Sample Collection, cDNA Array and TMA Construction and Evaluation

Clinical samples were taken from the radical prostatectomy series and from the Rapid Autopsy Program at the University of Michigan. Both are part of the University of Michigan Prostate Cancer Specialized Program of Research Excellence (S.P.O.R.E.). Primary PCA of metastatic cases as well as lymph node metastases were contributed in collaboration from the University of Ulm, Germany. Detailed clinical and expression analysis as well as TMA data was acquired and maintained on a secure relational database according to the Institutional Review Board protocol of both institutions. Tissue procurement for expression analysis on the RNA level is described in the above examples. For the development of TMA, samples were embedded in paraffin. The study pathologist reviewed slides of all cases and circled areas of interest. These slides were used as a template for construction of the six TMAs used in this study. All TMAs were assembled using a manual tissue arrayer (Beecher Instruments, Silver Spring, Md.). At least three tissue cores were sampled from each donor block. Histologic diagnosis of the tissue cores was verified by standard haematoxylin and eosin (H&E) staining of the initial TMA slide. Standard biotin-avidin complex immunohistochemistry (IHC) was performed using a polyclonal anti-AMACR antibody (Ronald Wanders, University of Amsterdam). Digital images were acquired using the BLISS Imaging System (Bacus Lab, Lombard, Ill.). Staining intensity was scored as negative (score=1), weak (score 2), moderate (3) and strong (4). For exploration of the treatment effect by the means of hormonal withdrawal before radical prostatectomy, standard slides were used for regular H&E staining and consecutive sections for detection of AMACR expression. In order to test AMACR expression in poorly differentiated colon cancers, cases were used from a cohort of well-described colon tumors. In addition to well-differentiated colon cancers, a recently described subset of poorly differentiated colon carcinomas with a distinctive histopathological appearance, termed large cell minimally differentiated carcinomas, was used. These poorly differentiated colon carcinomas had a high frequency of the microsatellite instability phenotype.

B. Cell Culture and Immunoblot Analysis

Prostate cell lines (RWPE-1, LNCaP, PC3 and DU145) were obtained from the American Tissue Culture Collection. Cells were maintained in RPMI-1640 with 8% decomplemented fetal bovine serum, 0.1% glutamine and 0.1% penicillin and streptomycin (BioWhittaker, Walkersville, Md.). Cells were grown to 75% confluence and then treated for 24 and 48 with the antiandrogen bicalutamide (CASODEX, Zeneca Pharmaceuticals, Plankstadt, Germany) at a final concentration of 20 μM or with methyltrienolone (synthetic androgen (R1881); NEN, Life Science Products, Boston, Mass.) at a final concentration of 1 nM. Cells were harvested and lysed in NP-40 lysis buffer containing 50 mmol/L Tris-HCl, pH 7.4, 1% Nonidet P-40 (Sigma, St. Louis, Mo.) and complete proteinase inhibitor cocktail (Roche, Ind., USA). 15 μg of protein extracts were mixed with SDS sample buffer and electrophoresed onto a 10% SDS-polyacrylamide gel under reducing conditions. After transferring, the membranes (Amersham Pharmacia Biotech, Piscataway, N.J.) were incubated for 1 hour in blocking buffer (Tris-buffered saline with 0.1% Tween and 5% nonfat dry milk). The AMACR antibody was applied at 1:10.000 diluted blocking buffer overnight at 4° C. After three washes with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.). For β-tubulin blots, membranes were stripped with Western Re-Probe buffer (Geno-tech, St. Louis, Mo.) and blocked in Tris-buffered saline with 0.1% Tween with 5% nonfat dry milk and incubated with rabbit anti β-tubulin antibodies (Santa Cruz Biotechnologies, Santa Cruz, Calif.) at 1:500 for two hours. For PSA expression the membranes were reprobed in the described manner with PSA antibody (rabbit polyclonal; DAKO Corporation, Carpinteria, Calif.) at 1: 1000 dilution and further processed.

C. Statistical Analysis

Primary analysis of the cDNA expression data was done with the Genepix software. Cluster analysis with the program Cluster and generation of figures with TreeView was performed as described above. AMACR protein expression was statistically evaluated using the mean score result for each prostate tissue type (i.e., benign prostate, naive localized or advanced prostate cancer, hormone treated and hormone refractory prostate cancer). To test for significant differences in AMACR protein expression between all tissue types, a one-way ANOVA test was performed. To determine differences between all pairs, a post-hoc analysis using the Scheffé method was applied as described above. For comparison of naive primaries to their corresponding lymph node metastases with respect to AMACR protein expression, a non parametric analysis (Mann Whitney test) was performed. To compare AMACR expression intensity to the scored hormonal effect of the pretreated localized prostate cancer cases the Mantel-Haenszel Chi-Square test was applied. AMACR expression scores are presented in a graphical format using error-bars with 95% confidence intervals. P-values<0.05 were considered statistically significant.

D. Results

Figure 15:
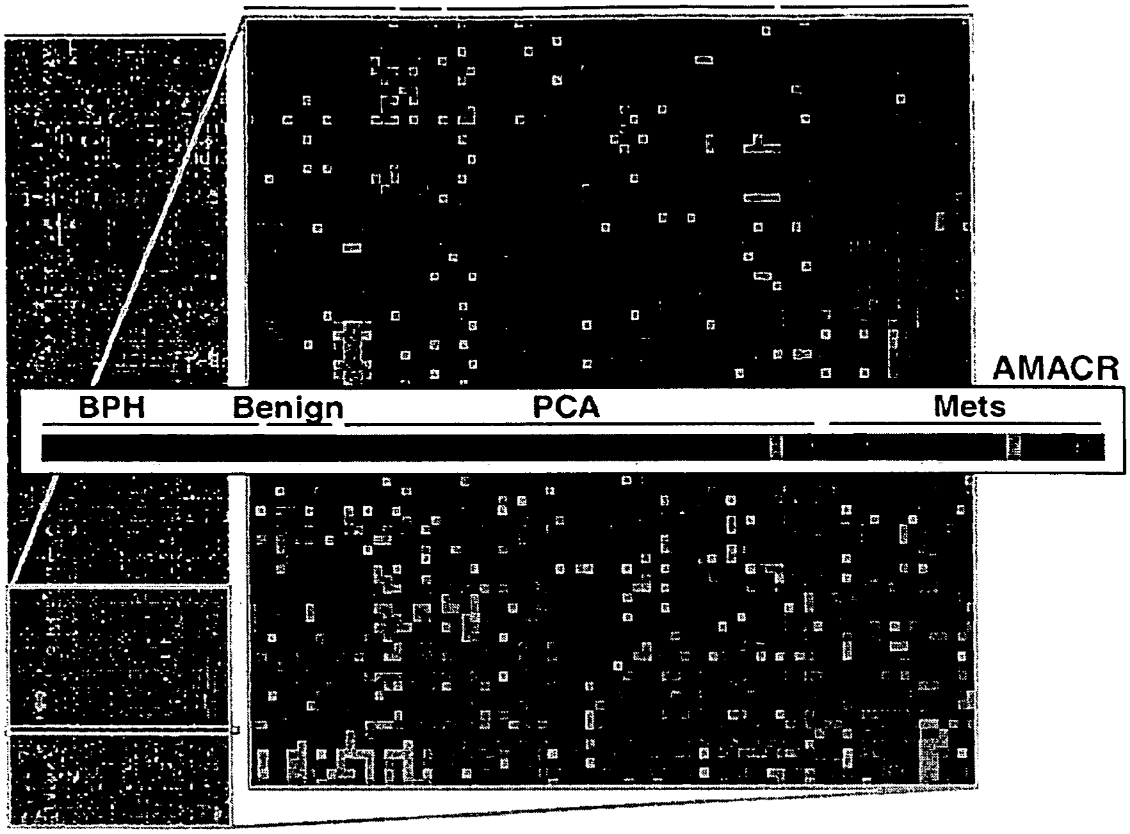
FIG. 15 shows relative gene expression of AMACR in several samples.

Hierarchical clustering of 76 prostate tissues including benign, BPH, localized PCA and metastatic PCA and filtering for only those genes with a 1.5 fold expression difference or greater, clustered the samples into histologically distinct groups as described above. As demonstrated by a TreeView presentation of this data (FIG. 15), AMACR was one of several genes that demonstrated over expression at the cDNA level of PCA samples with respect to benign pooled prostate tissue. The highest level of over expression by cDNA analysis was in the clinically localized PCA cases.

Figure 16:
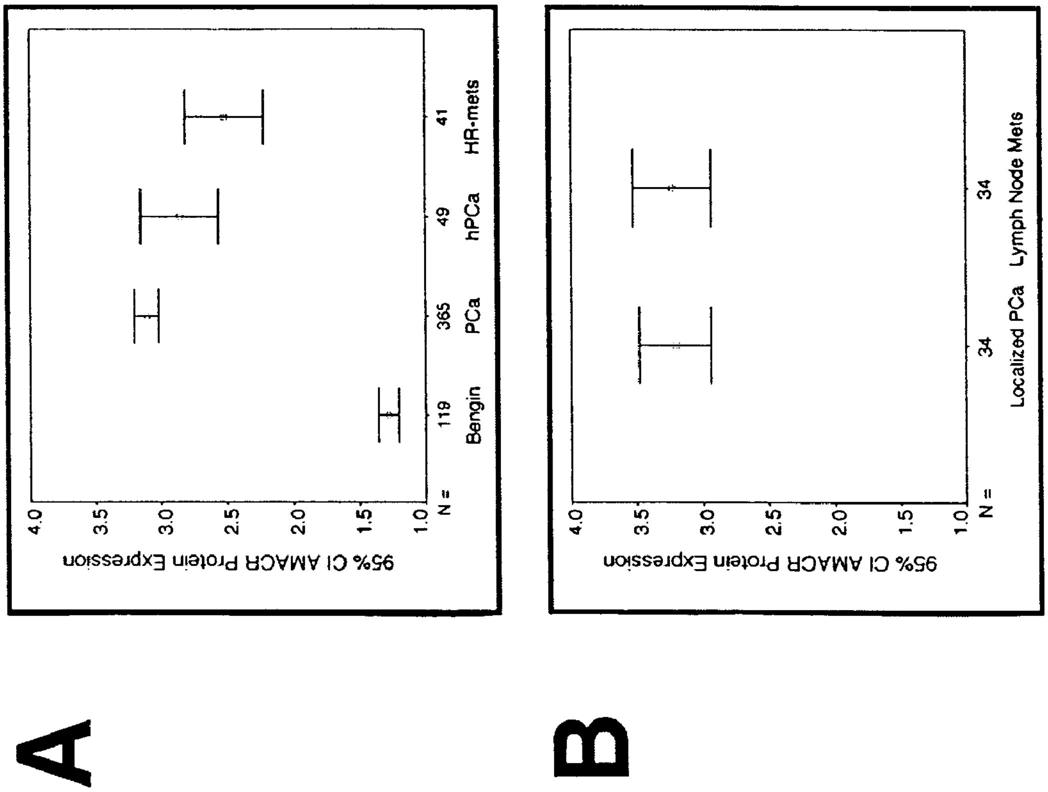
FIG. 16 shows AMACR protein expression PCA.

In order to further investigate the role of AMACR protein expression in samples with variable differentiation and exposure to anti-androgen treatment, several TMAs with a wide range of PCA were constructed: a total of 119 benign prostate samples, 365 primary hormone naive PCA samples, 37 naive prostate cancer lymph node metastases, and 41 hormone refractory metastatic PCA samples were evaluated. An additional 49 hormone treated primary prostate cancers (including 22 on standard slides) were examined for histologic changes associated with anti-androgen treatment and AMACR protein expression. The mean AMACR protein expression levels for each tissue category is presented in FIG. 16. Benign prostate, naive primary prostate cancer, hormone treated primary cancer, and hormone refractory metastatic tissue had a mean staining intensity of 1.28 (Standard Error SE 0.038, 95% Confidence Intervals CI 1.20-1.35), 3.11(SE 0.046, CI 3.02-3.20), 2.86 (SE 0.15, CI 2.56-3.15) and 2.52 (SE 0.15, CI 2.22-2.28), respectively). One-way ANOVA analysis revealed a p-value of <0.0001. To specifically examine the difference between different tissue types, a post-hoc pair-wise comparison was performed. Clinically localized PCA demonstrated a significantly stronger AMACR protein expression as compared to benign prostate tissue (post-hoc analysis using Scheffé method, mean difference=1.83, p<0.0001, CI 1.53-2.13). A significant decrease in AMACR protein expression was observed in the metastatic hormone refractory PCA samples with respect to clinically localized PCA (0.59, p=0.002, CI 0.15-1.03). Hormone treated primaries had a mean AMACR expression of 2.86, which was between the expression levels of naive primaries (3.11) and hormone refractory cases (2.52) (post-hoc analysis using Scheffé method, p=0.51, CI −0.66-0.16 and p=0.56, CI −0.23-0.91). There was no significant difference in AMACR expression in the 37 naive primary prostate samples and lymph node metastases derived from the same patient (Mann Whitney test, p=0.8). In other words, matched primaries and lymph node metastases showed similar AMACR expression pattern.

Figure 17:
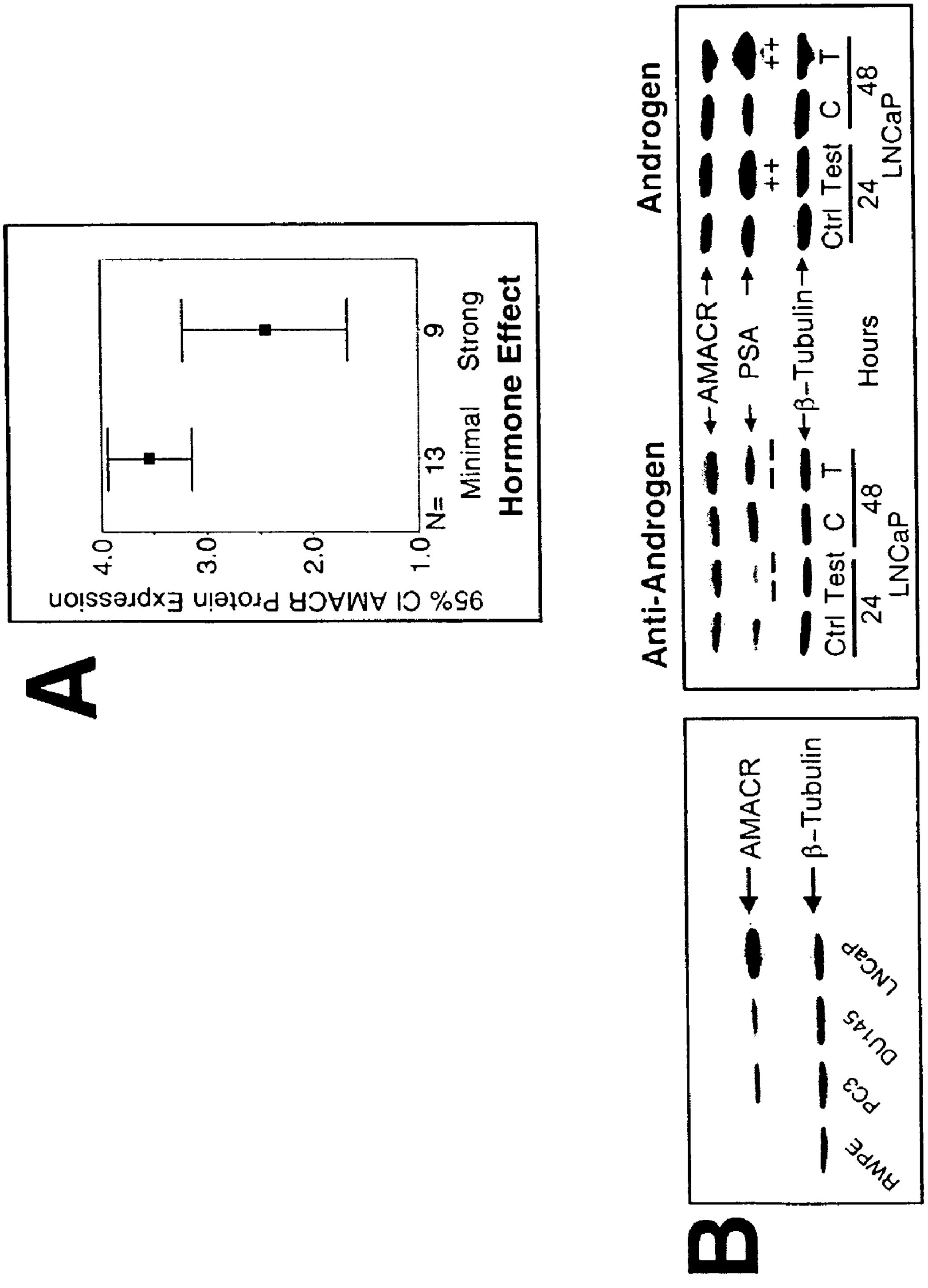
FIG. 17 shows the hormonal effect on AMACR expression.

A subset of 22 PCA cases in which the patients received variable amount and types of anti-androgen treatment prior to surgery was examined. These cases were evaluated blindly with respect to treatment protocol for histological evidence of hormone treatment (H&E slide) and AMACR protein expression. The hormonal effect visible on the H&E slides was classified from 1 to 4 with 1 representing "no effect" and 4 showing a "very strong effect". 13 cases demonstrated either no or moderate hormonal effect, and 9 cases had a very strong hormonal effect. Statistical analysis revealed a significant difference between these two groups with respect to AMACR expression intensity (FIG. 17, Mantel-Haenszel Chi-Square, p=0.009). FIG. 17 presents an example of a PCA case treated prior to surgery with anti-androgens that has a strong hormonal effect appreciated on H&E and decreased AMACR protein expression (FIG. 17A). In this dataset there was neither a correlation between treatment duration nor treatment type (monotherapy or complete hormonal withdrawal for hormone deprivation) and AMACR expression.

For further exploration of the hormonal effect on AMACR expression, primary cell culture experiments and Western blot analysis were performed. As demonstrated in FIG. 17 Panel B, LNCaP cells, derived from a metastatic lesion but considered hormone responsive, showed a higher baseline AMACR expression as compared to PC3 and DU-145 cells, which are both hormone independent cell lines derived from metastatic lesions. A benign cell line, RWPE-1 (Bello et al., Carcinogenesis 18:1215 [1997]), showed near absent AMACR expression, which is consistent with the in situ protein expression data. To simulate an anti-androgen treatment, the hormone responsive cell line LNCaP was treated with bicalutamide in a final concentration of 20 μM for a time period of 24 and 48 hours. AMACR expression in cell lysates of LNCaP cells did not change at either time point when exposed to anti-androgen therapy. Under the same conditions, PSA, a gene known to be regulated by the androgen receptor, showed decreased protein expression. In addition, when LNCaP cells were exposed to a synthetic androgen R1881, no increase in AMACR expression was observed (FIG. 17, Panel B). Therefore, these cell culture experiments provide evidence that AMACR expression is not regulated by the androgen pathway.

The present invention is not limited to a particular mechanism. Indeed, an understanding of the mechanism is not necessary to practice the present invention. Nonetheless, it is contemplated that another explanation for these observations was that AMACR over expression occurred in PCA, but as these tumors became poorly differentiated, as in the hormone refractory PCA, AMACR expression was down regulated either directly or indirectly due to the process of de-differentiation. To elucidate this potential correlation colon cancer samples were examined for AMACR expression (See Example 7). AMACR protein expression is also observed in some other tumor types, with the highest overall expression in colorectal cancers. Colorectal cancers are not known to be regulated by androgens and were therefore used as a control to test this hypothesis. Four well differentiated and seven anaplastic colon cancer samples were chosen. The poorly differentiated tumors have distinct molecular alterations distinguishing them from the common well to moderately differentiated colorectal tumors (Hinoi et al., Am. J. Pathol. 159:2239 [2001]). Strong AMACR protein expression in a moderately differentiated colon cancer was observed. This tumor still forms well defined glandular structures. The surrounding benign colonic tissue does not express AMACR. The anaplastic colon cancers demonstrated weak AMACR protein expression. Primarily data revealed positive AMACR expression in 4/4 well differentiated cases but only 4/7 anaplastic colonic cancers. Three of the anaplastic colon cancers had weak to moderate expression. Metastatic hormone refractory PCA demonstrated weak AMACR protein expression in tissue microarrays.

EXAMPLE 7

AMACR Expression in a Variety of Cancers

A. Analysis of Online EST and SAGE Database

The National Cancer Institute Cancer Genome Anatomy Project (CGAP) has several gene expression databases available online for comparing gene expression across multiple samples (See the Internet Web site of the National Cancer Institute). Both EST and SAGE databases offer Virtual Northern blots, which allow users to visualize and compare the expression level of a particular gene among multiple samples. The SAGE database includes over 5 million tags from 112 libraries of multiple benign and malignant tissues.

B. Selection of Study Cases

A total of 96 cases of cancers from different sites were selected for construction of a multi-tumor tissue microarray. The tissue microarray was constructed to perform a wide survey of multiple common tumor types. A minimum of three tissue cores (0.6 mm in diameter) was taken for each case. Tumors surveyed included colorectal adenocarcinoma (n=15 cases), renal cell carcinoma (6), prostatic adenocarcinoma (6), urothelial carcinoma (4), cervical squamous cell carcinoma (6), lung non-small cell carcinoma (4), lymphoma (15), melanoma (9) and several other cancer types. Normal adjacent tissue was taken when available. The prostate tissue microarray was constructed from selected patients who underwent radical prostatectomies as monotherapy for clinically localized prostate cancer. This tissue microarray contained a spectrum of prostatic tissue including prostatic atrophy, high-grade prostatic intraepithelial neoplasia (PIN), and clinically localized prostate cancer. In addition, standard slides were used to confirm results for colon cancer. Twenty-four cases of colorectal adenocarcinoma (16 well to moderately differentiated carcinoma and 8 large cell minimally differentiated carcinoma) and 8 endoscopically derived colorectal adenomas were selected for immunostaining for AMACR. For breast carcinoma, a TMA of 52 cases of invasive ductal carcinoma was used. Specimens were collected and analyzed in accordance with the Institutional Review Board guidelines.

C. Immunohistochemistry

Standard avidin-biotin complex immunohistochemistry was used. Pre-treatment was performed by steaming the slides for 10 minutes in sodium citrate buffer in a microwave oven. The slides were then incubated sequentially with primary antibody (1:2000 dilution, polyclonal rabbit anti-AMACR antibody), biotinylated secondary antibody, avidin-biotin complex and chromogenic substrate 3,3'-diaminobenzidine. Slides were evaluated for adequacy using a standard bright field microscope. Digital images were then acquired using the BLISS Imaging System (Bacus Lab, Lombard, Ill.) and evaluated by two pathologists. Protein expression was scored as negative, weak stain (faint cytoplasmic stain or granular apical staining), moderate (diffuse granular cytoplasmic stain) and strong (diffuse intense cytoplasmic stain). Only moderate and strong staining was considered as positive staining.

D. Laser Capture Microdissection

Sections of 2 radical prostatectomy samples were frozen in OCT in accordance with an Institutional Review Board protocol. Frozen sections (5 μm thick) were fixed in 70% alcohol for 10 minutes and then stained in hemotoxylin and eosin. Prostate cancer and benign prostate glands were dissected on a μCUT laser capture microdissector (MMI GmbH, Heidelberg, Germany). Approximately 6000 cells were harvested. Total RNA was isolated using Qiagen micro-isolation kit (Qiagen, San Diego, Calif.). Reverse transcription was performed using both oligo dT and random hexamer primers. Primers used to amplify specific gene products were: AMACR sense, 5'-CGTATGCCCCGCTGAATCTCGTG-3' (SEQ ID NO:100); AMACR antisense, 5'-TGGCCAATCATCCGTGCTCATCTG-3' (SEQ ID NO:105); GAPDH sense, 5'AGCCTTCTCCATGGTGGTGAAGAC-3' (SEQ ID NO:106); and GAPDH antisense, 5'-AGCCTTCTCCATGGTGGTGAAGAC-3' (SEQ ID NO:107). PCR conditions for AMACR and GAPDH were: heat denaturation at 94° C. for 5 mm, cycles of 940C for 1 mm 60° C. for 1 mm, and 72° C. for 1 mm (32 cycles for GAPDH, 40 cycles for AMACR), and a final extension step at 72° C. for 5 min. PCR products were then separated on 2% agarose gel and visualized by UV illumination.

E. Results

Using the Virtual Northern tool from the online CGAP program, AMACR expression was surveyed in two databases, EST and SAGE libraries. AMACR was found to be expressed in a wide range of tissues, including central and peripheral nervous system, colon, kidney, breast, pancreas, prostate and blood. Compared to their normal counterparts, a number of cancers have elevated AMACR expression, including tumors arising in bone marrow, breast, colon, genitourinary system, lung, lymph node, nervous system, pancreas, prostate, soft tissue and uterus.

Figure 18:
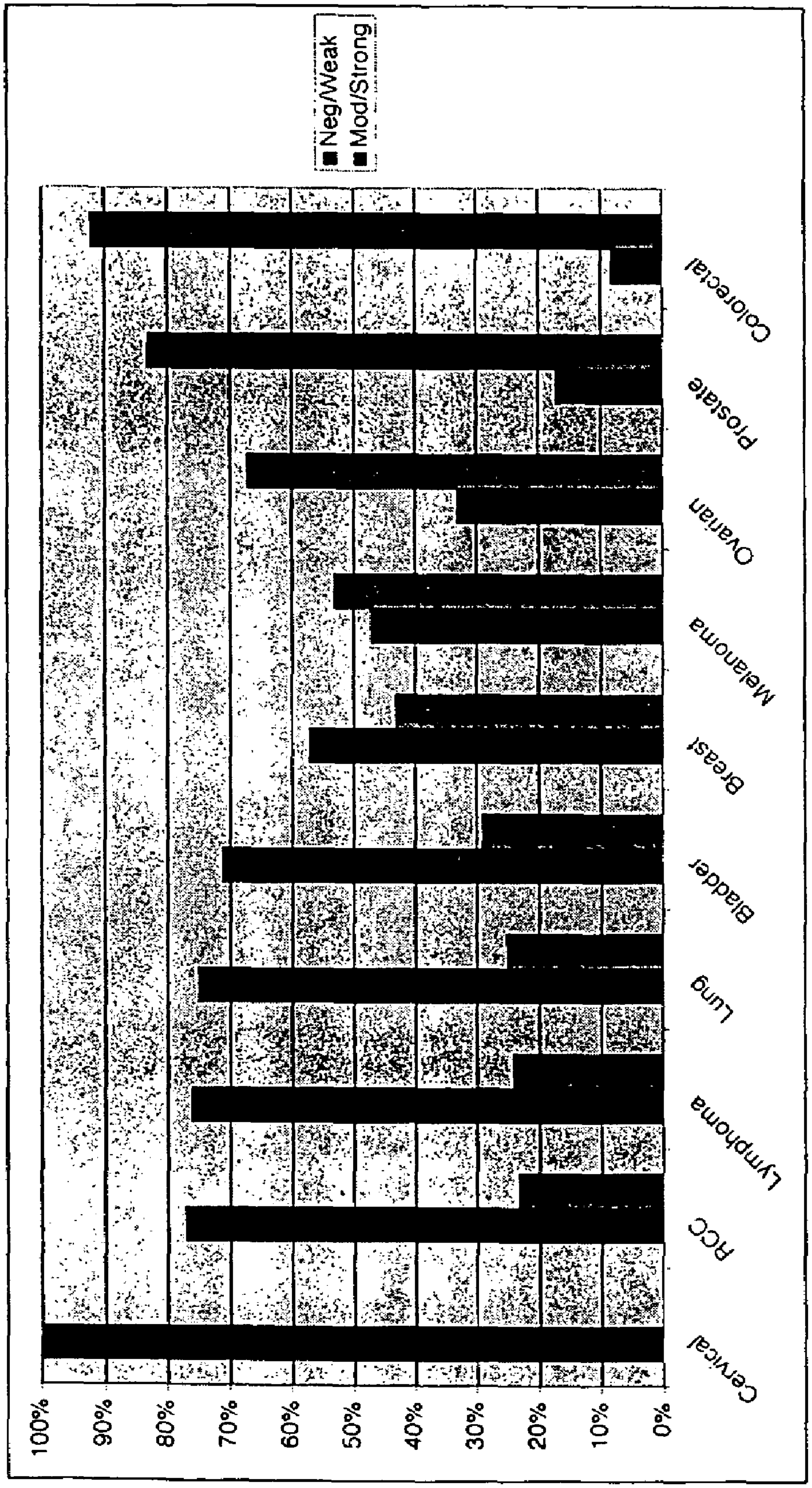
FIG. 18 shows AMACR over-expression in multiple tumors. AMACR protein expression was evaluated by immunohistochemistry on a multi-tumor and a breast cancer tissue microarray. Percentage of cases with positive staining (moderate and strong staining intensity) is summarized on the Y-axis. The left bar represents negative or weak staining and the right bar represents moderate or strong staining.

To confirm the gene expression data, AMACR immunohistochemistry was performed on a multi-tumor tissue array that included some of the most common cancers from multiple sites. AMACR protein level was increased in many cancers, including colorectal, prostate, ovarian, lung cancers, lymphoma and melanoma (FIG. 18). In particular, AMACR over-expression was observed in 92% and 83% of colorectal and prostate cancer, respectively. Using a breast cancer tissue microarray, it was found that AMACR over-expression was present in 44% of invasive ductal carcinomas. AMACR over expression was not observed in female cervical squamous cell carcinoma (6 cases).

Figure 19:
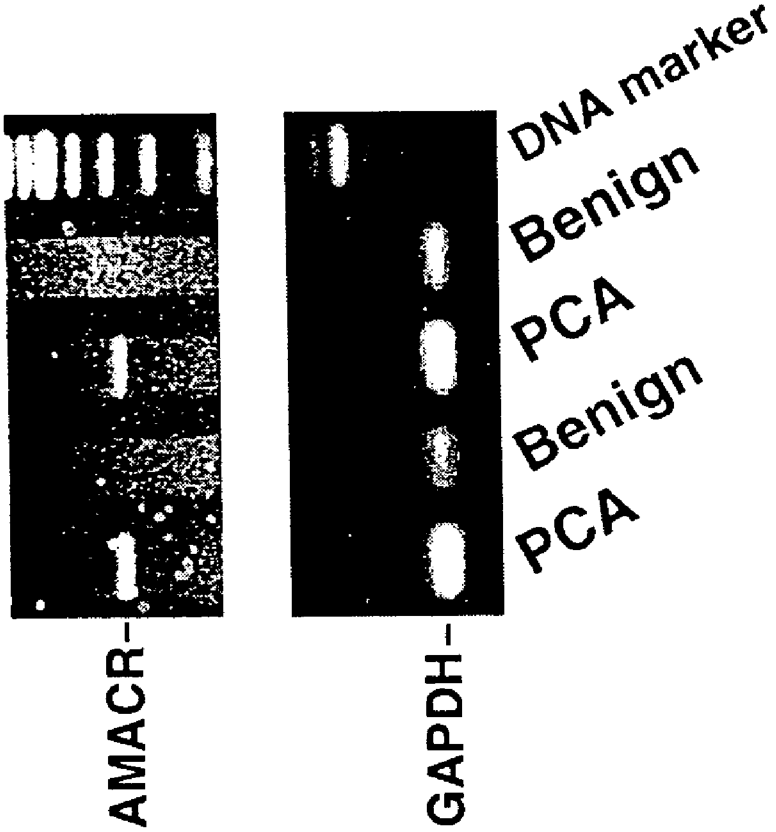
FIG. 19 shows the results of laser capture microdissection (LCM) and RT-PCR amplification of AMACR in prostate cancer. LCM was used to isolate pure prostate cancer and benign glands and AMACR gene expression was characterized by RT-PCR in 2 radical prostatectomies. A constitutively expressed gene, GAPDH, was used as quantitative control of input mRNA. AMACR expression is barely detectable in benign glands, and is elevated in prostate cancer.

To further characterize AMACR expression in a spectrum of proliferative prostate lesions, a prostate tissue microarray, which included prostate cancer, high grade PIN and atrophic glands, was utilized. Positive AMACR staining (moderate and strong staining) was observed in 83% and 64% of clinically localized prostate cancer and high-grade PIN, respectively. Focal AMACR expression was observed in 36% of the atrophic lesions and in rare morphologically benign glands. To confirm that AMACR protein over-expression was the result of increased gene transcription, laser capture microdissection was used to isolate cancerous and benign prostatic glands. RT-PCR was performed to assess the AMACR mRNA expression. Benign glands had very low baseline expression (FIG. 19). In contrast, prostate cancer had much higher mRNA level, confirming that increased AMACR gene transcription leads to elevated protein over expression in prostate cancer.

AMACR expression was studied in 24 colorectal adenocarcinomas, including 16 well to moderately differentiated, and 8 poorly differentiated large cell adenocarcinomas. Overall, 83% (20/24) demonstrated positive AMACR protein expression. All (16/16, 100%) cases of well to moderately differentiated carcinoma had positive staining, compared to 64% (5/8) of poorly differentiated carcinoma. AMACR expression was examined in 8 colorectal adenoma biopsies obtained by colonoscopy. Moderate staining was present in 6 (75%) cases. Compared with well-differentiated adenocarcinomas, adenomas usually showed more focal (10-60% of cells) and less intense staining.

EXAMPLE 8

Characterization of EZH2 Expression in Prostate Cancer

A. SAM Analysis

SAM analysis was performed by comparing gene expression profiles of 7 metastatic prostate cancer samples against 10 clinically localized prostate cancer samples. Data was normalized per array by multiplication by a factor to adjust the aggregate ratio of medians to one, then log base 2 transformed and median centered. This normalized data was divided into two groups for comparison using a two-class, unpaired t-test. Critical values for the analysis include: Iterations=500, Random Number Seed 1234567, a fold change cutoff of 1.5 and a delta cutoff of 0.985, resulting in a final largest median False Discovery Rate of 0.898% for the 535 genes selected as significant (55 relatively up and 480 relatively down regulated between MET and PCA). These 535 genes were analyzed using Cluster (Eisen et al., PNAS 95:14863 [1998]) implementing average linkage hierarchical clustering of genes. The output was visualized by Treeview (Eisen et al., [1998], supra).

B. RT-PCR

Reverse transcription and PCR amplification were performed with 1 μg total RNA isolated from the indicated prostate tissues and cell lines. Human EZH2 forward (5'-GCCAGACTGGGAAGAAATCTG-3' (SEQ ID NO:108)), reverse (5'-TGTGCTGGAAAATCCAAGTCA-3' (SEQ ID NO:109)) and GAPDH sense (5'-CGGAGTCAACGGATTTGGTCGTAT-3' (SEQ ID NO:110)), antisense 5'-AGCCTTCTCCATGGTGGTGAAGAC-3' (SEQ ID NO:111)) primers were used. The amplified DNA was resolved on agarose gels and visualized with ethidium bromide.

C. Immunoblot Analysis

Prostate tissue extracts were separated by SDS-PAGE and blotted onto nitrocellulose membranes. Anti-EZH2 (Sewalt et al., Mol. Cell. Biol. 18:3586 [1998]), anti-EED (Sewalt et al., supra), and polyclonal anti-tubulin (Santa Cruz biotechnology) antibodies were used at 1:1000 dilution for immunoblot analysis. The primary antibodies were detected using horseradish peroxidase-conjugated secondary antibodies and visualized by enhanced chemiluminescence as described by the manufacturer (Amersham-Pharmacia).

D. Tissue Microarray Analysis

Clinically stratified prostate cancer tissue microarrays used in this study have been described previously (See above examples). Tissues utilized were from the radical prostatectomy series at the University of Michigan and from the Rapid Autopsy Program, which are both part of University of Michigan Prostate Cancer Specialized Program of Research Excellence (S.P.O.R.E.) Tissue Core. Institutional Review Board approval was obtained to procure and analyze the tissues used in this study.

EZH-2 protein expression was evaluated on a wide range of prostate tissue to determine the intensity and extent in situ. Immunohistochemistry was performed on three tissue microarrays (TMA) containing samples of benign prostate, prostatic atrophy, high-grade prostatic intraepithelial neoplasia (PIN), clinically localized prostate cancer (PCA), and metastatic hormone refractory prostate cancer (HR-METSs). Standard biotin-avidin complex immunohistochemistry (IHC) was performed to evaluate EZH2 protein expression using a polyclonal anti-EZH2 antibody. Protein expression was scored as negative (score=1), weak (score 2), moderate (3) and strong (4).

Approximately 700 TMA samples (0.6 mm diameter) were evaluated for this study (3-4 tissue cores per case). The TMAs were assembled using a manual tissue arrayer (Beecher Instruments, Silver Spring, Md.) as previously described (See above examples). Four replicate tissue cores were sampled from each of the selected tissue types. After construction, 4 μm sections were cut and hematoxylin and eosin staining was performed on the initial slide to verify the histologic diagnosis. TMA hematoxylin and eosin images were acquired using the BLISS Imaging System (Bacus Lab, Lombard, Ill.). EZH2 protein expression was evaluated in a blinded manner by the study pathologist using a validated web-based tool (Manley et al., Am. J. Pathol. 159:837 [2001]; Bova et al., Hum. Pathol. 32:417 [2001]) and the median value of all measurements from a single patient were used for subsequent analysis.

E. Clinical Outcomes Analysis

To assess individual variables for risk of recurrence, Kaplan-Meier survival analysis was performed and a univariate Cox proportional hazards model was generated. PSA-recurrence was defined as 0.2 ng/ml following radical prostatectomy. Covariates included Gleason sum, preoperative PSA, maximum tumor dimension, tumor stage, and surgical margin status. To assess the influence of several variables simultaneously including EZH2 protein expression, a final multivariate Cox proportional hazards model of statistically significant covariates was generated. Statistical significance in univariate and multivariate Cox models were determined by Wald's test. A p-value<0.05 was considered statistically significant.

F. EZH2 Constructs

Myc-tagged EZH2-pCMV was used. The Myc-EZH2 fragment was released with BamHI/XhoI double digest and was sub-cloned into the mammalian expression vector pcDNA3 (Invitrogen). An EZH2-ER in-frame fusion expression construct was generated by replacing the FADD fragment released by Kpn I/Not I double digest of the FADD-ER construct (originally derived from Myc-ER (Littlewood et al., Nuc. Acids. Res. 23:1686 [1995]) with the PCR amplified human EZH2 devoid of its stop codon. The EZH2.SET mutant DNA was amplified using the primers 5'GGGGTACCATGGGCGGCCGCGAACAAAAGTTGATT 3' (SEQ ID NO:112) and 5'GGGGAATTCTCATGCCAGCAATAGATGCTTTTT3' (SEQ ID NO:113) and subsequently subcloned into pcDNA3 utilizing the in built KpnI/EcoRI sites. Expression of these constructs was verified by immunoblot analysis of the expressed proteins using either anti-Myc HRP (Roche, Inc) or anti-EZH2 antibodies.

G. RNA interference 21-nucleotide sense and antisense RNA oligonucleotides were chemically synthesized (Dharmacon Research Inc.) and annealed to form duplexes. The siRNA employed in the study were targeted to the region corresponding from 85 to 106 of the reported human EZH2 (NM004456). Control siRNA duplexes targeted luciferase, lamin and AMACR (NM014324). The human transformed prostate cell line RWPE (Webber et al., Carcinogenesis 18:1225 [1997]) and PC3 were plated at $2\times10^5$ cells per well in a 12 well plate (for immunoblot analysis, cell counts, and fluorescence activated cell sorting (FACS) analysis) and $1.5\times10^4$ cell per well in a 96 well plate (for WST-1 proliferation assays). Twelve hours after plating, the cells were transfected with 60 picomoles of siRNA duplex, sense or antisense oligonucleotides (targeting EZH2) using oligofectamine (Invitrogen). A second identical transfection was performed 24 hours later. Forty-eight hours after the first transfection, the cells were lysed for immunoblot analysis and trypsinized for cell number estimation or FACS analysis. Cell viability was assessed 60 hours after the initial transfection.

H. Cell Proliferation Assays

Cell proliferation was determined with the colorimetric assay of cell viability, based on the cleavage of tetrazolium salt WST-1 by mitochondrial dehydrogenases as per manufacturers instructions (Roche, Inc.). The absorbance of the formazan dye formed, which directly correlates with the number of metabolically active cells in the culture, was measured at 450 nm (Bio-Tek instruments), an hour after the addition of the reagent. Cell counts were estimated by trypsinizing cells and analysis by coulter cell counter.

I. Flow Cytometric Analysis

Trypsinized cells were washed with phosphate buffered saline (PBS) and cell number was determined by using a coulter cell counter. For FACS analysis, the washed cells were fixed in 70% ethanol overnight. Before staining with propidium iodide, the cells were washed again with PBS and analyzed by flow cytometry (Becton Dickinson).

J. Microarray Analysis of EZH2 Transfected Cells

Initial testing of this transient transfection/transcriptome analysis system demonstrated that transient overexpression of TNFR1 (p55), a receptor for tumor necrosis factor, induced similar expression profiles as was observed with incubation of cells with TNF (Kumar-Smith et al., J. Biol. Chem. 24:24 [2001]). Other molecules have been similarly tested with this approach. Cells were transfected with different EZH2 constructs and transfection efficiency was monitored by beta-galactosidase assay and was approximately 30-50%. EZH2.SET mutant expressing samples were compared to EZH2 expressing samples using the SAM analysis package (Tusher et al., PNAS 98:5116 [2001]). Data was pre-processed by multiplication by a normalization factor to adjust the aggregate ratio of medians to one, log base 2 transformed and median centered each array, individually. This pre-processed data was divided into 2 groups for comparison using a two-class, unpaired t-test. Critical values for the analysis include: iterations=5000, (720 at convergence) random Number Seed 1234567, a fold change of 1.5 and a delta cutoff of 0.45205, resulting in a final largest median False Discovery Rate of 0.45% for the 161 genes selected as significant. These 161 genes were supplemented by the values for EZH2 and then analyzed using Cluster implementing average linkage hierarchical clustering of genes. The output was visualized in Treeview. Selected genes identified as being repressed by EZH2 (e.g., EPC and cdc27) were re-sequenced to confirm identity.

The molecular identity of a cell is determined by the genes it expresses (and represses). Embryogenesis and cell differentiation intimately depend upon keeping certain genes "on" and other genes "off". When the transcriptional "memory" of a cell is perturbed this can lead to severe developmental defects (Jacobs et al., Semin. Cell Dev. Biol. 10:227 [1999]; Francis et al., Nat. Rev. Mol. Cell. Biol. 2:409 [2001]). Lack of differentiation, or anaplasia, is a hallmark of cancer, which results from normal cells "forgetting" their cellular identity. Thus, it is not surprising that dysregulation of the transcriptional maintenance system can lead to malignancy (Francis et al., supra; Jabobs et al., Nature 397:164 [1999]; Beuchle et al., Development 128:993 [2001]).

Studies in *Drosophila melanogaster* have been instrumental in the understanding of the proteins involved in transcriptional maintenance (Beuchle et al., [2001], supra; Strutt et al., Mol. Cell. Biol. 17:6773 [1997]; Tie et al., Development 128:275 [2001]). Two groups of proteins have been implicated in the maintenance of homeotic gene expression and include polycomb (PcG) and trithorax (trxG) group proteins (Mahmoudi et al., Oncogene 20:3055 [2001]; Lajeunesse et al., Development 122:2189 [1996]). PcG proteins act in large complexes and are thought to repress gene expression, while trxG proteins are operationally defined as antagonists of PcG proteins and thus activate gene expression (Francis et al., Nat. Rev. Mol. Cell. Biol. 2:409 [2001]; Mahmoudi et al., supra). There are at least twenty PcG and trxG proteins in *Drosophila*, and many have mammalian counterparts. In human malignancies, PcG and trxG proteins have primarily been found to be dysregulated in cells of hematopoietic origin (Yu et al., Nature 378:505 [1995]; Raaphorst et al., Am. J. Pathol., 157:709 [2000]; van Lohuizzen et al., Cell 65:737 [1991]). EZH2 is the human homolog of the *Drosophila* protein Enhancer of Zeste (E(z)) ((Laible et al., Embo. J. 16:3219 [1997]), for which genetic data defines as a PcG protein with additional trxG properties (LaJeunesse et al., supra). E(z) and EZH2 share homology in four regions including domain I, domain II, a cysteine-rich amino acid stretch, and a C-terminal SET domain (Laible et al., supra). The SET domain is a highly conserved domain found in chromatin-associated regulators of gene expression often modulating cell growth pathways (Jenuwein et al., Cell. Mol. Life Sci. 54:80 [1998]). EZH2 is thought to function in a PcG protein complex made up of EED, YY1 and HDAC2 (Satijn et al., Biochim. Biophys. Acta. 1447:1 [1999]). Disruption of the EZH2 gene in mice causes embryonic lethality suggesting a crucial role in development (O'Carroll et al., Mol. Cell. Biol. 21:4330 [2001]).

Figure 20:
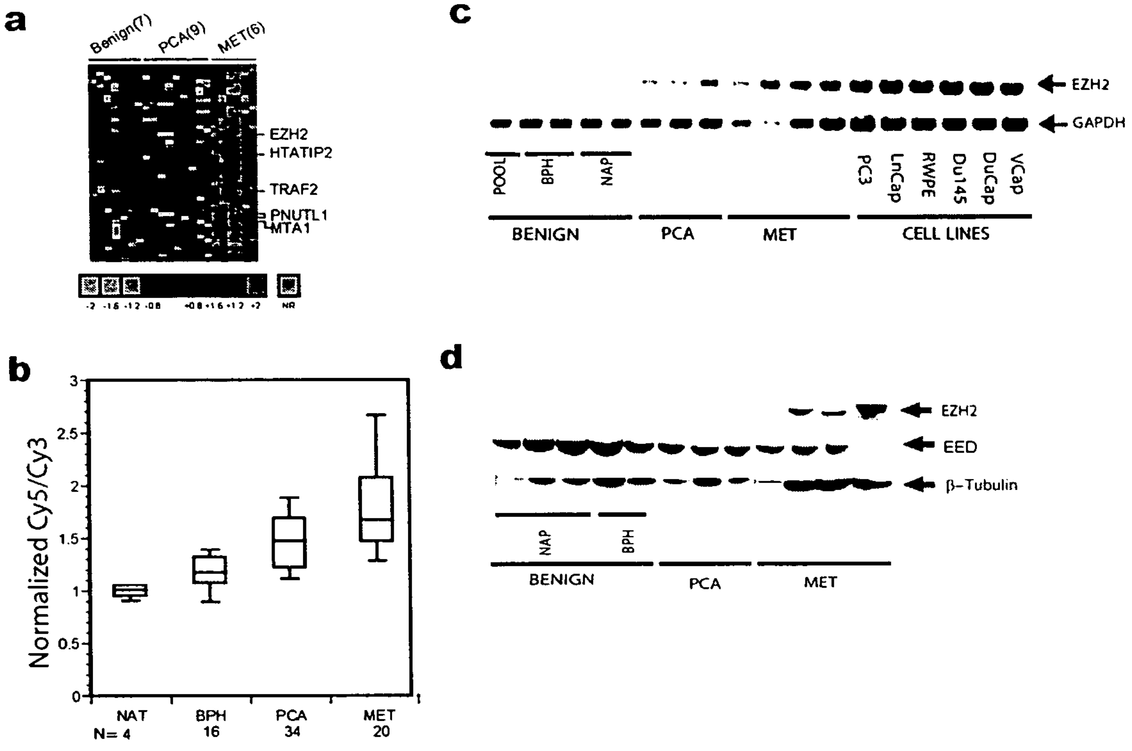
FIG. 20 describes the identification and validation of EZH2 over-expression in metastatic prostate cancer.

In previous studies (See e.g., Example 1), the gene at the top of the "list" of genes significantly up-regulated in metastatic prostate cancer was EZH2, which had a d-score (Tusher et al. PNAS 98:5116 [2001]) of 4.58 and a gene-specific FDR of 0.0012 (also called a "q-value" which is analogous to p-values, but adapted to multiple inference scenarios. FIG. 20*a* displays the 55 up-regulated genes identified by this approach. FIG. 20*b* summarizes the gene expression of EZH2 in 74 prostate tissue specimens analyzed on DNA microarrays made up of 10 K elements. The EZH2 transcript was significantly increased in metastatic prostate cancer with respect to clinically localized prostate cancer (Mann-Whitney test, p=0.001) and benign prostate (p=0.0001).

As independent experimental validation of DNA microarray results, RT-PCR was performed on 18 prostate samples and cell lines. As expected, EZH2 mRNA transcript levels were elevated in malignant prostate samples relative to benign (FIG. 20*c*). To determine whether EZH2 is up-regulated at the protein level in metastatic prostate cancer, tissue extracts were examined by immunoblotting. In the samples examined by immunoblot analysis, EZH2 protein was markedly elevated in metastatic prostate cancer relative to localized prostate cancer or benign prostate (FIG. 20*d*).

Figure 21:
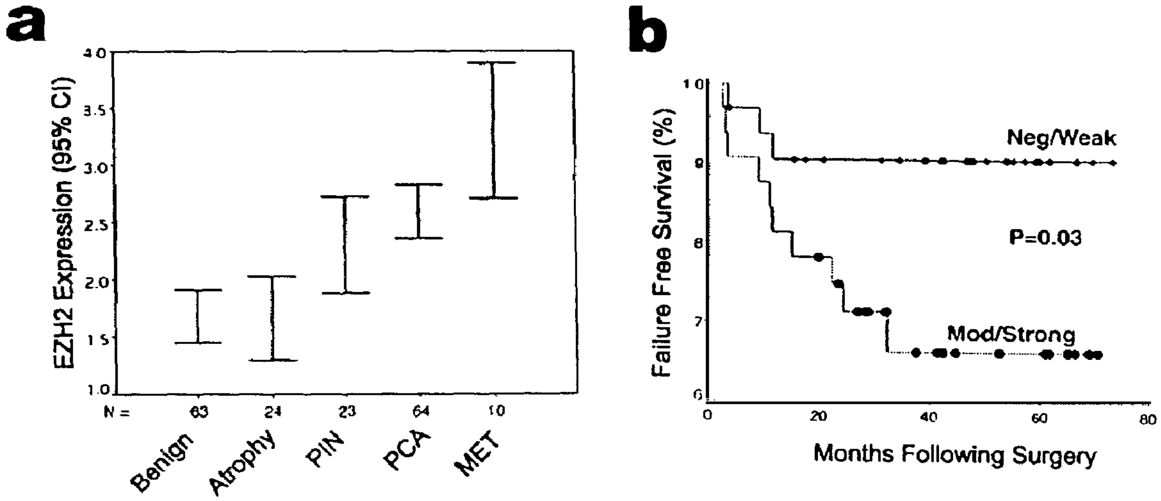
FIG. 21 shows that EZH2 protein levels correlate with the lethal progression and aggressiveness of prostate cancer.

Importantly, EED, a PcG protein that forms a complex with EZH2 (vanLohuizen et al., supra; Sewalt et al., supra), along with an un-related protein, 3-tubulin, did not exhibit similar protein dysregulation. EZH2 protein expression was evaluated on a wide range of prostate tissues (over 700 tissue microarray elements) to determine the intensity and extent of expression in situ (FIG. 21*a,b*). When highly expressed, EZH2 expression was primarily observed in the nucleus as suggested previously (Raaphorst et al., supra). The staining intensity was increased from benign, prostatic atrophy, prostatic intraepithelial neoplasia (PIN), to clinically localized prostate cancer with median staining intensity of 1.7 (standard error [SE], 0.1; 95% confidence interval [CI], 1.5-1.9), 1.7 (SE, 0.2; 95% CI, 1.3-2.0), 2.3 (SE, 0.2.; 95% CI, 1.9-2.7), and 2.6 (SE, 0.1; 95% CI, 2.4-2.8), respectively (FIG. 24*b*). The strongest EZH2 protein expression was observed in hormone-refractory metastatic prostate cancer with a median staining intensity of 3.3 (SE, 0.3; 95% CI, 2.7-3.9). There was a statistically significant difference in EZH2 staining intensity between benign prostate tissue and localized prostate cancer (ANOVA post-hoc analysis mean difference 0.9, p<0.0001). Although metastatic prostate cancer had a higher mean expression level than localized prostate cancer, the difference did not reach statistical significance (ANOVA post-hoc analysis mean difference 0.7, p=0.3). These findings suggest that as prostate neoplasia progresses there was a trend towards increased EZH2 protein expression, mimicking that seen by DNA expression array analysis. The present invention is not limited to a particular mechanism. Indeed, an understanding of the mechanism is not necessary to practice the present invention. Nonetheless, it is contemplated that this observation suggests that EZH2 levels may indicate how aggressive an individual's prostate cancer is given that the highest level of expression was observed in hormone-refractory, metastatic prostate cancer. Therefore, to test this hypothesis, the utility of EZH2 protein levels to predict clinical outcome in men treated with surgery for clinically localized prostate cancer was examined.

Two hundred and twenty-five (225) specimens from sixty-four patients (3-4 replicate samples per patient) with clinical follow up were interrogated on a single tissue microarray. These men had a median age of 61 years (range 43-76 years) and a 7.3 ng/ml median pre-operative serum prostate specific antigen (PSA) (range 0.8-21.0 ng/ml). Pathologic examination of their prostatectomy specimens indicated that 77% had organ-confined disease (pT2 stage) and 72% had negative surgical margins. The patient demographics and tumor stages were representative of the over 1500 radical prostatectomy patients. In order to test the utility of EZH2 as a potential tissue biomarker for prostate cancer, the clinical outcome of these 64 cases was examined, taking into account clinical and pathological parameters. Clinical failure was defined as either a 0.2 ng/ml PSA elevation or disease recurrence following prostatectomy (e.g., development of metastatic disease). By Kaplan-Meier analysis (FIG. 21*c*), EZH2 staining intensity of 3 and greater was significantly associated with clinical failure in 31% (10/32) of patients in contrast to 9% (3/32) of patients with an EZH2 protein levels below 3 (log rank p=0.03). There was no significant correlation between EZH2 levels and Gleason score (<7 versus=7), tumor stage (pT2 versus pT3), or surgical margin status (negative versus positive). There was a significant (p=0.048) albeit weak (Pearson coefficient=0.33) correlation between EZH2 protein levels and proliferation index in situ as assessed by Ki-67 labeling index. Multivariable Cox-Hazards regression analysis revealed that EZH2 protein expression (=3 versus <3) was the best predictor of clinical outcome with a recurrence ratio of 4.6 (95% CI 1.2-17.1, p=0.02), which was significantly better than surgical margin status, maximum tumor dimension, Gleason score, and pre-operative PSA. Thus, monitoring EZH2 protein levels in prostate specimens may provide additional prognostic information not discernible with current clinical and pathology parameters alone.

Figure 22:
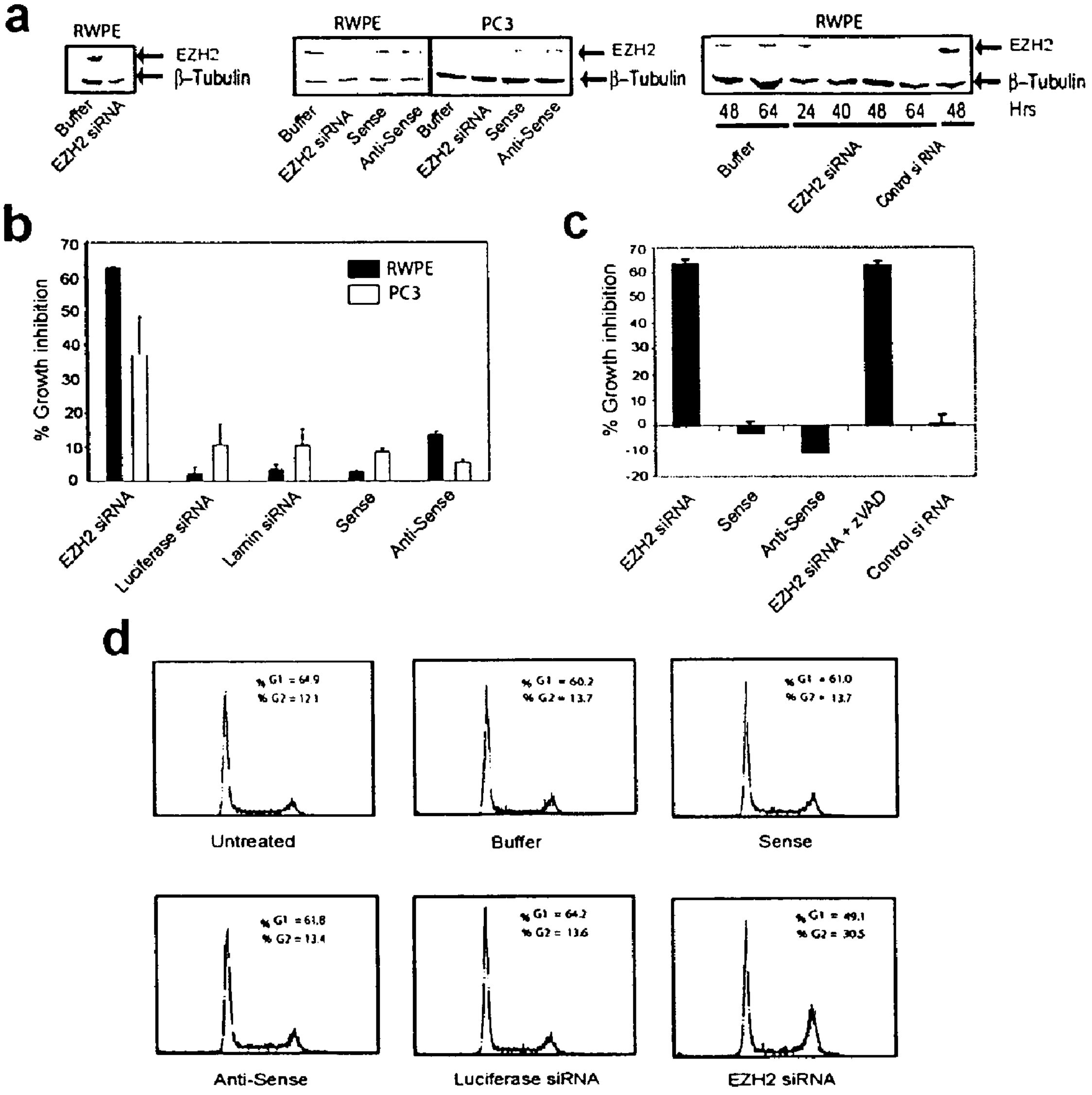
FIG. 22 shows the role of EZH2 in prostate cell proliferation.

To shed light into the functional role of EZH2 in prostate cancer progression, EZH2 expression in transformed prostate cells in vitro was disrupted using RNA interference. T. Tuschl and colleagues recently reported that duplexes of 21-nucleotide RNA (siRNAs) mediate RNA interference in cultured mammalian cells in a gene-specific fashion (Elbashir et al., Nature 411:494 [2001]). RNA interference has been used effectively in insect cell lines to "knock-down" the expression of specific proteins, owing to sequence-specific, double stranded-RNA mediated RNA degradation (Hammond et al., Nature 404:293 [2000]). siRNAs are potent mediators of gene silencing, several orders of magnitude more potent than conventional antisense or ribozyme approaches (Macejak et al., Hepatology 31:769 [2000]). Thus, a 21-nucleotide stretch of the EZH2 molecule was targeted using criteria provided by Elbashir et al. (supra), and RNA oligonucleotides were synthesized commercially. After the RNA oligos were annealed to form siRNA duplexes, they were tested on the transformed androgen-responsive prostate cell line RWPE (Webber et al., Carcinogenesis 18:1225 [1997]; Bello et al., Carcinogenesis 18:1215 [1997]) as well as the metastatic prostate cancer cell line PC3. Forty-eight hours after transfection with siRNA duplexes, the levels of endogenous EZH2 protein were quntitated. When EZH2 protein was specifically down-regulated in prostate cell lines, the levels of the un-related control protein, β-tubulin, remained unchanged (FIG. 22*a*). The sense or anti-sense oligonucleotides comprising the EZH2 duplex, as well as un-related siRNA duplexes, did not affect EZH2 protein levels (FIG. 22*a*, middle and right panels), verifying the specificity of the siRNA approach in both prostate cell lines.

The phenotype of EZH2 "knock-down" prostate cells was next examined. By phase contrast microscopy, it was observed that siRNA directed against EZH2 markedly inhibited cell number/confluency relative to buffer control. Cell counts taken 48 hrs after transfection with siRNA showed a 62% inhibition of RWPE cell growth mediated by the EZH2 siRNA duplex, which is in contrast to the corresponding sense and anti-sense EZH2 oligonucleotides or control duplexes (targeting luciferase and lamin) which exhibited minimal inhibition (FIG. 22*b*). The prostate cancer cell line, PC3, demonstrated a similar growth inhibition mediated by EZH2 siRNA, suggesting that the findings are not a peculiarity of the RWPE cell line (FIG. 22*b*). Using a commercially available cell proliferation reagent WST-1, which measures mitochondrial dehydrogenase activity, a decrease in cell proliferation mediated by the EZH2 siRNA duplex, but not by un-related duplexes, was observed (FIG. 22*c*). In the time frame considered (48 hrs), RNA interference of EZH2 did not induce apoptosis as assessed by propidium idodide staining of nuclei or PARP cleavage. Consistent with this, the broad-spectrum caspase inhibitor, z-VAD-fmk, failed to attenuate EZH2 siRNA induced inhibition of cell proliferation (FIG. 22*c*). Thus, activation of the apoptosis pathway does not account for the decreases in cell number observed by RNA interference of EZH2.

Various PcG Group proteins have been suggested to play a role in cell cycle progression (Jacobs et al., Nature 397:164 [1999]; Visser et al., Br. J. Hematol. 112:950 [2001]; Borck et al. Curr. Opin. Genet. Dev. 11:175 [2001]). Flow cytometric analysis of EZH2 siRNA-treated prostate cells demonstrated cell cycle arrest in the G2/M phase (FIG. 22*d*). Un-related control siRNA duplexes failed to induce a similar cell cycle dysregulation. Few apoptotic cells (sub-G1 cells) were present in any of the experimental samples tested as assessed by flow cytometry (FIG. 22*d*). The present invention is not limited to a particular mechanism. Indeed, an understanding of the mechanism is not necessary to practice the present invention. Nonetheless, it is contemplated that these observations suggest that EZH2 plays a role in prostate cell proliferation by mitigating the G2/M transition.

To further understand the functional role of EZH2 in prostate cells, an epitope-tagged version of wild-type EZH2 and a deletion mutant of EZH2 missing the conserved SET domain in the eukaryotic expression vector pcDNA3 were generated (FIG. 23*a*). An "inducible"-version of EZH2 was also generated by creating a fusion protein with a modified murine estrogen receptor (ER) (FIG. 26*a*) (Littlewood et al., Nuc. Acid. Res. 23:1686 [1995]; Juin et al., Genes Dev. 13:1367 [1999]). EZH2-ER fusion was expressed in cells (FIG. 26*b*) and is inactivated, presumably by sequestration/binding to hsp90 and other proteins (Littlewood et al., supra). Upon treatment of cells with 4-hydroxytamoxifen, hsp90 dissociates from the ER fusion and liberates its activity. Expression of the epitope-tagged EZH2 constructs was confirmed by transfection in 293 (FIG. 23*b*), RWPE and in other mammalian cell lines.

PcG proteins have been proposed to mediate their functions by repression of target genes (Laible et al., supra; Jacobs et al., Semin Cell Dev. Biol. 10:227 [1999]). To begin to test this hypothesis, RWPE prostate cells were transiently transfected with wild-type EZH2 and global gene expression alterations were monitored using DNA microarrays. While RNA from the experimental (transfected) cell line was labeled with one fluorescent dye, the paired reference sample was labeled with a second distinguishable fluorescent dye. By making direct comparisons between "gene"-transfected cell lines and control vector-transfected cell lines the molecular differences between the samples were observed. When EZH2 was over-expressed in RWPE cells or SUM149 breast carcinoma cells, there was a consistent repression of a cohort of genes (FIG. 23*c, d*). This exclusive repression of genes was unique compared to other molecules tested in this system including c-myc and TNFR1, among others. When compared to vector-transfected cells the only gene that was significantly up-regulated in EZH2-transfected cells was EZH2 itself (FIG. 23*c*).

EZH2-mediated transcriptional repression was dependent on an intact SET domain (FIG. 23*c*), as deletion of this domain did not produce a repressive phenotype and in some cases "de-repressed" genes. EZH2 has been shown to interact with histone deacetylase 2 (HDAC2) via the EED protein (van der Vlag et al., Nat. Genet. 23:474 [1999]). In the experiments described above, EZH2-mediated gene silencing was dependent on HDAC activity, as the commonly used HDAC inhibitor, trichostatin A (TSA) completely abrogated the effects of EZH2 (FIG. 23*c*). Thus, EZH2 function requires both an intact SET domain as well as endogenous HDAC activity.

To identify genes that are significantly repressed by EZH2, wild-type EZH2-transfected cells were compared with EZH2 SET-transfected cells. Using this approach, 163 genes were consistently repressed while no genes were activated at an FDR of 0.0045 (FIG. 23*d*). Examination of the significant gene list identified the PcG group protein EPC, which is the human homolog of the *drosophila* protein Enhancer of Polycomb (E(Pc)) as being consistently repressed by EZH2 (FIG. 23*c*). Of the *Drosophila* PcG proteins, E(Pc) and E(z) are related in that they both act as suppressors of variegation (Su(var)) (Sinclair et al., Genetics 148:211 [1998]) and are the only PcG proteins to have yeast homologs, emphasizing the evolutionary conservation of this PcG pair. In addition to EPC, a host of other transcriptional regulators/activators were transcriptionally silenced by EZH2 including MDNA, RNF5, RNF15, ZNF42, ZNF262, ZNFN1A1, RBM5, SPIB, and FOXF2, among others (FIG. 23*c*). MDNA, also known as myeloid cell nuclear differentiation antigen, mediates transcriptional repression by interacting with the transcription factor YY1, which is a PcG homolog of *Drosophila* Pho and shown to be part of the EZH2/EED complex of proteins (Satijin et al., Mol. Cell. Biol. 21:1360 [2001]).

Figure 23:
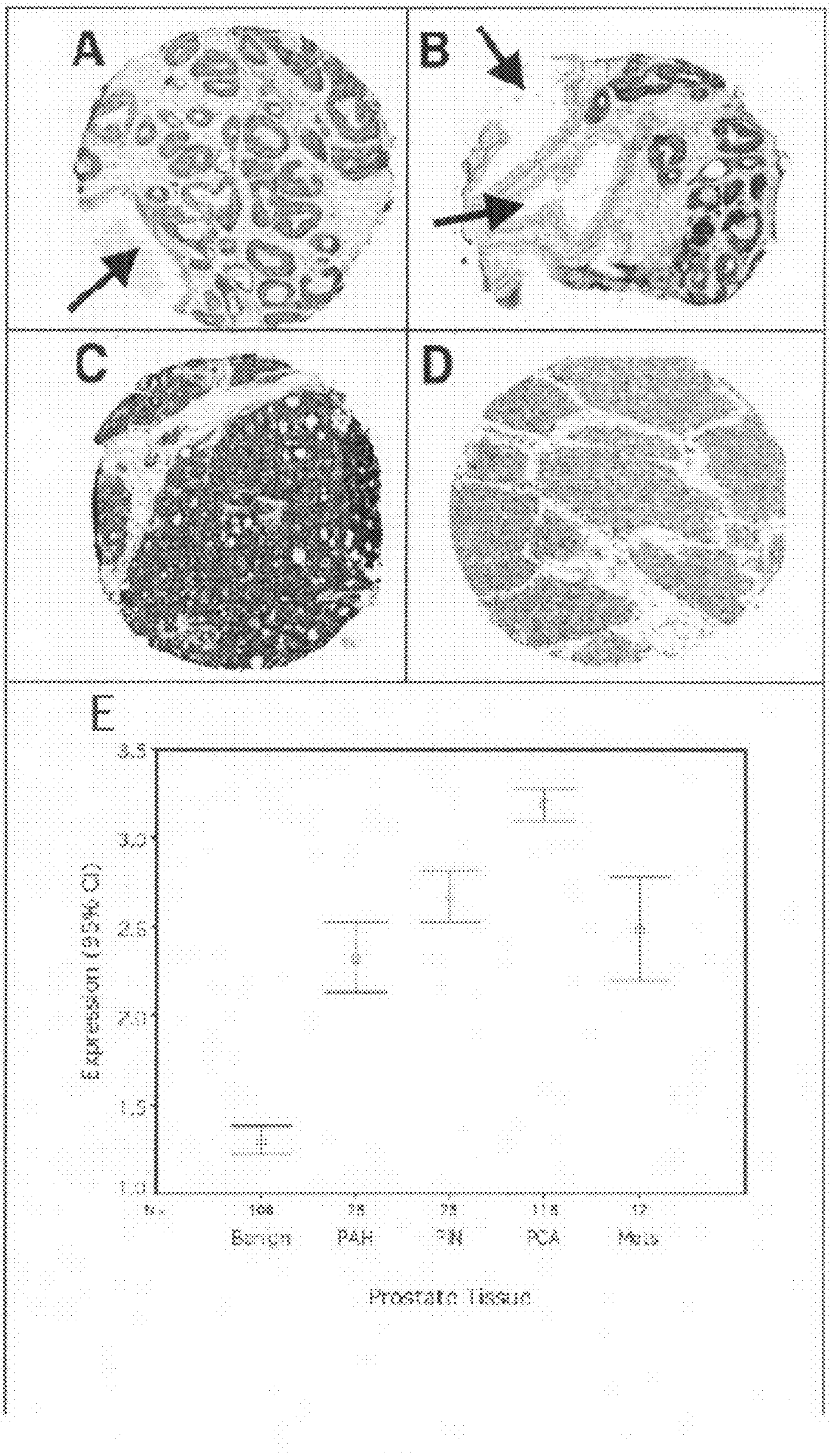
FIG. 23 shows that EZH2 functions as a transcriptional repressor in prostate cells.

In addition to transcriptional repression in prostate cells, the results also support a role for EZH2 in regulating cell growth (FIG. 23). Transcriptional repression of cdc27 (two independent Unigene clones) was also observed. Cdc27 is part of the anaphase-promoting complex (APC) which mediates ubiquitination of cyclin B1, resulting in cyclinB/cdk complex degradation (Jorgensen et al., Mol. Cell. Biol. 18:468 [1998]). Another family of proteins that was repressed when EZH2 was targeted was the solute carriers. At least 5 distinct members were shown to be repressed (i.e., SSLC34A2, SLC25A16, SLC25A6, SLC16A2, and SLC4A3).

EXAMPLE 9

Expression of AMACR in Serum and Urine

Figure 24:
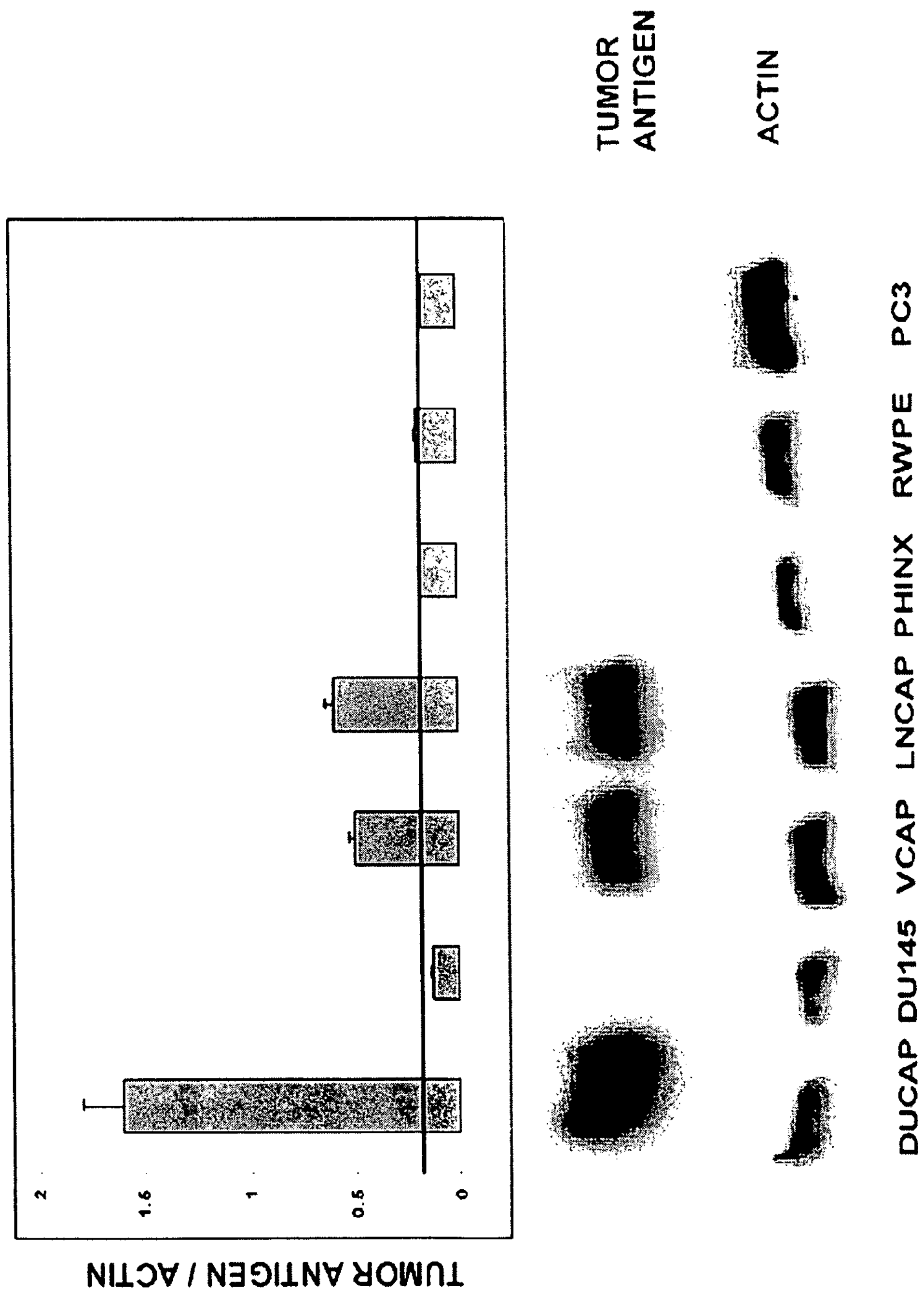
FIG. 24 shows the detection of AMACR in PCA cell lines.

This example describes the expression of AMACR in serum and urine. AMACR was detected by standard immunoblotting and by protein microarray using a polyclonal rabbit anti-AMACR antibody. The results are shown in FIGS. 24-27. FIG. 24 shows the detection of AMACR protein in PCA cell lines by quantitation of microarray data. DUCAP, DU145, and VCAP are prostate cancer cell lines. RWPE is a benign prostate cell line. PHINX is a human embryonic kidney cell line.

Figure 25:
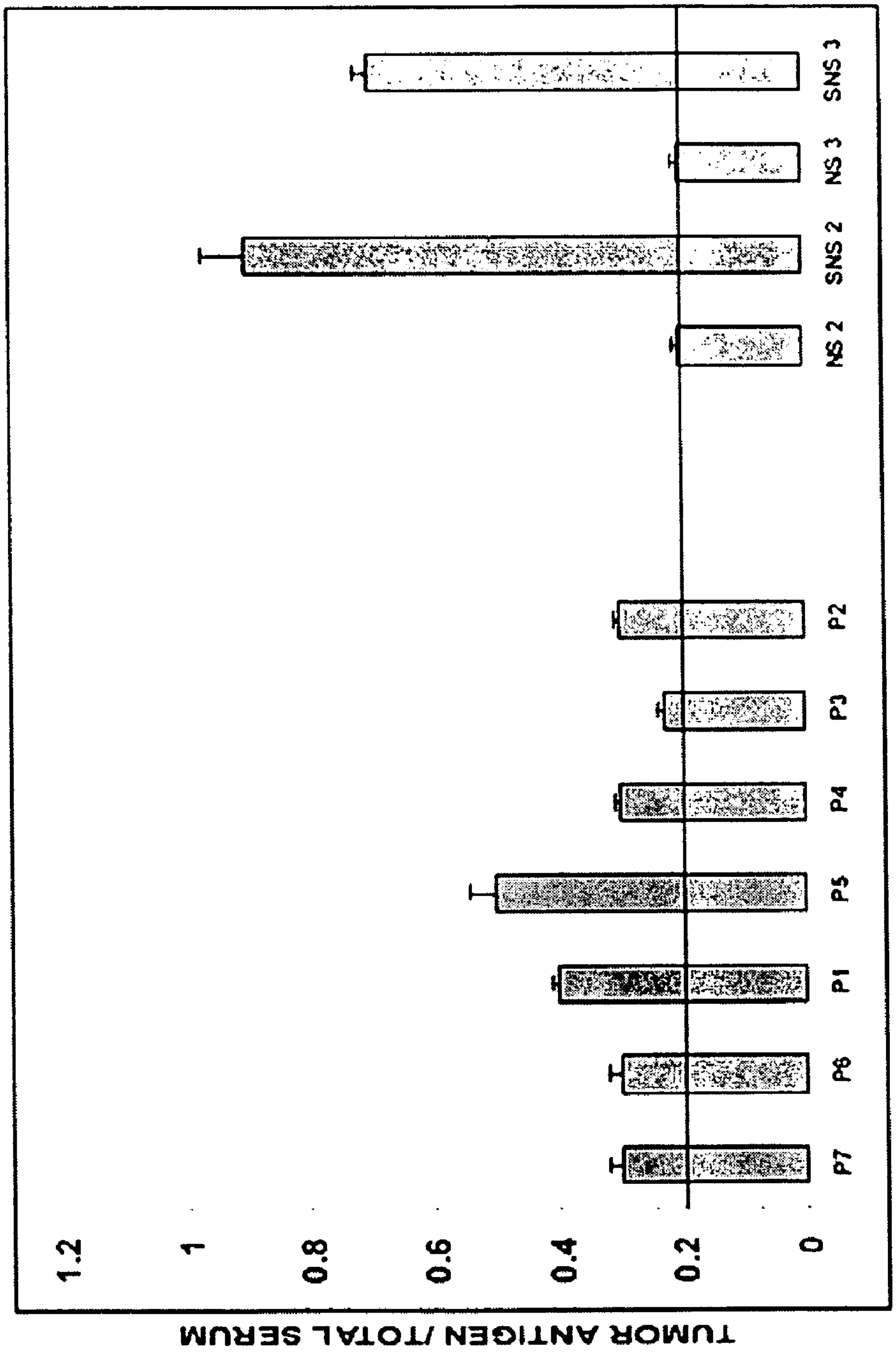
FIG. 25 shows the detection of AMACR protein in serum by quantitation of microarray data.
Figure 26:
FIG. 26 shows an immunoblot analysis of serum from patients with either negative or positive PSA antigen.
Figure 27:
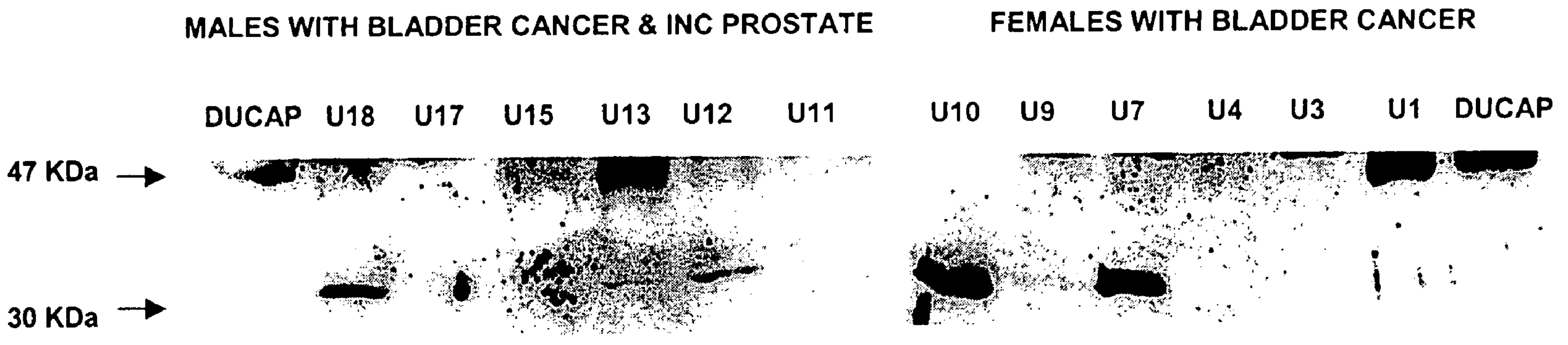
FIG. 27 shows an immunoblot analysis of the presence of AMACR in urine samples from patients with bladder cancer (females) or bladder cancer and increased PSA (males).

FIG. 25 shows the detection of AMACR protein in serum by quantitation of microarray data. P1-P7 represent serum from patients with prostate cancer. NS2 and NS3 represent serum from patients that do not have PCA. SNS2 and SNS3 represent serum from patients that do not have PCA that has been spiked with AMACR protein. FIG. 26 shows an immunoblot analysis of serum from patients with either negative or positive PSA antigen. FIG. 27 shows an immunoblot analysis of the presence of AMACR in urine samples from patients with bladder cancer (females) or bladder cancer and incidental prostate cancer (males). The results demonstrate that AMACR can be detected in the serum and urine of patients with bladder cancer or bladder cancer and prostate cancer.

EXAMPLE 10

AMACR as a Tumor Antigen

Figure 28:
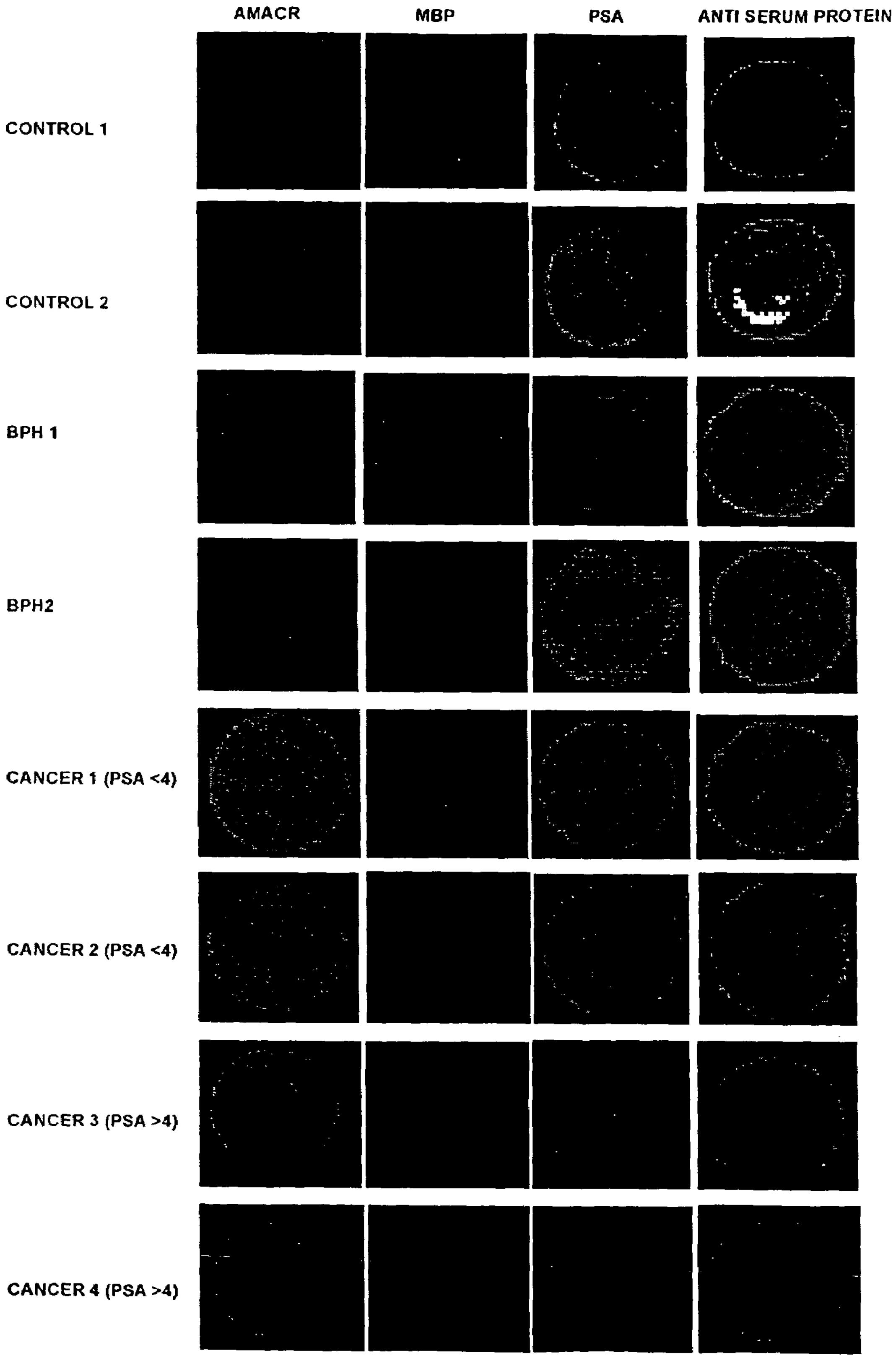
FIG. 28 shows representative data of a humoral response by protein microarray analysis.

This example describes the presence of an immune response against AMACR in serum. FIG. 28 shows representative data of a humoral response by protein microarray analysis. Tumor antigens including AMACR, PSA, CEA, HSPs were spotted onto nitrocellulose coated slides. The slides were incubated with sera from different patients to detect a humoral response. The microarray was then washed. A Cy5 labeled goat anti-human IgG was used to detect the humoral response. The slide was then scanned using a microarray scanner (Axon). After data normalization, intensity of spots reflects the presence, absence or strength of humoral response to specific tumor antigen. A specific humoral response to AMACR was detected in cancer patients but not in controls. Cancer refers to sera from prostate cancer patients. BPH refers to sera from patients with benign prostate hyperplasia.

FIG. 29 shows immunoblot analysis of the humoral response to AMACR. FIG. 29A shows an SDS-PAGE gel containing recombinant MBP (control protein=M) and recombinant AMACR-MBP (A) that was run and transferred to nitrocellulose paper. Each strip blot was then incubated with human sera. A humoral response to the AMACR was detected using an HRP-conjugated anti-human antibody. Only AMACR and fragments of AMACR were detected in sera from prostate cancer patients and not in controls. FIG. 29B shows a control experiment whereby the humoral response is blocked with recombinant AMACR (quenched) and thus shows the specificity of the response.

This example demonstrates that AMACR functions as a tumor antigen in human serum of prostate cancer patients. A specific immune response was generated to AMACR in the serum of PCA patients, but not in controls.

EXAMPLE 11

Expression of GP73 in Prostate Cancer

This example describes the association of GP73 with prostate cancer.

A. Methods

Microarray analysis, RT-PCR, Western blotting, and immunohistochemistry were performed as described in the above examples.

B. Results

Figure 30:
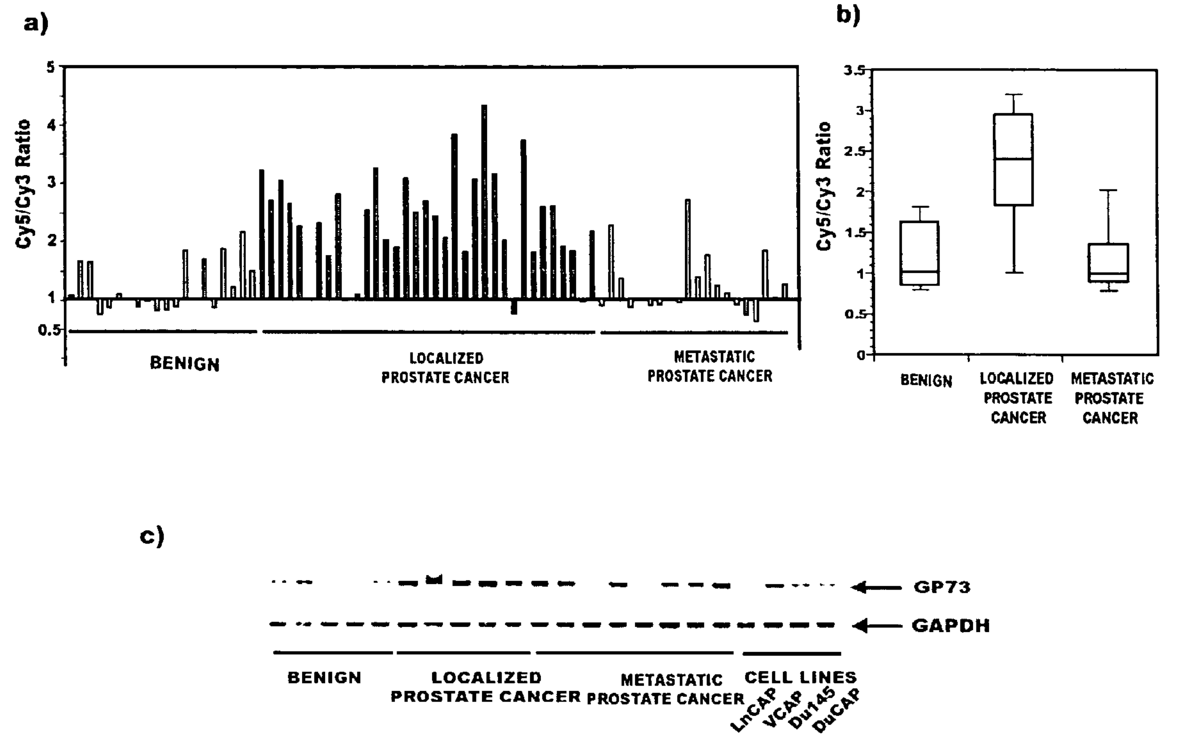
FIG. 30 shows GP73 Transcript levels in prostate cancer.

FIG. 30 shows GP73 Transcript levels in prostate cancer. FIG. 30*a* shows the level of GP73 in individual samples after microarray analysis. The graph shows the values of Cy5 versus Cy3 ratio wherein the prostate cancer tissue sample RNA were labeled with Cy5 fluorescent dye, while the reference sample (pool of benign tissue RNA) sample was labeled with Cy3 fluorescent dye. A total of 76 individual experiments from different prostate tissue are plotted and they are classified as benign, prostate cancer and metastatic cancer types. FIG. 30*b* shows the result of GP73 transcripts determined by DNA microarray analysis from 76 prostate samples grouped according to sample type and averaged. The experimental samples were labeled with Cy5 fluorescent dye, whereas the reference sample (pool of benign tissue sample) was labeled with Cy3 fluorescent dye. The box plot demonstrates the range of GP73 expression within each group. The middle horizontal bar indicates median values; the upper and lower limits of the boxes, interquartile ranges; and the error bars, 95% confidence intervals. FIG. 30*c* demonstrates that GP73 transcript levels are elevated in prostate cancer. RT-PCR was used to detect GP73 transcript levels in RNA preparations from prostate tissue extracts. GAPDH served as the loading control.

Figure 31:
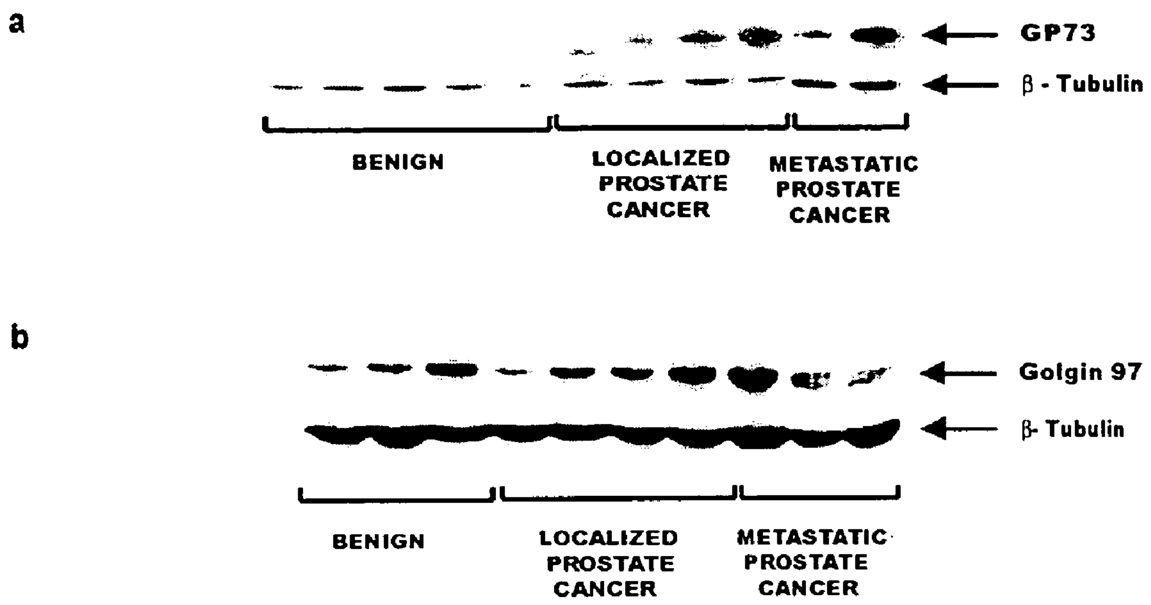
FIG. 31 shows that GP73 protein is upregulated in prostate cancer.

FIG. 31 shows that GP73 protein is upregulated in prostate cancer. FIG. 31*a* shows Western blot analysis of GP73 protein in prostate cancer. Total tissue proteins from benign, cancer and metastatic tissues (10 μg) were analyzed using anti-GP73 antiserum. β-Tubulin serves as control for sample loading. FIG. 3 lb shows an immunoblot analysis of the Golgi resident protein Golgin 97. The Golgin 97 protein levels were analyzed in the prostate tissue sample to indicate the level of Golgi structure in normal and cancerous prostate tissue. β-Tubulin serves as control for sample loading.

Tissue microarray analysis of GP73 protein in normal and cancerous prostate tissue was also performed. GP73 protein expression was analyzed by standard biotin-avidin immunohistochemical analysis using a polyclonal mouse antibody to GP73. Protein expression was evaluated on a wide range of prostate tissue using high-density tissue microarrays. High levels of staining were observed in prostate cancer tissue. Some normal epithelial cells did not stain for GP73 in a sub region of prostate cancer tissue.

Figure 32:
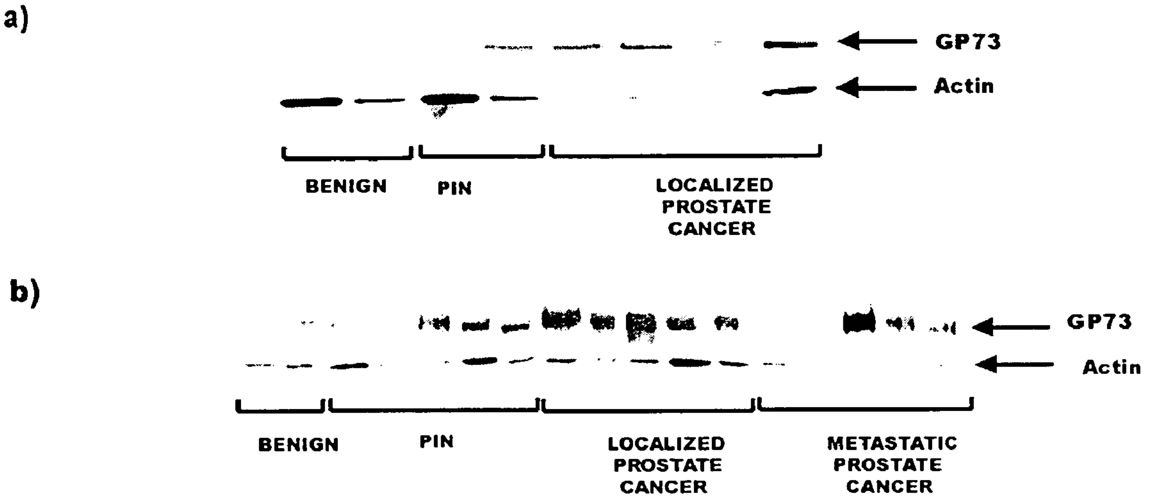
FIG. 32 shows immunoblot analysis of normal and prostate cancer epithelial cells.

FIG. 32 shows immunoblot analysis of normal and prostate cancer epithelial cells. The epithelial cells were isolated from normal prostate tissue and cancer tissue to specifically isolate the protein from epithelial cell for GP73 immunoblot analysis. For this purpose, laser capture microdissected samples were used. Actin western serves as control.

EXAMPLE 12

Lethal Markers and Targets

This example describes the identification of lethal markers. The markers serve as potential therapeutic targets. Markers were identified by correlating the number of samples with clinical parameters and gene expression. Specifically, the present study identified markers that have an expression profile similar to EZH2, which serves as a prototypic lethal biomarker of prostate cancer. These genes were identified by a scoring system that takes into account whether localized prostate cancer has recurred or not recurred. In addition, genes that have highly correlated expression with EZH2 were identified that may serve as markers to supplement EZH2.

| mean | dev | Total High | 16 bph_count | 13 pca_count | 16 pcau_count | 6 pcar_count | 20 met_count | score | UNIQID | NAME |
|---|---|---|---|---|---|---|---|---|---|---|
| −0.024 | 0.3725 | 0.7206 | 0 | 4 | 5 | 6 | 16 | 18 | 5814 | NULL ESTs Hs.30237 |
| −0.306 | 0.1707 | 0.0351 | 0 | 0 | 3 | 3 | 14 | 17 | 2506 | HN1 |
| −0.348 | 0.2394 | 0.1312 | 0 | 2 | 1 | 4 | 14 | 16 | 5112 | CSF2 |
| 0.0623 | 0.1578 | 0.3779 | 0 | 1 | 2 | 3 | 13 | 15 | 6053 | ASNS |
| −0.246 | 0.1689 | 0.0921 | 0 | 2 | 0 | 2 | 15 | 15 | 1520 | NULL ESTs Hs.16304 |
| −0.212 | 0.1386 | 0.0648 | 0 | 2 | 0 | 2 | 15 | 15 | 8273 | PRC1 |
| −0.352 | 0.1458 | −0.06 | 0 | 3 | 7 | 3 | 14 | 14 | 34 | GPAA1 |
| −0.292 | 0.2538 | 0.2153 | 0 | 0 | 1 | 3 | 10 | 13 | 5239 | KIAA1691 |
| −0.141 | 0.1572 | 0.1729 | 0 | 2 | 5 | 3 | 12 | 13 | 8562 | NULL Human clone 23614 |
| −0.21 | 0.1083 | 0.0067 | 0 | 4 | 4 | 2 | 15 | 13 | 3351 | FLJ11715 hypothetical protein |
| −0.22 | 0.1846 | 0.1495 | 0 | 5 | 4 | 5 | 13 | 13 | 2715 | NULL ESTs |
| −0.638 | 0.2696 | −0.099 | 1 | 5 | 4 | 3 | 15 | 13 | 9556 | FLJ12443 hypothetical protein |
| −0.142 | 0.1396 | 0.1371 | 0 | 0 | 2 | 2 | 10 | 12 | 1158 | TGFBI |
| −0.124 | 0.1606 | 0.1967 | 0 | 1 | 1 | 3 | 10 | 12 | 5292 | NULL ESTs |
| −0.444 | 0.2474 | 0.0504 | 0 | 1 | 2 | 2 | 11 | 12 | 3689 | NUF2R hypothetical protein |
| −0.205 | 0.2362 | 0.2674 | 0 | 2 | 1 | 2 | 12 | 12 | 1219 | ABCC5 |
| −0.09 | 0.2214 | 0.3526 | 0 | 4 | 2 | 4 | 12 | 12 | 1360 | MEN1 |
| −0.241 | 0.1541 | 0.0673 | 0 | 5 | 3 | 2 | 15 | 12 | 8476 | SARM and HEAT/ Armadillo motif |
| −0.874 | 0.3367 | −0.201 | 0 | 1 | 4 | 2 | 10 | 11 | 3747 | H2BFB |
| −0.196 | 0.254 | 0.3122 | 0 | 2 | 1 | 3 | 10 | 11 | 4941 | VAV2 |
| −0.166 | 0.1486 | 0.1307 | 0 | 2 | 4 | 2 | 11 | 11 | 8636 | NULL ESTs Hs.23268 |
| 0.0255 | 0.1542 | 0.3338 | 0 | 3 | 3 | 3 | 11 | 11 | 280 | TOP2A |
| −0.226 | 0.2536 | 0.2812 | 0 | 4 | 3 | 4 | 11 | 11 | 2156 | EZH2 |
| −0.031 | 0.1826 | 0.3346 | 0 | 4 | 4 | 2 | 13 | 11 | 1979 | NULL ESTs Hs.268921 |

-continued

| mean | dev | Total High | 16 bph_count | 13 pca_count | 16 pcau_count | 6 pcar_count | 20 met_count | score | UNIQID | NAME |
|---|---|---|---|---|---|---|---|---|---|---|
| −0.48 | 0.2967 | 0.1131 | 0 | 2 | 0 | 2 | 10 | 10 | 906 | MGC5627 hypothetical protein |
| −0.243 | 0.1421 | 0.0411 | 0 | 2 | 8 | 2 | 10 | 10 | 3728 | NULL ESTs |
| −0.133 | 0.1806 | 0.2279 | 0 | 2 | 2 | 2 | 10 | 10 | 8759 | RAB24 |
| −0.192 | 0.1782 | 0.1645 | 0 | 3 | 2 | 2 | 11 | 10 | 2029 | FLJ12876 hypothetical protein |
| −0.617 | 0 | −0.617 | 0 | 3 | 2 | 2 | 10 | 9 | 3928 | DGKD |
| 0.1079 | 0.1132 | 0.3343 | 0 | 3 | 2 | 2 | 10 | 9 | 5372 | ODF2 |
| −0.288 | 0.1221 | −0.043 | 0 | 4 | 3 | 3 | 10 | 9 | 7193 | KIAA0602 |
| −0.167 | 0.2278 | 0.2883 | 0 | 4 | 2 | 2 | 11 | 9 | 8535 | EHM2 |
| −0.95 | 0.3504 | −0.249 | 0 | 4 | 2 | 2 | 11 | 9 | 9824 | SLC19A1 |
| −0.314 | 0.187 | 0.06 | 1 | 4 | 2 | 2 | 11 | 9 | 9447 | LIG1 |
| 0.1366 | 0.1883 | 0.5132 | 1 | 4 | 3 | 2 | 10 | 8 | 327 | NULL ESTs |
| −0.586 | 0.2952 | 0.0044 | 0 | 5 | 2 | 2 | 11 | 8 | 1269 | DGKZ |

mean: mean expression in BPH
Dev: standard deviation in BPH
High: 2 SD's above the mean (threshold)
Bph: # of BPH samples > thresh
PCA: # of PCA samples > thresh (>1 yr no recur)
Pcau: # of PCA samples > thresh (<1 yr followup)
Pcar: # of PCA samples > thresh (recur)
Met: # of metastatic samples > thresh
Score: = met + pcar − pca
Total: # of samples in category Exemplary lethal markers identified using the above methods include ABCC5 (MDR5). This multi-drug resistance gene actively pumps cyclic nucleotides and other small molecules out of cells. An unrelated study found that this enzyme is potently Inhibited by phosphodiesterase inhibitors, including sildenafil (viagra). The present invention is not limited to a particular mechanism. Indeed, an understanding of the mechanism is not required to practice the present invention. Nonetheless, it is contemplated that sildenafil may be useful in the treatment of aggressive PCA.

Another lethal marker identified is asparagine synthetase (ASNS). Current therapeutics for the inhibition of ASNS include asparaginase, an enzyme that destroys asparagine in the body. It has been shown that cancers expressing the synthetase are resistant. Analogs are being developed to inhibit the synthetase.

Top2A (topoisomerase 2) and the Vav2 Oncogene were also identified using the methods of the present invention. Vav2 is required for cell spreading, but is dependent on src. The present invention is not limited to a particular mechanism. Indeed, an understanding of the mechanism is not required to practice the present invention. Nonetheless, it is contemplated src inhibitors can stop vav2 mediated cell spreading.

This example describes the identification of cancer markers overexpressed in prostate cancers. The present invention is not limited to a particular mechanism. Indeed, an understanding of the mechanism is not necessary to practice the present invention. Nonetheless, it is contemplated that therapeutic compounds that inhibit these lethal markers are useful in the treatment of prostate cancer.

EXAMPLE 13

Characterization of Annexin Expression in Prostate Cancer

This Example describes the expression of Annexins in prostate cancer.

A. Materials and Methods

Prostate Sample Collection

Prostate tissues were taken from the radical prostatectomy series and the rapid autopsy program available through the University of Michigan Prostate Cancer Specialized Program of Research Excellence (S.P.O.R.E.) Tissue Core. This program is approved by Institutional Review Board at the University of Michigan.

Hormone naïve, clinically localized PCA samples used for this study were taken from a cohort of men who underwent radical retropubic prostatectomy as a monotherapy (i.e., no hormonal or radiation therapy) for clinically localized PCA between the years 1994 and 1998. Processing of the prostatic tissues started within 20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol. 164:1583 [2000]). The snap frozen samples used for cDNA expression array analysis were all evaluated by one of the study pathologists. All samples were grossly trimmed to ensure greater than 95% of the sample represented the desired lesion.

Hormone refractory PCA samples were collected from the rapid autopsy program (Rubin et al., [2000], supra). Snap frozen samples were used for cDNA expression array analysis. Mirrored samples from the same lesion were placed in 10% buffered formalin. The fixed samples are embedded in paraffin. As with the prostatectomy samples, the study pathologist reviewed the glass slides, circled areas of viable prostate cancer, avoiding areas of necrosis, and used these slides as a template for tissue microarray construction. In this study, twenty (20) hormone refractory metastatic PCAs were extracted from 15 rapid autopsy cases performed from 1997 to 2000. The patients' ages ranged from 53 to 84 and time from diagnosis to death ranged from 21 to 193 months. All 15 patients died with widely metastatic PCA after extensive treatment, which included antiandrogens and chemotherapy.

Prostatectomy samples were evaluated for the presence or absence of surgical margin involvement by tumor (surgical margin status), the presence of extraprostatic extension, and seminal vesicle invasion. Tumors were staged using the TNM system, which includes extraprostatic extension and seminal vesicle invasion but does not take into account surgical margin status (Bostwick et al., Semin. Urol. Oncol. 17:222 [1999]). Tumors were graded using the Gleason grading system (Gleason, [1966], supra).

Immunohistochemistry

After paraffin removal and hydration, the tissue microarray slides were immersed in 10 mM citrate buffer placed in a pressure cooker chamber and microwaved for 10 minutes for optimal antigen retrieval. Immunostaining was performed using a Dako autostainer (DAKO, Carpinteria, Calif.). The primary antibody was incubated for 45 minutes at room temperature and a secondary biotin-labeled antibody for 30 minutes. Streptavidin-LSA amplification method (DAKO K0679) was carried out for 30 minutes followed by peroxidase/diaminobenzidine substrate/Chromagen. The slides were counterstained with hematoxylin. Polyclonal antibodies directed against the N-terminus of annexin 1 (dilution 1:50), annexin 2 (dilution 1:100), annexin 4 (dilution 1:100), annexin 7 (dilution 1:500), and annexin 11 (dilution 1:100) were obtained from a signal source (Santa Cruz Biotechnology, Santa Cruz, Calif.). Protein expression as determined by two pathologists immunohistochemistry was scored as negative (score=1), weak (score 2), moderate (3) or strong (4), using the system described above.

Tissue Microarray Construction, Digital Image Capture, and Analysis

Tissue microarrays were constructed as previously described to evaluate protein expression in a wide range of samples ranging from benign prostate tissue taken from the prostatectomy samples to hormone refractory PCA. Three tissue microarrays were used for this study consisting of benign prostate, localized PCAs, and hormone refractory PCA. The tissue microarrays were assembled using the manual tissue arrayer (Beecher Instruments, Silver Spring, Md.) as previously described (Kononen et al., [1998], supra; Pyrrone et al., [2000], supra). Tissue cores from the circled areas of interest were targeted for transfer to the recipient array blocks. The 0.6 mm diameter tissue microarray cores were each spaced at 0.8 mm from core-center to core-center. Tissue microarray images were acquired using the BLISS Imaging System (Bacus Lab, Lombard, Ill.).

Statistical Analyses

To investigate the statistical significance associated with the differential expression of annexins across 4 independent gene expression studies, standard methods (Hedges et al., Statistical Methods for Meta-analysis meta-analysis. Orlando, Academic Press 1985, pp xxii, 369) were used to combine the results. For each of the studies, a t-statistic was computed (with the two groups being benign tissue compared against localized prostate cancer) and the associated p-values were transformed using a negative logarithmic transformation. These numbers were then doubled and added together to arrive at a summary measure of differential gene expression across the three studies. To assess the statistical significance associated with this summary measure, a permutation-based approach was adopted (Hedges et al., supra). Namely, the tissue types were permutated within studies, and the summary measure was computed for the permutated data. A p-value was computed using the permutation distribution of the summary measure. The issue then arises of whether or not the t-statistics from the three studies are comparable.

Annexin protein expression was statistically evaluated using the mean score results from each tissue microarray sample for each prostate tissue type (i.e., benign, localized PCA, and hormone refractory PCA). To determine differences between all pairs (e.g., localized prostate cancer versus benign), an ANOVA with a post-hoc analysis was performed using the Scheffé method (Scheffae et al., supra). The mean expression scores for all examined cases were presented in a graphical format by using error-bars with 95% confidence intervals.

B. Results

Figure 33:
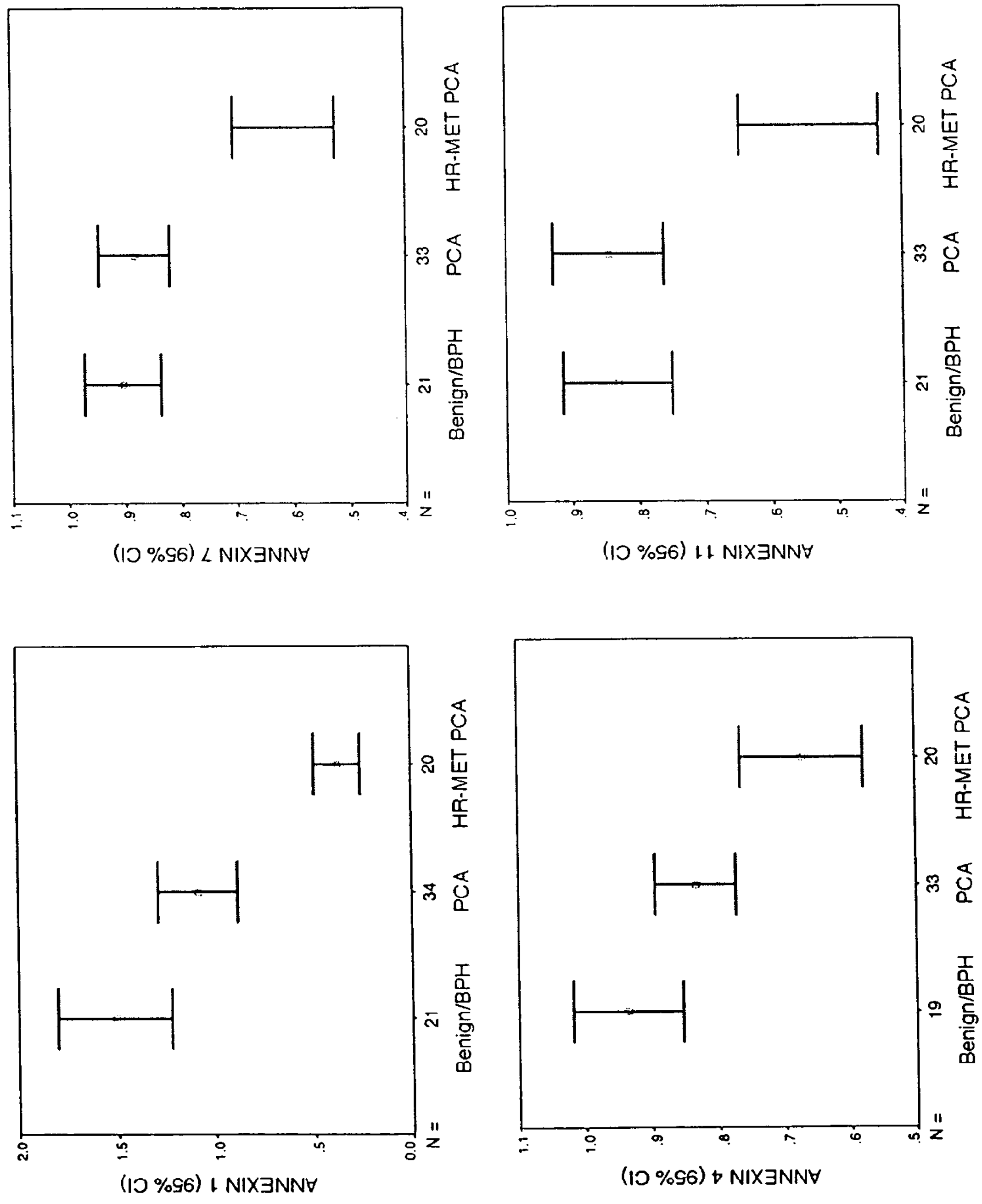
FIG. 33 shows the cDNA expression of select annexin gene family members.

Expression array analysis revealed a significant dysregulation of annexin family members with PCA progression. The cDNA expression of annexins 1, 2, 4, 7 and 11 were significantly decreased in the hormone refractory PCA samples as compared to localized hormone sensitive PCA samples with 2.2, 1.5, 1.3, 1.4 and 1.8 fold decrease, respectively (all p-values<0.01) (Table 8 and FIG. 33). Annexins 1 and 4 showed significant decreases of mRNA expression in localized PCA samples as compared to the benign samples. There were no significant differences between localized hormone naive PCA and the benign samples for annexin 2, 7, and 11. No cDNA dysregulation between the tested prostate samples and annexins 8 and 13 was observed. Annexin 6 demonstrated a slight decrease in cDNA expression between localized PCA and benign samples, which was not statistically significant (Table 8).

Figure 34:
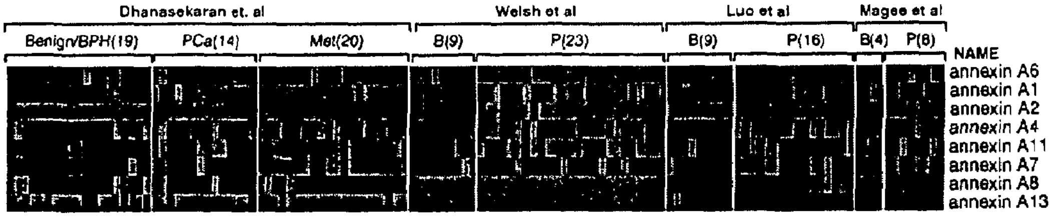
FIG. 34 shows a heat map representation of annexin family gene expression across four prostate cancer profiling studies. Over and under expression at the transcript level are represented by shades of red and green, respectively. Gray shading indicates that insufficient data was available. Each square represents an individual tissue sample.

In order to cross validate the cDNA expression results for these annexin family members, a meta-analysis of gene expression was performed. Annexin family members cDNA expression results were evaluated using a series of data sets (Welsh et al., Cancer Res. 61:5974 [2001]; Luo et al., Cancer Res. 61:4683 [2001]; Magee et al., Cancer Res. 61:5692 [2001]). The analysis evaluated annexins for each of the individual studies as well as performing a summary statistic, taking into account the significance of the gene expression across the 4 studies. The meta-analysis compared differences between clinically localized PCA and benign prostate tissue as not all of the studies had hormone refractory metastatic PCA. The meta-analysis (Table 9 and FIG. 34) demonstrated that annexins 1, 2, 4, and 6 were significantly down regulated across independent studies. Annexin 6 was down regulated to a significant level in 4 of 4 studies. Annexin 1 demonstrated down regulation in 3 of 4 studies. Annexins 2 and 4 were down regulated in 2 studies and overall considered to be significantly under expressed by the meta-analysis. Annexin 7 was not found to be significantly under expressed in any of the 4 studies at the transcript level.

Immunohistochemistry was performed to confirm these results at the protein level (Table 10). By immunohistochemistry, a significant decrease in protein expression for annexins 1, 2, 4, 7 and 11 in hormone refractory PCA samples as compared to localized PCA samples was identified with 2.5 (3.8 vs. 1.5 median expression), 2.4 (4 vs. 1.7 median expression), 3.6 (4 vs. 1.1 median expression) and 3.3 (4 vs. 1.2 median expression) fold decreases, respectively (Kruskal Wallis test, all p-values p<0.05). No statistically significant differences were seen between benign and localized PCA samples in any of the annexins tested.

TABLE 8

Gene Expression of Select Annexins.

| Annexin | Benign | | BPH[1] | | Loc-PCA[2] | | Met-PCA[3] | | Ratio PCA/Met | p Value* |
| --- | --- | --- | --- | --- | --- | --- | --- | --- | --- | --- |
| | Count | Median | Count | Median | Count | Median | Count | Median | | |
| 1 | 5 | 1.56 | 16 | 1.35 | 16 | 0.69 | 20 | 0.31 | 2.23 | <0.001 |
| 2 | 5 | 0.79 | 16 | 0.69 | 16 | 0.74 | 20 | 0.49 | 1.51 | 0.009 |
| 4 | 5 | 0.91 | 16 | 0.97 | 16 | 0.9 | 20 | 0.69 | 1.30 | 0.001 |
| 6 | 5 | 1.2 | 16 | 1.29 | 16 | 1.05 | 20 | 1.15 | 0.91 | 0.377 |
| 7 | 5 | 0.8 | 16 | 0.88 | 16 | 0.88 | 20 | 0.62 | 1.42 | <0.001 |
| 8 | 5 | 1.14 | 16 | 1.06 | 16 | 0.99 | 20 | 1.19 | 0.83 | 0.156 |
| 11 | 5 | 0.99 | 16 | 0.76 | 16 | 0.94 | 20 | 0.52 | 1.81 | <0.001 |
| 13 | 5 | 1.08 | 16 | 1.35 | 16 | 1.03 | 20 | 0.94 | 1.10 | 0.393 |

*Kruskal Wallis Test.
[1]BPH, benign prostatic hyperplasia.
[2]Loc-PCA, localized prostate cancer.
[3]Met-PCA, metastatic hormone refractory prostatic cancer. Ratio PCA/Met, ratio of expression of localized PCA over hormone refractory PCA.

TABLE 9

Meta-Analysis of cDNA Prostate Gene Expression Studies for Annexin Family Members

| Annexin | Present study | Welsh et al. | Luo et al. | Magee et al. | Summary p-Value |
| --- | --- | --- | --- | --- | --- |
| 6 | 0.024 | 0.0001 | 0.0001 | 0.026 | 0.0001 |
| 1 | 0.0001 | 0.031 | 0.0007 | 0.23 | 0.0001 |
| 2 | NA | 0.0001 | NA | 0.002 | 0.0001 |
| 11 | NA | 0.010 | NA | 0.6 | 0.17 |
| 7 | 0.25 | 0.48 | 0.38 | 0.088 | 0.20 |
| 4 | 0.33 | 0.023 | 0.0093 | 0.58 | 0.011 |
| 13 | 0.177 | NA | 1.00 | NA | 0.48 |
| 8 | 0.79 | NA | 0.104 | NA | 0.29 |

TABLE 10

Tissue Microarray Protein Expression for Annexins by Tissue Type

| Annexin | Benign | | Loc-PCA[2] | | Met-PCA[3] | | PCA/MET | p-value* |
| --- | --- | --- | --- | --- | --- | --- | --- | --- |
| | Count | Median | Count | Median | Count | Median | | |
| 1 | 37 | 2.59 | 360 | 2.45 | 162 | 1.46 | 1.68 | <0.001 |
| 2 | 57 | 3.95 | 82 | 3.62 | 214 | 1.47 | 2.46 | <0.001 |
| 4 | 23 | 3.65 | 357 | 3.96 | 141 | 1.57 | 2.52 | <0.001 |
| 7 | 26 | 3.77 | 350 | 3.97 | 126 | 1.32 | 3.01 | <0.001 |
| 11 | 23 | 4.00 | 360 | 3.99 | 163 | 1.30 | 3.01 | <0.001 |

*Kruskal Wallis Test.
1 BPH, benign prostatic hyperplasia.
[2]Loc-PCA, localized prostate cancer.
[3]Met-PCA, metastatic hormone refractory prostatic cancer.

EXAMPLE 14

Association of CtBP with Prostate Cancer

This example describes the expression of C-terminal binding proteins 1 and 2 (CtBP 1 and CtBP2) in prostate cancer. Microarray analysis, Western Blots, immunohistochemistry, and statistical analysis were performed as described in the above examples.

Figure 35:
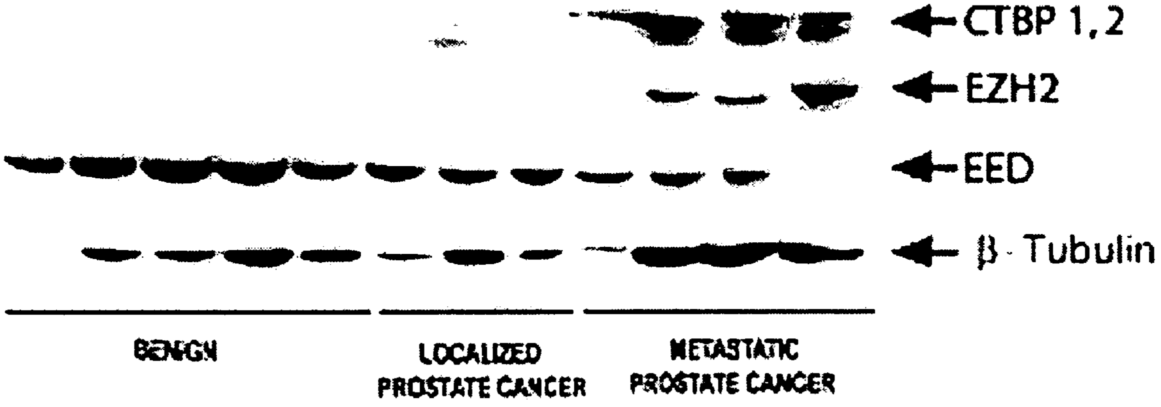
FIG. 35 shows the expression of CtBP proteins in PCA specimens.
Figure 38:
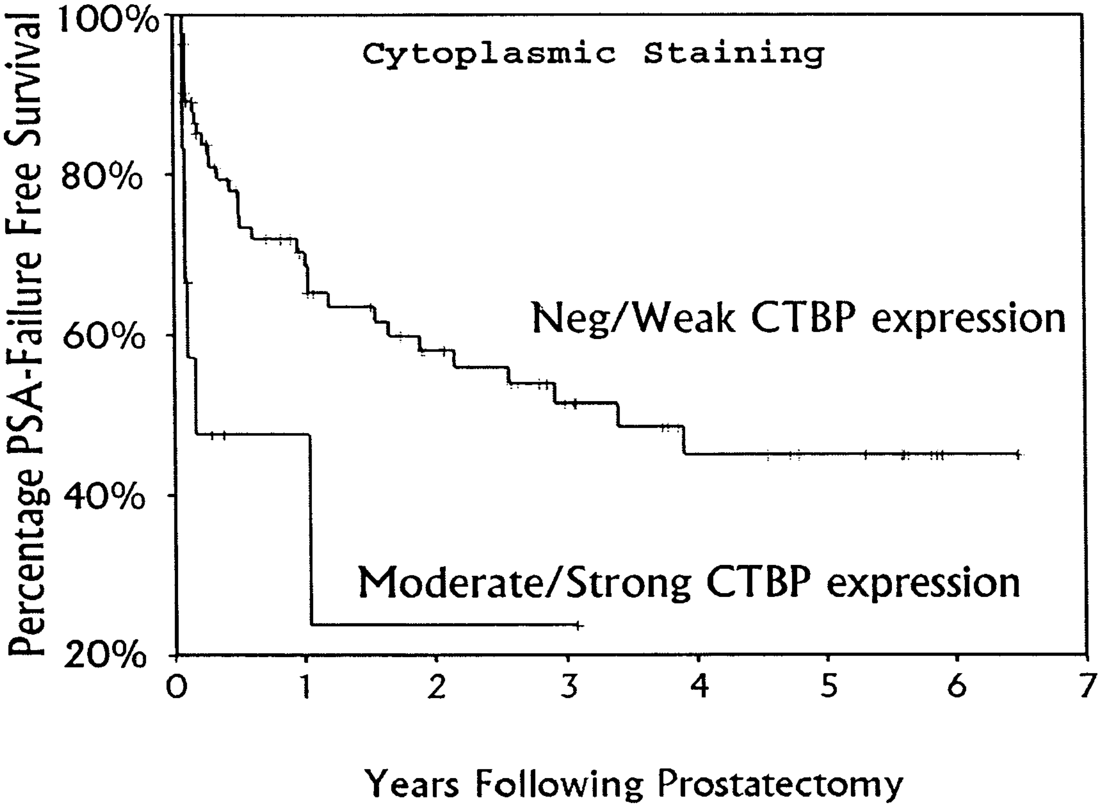
FIG. 38 shows a Kaplan-Meier Analysis of prostate cancer tissue microarray data.

The CtBP transcript was found to be up-regulated in metastatic prostate cancer (FIG. 38). Tissue extracts were used to validate this finding at the protein level using an antibody that recognizes CtBP1 and CtBP2 (Sewalt et al., Mol. Cell. Biol. 19:777 [1999]. The results are shown in FIG. 35. FIG. 35 shows the Expression of CtBP proteins in PCA specimens. Extracts from selected prostate specimens were assessed for expression of CtBP and PcG proteins by immunoblot analysis. Protein level was equalized in each extract before loading and blots were stained with Ponceau S to confirm equal loading. β-tubulin was used as a control protein.

Both CtBPs were over-expressed in metastatic prostate cancer relative to localized prostate cancer and benign tissue. EZH2 protein was also elevated in metastatic prostate cancer relative to localized prostate cancer or benign prostate (FIG. 35). EED, a PcG protein that forms a complex with EZH2, along with an un-related protein, β-tubulin, did not exhibit similar protein dysregulation. Thus, both transcriptional repressors (CtBP and EZH2) are mis-expressed in metastatic prostate cancer.

To determine in situ expression of CtBP, immunohistochemistry of prostate tissue sections were performed using prostate tissue microarrays. Benign prostatic epithelia exhibited exclusively nuclear staining consistent with CtBP's role as a transcriptional repressor. Both clinically localized and metastatic prostate cancer exhibited nuclear staining as well. Most of the metastatic prostate cancer cases and a fraction of the localized prostate cancer cases exhibited distinct cytoplasmic staining of CtBP.

Figure 36:
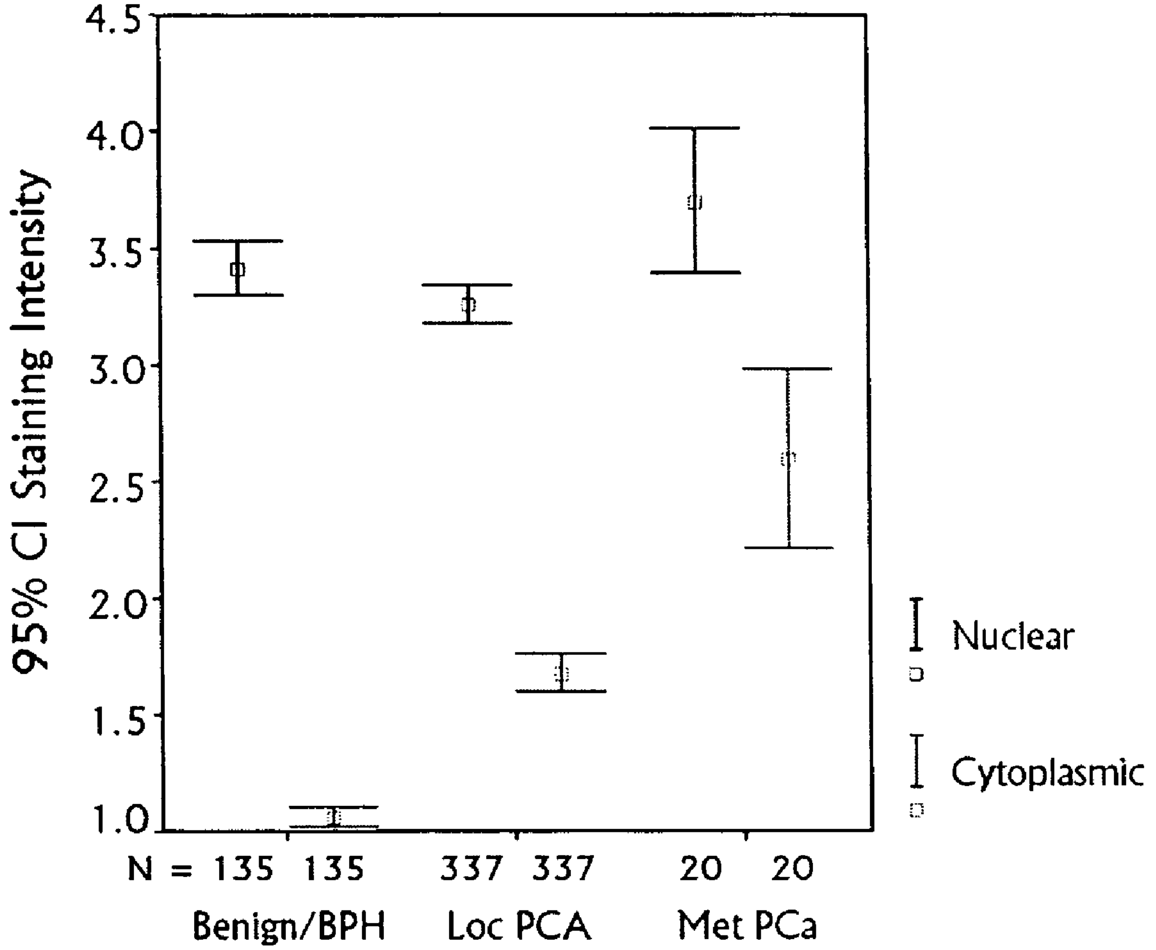
FIG. 36 shows tissue microarray analysis of CtBP in prostate cancer that suggests mis-localization during prostate cancer progression.
Figure 37:
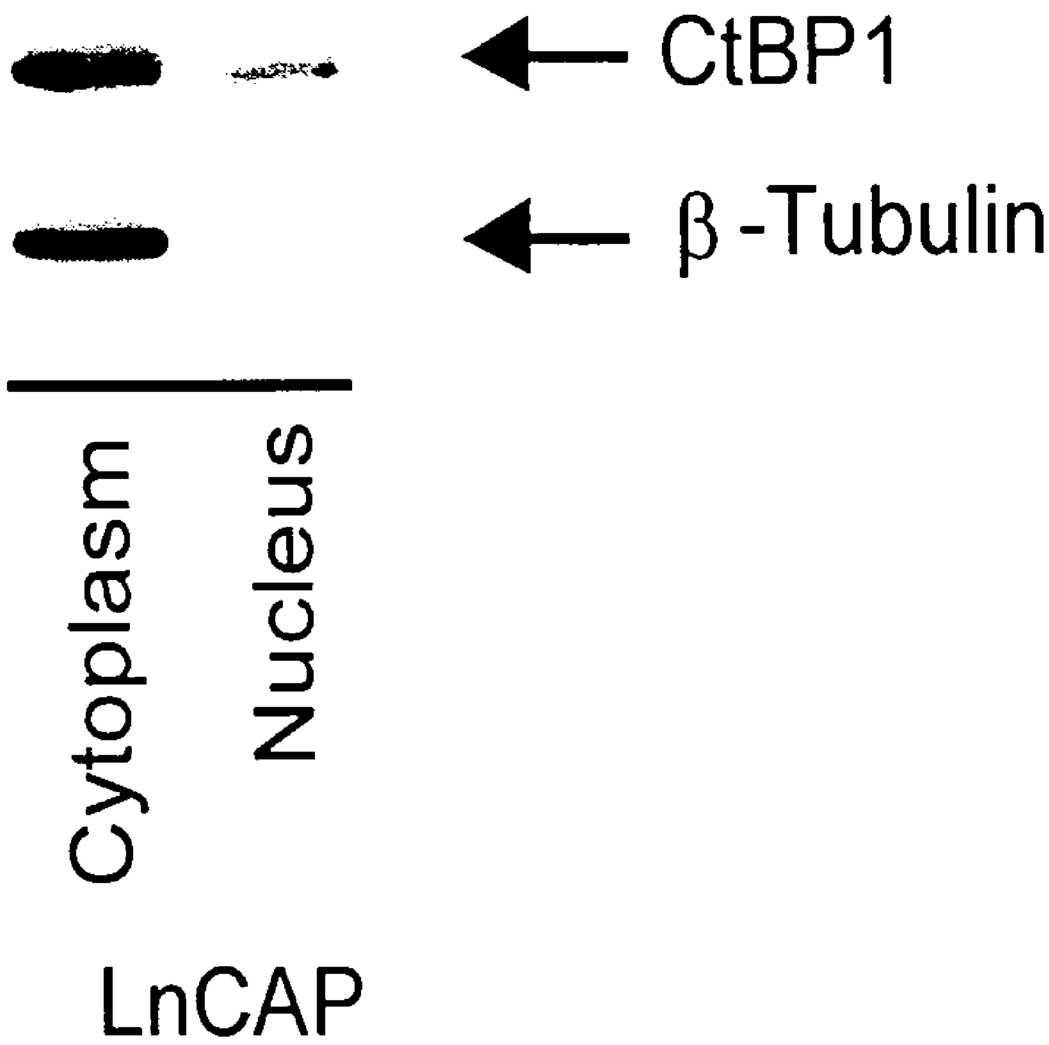
FIG. 37 shows the sub-cellular fractionation of LNCaP cells.

FIG. 36 shows tissue microarray analysis of CtBP in prostate cancer that suggests mis-localization during prostate cancer progression. The mean CtBP protein expression for the indicated prostate tissues and sub-cellular compartment is summarized using error bars with 95% confidence intervals. FIG. 37 shows the sub-cellular fractionation of LNCaP cells. The results show an increased level of CtBP 1 in the cytoplasm relative to the nucleus. CtBP2 is weakly expressed in the cell lines and is not easily apparent. β-tubulin, which is not expressed in the nucleus, is provided as a control. FIG. 38 shows a Kaplan-Meier Analysis of prostate cancer tissue microarray data. The results demonstrate that the presence of cytoplasmic CtBP may be associated with a poorer clinical outcome. The median follow up time for all patients was 1 year (range 2 month to 6.5 years). Over this follow up time, 38% of the patients developed a recurrence or PSA elevation greater than 0.2 ng/ml. Prostate tumors from 97 patients demonstrated near uniform nuclear protein expression for CTBP. Cytoplasmic expression was variable with 85 of 97 cases (88%) demonstrating weak cytoplasmic staining and 12 (12%) with moderate to strong CTBP expression. There was a significant association with increased CTBP cytoplasmic staining intensity and PSA recurrence or presence of recurrent disease following prostatectomy with a relative risk of 1.7 (Cox regression analysis p=0.034). The data presented demonstrates a Kaplan-Meier Analysis of outcome stratified by negative/weak cytoplasmic CTBP staining and moderate/strong staining. CTBP cytoplasmic expression predicted recurrence even when Gleason score was taken into account in a multivariable model, suggesting that CTBP is a prognostic predictor of poor outcome [Gleason relative risk 1.4 (p=0.005) and cCTBP rr 1.6 (p=0.042)].

CtBP has been shown to bind nitric oxide synthase (NOS), which is thought to shift the localization of CtBP from the nuclear compartment to the cytoplasmic compartment (Riefler et al., J. Biol. Chem. 276:48262 [2001]). Weigert and colleagues have proposed a cytoplasmic role for CtBP in the induction of Golgi membrane fission (Weigart et al., Nature 402:429 [1999]). To further support the preliminary immunohistochemical findings, LNCaP (metastatic) prostate cancer cells were fractionated and it was found that CtBP levels were higher in the cytosol relative to the nucleus (FIG. 38).

EXAMPLE 15

Methods of Characterizing Cancer Markers

This example describes exemplary methods for the characterization of new cancer markers of the present invention. These methods, in combination with the methods described in the above examples, are used to characterized new cancer markers and identify new diagnostic and therapeutic targets.

A. Determination of Quantitative mRNA Transcript Levels of Cancer Markers in Prostate Cancer Specimens In some embodiments, markers revealed to be over or under expressed in cancer microarrays (See e.g., Example 1 for a description of microarrays) are quantitated using real-time PCR (Wurmbach et al., J. Biol. Chem. 276:47195 [2001]).

In preferred embodiments, cDNA from over 100 prostate samples for archived cDNA samples and associated clinical data are available (See Example 1). The level of expression in the microarray is compared to those obtained by real-time PCR. To identify genes with dysregulation of expression, real-time PCR analysis of cDNA generated from laser-capture microdissected prostate cancer epithelia and benign epithelia is performed.

B. Detection of Mis-localized Transcripts

In some embodiments, in order to determine if a cancer marker normally present in the nucleus of a cell (e.g., a transcriptional repressor) is mis-localized to the cytoplasm (or other mis-locations) in cancer, the expression of the marker is examined in tissue extracts from preferably at least 20 benign prostate samples, 20 prostate cancer specimens, and 20 metastatic prostate specimens. Expression of the marker in benign prostate cell lines (RWPE), primary prostatic epithelial cells (Clonetics, Inc.) and a panel of prostate cancer cells including LNCaP, DU145, PC3, DUCaP, and VCaP cells is also examined. Once overall expression of prostate cell lines and tissues is established, the cellular localization of the marker is determined by 2 methods. In the first method, the cell and tissue extracts are fractionated into a nuclear fraction and a cytosolic fraction (NE-PER, Pierce-Endogen; Orth et al., J. Biol. Chem. 271:16443 [1996]). Quantitated protein is then analyzed by immunoblotting. Relative levels of cytosolic and nuclear cancer marker are determined by densitometry. To verify clean fractionation, antibodies to β-tubulin and PCNA (or lamin A) are used to assess cytosolic and nuclear fractions, respectively.

In the second method, cells are immunostained with antibodies to the cancer marker followed by detection using anti-rabbit FITC secondary antibody. Confocal microscopy (U of M Anatomy and Cell Biology Core Facility) is used to examine in situ localization of the cancer markers.

In some embodiments, mis-localization is further investigated by sequencing the gene in cells containing the mis-located transcript (e.g., metastatic cases) for mutations.

C. Correlation of Cancer Markers with Clinical Outcome

In some preferred embodiments, the association of expression or mis-localization of a cancer marker with clinical outcome is investigated. The ratio of total cancer marker to β-tubulin by immunoblot analysis of prostate cancer tissue extracts is first determined and associated with clinical outcome parameters. For markers suspected of being mis-localized in cancer (e.g., CtBP), the ratio of cytoplasmic marker to nuclear marker is next determined by immunoblot analysis of prostate cancer tissue extracts and associated with clinical outcome parameters. For example, it is contemplated that a high cytoplasmic/nuclear cancer marker ratio may portend a poor clinical outcome. In some embodiments (e.g., where a cancer marker is suspected of being mis-localized), immunohistochemistry of prostate cancer tissue microarrays is used to determine whether the presence of cytoplasmic marker correlates with poor clinical outcome. Tissue microarrays are prepared and performed as described in the above examples.

Briefly, high-density tissue microarrays (TMA) are constructed as previously described (Pyrrone et al, supra; Kononen et al., supra). Immunostaining intensity is scored by a genitourinary pathologist as absent, weak, moderate, or strong (or alternatively analyzed separately as for cytoplasmic and nuclear staining). Scoring is performed using a telepathology system in a blinded fashion without knowledge of overall Gleason score (e.g., tumor grade), tumor size, or clinical outcome (Pyrrone et al., supra). Tumor samples are derived from patients with clinically localized, advanced hormone refractory prostate cancer and naïve metastatic PCA. Cases of clinically localized prostate cancer are identified from the University of Michigan Prostate S.P.O.R.E. Tumor Bank. All patients were operated on between 1993 and 1998 for clinically localized prostate cancer as determined by preoperative PSA, digital-rectal examination, and prostate needle biopsy. All tissues used are collected with institutional review board approval. The advanced prostate tumors are collected from a series of 23 rapid autopsies performed at the University of Michigan on men who died of hormone refractory prostate cancer. The clinical and pathologic findings of these cases have been reported (Rubin et al., [2000], supra).

Statistical analysis of the array data is used to correlate the cancer marker protein measurements on the TMA with clinical outcomes, such as time to PSA recurrence and survival time. This analysis involves survival analysis methods for correlating the measurements with these censored response times. Kaplan-Meier curves are plotted for descriptive purposes. Univariate analyses is performed using the Cox model associating the biomarker with the survival time. In addition, multivariate Cox regression analysis is performed to test whether the biomarker adds any prognostic information over and above that available from known prognostic markers (i.e., Gleason score, tumor stage, margin status, PSA level before surgery).

D. RNA Interference

In some embodiments, RNA interference of cancer markers is used to investigate the role of the cancer marker in cell culture and well as for application as a therapeutic cancer treatment (See e.g., Example 8 for an example of RNA interference). 21-nucleotide RNAs (siACE-RNAi) are synthesized through a commercial vendor (Dharmacon Research, Inc.). RNA interference has been used in mammalian cells (Elbashir et al., Nature 411:494 [2001]). Several siRNA duplexes and controls are designed for each marker. The design of the siRNA duplexes uses criteria provided by Elbashir et al. (Elbashir et al., supra) and Dharmacon Research which include: starting approximately 75 bases downstream of the start codon, locating an adenine-adenine dimer, maintaining G/C content around 50%, and performing a BLAST-search against EST databases to ensure that only one gene is targeted. Multiple (e.g., two) siRNA duplexes are designed for each molecule of interest since whether the siRNA duplex is functional is a relatively empirical process. In addition, it is contemplated that using two siRNA duplexes may provide a combined "knock-down" effect. As a control, a "scrambled" siRNA, in which the order of nucleotides is randomized, is designed for each molecule of interest. Oligonucleotides are purchased deprotected and desalted. Upon arrival, the oligonucleotides are annealed to form a duplex using the manufacturer's provided protocol.

To test the efficacy of each siRNA duplex, prostate cell lines (RWPE, DU145, LnCAP, and PC3) are transfected with the OLIGOFECTAMINE reagent as described (Elbashir et al., supra). The cells are assayed for gene silencing 48 hrs post-transfection by immunoblotting with respective antibodies. A number of controls are included: buffer controls, sense siRNA oligo alone, anti-sense siRNA oligo alone, scrambled siRNA duplex, and siRNA duplexes directed against unrelated proteins. If significant silencing is not appreciated after single transfection, sequential transfection is performed and inhibition is monitored at later time points (i.e., 8 days later) as suggested by others (Breiling et al., Nature. 412: 51 [2001]). This may be necessary with proteins that have a long half-life.

In addition to the transient expression of siRNAs, a method for stable expression of siRNAs in mammalian cells is used (Brummelkamp et al., Science 296:550 [2002]). Prostate cancer cell lines are generated that express siRNA targeting cancer markers using the pSUPER system. Scrambled siRNA is used as a control. The cell lines facilitate downstream characterization of cancer markers that may be cumbersome using duplexes transiently. If inhibition of a specific cancer marker is found to be toxic to cells, the pSUPER cassette containing siRNA to the marker is cloned into an inducible vector system (e.g., Tet on/off).

E. Generation of Mutants

To study the function of cancer markers of the present invention, mutants of cancer markers are generated in eukaryotic expression vectors. myc-epitope tagged versions of cancer marker mutants are generated in both pcDNA3 and pcDNA3-ER (a modified estrogen receptor ligand binding domain). In the case of the ER constructs, the vectors produce an in-frame fusion protein with modified ER, thus generating a post-transcriptionally inducible vector (Littlewood et al., Nucleic Acids Res. 23: 686 [1995]). The ER-ligand domain is mutated and fails to bind endogenous estrogen, yet can be activated by 4-hydroxytamoxifen (Littlewood et al., supra). The ER-fusion proteins are inactivated in the absence of ligand presumably due to binding of proteins such as hsp90. In the presence of exogenously added 4-hydroxytamoxifen, ER-fusions become liberated. By using an inducible vector system, cell lines expressing a "toxic" or growth inhibitory version of a cancer marker can still be isolated.

Various N-terminal and C-terminal deletion mutants are generated that encompass function domains of the cancer marker (e.g., the PXDLS, dehydrogenase, and PDZ binding domains of CtBP; Chinnadurai, Mol Cell. 9: 213 [2002]). It is contemplated that some of the mutant versions of the cancer markers of the present invention act as dominant negative inhibitors of endogenous cancer marker function. Expression of epitope-tagged cancer markers and mutants is assessed by transient transfection of human embryonic kidney cells (using FUGENE) and subsequent Western blotting.

F. Establishing Stable Cell Lines Expressing Cancer Markers And Mutants

In some embodiments, cell lines stably expressing cancer markers of the present invention are generated for use in downstream analysis. FUGENE is used to transiently transfect prostate cell lines (RWPE, DU145, LnCAP, and PC3) with cancer markers and fusions or mutants using the above mentioned vectors and appropriate G418 selection. Prostate cell lines with varied expression levels of endogenous cancer marker protein are used. Both individual clones and pooled populations are derived and expression of cancer markers and mutants assessed by immunoblotting for the epitope tag. By also using an inducible system, clones expressing toxic versions of cancer markers or mutants can be isolated.

G. Cell Proliferation and Apoptosis Studies

In some embodiments, the role of cancer marker expression in prostate cell proliferation is investigated using a multi-faceted approach that includes 1. RNA interference, 2. transient transfection of cancer markers and potential dominant negative mutants, and 3. comparing stable transfectants of cancer markers and mutants. The following predictions are tested using these methods: 1. whether inhibition of cancer markers will block cell growth and 2. whether overexpression of cancer markers will enhance cell proliferation.

Cell proliferation is assessed by cell counting (Coulter counter) over a time course in culture by using the WST-1 reagent (Roche, Inc.), which is a non-radioactive alternative to [$^3$H]-thymidine incorporation and analogous to the MTT assay. The rate of incorporation of the DNA labeling dye bromodeoxyuridine (BrdU) will also be measured as described previously (Jacobs et al., Nature. 397:164 [1999]). Potential cell cycle arrest induced by siRNA or dominant negative inhibitors of is determined by conventional flow cytometric methods. By using stable cell lines that "activate" cancer markers and mutants in a 4-hydroxytamoxifen-dependent fashion, cell proliferation and cell cycle alterations are monitored in a highly controlled in vitro system. To confirm that overexpression or inhibition of cancer markers does not activate the apoptosis pathway, several assays are used including propidium iodide staining of nuclei, TUNEL assay and caspase activation.

If a cancer marker is found to be a regulator of cell proliferation in prostate cells, studies are designed to address how components of cell cycle machinery are modulated by the cancer marker. Thus, in order to study cancer marker mediated effects on the cell cycle machinery of prostate cells, cancer marker functions are modulated with the above mentioned tools (i.e., siRNA, dominant negative inhibition, etc.) and the expression levels (transcript and protein) of cyclins (cyclin D1,E,A), cyclins-dependent kinases (cdk2, cdk4, cdk6) and cyclin-dependent kinase inhibitors (p21CIP1, p27KIP1, p45SKP2, p16INK4) are monitored.

H. Cell Adhesion and Invasion Assays

If a cancer marker is suspected of altering cell adhesion (e.g., the transcriptional repression of an epithelial gene program such as E-cadherin), the methods described above are used to investigate whether over-expression of the cancer marker causes increased or decreased cell adhesion. Adhesion to extracellular matrix components, human bone marrow endothelium (HBME) as well as to human umbilical vein endothelial cells (HUVEC) is tested. Cancer markers are further tested for their ability to modulate invasion of PCA.

Known methods are used in these studies (Cooper et al., Clin. Cancer Res. 6:4839 [2000]). Briefly, snap-apart 96-well tissue culture plates are coated with crude bone and kidney matrices. Plates are incubated overnight at room temperature under sterile conditions and stored at 4° C. until needed. Assay plates are also coated with extracellular matrix components (e.g., human collagen I, human fibronectin, mouse laminin I) and human transferrin at various concentrations according to the manufacturer's instruction (Collaborative Biomedical Products, Bedford, Mass.). Endothelial cells (HBME or HUVEC) are seeded onto bone matrices or plastic substrata at a concentration of 900 cells/μl and grown to confluence. Tumor cells are removed from the flask by a 15-20 minute treatment with 0.5 mM EDTA in Hank's balanced salt solution. Once the EDTA solution is removed, the cells are resuspended in adhesion medium (e.g., minimum essential medium (MEM) with 1% bovine serum albumin (BSA) supplemented with 10 uCi $^{51}$Cr sodium salt (NEN, Boston, Mass.)) for 1 hour at 37° C. Cells are then washed three times in isotope free media and $1\times10^5$ radio-labeled tumor cells are resuspended in adhesion media and layered upon a confluent layer of endothelial cells for 30 min at 37° C. In addition, radiolabeled tumor cells are applied to crude bone matrices. Again, plates are washed three times in phosphate buffered saline and adhesion is determined by counting individual wells on a gamma counter. Cell adhesion is reported relative to the adhesion of controls (PC-3 cells on plastic), which are set to 100.

Cell invasion assays are performed using a classic Boyden chamber assay. Both strategies to inhibit and overexpress cancer markers are evaluated. Previous reports have correlated increased cell migration in a Boyden Chamber system with increased invasive properties in vivo (Klemke et al., J. Cell Biol. 140:61 [1998]). Commercially available 24-well invasion chambers are used (e.g., BD biosciences, Chemicon International).

I. Transcriptional Suppression in Prostate Cancer Cells

In some embodiments, the effect of cancer markers on gene silencing in prostate cells is assessed. Gene silencing is assayed in several ways. First, gene expression alterations induced by transient transfection of cancer markers and mutants in prostate cell lines (RWPE, DU145, LnCAP, and PC3) is assayed using FUGENE. Twelve to 48 hours after transfection, cells are harvested and a portion is processed to confirm expression of the transfectants by immunoblotting. Using vector-transfected cells as a reference sample, total RNA from transfected cells is then assessed on 20K cDNA microarrays.

In addition to transient transfections, stable cell lines overexpressing cancer markers and cancer marker mutants are generated. Patterns of gene expression from cancer marker and cancer marker mutant expressing cell lines are compared to vector-matched controls in order to identify a gene or group genes that is repressed by a given cancer marker. The present invention is not limited to a particular mechanism. Indeed, and understanding of the mechanism is not necessary to practice the present invention. Nonetheless, it is contemplated that genes identified as repressed by a given cancer marker will be increased (de-repressed) upon knock-down of the cancer marker (e.g., by siRNA inhibition).

EXAMPLE 16

AMACR as a Urine Biomarker for Non-Invasive Detection of Prostate Cancer

This example describes the investigation of AMACR as a diagnostic marker in biofluids.

A. Experimental Methods

Subjects and Samples

This study was approved by the Institutional Review Board (IRB) of the University of Michigan Medical School. At the time of diagnosis, serum (n=22), plasma (n=11) and urine (n=110) samples from biopsy-proven clinically localized prostate cancer patients were collected with written informed patient consent. The biofluids were stored in the University of Michigan Prostate S.P.O.R.E Tissue/Serum Bank. The average age of the prostate cancer patients in this study was 58.06±0.63. Clinical and pathology data from patients with biopsy-proven clinically localized prostate cancer used in this study is provided in FIG. 39 and the samples were obtained prior to prostatectomy at varying times after biopsy. As controls, urine samples from 116 control male subjects (average age 57.85±0.1) with no known history of prostate cancer were collected in the University of Michigan Clinical Pathology laboratories.

The urine samples were stored at 4° C. and concentrated within two days using a Biomax Ultrafree concentrator (5000 MW cutoff, Millipore Corporation, Bedford, Mass.) at 4° C. Multiple freeze-thaws of un-concentrated urine was avoided as a decrease in AMACR immunoreactivity of urine in these cases was observed. Protein content in each urine sample was estimated using Bradford reagent as per manufacturers instructions (Bio-Rad laboratories, Hercules, Calif.). The concentrated urine samples were frozen at −20° C. until use.

Prostatic fluids (n=13) were obtained ex vivo from resected prostates from prostate cancer patients in accordance with the IRB of Brigham and Women's Hospital. Within minutes of prostate removal, the gland was gently massaged ex vivo and the excretions collected from the prostatic urethra by aspiration using a 200 μl pipette. Care was taken not to damage the urethral lining or prostate tissue. The specimen (between 15 and 100 μl) was then snap-frozen in liquid nitrogen and stored at −20° C.

Antibody Production

Polyhistidine-tagged AMACR was purified from *Escherichia coli* containing HIS-AMACR plasmid in pET 28a(+) vector in a denatured state by using standard nickel affinity chromatography as per the manufacturer's instructions (Qiagen, Chatsworth, Calif.). The denatured protein was confirmed for purity by silver stain and antibodies were custom produced in rabbits (Proteintech Group Inc, Chicago, Ill.). The antiserum was obtained after four boosters, characterized by ELISA, and used for immunoblot analyses in this study.

Immunoblot Analysis

Serum, plasma, and prostatic secretions (each 1:10 diluted) or urine (20 μg total protein) were electrophoresed on a 10% pre-cast Bis-Tris gel (Invitrogen, Carlsbad, Calif.). The electrophoresis was carried out until the 39 kDa alcohol dehydrogenase (Seablue marker, Invitrogen, Carlsbad, Calif.) reached the end of the gel. The gel was then transferred onto nitrocellulose (in case of serum, plasma and prostatic fluid samples) or PVDF (urine samples) membranes using semi-dry transfer method (Bio-Rad, Hercules, Calif.). The blots were blocked in TBS (Bio-Rad, Hercules, Calif.) containing 5% non-fat milk, 5% normal goat serum (Sigma, St Louis, Mo.) and 0.1% Tween-20 (Sigma, St Louis, Mo.). The blots were probed with anti-AMACR antibodies at a dilution of 1:10,000. To test the specificity of the immunoreactivity, anti-AMACR antisera was quenched with either recombinant AMACR-MBP (Fusion protein of AMACR and Maltose Binding Protein) or MBP (New England BioLabs, Inc., Beverly, Mass.) at a final concentration of 10 g/ml and used as described above. Blots were washed for 30 minutes with TBS containing 0.1% tween-20 (Sigma, St Louis, Mo.) and then probed with 1:10,000 dilution of HRP-conjugated secondary antibody raised in goat (Southern Biotechnologies, Birmingham, Ala.) for 1 h at RT. The blots were washed as above and developed by ECL-Plus (Amersham Biosciences, Piscataway, N.J.).

Scoring of AMACR Reactivity

AMACR generally migrates at around 45 kDa. The intensity of this band in each sample was scored visually by a researcher who was unaware of the diagnosis of samples and the pattern of loading in the gels. An AMACR positive control sample (LNCaP total cell extract) was used for all immunoblot experiments. While scoring, the band in the sample lanes with highest reactivity was assigned a score of 4 (highest level of reactivity) while absence of a band was scored 0 (non reactivity). Intermediate band intensities were assigned as follows: weak (score=1), intermediate (score=2), and high (score=3). In all the immunoblots, the AMACR band in the LNCaP lane was scored as 4.

Statistical Analysis

All statistical analysis was performed with SPSS 11.1 (SPSS Inc. Chicago, Ill.). A graphical representation using bar graphs was used to show the distribution of AMACR-reactivity in both the control and prostate cancer sample from the urine cohort. Student's t test (two-sided) was used to test for statistically significant differences in AMACR reactivity between patients with prostate cancer and control subjects. No adjustment for multiple testing was made during the analysis. Associations between AMACR reactivity (as assessed by immunoblotting) and various clinical and pathology parameters were determined using Pearson's Correlation Test. The mean values for AMACR reactivity were presented with 95% confidence intervals. P values less than or equal to 0.05 were considered statistically significant. Receiver operating characteristic (ROC) curves were used to assess the sensitivity and specificity of urine-associated AMACR to detect prostate cancer. A cutoff point (AMACR reactivity>1.0) in the ROC curve was chosen at which urine-associated AMACR was best able to discriminate between prostate cancer and control groups.

B. Results

Figure 40:
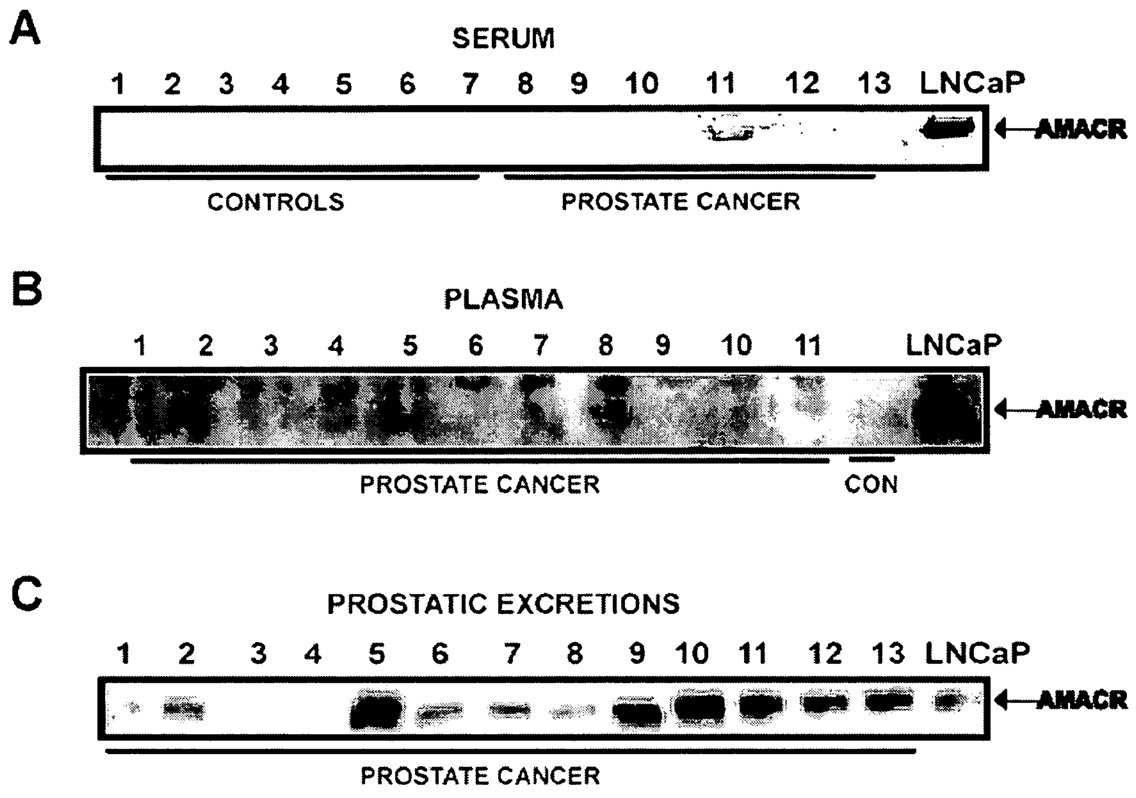
FIG. 40 shows evaluation of AMACR protein levels in serum, plasma and prostatic excretions.

Several biofluids were examined for the presence of AMACR protein. As a pilot study, immunoblot analysis of sera and plasma samples from prostate cancer patients and control subjects was performed. AMACR was detected in only a small fraction of prostate cancer sera analyzed (2 out of 22, FIG. 40A). Similarly, only 1 out of 11 plasma samples from prostate cancer patients showed AMACR reactivity (FIG. 40B). Since AMACR was initially reported to be up-regulated in prostate cancer epithelia relative to benign epithelia, the presence of this protein in prostatic excretions was assessed. Thus, prostatic excretions obtained ex vivo from prostate glands that were resected from prostate cancer patients following radical prostatectomy were analyzed. A total of 13 prostatic excretions were analyzed by immunoblot analysis and, all exhibited AMACR immunoreactivity (FIG. 40C).

Figure 41:
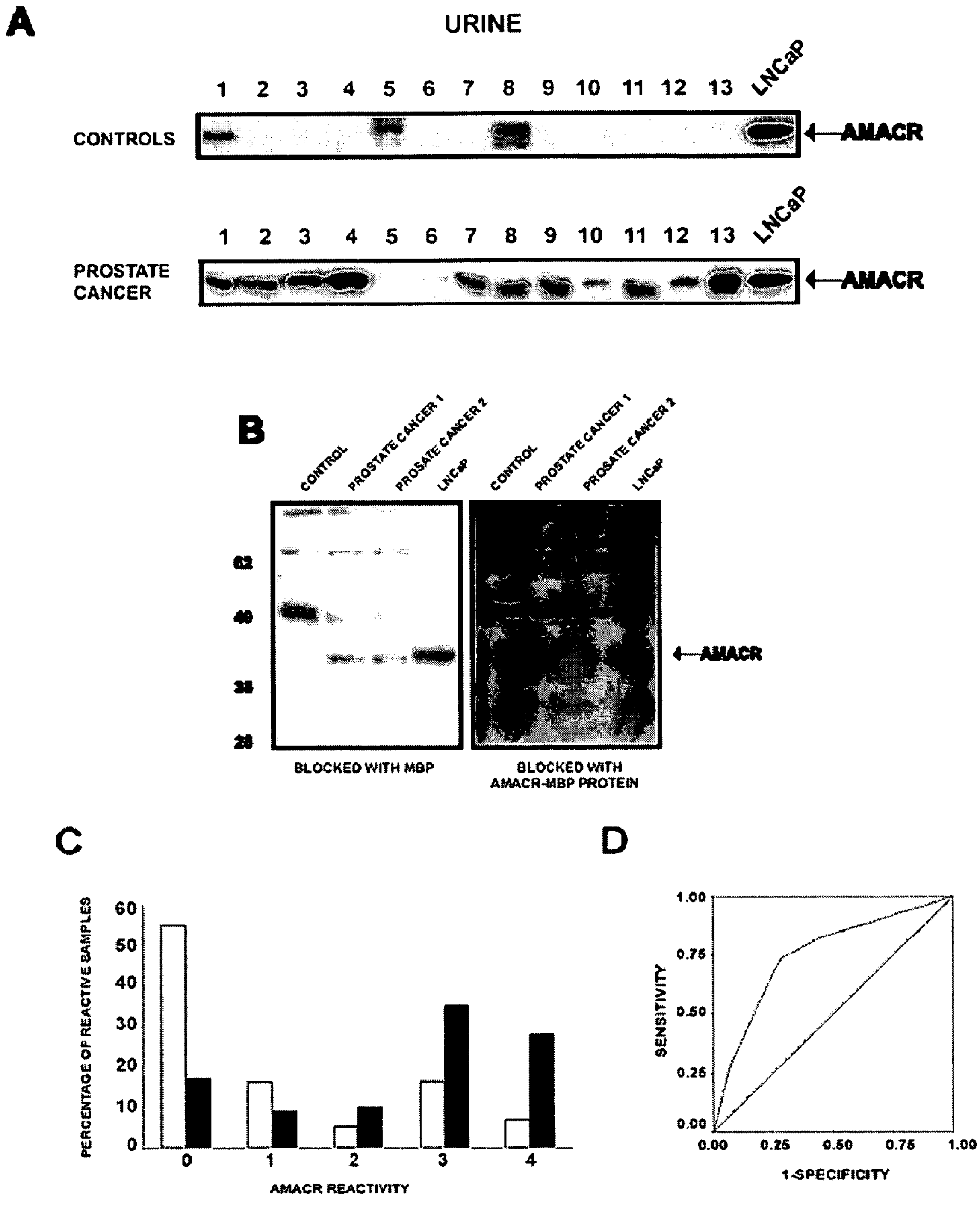
FIG. 41 shows data for the use of AMACR as a urine biomarker for the detection of prostate cancer.

Having detected AMACR in prostatic excretions, the possibility of detecting this antigen in the voided urine of prostate cancer patients was explored. AMACR immunoblot analysis was performed on urine samples from 226 individuals including 110 biopsy-proven clinically localized prostate cancer patients and 116 control subjects by immunoblotting. FIG. 41A shows a representative AMACR immunoreactivity pattern where in 11 out of 13 prostate cancer urine and 3 out of 13 control urine samples showed AMACR reactivity. To confirm the specificity of the AMACR immunoreactive band, AMACR anti-sera was presaturated (or quenched) with excess of either recombinant AMACR-MBP or as a control, MBP alone.

By immunoblot analysis, levels of AMACR in urine were then scored in a blinded fashion based on band intensities. Scoring ranged from 0 to 4, with 0 representing no band present and 4 representing a very strong band (see Experimental Methods above). The mean score for urine-associated AMACR reactivity in prostate cancer patients (mean=2.48, 95% CI=2.21 to 2.75) was significantly greater ($p<0.0001$) than in the control subjects (mean=1.03, 95% CI=0.78 to 1.29). A significantly greater percentage of prostate cancer urine samples (73.7%) had AMACR reactivity scored in the range of 2-4 in contrast to controls (28.5%) (FIG. 41C). A receiver operator characteristic (ROC) curve was generated for AMACR reactivity and an optimum cutoff point was selected at the region where the slope of the curve had the highest value (FIG. 41D). At this cutoff point, AMACR had the best discriminatory power in distinguishing between urine from prostate cancer patients and control populations (AUC: 0.753, 95% CI=0.688 to 0.817, p<0.0001) representing a sensitivity and specificity of 73.6% and 71.6%, respectively (FIG. 41D). Overall, 81 out of 110 urine samples from patients with clinically localized prostate cancer and 33 out of 116 control samples were considered positive for AMACR reactivity. In subjects with an AMACR reactivity greater than 1.0, the odds ratio of having prostate cancer was 7.03 (95% CI=3.91 to 12.61; p<0.00001). No statistically significant associations were found between AMACR reactivity in the urine of prostate cancer patients and various clinical and pathologic parameters, including PSA level at time of diagnosis, Gleason grade, pathologic stage, or gland weight (Table 11).

TABLE 11

Association between AMACR reactivity and various clinical and pathology parameters

| Variable | Analysis | PSA | Gleason Score | Pathological Stage | Prostate Weight |
|---|---|---|---|---|---|
| AMACR reactivity | Pearson Correlation | −0.105 | −0.163 | −0.155 | 0.099 |
| | p value | .325 | .120 | .178 | .389 |

Note:
the correlation was considered significant if p value ≦0.05.

EXAMPLE 17

Decreased AMACR Expression in Localized Prostate Cancer is Associated with An Increased Rate of Biochemical Recurrence and Cancer Specific Death This example describes using a semi-automated quantitative analysis of AMACR immunohistochemical staining that allows the determination of critical cutoffs to stratify patients into risk groups for biochemical failure or prostate cancer specific death.

A. Experimental Methods

Patient Cohorts

Surgical Cohort

This cohort consisted of 204 patients from the University of Michigan (Ann Arbor, Mich.), who underwent radical retro pubic prostatectomy as a primary therapy (i.e., no preceding hormonal or radiation therapy) for clinically localized prostate cancer between 1994 to 1998. Clinical and pathology data for all patients were acquired with approval from the Institutional Review Board at the University of Michigan. Clinical data regarding this cohort has been separately reported (Nelson et al., Urol. Oncol. 21:213-8 [2003]; Nelson et al., Urology 59:740-5; discussion 745-6 [2002]). A summary of the patient demographics is presented in Table 12. Disease progression was defined as a serum PSA increase greater than 0.2 ng./ml. after radical prostatectomy. Patients were considered censored if they have not had a PSA biochemical failure at the last follow up time evaluated for that individual.

Watchful Waiting Cohort

This cohort is the largest population-based watchful waiting cohort, and consists of patients from Örebro, Sweden with clinically localized prostate cancer, who underwent watchful waiting. This cohort, initially described in 1989 (Johansson et al., Lancet 1:799-803 [1989]), consists of all men who presented with voiding symptoms referred to the urology department to rule out the diagnosis of prostate carcinoma. From March 1977 through September 1991, 1,230 patients were diagnosed with prostate cancer in Örebro County. Among these, 253 were diagnosed through transurethral resection of the prostate (TURP) and these represent the study base for the watchful waiting cohort. None were diagnosed by PSA screening. For the current investigation, cases were excluded due to insufficient amount of tumor (N=39), inadequate immunohistochemistry (N=13), inability to confirm the original diagnosis of cancer (n=9), or initially presenting for cystoprostatectomy due to bladder cancer (n=1). Thus, data from 188 watchful waiting cases were included in this study.

The baseline evaluation of these patients at diagnosis included physical examination, chest radiography, intravenous pyelogram, bone scan and skeletal radiography (if needed). Lymph Node staging was not performed. In accordance with standard practices at that time in Örebro, these patients were initially followed expectantly ("watchful waiting"). Patients were treated with androgen deprivation therapy only if they exhibited symptoms. Patient follow up included clinical examinations, laboratory tests and bone scans every 6 months during the first 2 years following the initial prostate cancer diagnosis and subsequently every 2 years. Medical records of all deceased patients were reviewed to determine cause of death. As a validation, the classification of cause of death was compared with that recorded in the Swedish Death Register. Thus far, agreement on cause of death has been over 90%, with no evidence of systematic over- or under-estimation of prostate cancer as cause of death. As of March 2003, 36 (19.2%) of patients in this cohort died of prostate cancer. The remaining patients are considered censored having either died of other causes (126 or 67.0%) or were still alive without disease at time of last follow up (26 or 13.8%). No patients were lost to follow up.

In order to ensure a uniform review of the pathology, one of the study pathologists reviewed all cases from both series. Uniform pathology review included Gleason grading, an estimate of overall tumor involvement (tumor burden per tissue samples evaluated), and tumor type (peripheral zone versus transition zone). Although there are no strict criteria for distinguishing a transition zone tumor from a peripheral zone tumor that has invaded the transition zone, the transition zone tumors were defined for the sake of this analysis as tumors with Gleason score of 6 and below with a well-circumscribed growth pattern. For staging and grading of the tumors, the TNM-classification from 1992 (Barry et al., N. Engl. J. Med. 344:1373-7 [2001]) and the WHO classification (Kattan et al., J. Natl. Cancer Inst. 90:766-71 [1998]) were used. Of the 188 patients in the watchful waiting cohort, 75(39.9%) were stage T1a and 113 (60.1%) were found to have T1b. The mean age at diagnosis was 73 years.

Tissue Microarray Construction

The TMAs from both patient cohorts were assembled using the manual tissue arrayer (Beecher Instruments, Silver Spring, Md.) as previously described (Rubin et al., JAMA 287:1662-70 [2002]). Tissue cores from circled areas were targeted for transfer to the recipient array blocks. Three to five replicate tissue cores were sampled from each patient sample. In all cases, the dominant prostate cancer nodule or the nodule with the highest Gleason pattern was sampled for the tissue micorarray. The 0.6 mm diameter TMA cores were each spaced at 0.8 mm from core-center to core-center. Six tissue microarray blocks with an average of 480 cores per block were used for this study. All blocks contained benign prostate tissue as well as prostate cancer. Each block was assembled without prior knowledge of associated clinical or pathology staging information. After construction, 4 μm sections were cut and stained with hematoxylin and eosin on the initial slides to verify the histological diagnosis. All data is maintained on a relational database as previously described (Manley et al., Am. J. Pathol. 159:837-43 [2001]).

Immunohistochemistry

Pre-treatment conditions and incubations were worked out for AMACR immunostaining using the commercially available monoclonal antibody directed against AMACR (p504s, Zeta Co., CA). Pre-treatment included placing the slide in a 6.0 pH citrate buffer and microwaving for 30 minutes. Primary p504s antibody was incubated for 40 minutes at room temperature. Secondary anti-mouse antibodies applied for 30 minutes and the enzymatic reaction was completed using a streptavidin biotin detection kit (Dako developing system, Dako, Carpenteria, Calif.) for 5 minutes. Optimal primary antibody concentration was determined by serial dilutions, optimizing for maximal signal without background immunostaining.

Manual Scoring of AMACR

All TMA cores were assigned a diagnosis (i.e., benign, atrophy, PIN, or prostate cancer) by the two study pathologists. Prostate cancer samples were only included in the analysis if both reviewers agreed that it was cancer. All manual scoring was performed on an internet-based image evaluation tool that employs zoomable TMA images generated by the BLISS Imaging System (Bacus Lab, Lombard, Ill.). The AMACR protein expression was evaluated using a categorical scoring method ranging from negative to strong staining intensity as previously reported (Rubin et al., JAMA 287:1662-70 [2002]).

Semi-Automated Quantitative Image Analysis of AMACR

A semi-automated quantitative image analysis system, ACIS II (Chromavision, San Juan Capistrano, Calif.), was used to evaluate the same TMA slides from both cohorts. The ACIS II device consists of a microscope with a computer controlled mechanical stage. Software is used to detect the brown stain intensity of the chromogen used for the immunohistochemical analysis and compare this value to blue counterstain used as background. Theoretical intensity levels range from 0-255 chromogen intensity units (IU). In pilot experiments for this study, the reproducibility of the ACIS II system was tested and confirmed by scoring several TMAs on separate occasions. The correlation coefficient for these experiments was $r^2=0.973$. Because of tissue heterogeneity, one of the study pathologists electronically circled the areas of histologically recognizable prostate cancer using the ACIS II software for each TMA core. This process ensured that AMACR intensity measurements were from prostate cancer tissue only and not the surrounding benign glands or stroma.

Statistical Analysis

AMACR intensity readings were obtained for each of the TMA slides separately and were then normalized within each array before combining the data for analysis. After several pilot studies, it was determined that normalization of the data was preferred. Experiment-to-experiment variation was observed. Therefore, the AMACR intensity readings were normalized for each TMA core on a given array prior to merging all of the data for the final analysis. Preferred for the normalization process was the presence of approximately equally distributed numbers of normal and cancer samples on each TMA. AMACR staining intensity readings for each TMA core from a given array were subtracted by the mean intensity for that same array and then divided by the standard deviation:

$$Intensity_{ij}^{Normalized} = \frac{Intensity_{ij} - \text{mean}(Intensity_i)}{sd(Intensity_i)},$$

where j=1, . . . , $n_i$ ($n_i$ is the total number of cores on $TMA_i$). As a result, each of the normalized arrays had mean score of 0 and standard deviation equal to 1. Data were then combined using this normalized scale.

In order to determine an optimal cutpoint for AMACR, a modification of the method of regression trees (Breiman et al., Kluwer Academic Publishers; p. 368 [1984]) applied to censored data was used (LeBlanc et al., Biometrics 48:411-425 [1992]). The regression tree method is an estimation procedure that selects a cutpoint for AMACR based on optimizing a discriminating measure using the censored failure time outcome. The method employs a likelihood criterion to optimize the cutpoint, and assumes that the cost of a false positive and false negative are equal. An adjusted analysis was performed for determining a cutpoint, which involved obtaining Martingale residuals (Themeau et al., Biometrika 77:147-160 [1990]) at the first stage by adjusting for potential confounders and then applying the regression tree algorithm to find a cutpoint. The adjusted method allowed for the cutpoint to be determined accounting for clinical parameters.

The cutpoints for the AMACR intensity scores had a theoretical range between 0 and 255 IU. Using the regression tree method, the cutpoint that best differentiated PSA biochemical failure in the 204 patients from the PSA screened surgical series was determined. A similar process was repeated for the Örebro watchful waiting cohort (n=188 cases) using cancer specific death as the endpoint.

Once the cutpoints were determined for each cohort, the cutpoint was then applied to the other cohort. For example, the optimal cutpoint derived using the surrogate endpoint (PSA failure) was tested on the watchful waiting cohort to determine if it would predict a true endpoint (prostate cancer specific death). The cutpoint derived using prostate cancer specific death as the endpoint was then tested on the surgical series to see if it would predict PSA biochemical failure. Cox proportional hazards regression analysis was further employed to examine the association between the AMACR cutpoint and time to prostate cancer outcome, taking into account other clinical parameters.

B. Results

A summary of the patient demographics of the testing cohort from the University of Michigan is presented in Table 12.

TABLE 12

Prostate Cancer Patient Demographics: Men with Clinically Localized Prostate Cancer Treated by Radical Prostatectomy (n = 204) Stratified by Prostate Specific Antigen Biochemical Recurrence Status

| | PSA Recurrence | | |
|---|---|---|---|
| Parameter | Censored (n = 156) | Recurred (n = 48) | p-value |
| Age, years | 60 | 61 | 0.61 |
| DRE, % | | | |
| Negative | 61.5 | 21 43.8 | 0.03 |
| Positive | 38.5 | 27 56.3 | |
| Mean PSA, ng/ml | 7.2 | 12.7 | 0.0002 |

TABLE 12-continued

Prostate Cancer Patient Demographics: Men with Clinically Localized Prostate Cancer Treated by Radical Prostatectomy (n = 204) Stratified by Prostate Specific Antigen Biochemical Recurrence Status

| Parameter | PSA Recurrence Censored (n = 156) | Recurred (n = 48) | p-value |
|---|---|---|---|
| RP Gleason Score, % | | | <0.0001 |
| 5 | 3.8 | 12.1 | |
| 6 (3 + 3) | 44.2 | 12.5 | |
| 7 (3 + 4) | 42.3 | 47.9 | |
| 7 (4 + 3) | 7.7 | 27.1 | |
| 8 (4 + 4) | 0.6 | 6.3 | |
| 9 | 1.3 | 4.2 | |
| Tumor Size, % | | | 0.0001 |
| ≦2 cm. | 89.7 | 66.7 | |
| >2 cm. | 10.3 | 33.3 | |
| EPE | | | <0.0001 |
| Negative | 84.6 | 50 | |
| Positive | 15.4 | 50 | |
| SM Status | | | <0.0001 |
| Negative | 79.5 | 41.7 | |
| Positive | 20.5 | 58.3 | |
| AMACR (−1.11 cutoff) | | | 0.0002 |
| Low | 32.1 | 62.5 | |
| High | 67.9 | 37.5 | |

^ Prostate Specific Antigen (PSA) biochemical recurrence was defined as an elevation of serum PSA of greater than 0.2 ng./ml following surgery.
* P-value was calculated by Wilcoxon rank sum test for radical prostatectomy (RP) Gleason score and pathologic stage, by Chi-square test for surgical margin status (SM), tumor size (diameter), digital rectal examination results (DRE), and extraprostatic extension (EPE), by two-sample t-test for pre-treatment prostate specific antigen (PSA) serum levels, Age, and gland weight.

Manual Evaluation of AMACR

AMACR protein expression was evaluated manually by the study pathologist and graded on a 4-tiered scale. A significant difference was found in intensity between prostate cancer (mean score=3.14/4) and benign prostate epithelium (mean score=1.3/4) with a mean difference of 1.84 (ANOVA Post-hoc Scheffé Analysis p<0.00001). In the surgical series, no significant associations between AMACR intensity scores and biochemical failure were observed, consistent with previous observations (Rubin et al., JAMA 287(13):1662-70 [2002]).

Semi-Automated Quantitative AMACR Expression Analysis

Figure 42A:
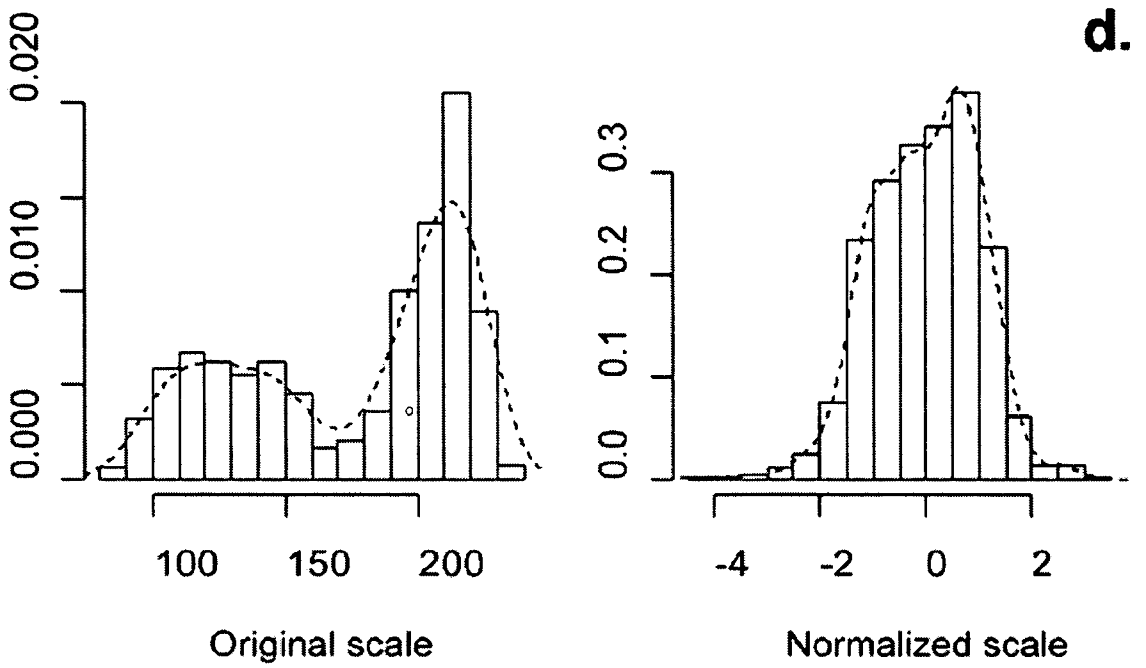
FIG. 42A shows two histograms demonstrating the distribution of scores for the raw (left, original scale) and normalized AMACR analysis.
Figure 42B:
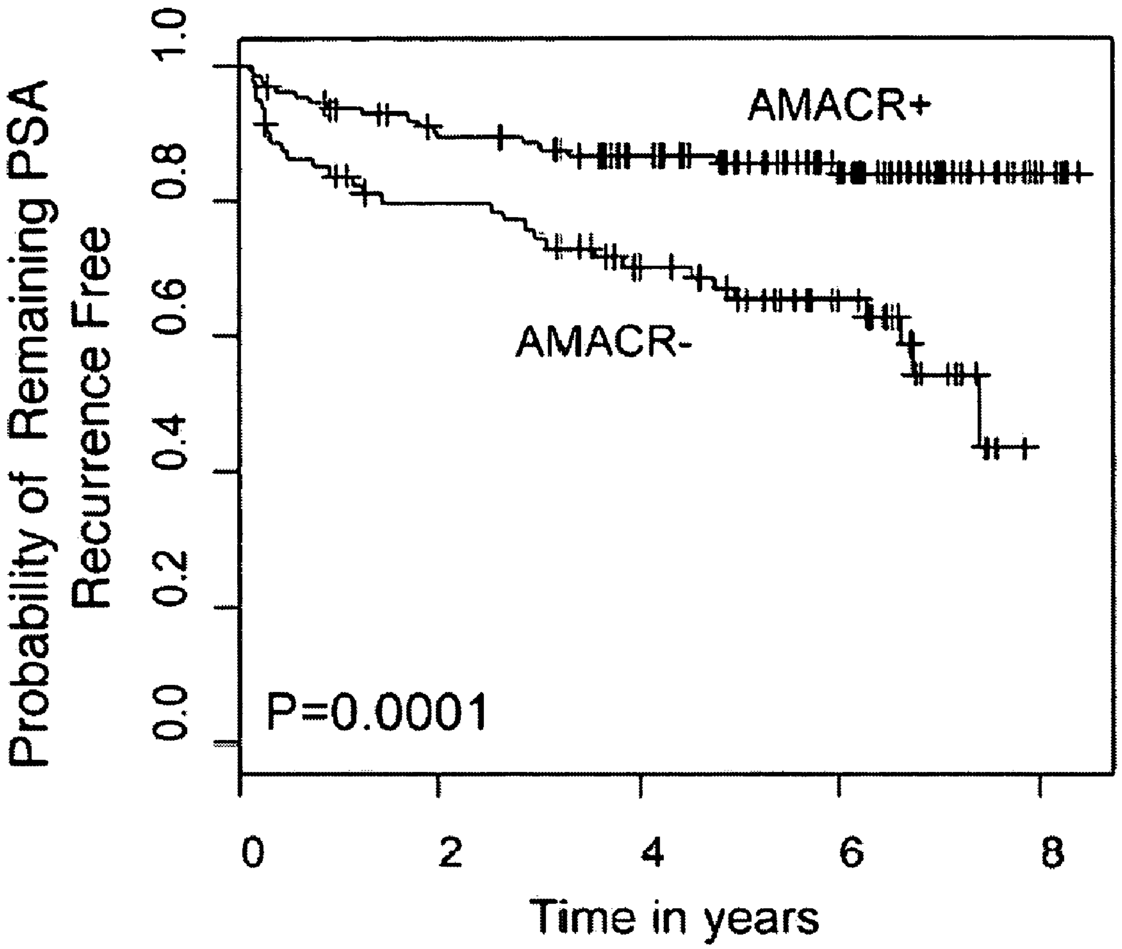
FIG. 42B shows that lower AMACR intensity was associated with prostate cancer progression as determined by PSA biochemical failure.

In the surgical series, lower AMACR intensity was associated with a greater likelihood of PSA biochemical failure (Tables 13 and 14). Using the adjusted regression tree method, a dichotomous cutpoint was established for AMACR intensity of 1.11 SD (i.e. samples with minimum AMACR intensity of 1.11 SD below that of the mean), wherein 37.5% of patients with AMACR intensity scores below the cutpoint had PSA biochemical failure compared to 14.5% of patients with AMACR intensity scores above the cutpoint (P=0.0002). This univariate association is visually illustrated by Kaplan-Meier analysis (FIG. 42). Using this AMACR cutpoint in multivariate analysis, patients with AMACR expression levels below the threshold were at a significantly higher risk of developing PSA recurrence (P=0.03, HR=2.15 95% CI 1.07-4.32) after adjusting for pre-operative PSA, Gleason score and surgical margin status.

TABLE 13

Univariate Cox Regression Analysis for Associations with Prostate Specific Biochemical Failure

| Parameters | Univariate Hazard Ratio | 95% CI for HR | P-value |
|---|---|---|---|
| AMACR < 1.11: Low | 2.89 | 1.47-5.68 | 0.002 |
| AMACR ≧ −1.11: High | REF | | |
| Gleason Score 7+ | 4.36 | 1.96-9.73 | 0.0003 |
| Gleason Score < 7 | REF | | |
| SM status positive | 3.61 | 2.26-5.76 | <.0001 |
| SM status negative | REF | | |
| pT Stage | 3.01 | 2.09-4.34 | <.0001 |
| | REF | | |
| Extra-prostatic extension | 2.79 | 1.97-3.94 | <.0001 |
| No extension | REF | | |
| In(PSA), per unit increase | 2.41 | 1.72-3.38 | <.0001 |
| Tumor size > 2 cm | 3.49 | 1.91-6.37 | <.0001 |
| Tumor size ≦ 2 cm | REF | | |
| DRE positive | 1.90 | 1.07-3.36 | 0.03 |
| DRE negative | REF | | |
| Age, per year | 1.01 | 0.97-1.05 | 0.61 |
| Gland Weight, per gram | 1.00 | 0.99-1.02 | 0.94 |

SM = surgical margin;
DRE = digital rectal examination;
In(PSA) = the natural logarithm of pre-treatment PSA

TABLE 14

Multivariate[1] Cox Regression Model: Independent Associations with PSA Recurrence for Men with Clinically Localized Prostate Cancer Following Radical Prostatectomy

| Parameter | Multivariate adjusted HR | 95% CI | pvalue |
|---|---|---|---|
| AMACR < 1.11: Low | 2.15 | 1.07-4.32 | 0.03 |
| AMACR ≧ −1.11: High | REF | | |
| Gleason Score 7+ | 3.50 | 1.00-12.19 | 0.049 |
| Gleason Score < 7 | REF | | |
| SM Status positive | 2.73 | 1.60-4.68 | 0.0002 |
| SM Status negative | REF | | |
| Ln (PSA) | 1.69 | 1.08-2.63 | 0.022 |

[1]Data in multivariate model are adjusted for AMACR cutpoint, Gleason score, SM status and natural log of PSA

Validation of the AMACR Cutpoint in the Watchful Waiting Cohort

After development of an optimal AMACR expression cutpoint to identify men at highest risk of developing PSA biochemical recurrence, this cutpoint developed with PSA relapses following radical prostatectomy was tested to determine if it also predicted cancer specific death among patients left without curative treatment. The −1.11 SD cutoff was then applied to the watchful waiting cohort. Using this cutpoint, AMACR intensity did not predict 5, 10, 15, and 20 years prostate cancer specific survival in univariate or multivariate analysis. For example, the multivariate adjusted hazard ratio for prostate cancer death after 20 years of follow-up was 1.09 (95% CI 0.33-3.60, p=0.89).

AMACR Cutpoint Using Cancer Specific Death as the Endpoint

Since the cutpoint developed for PSA failure did not predict cancer specific death, the optimal cutpoint for this latter endpoint was next determined. Using the adjusted regression tree method, the cutpoint was determined to be 0.18 SD. The patient demographics and AMACR staining intensity results for both cutpoints are presented in Table 15 stratifying the watchful waiting cohort by cancer specific death and censored patients. The univariate and multivariate analysis for the +0.18 SD cutpoint for 5, 10, 15, and 20-year prostate cancer specific survival are presented in Table 16. As demonstrated in Table 16 and FIG. 43, there was a significant association between the AMACR cutpoint and prostate cancer death in the multivariable analysis. For example, the hazard ratio for prostate cancer death after more than 20-years of follow-up was 3.04 (95% CI 1.43-6.49, p=0.004) comparing those with low AMACR levels to those with high levels. The effect of AMACR was independent of age at diagnosis, Gleason score, and tumor stage as evidenced in the multivariable analysis. The added value of AMACR in predicting prostate cancer death in this cohort over and beyond Gleason score and tumor stage was then examined. Among the 12 prostate cancer deaths with Gleason of 6 or less, using the AMACR cutpoint appropriately predicted 11 as deaths. Further, among the 4 prostate cancer deaths with Gleason 6 or less and tumor stage T1a, all were correctly predicted as death.

TABLE 15

Prostate Cancer (CaP) Patient Demographics by AMACR Expression from the Watchful Waiting Cohort, Örebro 1977-2003

| Parameter | Censored (N = 152) | CaP Specific Death (N = 36) |
|---|---|---|
| Mean age, years | 74.1 | 72.5 |
| T Stage, % | | |
| T1a | 46.1 | 13.9 |
| T1b | 53.9 | 86.1 |
| Gleason score, % | | |
| 4 | 0.2 | 0.0 |
| 5 | 2.6 | 8.3 |
| 6 (3 + 3) | 59.9 | 25.0 |
| 7 (3 + 4) | 18.4 | 22.2 |
| 7 (4 + 3) | 8.5 | 11.1 |
| 8 (4 + 4) | 7.2 | 30.6 |
| 9 | 1.3 | 2.8 |
| AMACR Cutoff (−1.11), % | | |
| Low | 12.8 | 8.3 |
| High | 87.2 | 91.7 |
| AMACR Cutoff (0.18), % | | |
| Low | 60.1 | 69.4 |
| High | 39.9 | 30.6 |

* AMACR intensity cutoffs were defined using either PSA biochemical failure as the endpoint (surrogate cutpoint equal −1.11) or prostate cancer specific death (true cutpoint equals 0.18)

TABLE 16

Univariate and Multivariate[1] Cox Models: Association between AMACR and Prostate Cancer Specific Death in Watchful Waiting Cohort, Örebro 1977-2003

| Parameter | Unadjusted HR | Unadjusted 95% CI | Unadjusted pvalue | Multivariate Adjusted HR | Multivariate Adjusted 95% CI | Multivariate Adjusted pvalue |
|---|---|---|---|---|---|---|
| 5 years of follow-up | | | | | | |
| AMACR < 0.18: Low | 3.32 | 0.74-14.98 | 0.12 | 7.36 | 1.56-34.74 | 0.012 |
| AMACR ≧ 0.18: High | REF | | | REF | | |
| Age (per year) | 1.04 | 0.97-1.11 | 0.30 | 1.03 | 0.95-1.12 | 0.51 |
| Stage T1b | 8.32 | 1.08-63.97 | 0.042 | 5.50 | 0.65-46.76 | 0.12 |
| Stage T1a | REF | | | REF | | |
| Gleason Score 7+ | 5.01 | 1.38-18.21 | 0.015 | 4.39 | 1.12-17.15 | 0.034 |
| Gleason Score < 7 | REF | | | REF | | |
| 10 years of follow-up | | | | | | |
| AMACR < 0.18: Low | 1.59 | 0.67-3.79 | 0.29 | 3.23 | 1.32-7.90 | 0.010 |
| AMACR ≧ 0.18: High | REF | | | REF | | |
| Age (per year) | 1.03 | 0.98-1.09 | 0.25 | 1.01 | 0.96-1.07 | 0.63 |
| T stage T1b | 10.25 | 2.42-43.48 | 0.0016 | 8.01 | 1.78-36.08 | 0.0068 |
| T stage T1a | REF | | | REF | | |
| Gleason 7+ | 4.09 | 1.77-9.43 | 0.001 | 2.84 | 1.17-6.93 | 0.022 |
| Gleason < 7 | REF | | | REF | | |
| 15 years of follow-up | | | | | | |
| AMACR < 0.18: Low | 1.91 | 0.86-4.25 | 0.11 | 3.97 | 1.71-9.17 | 0.0013 |
| AMACR ≧ 0.18: High | REF | | | REF | | |

TABLE 16-continued

Univariate and Multivariate[1] Cox Models: Association between AMACR and Prostate Cancer Specific Death in Watchful Waiting Cohort, Örebro 1977-2003

| | Unadjusted | | | Multivariate Adjusted | | |
|---|---|---|---|---|---|---|
| Parameter | HR | 95% CI | pvalue | HR | 95% CI | pvalue |
| Age (per year) | 1.04 | 0.99-1.09 | 0.12 | 1.03 | 0.98-1.08 | 0.30 |
| T stage T1b | 4.78 | 1.84-12.41 | 0.0013 | 3.59 | 1.29-9.99 | 0.014 |
| T stage T1a | REF | | | REF | | |
| Gleason 7+ | 3.63 | 1.77-7.44 | 0.0004 | 3.32 | 1.49-7.39 | 0.0033 |
| Gleason < 7 | REF | | | REF | | |
| | 20+ years of follow-up | | | | | |
| AMACR < 0.18: Low | 1.40 | 0.68-2.83 | 0.36 | 3.04 | 1.43-6.49 | 0.0039 |
| AMACR ≧ 0.18: High | REF | | | REF | | |
| Age (per year) | 1.03 | 0.99-1.08 | 0.17 | 1.02 | 0.97-1.01 | 0.46 |
| T stage T1b | 5.12 | 1.98-13.21 | 0.0007 | 3.45 | 1.25-9.56 | 0.017 |
| T stage T1a | REF | | | REF | | |
| Gleason 7+ | 4.40 | 2.18-8.89 | <0.0001 | 4.02 | 1.81-8.91 | 0.0006 |
| Gleason < 7 | REF | | | REF | | |

Figure 43A:
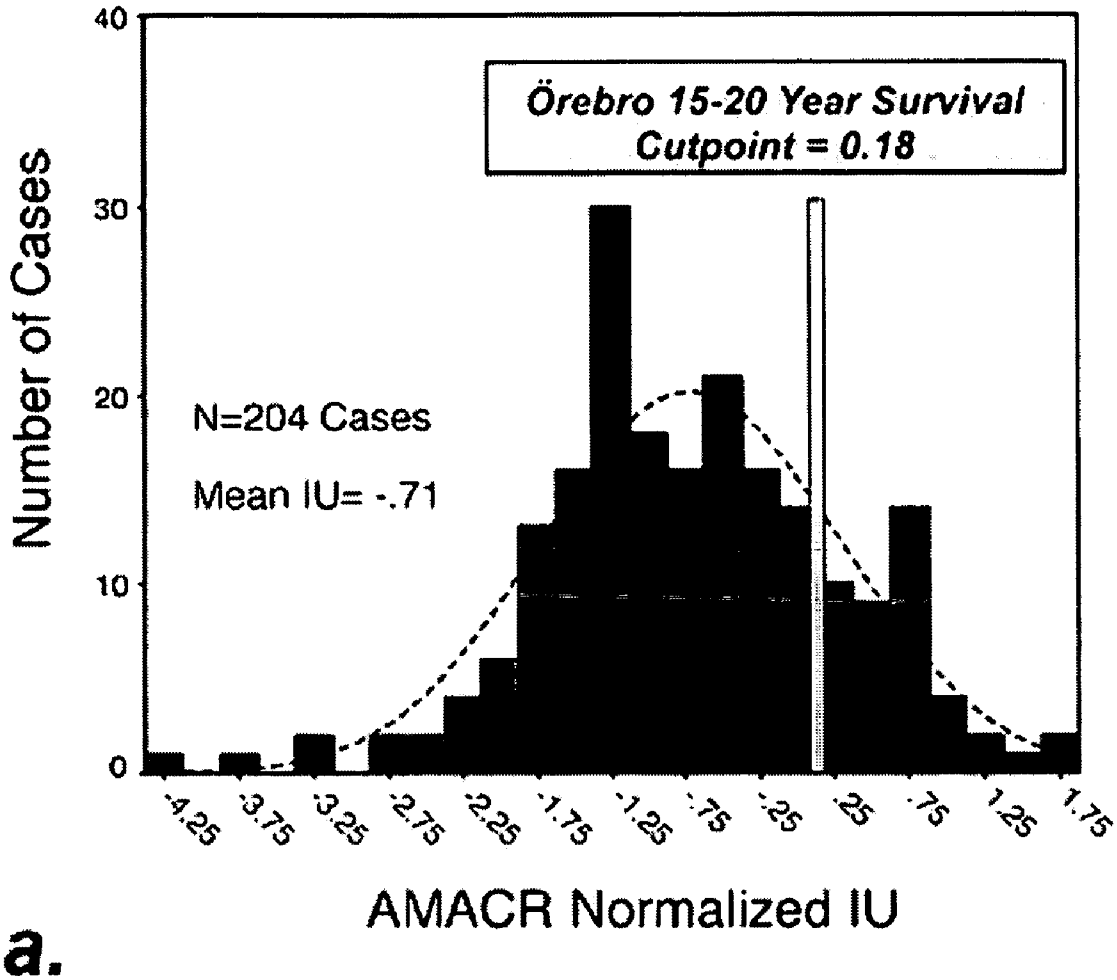
FIG. 43A shows AMACR levels and prostate cancer specific survival in a watchful waiting cohort with up to 20 years of clinical follow up using a cutpoint of 0.18.
Figure 43B:
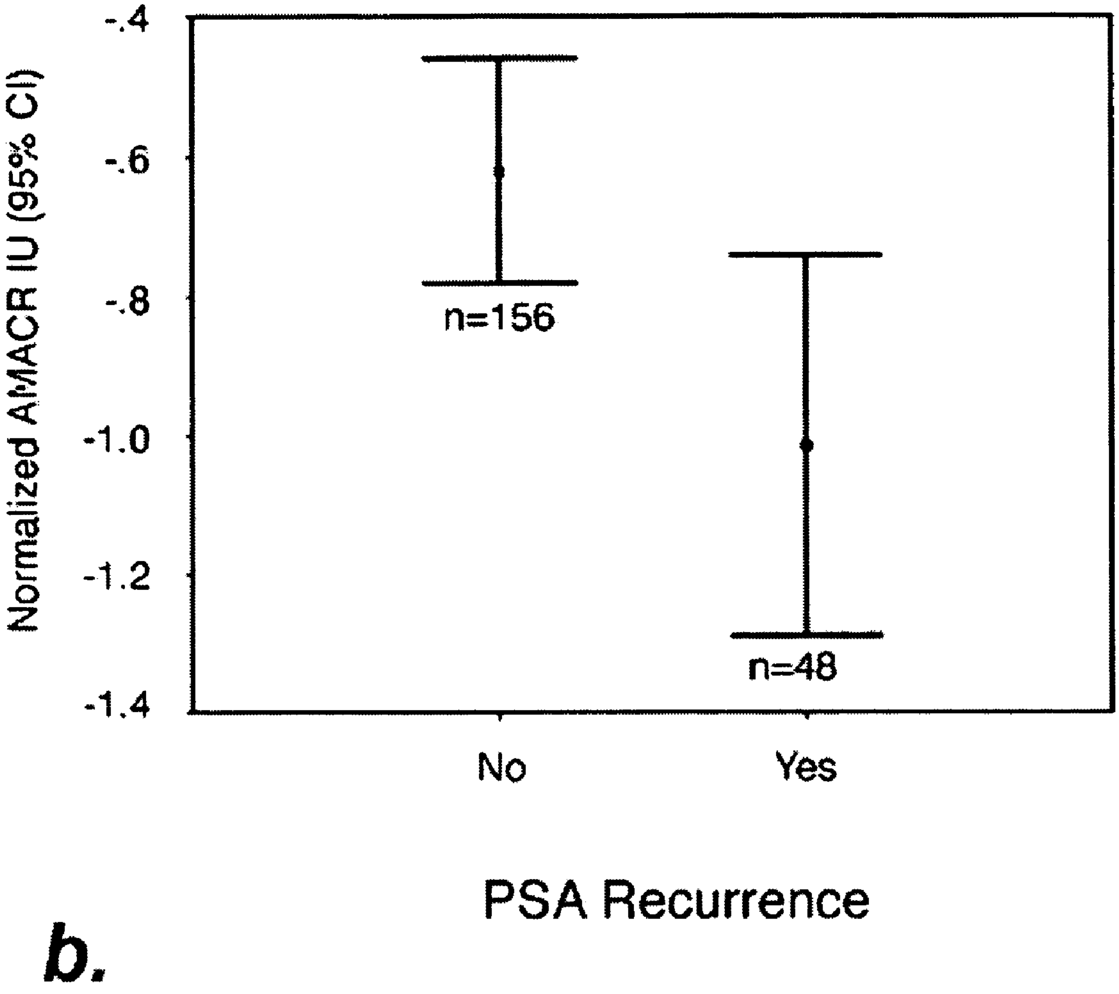
FIG. 43B shows lower AMACR expression in the 48 cases with a PSA biochemical failure versus the patients without disease progression (Error bars with 95% CI).
Figure 43C:
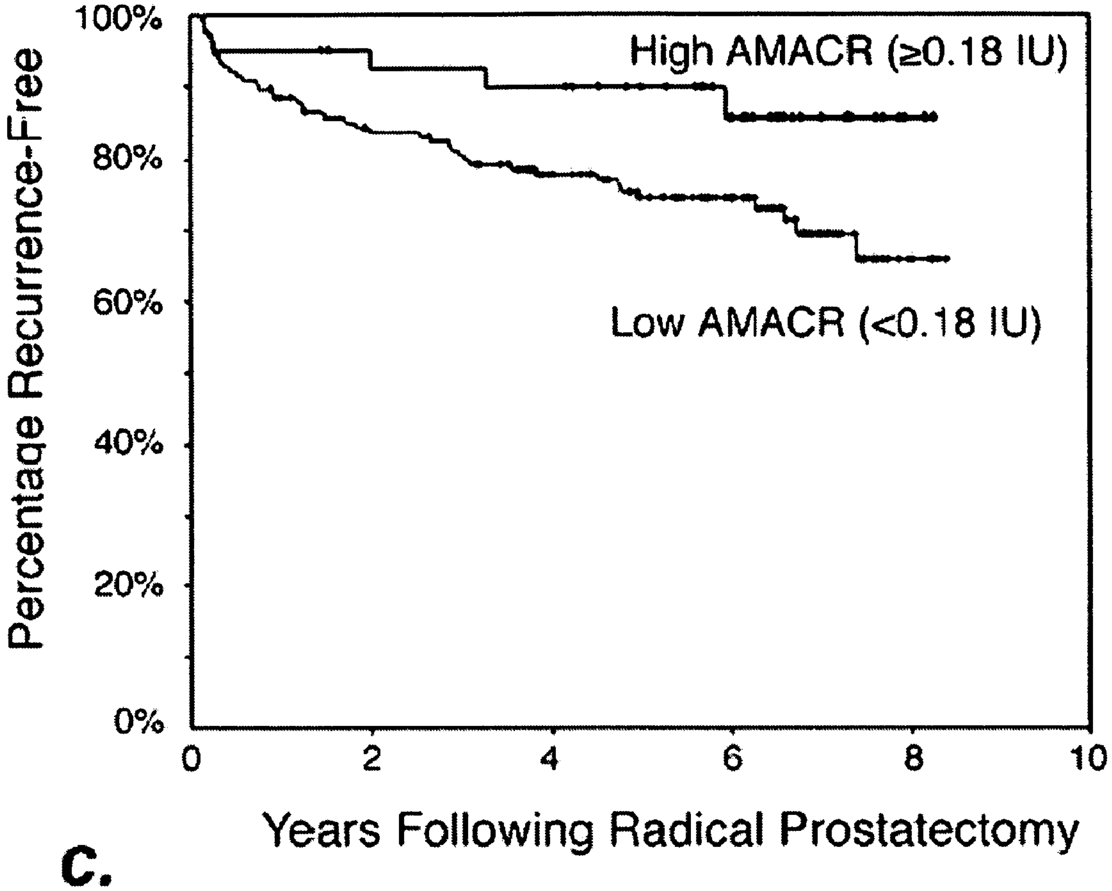
FIG. 43C shows a Kaplan-Meier curve for patients whose tumors had higher and lower AMACR protein expression using the 0.18 cutpoint.

[1]Data in multivariate model are adjusted for AMACR cutpoint, age, T stage and Gleason score Application of AMACR Cutpoint for Cancer Specific Death on the Surgical Series Using cancer specific death as the endpoint, the optimal normalized cutpoint was 0.18 (in contrast to −1.11 as determined by using PSA biochemical failure) (FIG. 43). It was then determined if this cutpoint could predict mean PSA biochemical failure following radical prostatectomy. Using the 0.18 cutpoint, 81% of the clinically localized tumors from the surgical series were below the AMACR cutpoint. There was evidence that AMACR levels below the cutpoint determined by prostate cancer death was significantly associated with time to PSA biochemical failure at the univariate level as demonstrated by the Kaplan-Meier analysis (FIG. 43). On multivariate analysis, low AMACR expression was a significant predictor of biochemical failure, independent of Gleason score, surgical margin status, and pre-treatment PSA, with a hazard ratio of 3.88 (95% CI=1.32-11.38, p<0.014) (Table 17).

TABLE 17

Multivariate[1] Cox Model: Independent associations with PSA Recurrence for Men with Clinically Localized Prostate Cancer Following Radical Prostatectomy Using Cancer Specific Death Cutoff for AMACR

| | Multivariate adjusted | | |
|---|---|---|---|
| Parameter | HR | 95% CI | pvalue |
| AMACR < 0.18 | 3.88 | 1.32-11.38 | 0.014 |
| AMACR ≧ 0.18 | REF | | |
| Gleason Score 7+ | 2.35 | 1.02-5.40 | 0.040 |
| Gleason Score < 7 | REF | | |
| SM Status positive | 2.78 | 1.53-5.03 | <0.001 |
| SM Status negative | REF | | |

TABLE 17-continued

Multivariate[1] Cox Model: Independent associations with PSA Recurrence for Men with Clinically Localized Prostate Cancer Following Radical Prostatectomy Using Cancer Specific Death Cutoff for AMACR

| | Multivariate adjusted | | |
|---|---|---|---|
| Parameter | HR | 95% CI | pvalue |
| Ln (PSA) | 1.89 | 1.31-2.74 | <0.001 |

AMACR intensity cutoffs were defined using prostate cancer specific death (true endpoint cutpoint equals 0.18).

[1]Data were adjusted for Gleason score; surgical margin status, and the natural log of pre-treatment serum PSA The application of a biomarker in the clinical setting accommodates clinical characteristics of patients as well assessment of prostate cancer prognosis. In Table 18, the joint association between AMACR expression and Gleason score on prostate cancer outcome in the two cohorts was examined. For this analysis, the AMACR cutpoint of 0.18 SD was relied upon. Compared to those with "better" biomarker and clinical measures (i.e. high AMACR expression and low Gleason score), those with both low AMACR expression and high Gleason score had an almost 4 times higher risk of PSA biochemical failure. In the watchful waiting cohort, however, individuals with the "poorer" measures had an 18-fold higher risk of prostate cancer death (p=0.006). These data indicate that the AMACR biomarker, in combination with clinical parameters, can substantially predict prostate cancer mortality.

TABLE 18

| Hazard ratio (95% CI) of prostate cancer outcome associated with AMACR expression and Gleason score, cross classified | | | | |
|---|---|---|---|---|
| | Surgical cohort PSA biochemical failure | | Watchful waiting cohort Prostate cancer death | |
| | Low AMACR | High AMACR | Low AMACR | High AMACR |
| Gleason ≧ 7 | 3.9 (0.53-29.2) | 1.7 (0.21-14.5) | 18.0 (2.3-140.8) | 4.9 (0.63-37.9) |
| Gleason < 7 | 1.2 (0.12-10.9) | REF | 6.4 (0.8-51.2) | REF |

Data are adjusted for surgical margins and PSA (surgical cohort) or age and T stage (watchful waiting cohort).
AMACR cutpoint = 0.18.

Figure 44:
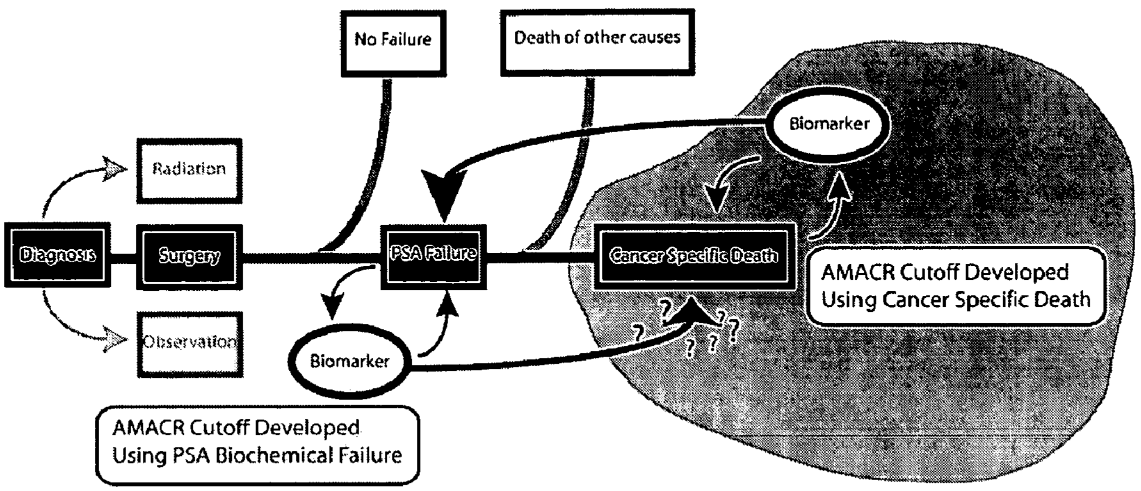
FIG. 44 illustrates the differing AMACR expression levels used as cutoff points for PSA biochemical failure versus cancer specific death.

Prostate cancer biomarker development requires selecting an endpoint for the study. Most studies have used PSA biochemical failure as a surrogate endpoint; however, this study indicates that PSA biochemical failure is not sufficient to define cutpoints for predicting cancer specific death. The AMACR cutpoint used to predict PSA biochemical failure did not predict cancer-specific death. The presence of two distinct cutpoints for the two distinct endpoints illustrates this principle (FIG. 44).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of detecting the presence or absence of prostate cancer in a subject, comprising:

a) providing i) urine from a subject;

ii) a reagent for detecting α-methylacyl-CoA racemase in said urine; and b) contacting said urine with said reagent under conditions such that said reagent detects the presence or absence of α-methylacyl-CoA racemase in said urine;

c) determining the presence or absence of prostate cancer in said subject based on said presence or absence of α-methylacyl-CoA racemase in said urine.

2. The method of claim 1, wherein level of said α-methylacyl-CoA racemase in said urine is determined.

3. The method of claim 2, wherein a minimum threshold level of expression of α-methylacyl-CoA racemase is set to 1, where 0 is absence of α-methylacyl-CoA racemase and 4 is highest level expression.

4. The method of claim 3, wherein the presence of said α-methylacyl-CoA racemase in said urine at a level above said minimum threshold level is indicative of a diagnosis of prostate cancer in said subject.

5. The method of claim 1, wherein said reagent is an antibody.

6. The method of claim 5, wherein said antibody is selected from the group consisting of a single chain antibody, an Fab, and an epitope-binding fragment.

7. The method of claim 1, wherein said reagent comprises a label.

8. The method of claim 7, wherein said label is selected from the group consisting of a radioactive label, a fluorescent label, a chemiluminescent label, and a bioluminescent label.

* * * * *

SEQUENCE LISTING

```
<160> NUMBER OF SEQ ID NOS: 123

<210> SEQ ID NO 1
<211> LENGTH: 1783
<212> TYPE: DNA
<213> ORGANISM: Homo sapiens

<400> SEQUENCE: 1

tcgagcccgc tttccaggga ccctacctga gggcccacag gtgaggcagc ctggcctagc     60

aggccccacg ccaccgcctc tgcctccagg ccgcccgctg ctgcggggcc accatgctcc    120

tgcccaggcc tggagactga cccgaccccg gcactacctc gaggctccgc ccccacctgc    180

tggaccccag ggtcccaccc tggcccagga ggtcagccag ggaatcatta acaagaggca    240

gtgacatggc gcagaaggag ggtggccgga ctgtgccatg ctgctccaga cccaaggtgg    300

cagctctcac tgcggggacc ctgctacttc tgacagccat cggggcggca tcctgggcca    360

ttgtggctgt tctcctcagg agtgaccagg agccgctgta cccagtgcag gtcagctctg    420

cggacgctcg gctcatggtc tttgacaaga cggaagggac gtggcggctg ctgtgctcct    480

cgcgctccaa cgccagggta gccggactca gctgcgagga gatgggcttc ctcagggcac    540

tgacccactc cgagctggac gtgcgaacgg cgggcgccaa tggcacgtcg ggcttcttct    600

gtgtggacga ggggaggctg ccccacaccc agaggctgct ggaggtcatc tccgtgtgtg    660

attgccccag aggccgtttc ttggccgcca tctgccaaga ctgtggccgc aggaagctgc    720

ccgtggaccg catcgtggga ggccgggaca ccagcttggg ccggtggccg tggcaagtca    780

gccttcgcta tgatggagca cacctctgtg ggggatccct gctctccggg gactgggtgc    840

tgacagccgc ccactgcttc ccggagcgga accgggtcct gtcccgatgg cgagtgtttg    900

ccggtgccgt ggcccaggcc tctccccacg gtctgcagct gggggtgcag gctgtggtct    960

accacggggg ctatcttccc tttcgggacc ccaacagcga ggagaacagc aacgatattg   1020
```

-continued

```
ccctggtcca cctctccagt cccctgcccc tcacagaata catccagcct gtgtgcctcc   1080

cagctgccgg ccaggccctg gtggatggca agatctgtac cgtgacgggc tggggcaaca   1140

cgcagtacta tggccaacag gccggggtac tccaggaggc tcgagtcccc ataatcagca   1200

atgatgtctg caatggcgct gacttctatg gaaaccagat caagcccaag atgttctgtg   1260

ctggctaccc cgagggtggc attgatgcct gccagggcga cagcggtggt ccctttgtgt   1320

gtgaggacag catctctcgg acgccacgtt ggcggctgtg tggcattgtg agttggggca   1380

ctggctgtgc cctggcccag aagccaggcg tctacaccaa agtcagtgac ttccgggagt   1440

ggatcttcca ggccataaag actcactccg aagccagcgg catggtgacc cagctctgac   1500

cggtggcttc tcgctgcgca gcctccaggg cccgaggtga tcccggtggt gggatccacg   1560

ctgggccgag gatgggacgt tttcttcttt gggcccggtc cacaggtcca aggacaccct   1620

ccctccaggg tcctctcttc cacagtggcg ggcccactca gccccgagac cacccaacct   1680

caccctcctg acccccatgt aaatattgtt ctgctgtctg ggactcctgt ctaggtgccc   1740

ctgatgatgg gatgctcttt aaataataaa gatggttttg att                     1783
```

<210> SEQ ID NO 2
<211> LENGTH: 2623
<212> TYPE: DNA
<213> ORGANISM: Homo sapiens

<400> SEQUENCE: 2

```
gaggaggccc gagaggagtc ggtggcagcg gcggcggcgg gaccggcagc agcagcagca     60

gcagcagcag caaccactag cctcctgccc cgcggcgttg cgacgagccc cacgagccgc    120

tcaccccgcc gttctcagcg ctgcccgacc ccgctggcgc gcctcccgcc gcagtcccgg    180

cagcgcctca gttgtcctcc gactcgccct cggccttcgc gcagcgcagc acagccgcac    240

gcaccgcagc acagcacagc acagcccagg catagcttcg gcacagcccc ggctccggct    300

cctgcggcag ctcctctggc acgtccctgc gccgacattc tggaggttgg atgctcttgt    360

ccaaaatcaa ctcgcttgcc cacctgcgcg ccgcgccctg caacgacctg cacgccacca    420

agctggcgcc cggcaaggag aaggagcccc tggagtcgca gtaccaggtg ggcccgctac    480

tgggcagcgg cggcttcggc tcggtctact caggcatccg cgtctccgac aacttgccgg    540

tggccatcaa acacgtggag aaggaccgga tttccgactg ggagagctg cctaatggca     600

ctcgagtgcc catggaagtg gtcctgctga agaaggtgag ctcgggtttc tccggcgtca    660

ttaggctcct ggactggttc gagaggcccg acagtttcgt cctgatcctg gagaggcccg    720

agccggtgca agatctcttc gacttcatca cggaaagggg agccctgcaa gaggagctgg    780

cccgcagctt cttctggcag gtgctggagg ccgtgcggca ctgccacaac tgcggggtgc    840

tacaccgcga catcaaggac gaaaacatcc ttatcgacct caatcgcggc gagctcaagc    900

tcatcgactt cgggtcgggg gcgctgctca aggacaccgt ctacacggac ttcgatggga    960

cccgagtgta tagccctcca gagtggatcc gctaccatcg ctaccatggc aggtcggcgg   1020

cagtctggtc cctggggatc ctgctgtatg atatggtgtg tggagatatt cctttcgagc   1080

atgacgaaga gatcatcagg ggccaggttt tcttcaggca gagggtctct tcagaatgtc   1140

agcatctcat tagatggtgc ttggccctga gaccatcaga taggccaacc ttcgaagaaa   1200

tccagaacca tccatggatg caagatgttc tcctgcccca ggaaactgct gagatccacc   1260

tccacagcct gtcgccgggg cccagcaaat agcagccttt ctggcaggtc ctcccctctc   1320
```

-continued

```
ttgtcagatg cccgagggag gggaagcttc tgtctccagc ttcccgagta ccagtgacac   1380
gtctcgccaa gcaggacagt gcttgataca ggaacaacat ttacaactca ttccagatcc   1440
caggcccctg gaggctgcct cccaacagtg gggaagagtg actctccagg ggtcctaggc   1500
ctcaactcct cccatagata ctctcttctt ctcataggtg tccagcattg ctggactctg   1560
aaatatcccg ggggtggggg gtgggggtgg gcagaaccct gccaatggaa ctctttcttc   1620
atcatgagtt ctgctgaatg ccgcgatggg tcaggtaggg gggaaacagg ttgggatggg   1680
ataggactag cacattttaa gtccctgtca cctcttccga ctctttctga gtgccttctg   1740
tggggactcc ggctgtgctg ggagaaatac ttgaacttgc ctcttttacc tgctgcttct   1800
ccaaaaatct gcctgggttt tgttccctat ttttctctcc tgtcctccct cacccccctcc   1860
ttcatatgaa aggtgccatg gaagaggcta cagggccaaa cgctgagcca cctgcccttt   1920
tttctgcctc ctttagtaaa actccgagtg aactggtctt cctttttggt ttttacttaa   1980
ctgtttcaaa gccaagacct cacacacaca aaaaaatgca caaaccaagc aatcaacaga   2040
aaagctgtaa atgtgtgtac agttggcatg gtagtataca aaaagattgt agtggatcta   2100
atttttaaga aattttgcct ttaagttatt ttacctgttt ttgtttcttg ttttgaaaga   2160
tgcgcattct aacctggagg tcaatgttat gtatttattt atttatttat ttggttccct   2220
tcctattcca agcttccata gctgctgccc tagttttctt tcctcctttc ctcctctgac   2280
ttggggacct tttgggggag ggctgcgacg cttgctctgt ttgtggggtg acgggactca   2340
ggcgggacag tgctgcagct ccctggcttc tgtggggccc ctcacctact tacccaggtg   2400
ggtcccggct ctgtgggtga tgggagggggc cattgctgac tgtgtatata ggataattat   2460
gaaacacagt tctggatggt gtgccttcca gatcctctct ggggctgtgt tttgagcagc   2520
aggtagcctg ctggttttat ctgagtgaaa tactgtacag gggaataaaa gagatcttat   2580
ttttttttta tacttgcgtt tggaataaaa accctttggc ttt                     2623
```

<210> SEQ ID NO 3
<211> LENGTH: 2226
<212> TYPE: DNA
<213> ORGANISM: Homo sapiens

<400> SEQUENCE: 3

```
gaacaatgaa gaaagcccca cagccactgt tgctgagcag ggagaggata ttacctccaa     60
aaaagacagg ggagtattaa agattgtcaa aagagtgggg aatggtgagg aaacgccgat    120
gattggagac aaagtttatg tccattacaa aggaaaattg tcaaatggaa agaagtttga    180
ttccagtcat gatagaaatg aaccatttgt ctttagtctt ggcaaaggcc aagtcatcaa    240
ggcatgggac attggggtgg ctaccatgaa gaaaggagag atatgccatt tactgtgcaa    300
accagaatat gcatatggct cggctggcag tctccctaaa attccctcga atgcaactct    360
ctttttttgag attgagctcc ttgatttcaa aggagaggat ttatttgaag atggaggcat    420
tatccggaga accaaacgga aaggagaggg atattcaaat ccaaacgaag gagcaacagt    480
agaaatccac ctggaaggcc gctgtggtgg aaggatgttt gactgcagag atgtggcatt    540
cactgtgggc gaaggagaag accacgacat tccaattgga attgacaaag ctctggagaa    600
aatgcagcgg gaagaacaat gtattttata tcttggacca agatatggtt ttggagaggc    660
agggaagcct aaatttggca ttgaacctaa tgctgagctt atatatgaag ttacacttaa    720
gagcttcgaa aaggccaaag aatcctggga gatggatacc aaagaaaaat tggagcaggc    780
tgccattgtc aaagagaagg gaaccgtata cttcaaggga ggcaaataca tgcaggcggt    840
```

-continued

```
gattcagtat gggaagatag tgtcctggtt agagatggaa tatggtttat cagaaaagga    900
atcgaaagct tctgaatcat ttctccttgc tgcctttctg aacctggcca tgtgctacct    960
gaagcttaga gaatacacca aagctgttga atgctgtgac aaggcccttg gactggacag   1020
tgccaatgag aaaggcttgt ataggagggg tgaagcccag ctgctcatga acgagtttga   1080
gtcagccaag ggtgactttg agaaagtgct ggaagtaaac ccccagaata aggctgcaag   1140
actgcagatc tccatgtgcc agaaaaaggc caaggagcac aacgagcggg accgcaggat   1200
atacgccaac atgttcaaga agtttgcaga gcaggatgcc aaggaagagg ccaataaagc   1260
aatgggcaag aagacttcag aaggggtcac taatgaaaaa ggaacagaca gtcaagcaat   1320
ggaagaagag aaacctgagg gccacgtatg acgccacgcc aaggagggaa gagtcccagt   1380
gaactcggcc cctcctcaat gggctttccc ccaactcagg acagaacagt gtttaatgta   1440
aagtttgtta tagtctatgt gattctggaa gcaaatggca aaaccagtag cttcccaaaa   1500
acagcccccc tgctgctgcc cggagggttc actgaggggt ggcacgggac cactccaggt   1560
ggaacaaaca gaaatgactg tggtgtggag ggagtgagcc agcagcttaa gtccagctca   1620
tttcagtttc tatcaacctt caagtatcca attcagggtc cctggagatc atcctaacaa   1680
tgtggggctg ttaggtttta cctttgaact ttcatagcac tgcagaaacc tttaaaaaaa   1740
aaatgcttca tgaatttctc ctttcctaca gttgggtagg gtaggggaag gaggataagc   1800
ttttgttttt taaatgactg aagtgctata aatgtagtct gttgcatttt taaccaacag   1860
aacccacagt agaggggtct catgtctccc cagttccaca gcagtgtcac agacgtgaaa   1920
gccagaacct cagaggccac ttgcttgctg acttagcctc ctcccaaagt ccccctcctc   1980
agccagcctc cttgtgagag tggctttcta ccacacacag cctgtccctg ggggagtaat   2040
tctgtcattc ctaaaacacc cttcagcaat gataatgagc agatgagagt ttctggatta   2100
gcttttccta ttttcgatga agttctgaga tactgaaatg tgaaaagagc aatcagaatt   2160
gtgctttttc tcccctcctc tattcctttt agggaataat attcaataca cagtacttcc   2220
tcccag                                                              2226
```

<210> SEQ ID NO 4
<211> LENGTH: 7515
<212> TYPE: DNA
<213> ORGANISM: Homo sapiens

<400> SEQUENCE: 4

```
atggaggagg tggtgattgc cggcatgttc gggaagctgc cagagtcgga gaacttgcag     60
gagttctggg acaacctcat cggcggtgtg gacatggtca cggacgatga ccgtcgctgg    120
aaggctgggc tctacggcct gccccggcgg tccggcaagc tgaaggacct gtctaggttt    180
gatgcctcct tcttcggagt ccaccccaag caggcacaca cgatggaccc tcagctgcgg    240
ctgctgctgg aagctaccta tgaagccatc gtggacggag gcatcaaccc agattcactc    300
cgaggaacac acactggcgt ctgggtgggc gtgagcggct ctgagacctc ggaggccctg    360
agccgagacc ccgagacact cgtgggctac agcatggtgg gctgccagcg agcgatgatg    420
gccaaccggc tctccttctt cttcgacttc agagggccca gcatcgcact ggacacagcc    480
tgctcctcca gcctgatggc cctgcagaac gcctaccagg ccatccacag cgggcagtgc    540
cctgccgcca tcgtgggggg catcaacgtc ctgctgaagc ccaacacctc cgtgcagttc    600
ttgaggctgg ggatgctcag ccccgagggc acctgcaagg ccttcgacac agcggggaat    660
```

-continued

```
gggtactgcc gctcggaggg tgtggtggct gtcctgctga ccaagaagtc cctggcccgg    720
aaggtctaca ccaccatcct gaacaaaggc accaatacag atggcttcaa ggagcaaggc    780
gtgaccttcc ctcaggatat ccaggagcag cctatccgct cgttgtacca gtcggccgga    840
gtggcccctg agtcatttga atacatcgaa gcccacggac caggcaccaa ggtgggcgac    900
ccccaggagc gtaatggcat cacccgagcc ctgtgcgcca cccgccagga gccgctgctc    960
atcggctcca ccaagtccaa catggggcac ccggagccag cctcggggct cgacgccctg   1020
gccaaggtgc tgctgtccct ggagcacggg ctctgggccc ccaacctgca cttccatagc   1080
cccaaccctg agatcccagc gctgttggat gggcggctgc aggtggtgga ccagcccctg   1140
cccgtccgtg gcggcaacgt gggcatcaac tcctttggct tcgggggctc caacatgcac   1200
atcatcctga ggcccaacac gcagtccgcc cccgcacccg ccccacatgc caccctgccc   1260
cgtctgctgc gggccagcgg acgcacccct gaggccgtgc agaagctgct ggagcagggc   1320
ctccggcaca gccagggcct ggctttcctg agcatgctga acgacatcgc ggctgtcccc   1380
gccaccgcca tgcccttccg tggctacgct gtgctgggtg gtgagacgcg gtggcccaga   1440
gtgcagcagg tgcccgctgg cgagcgcccg ctctggttca tctgctctgg gatgggcaca   1500
cagtggcgtg gaatggggct gagccttatg cgcctggacc gcttccgaga ttccatccta   1560
cgctccgatg aggctgtgaa ccgattcggc ctgaaggtgt cacagctgct gctgagcaca   1620
gacgagagca cctttgatga catcgtccat tcgtttgtga gcctgactgc catccagata   1680
ggcctcatag acctgctgag ctgcatggga cctgaggcag atggcatcgt cggccactcc   1740
ctgggggagt ggctgtcggt acgcgacggc tgcctgtccc aggaggaggc cgtcctcgct   1800
gcctactgga ggggacagtg catcaaagaa gccccacttc ccgccggcgc catggcagcc   1860
gtgggcttgt cctgggagga gtgtaaacag cgctgccccc ctgcggtggt gcccgcctgc   1920
cacaactcca aggacacagt caccatctcg ggacctcagg ccccggtgtt tgagttcgtg   1980
gagcagctga ggaaggaggg tgtgtttgcc aaggaggtgc ggaccggcgg tatggccttc   2040
cactcctact tcatggaggc catcgcaccc ccactgctgc aggagctcaa gaaggtgatc   2100
cgggagccga agccacgttc agcccgctgg ctcagcacct ctatccccga ggcccagtgg   2160
cacagcagcc tggcacgcac gtcttccgcc gagtacaatg tcaacaacct ggtgagccct   2220
gtgctgttcc aggaggccct gtggcacgtg cctgagcacg cggtggtgct ggagatcgcc   2280
ccgaccccgt gccctcaggc tgtcctgaag cgggtccgta agccgagctg caccatcatc   2340
ccccgtatga agaaggatca cagggacaac ctggagttct tcctggccgg catcggcagg   2400
ctgcacctct caggcatcga cgccaacccc aatgccttgt tcccacctgt ggagtcccca   2460
gctccccgag gaactcccct catctcccca ctcatcaagt gggaccacag cctggcctgg   2520
gacgcgccgg ccgccgagga cttccccaac ggttcaggtt ccccctcagc caccatctac   2580
acatgcacac caagctccga gtctcctgac cgctacctgg tggaccacac catcgacggt   2640
cgcgtcctct tccccgccac tggctacctg agcatagtgt ggaagacgct ggcccgcgcc   2700
tgggctgggc tcgagcagct gcctgtggtg tttgaggatg tggtgcagca ccaggccacc   2760
atcctgccca agactgggac agtgtccttg gaggtacggc tcctggaggc caccggtgcc   2820
ttcgaggtgt cagagaacgg caacctggta gtgagtggga aggtgtacca gtgggatgac   2880
cctgacccca ggctcttcga ccacccggaa agtccccacc ccaattcccc acggagtccc   2940
ctcttcctgg cccaggcaga agtttacaag gagctgcgtc tgcgtggcta cgactacggc   3000
cctcatttcc agggcatcct ggaggccagc ctggaaggtg actcggggag gctgctgtgg   3060
```

-continued

```
aaggataact gggtgagctt catggacacc atgctgcaga tgtccatcct gggctcggcc   3120
aagcacggcc tgtacctacc cacccgtgtc accgccatcc acatcgaccc tgccacccac   3180
aggcagaagc tgtacacact gcaggacaag gcccaagtgg ctgacgtggt ggtgagcagg   3240
tggccgaggg tcacagtggc gggaggcgtc cacatctccg ggctccacac tgagtcggcc   3300
ccgcggcggc acgaggagca gcaggtgccc atcctggaga agttttgctt cactccccac   3360
acggaggagg ggtgcctgtc tgagcacgct gccctcgagg aggagctgca actgtgcaag   3420
gggctggtcg aggcactcga gaccaaggtg acccagcagg ggctgaagat ggtggtgccg   3480
gactggacgg ggcccagatc cccccgggac ccctcacagc aggaactgcc ccggctgttg   3540
tcggctgcct gcaggcttca gctcaacggg aacctgcagc tggagctggc gcaggtgctg   3600
gcccaggaga ggcccaagct gccagaggac cctctgctca gcggcctcct ggactccccg   3660
gcactcaagg cctgcctgga cactgccgtg gagaacatgc ccagcctgaa gatgaaggtg   3720
gtggaggtgc tggccggcca cggtcacctg tattcccgca tcccaggcct gctcagcccc   3780
catcccctgc tgcagctgag ctacacggcc accgaccgcc acccccaggc cctggaggct   3840
gcccaggccg agctgcagca gcacgacgtt gcccagggcc agtgggatcc cgcagaccct   3900
gcccccagcg ccctgggcag cgcggacctc ctggtgtgca actgtgctgt ggctgccctc   3960
ggggacccgg cctcagctct cagcaacatg gtggctgccc tgagagaagg gggctttctg   4020
ctcctgcaca cactgctccg gggcaccct cgggacatcg tggccttcct cacctccact   4080
gagccgcagt atggccaggg catcctgagc caggacgcgt gggagagcct cttctccagg   4140
gtgtcgctgc gcctggtggg cctgaagaag tccttctacg gcgccacgct cttcctgtgc   4200
cgccggccca ccccgcagga cagccccatc ttcctgccgg tggacgatac cagcttccgc   4260
tgggtggagt ctctgaaggg catcctggct gacgaagact cttcccggcc tgtgtggctg   4320
aaggccatca actgtgccac ctcgggcgtg gtgggcttgg tgaactgtct ccgccgagag   4380
cccggcggaa ccgtccggtg tgtgctgctc tccaacctca gcagcacctc ccacgtcccg   4440
gaggtggacc cgggctccgc agaactgcag aaggtgttgc agggagacct ggtgatgaac   4500
gtctaccgcg acggggcctg gggggttttc cgccacttcc tgctggagga caagcctgag   4560
gagccgacgg cacatgcctt tgtgagcacc ctcacccggg gggacctgtc ctccatccgc   4620
tgggtctgct cctcgctgcg ccatgcccag cccacctgcc ctggcgccca gctctgcacg   4680
gtctactacg cctccctcaa cttccgcgac atcatgctgg ccactggcaa gctgtcccct   4740
gatgccatcc cagggaagtg gacctcccag gacagcctgc taggtatgga gttctcgggc   4800
cgagacgcca gcggcaagcg tgtgatggga ctggtgcctg ccaagggcct ggccacctct   4860
gtcctgctgt caccggactt cctctgggat gtgccttcca actggacgct ggaggaggcg   4920
gcctcggtgc ctgtcgtcta cagcacggcc tactacgcgc tggtggtgcg tgggcgggtg   4980
cgccccgggg agacgctgct catccactcg ggctcgggcg gcgtgggcca ggccgccatc   5040
gccatcgccc tcagtctggg ctgccgcgtc ttcaccaccg tggggtcggc tgagaagcgg   5100
gcgtacctcc aggccaggtt cccccagctc gacagcacca gcttcgccaa ctcccgggac   5160
acatccttcg agcagcatgt gctgtggcac acgggcggga agggcgttga cctggtcttg   5220
aactccttgg cggaagagaa gctgcaggcc agcgtgaggt gcttcggtac gcacggtcgc   5280
ttcctggaaa ttggcaaatt cgacctttct cagaaccacc cgctcggcat ggctatcttc   5340
ctgaagaacg tgacattcca cggggtccta ctggatgcgt tcttcaacga gagcagtgct   5400
```

-continued

```
gactggcggg aggtgtgggc gcttgtcgag gccgccatcc gggatggggt ggtacggccc   5460

ctcaagtgca cggtgttcca tggggcccag gtggaggacg ccttccgcta catggcccaa   5520

gggaagcaca ttggcaaagt cgtcgtgcag gtgcttgcgg aggagccggc agtgctgaag   5580

ggggccaaac ccaagctgat gtcggccatc tccaagacct tctgcccggc ccacaagagc   5640

tacatcatcg ctggtggtct gggtggcttc ggcctggagt tggcgcagtg gctgatacag   5700

cgtggggtgc agaagctcgt gttgacttct cgctccggga tccggacagg ctaccaggcc   5760

aagcaggtcc gccggtggag gcgccagggg ctacaggtgc aggtgtccac cagcaacatc   5820

agctcactgg agggggcccg ggcctcatt gccgaggcgg cgcagcttgg gcccgtgggg   5880

ggcgtcttca acctggccgt ggtcttgaga gatggcttgc tggagaacca gaccccagag   5940

ttcttccagg acgtctgcaa gcccaagtac agcggcaccc tgaacctgga cagggtgacc   6000

cgagaggcgt gccctgagct ggactacttt gtggtcttct cctctgtgag ctgcgggcgt   6060

ggcaatgcgg gacagagcaa ctacggcttt gccaattccg ccatggagcg tatctgtgag   6120

aaacgccggc acgaaggcct cccaggcctg gccgtgcagt ggggcgccat cggcaccgtg   6180

ggcattttgg tggagacgat gagcaccaac gacacgatcg tcagtggcac gctgcccacg   6240

cgcattggcg tccttggcct ggaggtgctg gacctcttcc tgaaccagcc ccacatggtc   6300

ctgagcagct ttgtgctggc tgagaaggct gcggcctata gggacaggga cagccagcgg   6360

gacctggtgg aggccgtggc acacatcctg ggcatccgcg acttggctgc tgtcaacctg   6420

ggcggctcac tggcggacct gggcctggac tcgctcatga gcgcgccggt gcgccagacg   6480

ctggagcgtg agctcaacct ggtgctgtcc gtgcgcgagg tgcggcaact cacgctccgg   6540

aaactgcagg agctgtcctc aaaggcggat gaagccagcg agctggcatg ccccacgccc   6600

aaggaggatg gtctggccca gcagcagact cagctgaacc tgcgctccct gctggtgaaa   6660

ccggagggcc ccaccctgat gcggctcaac tccgtgcaga gctcggagcg gcccctgttc   6720

ctggtgcacc caatcgaggc taccaccgtg ttccacagcc tcggtcccgg tctcagcatc   6780

cccacctatg gcctgcagtg caccccggct gcgccccttg acagcatcca cagcctggct   6840

gcctactaca tcgactgcat caggcaggtg cagcccgagg gcccctaccg cgtggccggc   6900

tactcctacg gggcctgcgt ggcctttgaa atgtgctccc agctgcaggc ccagcagagc   6960

ccagcccccca cccacaacag cctcttcctg ttcgacggct cgcccaccta cgtactggcc   7020

tacacccaga gctaccgggc aaagctgacc ccaggctgta aggctgaggc tgagacggag   7080

gccatatgct tcttcgtgca gcagttcacg gacatggagc acaacagggt gctggaggcg   7140

ctgctgccgc tgaagggcct agaggagcgt gtggcagccg ccgtggacct gatcatcaag   7200

agccaccagg gcctggaccg ccaggagctg agctttgcgg cccggtcctt ctactacagg   7260

ctgcgtgccg ctgaccagta tacacccaag gccaagtaca gtggcaacgt gatgctactg   7320

cgggccaaga cgggtggccg ctacggcgag gacctgggcg cggactacaa cctctcccag   7380

gtatgcgacg ggaaagtatc cgtccatatc atcgagggtg accaccgcac gctgctggag   7440

ggcagcggcc tggagtccat catcagcatc atccacagct ccctggctga gccacgtgtg   7500

agtcgggagg gctag                                                    7515
```

<210> SEQ ID NO 5
<211> LENGTH: 2653
<212> TYPE: DNA
<213> ORGANISM: Homo sapiens

<400> SEQUENCE: 5

-continued

```
ctcaaaaggg gccggatttc cttctcctgg aggcagatgt tgcctctctc tctcgctcgg     60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
gccggctctg ctcgcgccga gatgtggaat ctccttcacg aaaccgactc ggctgtggcc    300
accgcgcgcc gcccgcgctg gctgtgcgct ggggcgctgg tgctggcggg tggcttcttt    360
ctcctcggct tcctcttcgg gtggtttata aaatcctcca atgaagctac taacattact    420
ccaaagcata atatgaaagc atttttggat gaattgaaag ctgagaacat caagaagttc    480
ttatataatt ttacacagat accacattta gcaggaacag aacaaaactt tcagcttgca    540
aagcaaattc aatcccagtg gaaagaattt ggcctggatt ctgttgagct agcacattat    600
gatgtcctgt tgtcctaccc aaataagact catcccaact acatctcaat aattaatgaa    660
gatggaaatg agattttcaa cacatcatta tttgaaccac ctcctccagg atatgaaaat    720
gtttcggata ttgtaccacc tttcagtgct ttctctcctc aaggaatgcc agagggcgat    780
ctagtgtatg ttaactatgc acgaactgaa gacttcttta aattggaacg ggacatgaaa    840
atcaattgct ctgggaaaat tgtaattgcc agatatggga aagttttcag aggaaataag    900
gttaaaaatg cccagctggc aggggccaaa ggagtcattc tctactccga ccctgctgac    960
tactttgctc ctggggtgaa gtcctatcca gatggttgga atcttcctgg aggtggtgtc   1020
cagcgtggaa atatcctaaa tctgaatggt gcaggagacc ctctcacacc aggttaccca   1080
gcaaatgaat atgcttatag gcgtggaatt gcagaggctg ttggtcttcc aagtattcct   1140
gttcatccaa ttggatacta tgatgcacag aagctcctag aaaaaatggg tggctcagca   1200
ccaccagata gcagctggag aggaagtctc aaagtgccct acaatgttgg acctggcttt   1260
actggaaact tttctacaca aaaagtcaag atgcacatcc actctaccaa tgaagtgaca   1320
agaatttaca atgtgatagg tactctcaga ggagcagtgg aaccagacag atatgtcatt   1380
ctgggaggtc accgggactc atgggtgttt ggtggtattg accctcagag tggagcagct   1440
gttgttcatg aaattgtgag gagctttgga acactgaaaa aggaagggtg gagacctaga   1500
agaacaattt tgtttgcaag ctgggatgca gaagaatttg gtcttcttgg ttctactgag   1560
tgggcagagg agaattcaag actccttcaa gagcgtggcg tggcttatat taatgctgac   1620
tcatctatag aaggaaacta cactctgaga gttgattgta caccgctgat gtacagcttg   1680
gtacacaacc taacaaaaga gctgaaaagc cctgatgaag gctttgaagg caaatctctt   1740
tatgaaagtt ggactaaaaa aagtccttcc ccagagttca gtggcatgcc caggataagc   1800
aaattgggat ctggaaatga ttttgaggtg ttcttccaac gacttggaat tgcttcaggc   1860
agagcacggt atactaaaaa ttgggaaaca aacaaattca gcggctatcc actgtatcac   1920
agtgtctatg aaacatatga gttggtggaa aagttttatg atccaatgtt taaatatcac   1980
ctcactgtgg cccaggttcg aggagggatg gtgtttgagc tagccaattc catagtgctc   2040
ccttttgatt gtcgagatta tgctgtagtt ttaagaaagt atgctgacaa aatctacagt   2100
atttctatga aacatccaca ggaaatgaag acatacagtg tatcatttga ttcacttttt   2160
tctgcagtaa agaattttac agaaattgct tccaagttca gtgagagact ccaggacttt   2220
gacaaaagca acccaatagt attaagaatg atgaatgatc aactcatgtt tctggaaaga   2280
gcatttattg atccattagg gttaccagac aggccttttt ataggcatgt catctatgct   2340
```

-continued

```
ccaagcagcc acaacaagta tgcaggggag tcattcccag gaatttatga tgctctgttt   2400

gatattgaaa gcaaagtgga cccttccaag gcctggggag aagtgaagag acagatttat   2460

gttgcagcct tcacagtgca ggcagctgca gagactttga gtgaagtagc ctaagaggat   2520

tctttagaga atccgtattg aatttgtgtg gtatgtcact cagaaagaat cgtaatgggt   2580

atattgataa attttaaaat tggtatattt gaaataaagt tgaatattat atataaaaaa   2640

aaaaaaaaaa aaa                                                      2653


<210> SEQ ID NO 6
<211> LENGTH: 1750
<212> TYPE: DNA
<213> ORGANISM: Homo sapiens

<400> SEQUENCE: 6

cctcactgac tataaaagaa tagagaagga agggcttcag tgaccggctg cctggctgac     60

ttacagcagt cagactctga caggatcatg gctatgatgg aggtccaggg gggacccagc    120

ctgggacaga cctgcgtgct gatcgtgatc ttcacagtgc tcctgcagtc tctctgtgtg    180

gctgtaactt acgtgtactt taccaacgag ctgaagcaga tgcaggacaa gtactccaaa    240

agtggcattg cttgtttctt aaaagaagat gacagttatt gggaccccaa tgacgaagag    300

agtatgaaca gcccctgctg gcaagtcaag tggcaactcc gtcagctcgt tagaaagatg    360

attttgagaa cctctgagga aaccatttct acagttcaag aaaagcaaca aaatatttct    420

cccctagtga gagaaagagg tcctcagaga gtagcagctc acataactgg gaccagagga    480

agaagcaaca cattgtcttc tccaaactcc aagaatgaaa aggctctggg ccgcaaaata    540

aactcctggg aatcatcaag gagtgggcat tcattcctga gcaacttgca cttgaggaat    600

ggtgaactgg tcatccatga aaaagggttt tactacatct attcccaaac atactttcga    660

tttcaggagg aaataaaaga aaacacaaag aacgacaaac aaatggtcca atatatttac    720

aaatacacaa gttatcctga ccctatattg ttgatgaaaa gtgctagaaa tagttgttgg    780

tctaaagatg cagaatatgg actctattcc atctatcaag gggaatattt tgagcttaag    840

gaaaatgaca gaatttttgt ttctgtaaca aatgagcact tgatagacat ggaccatgaa    900

gccagttttt ttggggcctt tttagttggc taactgacct ggaaagaaaa agcaataacc    960

tcaaagtgac tattcagttt tcaggatgat acactatgaa gatgtttcaa aaaatctgac   1020

caaaacaaac aaacagaaaa cagaaaacaa aaaaaacctct atgcaatctg agtagagcag   1080

ccacaaccaa aaaattctac aacacacact gttctgaaag tgactcactt atcccaagag   1140

aatgaaattg ctgaaagatc tttcaggact ctacctcata tcagtttgct agcagaaatc   1200

tagaagactg tcagcttcca aacattaatg caatggttaa catcttctgt ctttataatc   1260

tactccttgt aaagactgta gaagaaagag caacaatcca tctctcaagt agtgtatcac   1320

agtagtagcc tccaggtttc cttaagggac aacatcctta agtcaaaaga gagaagaggc   1380

accactaaaa gatcgcagtt tgcctggtgc agtggctcac acctgtaatc ccaacatttt   1440

gggaacccaa ggtgggtaga tcacgagatc aagagatcaa gaccatagtg accaacatag   1500

tgaaaccccca tctctactga aagtacaaaa attagctggg tgtgttggca catgcctgta   1560

gtcccagcta cttgagaggc tgaggcaaga gaattgtttg aacccgggag gcagaggttg   1620

cagtgtggtg agatcatgcc actacactcc agcctggcga cagagcgaga cttggtttca   1680

aaaaaaaaaa aaaaaaaaac ttcagtaagt acgtgttatt tttttcaata aaattctatt   1740

acagtatgtc                                                          1750
```

-continued

<210> SEQ ID NO 7
<211> LENGTH: 6597
<212> TYPE: DNA
<213> ORGANISM: Homo sapiens

<400> SEQUENCE: 7
ggtcacatga ctccagtcta gctcgcattg cggctcccgc ccgggcgagt tctcgccccc 60
gcgcggccgt tgccgaggag acggcgcatg tcccgccgcg cgttgccccc tctgcagtac 120
ccccgcccct cttctcccac cacaatgaga tcctaagatg gcggtggctg cggcggttgg 180
cgctgcgtag ctgaggtcga aaaggcggcc actggggccg aggcagccag gaaacgtgtg 240
ggcctctctg ctgcggtctc cgagggccga ccgctgccgg cggcgggtcg tgggggctga 300
ctgtcgctct gcctttgaca ggagaggctg cttcttgtag aggaaacagc tttgaagtgt 360
ggagcgggaa aggagcagtt tctgagctgc aaaaactagt ttctaaacag agagttaatt 420
gttaaatcca gtatggccac aggaggaggt ccctttgaag atggcatgaa tgatcaggat 480
ttaccaaact ggagtaatga gaatgttgat gacaggctca acaatatgga ttggggtgcc 540
caacagaaga aagcaaatag atcatcagaa aagaataaga aaaagtttgg tgtagaaagt 600
gataaaagag taaccaatga tatttctccg gagtcgtcac caggagttgg aaggcgaaga 660
acaaagactc cacatacgtt cccacacagt agatacatga gtcagatgtc tgtcccagag 720
caggcagaat tagagaaact gaaacagcgg ataaacttca gtgatttaga tcagagaagc 780
attggaagtg attcccaagg tagagcaaca gctgctaaca acaaacgtca gcttagtgaa 840
aaccgaaagc ccttcaactt tttgcctatg cagattaata ctaacaagag caaagatgca 900
tctacaagtc cccccaaacag agaaacgatt ggatcagcac agtgtaaaga gttgtttgct 960
tctgctttaa gtaatgacct cttgcaaaac tgtcaggtgt ctgaagaaga tgggagggga 1020
gaacctgcaa tggagagcag ccagattgta agcaggcttg ttcaaattcg cgattatatt 1080
actaaagcta gttccatgcg ggaagatctt gtagagaaaa atgagagatc tgctaatgtt 1140
gagcgcctta ctcatctaat agatcacctt aaagaacaag agaagtcata tatgaaattt 1200
cttaaaaaaa tccttgccag agatcctcag caggagccta tggaagagat agaaaatttg 1260
aagaaacaac atgatttatt aaaaagaatg ttacaacagc aggagcaact aagagctcta 1320
cagggacggc aggctgcact tctagctctg caacataaag cagagcaagc tattgcagtg 1380
atggatgatt ctgttgttgc agaaactgca ggtagcttat ctggcgtcag tatcacatct 1440
gaactaaatg aagaattgaa tgacttaatt cagcgttttc ataatcagct tcgtgattct 1500
cagcctccag ctgttccaga caatagaaga caggcagaaa gtctttcatt aactagggag 1560
gtttcccaga gcaggaaacc atcagcttca gaacgtttac ctgatgagaa agtcgaactt 1620
tttagcaaaa tgagagtgct acaggaaaag aaacaaaaaa tggacaaatt gcttggagaa 1680
cttcatacac ttcgagatca gcatcttaac aattcatcat cctctccaca aaggagtgtc 1740
gatcagagaa gtacttcagc tccctctgct tctgtaggct tggcaccggt tgtcaatgga 1800
gaatccaata gcctcacatc atctgttcct tatcctactg cttctctagt atctcagaat 1860
gagagtgaaa acgaaggcca cctcaatcca tctgaaaaac tccagaagtt aaatgaagtt 1920
cgaaagagat tgaatgagct aagagaatta gttcattatt atgaacaaac gtcagacatg 1980
atgacagatg ctgtgaatga aaacaggaaa gatgaagaaa ctgaagagtc agaatatgat 2040
tctgagcatg aaaattccga gcctgttact aacattcgaa atccacaagt agcttccact 2100

-continued

```
tggaatgaag taaatagtca tagtaatgca cagtgtgttt ctaataatag agatgggcga   2160
acagttaatt ctaattgtga aattaacaac agatctgctg ccaacataag ggctctaaac   2220
gtgcctcctt ctttagattg tcgatataat agagaagggg aacaggagat tcatgttgca   2280
caaggtgaag atgatgagga ggaggaggaa gaagcagaag aggagggagt cagtggagct   2340
tcattatcta gtcacaggag cagtctggtt gatgagcatc cagaagatgc tgaatttgaa   2400
cagaagatca accgacttat ggctgcaaaa cagaaactta gacagttaca agatcttgtt   2460
gctatggtac aggatgatga tgcagctcaa ggagttatct ctgccagtgc atcaaatttg   2520
gatgatttct acccagcaga agaagacacc aagcaaaatt caaataacac tagaggaaat   2580
gccaataaaa cacagaaaga tactggagta aatgaaaagg caagagagaa attttatgag   2640
gctaaactac agcagcaaca gagagagcta aaacaattgc aggaagaaag aaagaaactg   2700
attgacattc aggagaaaat tcaagcattg caaacggcat gccctgactt acagctgtca   2760
gctgctagtg tgggtaactg tcccaccaaa aaatatatgc cagctgttac ttcaacccca   2820
actgttaatc aacacgagac cagtacaagc aaatctgttt ttgagcctga agattcttca   2880
atagtagata atgagttgtg gtcagaaatg agaagacatg aaatgttgag ggaggagctg   2940
cgacagagaa gaaagcagct tgaagctctg atggctgaac atcagaggag gcaaggtcta   3000
gctgaaactg catctccagt ggctgtgtca ttgagaagtg atggatctga gaacctatgt   3060
actcctcagc aaagtagaac agaaaaaacg atggcaactt ggggagggtc tacccagtgt   3120
gcactagatg aagaaggaga tgaagacggt tacctttctg aaggaattgt tcggacagat   3180
gaagaggagg aagaagagca agatgccagt tccaatgata acttttctgt gtgtccttct   3240
racagtgtga atcataactc ctacaatgga aaggaaacta aaaataggtg gaagaacaat   3300
tgcccttttt cggcagatga aaattatcgt cctttagcca agacaaggca acagaatatc   3360
agcatgcaac ggcaagaaaa ccttcgttgg gtgtcagagc tctcttacgt agaagagaaa   3420
gaacaatggc aagaacaaat caatcagcta aagaaacagc ttgattttag tgtcagtatt   3480
tgtcagactt tgatgcaaga ccagcagact ctatcttgtc tgctacaaac tcttctcacg   3540
ggtccttaca gtgttatgcc cagcaatgtt gcatctcctc aagtacactt cataatgcac   3600
cagttgaacc agtgctatac tcagctaaca tggcaacaga ataatgttca gaggttgaaa   3660
caaatgctaa atgaacttat gcgccagcaa aatcagcatc cagaaaaacc tggaggcaag   3720
gaaagaggca gtagtgcatc gcaccctcct tctcccagtt tattttgtcc tttcagcttt   3780
ccaacacagc ctgtaaatct cttcaatata cctggattta ctaacttttc atcatttgca   3840
ccaggtatga atttcagccc tttatttcct tctaattttg gagatttttc tcagaatatc   3900
tctacaccca gtgaacagca gcaaccctta gcccagaatt cttcaggaaa aacagaatat   3960
atggcttttc caaaaccttt tgaaagcagt tcctctattg gagcagagaa accaaggaat   4020
aaaaaactgc ctgaagagga ggtggaaagc agtaggacac catggttata tgaacaagaa   4080
ggtgaagtag agaaaccatt tatcaagact ggattttcag tgtctgtaga aaaatctaca   4140
agtagtaacc gcaaaaatca attagataca aacggaagaa gacgccagtt tgatgaagaa   4200
tcactggaaa gctttagcag tatgcctgat ccagtagatc caacaacagt gactaaaaca   4260
ttcaagacaa gaaaagcgtc tgcacaggcc agcctggcat ctaaagataa aactcccaag   4320
tcaaaaagta agaagaggaa ttctactcag ctgaaaagca gagttaaaaa catcaggtat   4380
gaaagtgcca gtatgtctag cacatgtgaa ccttgcaaaa gtaggaacag acattcagcc   4440
cagactgaag agcctgttca agcaaaagta ttcagcagaa agaatcatga gcaactggaa   4500
```

-continued

```
aaaataataa aatgtaatag gtctacagaa atatcttcag aaactgggag tgatttttcc   4560
atgtttgaag ctttgcgaga tactatttat tctgaagtag ctacattaat ttctcaaaat   4620
gaatctcgtc cacattttct tattgaactc ttccatgagc tgcagctact aaacacagac   4680
tacttgagac agagggcttt atatgcattg caggacatag tatccagaca tatttctgag   4740
agccatgaaa aaggagaaaa tgtaaagtca gtaaactctg gtacttggat agcatcaaac   4800
tcagaactta ctcctagtga gagccttgct actactgatg atgaaacttt tgagaagaac   4860
tttgaaagag aaacccataa aataagtgag caaaatgatg ctgataatgc tagtgtcctg   4920
tctgtatcat caaattttga gccttttgca acagatgatc taggtaacac cgtgattcac   4980
ttagatcaag cattagccag aatgagagaa tatgagcgta tgaagactga ggctgaaagt   5040
aactcaaata tgagatgcat ctgcaggatt attgaggatg gagatggtgc tggtgcaggt   5100
actacagtta ataatttaga agaaactccc gttattgaaa atcgtagttc acaacaacct   5160
gtaagtgaag tttctaccat cccatgtcct agaattgata ctcagcagct ggaccggcaa   5220
attaaagcaa ttatgaaaga agtcattcct tttttgaagg agcacatgga tgaagtatgc   5280
tcctcgcagc ttctaacttc agtaaggcgc atggttttga cccttaccca gcaaaatgat   5340
gagagcaaag agtttgtaaa gttctttcat aaacaacttg gaagtatatt acaggattca   5400
ctggcaaaat ttgctggcag aaaactgaaa gactgtggag aagatcttct tgtagagata   5460
tctgaagtgt tgttcaatga attggctttc tttaagctta tgcaagattt ggataataat   5520
agtataactg ttaaacagag atgcaaaagg aaaatagaag caactggagt gatacaatct   5580
tgtgccaaag agctaaaagg attcttgaag atcatggctc acctgctgga gagattgatg   5640
atgaagacaa agacaaggat gaaactgaaa cagttaagca gactcaaaca tctgaggtgt   5700
atgatggtcc caaaaatgta agatctgata tttctgatca agaggaagat gaagaaagtg   5760
aaggatgtcc agtgtctatt aatttgtcta aagctgaaac tcaggcttta actaattatg   5820
gaagtggaga agatgaaaat gaggatgaag aaatggaaga atttgaagaa ggccctgtgg   5880
atgtccagac ttccctccag gctaacactg aagctactga agaaaatgaa catgatgaac   5940
aggtcctaca acgtgacttt aaaaagacag cagaaagcaa aaatgtccca ttggaacgag   6000
aagccactag taaaaatgac caaaataact gtcctgtgaa accctgttac ctcaatatct   6060
tggaagatga gcaaccttta aatagtgctg cccataagga gtcacctcct actgttgatt   6120
caactcaaca gcctaaccct ttgccgttac gtttacctga aatggaaccc ttagtgccta   6180
gagtcaaaga agttaaatct gctcaggaaa ctcctgaaag ctctctggct ggaagtcctg   6240
atactgaatc tccagtgtta gtgaatgact atgaagcaga atctggtaat ataagtcaaa   6300
agtctgatga agaagatttt gtaaaagttg aagatttacc actgaaactg acaatatatt   6360
cagaggcaga tctaagaaag aaaatggtag aagaagaaca gaaaaaccat ttatctggtg   6420
aaatatgtga aatgcagacc gaagaattag ctggaaattc tgagacacta aaagaacctg   6480
aaacggtggg agcccagagt atatgagatg tcttcagagg ctcatctaac tctgtcctta   6540
catactcaat gcatatatga aaacaatact aaataaacat ctgatctgta taaaaat      6597
```

<210> SEQ ID NO 8
<211> LENGTH: 479
<212> TYPE: DNA
<213> ORGANISM: Homo sapiens

<400> SEQUENCE: 8

-continued

```
ctccaaaggc aaaaatctcc agccctacag agactgagcg gtgcatcgag tccctgattg     60

ctgtcttcca gaagtatgct ggaaaggatg gttataacta cactctctcc aagacagagt    120

tcgtaagctt catgaataca gaactagctg ccttcacaaa gaaccagaag gaccctggtg    180

tccttgaccg catgatgaag aaactggaca ccaacagtga tggtcagcta gatttctcag    240

aatttcttaa tctgattggt ggcctagcta tggcttgcca tgactccttc ctcaaggctg    300

tcccttccca gaagcggacc tgaggacccc ttggccctgg ccttcaaacc caccccccttt    360

ccttccagcc tttctgtcat catctccaca gcccacccat cccctgagca cactaaccac    420

ctcatgcagg ccccacctgc caatagtaat aaagcaatgt cacttttttta aaacatgaa    479
```

<210> SEQ ID NO 9
<211> LENGTH: 2465
<212> TYPE: DNA
<213> ORGANISM: Homo sapiens

<400> SEQUENCE: 9

```
gccgcttcct gcctggattc cacagcttcg cgccgtgtac tgtcgcccca tccctgcgcg     60

cccagcctgc caagcagcgt gccccggttg caggcgtcat gcagcgggcg cgacccacgc    120

tctgggccgc tgcgctgact ctgctggtgc tgctccgcgg gccgccggtg gcgcgggctg    180

gcgcgagctc ggcgggcttg ggtcccgtgg tgcgctgcga gccgtgcgac gcgcgtgcac    240

tggcccagtg cgcgcctccg cccgccgtgt gcgcggagct ggtgcgcgag ccgggctgcg    300

gctgctgcct gacgtgcgca ctgagcgagg gccagccgtg cggcatctac accgagcgct    360

gtggctccgg ccttcgctgc cagccgtcgc ccgacgaggc gcgaccgctg caggcgctgc    420

tggacggccg cgggctctgc gtcaacgcta gtgccgtcag ccgcctgcgc gcctacctgc    480

tgccagcgcc gccagctcca ggaaatgcta gtgagtcgga ggaagaccgc agcgccggca    540

gtgtggagag cccgtccgtc tccagcacgc accgggtgtc tgatcccaag ttccaccccc    600

tccattcaaa gataatcatc atcaagaaag ggcatgctaa agacagccag cgctacaaag    660

ttgactacga gtctcagagc acagataccc agaacttctc ctccgagtcc aagcgggaga    720

cagaatatgg tccctgccgt agagaaatgg aagacacact gaatcacctg aagttcctca    780

atgtgctgag tcccaggggt gtacacattc ccaactgtga caagaaggga ttttataaga    840

aaaagcagtg tcgcccttcc aaaggcagga agcggggctt ctgctggtgt gtggataagt    900

atgggcagcc tctcccaggc tacaccacca aggggaagga ggacgtgcac tgctacagca    960

tgcagagcaa gtagacgcct gccgcaaggt taatgtggag ctcaaatatg ccttattttg   1020

cacaaaagac tgccaaggac atgaccagca gctggctaca gcctcgattt atatttctgt   1080

ttgtggtgaa ctgatttttt ttaaaccaaa gtttagaaag aggtttttga aatgcctatg   1140

gtttctttga atggtaaact tgagcatctt ttcactttcc agtagtcagc aaagagcagt   1200

ttgaattttc ttgtcgcttc ctatcaaaat attcagagac tcgagcacag cacccagact   1260

tcatgcgccc gtggaatgct caccacatgt tggtcgaagc ggccgaccac tgactttgtg   1320

acttaggcgg ctgtgttgcc tatgtagaga acacgcttca cccccactcc ccgtacagtg   1380

cgcacaggct ttatcgagaa taggaaaacc tttaaacccc ggtcatccgg acatcccaac   1440

gcatgctcct ggagctcaca gccttctgtg gtgtcatttc tgaaacaagg gcgtggatcc   1500

ctcaaccaag aagaatgttt atgtcttcaa gtgacctgta ctgcttgggg actattggag   1560

aaaataaggt ggagtcctac ttgtttaaaa aatatgtatc taagaatgtt ctagggcact   1620

ctgggaacct ataaaggcag gtatttcggg ccctcctctt caggaatctt cctgaagaca   1680
```

-continued

```
tggcccagtc gaaggcccag gatggctttt gctgcggccc cgtggggtag gagggacaga   1740

gagacaggga gagtcagcct ccacattcag aggcatcaca agtaatggca caattcttcg   1800

gatgactgca gaaaatagtg ttttgtagtt caacaactca agacgaagct tatttctgag   1860

gataagctct ttaaaggcaa agctttattt tcatctctca tcttttgtcc tccttagcac   1920

aatgtaaaaa agaatagtaa tatcagaaca ggaaggagga atggcttgct ggggagccca   1980

tccaggacac tgggagcaca tagagattca cccatgtttg ttgaacttag agtcattctc   2040

atgcttttct ttataattca cacatatatg cagagaagat atgttcttgt taacattgta   2100

tacaacatag ccccaaatat agtaagatct atactagata atcctagatg aaatgttaga   2160

gatgctattt gatacaactg tggccatgac tgaggaaagg agctcacgcc cagagactgg   2220

gctgctctcc cggaggccaa acccaagaag gtctggcaaa gtcaggctca gggagactct   2280

gccctgctgc agacctcggt gtggacacac gctgcataga gctctccttg aaaacagagg   2340

ggtctcaaga cattctgcct acctattagc ttttctttat ttttttaact ttttgggggg   2400

aaaagtattt ttgagaagtt tgtcttgcaa tgtatttata aatagtaaat aaagttttta   2460

ccatt                                                               2465
```

<210> SEQ ID NO 10
<211> LENGTH: 807
<212> TYPE: DNA
<213> ORGANISM: Homo sapiens

<400> SEQUENCE: 10

```
atgccgcgct ccttcctggt caagaagcat ttcaacgcct ccaaaaagcc aaactacagc     60

gaactggaca cacatacagt gattatttcc ccgtatctct atgagagtta ctccatgcct    120

gtcataccac aaccagagat cctcagctca ggagcataca gccccatcac tgtgtggact    180

accgctgctc cattccacgc ccagctaccc aatggcctct ctcctctttc cggatactcc    240

tcatctttgg ggcgagtgag tccccctcct ccatctgaca cctcctccaa ggaccacagt    300

ggctcagaaa gccccattag tgatgaagag gaaagactac agtccaagct ttcagacccc    360

catgccattg aagctgaaaa gtttcagtgc aatttatgca ataagaccta ttcaactttt    420

tctgggctgg ccaaacataa gcagctgcac tgcgatgccc agtctagaaa atctttcagc    480

tgtaaatact gtgacaagga atatgtgagc ctgggcgccc tgaagatgca tattcggacc    540

cacacattac cttgtgtttg caagatctgc ggcaaggcgt tttccagacc ctggttgctt    600

caaggacaca ttagaactca cacgggggag aagccttttt cttgccctca ctgcaacaga    660

gcatttgcag acaggtcaaa tctgagggct catctgcaga cccattctga tgtaaagaaa    720

taccagtgca aaaactgctc caaaaccttc tccagaatgt ctctcctgca caaacatgag    780

gaatctggct gctgtgtagc acactga                                        807
```

<210> SEQ ID NO 11
<211> LENGTH: 1266
<212> TYPE: DNA
<213> ORGANISM: Homo sapiens

<400> SEQUENCE: 11

```
ctcggaagcc cgtcaccatg tcgtgcgagt cgtctatggt tctcgggtac tgggatattc     60

gtgggctggc gcacgccatc cgcctgctcc tggagttcac ggatacctct tatgaggaga    120

aacggtacac gtgcggggaa gctcctgact atgatcgaag ccaatggctg gatgtgaaat    180
```

-continued tcaagctaga cctggacttt cctaatctgc cctacctcct ggatgggaag aacaagatca 240
cccagagcaa tgccatcttg cgctacatcg ctcgcaagca caacatgtgt ggtgagactg 300
aagaagaaaa gattcgagtg gacatcatag agaaccaagt aatggatttc cgcacacaac 360
tgataaggct ctgttacagc tctgaccacg aaaaactgaa gcctcagtac ttggaagagc 420
tacctggaca actgaaacaa ttctccatgt ttctgtggaa attctcatgg tttgccgggg 480
aaaagctcac ctttgtggat tttctcacct atgatatctt ggatcagaac cgtatatttg 540
accccaagtg cctggatgag ttcccaaacc tgaaggcttt catgtgccgt tttgaggctt 600
tggagaaaat cgctgcctac ttacagtctg atcagttctg caagatgccc atcaacaaca 660
agatggccca gtggggcaac aagcctgtat gctgagcagg aggcagactt gcagagcttg 720
ttttgtttca tcctgtccgt aaggggtcag cgctcttgct ttgctctttt caatgaatag 780
cacttatgtt actggtgtcc agctgagttt ctcttgggta taaaggctaa aagggaaaaa 840
ggatatgtgg agaatcatca agatatgaat tgaatcgctg cgatactgtg gcatttccct 900
actccccaac tgagttcaag ggctgtaggt tcatgcccaa gccctgagag tgggtactag 960
aaaaaacgag attgcacagt tggagagagc aggtgtgtta aatggactgg agtccctgtg 1020
aagactgggt gaggataaca caagtaaaac tgtggtactg atggacttaa ccggagttcg 1080
gaaaccgtcc tgtgtacaca tgggagttta gtgtgataaa ggcagtattt cagactggtg 1140
ggctagccaa tagagttggc aattgcttat tgaaactcat taaaaataat agagccccac 1200
ttgacactat tcactaaaat taatctggaa tttaaggccc aacattaaac acaaagctgt 1260
attgat 1266

<210> SEQ ID NO 12
<211> LENGTH: 1308
<212> TYPE: DNA
<213> ORGANISM: Homo sapiens

<400> SEQUENCE: 12
gccacgtgct gctgggtctc agtcctccac ttcccgtgtc ctctggaagt tgtcaggagc 60
aatgttgcgc ttgtacgtgt tggtaatggg agtttctgcc ttcacccttc agcctgcggc 120
acacacaggg gctgccagaa gctgccggtt tcgtgggagg cattacaagc gggagttcag 180
gctggaaggg gagcctgtag ccctgaggtg cccccaggtg ccctactggt tgtgggcctc 240
tgtcagcccc cgcatcaacc tgacatggca taaaaatgac tctgctagga cggtcccagg 300
agaagaagag acacggatgt gggcccagga cggtgctctg tggcttctgc cagccttgca 360
ggaggactct ggcacctacg tctgcactac tagaaatgct tcttactgtg acaaaatgtc 420
cattgagctc agagtttttg agaatacaga tgctttcctg ccgttcatct catacccgca 480
aattttaacc ttgtcaacct ctggggtatt agtatgccct gacctgagtg aattcacccg 540
tgacaaaact gacgtgaaga ttcaatggta caaggattct cttcttttgg ataaagacaa 600
tgagaaattt ctaagtgtga gggggaccac tcacttactc gtacacgatg tggccctgga 660
agatgctggc tattaccgct gtgtcctgac atttgcccat gaaggccagc aatacaacat 720
cactaggagt attgagctac gcatcaagaa aaaaaaagaa gagaccattc ctgtgatcat 780 ttccccccctc aagaccatat cagcttctct ggggtcaaga ctgacaatcc cgtgtaaggt 840
gtttctggga accggcacac ccttaaccac catgctgtgg tggacggcca atgacaccca 900
catagagagc gcctacccgg gaggccgcgt gaccgagggg ccacgccagg aatattcaga 960
aaataatgag aactacattg aagtgccatt gattttgat cctgtcacaa gagaggattt 1020

-continued

```
gcacatggat tttaaatgtg ttgtccataa taccctgagt tttcagacac tacgcaccac   1080

agtcaaggaa gcctcctcca cgttctcctg gggcattgtg ctggccccac tttcactggc   1140

cttcttggtt ttggggggaa tatggatgca cagacggtgc aaacacagaa ctggaaaagc   1200

agatggtctg actgtgctat ggcctcatca tcaagacttt caatcctatc ccaagtgaaa   1260

taaatggaat gaaataattc aaacacaaaa aaaaaaaaaa aaaaaaaa               1308
```

<210> SEQ ID NO 13
<211> LENGTH: 5994
<212> TYPE: DNA
<213> ORGANISM: Homo sapiens

<400> SEQUENCE: 13

```
gcgctgcccg cctcgtcccc accccccaac cccccgcgcc cgccctcgga cagtccctgc     60

tcgcccgcgc gctgcagccc catctcctag cggcagccca ggcgcggagg gagcgagtcc    120

gccccgaggt aggtccagga cgggcgcaca gcagcagccg aggctggccg ggagagggag    180

gaagaggatg gcagggccac gccccagccc atgggccagg ctgctcctgg cagccttgat    240

cagcgtcagc ctctctggga ccttggcaaa ccgctgcaag aaggccccag tgaagagctg    300

cacggagtgt gtccgtgtgg ataaggactg cgcctactgc acagacgaga tgttcaggga    360

ccggcgctgc aacacccagg cggagctgct ggccgcgggc tgccagcggg agagcatcgt    420

ggtcatggag agcagcttcc aaatcacaga ggagacccag attgacacca ccctgcggcg    480

cagccagatg tccccccaag gcctgcgggt ccgtctgcgg cccggtgagg agcggcattt    540

tgagctggag gtgtttgagc cactggagag ccccgtggac ctgtacatcc tcatggactt    600

ctccaactcc atgtccgatg atctggacaa cctcaagaag atggggcaga acctggctcg    660

ggtcctgagc cagctcacca gcgactacac tattggattt ggcaagtttg tggacaaagt    720

cagcgtcccg cagacggaca tgaggcctga gaagctgaag gagccctggc ccaacagtga    780

cccccccttc tccttcaaga acgtcatcag cctgacagaa gatgtggatg agttccggaa    840

taaactgcag ggagagcgga tctcaggcaa cctggatgct cctgagggcg gcttcgatgc    900

catcctgcag acagctgtgt gcacgaggga cattggctgg cgcccggaca gcacccacct    960

gctggtcttc tccaccgagt cagccttcca ctatgaggct gatggcgcca acgtgctggc   1020

tggcatcatg agccgcaacg atgaacggtg ccacctggac accacgggca cctacaccca   1080

gtacaggaca caggactacc cgtcggtgcc caccctggtg cgcctgctcg ccaagcacaa   1140

catcatcccc atctttgctg tcaccaacta ctcctatagc tactacgaga agcttcacac   1200

ctatttccct gtctcctcac tgggggtgct gcaggaggac tcgtccaaca tcgtggagct   1260

gctggaggag gccttcaatc ggatccgctc caacctggac atccgggccc tagacagccc   1320

ccgaggcctt cggacagagg tcacctccaa gatgttccag aagacgagga ctgggtcctt   1380

tcacatccgg cggggggaag tgggtatata ccaggtgcag ctgcgggccc ttgagcacgt   1440

ggatgggacg cacgtgtgcc agctgccgga ggaccagaag ggcaacatcc atctgaaacc   1500

ttccttctcc gacggcctca agatggacgc gggcatcatc tgtgatgtgt gcacctgcga   1560

gctgcaaaaa gaggtgcggt cagctcgctg cagcttcaac ggagacttcg tgtgcggaca   1620

gtgtgtgtgc agcgagggct ggagtggcca gacctgcaac tgctccaccg gctctctgag   1680

tgacattcag ccctgcctgc gggagggcga ggacaagccg tgctccggcc gtggggagtg   1740

ccagtgcggg cactgtgtgt gctacggcga aggccgctac gagggtcagt tctgcgagta   1800
```

-continued

```
tgacaacttc cagtgtcccc gcacttccgg gttcctgtgc aatgaccgag gacgctgctc   1860
catgggccag tgtgtgtgtg agcctggttg gacaggccca agctgtgact gtcccctcag   1920
caatgccacc tgcatcgaca gcaatggggg catctgtaat ggacgtggcc actgtgagtg   1980
tggccgctgc cactgccacc agcagtcgct ctacacggac accatctgcg agatcaacta   2040
ctcggcgatc cacccgggcc tctgcgagga cctacgctcc tgcgtgcagt gccaggcgtg   2100
gggcaccggc gagaagaagg ggcgcacgtg tgaggaatgc aacttcaagg tcaagatggt   2160
ggacgagctt aagagagccg aggaggtggt ggtgcgctgc tccttccggg acgaggatga   2220
cgactgcacc tacagctaca ccatggaagg tgacggcgcc cctgggccca acagcactgt   2280
cctggtgcac aagaagaagg actgccctcc gggctccttc tggtggctca tcccccctgct   2340
cctcctcctc ctgccgctcc tggccctgct actgctgcta tgctggaagt actgtgcctg   2400
ctgcaaggcc tgcctggcac ttctcccgtg ctgcaaccga ggtcacatgg tgggctttaa   2460
ggaagaccac tacatgctgc gggagaacct gatggcctct gaccacttgg acacgcccat   2520
gctgcgcagc gggaacctca agggccgtga cgtggtccgc tggaaggtca ccaacaacat   2580
gcagcggcct ggctttgcca ctcatgccgc cagcatcaac ccccacagagc tggtgcccta   2640
cgggctgtcc ttgcgcctgg cccgcctttg caccgagaac ctgctgaagc ctgacactcg   2700
ggagtgcgcc cagctgcgcc aggaggtgga ggagaacctg aacgaggtct acaggcagat   2760
ctccggtgta cacaagctcc agcagaccaa gttccggcag cagcccaatg ccgggaaaaa   2820
gcaagaccac accattgtgg acacagtgct gatggcgccc cgctcggcca agccggccct   2880
gctgaagctt acagagaagc aggtggaaca gagggccttc cacgacctca aggtggcccc   2940
cggctactac accctcactg cagaccagga cgcccggggc atggtggagt tccaggaggg   3000
cgtggagctg gtggacgtac gggtgcccct ctttatccgg cctgaggatg acgacgagaa   3060
gcagctgctg gtggaggcca tcgacgtgcc cgcaggcact gccaccctcg gccgccgcct   3120
ggtaaacatc accatcatca aggagcaagc cagagacgtg gtgtcctttg agcagcctga   3180
gttctcggtc agccgcgggg accaggtggc ccgcatccct gtcatccggc gtgtcctgga   3240
cggcgggaag tcccaggtct cctaccgcac acaggatggc accgcgcagg gcaaccggga   3300
ctacatcccc gtggagggtg agctgctgtt ccagcctggg gaggcctgga aagagctgca   3360
ggtgaagctc ctggagctgc aagaagttga ctccctcctg cggggccgcc aggtccgccg   3420
tttccacgtc cagctcagca accctaagtt tggggcccac ctgggccagc cccactccac   3480
caccatcatc atcagggacc cagatgaact ggaccggagc ttcacgagtc agatgttgtc   3540
atcacagcca ccccctcacg gcgacctggg cgccccgcag aaccccaatg ctaaggccgc   3600
tgggtccagg aagatccatt tcaactggct gccccccttct ggcaagccaa tggggtacag   3660
ggtaaagtac tggattcagg gcgactccga atccgaagcc cacctgctcg acagcaaggt   3720
gccctcagtg gagctcacca acctgtaccc gtattgcgac tatgagatga aggtgtgcgc   3780
ctacggggct cagggcgagg gaccctacag ctccctggtg tcctgccgca cccaccagga   3840
agtgcccagc gagccagggc gtctggcctt caatgtcgtc tcctccacgg tgacccagct   3900
gagctgggct gagccggctg agaccaacgg tgagatcaca gcctacgagg tctgctatgg   3960
cctggtcaac gatgacaacc gacctattgg gcccatgaag aaagtgctgg ttgacaaccc   4020
taagaaccgg atgctgctta ttgagaacct tcgggagtcc cagccctacc gctacacggt   4080
gaaggcgcgc aacggggccg gctgggggcc tgagcgggag gccatcatca acctggccac   4140
ccagcccaag aggcccatgt ccatccccat catccctgac atccctatcg tggacgccca   4200
```

-continued gagcggggag gactacgaca gcttccttat gtacagcgat gacgttctac gctctccatc 4260
gggcagccag aggcccagcg tctccgatga cactggctgc ggctggaagt tcgagcccct 4320
gctgggggag gagctggacc tgcggcgcgt cacgtggcgg ctgcccccgg agctcatccc 4380
gcgcctgtcg gccagcagcg ggcgctcctc cgacgccgag gcccccacgg ccccccggac 4440
gacggcggcg cgggcgggaa gggcggcagc cgtgccccgc agtgcgacac ccgggccccc 4500
cggagagcac ctggtgaatg gccggatgga ctttgccttc ccgggcagca ccaactccct 4560
gcacaggatg accacgacca gtgctgctgc ctatggcacc cacctgagcc cacacgtgcc 4620
ccaccgcgtg ctaagcacat cctccaccct cacacgggac tacaactcac tgacccgctc 4680
agaacactca cactcgacca cactgcccag ggactactcc accctcacct ccgtctcctc 4740
ccacgactct cgcctgactg ctggtgtgcc cgacacgccc acccgcctgg tgttctctgc 4800
cctggggccc acatctctca gagtgagctg gcaggagccg cggtgcgagc ggccgctgca 4860
gggctacagt gtggagtacc agctgctgaa cggcggtgag ctgcatcggc tcaacatccc 4920
caaccctgcc cagacctcgg tggtggtgga agacctcctg cccaaccact cctacgtgtt 4980
ccgcgtgcgg gcccagagcc aggaaggctg gggccgagag cgtgagggtg tcatcaccat 5040
tgaatcccag gtgcacccgc agagcccact gtgtcccctg ccaggctccg ccttcacttt 5100
gagcactccc agtgccccag gcccgctggt gttcactgcc ctgagcccag actcgctgca 5160
gctgagctgg gagcggccac ggaggcccaa tggggatatc gtcggctacc tggtgacctg 5220
tgagatggcc caaggaggag ggccagccac cgcattccgg gtggatggag acagccccga 5280
gagccggctg accgtgccgg gcctcagcga gaacgtgccc tacaagttca aggtgcaggc 5340
caggaccact gagggcttcg ggccagagcg cgagggcatc atcaccatag agtcccagga 5400
tggaggaccc ttcccgcagc tgggcagccg tgccgggctc ttccagcacc cgctgcaaag 5460
cgagtacagc agcatcacca ccacccacac cagcgccacc gagcccttcc tagtggatgg 5520
gctgaccctg gggggcccagc acctggaggc aggcggctcc ctcacccggc atgtgaccca 5580
ggagtttgtg agccggacac tgaccaccag cggaaccctt agcacccaca tggaccaaca 5640
gttcttccaa acttgaccgc accctgcccc acccccgcca tgtcccacta ggcgtcctcc 5700
cgactcctct cccggagcct cctcagctac tccatccttg cacccctggg ggcccagccc 5760
acccgcatgc acagagcagg ggctaggtgt ctcctgggag gcatgaaggg ggcaaggtcc 5820
gtcctctgtg ggcccaaacc tatttgtaac caaagagctg ggagcagcac aaggacccag 5880
cctttgttct gcacttaata aatggttttg ctactgctaa aaaaaaaaaa aaaaaaaaaa 5940
aaaaaaaaaa aaaaaaaaaa aaaaaaaaaa aaaaaaaaaa aaaaaaaaaa aaaa 5994

<210> SEQ ID NO 14
<211> LENGTH: 1898
<212> TYPE: DNA
<213> ORGANISM: Homo sapiens

<400> SEQUENCE: 14
ccgccgggct ggccatggag ctgctgtgcc acgaggtgga cccggtccgc agggccgtgc 60
gggaccgcaa cctgctccga gacgaccgcg tcctgcagaa cctgctcacc atcgaggagc 120
gctaccttcc gcagtgctcc tacttcaagt gcgtgcagaa ggacatccaa ccctacatgc 180
gcagaatggt ggccacctgg atgctggagg tctgtgagga acagaagtgc gaagaagagg 240
tcttccctct ggccatgaat tacctggacc gtttcttggc tggggtcccg actccgaagt 300

-continued

```
cccatctgca actcctgggt gctgtctgca tgttcctggc ctccaaactc aaagagacca    360

gcccgctgac cgcggagaag ctgtgcattt acaccgacaa ctccatcaag cctcaggagc    420

tgctggagtg ggaactggtg gtgctgggga agttgaagtg gaacctggca gctgtcactc    480

ctcatgactt cattgagcac atcttgcgca agctgcccca gcagcgggag aagctgtctc    540

tgatccgcaa gcatgctcag accttcattg ctctgtgtgc caccgacttt aagtttgcca    600

tgtacccacc gtcgatgatc gcaactggaa gtgtgggagc agccatctgt gggctccagc    660

aggatgagga agtgagctcg ctcacttgtg atgccctgac tgagctgctg gctaagatca    720

ccaacacaga cgtggattgt ctcaaagctt gccaggagca gattgaggcg gtgctcctca    780

atagcctgca gcagtaccgt caggaccaac gtgacggatc caagtcggag gatgaactgg    840

accaagccag caccccctaca gacgtgcggg atatcgacct gtgaggatgc cagttgggcc    900

gaaagagaga gacgcgtcca taatctggtc tcttcttctt tctggttgtt tttgttcttt    960

gtgttttagg gtgaaactta aaaaaaaaat tctgccccca cctagatcat atttaaagat   1020

cttttagaag tgagagaaaa aggtcctacg aaaacggaat aataaaaagc atttggtgcc   1080

tatttgaagt acagcataag ggaatccctt gtatatgcga acagttattg tttgattatg   1140

taaaagtaat agtaaaatgc ttacaggaaa acctgcagag tagttagaga atatgtatgc   1200

ctgcaatatg ggaacaaatt agaggagact tttttttttc atgttatgag ctagcacata   1260

caccccccttg tagtataatt tcaaggaact gtgtacgcca tttatggcat gattagattg   1320

caaagcaatg aactcaagaa ggaattgaaa taaggaggga catgatgggg aaggagtaca   1380

aaacaatctc tcaacatgat tgaaccattt gggatggaga agcacctttg ctctcagcca   1440

cctgttacta agtcaggagt gtagttggat ctctacatta atgtcctctt gctgtctaca   1500

gtagctgcta cctaaaaaaa gatgttttat tttgccagtt ggacacaggt gattggctcc   1560

tgggtttcat gttctgtgac atcctgcttc ttcttccaaa tgcagttcat tgcagacacc   1620

accatattgc tatctaatgg ggaaatgtag ctatgggcca taaccaaaac tcacatgaaa   1680

cggaggcaga tggagaccaa gggtgggatc cagaatggag tcttttctgt tattgtattt   1740

aaaagggtaa tgtggccttg gcatttcttc ttagaaaaaa actaattttt ggtgctgatt   1800

ggcatgtctg gttcacagtt tagcattgtt ataaaccatt ccattcgaaa agcactttga   1860

aaaattgttc ccgagcgata gatgggatgg tttatgca                            1898
```

<210> SEQ ID NO 15
<211> LENGTH: 4286
<212> TYPE: DNA
<213> ORGANISM: Homo sapiens

<400> SEQUENCE: 15

```
gagacattcc ggtgggggac tctggccagc ccgagcaacg tggatcctga gagcactccc     60

aggtaggcat ttgccccggt gggacgcctt gccagagcag tgtgtggcag gccccccgtgg    120

aggatcaaca cagtggctga acactgggaa ggaactggta cttggagtct ggacatctga    180

aacttggctc tgaaactgcg cagcggccac cggacgcctt ctggagcagg tagcagcatg    240

cagccgcctc caagtctgtg cggacgcgcc ctggttgcgc tggttcttgc ctgcggcctg    300

tcgcggatct ggggagagga gagaggcttc ccgcctgaca gggccactcc gcttttgcaa    360

accgcagaga taatgacgcc acccactaag accttatggc ccaagggttc caacgccagt    420

ctggcgcggt cgttggcacc tgcggaggtg cctaaaggag acaggacggc aggatctccg    480

ccacgcacca tctcccctcc cccgtgccaa ggacccatcg agatcaagga gactttcaaa    540
```

-continued

```
tacatcaaca cggttgtgtc ctgccttgtg ttcgtgctgg ggatcatcgg gaactccaca    600
cttctgagaa ttatctacaa gaacaagtgc atgcgaaacg gtcccaatat cttgatcgcc    660
agcttggctc tgggagacct gctgcacatc gtcattgaca tccctatcaa tgtctacaag    720
ctgctggcag aggactggcc atttggagct gagatgtgta agctggtgcc tttcatacag    780
aaagcctccg tgggaatcac tgtgctgagt ctatgtgctc tgagtattga cagatatcga    840
gctgttgctt cttggagtag aattaaagga attggggttc caaaatggac agcagtagaa    900
attgttttga tttgggtggt ctctgtggtt ctggctgtcc ctgaagccat aggttttgat    960
ataattacga tggactacaa aggaagttat ctgcgaatct gcttgcttca tcccgttcag   1020
aagacagctt tcatgcagtt ttacaagaca gcaaaagatt ggtggctgtt cagtttctat   1080
ttctgcttgc cattggccat cactgcattt ttttatacac taatgacctg tgaaatgttg   1140
agaaagaaaa gtggcatgca gattgcttta aatgatcacc taaagcagag acgggaagtg   1200
gccaaaaccg tcttttgcct ggtccttgtc tttgccctct gctggcttcc ccttcacctc   1260
agcaggattc tgaagctcac tctttataat cagaatgatc ccaatagatg tgaacttttg   1320
agctttctgt tggtattgga ctatattggt atcaacatgg cttcactgaa ttcctgcatt   1380
aacccaattg ctctgtattt ggtgagcaaa agattcaaaa actgctttaa gtcatgctta   1440
tgctgctggt gccagtcatt tgaagaaaaa cagtccttgg aggaaaagca gtcgtgctta   1500
aagttcaaag ctaatgatca cggatatgac aacttccgtt ccagtaataa atacagctca   1560
tcttgaaaga agaactattc actgtatttc attttcttta tattggaccg aagtcattaa   1620
aacaaaatga aacatttgcc aaaacaaaac aaaaaactat gtatttgcac agcacactat   1680
taaaatatta agtgtaatta ttttaacact cacagctaca tatgacattt tatgagctgt   1740
ttacggcatg gaaagaaaat cagtgggaat taagaaagcc tcgtcgtgaa agcacttaat   1800
tttttacagt tagcacttca acatagctct taacaacttc caggatattc acacaacact   1860
taggcttaaa aatgagctca ctcagaattt ctattctttc taaaaagaga tttattttta   1920
aatcaatggg actctgatat aaaggaagaa taagtcactg taaaacagaa cttttaaatg   1980
aagcttaaat tactcaattt aaaattttaa aatcctttaa aacaactttt caattaatat   2040
tatcacacta ttatcagatt gtaattagat gcaaatgaga gagcagttta gttgttgcat   2100
ttttcggaca ctggaaacat ttaaatgatc aggagggagt aacagaaaga gcaaggctgt   2160
ttttgaaaat cattacactt tcactagaag cccaaacctc agcattctgc aatatgtaac   2220
caacatgtca caaacaagca gcatgtaaca gactggcaca tgtgccagct gaatttaaaa   2280
tataatactt ttaaaaagaa aattattaca tcctttacat tcagttaaga tcaaacctca   2340
caaagagaaa tagaatgttt gaaaggctat cccaaaagac ttttttgaat ctgtcattca   2400
cataccctgt gaagacaata ctatctacaa tttttttcagg attattaaaa tcttcttttt   2460
tcactatcgt agcttaaact ctgtttggtt ttgtcatctg taaatactta cctacataca   2520
ctgcatgtag atgattaaat gagggcaggc cctgtgctca tagctttacg atggagagat   2580
gccagtgacc tcataataaa gactgtgaac tgcctggtgc agtgtccaca tgacaaaggg   2640
gcaggtagca ccctctctca cccatgctgt ggttaaaatg gtttctagca tatgtataat   2700
gctatagtta aaatactatt tttcaaaatc atacagatta gtacatttaa cagctacctg   2760
taaagcttat tactaatttt tgtattattt ttgtaaatag ccaatagaaa agtttgcttg   2820
acatggtgct tttctttcat ctagaggcaa aactgctttt tgagaccgta agaacctctt   2880
```

-continued

```
agctttgtgc gttcctgcct aatttttata tcttctaagc aaagtgcctt aggatagctt   2940
gggatgagat gtgtgtgaaa gtatgtacaa gagaaaacgg aagagagagg aaatgaggtg   3000
gggttggagg aaacccatgg ggacagattc ccattcttag cctaacgttc gtcattgcct   3060
cgtcacatca atgcaaaagg tcctgatttt gttccagcaa aacacagtgc aatgttctca   3120
gagtgacttt cgaaataaat tgggcccaag agctttaact cggtcttaaa atatgcccaa   3180
atttttactt tgtttttctt ttaataggct gggccacatg ttggaaataa gctagtaatg   3240
ttgttttctg tcaatattga atgtgatggt acagtaaacc aaaacccaac aatgtggcca   3300
gaaagaaaga gcaataataa ttaattcaca caccatatgg attctattta taaatcaccc   3360
acaaacttgt tctttaattt catcccaatc actttttcag aggcctgtta tcatagaagt   3420
cattttagac tctcaatttt aaattaattt tgaatcacta atattttcac agtttattaa   3480
tatatttaat ttctatttaa attttagatt atttttatta ccatgtactg aatttttaca   3540
tcctgatacc ctttccttct ccatgtcagt atcatgttct ctaattatct tgccaaattt   3600
tgaaactaca cacaaaaagc atacttgcat tatttataat aaaattgcat tcagtggctt   3660
tttaaaaaaa atgtttgatt caaaacttta acatactgat aagtaagaaa caattataat   3720
ttctttacat actcaaaacc aagatagaaa aaggtgctat cgttcaactt caaaacatgt   3780
ttcctagtat taaggacttt aatatagcaa cagacaaaat tattgttaac atggatgtta   3840
cagctcaaaa gatttataaa agattttaac ctattttctc ccttattatc cactgctaat   3900
gtggatgtat gttcaaacac cttttagtat tgatagctta catatggcca aaggaataca   3960
gtttatagca aaacatgggt atgctgtagc taactttata aaagtgtaat ataacaatgt   4020
aaaaaattat atatctggga ggattttttg gttgcctaaa gtggctatag ttactgattt   4080
tttattatgt aagcaaaacc aataaaaatt taagtttttt taacaactac cttatttttc   4140
actgtacaga cactaattca ttaaatacta attgattgtt taaaagaaat ataaatgtga   4200
caagtggaca ttatttatgt taaatataca attatcaagc aagtatgaag ttattcaatt   4260
aaaatgccac atttctggtc tctggg                                        4286
```

<210> SEQ ID NO 16
<211> LENGTH: 3148
<212> TYPE: DNA
<213> ORGANISM: Homo sapiens

<400> SEQUENCE: 16

```
gaattcccgc ggagcagcgt gcgcggggcc ccgggagacg gcggcggtag cggcgcgggc     60
agagcaagga cgcggcggat cccactcgca cagcagcgca ctcggtgccc cgcgcagggt    120
cgcgatgctg cccggtttgg cactgctcct gctggccgcc tggacggctc gggcgctgga    180
ggtacccact gatggtaatg ctggcctgct ggctgaaccc cagattgcca tgttctgtgg    240
cagactgaac atgcacatga atgtccagaa tgggaagtgg gattcagatc catcagggac    300
caaaacctgc attgatacca aggaaggcat cctgcagtat tgccaagaag tctaccctga    360
actgcagatc accaatgtgg tagaagccaa ccaaccagtg accatccaga actggtgcaa    420
gcggggccgc aagcagtgca agacccatcc ccactttgtg attccctacc gctgcttagt    480
tggtgagttt gtaagtgatg cccttctcgt tcctgacaag tgcaaattct tacaccagga    540
gaggatggat gtttgcgaaa ctcatcttca ctggcacacc gtcgccaaag agacatgcag    600
tgagaagagt accaacttgc atgactacgg catgttgctg ccctgcggaa ttgacaagtt    660
ccgaggggta gagtttgtgt gttgcccact ggctgaagaa agtgacaatg tggattctgc    720
```

-continued

```
tgatgcggag gaggatgact cggatgtctg gtggggcgga gcagacacag actatgcaga    780
tgggagtgaa gacaaagtag tagaagtagc agaggaggaa gaagtggctg aggtggaaga    840
agaagaagcc gatgatgacg aggacgatga ggatggtgat gaggtagagg aagaggctga    900
ggaaccctac gaagaagcca cagagagaac caccagcatt gccaccacca ccaccaccac    960
cacagagtct gtggaagagg tggttcgaga ggtgtgctct gaacaagccg agacggggcc   1020
gtgccgagca atgatctccc gctggtactt tgatgtgact gaagggaagt gtgccccatt   1080
cttttacggc ggatgtggcg gcaaccggaa caactttgac acagaagagt actgcatggc   1140
cgtgtgtggc agcgccattc ctacaacagc agccagtacc cctgatgccg ttgacaagta   1200
tctcgagaca cctggggatg agaatgaaca tgcccatttc cagaaagcca aagagaggct   1260
tgaggccaag caccgagaga gaatgtccca ggtcatgaga gaatgggaag aggcagaacg   1320
tcaagcaaag aacttgccta aagctgataa gaaggcagtt atccagcatt tccaggagaa   1380
agtggaatct ttggaacagg aagcagccaa cgagagacag cagctggtgg agacacacat   1440
ggccagagtg gaagccatgc tcaatgaccg ccgccgcctg gccctggaga actacatcac   1500
cgctctgcag gctgttcctc ctcggcctcg tcacgtgttc aatatgctaa agaagtatgt   1560
ccgcgcagaa cagaaggaca gacagcacac cctaaagcat ttcgagcatg tgcgcatggt   1620
ggatcccaag aaagccgctc agatccggtc ccaggttatg acacacctcc gtgtgattta   1680
tgagcgcatg aatcagtctc tctccctgct ctacaacgtg cctgcagtgg ccgaggagat   1740
tcaggatgaa gttgatgagc tgcttcagaa agagcaaaac tattcagatg acgtcttggc   1800
caacatgatt agtgaaccaa ggatcagtta cggaaacgat gctctcatgc catctttgac   1860
cgaaacgaaa accaccgtgg agctccttcc cgtgaatgga gagttcagcc tggacgatct   1920
ccagccgtgg cattcttttg gggctgactc tgtgccagcc aacacagaaa acgaagttga   1980
gcctgttgat gcccgccctg ctgccgaccg aggactgacc actcgaccag gttctgggtt   2040
gacaaatatc aagacggagg agatctctga agtgaagatg gatgcagaat tccgacatga   2100
ctcaggatat gaagttcatc atcaaaaatt ggtgttcttt gcagaagatg tgggttcaaa   2160
caaaggtgca atcattggac tcatggtggg cggtgttgtc atagcgacag tgatcgtcat   2220
caccttggtg atgctgaaga agaaacagta cacatccatt catcatggtg tggtggaggt   2280
tgacgccgct gtcaccccag aggagcgcca cctgtccaag atgcagcaga acggctacga   2340
aaatccaacc tacaagttct ttgagcagat gcagaactag acccccgcca cagcagcctc   2400
tgaagttgga cagcaaaacc attgcttcac tacccatcgg tgtccattta tagaataatg   2460
tgggaagaaa caaacccgtt ttatgattta ctcattatcg ccttttgaca gctgtgctgt   2520
aacacaagta gatgcctgaa cttgaattaa tccacacatc agtaatgtat tctatctctc   2580
tttacatttt ggtctctata ctacattatt aatgggtttt gtgtactgta aagaatttag   2640
ctgtatcaaa ctagtgcatg aatagattct ctcctgatta tttatcacat agccccttag   2700
ccagttgtat attattcttg tggtttgtga cccaattaag tcctacttta catatgcttt   2760
aagaatcgat gggggatgct tcatgtgaac gtgggagttc agctgcttct cttgcctaag   2820
tattcctttc ctgatcacta tgcattttaa agttaaacat ttttaagtat ttcagatgct   2880
ttagagagat tttttttcca tgactgcatt ttactgtaca gattgctgct tctgctatat   2940
ttgtgatata ggaattaaga ggatacacac gtttgtttct tcgtgcctgt tttatgtgca   3000
cacattaggc attgagactt caagcttttc ttttttgtc cacgtatctt tgggtctttg   3060
```

-continued ataaagaaaa gaatccctgt tcattgtaag cacttttacg gggcgggtgg ggaggggtgc 3120
tctgctggtc ttcaattacc aagaattc 3148

<210> SEQ ID NO 17
<211> LENGTH: 4434
<212> TYPE: DNA
<213> ORGANISM: Homo sapiens

<400> SEQUENCE: 17
gccgccctcg ccaccgctcc cggccgccgc gctccggtac acacaggatc cctgctgggc 60
accaacagct ccaccatggg gctggcctgg ggactaggcg tcctgttcct gatgcatgtg 120
tgtggcacca accgcattcc agagtctggc ggagacaaca gcgtgtttga catctttgaa 180
ctcaccgggg ccgcccgcaa ggggtctggg cgccgactgg tgaagggccc cgacccttcc 240
agcccagctt tccgcatcga ggatgccaac ctgatccccc ctgtgcctga tgacaagttc 300
caagacctgg tggatgctgt gcggacagaa aagggtttcc tccttctggc atccctgagg 360
cagatgaaga agacccgggg cacgctgctg gccctggagc ggaaagacca ctctggccag 420
gtcttcagcg tggtgtccaa tggcaaggcg ggcaccctgg acctcagcct gaccgtccaa 480
ggaaagcagc acgtggtgtc tgtggaagaa gctctcctgg caaccggcca gtggaagagc 540
atcaccctgt ttgtgcagga agacagggcc cagctgtaca tcgactgtga aaagatggag 600
aatgctgagt tggacgtccc catccaaagc gtcttcacca gagacctggc cagcatcgcc 660
agactccgca tcgcaaaggg gggcgtcaat gacaatttcc aggggggtgct gcagaatgtg 720 aggtttgtct ttggaaccac accagaagac atcctcagga acaaaggctg ctccagctct 780
accagtgtcc tcctcaccct tgacaacaac gtggtgaatg gttccagccc tgccatccgc 840
actaactaca ttggccacaa gacaaaggac ttgcaagcca tctgcggcat ctcctgtgat 900
gagctgtcca gcatggtcct ggaactcagg ggcctgcgca ccattgtgac cacgctgcag 960
gacagcatcc gcaaagtgac tgaagagaac aaagagttgg ccaatgagct gaggcggcct 1020
cccctatgct atcacaacgg agttcagtac agaaataacg aggaatggac tgttgatagc 1080
tgcactgagt gtcactgtca gaactcagtt accatctgca aaaaggtgtc ctgccccatc 1140
atgccctgct ccaatgccac agttcctgat ggagaatgct gtcctcgctg ttggcccagc 1200
gactctgcgg acgatggctg gtctccatgg tccgagtgga cctcctgttc tacgagctgt 1260
ggcaatggaa ttcagcagcg cggccgctcc tgcgatagcc tcaacaaccg atgtgagggc 1320
tcctcggtcc agacacggac ctgccacatt caggagtgtg acaagagatt taaacaggat 1380
ggtggctgga gccactggtc cccgtggtca tcttgttctg tgacatgtgg tgatggtgtg 1440
atcacaagga tccggctctg caactctccc agcccccaga tgaacgggaa accctgtgaa 1500
ggcgaagcgc gggagaccaa agcctgcaag aaagacgcct gccccatcaa tggaggctgg 1560
ggtccttggt caccatggga catctgttct gtcacctgtg gaggaggggt acagaaacgt 1620
agtcgtctct gcaacaaccc cacaccccag tttggaggca aggactgcgt tggtgatgta 1680
acagaaaacc agatctgcaa caagcaggac tgtccaattg atggatgcct gtccaatccc 1740
tgctttgccg gcgtgaagtg tactagctac cctgatggca gctggaaatg tggtgcttgt 1800
ccccctggtt acagtggaaa tggcatccag tgcacagatg ttgatgagtg caaagaagtg 1860
cctgatgcct gcttcaacca caatggagag caccggtgtg agaacacgga ccccggctac 1920
aactgcctgc cctgccccc acgcttcacc ggctcacagc ccttcggcca gggtgtcgaa 1980
catgccacgg ccaacaaaca ggtgtgcaag ccccgtaacc cctgcacgga tgggacccac 2040

-continued

```
gactgcaaca agaacgccaa gtgcaactac ctgggccact atagcgaccc catgtaccgc   2100
tgcgagtgca agcctggcta cgctggcaat ggcatcatct gcggggagga cacagacctg   2160
gatggctggc ccaatgagaa cctggtgtgc gtggccaatg cgacttacca ctgcaaaaag   2220
gataattgcc ccaaccttcc caactcaggg caggaagact atgacaagga tggaattggt   2280
gatgcctgtg atgatgacga tgacaatgat aaaattccag atgacaggga caactgtcca   2340
ttccattaca acccagctca gtatgactat gacagagatg atgtgggaga ccgctgtgac   2400
aactgtccct acaaccacaa cccagatcag gcagacacag acaacaatgg ggaaggagac   2460
gcctgtgctg cagacattga tggagacggt atcctcaatg aacgggacaa ctgccagtac   2520
gtctacaatg tggaccagag agacactgat atggatgggg ttggagatca gtgtgacaat   2580
tgccccttgg aacacaatcc ggatcagctg gactctgact cagaccgcat tggagatacc   2640
tgtgacaaca atcaggatat tgatgaagat ggccaccaga acaatctgga caactgtccc   2700
tatgtgccca atgccaacca ggctgaccat gacaaagatg gcaagggaga tgcctgtgac   2760
cacgatgatg acaacgatgg cattcctgat gacaaggaca actgcagact cgtgcccaat   2820
cccgaccaga aggactctga cggcgatggt cgaggtgatg cctgcaaaga tgattttgac   2880
catgacagtg tgccagacat cgatgacatc tgtcctgaga atgttgacat cagtgagacc   2940
gatttccgcc gattccagat gattcctctg gaccccaaag ggacatccca aaatgaccct   3000
aactgggttg tacgccatca gggtaaagaa ctcgtccaga ctgtcaactg tgatcctgga   3060
ctcgctgtag gttatgatga gtttaatgct gtggacttca gtggcacctt cttcatcaac   3120
accgaaaggg acgatgacta tgctggattt gtctttggct accagtccag cagccgcttt   3180
tatgttgtga tgtggaagca agtcacccag tcctactggg acaccaaccc cacgagggct   3240
cagggatact cgggcctttc tgtgaaagtt gtaaactcca ccacagggcc tggcgagcac   3300
ctgcggaacg ccctgtggca cacaggaaac acccctggcc aggtgcgcac cctgtggcat   3360
gaccctcgtc acataggctg gaaagatttc accgcctaca gatggcgtct cagccacagg   3420
ccaaagacgg gtttcattag agtggtgatg tatgaaggga agaaaatcat ggctgactca   3480
ggacccatct atgataaaac ctatgctggt ggtagactag ggttgtttgt cttctctcaa   3540
gaaatggtgt tcttctctga cctgaaatac gaatgtagag atccctaatc atcaaattgt   3600
tgattgaaag actgatcata aaccaatgct ggtattgcac cttctggaac tatgggcttg   3660
agaaaacccc caggatcact tctccttggc ttccttcttt tctgtgcttg catcagtgtg   3720
gactcctaga acgtgcgacc tgcctcaaga aaatgcagtt ttcaaaaaca gactcagcat   3780
tcagcctcca atgaataaga catcttccaa gcatataaac aattgctttg gtttcctttt   3840
gaaaaagcat ctacttgctt cagttgggaa ggtgcccatt ccactctgcc tttgtcacag   3900
agcagggtgc tattgtgagg ccatctctga gcagtggact caaaagcatt ttcaggcatg   3960
tcagagaagg gaggactcac tagaattagc aaacaaaacc accctgacat cctccttcag   4020
gaacacgggg agcagaggcc aaagcactaa ggggagggcg catacccgag acgattgtat   4080
gaagaaaata tggaggaact gttacatgtt cggtactaag tcattttcag ggattgaaa    4140
gactattgct ggatttcatg atgctgactg gcgttagctg attaacccat gtaaataggc   4200
acttaaatag aagcaggaaa gggagacaaa gactggcttc tggacttcct ccctgatccc   4260
caccccttact catcacctgc agtggccaga attagggaat cagaatcgaa accagtgtaa   4320
ggcagtgctg gctgccattg cctggtcaca ttgaaattgg tggcttcatt ctagatgtag   4380
```

-continued

```
cttgtgcaga tgtagcagga aaataggaaa acctaccatc tcagtgagca ccag         4434
```

<210> SEQ ID NO 18
<211> LENGTH: 1377
<212> TYPE: DNA
<213> ORGANISM: Homo sapiens

<400> SEQUENCE: 18

```
atttctcttt agttctttgc aagaaggtag agataaagac actttttcaa aaatggcaat     60
ggtatcagaa ttcctcaagc aggcctggtt tattgaaaat gaagagcagg aatatgttca    120
aactgtgaag tcatccaaag gtggtcccgg atcagcggtg agcccctatc ctaccttcaa    180
tccatcctcg gatgtcgctg ccttgcataa ggccataatg gttaaaggtg tggatgaagc    240
aaccatcatt gacattctaa ctaagcgaaa caatgcacag cgtcaacaga tcaaagcagc    300
atatctccag gaaacaggaa agcccctgga tgaaacactg aagaaagccc ttacaggtca    360
ccttgaggag gttgttttag ctctgctaaa aactccagcg caatttgatg ctgatgaact    420
tcgtgctgcc atgaagggcc ttggaactga tgaagatact ctaattgaga ttttggcatc    480
aagaactaac aaagaaatca gagacattaa cagggtctac agagaggaac tgaagagaga    540
tctggccaaa gacataacct cagacacatc tggagatttt cggaacgctt tgctttctct    600
tgctaagggt gaccgatctg aggactttgg tgtgaatgaa gacttggctg attcagatgc    660
cagggccttg tatgaagcag gagaaaggag aaaggggaca gacgtaaacg tgttcaatac    720
catccttacc accagaagct atccacaact tcgcagagtg tttcagaaat acaccaagta    780
cagtaagcat gacatgaaca aagttctgga cctggagttg aaaggtgaca ttgagaaatg    840
cctcacagct atcgtgaagt gcgccacaag caaaccagct ttctttgcag agaagcttca    900
tcaagccatg aaaggtgttg gaactcgcca taaggcattg atcaggatta tggtttcccg    960
ttctgaaatt gacatgaatg atatcaaagc attctatcag aagatgtatg gtatctccct   1020
ttgccaagcc atcctggatg aaaccaaagg agattatgag aaaatcctgg tggctctttg   1080
tggaggaaac taaacattcc cttgatggtc tcaagctatg atcagaagac tttaattata   1140
tattttcatc ctataagctt aaataggaaa gtttcttcaa caggattaca gtgtagctac   1200
ctacatgctg aaaaatatag cctttaaatc atttttatat tataactctg tataatagag   1260
ataagtccat tttttaaaaa tgttttcccc aaaccataaa accctataca agttgttcta   1320
gtaacaatac atgagaaaga tgtctatgta gctgaaaata aaatgacgtc acaagac      1377
```

<210> SEQ ID NO 19
<211> LENGTH: 3370
<212> TYPE: DNA
<213> ORGANISM: Homo sapiens

<400> SEQUENCE: 19

```
gcccccgccc ggcccgcccc gctctcctag tcccttgcaa cctggcgctg catccgggcc     60
actgtcccag gtcccaggtc ccggcccgga gctatggagc ggcgctggcc cctggggcta    120
gggctggtgc tgctgctctg cgccccgctg cccccggggg cgcgcgccaa ggaagttact    180
ctgatggaca caagcaaggc acagggagag ctgggctggc tgctggatcc cccaaaagat    240
gggtggagtg aacagcaaca gatactgaat gggacacccc tctacatgta ccaggactgc    300
ccaatgcaag gacgcagaga cactgaccac tggcttcgct ccaattggat ctaccgcggg    360
gaggaggctt cccgcgtcca cgtggagctg cagttcaccg tgcgggactg caagagtttc    420
cctgggggag ccgggcctct gggctgcaag gagaccttca accttctgta catggagagt    480
```

-continued

```
gaccaggatg tgggcattca gctccgacgg cccttgttcc agaaggtaac cacggtggct    540
gcagaccaga gcttcaccat tcgagacctt gcgtctggct ccgtgaagct gaatgtggag    600
cgctgctctc tgggccgcct gacccgccgt ggcctctacc tcgctttcca caacccgggt    660
gcctgtgtgg ccctggtgtc tgtccgggtc ttctaccagc gctgtcctga gaccctgaat    720
ggcttggccc aattcccaga cactctgcct ggccccgctg ggttggtgga agtggcgggc    780
acctgcttgc cccacgcgcg ggccagcccc aggccctcag gtgcaccccg catgcactgc    840
agccctgatg gcgagtggct ggtgcctgta ggacggtgcc actgtgagcc tggctatgag    900
gaaggtggca gtggcgaagc atgtgttgcc tgccctagcg gctcctaccg gatggacatg    960
gacacacccc attgtctcac gtgcccccag cagagcactg ctgagtctga gggggccacc   1020
atctgtacct gtgagagcgg ccattacaga gctcccgggg agggccccca ggtggcatgc   1080
acaggtcccc cctcggcccc ccgaaacctg agcttctctg cctcagggac tcagctctcc   1140
ctgcgttggg aacccccagc agatacgggg ggacgccagg atgtcagata cagtgtgagg   1200
tgttcccagt gtcagggcac agcacaggac ggggggccct gccagccctg tggggtgggc   1260
gtgcacttct cgccgggggc ccgggcgctc accacacctg cagtgcatgt caatggcctt   1320
gaaccttatg ccaactacac ctttaatgtg gaagcccaaa atggagtgtc agggctgggc   1380
agctctggcc atgccagcac ctcagtcagc atcagcatgg ggcatgcaga gtcactgtca   1440
ggcctgtctc tgagactggt gaagaaagaa ccgaggcaac tagagctgac ctgggcgggg   1500
tcccggcccc gaagccctgg ggcgaacctg acctatgagc tgcacgtgct gaaccaggat   1560
gaagaacggt accagatggt tctagaaccc agggtcttgc tgacagagct gcagcctgac   1620
accacataca tcgtcagagt ccgaatgctg accccactgg gtcctggccc tttctcccct   1680
gatcatgagt ttcggaccag cccaccagtg tccaggggcc tgactggagg agagattgta   1740
gccgtcatct ttgggctgct gcttggtgca gccttgctgc ttgggattct cgttttccgg   1800
tccaggagag cccagcggca gaggcagcag aggcacgtga ccgcgccacc gatgtggatc   1860
gagaggacaa gctgtgctga agccttatgt ggtacctcca ggcatacgag gaccctgcac   1920
agggagcctt ggactttacc cggaggctgg tctaattttc cttcccggga gcttgatcca   1980
gcgtggctga tggtggacac tgtcatagga gaaggagagt ttggggaagt gtatcgaggg   2040
accctcaggc tccccagcca ggactgcaag actgtggcca ttaagacctt aaaagacaca   2100
tccccaggtg gccagtggtg gaacttcctt cgagaggcaa ctatcatggg ccagtttagc   2160
cacccgcata ttctgcatct ggaaggcgtc gtcacaaagc gaaagccgat catgatcatc   2220
acagaattta tggagaatgc agccctggat gccttcctga gggagcggga ggaccagctg   2280
gtccctgggc agctagtggc catgctgcag ggcatagcat ctggcatgaa ctacctcagt   2340
aatcacaatt atgtccaccg ggacctggct gccagaaaca tcttggtgaa tcaaaacctg   2400
tgctgcaagg tgtctgactt tggcctgact cgcctcctgg atgactttga tggcacatac   2460
gaaacccagg gaggaaagat ccctatccgt tggacagccc ctgaagccat tgcccatcgg   2520
atcttcacca cagccagcga tgtgtggagc tttgggattg tgatgtggga ggtgctgagc   2580
tttggggaca agccttatgg ggagatgagc aatcaggagg ttatgaagag cattgaggat   2640
gggtaccggt tgccccctcc tgtggactgc cctgcccctc tgtatgagct catgaagaac   2700
tgctgggcat atgaccgtgc ccgccggcca cacttccaga agcttcaggc acatctggag   2760
caactgcttg ccaaccccca ctccctgcgg accattgcca actttgaccc cagggtgact   2820
```

-continued

```
cttcgcctgc ccagcctgag tggctcagat gggatcccgt atcgaaccgt ctctgagtgg   2880

ctcgagtcca tacgcatgaa acgctacatc ctgcacttcc actcggctgg gctggacacc   2940

atggagtgtg tgctggagct gaccgctgag gacctgacgc agatgggaat cacactgccc   3000

gggcaccaga agcgcattct ttgcagtatt cagggattca aggactgatc cctcctctca   3060

ccccatgccc aatcagggtg caaggagcaa ggacggggcc aaggtcgctc atggtcactc   3120

cctgcgcccc ttcccacaac ctgccagact aggctatcgg tgctgcttct gcccgcttta   3180

aggagaaccc tgctctgcac cccagaaaac ctctttgttt taaaagggag gtgggggtag   3240

aagtaaaagg atgatcatgg gagggagctc aggggttaat atatatacat acatacacat   3300

atatatattg ttgtaaataa acaggaaatg attttctgcc tccatcccac ccatcagggc   3360

tgcaggcact                                                          3370
```

<210> SEQ ID NO 20
<211> LENGTH: 1913
<212> TYPE: DNA
<213> ORGANISM: Homo sapiens

<400> SEQUENCE: 20

```
ccaagagcta cgcggcggcg gcggagcgca ggcctcgtgc cgttacggcc atcacggcgg     60

ccgcagtggc gtcctggagc cctcctcagt gctgaagctg ctgaaagatg gcagaagaag    120

tggtggtagt agccaaattt gattatgtgg cccaacaaga acaagagttg gacatcaaga    180

agaatgagag attatggctt ctggatgatt ctaagtcctg gtggcgagtt cgaaattcca    240

tgaataaaac aggttttgtg ccttctaact atgtggaaag gaaaaacagt gctcggaaag    300

catctattgt gaaaaaccta aaggatacct taggcattgg aaaagtgaaa agaaaaccta    360

gtgtgccaga ttctgcatct cctgctgatg atagttttgt tgacccaggg gaacgtctct    420

atgacctcaa catgcccgct tatgtgaaat ttaactacat ggctgagaga gaggatgaat    480

tatcattgat aaaggggaca aaggtgatcg tcatggagaa atgcagtgat gggtggtggc    540

gtggtagcta caatggacaa gttggatggt tcccttcaaa ctatgtaact gaagaaggtg    600

acagtccttt gggtgaccat gtgggttctc tgtcagagaa attagcagca gtcgtcaata    660

acctaaatac tgggcaagtg ttgcatgtgg tacaggctct ttacccattc agctcatcta    720

atgatgaaga acttaatttc gagaaaggag atgtaatgga tgttattgaa aaacctgaaa    780

atgacccaga gtggtggaaa tgcaggaaga tcaatggtat ggttggtcta gtaccaaaaa    840

actatgttac cgttatgcag aataatccat taacttcagg tttggaacca tcacctccac    900

agtgtgatta cattaggcct tcactcactg gaaagtttgc tggcaatcct tggtattatg    960

gcaaagtcac caggcatcaa gcagaaatgg cattaaatga aagaggacat gaaggggatt   1020

tcctcattcg tgatagtgaa tcttcgccaa atgatttctc agtatcacta aaagcacaag   1080

ggaaaaacaa gcattttaaa gtccaactaa aagagactgt ctactgcatt gggcagcgta   1140

aattcagcac catggaagaa cttgtagaac attacaaaaa ggcaccaatt tttacaagtg   1200

aacaaggaga aaaattatat cttgtcaagc atttatcatg atactgctga ccagaagtga   1260

ctgctgtgta gctgtaattt gtcatgtaat tgaagactga gaaaatgttg ggtccagtcg   1320

tgcttgattg gaaattgttg tttctaaatc tatatgagaa ttgacaataa gtatttttat   1380

tataactcag cccatacata tatactatgt atgcagtgca tctgcataga acagttcctt   1440

atccttggcc ttctgtttta ttgttttttt ctttgctgtt ttccctttgc ttctaatatt   1500

acagttttgt attttgtaaa caaaaatcaa ataatgcata tcagaatctt tatatggaag   1560
```

-continued

```
aaatccttta ttgcctttcc tttgtttcct tgtaaaggca ccctgttctg ttatggtttt   1620

tcattatata aaattattat atctatatat gacatatgct aaaatttctt ggagagtgtt   1680

aatcttttct gtgactaaat agcaataata agtggaaaat tagaaattat ttccaggtat   1740

tatatttgtc acaggccatt gtaaatacca agtatattgt gtctgccata atttttaaaa   1800

atacattcat tgtcttcagt catacagcaa gacacatgag acatagatta gaaaacatgt   1860

tgtacaattt taatttacaa ctgttggaaa taaaaatcac ttaatttttt tcc          1913
```

<210> SEQ ID NO 21
<211> LENGTH: 3257
<212> TYPE: DNA
<213> ORGANISM: Homo sapiens

<400> SEQUENCE: 21

```
catggcggcg actgcggcaa agcgagagcc tcggagacgc cgctgccgcc agcacagccg     60

gagacctgag ccgacactgg gggcagtccg cgagccccgc actctctcga tgagtcggag    120

aagtcccgtt gtatcagagt aagatggacg gtagctttga ttgtgattgt ggtgagctgg    180

agccacctga tcactaacaa aagacatctt ctgttaacca acagccgcca gggcttcctg    240

ttgaaataaa tatatagcaa caaaggaaaa aaagaagcaa aacggaaata gtgcttacca    300

gcaccttaga atgatgctgc tcaggaccag tccaacactg aatgtatctg cactgtgagg    360

agaatgttca tagaagcctg ttgtgtgcat atttattcac atttttgtta aatgttaaat    420

cgtttagcac ggtaatctga gtgcacagta tgtcatttca ttccgtttga gtttcttgtt    480

ttcgttaaat gtctgcagag ttgctgcccc tttcttgaac tatgagtact gcaatctttt    540

taattctcaa tatgaataga gctttttgag ctttaaatct aaggggaact cgacaggcct    600

gtttggcata tgcaatgaac atcaagaaac catcttgctg tggaagcata attatttttc    660

ttctcccttt ttgaaagatc tttccttttg atgccagttt tcttccttgt ttacacaagt    720

tcaatttgaa aggaaaaggc aatagtaagg gtttcaaaat ggcagagaaa tttgaaagtc    780

tcatgaacat tcatggtttt gatctgggtt ctaggtatat ggacttaaaa ccattgggtt    840

gtggaggcaa tggcttggtt ttttctgctg tagacaatga ctgtgacaaa agagtagcca    900

tcaagaaaat tgtccttact gatccccaga gtgtcaaaca tgctctacgt gaaatcaaaa    960

ttattagaag acttgaccat gataacattg tgaaagtgtt tgagattctt ggtcccagtg   1020

gaagccaatt aacagacgat gtgggctctc ttacggaact gaacagtgtt tacattgttc   1080

aggagtacat ggagacagac ttggctaatg tgctggagca gggcccttta ctggaagagc   1140

atgccaggct tttcatgtat cagctgctac gggggctcaa gtatattcac tctgcaaatg   1200

tactgcacag agatctcaaa ccagctaatc ttttcattaa tacggaagac ttggtgctga   1260

agataggtga ctttggtctt gcacggatca tggatcctca ttattcccat aagggtcatc   1320

tttctgaagg attggttact aaatggtaca gatctccacg tcttttactt tctcctaata   1380

attatactaa agccattgac atgtgggctg caggctgcat ctttgctgaa atgctgactg   1440

gtaaaaccct tttgcaggt gcacatgaac ttgaacagat gcagctgatt ttagaatcta    1500

ttcctgttgt acatgaggaa gatcgtcagg agcttctcag cgtaattcca gtttacatta   1560

gaaatgacat gactgagcca cacaaacctt taactcagct gcttccagga attagtcgag   1620

aagcactgga tttcctggaa caaattttga catttagccc catggatcgg ttaacagcag   1680

aagaagcact ctcccatcct tacatgagca tatattcttt tccaatggat gagccaattt   1740
```

-continued

```
caagccatcc ttttcatatt gaagatgaag ttgatgatat tttgcttatg gatgaaactc   1800

acagtcacat ttataactgg gaaaggtatc atgattgtca gttttcagag catgattggc   1860

ctgtacataa caactttgat attgatgaag ttcagcttga tccaagagct ctgtccgatg   1920

tcactgatga agaagaagta caagttgatc cccgaaaata tttggatgga gatcgggaaa   1980

agtatctgga ggatcctgct tttgatacca attactctac tgagccttgt tggcaatact   2040

cagatcatca tgaaaacaaa tattgtgatc tggagtgtag ccatacttgt aactacaaaa   2100

cgaggtcatc atcatattta gataacttag tttggagaga gagtgaagtt aaccattact   2160

atgaacccaa gcttattata gatctttcca attggaaaga acaaagcaaa gaaaaatctg   2220

ataagaaagg caaatcaaaa tgtgaaagga atggattggt taaagcccag atagcgctag   2280

aggaagcatc acagcaactg gctggaaaag aaagggaaaa gaatcaggga tttgattttg   2340

attcctttat tgcaggaact attcagctta gttcccagca tgagcctact gatgttgttg   2400

ataaattaaa tgacttgaat agctcagtgt cccaactaga attgaaaagt ttgatatcaa   2460

agtcagtaag ccaagaaaaa caggaaaaag gaatggcaaa tctggctcaa ttagaagcct   2520

tgtaccagtc ttcttgggac agccagtttg tgagtggtgg ggaggactgt tttttcataa   2580

atcagttttg tgaggtaagg aaggatgaac aagttgagaa ggaaaacact tacactagtt   2640

acttggacaa gttctttagc aggaaagaag atactgaaat gctagaaact gagccagtag   2700

aggatgggaa gcttggggag agaggacatg aggaaggatt tctgaacaac agtggggagt   2760

tcctctttaa caagcagctc gagtccatag gcatcccaca gtttcacagt ccagttgggt   2820

caccacttaa gtcaatacag gccacattaa caccttctgc tatgaaatct tcccctcaaa   2880

ttcctcatca aacatacagc agcattctga aacatctgaa ctaaaacact cagcagacat   2940

ttatctttgt attcttcatg aaatgtgttt tgtctttttt tattactagt gtttaagtca   3000

tttttttactt gaatcagatg gtgtcattta gtaaggattt tatgagttct tgttttttaa   3060

aatccagact ttcttttttct acatgtgaga tagttttcat tttaactggc atgtcatttg   3120

cacacaaaaa taaagactag agcaaaataa tgcaacgcag gaggagaaaa gaaatgcact   3180

aagacaagaa cattctctca tagaacattg atctgtttta caggaaacaa accttgcctt   3240

gaaatttaca cagtgag                                                  3257
```

<210> SEQ ID NO 22
<211> LENGTH: 2354
<212> TYPE: DNA
<213> ORGANISM: Homo sapiens

<400> SEQUENCE: 22

```
ggtctttgag cgctaacgtc tttctgtctc cccgcggtgg tgatgacggt gaaaactgag     60

gctgctaagg gcaccctcac ttactccagg atgaggggca tggtggcaat tctcatcgct    120

ttcatgaagc agaggaggat gggtctgaac gactttattc agaagattgc caataactcc    180

tatgcatgca aacaccctga agttcagtcc atcttgaaga tctcccaacc tcaggagcct    240

gagcttatga atgccaaccc ttctcctcca ccaagtcctt ctcagcaaat caaccttggc    300

ccgtcgtcca atcctcatgc taaaccatct gactttcact tcttgaaagt gatcggaaag    360

ggcagttttg gaaaggttct tctagcaaga cacaaggcag aagaagtgtt ctatgcagtc    420

aaagttttac agaagaaagc aatcctgaaa aagaaagagg agaagcatat tatgtcggag    480

cggaatgttc tgttgaagaa tgtgaagcac cctttcctgg tgggccttca cttctctttc    540

cagactgctg acaaattgta ctttgtccta gactacatta atggtggaga gttgttctac    600
```

-continued catctccaga gggaacgctg cttcctggaa ccacgggctc gtttctatgc tgctgaaata 660
gccagtgcct tgggctacct gcattcactg aacatcgttt atagagactt aaaaccagag 720
aatattttgc tagattcaca gggacacatt gtccttactg acttcggact ctgcaaggag 780
aacattgaac acaacagcac aacatccacc ttctgtggca cgccggagta tctcgcacct 840
gaggtgcttc ataagcagcc ttatgacagg actgtggact ggtggtgcct gggagctgtc 900
ttgtatgaga tgctgtatgg cctgccgcct tttatagcc gaaacacagc tgaaatgtac 960
gacaacattc tgaacaagcc tctccagctg aaaccaaata ttacaaattc cgcaagacac 1020
ctcctggagg gcctcctgca gaaggacagg acaaagcggc tcggggccaa ggatgacttc 1080
atggagatta agagtcatgt cttcttctcc ttaattaact gggatgatct cattaataag 1140
aagattactc cccttttaa cccaaatgtg agtgggccca acgacctacg gcactttgac 1200
cccgagttta ccgaagagcc tgtccccaac tccattggca agtcccctga cagcgtcctc 1260
gtcacagcca gcgtcaagga agctgccgag gctttcctag gcttttccta tgcgcctccc 1320
acggactctt tcctctgaac cctgttaggg cttggtttta aaggatttta tgtgtgtttc 1380
cgaatgtttt agttagcctt ttggtggagc cgccagctga caggacatct tacaagagaa 1440
tttgcacatc tctggaagct tagcaatctt attgcacact gttcgctgga agctttttga 1500
agagcacatt ctcctcagtg agctcatgag gttttcattt ttattcttcc ttccaacgtg 1560
gtgctatctc tgaaacgagc gttagagtgc cgccttagac ggaggcagga gtttcgttag 1620
aaagcggacg ctgttctaaa aaggtctcc tgcagatctg tctgggctgt gatgacgaat 1680
attatgaaat gtgccttttc tgaagagatt gtgttagctc caaagctttt cctatcgcag 1740
tgtttcagtt ctttattttc ccttgtggat atgctgtgtg aaccgtcgtg tgagtgtggt 1800
atgcctgatc acagatggat tttgttataa gcatcaatgt gacacttgca ggacactaca 1860
acgtgggaca ttgtttgttt cttccatatt tggaagataa atttatgtgt agactttttt 1920
gtaagatacg gttaataact aaaatttatt gaaatggtct tgcaatgact cgtattcaga 1980
tgcttaaaga aagcattgct gctacaaata tttctatttt tagaaagggt ttttatggac 2040
caatgcccca gttgtcagtc agagccgttg gtgtttttca ttgtttaaaa tgtcacctgt 2100
aaaatgggca ttatttatgt tttttttttt gcattcctga taattgtatg tattgtataa 2160
agaacgtctg tacattgggt tataacacta gtatatttaa acttacaggc ttatttgtaa 2220
tgtaaaccac cattttaatg tactgtaatt aacatggtta taatacgtac aatccttccc 2280
tcatcccatc acacaacttt ttttgtgtgt gataaactga ttttggtttg caataaaacc 2340
ttgaaaaata ttta 2354

<210> SEQ ID NO 23
<211> LENGTH: 1728
<212> TYPE: DNA
<213> ORGANISM: Homo sapiens

<400> SEQUENCE: 23
gagcagcaga atttcaactc cagtagactt gaatatgcct ctgggcaaag aagcagagct 60
aacgaggaaa gggatttaaa gagtttttct tgggtgtttg tcaaactttt attccctgtc 120
tgtgtgcaga ggggattcaa cttcaatttt tctgcagtgg ctctgggtcc agccccttac 180
ttaaagatct ggaaagcatg aagactgggc tttttttcct atgtctcttg ggaactgcag 240
ctgcaatccc gacaaatgca agattattat ctgatcattc caaaccaact gctgaaacgg 300

-continued

```
tagcacctga caacactgca atccccagtt taagggctga agctgaagaa aatgaaaaag    360

aaacagcagt atccacagaa gacgattccc accataaggc tgaaaaatca tcagtactaa    420

agtcaaaaga ggaaagccat gaacagtcag cagaacaggg caagagttct agccaagagc    480

tgggattgaa ggatcaagag gacagtgatg gtcacttaag tgtgaatttg gagtatgcac    540

caactgaagg tacattggac ataaaagaag atatgagtga gcctcaggag aaaaaactct    600

cagagaacac tgattttttg gctcctggtg ttagttcctt cacagattct aaccaacaag    660

aaagtatcac aaagagagag gaaaaccaag aacaacctag aaattattca catcatcagt    720

tgaacaggag cagtaaacat agccaaggcc taagggatca aggaaaccaa gagcaggatc    780

caaatatttc caatggagaa gaggaagaag aaaaagagcc aggtgaagtt ggtacccaca    840

atgataacca agaaagaaag acagaattgc ccagggagca tgctaacagc aagcaggagg    900

aagacaatac ccaatctgat gatattttgg aagagtctga tcaaccaact caagtaagca    960

agatgcagga ggatgaattt gatcagggta accaagaaca agaagataac tccaatgcag   1020

aaatggaaga ggaaaatgca tcgaacgtca ataagcacat tcaagaaact gaatggcaga   1080

gtcaagaggg taaaactggc ctagaagcta tcagcaacca caaagagaca gaagaaaaga   1140

ctgtttctga ggctctgctc atggaaccta ctgatgatgg taataccacg cccagaaatc   1200

atggagttga tgatgatggc gatgatgatg gcgatgatgg cggcactgat ggccccaggc   1260

acagtgcaag tgatgactac ttcatcccaa gccaggcctt tctggaggcc gagagagctc   1320

aatccattgc ctatcacctc aaaattgagg agcaaagaga aaaagtacat gaaaatgaaa   1380

atataggtac cactgagcct ggagagcacc aagaggccaa gaaagcagag aactcatcaa   1440

atgaggagga aacgtcaagt gaaggcaaca tgagggtgca tgctgtggat tcttgcatga   1500

gcttccagtg taaaagaggc cacatctgta aggcagacca acagggaaaa cctcactgtg   1560

tctgccagga tccagtgact tgtcctccaa caaaacccct tgatcaagtt tgtggcactg   1620

acaatcagac ctatgctagt tcctgtcatc tattcgctac taaatgcaga ctggagggga   1680

ccaaaaaggg gcatcaactc cagctggatt attttggagc ctgcaaat                1728


<210> SEQ ID NO 24
<211> LENGTH: 1848
<212> TYPE: DNA
<213> ORGANISM: Homo sapiens

<400> SEQUENCE: 24

cggataagga caaaaaacgc cagaagaaaa gaggcatttt ccccaaagta gcaacaaata     60

tcatgagagc atggctcttc cagcatctca cacatccgta cccttccgaa gagcagaaga    120

aacagttagc gcaagacaca ggacttacaa ttctccaagt aaacaactgg tttattaatg    180

ccagaagaag aatagtacag cccatgattg accagtcaaa tcgagcagtg agccaaggag    240

cagcatatag tccagagggt cagcccatgg ggagctttgt gttggatggt cagcaacaca    300

tggggatccg gcctgcagga cctatgagtg gaatgggcat gaatatgggc atggatgggc    360

aatggcacta catgtaacct tcatcatgta aagcaatcgc aaagcaaggg ggaagtttgc    420

agagcatgcc aggggactac gtttctcagg gtggtcctat gggaatgagt atggcacagc    480

caagttacac tcctccccag atgaccccac accctactca attaagacat ggaccccccaa   540

tgcattcata tttgccaagc catccccacc acccagccat gatgatgcac ggaggacccc    600

ctacccaccc tggaatgact atgtcagcac agagccccac aatgttaaat tctgtagatc    660

ccaatgttgg cggacaggtt atggacattc atgcccaata gtataaggga actcaaggga    720
```

-continued

```
aaaggaaaca cacgcaaaaa ctattttaag actttctgaa ctttgaccag atgttgacac    780
ttaatatgaa attccagaca gctgtgatta ttttttactt ttgtcatttt tcatcaagca    840
acagaggacc aatgcaacaa gaacacaaat gtgaaatcat gggctgactg agacaattct    900
gtccatgtaa agatcctctg gaaaaagact ccgagagtta taactactgt agtataaata    960
taggaactaa gttaaacttg tacatttctg ttgatcacgc cgttatgttg cctcaaatag   1020
ttttagaaga gaaaaaaaaa tatatccttg ttttccacac tatgtgtgtt gttcccaaaa   1080
gaatgactgt tttggttcat cagtgaattc accatccagg agagactgtg gtatatattt   1140
taaacctgtt gggccaatga gaaaagaacc acactggaga tcatgatgaa cttttggctg   1200
aacctcatca ctcgaactcc agcttcaaga atgtgttttc atgcccggcc tttgttcctc   1260
cataaatgtg tcctttagtt tcaaacagat ctttatagtt cgtgcttcat aagccaattc   1320
ttattattat ttttgggggga ctcttcttca aagagcttgc caatgaagat ttaaagacag   1380
agcaggagct tcttccagga gttctgagcc ttggttgtgg acaaaacaat cttaagttgg   1440
gcagctttcc tcaacacaaa aaaaagttat taatggtcat tgaaccataa ctaggacttt   1500
atcagaaact caaagcttgg gggataaaaa ggagcaagag aatactgtaa caaacttcgt   1560
acagagttcg gtctattaat tgtttcatgt tagatattct atgtgtttac ctcaattgaa   1620
aaaaaaaaga atgtttttgc tagtatcaga tctgctgtgg aattggtatt gtatgtccat   1680
gaattcttct tttctcagca cgtgttcctc actagaagaa aatgctgtta cctttaagct   1740
ttgtcaaatt tacattaaaa tacttgtatg aggactgtga cgttatgtta aaaaaaaaaa   1800
ggtgttaagt cacaaaaagc ggtaataaat atttcatttt tgattttt                1848
```

```
<210> SEQ ID NO 25
<211> LENGTH: 3164
<212> TYPE: DNA
<213> ORGANISM: Homo sapiens

<400> SEQUENCE: 25

agcacactga ggaggcgatc cgccagcagg aggtggagca gctggacttc cgagacctcc     60
tggggaagaa ggtgagtaca aagaccctat cggaagacga cctgaaggag atcccagccg    120
agcagatgga tttccgtgcc aacctgcagc ggcaagtgaa gccaaagact gtgtctgagg    180
aagagaggaa ggtgcacagc ccccagcagg tcgattttcg ctctgtcctg gccaagaagg    240
ggacttccaa gacccccgtg cctgagaagg tgccaccgcc aaaacctgcc accccggatt    300
ttcgctcagt gctgggtggc aagaagaaat taccagcaga gaatggcagc agcagtgccg    360
agaccctgaa tgccaaggca gtggagagtt ccaagcccct gagcaatgca cagccttcag    420
ggcccttgaa acccgtgggc aacgccaagc ctgctgagac cctgaagcca atgggcaacg    480
ccaagcctgc cgagaccctg aagcccatgg gcaatgccaa gcctgatgag aacctgaaat    540
ccgctagcaa agaagaactc aagaaagacg ttaagaatga tgtgaactgc aagagaggcc    600
atgcagggac cacagataat gaaaagagat cagagagcca ggggacagcc ccagccttca    660
agcagaagct gcaagatgtt catgtggcag agggcaagaa gctgctgctc cagtgccagg    720
tgtcttctga ccccccagcc accatcatct ggacgctgaa cggaaagacc atcaagacca    780
ccaagttcat catcctctcc caggaaggct cactctgctc cgtctccatc gagaaggcac    840
tgcctgagga cagaggctta tacaagtgtg tagccaagaa tgacgctggc caggcggagt    900
gctcctgcca agtcaccgtg gatgatgctc cagccagtga gaacaccaag gccccagaga    960
```

-continued

```
tgaaatcccg gaggcccaag agctctcttc ctcccgtgct aggaactgag agtgatgcga   1020
ctgtgaaaaa gaaacctgcc cccaagacac ctccgaaggc agcaatgccc cctcagatca   1080
tccagttccc tgaggaccag aaggtacgcg caggagagtc agtggagctg tttggcaaag   1140
tgacaggcac tcagcccatc acctgtacct ggatgaagtt ccgaaagcag atccaggaaa   1200
gcgagcacat gaaggtggag aacagcgaga atggcagcaa gctcaccatc ctggccgcgc   1260
gccaggagca ctgcggctgc tacacactgc tggtggagaa caagctgggc agcaggcagg   1320
cccaggtcaa cctcactgtc gtggataagc cagacccccc agctggcaca ccttgtgcct   1380
ctgacattcg gagctcctca ctgaccctgt cctggtatgg ctcctcatat gatgggggca   1440
gtgctgtaca gtcctacagc atcgagatct gggactcagc caacaagacg tggaaggaac   1500
tagccacatg ccgcagcacc tctttcaacg tccaggacct gctgcctgac cacgaatata   1560
agttccgtgt acgtgcaatc aacgtgtatg gaaccagtga gccaagccag gagtctgaac   1620
tcacaacggt aggagagaaa cctgaagagc cgaaggatga agtggaggtg tcagacgatg   1680
atgagaagga gcccgaggtt gattaccgga cagtgacaat caatactgaa caaaaagtat   1740
ctgacttcta cgacattgag gagagattag gatctgggaa atttggacag gtctttcgac   1800
ttgtagaaaa gaaaactcga aaagtctggg cagggaagtt cttcaaggca tattcagcaa   1860
aagagaaaga gaatatccgg caggagatta gcatcatgaa ctgcctccac caccctaagc   1920
tggtccagtg tgtggatgcc tttgaagaaa aggccaacat cgtcatggtc ctggagatcg   1980
tgtcaggagg ggagctgttt gagcgcatca ttgacgagga ctttgagctg acggagcgtg   2040
agtgcatcaa gtacatgcgg cagatctcgg agggagtgga gtacatccac aagcagggca   2100
tcgtgcacct ggacctcaag ccggagaaca tcatgtgtgt caacaagacg ggcaccagga   2160
tcaagctcat cgactttggt ctggccagga ggctggagaa cgcggggtct ctgaaggtcc   2220
tctttggcac cccagaattt gtggctcctg aagtgatcaa ctatgagccc atcggctacg   2280
ccacagacat gtggagcatc ggggtcatct gctacatcct agtcagtggc ctttcccccct  2340
tcatgggaga caacgataac gaaaccttgg ccaacgttac ctcagccacc tgggacttcg   2400
acgacgaggc attcgatgag atctccgacg atgccaagga tttcatcagc aatctgctga   2460
agaaagatat gaaaaaccgc ctggactgca cgcagtgcct tcagcatcca tggctaatga   2520
aagataccaa gaacatggag gccaagaaac tctccaagga ccggatgaag aagtacatgg   2580
caagaaggaa atggcagaaa acgggcaatg ctgtgagagc cattggaaga ctgtcctcta   2640
tggcaatgat ctcagggctc agtggcagga aatcctcaac agggtcacca accagcccgc   2700
tcaatgcaga aaaactagaa tctgaagaag atgtgtccca agctttcctt gaggctgttg   2760
ctgaggaaaa gcctcatgta aaaccctatt tctctaagac cattcgcgat ttagaagttg   2820
tggagggaag tgctgctaga tttgactgca agattgaagg atacccagac cccgaggttg   2880
tctggttcaa agatgaccag tcaatcaggg agtcccgcca cttccagata gactacgatg   2940
aggacgggaa ctgctcttta attattagtg atgtttgcgg ggatgacgat gccaagtaca   3000
cctgcaaggc tgtcaacagt cttggagaag ccacctgcac agcagagctc attgtggaaa   3060
cgatggagga aggtgaaggg gaaggggaag aggaagaaga gtgaaacaaa gccagagaaa   3120
agcagtttct aagtcatatt aaaaggacta tttctctaaa actc                    3164
```

<210> SEQ ID NO 26
<211> LENGTH: 3851
<212> TYPE: DNA
<213> ORGANISM: Homo sapiens -continued

<400> SEQUENCE: 26

```
ctctcccaac cgcctcgtcg cactcctcag gctgagagca ccgctgcact cgcggccggc     60
gatgcgggac cccggcgcgg ccgctccgct ttcgtccctg ggcctctgtg ccctggtgct    120
ggcgctgctg ggcgcactgt ccgcgggcgc cggggcgcag ccgtaccacg gagagaaggg    180
catctccgtg ccggaccacg gcttctgcca gcccatctcc atcccgctgt gcacggacat    240
cgcctacaac cagaccatcc tgcccaacct gctgggccac acgaaccaag aggacgcggg    300
cctcgaggtg caccagttct acccgctggt gaaggtgcag tgttctcccg aactccgctt    360
tttcttatgc tccatgtatg cgcccgtgtg caccgtgctc gatcaggcca tcccgccgtg    420
tcgttctctg tgcgagcgcg cccgccaggg ctgcgaggcg ctcatgaaca agttcggctt    480
ccagtggccc gagcggctgc gctgcgagaa cttcccggtg cacggtgcgg gcgagatctg    540
cgtgggccag aacacgtcgg acggctccgg gggcccaggc ggcggcccca ctgcctaccc    600
taccgcgccc tacctgccgg acctgccctt caccgcgctg cccccggggg cctcagatgg    660
caggggggcgt cccgccttcc ccttctcatg cccccgtcag ctcaaggtgc ccccgtacct    720
gggctaccgc ttcctgggtg agcgcgattg tggcgccccg tgcgaaccgg gccgtgccaa    780
cggcctgatg tactttaagg aggaggagag gcgcttcgcc cgcctctggg tgggcgtgtg    840
gtccgtgctg tgctgcgcct cgacgctctt taccgttctc acctacctgg tggacatgcg    900
gcgcttcagc tacccagagc ggcccatcat cttcctgtcg ggctgctact tcatggtggc    960
cgtggcgcac gtggccggct tccttctaga ggaccgcgcc gtgtgcgtgg agcgcttctc   1020
ggacgatggc taccgcacgg tggcgcaggg caccaagaag gagggctgca ccatcctctt   1080
catggtgctc tacttcttcg gcatggccag ctccatctgg tgggtcattc tgtctctcac   1140
ttggttcctg gcggccggca tgaagtgggg ccacgaggcc atcgaggcca actcgcagta   1200
cttccacctg gccgcgtggg ccgtgcccgc cgtcaagacc atcactatcc tggccatggg   1260
ccaggtagac ggggacctgc tgagcggggt gtgctacgtt ggcctctcca gtgtggacgc   1320
gctgcggggc ttcgtgctgg cgcctctgtt cgtctacctc ttcataggca cgtccttctt   1380
gctggccggc ttcgtgtccc tcttccgtat ccgcaccatc atgaaacacg acggcaccaa   1440
gaccgagaag ctggagaagc tcatggtgcg catcggcgtc ttcagcgtgc tctacacagt   1500
gcccgccacc atcgtcctgg cctgctactt ctacgagcag gccttccgcg agcactggga   1560
gcgcacctgg ctcctgcaga cgtgcaagag ctatgccgtg ccctgcccgc ccggccactt   1620
cccgcccatg agccccgact tcaccgtctt catgatcaag tacctgatga ccatgatcgt   1680
cggcatcacc actggcttct ggatctggtc gggcaagacc ctgcagtcgt ggcgccgctt   1740
ctaccacaga cttagccaca gcagcaaggg ggagactgcg gtatgagccc cggcccctcc   1800
ccacctttcc caccccagcc ctcttgcaag aggagaggca cggtagggaa aagaactgct   1860
gggtgggggc ctgtttctgt aactttctcc ccctctactg agaagtgacc tggaagtgag   1920
aagttctttg cagatttggg gcgaggggtg atttggaaaa gaagacctgg gtggaaagcg   1980
gtttggatga aaagatttca ggcaaagact tgcaggaaga tgatgataac ggcgatgtga   2040
atcgtcaaag gtacgggcca gcttgtgcct aatagaaggt tgagaccagc agagactgct   2100
gtgagtttct cccggctccg aggctgaacg gggactgtga gcgatccccc tgctgcaggg   2160
cgagtggcct gtccagaccc ctgtgaggcc ccgggaaagg tacagccctg tctgcggtgg   2220
ctgctttgtt ggaaagaggg agggcctcct gcggtgtgct tgtcaagcag tggtcaaacc   2280
```

-continued

```
ataatctctt ttcactgggg ccaaactgga gcccagatgg gttaatttcc agggtcagac   2340

attacggtct ctcctcccct gccccctccc gcctgttttt cctcccgtac tgctttcagg   2400

tcttgtaaaa taagcatttg gaagtcttgg gaggcctgcc tgctagaatc ctaatgtgag   2460

gatgcaaaag aaatgatgat aacattttga gataaggcca aggagacgtg gagtaggtat   2520

ttttgctact ttttcatttt ctggggaagg caggaggcag aaagacgggt gttttatttg   2580

gtctaatacc ctgaaaagaa gtgatgactt gttgcttttc aaaacaggaa tgcatttttc   2640

cccttgtctt tgttgtaaga gacaaaagag gaaacaaaag tgtctccctg tggaaaggca   2700

taactgtgac gaaagcaact tttataggca aagcagcgca aatctgaggt ttcccgttgg   2760

ttgttaattt ggttgagata aacattcctt tttaaggaaa agtgaagagc agtgtgctgt   2820

cacacaccgt taagccagag gttctgactt cgctaaagga aatgtaagag gttttgttgt   2880

ctgttttaaa taaatttaat tcggaacaca tgatccaaca gactatgtta aaatattcag   2940

ggaaatctct cccttcattt actttttctt gctataagcc tatatttagg tttcttttct   3000

atttttttct cccatttgga tcctttgagg taaaaaaaca taatgtcttc agcctcataa   3060

taaaggaaag ttaattaaaa aaaaaaagca aagagccatt ttgtcctgtt ttcttggttc   3120

catcaatctg tttattaaac atcatccata tgctgaccct gtctctgtgt ggttgggttg   3180

ggaggcgatc agcagatacc atagtgaacg aagaggaagg tttgaaccat gggccccatc   3240

tttaaagaaa gtcattaaaa gaaggtaaac ttcaaagtga ttctggagtt ctttgaaatg   3300

tgctggaaga cttaaattta ttaatcttaa atcatgtact ttttttctgt aatagaactc   3360

ggattctttt gcatgatggg gtaaagctta gcagagaatc atgggagcta acctttatcc   3420

cacctttgac actaccctcc aatcttgcaa cactatcctg tttctcagaa cagtttttaa   3480

atgccaatca tagagggtac tgtaaagtgt acaagttact ttatatatgt aatgttcact   3540

tgagtggaac tgctttttac attaaagtta aaatcgatct tgtgtttctt caaccttcaa   3600

aactatctca tctgtcagat ttttaaaact ccaacacagg ttttggcatc ttttgtgctg   3660

tatcttttaa gtgcatgtga aatttgtaaa atagagataa gtacagtatg tatattttgt   3720

aaatctccca tttttgtaag aaaatatata ttgtatttat acatttttac tttggatttt   3780

tgttttgttg gctttaaagg tctaccccac tttatcacat gtacagatca caaataaatt   3840

tttttaaata c                                                        3851
```

<210> SEQ ID NO 27
<211> LENGTH: 1476
<212> TYPE: DNA
<213> ORGANISM: Homo sapiens

<400> SEQUENCE: 27

```
ggggctcggg acggccgggc tgggagctgg agcccacagc gggaagcggc cgccgcccgg     60

gcctcgcagg gctaggcgag gcgagggggg gcggggccgg gcgctacggg aaggggaggc    120

cgcgcggacc gggagccgca ccgcgccagc cgggctgcag cggccgcgca ccaaggctgc    180

gatggggctg gagacggaga aggcggacgt acagctcttc atggacgacg actcctacag    240

ccaccacagc ggcctcgagt acgccgaccc cgagaagttc gcggactcgg accaggaccg    300

ggatccccac cggctcaact cgcatctcaa gctgggcttc gaggatgtga tcgcagagcc    360

ggtgactacg cactcctttg acaaagtgtg gatctgcagc catgccctct ttgaaatcag    420

caaatacgta atgtacaagt tcctgacggt gttcctggcc attcccctgg ccttcattgc    480

gggaattctc tttgccaccc tcagctgtct gcacatctgg attttaatgc cttttgtaaa    540
```

-continued

```
gacctgccta atggttctgc cttcagtgca gacaatatgg aagagtgtga cagatgttat    600
cattgctcca ttgtgtacga gcgtaggacg atgcttctct tctgtcagcc tgcaactgag    660
ccaggattga atacttggac cccaggtctg gagattggga tactgtaata cttctttgtt    720
attataacat aaaagcacca ctgttctgtt catttcctag ctgttctaat taagaaaact    780
attaagatga gcaaccacat ttagaaatgt ttattgacag gtcttttcaa ataatgcttt    840
tctaattaat agccaaagat ttcatatcta actttgtaac cagaattata cagtaagttg    900
acaccactta gatttaaagg cagacagttt tgctttagta caatagtata cattttataa    960
tgatgaactt ataatgatta agggacattt ctataaaaat actacaatag ttttatgcac   1020
aacttcccat taaaaatgag atttcttatt tgtttgtctg tttttactct gggagtaata   1080
ctttttaaat tacctttaca tatatagtca ctggcatact gagaatatac aatgatcctg   1140
gaaattgcag taacaaaagc acacaacgat tatagtaact ataagataca ataaaacaaa   1200
taaatatgaa agtagattca tgaaaatgta ttcctttaaa atattgtttt cctacaggcc   1260
tatttaacaa gatgtttcat tttactgtat attttgtagt taatataaat gttgctctaa   1320
tcagattgct taaaagcatt tttattatat ttatgttgtt gaactaatat atgaaataag   1380
taaatgtagc tcccacaagg taaacttcat tggtaagatt gcactgttct gattatgtaa   1440
gcatttgtac atcttctttg gaaataaaag ataaaa                              1476

<210> SEQ ID NO 28
<211> LENGTH: 4116
<212> TYPE: DNA
<213> ORGANISM: Homo sapiens

<400> SEQUENCE: 28

gtttagaaca gcctacagac ccagtggcac gagacgggcc tctctcccaa acatcttcca     60
agccagatcc tagtcagtgg gaaagcccca gcttcaaccc ctttgggagc cactctgttc    120
tgcagaactc cccacccctc tcttctgagg gctcctacca ctttgaccca gataactttg    180
acgaatccat ggatcccttt aaaccaacta cgaccttaac aagcagtgac ttttgttctc    240
ccactggtaa tcacgttaat gaaatcttag aatcacccaa gaaggcaaag tcgcgtttaa    300
taacgactac tgaacaagtg aaatttctct gttttctgtt gagtggctgt aaggtgaaga    360
agcatgaaac tcagtctctc gccctggatg catgttctcg ggatgaaggg gcagtgatct    420
cccagatttc agacatttct aatagggatg gccatgctac tgatgaggag aaactggcat    480
ccacgtcatg tggtcagaaa tcagctggtg ccgaggtgaa aggtgagcca gaggaagacc    540
tggagtactt tgaatgttcc aatgttcctg tgtctaccat aaatcatgcg ttttcatcct    600
cagaagcagg catagagaag gagacgtgcc agaagatgga agaagacggg tccactgtgc    660
ttgggctgct ggagtcctct gcagagaagg cccctgtgtc ggtgtcctgt ggaggtgaga    720
gccccctgga tgggatctgc ctcagcgaat cagacaagac agccgtgctc accttaataa    780
gagaagagat aattactaaa gagattgaag caaatgaatg gaagaagaaa tacgaagaga    840
cccggcaaga agttttggag atgaggaaaa ttgtagctga atatgaaaag actattgctc    900
aaatgattga tgaacaaagg acaagtatga cctctcagaa gagcttccag caactgacca    960
tggagaagga acaggccctg gctgacctta actctgtgga aaggtccctt tctgatctct   1020
tcaggagata tgagaacctg aaaggtgttc tggaagggtt caagaagaat gaagaagcct   1080
tgaagaaatg tgctcaggat tacttagcca gagttaaaca agaggagcag cgataccagg   1140
```

-continued

```
ccctgaaaat ccacgcagaa gagaaactgg acaaagccaa tgaagagatt gctcaggttc   1200
gaacaaaagc aaaggctgag agtgcagctc tccatgctgg actccgcaaa gagcagatga   1260
aggtggagtc cctggaaagg gccctgcagc agaagaacca agaaattgaa gaactgacaa   1320
aaatctgtga tgagctgatt gcaaagctgg gaaagactga ctgagacact ccccctgtta   1380
gctcaacaga tctgcatttg gctgcttctc ttgtgaccac aattatcttg ccttatccag   1440
gaataattgc ccctttgcag agaaaaaaaa aaacttaaaa aaagcacatg cctactgctg   1500
cctgtcccgc tttgctgcca atgcaacagc cctggaagaa accctagagg gttgcatagt   1560
ctagaaagga gtgtgacctg acagtgctgg agcctcctag tttcccccta tgaaggttcc   1620
cttaggctgc tgagtttggg tttgtgattt atctttagtt tgttttaaag tcatctttac   1680
tttcccaaat gtgttaaatt tgtaactcct ctttggggtc ttctccacca cctgtctgat   1740
tttttgtga tctgtttaat cttttaattt tttagtatca gtggttttat ttaaggagac   1800
agtttggcct attgttactt ccaatttata atcaagaagg ggctctggat cccctttttaa  1860
attacacaca ctctcacaca catacatgta tgtttataga tgctgctgct cttttccctg   1920
aagcatagtc aagtaagaac tgctctacag aaggacatat ttccttggat gtgagaccct   1980
attttgaaat agagtcctga ctcagaacac caacttaaga atttggggga ttaaagatgt   2040
gaagaccaca gtcttgggtt ttcatatctg gagaagacta tttgccatga cgttttgttg   2100
ccctggtatt tggacactcc tcagctttaa tgggtgtggc ccctttaggg ttagtcctca   2160
gactaatgat agtgtctgct ttctgcatga acggcaatat gggactccct ccaagctagg   2220
gtttggcaag tctgccctag agtcatttac tctcctctgc ctccatttgt taatacagaa   2280
tcaacattta gtcttcatta tctttttttt tttttttgag acagagtttc gatctatttt   2340
aagtatgtga agaaaatcta cttgtaaaag gctcagatct taattaaaag gtaattgtag   2400
cacattacca attataaggt gaagaaatgt ttttttccca agtgtgatgc attgttcttc   2460
agatgttgaa aagaaagcaa aaaataccct ctaacttaag acagaatttt taacaaaatg   2520
agcagtaaaa gtcacatgaa ccactccaaa aatcagtgca ttttgcatat ttttaaacaa   2580
agacagcttg ttgaatactg agaagaggag tgcaaggaga aggtctgtac taacaaagcc   2640
aaattcctca agctcttact ggactcagtt cagagtggtg ggccattaac cccaacatgg   2700
aatttttcca tataaatctc aatgaattcc ctttcatttg aataggcaaa cccaaatcca   2760
tgcaagtgtt ttaaagcact gtcctgtctt aatcttacat gctgaaagtc ttcatggtga   2820
tatgcactat attcagtata cgtatgtttt cctacttctc ttgtaaaact gttgcatgat   2880
ccaacttcag caatgaattg tgcctagtgg agaacctcta tagatcttaa aaaatgaatt   2940
attctttagc agtgtattac tcacatgggt gcaatcttta gccccaggga ggtcaataat   3000
gtcttttaaa gccagaagtc acattttacc aatatgcatt tatcataatt ggtgcttagg   3060
ctgtatattc aagcctgttg tcttaacatt ttgtataaaa aagaacaaca gaaattatct   3120
gtcatttgag aagtggcttg acaatcattt gagctttgaa agcagtcact gtggtgtaat   3180
atgaatgctg tcctagtggt catagtacca agggcacgtg tctccccttg gtataactga   3240
tttcctttttt agtcctctac tgctaaataa gttaattttg cattttgcag aaagaaacat  3300
tgattgctaa atctttttgc tgctgtgttt tggtgttttc atgtttactt gttttatatt   3360
gatctgtttt aagtatgaga ggcttatagt gccctccatt gtaaatccat agtcatcttt   3420
ttaagcttat tgtgtttaag aaagtagcta tgtgttaaac agaggtgatg gcagcccttc   3480
cctagcacac tggtggaaga gacccccttaa gaacctgacc ccagtgaatg aagctgatgc  3540
```

-continued

```
acagggagca ccaaaggacc ttcgttaagt gataattgtc ctggcctctc agccatgacc   3600

gttatgagga aatatccccc attcgaactt aacagatgcc tcctctccaa agagaattaa   3660

aatcgtagct tgtacagatc aagagaatat actgggcaga atgaagtatg tttgtttatt   3720

tttctttaaa aataaaggat tttggaactc tggagagtaa gaatatagta tagagtttgc   3780

ctcaacacat gtgagggcca aataacctgc tagctaggca gtaataaact ctgttacaga   3840

agagaaaaag ggccgggcac agtggcttat tcctgtaatc ccaacactgt ggaaggccga   3900

ggcaggagga tcacttgagt ccaggagttt gaaacctacc taggcaacat ggtgaaacct   3960

tgtctctacc aaaataaaaa ttagctgggc atggtggcac gtgcctgtgg tcccagctac   4020

ttgggaggct gaggtgggag cctgggaggt caaggctgca gtgagccatg atcatgccac   4080

tgcactccat cctgggtgac agcaagatct tgtctc                            4116
```

<210> SEQ ID NO 29
<211> LENGTH: 540
<212> TYPE: DNA
<213> ORGANISM: Homo sapiens

<400> SEQUENCE: 29

```
cgagttcccc gaggtgtacg tgcccaccgt cttcgagaac tatgtggccg acattgaggt     60

ggacggcaag caggtggagc tggcgctgtg ggacacggcg ggccaggagg actacgaccg    120

cctgcggccg ctctcctacc cggacaccga cgtcattctc atgtgcttct cggtggacag    180

cccggactcg ctggagaaca tccccgagaa gtgggtcccc gaggtgaagc acttctgtcc    240

caatgtgccc atcatcctgg tggccaacaa aaaagacctg cgcagcgacg agcatgtccg    300

cacagagctg gcccgcatga agcaggaacc cgtgcgcacg gatgacggcc gcgccatggc    360

cgtgcgcatc caagcctacg actacctcga gtgctctgcc aagaccaagg aaggcgtgcg    420

cgaggtcttc gagacggcca cgcgcgccgc gctgcagaag cgctacggct cccagaacgg    480

ctgcatcaac tgctgcaagg tgctatgagg gccgcgcccg tcgcgcctgc ccctgccggc    540
```

<210> SEQ ID NO 30
<211> LENGTH: 1063
<212> TYPE: DNA
<213> ORGANISM: Homo sapiens

<400> SEQUENCE: 30

```
cggggagacc atggggcccc tctcagcccc ttcctgcaca cacctcatca cttggaaggg     60

ggtcctgctc acagcatcac ttttaaactt ctggaatccg cccaccactg ccgaagtcac    120

gattgaagcc cagccaccca aagtttctga ggggaaggat gttcttctac ttgttcacaa    180

tttgccccag aatcttcctg gctacttctg gtacaaaggg gaaatgacgg acctctacca    240

ttacattata tcgtatatag ttgatggtaa aataattata tatgggcctg catacagtgg    300

aagagaaaca gtatattcca acgcatccct gctgatccag aatgtcaccc ggaaggatgc    360

aggaacctac accttacaca tcataaagcg aggtgatgag actagagaag aaattcgaca    420

tttcaccttc accttatact atggtccaga cctccccaga atttaccctt cattcaccta    480

ttacggttca ggagaaaacc tcgacttgtc ctgcttcacg gaatctaacc caccggcaga    540

gtatttttgg acaattaatg ggaagtttca gcaatcagga caaaagctct ttatccccca    600

aattactaga aatcatagcg ggctctatgt ttgctctgtt cataactcag ccactggcaa    660

ggaaatctcc aaatccatga cagtcaaagt ctctggtccc tgccatggag acctgacaga    720
```

-continued

```
gtttcagtca tgactgcaac aactgagaca ctgagaaaaa gaacaggctg ataccttcat    780

gaaattcaag acaaagaaga aaaaaactca atgttattgg actaaataat caaaaggata    840

atgttttcat aattttttat tggaaaatgt gctgattctt tgaatgtttt attctccaga    900

tttatgaact ttttttcttc agcaattggt aaagtatact tttgtaaaca aaaattgaaa    960

tatttgcttt tgctgtctat ctgaatgccc cagaattgtg aaactactca tgagtactca   1020

taggtttatg gtaataaagt tatttgcaca tgttccgtag ttt                     1063


<210> SEQ ID NO 31
<211> LENGTH: 1117
<212> TYPE: DNA
<213> ORGANISM: Homo sapiens

<400> SEQUENCE: 31

gcaccaacca gcaccatgcc catgatactg gggtactggg acatccgcgg gctggcccac     60

gccatccgcc tgctcctgga atacacagac tcaagctatg aggaaaagaa gtacacgatg    120

ggggacgctc ctgattatga cagaagccag tggctgaatg aaaaattcaa gctgggcctg    180

gactttccca atctgcccta cttgattgat ggggctcaca agatcaccca gagcaacgcc    240

atcttgtgct acattgcccg caagcacaac ctgtgtgggg agacagaaga ggagaagatt    300

cgtgtggaca ttttggagaa ccagaccatg gacaaccata tgcagctggg catgatctgc    360

tacaatccag aatttgagaa actgaagcca aagtacttgg aggaactccc tgaaaagcta    420

aagctctact cagagtttct ggggaagcgg ccatggtttg caggaaacaa gatcactttt    480

gtagattttc tcgtctatga tgtccttgac ctccaccgta tatttgagcc caactgcttg    540

gacgccttcc caaatctgaa ggacttcatc tcccgctttg agggcttgga gaagatctct    600

gcctacatga agtccagccg cttcctccca agacctgtgt tctcaaagat ggctgtctgg    660

ggcaacaagt agggccttga aggcaggagg tgggagtgag gagcccatac tcagcctgct    720

gcccaggctg tgcagcgcag ctggactctg catcccagca cctgcctcct cgttcctttc    780

tcctgtttat tcccatcttt actcccaaga cttcattgtc cctcttcact ccccctaaac    840

ccctgtccca tgcaggccct ttgaagcctc agctacccac tatccttcgt gaacatcccc    900

tcccatcatt acccttccct gcactaaagc cagcctgacc ttccttcctg ttagtggttg    960

tgtctgcttt aaagcctgcc tggcccctcg cctgtggagc tcagccccga gctgtccccg   1020

tgttgcatga aggagcagca ttgactggtt tacaggccct gctcctgcag catggtccct   1080

gcctaggcct acctgatgga agtaaagcct caaccac                            1117


<210> SEQ ID NO 32
<211> LENGTH: 1869
<212> TYPE: DNA
<213> ORGANISM: Homo sapiens

<400> SEQUENCE: 32

ttcaggaacc ggtttggtgc tggtgctgga ggcggctatg gctttggagg tggtgccggt     60

agtggatttg gtttcggcgg tggagctggt ggtggctttg ggctcggtgg cggagctggc    120

tttggaggtg gcttcggtgg ccctggcttt cctgtctgcc ctcctggagg tatccaagag    180

gtcactgtca accagagtct cctgactccc ctcaacctgc aaatcgaccc cagcatccag    240

agggtgagga ccgaggagcg cgagcagatc aagaccctca acaataagtt tgcctccttc    300

atcgacaagg tgcggttcct ggagcagcag aacaaggttc tggacaccaa gtggaccctg    360

ctgcaggagc agggcaccaa gactgtgagg cagaacctgg agccgttgtt cgagcagtac    420
```

-continued atcaacaacc tcaggaggca gctggacagc atcgtggggg aacggggccg cctggactca 480
gagctgagaa acatgcagga cctggtggaa gacttcaaga acaagtatga ggatgaaatc 540
aacaagcgta ccactgctga gaatgagttt gtgatgctga agaaggatgt agatgctgcc 600
tacatgaaca aggtggagct ggaggccaag gttgatgcac tgatggatga gattaacttc 660
atgaagatgt tctttgatgc ggagctgtcc cagatgcaga cgcatgtctc tgacacctca 720
gtggtcctct ccatggacaa caaccgcaac ctggacctgg atagcatcat cgctgaggtc 780
aaggcccagt atgaggagat tgccaaccgc agccggacag aagccgagtc ctggtatcag 840
accaagtatg aggagctgca gcagacagct ggccggcatg gcgatgacct ccgcaacacc 900
aagcatgaga tctctgagat gaaccggatg atccagaggc tgagagccga gattgacaat 960
gtcaagaaac agtgcgccaa tctgcagaac gccattgcgg atgccgagca gcgtggggag 1020
ctggccctca aggatgccag gaacaagctg gccgagctgg aggaggccct gcagaaggcc 1080
aagcaggaca tggcccggct gctgcgtgag taccaggagc tcatgaacac caagctggcc 1140
ctggacgtgg agatcgccac ttaccgcaag ctgctggagg gcgaggaatg cagactcagt 1200
ggagaaggag ttggaccagt caacatctct gttgtcacaa gcagtgtttc ctctggatat 1260
ggcagtggca gtggctatgg cggtggcctc ggtggaggtc ttggcggcgg cctcggtgga 1320
ggtcttgccg gaggtagcag tggaagctac tactccagca gcagtggggg tgtcggccta 1380
ggtggtgggc tcagtgtggg gggctctggc ttcagtgcaa gcagtggccg agggctgggg 1440
gtgggctttg gcagtggcgg gggtagcagc tccagcgtca aatttgtctc caccacctcc 1500
tcctcccgga agagcttcaa gagctaagaa cctgctgcaa gtcactgcct tccaagtgca 1560
gcaacccagc ccatggagat tgcctcttct aggcagttgc tcaagccatg ttttatcctt 1620
ttctggagag tagtctagac caagccaatt gcagaaccac attctttggt tcccaggaga 1680
gccccattcc cagcccctgg tctcccgtgc cgcagttcta tattctgctt caaatcagcc 1740
ttcaggtttc ccacagcatg gcccctgctg acacgagaac ccaaagtttt cccaaatcta 1800
aatcatcaaa acagaatccc caccccaatc ccaaattttg ttttggttct aactacctcc 1860
agaatgtgt 1869

<210> SEQ ID NO 33
<211> LENGTH: 664
<212> TYPE: DNA
<213> ORGANISM: Homo sapiens

<400> SEQUENCE: 33
agtgatcagg gccaaagcgg tcagtgagaa ggaagtggac tctggaaacg acatttatgg 60
caaccctatc aagaggatcc agtatgagat caagcagata aagatgttca aagggcctga 120
gaaggatata gagtttatct acacggcccc ctcctcggca gtgtgtgggg tctcgctgga 180
cgttggagga aagaaggaat atctcattgc aggaaaggcc gagggggacg gcaagatgca 240
catcaccctc tgtgacttca tcgtgccctg ggacaccctg agcaccaccc agaagaagag 300
cctgaaccac aggtaccaga tgggctgcga gtgcaagatc acgcgctgcc ccatgatccc 360
gtgctacatc tcctccccgg acgagtgcct ctggatggac tgggtcacag agaagaacat 420
caacgggcac caggccaagt tcttcgcctg catcaagaga agtgacggct cctgtgcgtg 480
gtaccgcggc gcggcgcccc ccaagcagga gtttctcgac atcgaggacc cataagcagg 540
cctccaacgc ccctgtggcc aactgcaaaa aaagcctcca agggtttcga ctggtccagc 600

-continued

```
tctgacatcc cttcctggaa acagcatgaa taaaacactc atcccatggg tccaaattaa    660

tatg                                                                 664
```

<210> SEQ ID NO 34
<211> LENGTH: 2598
<212> TYPE: DNA
<213> ORGANISM: Homo sapiens

<400> SEQUENCE: 34

```
tgtcgccacc atggctccgc accgccccgc gcccgcgctg ctttgcgcgc tgtccctggc     60

gctgtgcgcg ctgtcgctgc ccgtccgcgc ggccactgcg tcgcgggggg cgtcccaggc    120

gggggcgccc caggggcggg tgcccgaggc gcggcccaac agcatggtgg tggaacaccc    180

cgagttcctc aaggcaggga aggagcctgg cctgcagatc tggcgtgtgg agaagttcga    240

tctggtgccc gtgcccacca acctttatgg agacttcttc acgggcgacg cctacgtcat    300

cctgaagaca gtgcagctga ggaacggaaa tctgcagtat gacctccact actggctggg    360

caatgagtgc agccaggatg agagcggggc ggccgccatc tttaccgtgc agctggatga    420

ctacctgaac ggccgggccg tgcagcaccg tgaggtccag ggcttcgagt cggccacctt    480

cctaggctac ttcaagtctg gcctgaagta caagaaagga ggtgtggcat caggattcaa    540

gcacgtggta cccaacgagg tggtggtgca gagactcttc caggtcaaag ggcggcgtgt    600

ggtccgtgcc accgaggtac ctgtgtcctg ggagagcttc aacaatggcg actgcttcat    660

cctggacctg ggcaacaaca tccaccagtg gtgtggttcc aacagcaatc ggtatgaaag    720

actgaaggcc acacaggtgt ccaagggcat ccgggacaac gagcggagtg gccgggcccg    780

agtgcacgtg tctgaggagg gcactgagcc cgaggcgatg ctccaggtgc tgggccccaa    840

gccggctctg cctgcaggta ccgaggacac cgccaaggag gatgcggcca accgcaagct    900

ggccaagctc tacaaggtct ccaatggtgc agggaccatg tccgtctccc tcgtggctga    960

tgagaacccc ttcgcccagg gggccctgaa gtcagaggac tgcttcatcc tggaccacgg   1020

caaagatggg aaaatctttg tctggaaagg caagcaggca aacacggagg agaggaaggc   1080

tgccctcaaa acagcctctg acttcatcac caagatggac taccccaagc agactcaggt   1140

ctcggtcctt cctgagggcg gtgagacccc actgttcaag cagttcttca agaactggcg   1200

ggacccagac cagacagatg gcctgggctt gtcctacctt tccagccata tcgccaacgt   1260

ggagcgggtg cccttcgacg ccgccaccct gcacacctcc actgccatgg ccgcccagca   1320

cggcatggat gacgatggca caggccagaa acagatctgg agaatcgaag gttccaacaa   1380

ggtgcccgtg gaccctgcca catatggaca gttctatgga ggcgacagct acatcattct   1440

gtacaactac cgccatggtg gccgccaggg gcagataatc tataactggc agggtgccca   1500

gtctacccag gatgaggtcg ctgcatctgc catcctgact gctcagctgg atgaggagct   1560

gggaggtacc cctgtccaga gccgtgtggt ccaaggcaag gagcccgccc acctcatgag   1620

cctgtttggt gggaagccca tgatcatcta caagggcggc acctcccgcg agggcgggca   1680

gacagcccct gccagcaccc gcctcttcca ggtccgcgcc aacagcgctg gagccacccg   1740

ggctgttgag gtattgccta aggctggtgc actgaactcc aacgatgcct ttgttctgaa   1800

aacccctca gccgcctacc tgtgggtggg tacaggagcc agcgaggcag agaagacggg    1860

ggcccaggag ctgctcaggg tgctgcgggc ccaacctgtg caggtggcag aaggcagcga   1920

gccagatggc ttctgggagg ccctgggcgg gaaggctgcc taccgcacat ccccacggct   1980

gaaggacaag aagatggatg cccatcctcc tcgcctcttt gcctgctcca acaagattgg   2040
```

-continued

```
acgttttgtg atcgaagagg ttcctggtga gctcatgcag gaagacctgg caacggatga   2100

cgtcatgctt ctggacacct gggaccaggt ctttgtctgg gttggaaagg attctcaaga   2160

agaagaaaag acagaagcct tgacttctgc taagcggtac atcgagacgg acccagccaa   2220

tcgggatcgg cggacgccca tcaccgtggt gaagcaaggc tttgagcctc cctcctttgt   2280

gggctggttc cttggctggg atgatgatta ctggtctgtg gaccccttgg acagggccat   2340

ggctgagctg gctgcctgag gaggggcagg gcccacccat gtcaccggtc agtgcctttt   2400

ggaactgtcc ttccctcaaa gaggccttag agcgagcaga gcagctctgc tatgagtgtg   2460

tgtgtgtgtg tgtgttgttt cttttttttt tttttacagt atccaaaaat agccctgcaa   2520

aaattcagag tccttgcaaa attgtctaaa atgtcagtgt ttgggaaatt aaatccaata   2580

aaaacatttt gaagtgtg                                                 2598
```

```
<210> SEQ ID NO 35
<211> LENGTH: 329
<212> TYPE: DNA
<213> ORGANISM: Homo sapiens
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 35

gaagtaaaag atttttattg ttctatagac acttctgaaa agagatctaa ttgagaaaat     60

atacaaagca tttaagagtt tcatccccag agactgactg aaggcgttac agccctcctc    120

tccaaggctc agggctgaga acggttagca tatcgaatga tcagtaaaaa catgcaaaag    180

tgagaaggaa agggaaaaag gtgcattccc ctaagctgag ggggatggaa tttcagaaca    240

gaggangcag ggtggacaag taccaaggtg gctctccctt tccctctgtg tnatctttca    300

aaaccanttc caagcntgga tnaaagcaa                                      329
```

```
<210> SEQ ID NO 36
<211> LENGTH: 1555
<212> TYPE: DNA
<213> ORGANISM: Homo sapiens

<400> SEQUENCE: 36

caaagtctga gccccgctcc gctgatgcct gtctgcagaa tccgcaccaa ccagcaccat     60

gcccatgact ctggggtact gggacatccg tgggctggcc cacgccatcc gcttgctcct    120

ggaatacaca gactcaagct atgtggaaaa gaagtacacg ctgggggacg ctcctgacta    180

tgacagaagc cagtggctga atgaaaaatt caagctgggc ctggactttc ccaatctgcc    240

ctacttgatt gatggggctc acaagatcac ccagagcaat gccatcctgc gctacattgc    300
```

-continued

```
ccgcaagcac aacctgtgtg gggagacaga agaggagaag attcgtgtgg acattttgga    360

gaaccaggtt atggataacc acatggagct ggtcagactg tgctatgacc cagattttga    420

gaaactgaag ccaaaatact tggaggaact ccctgaaaag ctaaagctct actcagagtt    480

tctggggaag cggccatggt ttgcaggaga caagatcacc tttgtggatt tccttgccta    540

tgatgtcctt gacatgaagc gtatatttga gcccaagtgc ttggacgcct tcctaaactt    600

gaaggacttc atctcccgct ttgagggttt gaagaagatc tctgcctaca tgaagtccag    660

ccaattcctc cgaggtcttt tgtttggaaa gtcagctaca tggaacagca aatagggccc    720

agtgatgcca gaagatggga gggaggagcc aaccttgctg cctgcgaccc tggaggacag    780

cctgactccc tggacctgcc ttcttccttt ttccttcttt ctactctctt ctcttcccca    840

aggcctcatt ggcttccttt cttctaacat catccctccc cgcatcgagg ctctttaaag    900

cttcagctcc ccactgtcct ccatcaaagt cccccteccta acgtcttcct ttccctgcac    960

taacgccaac ctgactgctt ttcctgtcag tgcttttctc ttctttgaga agccagactg   1020

atctctgagc tccctagcac tgtcctcaaa gaccatctgt atgccctgct ccctttgctg   1080

ggtccctacc ccagctccgt gtgatgccca gtaaagcctg aaccatgcct gccatgtctt   1140

gtcttattcc ctgaggctcc cttgactcag gactgtgctc gaattgtggg tggttttttg   1200

tcttctgttg tccacagcca gagcttagtg gatgggtgtg tgtgtgtgtg tgttgggggt   1260

ggtgatcagg caggttcata aatttccttg gtcatttctg ccctctagcc acatccctct   1320

gttcctcact gtggggatta ctacagaaag gtgctctgtg ccaagttcct cactcattcg   1380

cgctcctgta ggccgtctag aactggcatg gttcaaagag gggctaggct gatggggaag   1440

ggggctgagc agctcccagg cagactgcct tctttcaccc tgtcctgata gacttccctg   1500

atctagatat ccttcgtcat gacacttctc aataaaacgt atcccaccgt attgt        1555
```

<210> SEQ ID NO 37
<211> LENGTH: 4812
<212> TYPE: DNA
<213> ORGANISM: Homo sapiens
<220> FEATURE:
<221> NAME/KEY: misc_feature
<222> LOCATION: (784)..(1133)
<223> OTHER INFORMATION: n is a, c, g, or t

<400> SEQUENCE: 37

```
ggttgagaat gcttgcacca agcttgtcca ggcagctcag atgcttcagt cagaccctta     60

ctcagtgcct gctcgagatt atctaattga tgggtcaagg ggcatcctct ctggaacatc    120

agacctgctc cttaccttcg atgaggctga ggtccgtaaa attattagag tttgcaaagg    180

aattttggaa tatcttacag tggcagaggt ggtggagact atggaagatt tggtcactta    240

cacaaagaat cttgggccag gaatgactaa gatggccaag atgattgacg agagacagca    300

ggagctcact caccaggagc accgagtgat gttggtgaac tcgatgaaca ccgtgaaaga    360

gttgctgcca gttctcattt cagctatgaa gatttttgta acaactaaaa actcaaaaaa    420

ccaaggcata gaggaagctt taaaaaatcg caattttact gtagaaaaaa tgagtgctga    480

aattaatgag ataattcgtg tgttacaact cacctcttgg gatgaagatg cctgggccag    540

caaggacact gaagccatga agagagcatt ggcctccata gactccaaac tgaaccaggc    600

caaaggttgg ctccgtgacc ctagtgcctc cccaggggat gctggtgagc aggccatcag    660

acagatctta gatgaagctg gaaaagttgg tgaactctgt gcaggcaaag aacgcaggga    720

gattctggga acttgcaaaa tgctagggca gatgactgat caagtggctg acctccgtgc    780
```

-continued

```
cagnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnaggctcg   1140
agccttggcc aaacaggtgg ccacggccct gcagaacctg cagaccaaaa ccaaccgggc   1200
tgtggccaac agcagaccgg ccaaagcagc tgtacacctt gagggcaaga ttgagcaagc   1260
acagcggtgg attgataatc ccacagtgga tgaccgtgga gtcggtcagg ctgccatccg   1320
ggggcttgtg gccgaagggc atcgtctggc taatgttatg atggggcctt atcggcaaga   1380
tcttctcgcc aagtgtgacc gagtggacca gctgacagcc cagctggctg acctggctgc   1440
cagaggggaa ggggagagtc ctcaggcacg agcacttgca tctcagctcc aagactcctt   1500
aaaggatcta aaagctcgga tgcaggaggc catgactcag gaagtgtcag atgttttcag   1560
cgataccaca actcccatca agctgttggc agtggcagcc acggcgcctc ctgatgcgcc   1620
taacagggaa gaggtatttg atgagagggc agctaacttt gaaaaccatt caggaaagct   1680
tggtgctacg gccgagaagg cggctgcggt tggtactgct aataaatcaa cagtggaagg   1740
cattcaggcc tcagtgaaga cggcccgaga actcacaccc caggtggtct cggctgctcg   1800
tatcttactt aggaaccctg gaaatcaagc tgcttatgaa cattttgaga ccatgaagaa   1860
ccagtggatc gataatgttg aaaaaatgac agggctggtg gacgaagcca ttgataccaa   1920
atctctgttg gatgcttcag aagaagcaat taaaaaagac ctggacaagt gcaaggtagc   1980
tatggccaac attcagcctc agatgctggt tgctggggca accagtattg ctcgtcgggc   2040
caaccggatc ctgctggtgg ctaagaggga ggtggagaat tccgaggatc ccaagttccg   2100
tgaggctgtg aaagctgcct ctgatgaatt gagcaaaacc atctccccga tggtgatgga   2160
tgcaaaagct gtggctggaa acatttccga ccctggactg caaaagagct tcctggactc   2220
aggatatcgg atcctgggag ctgtggccaa ggtcagagaa gccttccaac ctcaggagcc   2280
tgacttcccg ccgcctccac cagaccttga acaactccga ctaacagatg agcttgctcc   2340
tcccaaacca cctctgcctg aaggtgaggt ccctccacct aggcctccac caccagagga   2400
aaaggatgaa gagttccctg agcagaaggc cggggaggtg attaaccagc caatgatgat   2460
ggctgccaga cagctccatg atgaagctcg caaatggtcc agcaagggca atgacatcat   2520
tgcagcagcc aagcgcatgg ctctgctgat ggctgagatg tctcggctgg taagaggggg   2580
cagtggtacc aagcgggcac tcattcagtg tgccaaggac atcgccaagg cctcagatga   2640
ggtgactcgg ttggccaagg aggttgccaa gcagtgcaca gataaacgga ttagaaccaa   2700
cctcttacag gtatgtgagc gaatcccaac cataagcacc cagctcaaaa tcctgtccac   2760
agtgaaggcc accatgctgg gccggaccaa catcagtgat gaggagtctg agcaggccac   2820
agagatgctg gttcacaatg cccagaacct catgcagtct gtgaaggaga ctgtgcggga   2880
agctgaagct gcttcaatca aaattcgaac agatgctgga tttacactgc gctgggttag   2940
aaagactccc tggtaccagt aggcacctgg ctgagcctgg ctggcacaga aacctctact   3000
aaaaagaagg aaaatgatct gagtcccagg agctgcccag agttgctggg agctgaaaaa   3060
tcacatcctg gcctggcaca tcagaaagga atgggggcct cttcaaatta gaagacattt   3120
```

-continued

```
atactctttt ttcatggaca ctttgaaatg tgtttctgta taaagcctgt attctcaaac   3180

acagttacac ttgtgcaccc tctatcccaa taggcagact gggtttctag cccatggact   3240

tcacataagc tcagaatcca agtgaacact agccagacac tctgctctgc ccttgttccc   3300

taggggacac ttccctctgt ttctctttcc ttggctccca ttcactcttc cagaatccca   3360

agacccaggg cccaggcaaa tcagttacta agaagaaaat tgctgtgcct cccaaaattg   3420

ttttgagctt tccatgttgc tgccaaccat accttccttc cctgggctgt gctacctggg   3480

tccttttcag aagtgagctt tgctgctaca ggggaaggtg gcctctgtgg agccccagca   3540

tatgggggcc tggattcatt tcctgccctt cctcagttta atccttctag tttcccacaa   3600

tataaaactg tacttcactg tcaggaagaa atcacagaat catatgattc tgcttttacc   3660

atgcccctga gcaatgtctg tgctagggaa acttcccgtc ccatatcctg cctcagcccg   3720

ccaaggtagc catcccatga acacactgtg tcctggtgct ctctgccact ggaagggcag   3780

agtagccagg gtgtggccct gccatcttcc cagcagggcc actcccggca ctccatgctt   3840

agtcactgcc tgcagaggtc tgtgctgagg ccttatcatt cattcttagc tcttaattgt   3900

tcattttgag ctgaaatgct gcattttaat tttaaccaaa acatgtctcc tatcctggtt   3960

tttgtagcct tcctccacat cctttctaaa caagatttta aagacatgta ggtgtttgtt   4020

catctgtaac tctaaaagat cctttttaaa ttcagtccta agaaagagga gtgcttgtcc   4080

cctaagagtg tttaatggca aggcagccct gtctgaagga cacttcctgc ctaagggaga   4140

gtggtatttg cagactagaa ttctagtgct gctgaagatg aatcaatggg aaatactact   4200

cctgtaattc ctacctccct gcaaccaact acaaccaagc tctctgcatc tactcccaag   4260

tatggggttc aagagagtaa tgggtttcat atttcttatc accacagtaa gttcctacta   4320

ggcaaaatga gagggcagtg tttccttttt ggtacttatt actgctaagt atttcccagc   4380

acatgaaacc ttattttttc ccaaagccag aaccagatga gtaaaggagt aagaaccttg   4440

cctgaacatc cttccttccc acccatcgct gtgtgttagt tcccaacatc gaatgtgtac   4500

aacttaagtt ggtcctttac actcaggctt tcactatttc ctttataatg aggatgatta   4560

ttttcaaggc cctcagcata tttgtatagt tgcttgcctg atataaatgc aatattaatg   4620

cctttaaagt atgaatctat gccaaagatc acttgttgtt ttactaaaga aagattactt   4680

agaggaaata agaaaaatca tgtttgctct cccggttctt ccagtggttt gagacactgg   4740

tttacacttt atgccggatg tgcttttctc caatatcagt gctcgagaca cagtgaagca   4800

aattaaaaaa aa                                                        4812
```

<210> SEQ ID NO 38
<211> LENGTH: 2038
<212> TYPE: DNA
<213> ORGANISM: Homo sapiens

<400> SEQUENCE: 38

```
atatccagcc tttgccgaat acatcctatc tgccacacat ccagcgtgag gtccctccag     60

ctacaaggtg ggcaccatgg cggagaagtt tgactgccac tactgcaggg atcccttgca    120

ggggaagaag tatgtgcaaa aggatggcca ccactgctgc ctgaaatgct ttgacaagtt    180

ctgtgccaac acctgtgtgg aatgccgcaa gcccatcggt gcggactcca aggaggtgca    240

ctataagaac cgcttctggc atgacacctg cttccgctgt gccaagtgcc ttcacccctt    300

ggccaatgag acctttgtgg ccaaggacaa caagatcctg tgcaacaagt gcaccactcg    360

ggaggactcc cccaagtgca aggggtgctt caaggccatt gtggcaggag atcaaaacgt    420
```

-continued

```
ggagtacaag gggaccgtct ggcacaaaga ctgcttcacc tgtagtaact gcaagcaagt    480

catcgggact ggaagcttct tccctaaagg ggaggacttc tactgcgtga cttgccatga    540

gaccaagttt gccaagcatt gcgtgaagtg caacaaggcc atcacatctg gaggaatcac    600

ttaccaggat cagccctggc atgccgattg ctttgtgtgt gttacctgct ctaagaagct    660

ggctgggcag cgtttcaccg ctgtggagga ccagtattac tgcgtggatt gctacaagaa    720

ctttgtggcc aagaagtgtg ctggatgcaa gaaccccatc actgggaaaa ggactgtgtc    780

aagagtgagc cacccagtct ctaaagctag gaagcccccca gtgtgccacg ggaaacgctt    840

gcctctcacc ctgtttccca gcgccaacct ccggggcagg catccgggtg gagagaggac    900

ttgtccctcg tgggtggtgg ttctttatag aaaaaatcga agcttagcag ctcctcgagg    960

cccgggtttg gtaaaggctc cagtgtggtg gcctatgaag gacaatcctg gcacgactac   1020

tgcttccact gcaaaaaatg ctccgtgaat ctggccaaca agcgctttgt tttccaccag   1080

gagcaagtgt attgtcccga ctgtgccaaa aagctgtaaa ctgacagggg ctcctgtcct   1140

gtaaaatggc atttgaatct cgttctttgt gtccttactt tctgccctat accatcaata   1200

ggggaagagt ggtccttccc ttctttaaag ttctccttcc gtcttttctc ccattttaca   1260

gtattactca aataagggca cacagtgatc atattagcat ttagcaaaaa gcaaccctgc   1320

agcaaagtga atttctgtcc ggctgcaatt taaaaatgaa aacttaggta gattgactct   1380

tctgcatgtt tctcatagag cagaaaagtg ctaatcattt agccacttag tgatgtaagc   1440

aagaagcata ggagataaaa cccccactga gatgcctctc atgcctcagc tgggacccac   1500

cgtgtagaca cacgacatgc aagagttgca gcggctgctc caactcactg ctcaccctct   1560

tctgtgagca ggaaaagaac cctactgaca tgcatggttt aacttcctca tcagaactct   1620

gcccttcctt ctgttctttt gtgctttcaa ataactaaca cgaacttcca gaaaattaac   1680

atttgaactt agctgtaatt ctaaactgac ctttccccgt actaacgttt ggtttccccg   1740

tgtggcatgt tttctgagcg ttcctacttt aaagcatgga acatgcaggt gatttgggaa   1800

gtgtagaaag acctgagaaa acgagcctgt ttcagaggaa catcgtcaca acgaatactt   1860

ctggaagctt aacaaaacta accctgctgt cctttttatt gtttttaatt aatatttttg   1920

ttttaattga tagcaaaata gtttatgggt ttggaaactt gcatgaaaat attttagccc   1980

cctcagatgt tcctgcagtg ctgaaattca tcctacggaa gtaaccgcaa aactctag     2038
```

<210> SEQ ID NO 39
<211> LENGTH: 691
<212> TYPE: DNA
<213> ORGANISM: Homo sapiens
<220> FEATURE:
<221> NAME/KEY: misc_feature
<222> LOCATION: (37)..(78)
<223> OTHER INFORMATION: n is a, c, g, or t
<220> FEATURE:
<221> NAME/KEY: misc_feature
<222> LOCATION: (240)..(268)
<223> OTHER INFORMATION: n is a, c, g, or t

<400> SEQUENCE: 39

```
tgccgcccta caccgtggtc tatttcccag ttcgagnnnn nnnnnnnnnn nnnnnnnnnn     60

nnnnnnnnnn nnnnnnnngc tgctggcaga tcagggccag agctggaagg aggaggtggt    120

gaccgtggag acgtggcagg agggctcact caaagcctcc tgcctatacg ggcagctccc    180

caagttccag gacggagacc tcaccctgta ccagtccaat accatcctgc gtcacctggn    240
```

-continued

```
nnnnnnnnnn nnnnnnnnnn nnnnnnnngg ctctatggga aggaccagca ggaggcagcc    300

ctggtggaca tggtgaatga cggcgtggag gacctccgct gcaaatacat ctccctcatc    360

tacaccaact atgaggcggg caaggatgac tatgtgaagg cactgcccgg gcaactgaag    420

ccttttgaga ccctgctgtc ccagaaccag ggaggcaaga ccttcattgt gggagaccag    480

atctccttcg ctgactacaa cctgctggac ttgctgctga tccatgaggt cctagcccct    540

ggctgcctgg atgcgttccc cctgctctca gcatatgtgg ggcgcctcag tgcccggccc    600

aagctcaagg ccttcctggc ctcccctgag tacgtgaacc tccccatcaa tggcaacggg    660

aaacagtgag ggttgggggg actctgagcg g                                   691


<210> SEQ ID NO 40
<211> LENGTH: 2511
<212> TYPE: DNA
<213> ORGANISM: Homo sapiens
<220> FEATURE:
<221> NAME/KEY: misc_feature
<222> LOCATION: (799)..(953)
<223> OTHER INFORMATION: n is a, c, g, or t

<400> SEQUENCE: 40

cttttcacac tggccttaaa gaggatatat tagaagttga agtaggaagg gagccagaga     60

ggccgatggc gcaaaggtac gacgatctac cccattacgg gggcatggat ggagtaggca    120

tcccctccac gatgtatggg gacccgcatg cagccaggtc catgcagccg gtccaccacc    180

tgaaccacgg gcctcctctg cactcgcatc agtacccgca cacagctcat accaacgcca    240

tggcccccag catgggctcc tctgtcaatg acgctttaaa gagagataaa gatgccattt    300

atggacaccc cctcttccct ctcttagcac tgatttttga gaaatgtgaa ttagctactt    360

gtaccccccg cgagccgggg gtggcgggcg gggacgtctg ctcgtcagag tcattcaatg    420

aagatatagc cgtgttcgcc aaacagattc gcgcagaaaa acctctattt tcttctaatc    480

cagaactgga taacttgatg attcaagcca tacaagtatt aaggtttcat ctattggaat    540

tagagaaggt acacgaatta tgtgacaatt tctgccaccg gtatattagc tgtttgaaag    600

ggaaaatgcc tatcgatttg gtgatagacg atagagaagg aggatcaaaa tcagacagtg    660

aagatataac aagatcagca aatctaactg accagccctc ttggaacaga gatcatgatg    720

acacggcatc tactcgttca ggaggaaccc caggcccttc cagcggtggc cacacgtcac    780

acagtgggga caacagcann nnnnnnnnnn nnnnnnnnnn nnnnnnnnnn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnnnnnnn nnnnnnnnnn nnnnnnnnnn nnncaccctt    960

acccttctga agaacagaaa aagcagttgg cacaagacac gggactcacc atccttcaag   1020

tgaacaattg gtttattaat gcccggagaa gaatagtgca gcccatgata gaccagtcca   1080

accgagcagt aagtcaagga acaccttata atcctgatgg acagcccatg ggaggtttcg   1140

taatggacgg tcagcaacat atgggaatta gagcaccagg acctatgagt ggaatgggca   1200

tgaatatggg catggagggg cagtggcact acatgtaacc ttcatctagt taaccaatcg   1260

caaagcaagg gggaaggctg caaagtatgc caggggagta tgtagcccgg ggtggtccaa   1320

tgggtgtgag tatgggacag ccaagttata cccaacccca gatgcccccc catcctgctc   1380

agctgcgtca tgggcccccc atgcatacgt acattcctgg acaccctcac cacccaacag   1440

tgatgatgca tggaggaccg ccccaccctg gaatgccaat gtcagcatca agccccacag   1500

ttcttaatac aggagaccca acaatgagtg gacaagtcat ggacattcat gctcagtagc   1560
```

-continued ttaagggaat atgcattgtc tgcaatggtg actgatttca aatcatgttt tttctgcaat 1620
gactgtggag ttccattctt ggcatctact ctggaccaag gagcatccct aattcttcat 1680
agggaccttt aaaaagcagg aaataccaac tgaagtcaat ttgggggaca tgctaaataa 1740
ctatataaga cattaagaga acaaagagtg aaatattgta aatgctatta tactgttatc 1800
catattacgt tgtttcttat agatttttta aaaaaaatgt gaaatttttc cacactatgt 1860
gtgttgtttc catagctctt cacttcctcc agaagcctcc ttacattaaa aagccttaca 1920
gttatcctgc aagggacagg aaggtctgat ttgcaggatt tttagagcat taaaataact 1980
atcaggcaga agaatctttc ttctcgccta ggatttcagc catgcgcgcg ctctctctct 2040
ttctctctct tttcctctct ctccctcttt ctagcctggg gcttgaattt gcatgtctaa 2100
ttcatttact caccatattt gaattggcct gaacagatgt aaatcgggaa ggatgggaaa 2160
aactgcagtc atcaacaatg attaatcagc tgttgcaggc agtgtcttaa ggagactggt 2220
aggaggaggc atggaaacca aaaggccgtg tgtttagaag cctaattgtc acatcaagca 2280
tcattgtccc catgcaacaa ccaccacctt atacatcact tcctgtttta agcagctcta 2340
aaacatagac tgaagattta tttttaatat gttgacttta tttctgagca aagcatcggt 2400
catgtgtgta ttttttcata gtcccacctt ggagcattta tgtagacatt gtaaataaat 2460
tttgtgcaaa aaggactgga aaaatgaact gtattattgc aattttttttt t 2511

<210> SEQ ID NO 41
<211> LENGTH: 441
<212> TYPE: DNA
<213> ORGANISM: Homo sapiens

<400> SEQUENCE: 41
ctcaataagc caaccatgtc tttcaaggat tacatccaag agaggagtga cccagtggag 60
caaggcaaac cagttatacc tgcagctgtg ctggccggct tcacaggaag tggacctatt 120
cagctgtggc agtttctcct ggagctgcta tcagacaaat cctgccagtc attcatcagc 180
tggactggag acggatggga gtttaagctc gccgaccccg atgaggtggc ccgccggtgg 240
ggaaagagga aaaataagcc caagatgaac tacgagaagc tgagccgggg cttacgctac 300
tattacgaca agaacatcat ccacaagacg tcggggaagc gctacgtgta ccgcttcgtg 360
tgcgacctcc agaacttgct ggggttcacg cccgaggaac tgcacgccat cctgggcgtc 420
cagcccgaca cggaggactg a 441

<210> SEQ ID NO 42
<211> LENGTH: 1531
<212> TYPE: DNA
<213> ORGANISM: Homo sapiens

<400> SEQUENCE: 42
ggacgacaag gcgttcacca aggagctgga ccagtgggtc gagcagctga acgagtgtaa 60
gcagctgaac gagaaccaag tgcggacgct gtgcgagaag gcaaaggaaa ttttaacaaa 120
agaatcaaat gtgcaagagg ttcgttgccc tgttactgtc tgtggagatg tgcatggtca 180
atttcatgat cttatggaac tctttagaat tggtggaaaa tcaccggata caaactactt 240
attcatgggt gactatgtag acagaggata ttattcagtg gagactgtga ctcttcttgt 300
agcattaaag gtgcgttatc cagaacgcat tacaatattg agaggaaatc acgaaagccg 360
acaaattacc caagtatatg gcttttatga tgaatgtctg cgaaagtatg ggaatgccaa 420

-continued

```
cgtttggaaa tattttacag atctctttga ttatcttcca cttacagctt tagtagatgg    480

acagatattc tgcctccatg gtggcctctc tccatccata gacacactgg atcatataag    540

agccctggat cgtttacagg aagttccaca tgagggccca atgtgtgatc tgttatggtc    600

agatccagat gatcgtggtg gatggggtat ttcaccacgt ggtgctggct acacatttgg    660

acaagacatt tctgaaacct ttaaccatgc caatggtctc acactggttt ctcgtgccca    720

ccagcttgta atggagggat acaattggtg tcatgatcgg aatgtggtta ccattttcag    780

tgcacccaat tactgttatc gttgtgggaa ccaggctgct atcatggaat tagatgacac    840

tttaaaatat tccttccttc aatttgaccc agcgcctcgt cgtggtgagc ctcatgttac    900

acggcgcacc ccagactact tcctataaat ttctcctggg aaacctgcct ttgtatgtgg    960

aagtatacct ggctttttaa aatatatgta tttaaaaaca aaaagcaaca gtaatctatg   1020

tgtttctgta acaaattggg atctgtcttg gcattaaacc acatcatgga ccaaatgtgc   1080

catactaatg atgagcattt agcacaattt gagactgaaa tttagtacac tatgttctag   1140

gtcagtctaa cagtttgcct gctgtattta tagtaaccat tttcctttgg actgttcaag   1200

caaaaaaggt aactaactgc ttcatctcct tttgcgctta tttggaaatt ttagttatag   1260

tgtttaactg gcatggatta atagagttgg agttttattt ttaagaaaaa ttcacaagct   1320

aacttccact aatccattat cctttatttt attgaaatgt ataattaact taactgaaga   1380

aaaggttctt cttgggagta tgttgtcata acatttaaag agatttccct tcatttaaac   1440

taaattactg ttttatgttg atctgcatat ttctgtatat ttgtcatgac agtgcttgca   1500

tcctatttgg tgtactcagc aaataaactt t                                  1531
```

```
<210> SEQ ID NO 43
<211> LENGTH: 1260
<212> TYPE: DNA
<213> ORGANISM: Homo sapiens

<400> SEQUENCE: 43
```

```
cctgtgagca ccacgtcaac ggctcccggc ccccatgcac gggggaggga gatacccccca     60

agtgtagcaa gatctgtgag cctggctaca gcccgaccta caaacaggac aagcactacg    120

gatacaattc ctacagcgtc tccaatagcg agaaggacat catggccgag atctacaaaa    180

acggccccgt ggagggagct ttctctgtgt attcggactt cctgctctac aagtcaggag    240

tgtaccaaca cgtcaccgga gagatgatgg gtggccatgc catccgcatc ctgggctggg    300

gagtggagaa tggcacaccc tactggctgg ttgccaactc ctggaacact gactggggtg    360

acaatggctt ctttaaaata ctcagaggac aggatcactg tggaatcgaa tcagaagtgg    420

tggctggaat tccacgcacc gatcagtact gggaaaagat ctaatctgcc gtgggcctgt    480

cgtgccagtc ctgggggcga gatgggggta gaaatgcatt ttattcttta agttcacgta    540

agatacaagt ttcagacagg gtctgaagga ctggattggc caaacatcag acctgtcttc    600

caaggagacc aagtcctggc tacatcccag cctgtggtta cagtgcagac aggccatgtg    660

agccaccgct gccagcacag agcgtccttc cccctgtaga ctagtgccgt agggagtacc    720

tgttgcccca gctgactgtg gccccctccg tgatccatcc atctccaggg agcaagacag    780

agacccagga atggaaagcg gagttcctaa caggatgaaa gttcccccat cagttccccc    840

agtacctcca agcaagtagc tttccacatt tgtcacagaa atcagaggag agatggtgtt    900

gggagccctt tggagaacgc cagtctccca ggccccctgc atctatcgag tttgcaatgt    960

cacaacctct ctgatcttgt gctcagcatg attctttaat agaagtttta ttttttcgtg   1020
```

-continued

```
cactctgcta atcatgtggg tgagccagtg gaacagcggg agacctgtgc tagttttaca   1080

gattgcctcc ttatgacgcg gctcaaaagg aaaccaagtg gtcaggagtt gtttctgacc   1140

cactgatctc tactaccaca aggagaatag tttaggagaa accagctttt actgtttttg   1200

aaaaattaca gcttcaccct gtcaagttaa caaggaatgc ctgtgccaat aaaaggtttc   1260
```

<210> SEQ ID NO 44
<211> LENGTH: 5418
<212> TYPE: DNA
<213> ORGANISM: Homo sapiens
<220> FEATURE:
<221> NAME/KEY: misc_feature
<222> LOCATION: (1210)..(1219)
<223> OTHER INFORMATION: n is a, c, g, or t

<400> SEQUENCE: 44

```
gtgtcccata gtgtttccaa acttggaaag ggcgggggag ggcgggagga tgcggagggc     60

ggaggtatgc agacaacgag tcagagtttc cccttgaaag cctcaaaagt gtccacgtcc    120

tcaaaaagaa tggaaccaat ttaagaagcc agccccgtgg ccacgtccct tcccccattc    180

gctccctcct ctgcgccccc gcaggctcct cccagctgtg gctgcccggg cccccagccc    240

cagccctccc attggtggag gcccttttgg aggcacccta gggccaggga aacttttgcc    300

gtataaatag ggcagatccg ggctttatta ttttagcacc acggcagcag gaggtttcgg    360

ctaagttgga ggtactggcc acgactgcat gcccgcgccc gccaggtgat acctccgccg    420

gtgacccagg ggctctgcga cacaaggagt ctgcatgtct aagtgctaga catgctcagc    480

tttgtggata cgcggacttt gttgctgctt gcagtaacct tatgcctagc aacatgccaa    540

tctttacaag aggaaactgt aagaaagggc ccagccggag atagaggacc acgtggagaa    600

aggggtccac caggcccccc aggcagagat ggtgaagatg gtcccacagg ccctcctggt    660

ccacctggtc ctcctggccc ccctggtctc ggtgggaact ttgctgctca gtatgatgga    720

aaaggagttg gacttggccc tggaccaatg ggcttaatgg gacctagagg cccacctggt    780

gcagctggag ccccaggccc tcaaggtttc caaggacctg ctggtgagcc tggtgaacct    840

ggtcaaactg gtcctgcagg tgctcgtggt ccagctggcc ctcctggcaa ggctggtgaa    900

gatggtcacc ctggaaaacc cggacgacct ggtgagagag gagttgttgg accacagggt    960

gctcgtggtt tccctggaac tcctggactt cctggcttca aaggcattag gggacacaat   1020

ggtctggatg gattgaaggg acagcccggt gctcctggtg tgaagggtga acctggtgcc   1080

cctggtgaaa atggaactcc aggtcaaaca ggagcccgtg ggcttcctgg tgagagagga   1140

cgtgttggtg cccctggccc agctggtgcc cgtggcagtg atggaagtgt gggtcccgtg   1200

ggtcctgctn nnnnnnnnng gtctgctggc cctccaggct tcccaggtgc ccctggcccc   1260

aagggtgaaa ttggagctat tggtaacgct ggtcctgctg gtcccgccgg tccccgtggt   1320

gaagtgggtc ttccaggcct ctccggcccc gttggacctc ctggtaatcc tggagcaaac   1380

ggccttactg gtgccaaggg tgctgctggc cttcccggcg ttgctggggc tcccggcctc   1440

cctggacccc gcggtattcc tggccctgtt ggtgctgccg gtgctactgg tgccagagga   1500

cttgttggtg agcctggtcc agctggctcc aaaggagaga gcggtaacaa gggtgagccc   1560

ggctctgctg ggccccaagg tcctcctggt cccagtggtg aagaaggaaa gagaggccct   1620

aatggggaag ctggatctgc cggccctcca ggacctcctg ggctgagagg tagtcctggt   1680

tctcgtggtc ttcctggagc tgatggcaga gctggcgtca tgggccctcc tggtagtcgt   1740
```

-continued

```
ggtgcaagtg gccctgctgg agtccgagga cctaatggag atgctggtcg ccctggggag   1800
cctggtctca tgggacccag aggtcttcct ggttcccctg gaaatatcgg ccccgctgga   1860
aaagaaggtc ctgtcggcct ccctggcatc gacggcaggc ctggcccaat tggccccgtt   1920
ggagcaagag gagagcctgg caacattgga ttccctggac ccaaaggccc cactggtgac   1980
cctggcaaaa acggtgataa aggtcatgct ggtcttgctg gtgctcgggg tgctccaggt   2040
cctgatggaa acaatggtgc tcagggacct cctggaccac agggtgttca aggtggaaaa   2100
ggtgaacagg gtcccgctgg tcctccaggc ttccagggtc tgcctggccc ctcaggtccc   2160
gctggtgaag ttggcaaacc aggagaaagg ggtctccatg gtgagtttgg tctccctggt   2220
cctgctggtc caagagggga acgcggtccc ccaggtgaga gtggtgctgc cggtcctact   2280
ggtcctattg gaagccgagg tccttctgga cccccagggc ctgatggaaa caagggtgaa   2340
cctggtgtgg ttggtgctgt gggcactgct ggtccatctg gtcctagtgg actcccagga   2400
gagaggggtg ctgctggcat acctggaggc aagggagaaa agggtgaacc tggtctcaga   2460
ggtgaaattg gtaaccctgg cagagatggt gctcgtggtg ctcatggtgc tgtaggtgcc   2520
cctggtcctg ctggagccac aggtgaccgg ggcgaagctg gggctgctgg tcctgctggt   2580
cctgctggtc ctcggggaag ccctggtgaa cgtggcgagg tcggtcctgc tggccccaac   2640
ggatttgctg gtccggctgg tgctgctggt caaccgggtg ctaaaggaga aagaggaggc   2700
aaagggccta agggtgaaaa cggtgttgtt ggtcccacag gccccgttgg agctgctggc   2760
ccagctggtc caaatggtcc ccccggtcct gctggaagtc gtggtgatgg aggccccccct   2820
ggtatgactg gtttccctgg tgctgctgga cggactggtc ccccaggacc ctctggtatt   2880
tctggccctc ctggtccccc tggtcctgct gggaaagaag ggcttcgtgg tcctcgtggt   2940
gaccaaggtc cagttggccg aactggagaa gtaggtgcag ttggtccccc tggcttcgct   3000
ggtgagaagg gtccctctgg agaggctggt actgctggac ctcctggcac tccaggtcct   3060
cagggtcttc ttggtgctcc tggtattctg ggtctccctg gctcgagagg tgaacgtggt   3120
ctacctggtg ttgctggtgc tgtgggtgaa cctggtcctc ttggcattgc cggccctcct   3180
ggggcccgtg gtcctcctgg tgctgtgggt agtcctggag tcaacggtgc tcctggtgaa   3240
gctggtcgtg atggcaaccc tgggaacgat ggtcccccag gtcgcgatgg tcaacccgga   3300
cacaagggag agcgcggtta ccctggcaat attggtcccg ttggtgctgc aggtgcacct   3360
ggtcctcatg gccccgtggg tcctgctggc aaacatggaa accgtggtga aactggtcct   3420
tctggtcctg ttggtcctgc tggtgctgtt ggcccaagag gtcctagtgg cccacaaggc   3480
attcgtggcg ataagggaga gcccggtgaa aaggggccca gaggtcttcc tggcttcaag   3540
ggacacaatg gattgcaagg tctgcctggt atcgctggtc accatggtga tcaaggtgct   3600
cctggctccg tgggtcctgc tggtcctagg ggccctgctg gtccttctgg ccctgctgga   3660
aaagatggtc gcactggaca tcctggtacg gttggacctg ctggcattcg aggccctcag   3720
ggtcaccaag gccctgctgg cccccctggt ccccctggcc ctcctggacc tccaggtgta   3780
agcggtggtg gttatgactt tggttacgat ggagacttct acagggctga ccagcctcgc   3840
tcagcacctt ctctcagacc caaggactat gaagttgatg ctactctgaa gtctctcaac   3900
aaccagattg agacccttct tactcctgaa ggctctagaa agaacccagc tcgcacatgc   3960
cgtgacttga gactcagcca cccagagtgg agcagtggtt actactggat tgaccccaac   4020
caaggatgca ctatggaagc catcaaagta tactgtgatt tccctaccgg cgaaacctgt   4080
atccgggccc aacctgaaaa catcccagcc aagaactggt ataggagctc caaggacaag   4140
```

```
aaacacgtct ggctaggaga aactatcaat gctggcagcc agtttgaata taatgttgaa   4200
ggagtgactt ccaaggaaat ggctacccaa cttgccttca tgcgcctgct ggccaactat   4260
gcctctcaga acatcaccta ccactgcaag aacagcattg catacatgga tgaggagact   4320
ggcaacctga aaaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
attgcacctt tggacatcgg tggtgctgac catgaattct ttgtggacat tggcccagtc   4560
tgtttcaaat aaatgaactc aatctaaatt aaaaaagaaa gaaatttgaa aaaactttct   4620
ctttgccatt tcttcttctt cttttttaac tgaaagctga atccttccat ttcttctgca   4680
catctacttg cttaaattgt gggcaaaaga gaaaaagaag gattgatcag agcattgtgc   4740
aatacagttt cattaactcc ttcccccgct cccccaaaaa tttgaatttt tttttcaaca   4800
ctcttacacc tgttatggaa aatgtcaacc tttgtaagaa aaccaaaata aaaattgaaa   4860
aataaaaacc ataaacattt gcaccacttg tggcttttga atatcttcca cagagggaag   4920
tttaaaaccc aaacttccaa aggtttaaac tacctcaaaa cactttccca tgagtgtgat   4980
ccacattgtt aggtgctgac ctagacagag atgaactgag gtccttgttt tgttttgttc   5040
ataatacaaa ggtgctaatt aatagtattt cagatacttg aagaatgttg atggtgctag   5100
aagaatttga gaagaaatac tcctgtattg agttgtatcg tgtggtgtat tttttaaaaa   5160
atttgattta gcattcatat tttccatctt attcccaatt aaaagtatgc agattatttg   5220
cccaaagttg tcctcttctt cagattcagc atttgttctt tgccagtctc attttcatct   5280
tcttccatgg ttccacagaa gctttgtttc ttgggcaagc agaaaaatta aattgtacct   5340
attttgtata tgtgagatgt ttaaataaat tgtgaaaaaa atgaaataaa gcatgtttgg   5400
ttttccaaaa gaacatat                                                 5418
```

<210> SEQ ID NO 45
<211> LENGTH: 2566
<212> TYPE: DNA
<213> ORGANISM: Homo sapiens

<400> SEQUENCE: 45

```
cagaccacag gaatacctaa tgcctttttt ctcttcctgt ctttgtccct cacactacag     60
caggcccctc ccttccctct tcaacctcat cctccctccc cacaggccca gagaaccagt    120
tgggctttgt tctcctgcag gctatggttc atcatgcaaa tagctcctgt gtcagaaatg    180
ctttttggct tcaaataaca gaaaagctaa caccagcttt atcaataata atatcggtgg    240
tttacttaag gtgtccagag atggtggaga acaggattgg tttcctcctc aatgtcaagg    300
actcaaagac tctttctgtg gtagggccac atcctaaacc ctgtatcctg tgattattta    360
cctgacaggg caaaagagat tttgcagatg caattaaggt taaggacctt gacgtgggaa    420
gattgtgatt atttacctga cagggcaaaa gagattttgc agatgcaatt aaggttaagg    480
accttgacgt gggaagatta ttctggatta tctaggtggg cgcaatttga tcacatgggt    540
ccccagaagt ggagaacctt tcccacctgt agaaagccag agagctggca cctgagaagg    600
acagaactgt cactgcagga tttgaagatg aaggggccca tgagccaagg aatgccagtg    660
acctatagag gctaaaaaac agcaaggaaa tggactctcc ccagagcctc cagaggaatg    720
cagccctgtt gatcacatga tcaccagatg gctgccccag agccaaatgt cgcttcctga    780
```

-continued

```
gcaccatact caaaggcagg ggaagtggat ggagggcagg agctccattc ttgtttgcca    840

ctctcctttt gtcaattggg aaaaaattcc agaaactctg ggagccctcc ccttacattt    900

cctgggtcat ggggccagcc ctagctgctg gagggactga gaactgctgt tgagcagttt    960

acctgacggc atctgccatg gcttggcagg aactctggct ttgggagaga gcagcagcaa   1020

ggtattcaag caccacctcc acccagcccc tcccacattt cactcaggac tgagtaaagg   1080

agacactcag atgctactca gatgctggct tcagctaagt attttgcaaa gcctctcgtg   1140

ttcttacaag tttgtggcta tcatgacaaa atggagcagc ctactatatc tacatataca   1200

actatggggg acctagtttt atctcattta ccacaatgtt ttcaatcatt ttttggatga   1260

cataattttt agcctcttct ctaaatgctt cctcaagctt tccttgcctt ccagccactg   1320

caaatgactt gcagtttccc ctacatggca cctgaccctt gtgcctccct ccctctgccc   1380

atggcccaga aagccctttc ctgtgccctc tggcttcctg ataaactcct atcatcttca   1440

agagccagtt cccatgccag ctctccccaa gtgctccact gaggcttccg taacacctct   1500

gttcccacat cgggttgact gtctttgttt tgtcattgct tgctctggct gtgtctccct   1560

cattagactg ggatgccttc aaggtaggga ccctatctgg gtcagcttgg caccccaaag   1620

cgtaccacag cacctgattc tgaggaggct ctcagtagat atctgttgag taaccagaat   1680

gtagggtggt cctgatggtt tctgacattg aatagaaaac agctccctat ttgatcttaa   1740

aataatcact ataacctgga catactgtac tagatgctgt ttttgtctga cttctactct   1800

gtcaatctct ttgcacctcc atttgttcat ctgtgaaatg aagaaaatgc tcatggagtt   1860

cagtgaagat taaatgaatg aatataggta gactgcctaa tctggcactt gccacgcagc   1920

tgacttcaat atagtagctc taatattatg gtccttgagg atcttactgt cttatggccc   1980

agaactgcat ttgattaaag aaggctcccc taaaaaaaga gtcatacata ttccatttgt   2040

cctttcagaa ggccgtgaag catttacact ctttaagaca aattcccatc caaaaatagt   2100

taagatttct aaaatatttt gatgctgaaa gaggtgtgct tcagttgggt ggcaaatttg   2160

cttctatgga agatttttaa tacaggttgt ttctatttta ctttttctgg ctgaaaggat   2220

tttacattta ttcaaagtca aaagggaaaa gaaatccaag aactacagaa gagcagttga   2280

agtgatttat gcttgatttc taaatgcaac ttatgtttat acataattta aaactcaaag   2340

aaagcatgct tatacaatca tgtgcaactt taaactttaa gaactctgga tgaatacatg   2400

gtggcaacag tccatgacac ctgaaaacat catttgtgga gtggcgtaga gttcagtgtt   2460

cgcagtcgca tattacaacc atgtttcaca cagccctgct cggtttgatt ttctccacgt   2520

ggttgataat tgtcttcagt tgctgctaag tgattttgca aatttc                  2566
```

<210> SEQ ID NO 46
<211> LENGTH: 1847
<212> TYPE: DNA
<213> ORGANISM: Homo sapiens

<400> SEQUENCE: 46

```
gtccccgcgc cagagacgca gccgcgctcc caccacccac acccaccgcg ccctcgttcg     60

cctcttctcc gggagccagt ccgcgccacc gccgccgccc aggccatcgc caccctccgc    120

agccatgtcc accaggtccg tgtcctcgtc ctcctaccgc aggatgttcg gcggcccggg    180

caccgcgagc cggccgagct ccagccggag ctacgtgact acgtccaccc gcacctacag    240

cctgggcagc gcgctgcgcc ccagcaccag ccgcagcctc tacgcctcgt ccccgggcgg    300

cgtgtatgcc acgcgctcct ctgccgtgcg cctgcggagc agcgtgcccg gggtgcggct    360
```

-continued cctgcaggac tcggtggact tctcgctggc cgacgccatc aacaccgagt tcaagaacac 420
ccgcaccaac gagaaggtgg agctgcagga gctgaatgac cgcttcgcca actacatcga 480
caaggtgcgc ttcctggagc agcagaataa gatcctgctg gccgagctcg agcagctcaa 540
gggccaaggc aagtcgcgcc tgggggacct ctacgaggag gagatgcggg agctgcgccg 600
gcaggtggac cagctaacca acgacaaagc ccgcgtcgag gtggagcgcg acaacctggc 660
cgaggacatc atgcgcctcc gggagaaatt gcaggaggag atgcttcaga gagaggaagc 720
cgaaaacacc ctgcaatctt tcagacagga tgttgacaat gcgtctctgg cacgtcttga 780
ccttgaacgc aaagtggaat ctttgcaaga agagattgcc tttttgaaga aactccacga 840
agaggaaatc caggagctgc aggctcagat tcaggaacag catgtccaaa tcgatgtgga 900
tgtttccaag cctgacctca cggctgccct gcgtgacgta cgtcagcaat atgaaagtgt 960
ggctgccaag aacctgcagg aggcagaaga atggtacaaa tccaagtttg ctgacctctc 1020
tgaggctgcc aaccggaaca atgacgccct gcgccaggca aagcaggagt ccactgagta 1080
ccggagacag gtgcagtccc tcacctgtga agtggatgcc cttaaaggaa ccaatgagtc 1140
cctggaacgc cagatgcgtg aaatggaaga gaactttgcc gttgaagctg ctaactacca 1200
agacactatt ggccgcctgc aggatgagat tcagaatatg aaggaggaaa tggctcgtca 1260
ccttcgtgaa taccaagacc tgctcaatgt taagatggcc cttgacattg agattgccac 1320
ctacaggaag ctgctggaag gcgaggagag caggatttct ctgcctcttc caaacttttc 1380
ctccctgaac ctgagggaaa ctaatctgga ttcactccct ctggttgata cccactcaaa 1440
aaggacactt ctgattaaga cggttgaaac tagagatgga caggttatca acgaaacttc 1500
tcagcatcac gatgaccttg aataaaaatt gcacacactc agtgcagcaa tatattacca 1560
gcaagaataa aaaagaaatc catatcttaa agaaacagct ttcaagtgcc tttctgcagt 1620
ttttcaggag cgcaagatag atttggaata ggaataagct ctagttctta acaaccgaca 1680
ctcctacaag atttagaaaa aagtttacaa cataatctag tttacagaaa aatcttgtgc 1740
tagaatactt tttaaaaggt attttgaata ccattaaaac tgcttttttt tttccagcaa 1800
gtatccaacc aacttggttc tgcttcaata aatctttgga aaaactc 1847

<210> SEQ ID NO 47
<211> LENGTH: 3864
<212> TYPE: DNA
<213> ORGANISM: Homo sapiens

<400> SEQUENCE: 47
ggccagccga atccaagccg tgtgtactgc gtgctcagca ctgcccgaca gtcctagcta 60
aacttcgcca actccgctgc ctttgccgcc accatgccca aaacgatcag tgtgcgtgtg 120
accaccatgg atgcagagct ggagtttgcc atccagccca acaccaccgg gaagcagcta 180
tttgaccagg tggtgaaaac tattggcttg agggaagttt ggttctttgg tctgcagtac 240
caggacacta aaggtttctc cacctggctg aaactcaata agaaggtgac tgcccaggat 300
gtgcggaagg aaagccccct gctctttaag ttccgtgcca agttctaccc tgaggatgtg 360
tccgaggaat tgattcagga catcactcag cgcctgttct ttctgcaagt gaaagagggc 420
attctcaatg atgatattta ctgcccgcct gagaccgctg tgctgctggc ctcgtatgct 480
gtccagtcta agtatggcga cttcaataag gaagtgcata agtctggcta cctggccgga 540
gacaagttgc tcccgcagag agtcctggaa cagcacaaac tcaacaagga ccagtgggag 600

-continued

```
gagcggatcc aggtgtggca tgaggaacac cgtggcatgc tcagggagga tgctgtcctg    660
gaatatctga agattgctca agatctggag atgtatggtg tgaactactt cagcatcaag    720
aacaagaaag gctcagagct gtggctgggg gtggatgccc tgggtctcaa catctatgag    780
cagaatgaca gactaactcc caagataggc ttcccctgga gtgaaatcag gaacatctct    840
ttcaatgata agaaatttgt catcaagccc attgacaaaa aagccccgga cttcgtcttc    900
tatgctcccc ggctgcggat taacaagcgg atcttggcct tgtgcatggg gaaccatgaa    960
ctatacatgc gccgtcgcaa gcctgatacc attgaggtgc agcagatgaa ggcacaggcc   1020
cgggaggaga agcaccagaa gcagatggag cgtgctatgc tggaaaatga gaagaagaag   1080
cgtgaaatgg cagagaagga gaaagagaag attgaacggg agaaggagga gctgatggag   1140
aggctgaagc agatcgagga acagactaag aaggctcagc aagaactgga agaacagacc   1200
cgtagggctc tggaacttga gcaggaacgg aagcgtgccc agagcgaggc tgaaaagctg   1260
gccaaggagc gtcaagaagc tgaagaggcc aaggaggcct tgctgcaggc ctcccgggac   1320
cagaaaaaga ctcaggaaca gctggccttg gaaatggcag agctgacagc tcgaatctcc   1380
cagctggaga tggcccgaca gaagaaggag agtgaggctg tggagtggca gcagaaggcc   1440
cagatggtac aggaagactt ggagaagacc cgtgctgagc tgaagactgc catgagtaca   1500
cctcatgtgg cagagcctgc tgagaatgag caggatgagc aggatgagaa tggggcagag   1560
gctagtgctg acctacgggc tgatgctatg gccaaggacc gcagtgagga ggaacgtacc   1620
actgaggcag agaagaatga gcgtgtgcag aagcacctga aggccctcac ttcggagctg   1680
gccaatgcca gagatgagtc caagaagact gccaatgaca tgatccatgc tgagaacatg   1740
cgactgggcc gagacaaata caagaccctg cgccagatcc ggcagggcaa caccaagcag   1800
cgcattgacg aatttgagtc tatgtaatgg gcacccagcc tctagggacc cctcctccct   1860
ttttccttgt ccccacactc ctacacctaa ctcacctaac tcatactgtg ctggagccac   1920
taactagagc agccctggag tcatgccaag catttaatgt agccatggga ccaaacctag   1980
ccccttagcc cccacccact tccctgggca aatgaatggc tcactatggt gccaatggaa   2040
cctcctttct cttctctgtt ccattgaatc tgtatggcta gaatatccta cttctccagc   2100
ctagaggtac tttccacttg attttgcaaa tgcccttaca cttactgttg tcctatggga   2160
gtcaagtgtg gagtaggttg gaagctagct cccctcctct cccctaccac tgtcttcttc   2220
agggtcctga gatttacacg gttggagtgt tatgcggtct agggaatgag acaggaccta   2280
ggatatcttc tccaggatgt caactgacct aaaatttgcc ctcccatccc gtttagagtt   2340
atttaggctt tgtaacgatt gggggataaa aagatgttca gtcatttttg tttctacctc   2400
ccagatcgga tctgttgcaa actcagcctc aataagcctt gtcgttgact ttagggactc   2460
aatttctccc cagggtggat gggggaaatg gtgccttcaa gaccttcacc aaacatacta   2520
gaagggcatt ggccattcta ttgtggcaag gctgagtaga agatcctacc ccaattcctt   2580
gtaggagtat aggccggtct aaagtgagct ctatgggcag atctacccct tacttattat   2640
tccagatctg cagtcacttc gtgggatctg cccctccctg cttcaatacc caaatcctct   2700
ccagctataa cagtagggat gagtacccaa aagctcagcc agccccatca ggactcttgt   2760
gaaaagagag gatatgttca cacctagcgt cagtattttc cctgctaggg gttttaggtc   2820
tcttcccctc tcagagctac ttgggccata gctcctgctc cacagccatc ccagccttgg   2880
catctagagc ttgatgccag taggctcaac tagggagtga gtgcaaaaag ctgagtatgg   2940
tgagagaagc ctgtgccctg atccaagttt actcaaccct ctcaggtgac caaaatcccc   3000
```

-continued ttctcatcac tcccctccaa agaggtgact gggccctgcc tctgtttgac aaacctctaa 3060
cccaggtctt gacaccagct gttctgtccc ttggagctgt aaaccagaga gctgctgggg 3120
attctggcct agtcccttcc acaccccccac cccttgctct caacccagga gcatccacct 3180
ccttctctgt ctcatgtgtg ctcttcttct ttctacagta ttatgtactc tactgatatc 3240
taaatattga tttctgcctt ccttgctaat gcaccattag aagatattag tcttggggca 3300
ggatgatttt ggcctcatta ctttaccacc cccacacctg gaaagcatat actatattac 3360
aaaatgacat tttgccaaaa ttattaatat aagaagcttt cagtattagt gatgtcatct 3420
gtcactatag gtcatacaat ccattcttaa agtacttgtt atttgttttt attattactg 3480
tttgtcttct ccccagggtt cagtcctcaa ggggccatcc tgtcccacca tgcagtgccc 3540
ctagcttaga gcctccctca attccccctg gccaccaccc cccactctgt gcctgacctt 3600
gaggagtctt gtgtgcattg ctgtgaatta gctcacttgg tgatatgtcc tatattggct 3660
aaattgaaac ctggaattgt ggggcaatct attaatagct gccttaaagt cagtaactta 3720
cccttaggga ggctggggga aaaggttaga ttttgtattc aggggttttt tgtgtacttt 3780
ttgggttttt taaaaattgt ttttggaggg gtttatgctc aatccatgtt ctatttcagt 3840
gccaataaaa tttaggaaga cttc 3864

<210> SEQ ID NO 48
<211> LENGTH: 2270
<212> TYPE: DNA
<213> ORGANISM: Homo sapiens

<400> SEQUENCE: 48
ggtgtgcccg gagaggctga gcagcctgcg cctgagctgg tggaggtgga agtgggcagc 60
acagcccttc tgaagtgcgg cctctcccag tcccaaggca acctcagcca tgtcgactgg 120
ttttctgtcc acaaggagaa gcggacgctc atcttccgtg tgcgccaggg ccagggccag 180
agcgaacctg gggagtacga gcagcggctc agcctccagg acagaggggc tactctggcc 240
ctgactcaag tcacccccca agacgagcgc atcttcttgt gccagggcaa gcgccctcgg 300
tcccaggagt accgcatcca gctccgcgtc tacaaagctc cggaggagcc aaacatccag 360
gtcaaccccc tgggcatccc tgtgaacagt aaggagcctg aggaggtcgc tacctgtgta 420
gggaggaacg ggtaccccat tcctcaagtc atctggtaca agaatggccg gcctctgaag 480
gaggagaaga accgggtcca cattcagtcg tcccagactg tggagtcgag tggtttgtac 540
accttgcaga gtattctgaa ggcacagctg gttaaagaag acaaagatgc ccagttttac 600
tgtgagctca actaccggct gcccagtggg aaccacatga aggagtccag ggaagtcacc 660
gtccctgttt tctacccgac agaaaaagtg tggctggaag tggagcccgt gggaatgctg 720
aaggaagggg accgcgtgga aatcaggtgt ttggctgatg gcaaccctcc accacacttc 780
agcatcagca agcagaaccc cagcaccagg gaggcagagg aagagacaac caacgacaac 840
ggggtcctgg tgctggagcc tgcccggaag gaacacagtg ggcgctatga atgtcagggc 900
ctggacttgg acaccatgat atcgctgctg agtgaaccac aggaactact ggtgaactat 960
gtgtctgacg tccgagtgag tcccgcagca cactgagaga caggaaggca gcagcctcac 1020
cctgacctgt gaggcagaga gtagccagga cctcgagttc cagtggctga gagaagagac 1080
aggccaggtg ctggaaaggg ggcctgtgct tcagttgcat gacctgaaac gggaggcagg 1140
aggcggctat cgctgcgtgg cgtctgtgcc cagcataccc ggcctgaacc gcacacagct 1200

-continued

```
ggtcaacgtg gccatttttg gcccccccttg gatggcattc aaggagagga aggtgtgggt   1260

gaaagagaat atggtgttga atctgtcttg tgaagcgtca gggcaccccc ggcccaccat   1320

ctcctggaac gtcaacggca cggcaagtga acaagaccaa gatccacagc gagtcctgag   1380

caccctgaat gtcctcgtga ccccggagct gttggagaca ggtgttgaat gcacggcctc   1440

caacgacctg ggcaaaaaca ccagcatcct cttcctggag ctggtcaatt taaccaccct   1500

cacaccagac tccaacacaa ccactggcct cagcacttcc actgccagtc ctcataccag   1560

agccaacagc acctccacag agagaaagct gccggagccg gagagccggg gcgtggtcat   1620

cgtggctgtg attgtgtgca tcctggtcct ggcggtgctg ggcgctgtcc tctatttcct   1680

ctataagaag ggcaagctgc cgtgcaggcg ctcagggaag caggagatca cgctgccccc   1740

gtctcgtaag agcgaacttg tagttgaagt taagtcagat aagctcccag aagagatggg   1800

cctcctgcag ggcagcagcg gtgacaagag ggctccggga gaccagggag agaaatacat   1860

cgatctgagg cattagcccc gaatcacttc agctcccttc cctgcctgga ccattcccag   1920

ctccctgctc actcttctct cagccaaagc ctccaaaggg actagagaga agcctcctgc   1980

tcccctcgcc tgcacacccc ctttcagagg gccactgggt taggacctga ggacctcact   2040

tggccctgca aggcccgctt ttcagggacc agtccaccac catctccacg ttgagtgaag   2100

ctcatcccaa gcaaggagcc ccagtctccc gagcgggtag gagagtttct tgtagaacgt   2160

gtttttttctt tacacacatt atggctgtaa atacctggct cctgccagca gctgagctgg   2220

gtagcctctc tgagctggga ttacaggtgt gagccactgc gcccagccaa              2270
```

<210> SEQ ID NO 49
<211> LENGTH: 2127
<212> TYPE: DNA
<213> ORGANISM: Homo sapiens

<400> SEQUENCE: 49

```
caaacttggt ggcaacttgc ctcccggtgc gggcgtctct cccccaccgt ctcaacatgc     60

ttaggggtcc ggggcccggg ctgctgctgc tggccgtcct gtgcctgggg acagcggtgc    120

cctccacggg agcctcgaag agcaagaggc aggctcagca aatggttcag ccccagtccc    180

cggtggctgt cagtcaaagc aagcccggtt gttatgacaa tggaaaacac tatcagataa    240

atcaacagtg ggagcggacc tacctaggca atgcgttggt ttgtacttgt tatggaggaa    300

gccgaggttt taactgcgag agtaaacctg aagctgaaga gacttgcttt gacaagtaca    360

ctgggaacac ttaccgagtg ggtgacactt atgagcgtcc taaagactcc atgatctggg    420

actgtacctg catcggggct gggcgaggga gaataagctg taccatcgca aaccgctgcc    480

atgaaggggg tcagtcctac aagattggtg acacctggag gagaccacat gagactggtg    540

gttacatgtt agagtgtgtg tgtcttggta atggaaaagg agaatggacc tgcaagccca    600

tagctgagaa gtgttttgat catgctgctg ggacttccta tgtggtcgga gaaacgtggg    660

agaagcccta ccaaggctgg atgatggtag attgtacttg cctgggagaa ggcagcggac    720

gcatcacttg cacttctaga aatagatgca acgatcagga cacaaggaca tcctatagaa    780

ttggagacac ctggagcaag aaggataatc gaggaaacct gctccagtgc atctgcacag    840

gcaacggccg aggagagtgg aagtgtgaga ggcacacctc tgtgcagacc acatcgagcg    900

gatctggccc cttcaccgat gttcgtgcag ctgtttacca accgcagcct cacccccagc    960

ctcctcccta tggccactgt gtcacagaca gtggtgtggt ctactctgtg gggatgcagt   1020

ggctgaagac acaaggaaat aagcaaatgc tttgcacgtg cctgggcaac ggagtcagct   1080
```

-continued

```
gccaagagac agctgtaacc cagacttacg gtggcaactc aaatggagag ccatgtgtct   1140

taccattcac ctacaatggc aggacgtgca gcacaacttc gaattatgag caggaccaga   1200

aatactcttt ctgcacagac cacactgttt tggttcagac tcgaggagga aattccaatg   1260

gtgccttgtg ccacttcccc ttcctataca acaaccacaa ttacactgat tgcacttctg   1320

agggcagaag agacaacatg aagtggtgtg ggaccacaca gaactatgat gccgaccaga   1380

agtttgggtt ctgccccatg gctgcccacg aggaaatctg cacaaccaat gaaggggtca   1440

tgtaccgcat tggagatcag tgggataagc agcatgacat gggtcacatg atgaggtgca   1500

cgtgtgttgg gaatggtcgt ggggaatgga catgcattgc ctactcgcag cttcgagatc   1560

agtgcattgt tgatgacatc acttacaatg tgaacgacac attccacaag cgtcatgaag   1620

aggggcacat gctgaactgt acatgcttcg gtcagggtcg ggcaggtgg aagtgtgatc   1680

ccgtcgacca atgccaggat tcagagactg ggacgtttta tcaaattgga gattcatggg   1740

agaagtatgt gcatggtgtc agataccagt gctactgcta tggccgtggc attggggagt   1800

ggcattgcca acctttacag acctatccaa gctcaagtgg tcctgtcgaa gtatttatca   1860

ctgagactcc gagtcagccc aactcccacc ccatccagtg gaatgcacca cagccatctc   1920

acatttccaa gtacattctc aggtggagac ctgtgagtat cccacccaga aaccttggat   1980

actgagtctc ctaatcttat caattctgat ggtttctttt tttcccagct tttgagccaa   2040

caactctgat taactattcc tatagcattt actatatttg tttagtgaac aaacaatatg   2100

tggtcaatta aattgacttg tagactg                                       2127
```

<210> SEQ ID NO 50
<211> LENGTH: 1918
<212> TYPE: DNA
<213> ORGANISM: Homo sapiens

<400> SEQUENCE: 50

```
acccccgcac ccagctccgc aggaccggcg ggcgcgcgcg ggctctggag gccacgggca     60

tgatgcttcg ggtcctggtg ggggctgtcc tccctgccat gctactggct gccccaccac    120

ccatcaacaa gctggcactg ttcccagata agagtgcctg gtgcgaagcc aagaacatca    180

cccagatcgt gggccacagc ggctgtgagg ccaagtccat ccagaacagg gcgtgcctag    240

gacagtgctt cagctacagc gtccccaaca ccttccccaca gtccacagag tccctggttc    300

actgtgactc ctgcatgcca gcccagtcca tgtgggagat tgtgacgctg gagtgcccgg    360

gccacgagga ggtgcccagg gtggacaagc tggtggagaa gatcctgcac tgtagctgcc    420

aggcctgcgg caaggagcct agtcacgagg ggctgagcgt ctatgtgcag ggcgaggacg    480

ggccgggatc ccagcccggc acccaccctc acccccatcc ccacccccat cctggcgggc    540

agacccctga gcccgaggac ccccctgggg ccccccacac agaggaagag ggggctgagg    600

actgaggccc ccccaactct tcctcccctc tcatcccccct gtggaatgtt gggtctcact    660

ctctggggaa gtcaggggag aagctgaagc ccccctttgg cactggatgg acttggcttc    720

agactcggac ttgaatgctg cccggttgcc atggagatct gaaggggcgg ggttagagcc    780

aagctgcaca atttaatata ttcaagagtg gggggaggaa gcagaggtct tcagggctct    840

ttttttgggg ggggtggtct cttcctgtct ggcttctaga gatgtgcctg tgggaggggg    900

aggaagttgg ctgagccatt gagtgctggg ggaggccatc caagatggca tgaatcgggc    960

taaggtccct gggggtgcag atggtactgc tgaggtcccg ggcttagtgt gagcatcttg   1020
```

-continued

```
ccagcctcag gcttgaggga gggctgggct agaaagacca ctggcagaaa caggaggctc   1080
cggcccacag gtttccccaa ggcctctcac cccacttccc atctccaggg aagcgtcgcc   1140
ccagtggcac tgaagtggcc ctccctcagc ggaggggttt gggagtcagg cctgggcagg   1200
accctgctga ctcgtggcgc gggagctggg agccaggctc tccgggcctt tctctggctt   1260
ccttggcttg cctggtgggg gaaggggagg aggggaagaa ggaaagggaa gagtcttcca   1320
aggccagaag gagggggaca accccccaag accatccctg aagacgagca tccccctcct   1380
ctccctgtta gaaatgttag tgccccgcac tgtgccccaa gttctaggcc ccccagaaag   1440
ctgccagagc cggccgcctt ctcccctctc ccagggatgc tctttgtaaa tatcggatgg   1500
gtgtgggagt gaggggttac ctccctcgcc ccaaggttcc agaggcccta ggcgggatgg   1560
gctcgctgaa cctcgaggaa ctccaggacg aggaggacat gggacttgcg tggacagtca   1620
gggttcactt gggctctctc tagctcccca attctgcctg cctcctccct cccagctgca   1680
ctttaaccct agaaggtggg gacctggggg gagggacagg gcaggcgggc ccatgaagaa   1740
agcccctcgt tgcccagcac tgtctgcgtc tgctcttctg tgcccagggt ggctgccagc   1800
ccactgcctc ctgcctgggg tggcctggcc ctcctggctg ttgcgacgcg ggcttctgga   1860
gcttgtcacc attggacagt ctccctgatg gaccctcagt cttctcatga ataaattc     1918
```

<210> SEQ ID NO 51
<211> LENGTH: 1222
<212> TYPE: DNA
<213> ORGANISM: Homo sapiens

<400> SEQUENCE: 51

```
atccgtcccg gataagaccc gctgtctggc cctgagtagg gtgtgacctc cgcagccgca     60
gaggaggagc gcagcccggc ctcgaagaac ttctgcttgg gtggctgaac tctgatcttg    120
acctagagtc atggccatgg caaccaaagg aggtactgtc aaagctgctt caggattcaa    180
tgccatggaa gatgcccaga ccctgaggaa ggccatgaaa gggctcggca ccgatgaaga    240
cgccattatt agcgtccttg cctaccgcaa caccgcccag cgccaggaga tcaggacagc    300
ctacaagagc accatcggca gggacttgat agacgacctg aagtcagaac tgagtggcaa    360
cttcgagcag gtgattgtgg ggatgatgac gcccacggtg ctgtatgacg tgcaagagct    420
gcgaagggcc atgaagggag ccggcactga tgagggctgc ctaattgaga tcctggcctc    480
ccggacccct gaggagatcc ggcgcataag ccaaacctac cagcagcaat atggacggag    540
ccttgaagat gacattcgct ctgacacatc gttcatgttc cagcgagtgc tggtgtctct    600
gtcagctggt gggagggatg aaggaaatta tctggacgat gctctcgtga gacaggatgc    660
ccaggacctg tatgaggctg gagagaagaa atgggggaca gatgaggtga aatttctaac    720
tgttctctgt tcccggaacc gaaatcacct gttgcatggt ttgatgaata caaaaggata    780
tcacagaagg atattgaaca gagtattaaa tctgaaacat ctggtagctt tgaagatgct    840
ctgctggcta tagtaaagtg catgaggaac aaatctgcat attttgctga aaagctctat    900
aaatcgatga agggcttggg caccgatgat aacaccctca tcagagtgat ggtttctcga    960
gcagaaattg acatgttgga tatccgggca cacttcaaga gactctatgg aaagtctctg   1020
tactcgttca tcaagggtga cacatctgga gactacagga aagtactgct tgttctctgt   1080
ggaggagatg attaaaataa aaatcccaga aggacaggag gattctcaac actttgaatt   1140
tttttaactt catttttcta cactgctatt atcattatct cagaatgctt atttccaatt   1200
aaaacgccta cagctgcctc ct                                            1222
```

-continued

<210> SEQ ID NO 52
<211> LENGTH: 2468
<212> TYPE: DNA
<213> ORGANISM: Homo sapiens

<400> SEQUENCE: 52
tggggcagcc gcgcccgcgg tgttttccgc ccggcgctgg cggctgctgc gcccgcggct 60
ccccagtgcc ccgagtgccc cgcgggcccc gcgagcggga gtgggaccca gcccctaggc 120
agaacccagg cgccgcgccc gggacgcccg cggagagagc cactcccgcc cacgtcccat 180
ttcgcccctc gcgtccggag tcctcgtggc cagatctaac catgagctac cctggctatc 240
ccccgccccc aggtggctac ccaccagctg caccaggtgg tggtccctgg ggaggtgctg 300
cctaccctcc tccgcccagc atgcccccca tcgggctgga taacgtggcc acctatgcgg 360
ggcagttcaa ccaggactat ctctcgggaa tggcggccaa catgtctggg acatttggag 420
gagccaacat gcccaacctg taccctgggg cccctggggc tggctaccca ccagtgcccc 480
ctggcggctt tgggcagccc ccctctgccc agcagcctgt tcctccctat gggatgtatc 540
cacccccagg aggaaaccca ccctccagga tgccctcata tccgccatac ccaggggccc 600
ctgtgccggg ccagcccatg ccacccccg gacagcagcc cccaggggcc taccctgggc 660
agccaccagt gacctaccct ggtcagcctc cagtgccact ccctgggcag cagcagccag 720
tgccgagcta cccaggatac ccggggtctg ggactgtcac ccccgctgtg cccccaaccc 780
agtttggaag ccgaggcacc atcactgatg ctcccggctt tgaccccctg cgagatgccg 840
aggtcctgcg gaaggccatg aaaggcttcg ggacggatga gcaggccatc attgactgcc 900
tggggagtcg ctccaacaag cagcggcagc agatcctact ttccttcaag acggcttacg 960
gcaaggattt gatcaaagat ctgaaatctg aactgtcagg aaactttgag aagacaatct 1020
tggctctgat gaagacccca gtcctctttg acatttatga gataaaggaa gccatcaagg 1080
gggttggcac tgatgaagcc tgcctgattg agatcctcgc ttcccgcagc aatgagcaca 1140
tccgagaatt aaacagagcc tacaaagcag aattcaaaaa gaccctggaa gaggccattc 1200
gaagcgacac atcagggcac ttccagcggc tcctcatctc tctctctcag ggaaaccgtg 1260
atgaaagcac aaacgtggac atgtcactcg cccagagaga tgcccaggag ctgtatgcgg 1320
ccggggagaa ccgcctggga acagacgagt ccaagttcaa tgcggttctg tgctcccgga 1380
gccgggccca cctggtagca gttttcaatg agtaccagag aatgacaggc cgggacattg 1440
agaagagcat ctgccgggag atgtccgggg acctggagga gggcatgctg gccgtggtga 1500
aatgtctcaa gaatacccca gccttctttg cggagaggct caacaaggcc atgagggggg 1560
caggaacaaa ggaccggacc ctgattcgca tcatggtgtc tcgcagcgag accgacctcc 1620
tggacatcag atcagagtat aagcggatgt acggcaagtc gctgtaccac gacatctcgg 1680
gagatacttc aggggattac cggaagattc tgctgaagat ctgtggtggc aatgactgaa 1740
cagtgactgg tggctcactt ctgcccacct gccggcaaca ccagtgccag gaaaaggcca 1800
aaagaatgtc tgtttctaac aaatccacaa atagccccga gattcaccgt cctagagctt 1860
aggcctgtct tccacccctc ctgacccgta tagtgtgcca caggacctgg gtcggtctag 1920
aactctctca ggatgccttt tctaccccat ccctcacagc ctcttgctgc taaaatagat 1980
gtttcatttt tctgactcat gcaatcattc ccctttgcct gtggctaaga cttggcttca 2040
tttcgtcatg taattgtata tttttatttg gaggcatatt ttcttttctt acagtcattg 2100

-continued

```
ccagacagag gcatacaagt ctgtttgctg catacacatt tctggtgagg gcgactgggt   2160

gggtgaagca ccgtgtcctc gctgaggaga gaaagggagg cgtgcctgag aaggtagcct   2220

gtgcatctgg tgagtgtgtc acgagctttg ttactgccaa actcactcct ttttagaaaa   2280

aacaaaaaaa aagggccaga aagtcattcc ttccatcttc cttgcagaaa ccacgagaac   2340

aaagccagtt ccctgtcagt gacagggctt cttgtaattt gtggtatgtg ccttaaacct   2400

gaatgtctgt agccaaaact tgtttccaca ttaagagtca gccagctctg gaatggtctg   2460

gaaatgtc                                                             2468
```

<210> SEQ ID NO 53
<211> LENGTH: 4907
<212> TYPE: DNA
<213> ORGANISM: Homo sapiens

<400> SEQUENCE: 53

```
tagacgcacc ctctgaagat ggtgactccc tcctgagaag ctggacccct tggtaaaaga     60

caaggccttc tccaagaaga atatgaaagt gttactcaga cttatttgtt tcatagctct    120

actgatttct tctctggagg ctgataaatg caaggaacgt gaagaaaaaa taattttagt    180

gtcatctgca aatgaaattg atgttcgtcc ctgtcctctt aacccaaatg aacacaaagg    240

cactataact tggtataaag atgacagcaa gacacctgta tctacagaac aagcctccag    300

gattcatcaa cacaaagaga aactttggtt tgttcctgct aaggtggagg attcaggaca    360

ttactattgc gtggtaagaa attcatctta ctgcctcaga attaaaataa gtgcaaaatt    420

tgtggagaat gagcctaact tatgttataa tgcacaagcc atatttaagc agaaactacc    480

cgttgcagga gacggaggac ttgtgtgccc ttatatggag ttttttaaaa atgaaaataa    540

tgagttacct aaattacagt ggtataagga ttgcaaacct ctacttcttg acaatataca    600

ctttagtgga gtcaaagata ggctcatcgt gatgaatgtg gctgaaaagc atagagggaa    660

ctatacttgt catgcatcct acacatactt gggcaagcaa tatcctatta cccgggtaat    720

agaatttatt actctagagg aaaacaaacc cacaaggcct gtgattgtga gcccagctaa    780

tgagacaatg gaagtagact tgggatccca gatacaattg atctgtaatg tcaccggcca    840

gttgagtgac attgcttact ggaagtggaa tgggtcagta attgatgaag atgacccagt    900

gctaggggaa gactattaca gtgtggaaaa tcctgcaaac aaaagaagga gtaccctcat    960

cacagtgctt aatatatcgg aaattgaaag tagattttat aaacatccat ttacctgttt   1020

tgccaagaat acacatggta tagatgcagc atatatccag ttaatatatc cagtcactaa   1080

tttccagaag cacatgattg gtatatgtgt cacgttgaca gtcataattg tgtgttctgt   1140

tttcatctat aaaatcttca agattgacat tgtgctttgg tacagggatt cctgctatga   1200

ttttctccca ataaaagctt cagatggaaa gacctatgac gcatatatac tgtatccaaa   1260

gactgttggg gaagggtcta cctctgactg tgatattttt gtgtttaaag tcttgcctga   1320

ggtcttggaa aaacagtgtg gatataagct gttcatttat ggaagggatg actacgttgg   1380

ggaagacatt gttgaggtca ttaatgaaaa cgtaaagaaa agcagaagac tgattatcat   1440

tttagtcaga gaaacatcag gcttcagctg gctgggtggt tcatctgaag agcaaatagc   1500

catgtataat gctcttgttc aggatggaat taaagttgtc ctgcttgagc tggagaaaat   1560

ccaagactat gagaaaatgc cagaatcgat taaattcatt aagcagaaac atggggctat   1620

ccgctggtca ggggacttta cacagggacc acagtctgca aagacaaggt tctggaagaa   1680

tgtcaggtac cacatgccag tccagcgacg gtcaccttca tctaaacacc agttactgtc   1740
```

-continued

```
accagccact aaggagaaac tgcaaagaga ggctcacgtg cctctcgggt agcatggaga   1800
agttgccaag agttctttag gtgcctcctg tcttatggcg ttgcaggcca ggttatgcct   1860
catgctgact tgcagagttc atggaatgta actatatcat cctttatccc tgaggtcacc   1920
tggaatcaga ttattaaggg aataagccat gacgtcaata gcagcccagg gcacttcaga   1980
gtagagggct tgggaagatc ttttaaaaag gcagtaggcc cggtgtggtg gctcacgcct   2040
ataatcccag cactttggga ggctgaagtg ggtggatcac cagaggtcag gagttcgaga   2100
ccagcccagc caacatggca aaaccccatc tctactaaaa atacaaaaat gagctaggca   2160
tggtggcaca cgcctgtaat cccagctaca cctgaggctg aggcaggaga attgcttgaa   2220
ccggggagac ggaggttgca gtgagccgag tttgggccac tgcactctag cctggcaaca   2280
gagcaagact ccgtctcaaa aaaagggcaa taaatgccct ctctgaatgt ttgaactgcc   2340
aagaaaaggc atggagacag cgaactagaa gaaagggcaa gaaggaaata gccaccgtct   2400
acagatggct tagttaagtc atccacagcc caagggcggg gctatgcctt gtctggggac   2460
cctgtagagt cactgaccct ggagcggctc tcctgagagg tgctgcaggc aaagtgagac   2520
tgacacctca ctgaggaagg gagacatatt cttggagaac tttccatctg cttgtatttt   2580
ccatacacat ccccagccag aagttagtgt ccgaagaccg aattttattt tacagagctt   2640
gaaaactcac ttcaatgaac aaagggattc tccaggattc caaagttttg aagtcatctt   2700
agctttccac aggagggaga gaacttaaaa aagcaacagt agcagggaat tgatccactt   2760
cttaatgctt tcctccctgg catgaccatc ctgtcctttg ttattatcct gcattttacg   2820
tctttggagg aacagctccc tagtggcttc ctccgtctgc aatgtccctt gcacagccca   2880
cacatgaacc atccttccca tgatgccgct cttctgtcat cccgctcctg ctgaaacacc   2940
tcccaggggc tccacctgtt caggagctga agcccatgct ttcccaccag catgtcactc   3000
ccagaccacc tccctgccct gtcctccagc ttcccctcgc tgtcctgctg tgtgaattcc   3060
caggttggcc tggtggccat gtcgcctgcc cccagcactc ctctgtctct gctcttgcct   3120
gcacccttcc tcctcctttg cctaggaggc cttctcgcat tttctctagc tgatcagaat   3180
tttaccaaaa ttcagaacat cctccaattc cacagtctct gggagacttt ccctaagagg   3240
cgacttcctc tccagccttc tctctctggt caggcccact gcagagatgg tggtgagcac   3300
atctgggagg ctggtctccc tccagctgga attgctgctc tctgagggag aggctgtggt   3360
ggctgtctct gtccctcact gccttccagg agcaatttgc acatgtaaca tagatttatg   3420
taatgcttta tgtttaaaaa cattccccaa ttatcttatt taatttttgc aattattcta   3480
attttatata tagagaaagt gacctatttt ttaaaaaaat cacactctaa gttctattga   3540
acctaggact tgagcctcca tttctggctt ctagtctggt gttctgagta cttgatttca   3600
ggtcaataac ggtccccccct cactccacac tggcacgttt gtgagaagaa atgacatttt   3660
gctaggaagt gaccgagtct aggaatgctt ttattcaaga caccaaattc caaacttcta   3720
aatgttggaa ttttcaaaaa ttgtgtttag attttatgaa aaactcttct actttcatct   3780
attctttccc tagaggcaaa catttcttaa aatgtttcat tttcattaaa aatgaaagcc   3840
aaatttatat gccaccgatt gcaggacaca agcacagttt taagagttgt atgaacatgg   3900
agaggacttt tggtttttat atttctcgta tttaatatgg gtgaacacca acttttattt   3960
ggaataataa ttttcctcct aaacaaaaac acattgagtt taagtctctg actcttgcct   4020
ttccacctgc tttctcctgg gcccgctttg cctgcttgaa ggaacagtgc tgttctggag   4080
```

| | | | |
|---|---|---|---|
| ctgctgttcc | aacagacagg | gcctagcttt catttgacac acagactaca gccagaagcc | 4140 |
| catggagcag | ggatgtcacg | tcttgaaaag cctattagat gttttacaaa tttaattttg | 4200 |
| cagattattt | tagtctgtca | tccagaaaat gtgtcagcat gcatagtgct aagaaagcaa | 4260 |
| gccaatttgg | aaacttaggt | tagtgacaaa attggccaga gagtgggggt gatgatgacc | 4320 |
| aagaattaca | agtagaatgg | cagctggaat ttaaggaggg acaagaatca atggataagc | 4380 |
| gtgggtggag | gaagatccaa | acagaaaagt gcaaagttat tccccatctt ccaagggttg | 4440 |
| aattctggag | gaagaagaca | cattcctagt tccccgtgaa cttcctttga cttattgtcc | 4500 |
| ccactaaaac | aaaacaaaaa | acttttaatg ccttccacat taattagatt ttcttgcagt | 4560 |
| ttttttatgg | cattttttta | aagatgccct aagtgttgaa gaagagtttg caaatgcaac | 4620 |
| aaaatattta | attaccggtt | gttaaaactg gtttagcaca atttatattt tccctctctt | 4680 |
| gcctttctta | tttgcaataa | aaggtattga gccattttt aaatgacatt tttgataaat | 4740 |
| tatgtttgta | ctagttgatg | aaggagtttt ttttaacctg tttatataat tttgcagcag | 4800 |
| aagccaaatt | ttttgtatat | taaagcacca aattcatgta cagcatgcat cacggatcaa | 4860 |
| tagactgtac | ttattttcca | ataaaatttt caaactttgt actgtta | 4907 |

<210> SEQ ID NO 54
<211> LENGTH: 1004
<212> TYPE: DNA
<213> ORGANISM: Homo sapiens

<400> SEQUENCE: 54

| | | | |
|---|---|---|---|
| ccctgcactc | tcgctctcct | gccccacccc gaggtaaagg gggcgactaa gagaagatgg | 60 |
| tgttgctcac | cgcggtcctc | ctgctgctgg ccgcctatgc ggggccggcc cagagcctgg | 120 |
| gctccttcgt | gcactgcgag | ccctgcgacg agaaagccct ctccatgtgc ccccccagcc | 180 |
| ccctgggctg | cgagctggtc | aaggagccgg gctgcggctg ctgcatgacc tgcgccctgg | 240 |
| ccgaggggca | gtcgtgcggc | gtctacaccg agcgctgcgc ccaggggctg cgctgcctcc | 300 |
| cccggcagga | cgaggagaag | ccgctgcacg ccctgctgca cggccgcggg gtttgcctca | 360 |
| acgaaaagag | ctaccgcgag | caagtcaaga tcgagagaga ctcccgtgag cacgaggagc | 420 |
| ccaccacctc | tgagatggcc | gaggagacct actcccccaa gatcttccgg cccaaacaca | 480 |
| cccgcatctc | cgagctgaag | gctgaagcag tgaagaagga ccgcagaaag aagctgaccc | 540 |
| agtccaagtt | tgtcggggga | gccgagaaca ctgcccaccc ccggatcatc tctgcacctg | 600 |
| agatgagaca | ggagtctgag | cagggcccct gccgcagaca catggaggct tccctgcagg | 660 |
| agctcaaagc | cagcccacgc | atggtgcccc gtgctgtgta cctgcccaat tgtgaccgca | 720 |
| aaggattcta | caagagaaag | cagtgcaaac cttcccgtgg ccgcaaacgt ggcatctgct | 780 |
| ggtgcgtgga | caagtacggg | atgaagctgc caggcatgga gtacgttgac ggggactttc | 840 |
| agtgccacac | cttcgacagc | agcaacgttg agtgatgcgt ccccccccaa cctttccctc | 900 |
| accccctccc | accccagcc | ccgactccag ccagcgcctc cctccacccc aggacgccac | 960 |
| tcatttcatc | tcatttaagg | gaaaaatata tatctatcta tttg | 1004 |

<210> SEQ ID NO 55
<211> LENGTH: 772
<212> TYPE: DNA
<213> ORGANISM: Homo sapiens

<400> SEQUENCE: 55

| | | | |
|---|---|---|---|
| cgcagcgggt | cctctctatc | tagctccagc ctctcgcctg cgccccactc cccgcgtccc | 60 |

-continued gcgtcctagc cgaccatggc cgggcccctg cgcgccccgc tgctcctgct ggccatcctg 120
gccgtggccc tggccgtgag ccccgcggcc ggctccagtc ccggcaagcc gccgcgccta 180
gtgggaggcc ccatggacgc cagcgtggag gaggagggtg tgcggcgtgc actggacttt 240
gccgtcggcg agtacaacaa agccagcaac gacatgtacc acagccgcgc gctgcaggtg 300
gtgcgcgccc gcaagcagat cgtagctggg gtgaactact tcttggacgt ggagctgggc 360
cgaaccacgt gtaccaagac ccagcccaac ttggacaact gccccttcca tgaccagcca 420
catctgaaaa ggaaagcatt ctgctctttc cagatctacg ctgtgccttg gcagggcaca 480
atgaccttgt cgaaatccac ctgtcaggac gcctaggggt ctgtaccggg ctggcctgtg 540
cctatcacct cttatgcaca cctcccaccc cctgtattcc cacccctgga ctggtggccc 600
ctgccttggg gaaggtctcc ccatgtgcct gcaccaggag acagacagag aaggcagcag 660
gcggcctttg ttgctcagca aggggctctg ccctccctcc ttccttcttg cttctcatag 720
ccccggtgtg cggtgcatac acccccacct cctgcaataa aatagtagca tc 772

<210> SEQ ID NO 56
<211> LENGTH: 2128
<212> TYPE: DNA
<213> ORGANISM: Homo sapiens

<400> SEQUENCE: 56
gaaagatgga tcactccagc tcaaagagaa catgtgggaa tgaaaggaca ggctgggccc 60
aaaggagaaa agggtgatgc tggggaggag cttcctggcc ctcctgaacc ttctgggcct 120
gttggaccca cggcaggagc agaagcagag ggctctggcc taggctgggg ctcggacgtc 180
ggctctggct ctggtgacct ggtgggcagt gagcagctgc tgagaggtcc tccaggaccc 240
ccagggccac ctggcttacc tgggattcca ggaaaaccag gaactgatgt tttcatggga 300
ccccctggat ctcctggaga ggatggacct gctggtgaac ctgggccccc gggccctgag 360
ggacagcctg gagttgatgg agccaccggc cttcccggga tgaaagggga gaagggagca 420
agagggccta atggctcagt tggtgaaaag ggtgaccctg gcaacagagg cttacctgga 480
cccccgggga aaaagggaca agctggccct cctggggtca tgggaccccc agggcctcct 540 ggacccccctg ggcccccagg ccctggatgc acaatgggac ttggattcga ggataccgaa 600
ggctctggaa gcacccagct attgaatgaa cccaaactct ccagaccaac ggctgcaatt 660
ggtctcaaag gagagaaagg agaccgggga cccaagggag aaagggggat ggatggagcc 720
agtattgtgg gacccccctgg gccgagaggg ccacctgggc acatcaaggt cttgtctaat 780
tccttgatca atatcaccca tggattcatg aatttctcgg acattcctga gctggtgggg 840
cctccggggc cggacgggtt gcctgggctg ccaggatttc cagggtccta gaggaccaaa 900
aggtgacact ggtttacctg gctttccagg actaaaagga gaacagggcg agaagggaga 960
gccgggtgcc atcctgacag aggacattcc tctggaaagg ctgatgggga aaaagggtga 1020
acctggaatg catggagccc caggaccaat ggggcccaaa ggaccaccag gacataaagg 1080
agaatttggc cttcccgggc gacctggtcg cccaggactg aatggcctca agggtaccaa 1140
aggagatcca ggggtcatta tgcagggccc acctggctta cctggccctc caggcccccc 1200
tgggccacct ggagctgtga ttaacatcaa aggagccatt ttcccaatac ccgtccgacc 1260
acactgcaaa atgccagttg atactgctca tcctgggagt ccagagctca tcacttttca 1320
cggtgttaaa ggagagaaag gatcctgggg tcttcctggc tcaaagggag aaaaaggcga 1380

-continued

```
ccagggagcc cagggaccac caggtcctcc acttgatcta gcttacctga gacactttct   1440

gaacaacttg aagggggaga atggagacaa ggggttcaaa ggtgaaaaag gagaaaaagg   1500

agacattaat ggcagcttcc ttatgtctgg gcctccaggc ctgcccggaa atccaggccc   1560

ggctggccaa aaaggggaga cagtcgttgg gccccaagga cccccaggtg ctcctggtct   1620

gcctgggcca cctggctttg gaagacctgg tgatcctggg ccaccggggc ccccggggcc   1680

accaggacct ccagctatcc tgggagcagc tgtggccctt ccaggtcccc ctggccctcc   1740

aggacagcca gggcttcccg gatccagaaa cctggtcaca gcattcagca acatggatga   1800

catgctgcag aaagcgcatt tggttataga aggaacattc atctacctga gggacagcac   1860

tgagtttttc attcgtgtta gagatggctg gaaaaaatta cagctgggag aactgatccc   1920

cattcctgcc gacagccctc caccccctgc gctttccagc aacccacatc agcttctgcc   1980

tccaccaaac cctatttcaa gtgccaatta tgagaagcct gctctgcatt tggctgctct   2040

gaacatgcca ttttctgggg acattcgagc tgattttcag tgcttcaagc aggccagagc   2100

tgcaggactg ttgtccacct accgagca                                     2128
```

<210> SEQ ID NO 57
<211> LENGTH: 4309
<212> TYPE: DNA
<213> ORGANISM: Homo sapiens

<400> SEQUENCE: 57

```
tagaaattgt taattttaac aatccagagc aggccaacga ggctttgctc tcccgacccg     60

aactaaaggt ccctcgctcc gtgcgctgct acgagcggtg tctcctgggg ctccaatgca    120

gcgagctgtg cccgaggggt tcggaaggcg caagctgggc agcgacatgg ggaacgcgga    180

gcgggctccg gggtctcgga gctttgggcc agtacccacg ctgctgctgc tcgccgcggc    240

gctactggcc gtgtcggacg cactcgggcg cccctccgag gaggacgagg agctagtggt    300

gccggagctg gagcgcgccc cgggacacgg gaccacgcgc ctccgcctgc acgcctttga    360

ccagcagctg gatctggagc tgcggcccga cagcagcttt ttggcgcccg gcttcacgct    420

ccagaacgtg gggcgcaaat ccgggtccga gacgccgctt ccggaaaccg acctggcgca    480

ctgcttctac tccggcaccg tgaatggcga tcccagctcg gctgccgccc tcagcctctg    540

cgagggcgtg cgcggcgcct tctacctgct gggggaggcg tatttcatcc agccgctgcc    600

cgccgccagc gagcgcctcg ccaccgccgc cccaggggag aagccgccgg caccactaca    660

gttccacctc ctgcggcgga atcggcaggg cgacgtcggc ggcacgtgcg gggtcgtgga    720

cgacgagccc cggccgactg ggaaagcgga gaccgaagac gaggacgaag ggactgaggg    780

cgaggacgaa ggggctcagt ggtcgccgca ggacccggca ctgcaaggcg taggacagcc    840

cacaggaact ggaagcataa gaaagaagcg atttgtgtcc agtcaccgct atgtggaaac    900

catgcttgtg gcagaccagt cgatggcaga attccacggc agtggtctaa agcattacct    960

tctcacgttg ttttcggtgg cagccagatt gtacaaacac cccagcattc gtaattcagt   1020

tagcctggtg gtggtgaaga tcttggtcat ccacgatgaa cagaaggggc cggaagtgac   1080

ctccaatgct gccctcactc tgcggaactt ttgcaactgg cagaagcagc acaacccacc   1140

cagtgaccgg gatgcagagc actatgacac agcaattctt ttcaccagac aggacttgtg   1200

tgggtcccag acatgtgata ctcttgggat ggctgatgtt ggaactgtgt gtgatccgag   1260

cagaagctgc tccgtcatag aagatgatgg tttacaagct gccttcacca cagcccatga   1320

attaggccac gtgtttaaca tgccacatga tgatgcaaag cagtgtgcca gccttaatgg   1380
```

-continued

```
tgtgaaccag gattcccaca tgatggcgtc aatgctttcc aacctggacc acagccagcc   1440
ttggtctcct tgcagtgcct acatgattac atcatttctg gataatggtc atggggaatg   1500
tttgatggac aagcctcaga atcccataca gctcccaggc gatctccctg gcacctcgta   1560
cgatgccaac cggcagtgcc agtttacatt tggggaggac tccaaacact gccccgatgc   1620
agccagcaca tgtagcacct tgtggtgtac cggcacctct ggtggggtgc tggtgtgtca   1680
aaccaaacac ttcccgtggg cggatggcac cagctgtgga gaagggaaat ggtgtatcaa   1740
cggcaagtgt gtgaacaaaa ccgacagaaa gcattttgat acgccttttc atggaagctg   1800
gggaatgtgg gggccttggg gagactgttc gagaacgtgc ggtggaggag tccagtacac   1860
gatgagggaa tgtgacaacc cagtcccaaa gaatggaggg aagtactgtg aaggcaaacg   1920
agtgcgctac agatcctgta accttgagga ctgtccagac aataatggaa aaacctttag   1980
agaggaacaa tgtgaagcac acaacgagtt ttcaaaagct tcctttggga gtgggcctgc   2040
ggtggaatgg attcccaagt acgctggcgt ctcaccaaag gacaggtgca agctcatctg   2100
ccaagccaaa ggcattggct acttcttcgt tttgcagccc aaggttgtag atggtactcc   2160
atgtagccca gattccacct ctgtctgtgt gcaaggacag tgtgtaaaag ctggttgtga   2220
tcgcatcata gactccaaaa agaagtttga taaatgtggt gtttgcgggg gaaatggatc   2280
tacttgtaaa aaaatatcag gatcagttac tagtgcaaaa cctggatatc atgatatcat   2340
cacaattcca actggagcca ccaacatcga agtgaaacag cggaaccaga ggggatccag   2400
gaacaatggc agctttcttg ccatcaaagc tgctgatggc acatatattc ttaatggtga   2460
ctacactttg tccaccttag agcaagacat tatgtacaaa ggtgttgtct tgaggtacag   2520
cggctcctct gcggcattgg aaagaattcg cagctttagc cctctcaaag agcccttgac   2580
catccaggtt cttactgtgg gcaatgccct tcgacctaaa attaaataca cctacttcgt   2640
aaagaagaag aaggaatctt tcaatgctat ccccactttt tcagcatggg tcattgaaga   2700
gtggggcgaa tgttctaagt catgtgaatt gggttggcag agaagactgg tagaatgccg   2760
agacattaat ggacagcctg cttccgagtg tgcaaaggaa gtgaagccag ccagcaccag   2820
accttgtgca gaccatccct gcccccagtg gcagctgggg gagtggtcat catgttctaa   2880
gacctgtggg aagggttaca aaaaaagaag cttgaagtgt ctgtcccatg atggaggggt   2940
gttatctcat gagagctgtg atcctttaaa gaaacctaaa catttcatag acttttgcac   3000
aatggcagaa tgcagttaag tggtttaagt ggtgttagct ttgagggcaa ggcaaagtga   3060
ggaagggctg gtgcagggaa agcaagaagg ctggagggat ccagcgtatc ttgccagtaa   3120
ccagtgaggt gtatcagtaa ggtgggatta tgggggtaga tagaaaagga gttgaatcat   3180
cagagtaaac tgccagttgc aaatttgata ggatagttag tgaggattat taacctctga   3240
gcagtgatat agcataataa agccccgggc attattatta ttatttcttt tgttacatct   3300
attacaagtt tagaaaaaac aaagcaattg tcaaaaaaag ttagaactat tacaacccct   3360
gtttcctggt acttatcaaa tacttagtat catgggggtt gggaaatgaa aagtaggaga   3420
aaagtgagat tttactaaga cctgttttac tttacctcac taacaatggg gggagaaagg   3480
agtacaaata ggatctttga ccagcactgt ttatggctgc tatggtttca gagaatgttt   3540
atacattatt tctaccgaga attaaaactt cagattgttc aacatgagag aaaggctcag   3600
caacgtgaaa taacgcaaat ggcttcctct ttcctttttt ggaccatctc agtctttatt   3660
tgtgtaattc attttgagga aaaaacaact ccatgtattt attcaagtgc attaaagtct   3720
```

-continued

```
acaatggaaa aaaagcagtg aagcattaga tgctggtaaa agctagagga gacacaatga   3780
gcttagtacc tccaacttcc tttctttcct accatgtaac cctgctttgg gaatatggat   3840
gtaaagaagt aacttgtgtc tcatgaaaat cagtacaatc acacaaggag gatgaaacgc   3900
cggaacaaaa atgaggtgtg tagaacaggg tcccacaggt ttggggacat tgagatcact   3960
tgtcttgtgg tggggaggct gctgaggggt agcaggtcca tctccagcag ctggtccaac   4020
agtcgtatcc tggtgaatgt ctgttcagct cttctgtgag aatatgattt tttccatatg   4080
tatatagtaa aatatgttac tataaattac atgtacttta taagtattgg tttgggtgtt   4140
ccttccaaga aggactatag ttagtaataa atgcctataa taacatattt atttttatac   4200
atttatttct aatgaaaaaa acttttaaat tatatcgctt ttgtggaagt gcatataaaa   4260
tagagtattt atacaatata tgttactaga aataaaagaa cacttttgg              4309
```

<210> SEQ ID NO 58
<211> LENGTH: 3488
<212> TYPE: DNA
<213> ORGANISM: Homo sapiens

<400> SEQUENCE: 58

```
gggcccgggc gcgcgggagc gggagcggcc gggggagccg gagcgcacca tggaggcggc     60
ggcaggcggc cgcggctgtt tccagccgca cccggggctg cagaagacgc tggagcagtt    120
ccacctgagc tccatgagct cgctgggcgg cccggccgct ttctcggcgc gctgggcgca    180
ggaggcctac aagaaggaga gcgccaagga ggcgggcgcg gccgcggtgc cggcgccggt    240
gcccgcagcc accgagccgc cgcccgtgct gcacctgccc gccatccagc cgccgccgcc    300
cgtgctgccc gggcccttct tcatgccgtc cgaccgctcc accgagcgct gcgagaccgt    360
actggaaggc gagaccatct cgtgcttcgt ggtgggaggc gagaagcgcc tgtgtctgcc    420
gcagattctc aactcggtgc tgcgcgactt ctcgctgcag cagatcaacg cggtgtgcga    480
cgagctccac atctactgct cgcgctgcac ggccgaccag ctggagatcc tcaaagtcat    540
gggcatcctg cccttctcgg cgccctcgtg cgggctcatc accaagacgg acgccgagcg    600
cctgtgcaac gcgctgctct acggcggcgc ctacccgccg ccctgcaaga aggagctggc    660
cgccagcctg gcgctgggcc tggagctcag cgagcgcagc gtccgcgtgt accacgagtg    720
cttcggcaag tgtaaggggc tgctggtgcc cgagctctac agcagcccga gcgccgcctg    780
catccagtgc ctggactgcc gcctcatgta cccgccgcac aagttcgtgg tgcactcgca    840
caaggccctg gagaaccgga cctgccactg ggggcttcgac tcggccaact ggcgggccta    900
catcctgctg agccaggatt acacgggcaa ggaggagcag gcgcgcctcg gccgctgcct    960
ggacgacgtg aaggagaaat tcgactatgg caacaagtac aagcggcggg tgccccgggt   1020
ctcctctgag cctccggcct ccataagacc caaaacagat gacacctctt cccagtcccc   1080
cgcgccttcc gaaaaggaca agccgtccag ctggctgcgg accttggccg gctcttccaa   1140
taagagcctg ggctgtgttc accctcgcca gcgcctctct gctttccgac cctggtcccc   1200
cgcagtgtca gcgagtgaga aagagctctc cccacacctc ccggccctca tccgagacag   1260
cttctactcc tacaagagct ttgagacagc cgtggcgccc aacgtggccc tcgcaccgcc   1320
ggcccagcag aaggttgtga gcagccctcc gtgtgccgcc gccgtctccc gggcccccga   1380
gcctctcgcc acttgcaccc agcctcggaa gcggaagctg actgtggaca ccccaggagc   1440
cccagagacg ctggcgcccg tggctgcccc agaggaggac aaggactcgg aggcggaggt   1500
ggaagttgaa agcagggagg aattcacctc ctccttgtcc tcgctctctt ccccgtcctt   1560
```

-continued

```
tacctcatcc agctccgcca aggacctggg ctccccgggt gcgcgtgccc tgccctcggc   1620

cgtccctgat gctgcggccc ctgccgacgc ccccagtggg ctggaggcgg agctggagca   1680

cctgcggcag gcactggagg gcggcctgga caccaaggaa gccaaagaga agttcctgca   1740

tgaggtggtc aagatgcgcg tgaagcagga ggagaagctc agcgcagccc tgcaggccaa   1800

gcgcagcctc caccaggagc tggagttcct acgcgtggcc aagaaggaga agctgcggga   1860

ggccacggag gccaagcgta acctgcggaa ggagatcgag cgtctccgcg ccgagaacga   1920

gaagaagatg aaagaggcca acgagtcacg gctgcgcctg aagcgggagc tggagcaggc   1980

gcggcaggcc cgggtgtgcg acaagggctg cgaggcgggc cgcctgcgcg ccaagtactc   2040

ggcccagatc gaagacctgc aggtgaagct gcagcacgcg gaggcggacc gggagcagct   2100

gcgggccgac ctgctgcggg agcgcgaggc ccgggagcac ctggagaagg tggtgaagga   2160

gctgcaggaa cagctgtggc cgcgggcccg ccccgaggct gcgggcagcg agggcgctgc   2220

ggagctggag ccgtagattc cgtgcctgcc gccgcagcgc cgccgacaac gcgggtgcag   2280

gggggcgcgg ctgggcggtg cagctccgcc cggctccgcc cctgcagccc acacagcaca   2340

acgtcttacc gtgcctatta ccaagcgagt gtttgtaacc atgtagtttt ggaacccact   2400

gcaaaatttt ctactggcca agttcaagtg agtaagccgc gtcccccaac tacagctgga   2460

gacggggcca gctcggcggc ctgctggtcc tctgcttgct ggaacattct aacatttaca   2520

cttttgttat aagctattta aaaccagtaa ggagacttga aattcagaaa atcaacacat   2580

ttttaaatga ctaacttcta aaagccccaa cacatgacgc catctgaaga cccgcaacgg   2640

agtgggggtg gcggccgccc caccctcccc acccggggaa gccatcacag ctcatctgcc   2700

cgcggctgcg tgaggacagc aggggttttt cttcagagtc tatttttttca gcgacaagga   2760

cccaggtctt cctgctgctg ccagggagag cagggacagt gccgcgtgcg agatgagctc   2820

gaacactgcc cgccttactg ccgcctaccc cgcccgccac gccgccgtcg atgccagcgc   2880

tgtccccacg ggtaccagga agtgcagagc cgcacaggag ctgccccgga gctgagggga   2940

cggtcttcgg ctcctctgca ccccgtgatt ctgcccacgc tcctccacca cgaggcactg   3000

acctgcgtcg ggtggtgacc gtggctggcg gtcacgccct cagcccctcc gggcacacgt   3060

gccgcctgac cgggcgaccc ttttcagttc ggcaaacgtc gctcccttca ttttgggact   3120

gaggctgcag cattggaaca aaagagcatt atttcaattt ttctttcttt ttttttgttc   3180

gttcatttaa acgtatattt agaactgcac tttgtccaca accttccctt ctctttctat   3240

tccccagtga actgaggttt ttaccgattt atagagcagt caaatccgaa gtgctcgagt   3300

gcttagaaac cccctctggt gcttggttga acaagggaat cacaagaaaa cgaaaatgca   3360

aaaactgaac ttcgggggtc gttctgtgcc ttccagcatc ttgtacagca aatcctgact   3420

cgtgtctttt tacccccaag atatctgtct tcagtagcga ctgaatctgc cactctcaga   3480

ataagttc                                                             3488


<210> SEQ ID NO 59
<211> LENGTH: 3108
<212> TYPE: DNA
<213> ORGANISM: Homo sapiens

<400> SEQUENCE: 59

gccgccgccg ccatccgccg ccgcagccag cttccgccgc cgcaggaccg gcccctgccc     60

cagcctccgc agccgcggcg cgtccacgcc cgcccgcgcc cagggcgagt cggggtcgcc    120
```

-continued

```
gcctgcacgc ttctcagtgt tccccgcgcc ccgcatgtaa cccggccagg cccccgcaac    180
tgtgtcccct gcagctccag ccccgggctg catccccccg ccccgacacc agctctccag    240
cctgctcgtc caggatggcc gcggccaagg ccgagatgca gctgatgtcc ccgctgcaga    300
tctctgaccc gttcggatcc tttcctcact cgcccaccat ggacaactac cctaagctgg    360
aggagatgat gctgctgagc aacggggctc cccagttcct cggcgccgcc ggggccccag    420
agggcagcgg cagcaacagc agcagcagca gcagcggggg cggtggaggc ggcgggggcg    480
gcagcaacag cagcagcagc agcagcacct tcaaccctca ggcggacacg ggcgagcagc    540
cctacgagca cctgaccgca gagtcttttc ctgacatctc tctgaacaac gagaaggtgc    600
tggtggagac cagttacccc agccaaacca ctcgactgcc ccccatcacc tatactggcc    660
gcttttccct ggagcctgca cccaacagtg gcaacacctt gtggcccgag cccctcttca    720
gcttggtcag tggcctagtg agcatgacca acccaccggc ctcctcgtcc tcagcaccat    780
ctccagcggc ctcctccgcc tccgcctccc agagcccacc cctgagctgc gcagtgccat    840
ccaacgacag cagtcccatt tactcagcgg cacccacctt ccccacgccg aacactgaca    900
ttttccctga gccacaaagc caggccttcc cgggctcggc agggacagcg ctccagtacc    960
cgcctcctgc ctaccctgcc gccaagggtg gcttccaggt tcccatgatc cccgactacc   1020
tgtttccaca gcagcagggg gatctgggcc tgggcacccc agaccagaag cccttccagg   1080
gcctggagag ccgcacccag cagccttcgc taacccctct gtctactatt aaggcctttg   1140
ccactcagtc gggctcccag gacctgaagg ccctcaatac cagctaccag tcccagctca   1200
tcaaacccag ccgcatgcgc aagtacccca accggcccag caagacgccc ccccacgaac   1260
gcccttacgc ttgcccagtg gagtcctgtg atcgccgctt ctcccgctcc gacgagctca   1320
cccgccacat ccgcatccac acaggccaga agcccttcca gtgccgcatc tgcatgcgca   1380
acttcagccg cagcgaccac ctcaccaccc acatccgcac ccacacaggc gaaaagccct   1440
tcgcctgcga catctgtgga agaaagtttg ccaggagcga tgaacgcaag aggcatacca   1500
agatccactt gcggcagaag gacaagaaag cagacaaaag tgttgtggcc tcttcggcca   1560
cctcctctct ctcttcctac ccgtccccgg ttgctacctc ttacccgtcc ccggttacta   1620
cctcttatcc atccccggcc accacctcat acccatcccc tgtgcccacc tccttctcct   1680
ctcccggctc ctcgacctac ccatcccctg tgcacagtgg cttcccctcc ccgtcggtgg   1740
ccaccacgta ctcctctgtt ccccctgctt tcccggccca ggtcagcagc ttcccttcct   1800
cagctgtcac caactccttc agcgcctcca cagggctttc ggacatgaca gcaacctttt   1860
ctcccaggac aattgaaatt tgctaaaggg aaaggggaaa gaaagggaaa agggagaaaa   1920
agaaacacaa gagacttaaa ggacaggagg aggagatggc cataggagag gagggttcct   1980
cttaggtcag atggaggttc tcagagccaa gtcctccctc tctactggag tggaaggtct   2040
attggccaac aatcctttct gcccacttcc ccttccccaa ttactattcc ctttgacttc   2100
agctgcctga aacagccatg tccaagttct tcacctctat ccaaagaact tgatttgcat   2160
ggattttgga taaatcattt cagtatcatc tccatcatat gcctgacccc ttgctccctt   2220
caatgctaga aaatcgagtt ggcaaaatgg ggtttgggcc cctcagagcc ctgccctgca   2280
cccttgtaca gtgtctgtgc catggatttc gtttttcttg ggtactcttg gatgtgaaga   2340
taatttgcat attctattgt attatttgga gttaggtcct cacttggggg aaaaaaaaaa   2400
aagaaaagcc aagcaaacca atggtgatcc tctattttgt gatgatgctg tgacaataag   2460
tttgaacctt ttttttgaa acagcagtcc cagtattctc agagcatgtg tcagagtgtt    2520
```

-continued

```
gttccgttaa cctttttgta aatactgctt gaccgtactc tcacatgtgg caaaatatgg   2580
tttggttttt cttttttttt tttttgaaa gtgtttttc ttcgtccttt tggtttaaaa   2640
agtttcacgt cttggtgcct tttgtgtgat gcgccttgct gatggcttga catgtgcaat   2700
tgtgagggac atgctcacct ctagccttaa ggggggcagg gagtgatgat ttgggggagg   2760
ctttgggagc aaaataagga agagggctga gctgagcttc ggttctccag aatgtaagaa   2820
aacaaaatct aaaacaaaat ctgaactctc aaaagtctat ttttttaact gaaaatgtaa   2880
atttataaat atattcagga gttggaatgt tgtagttacc tactgagtag gcggcgattt   2940
ttgtatgtta tgaacatgca gttcattatt ttgtggttct attttacttt gtacttgtgt   3000
ttgcttaaac aaagtgactg tttggcttat aaacacattg aatgcgcttt attgcccatg   3060
ggatatgtgg tgtatatcct tccaaaaaat taaaacgaaa ataaagta               3108
```

<210> SEQ ID NO 60
<211> LENGTH: 3775
<212> TYPE: DNA
<213> ORGANISM: Homo sapiens

<400> SEQUENCE: 60

```
cattcataag actcagagct acggccacgg cagggacacg cggaaccaag acttggaaac     60
ttgattgttg tggttcttct tgggggttat gaaatttcat taatcttttt tttttccggg    120
gagaaagttt ttggaaagat tcttccagat atttcttcat tttcttttgg aggaccgact    180
tacttttttt ggtcttcttt attactcccc tccccccgtg ggacccgccg gacgcgtgga    240
ggagaccgta gctgaagctg attctgtaca gcgggacagc gctttctgcc cctgggggag    300
caacccctcc ctcgcccctg ggtcctacgg agcctgcact ttcaagaggt acagcggcat    360
cctgtggggg cctgggcacc gcaggaagac tgcacagaaa ctttgccatt gttggaacgg    420
gacgttgctc cttccccgag cttccccgga cagcgtactt tgaggactcg ctcagctcac    480
cggggactcc cacggctcac cccggacttg caccttactt ccccaacccg gccatagcct    540
tggcttcccg gcgacctcag cgtggtcaca ggggcccccc tgtgcccagg gaaatgtttc    600
aggctttccc cggagactac gactccggct cccggtgcag ctcctcaccc tctgccgagt    660
ctcaatatct gtcttcggtg gactccttcg gcagtccacc caccgccgcg gcctcccagg    720
agtgcgccgg tctcggggaa atgcccggtt ccttcgtgcc cacggtcacc gcgatcacaa    780
ccagccagga cctccagtgg cttgtgcaac ccaccctcat ctcttccatg gcccagtccc    840
aggggcagcc actggcctcc cagcccccgg tcgtcgaccc ctacgacatg ccgggaacca    900
gctactccac accaggcatg agtggctaca gcagtggcgg agcgagtggc agtggtgggc    960
cttccaccag cggaactacc agtgggcctg ggcctgcccg cccagcccga gcccggccta   1020
ggagaccccg agaggagacg ctcaccccag aggaagagga gaagcgaagg gtgcgccggg   1080
aacgaaataa actagcagca gctaaatgca ggaaccggcg gagggagctg accgaccgac   1140
tccaggcgga gacagatcag ttggaggaag aaaaagcaga gctggagtcg gagatcgccg   1200
agctccaaaa ggagaaggaa cgtctggagt ttgtgctggt ggcccacaaa ccgggctgca   1260
agatccccta cgaagagggg cccgggccgg gcccgctggc ggaggtgaga gatttgccgg   1320
gctcagcacc ggctaaggaa gatggcttca gctggctgct gccgcccccg ccaccaccgc   1380
ccctgccctt ccagaccagc caagacgcac cccccaacct gacggcttct ctctttacac   1440
acagtgaagt tcaagtcctc ggcgacccct tccccgttgt taacccttcg tacacttctt   1500
```

-continued

```
cgtttgtcct cacctgcccg gaggtctccg cgttcgccgg cgcccaacgc accagcggca   1560
gtgaccagcc ttccgatccc ctgaactcgc cctccctcct cgctcggtga actctttaga   1620
cacacaaaac aaacaaacac atgggggaga gagacttgga agaggaggag gaggaggaga   1680
aggaggagag agaggggaag agacaaagtg ggtgtgtggc ctccctggct cctccgtctg   1740
accctctgcg gccactgcgc cactgccatc ggacaggagg attccttgtg ttttgtcctg   1800
cctcttgttt ctgtgccccg gcgaggccgg agagctggtg actttgggga caggggggtgg   1860
gaaggggatg gacaccccca gctgactgtt ggctctctga cgtcaaccca agctctgggg   1920
atgggtgggg aggggggcgg gtgacgccca ccttcgggca gtcctgtgtg aggatgaagg   1980
gacgggggtg ggaggtaggc tgtggggtgg gctggagtcc tctccagaga ggctcaacaa   2040
ggaaaaatgc cactccctac ccaatgtctc ccacacccac cctttttttg gggtgcccag   2100
gttggtttcc cctgcactcc cgaccttagc ttattgatcc cacatttcca tggtgtgaga   2160
tcctctttac tctgggcaga agtgagcccc cccttaaagg gaattcgatg ccccccctaga   2220
ataatctcat ccccccaccc gacttctttt gaaatgtgaa cgtccttcct tgactgtcta   2280
gccactccct cccagaaaaa ctggctctga ttggaatttc tggcctccta aggctcccca   2340
ccccgaaatc agcccccagc cttgtttctg atgacagtgt tatcccaaga ccctgccccc   2400
tgccagccga ccctcctggc cttcctcgtt gggccgctct gatttcaggc agcaggggct   2460
gctgtgatgc cgtcctgctg gagtgattta tactgtgaaa tgagttggcc agattgtggg   2520
gtgcagctgg gtggggcagc acacctctgg ggggataatg tccccactcc cgaaagcctt   2580
tcctcggtct cccttccgtc catccccctt cttcctcccc tcaacagtga gttagactca   2640
agggggtgac agaaccgaga agggggtgac agtcctccat ccacgtggcc tctctctctc   2700
tcctcaggac cctcagccct ggcctttttc tttaaggtcc cccgaccaat ccccagccta   2760
ggacgccaac ttctcccacc ccttggcccc tcacatcctc tccaggaagg cagtgagggg   2820
ctgtgacatt tttccggaga agatttcaga gctgaggctt tggtaccccc aaaccccaa   2880
tatttttgga ctggcagact caaggggctg gaatctcatg attccatgcc cgagtccgcc   2940
catccctgac catggttttg gctctcccac cccgccgttc cctgcgcttc atctcatgag   3000
gatttcttta tgaggcaaat ttatattttt taatatcggg gggtggacca cgccgccctc   3060
catccgtgct gcatgaaaaa cattccacgt gccccttgtc gcgcgtctcc catcctgatc   3120
ccagacccat tccttagcta tttatccctt tcctggtttc cgaaaggcaa ttatatctat   3180
tatgtataag taaatatatt atatatggat gtgtgtgtgt gcgtgcgcgt gagtgtgtga   3240
gcgcttctgc agcctcggcc taggtcacgt tggccctcaa agcgagccgt tgaattggaa   3300
actgcttcta gaaactctgg ctcagcctgt ctcgggctga ccctttttctg atcgtctcgg   3360
cccctctgat tgttcccgat ggtctctctc cctctgtctt ttctcctccg cctgtgtcca   3420
tctgaccgtt ttcacttgtc tcctttctga ctgtccctgc caatgctcca gctgtcgtct   3480
gactctgggt tcgttgggga catgagattt tattttttgt gagtgagact gagggatcgt   3540
agatttttac aatctgtatc tttgacaatt ctgggtgcga gtgtgagagt gtgagcaggg   3600
cttgctcctg ccaaccacaa ttcaatgaat ccccgacccc cctaccccat gctgtacttg   3660
tggttctctt tttgtatttt gcatctgacc ccggggggct gggacagatt ggcaatgggc   3720
cgtcccctct ccccttggtt ctgcactgtt gccaataaaa agctcttaaa aacgc         3775
```

<210> SEQ ID NO 61
<211> LENGTH: 2021

-continued

<212> TYPE: DNA
<213> ORGANISM: Homo sapiens

<400> SEQUENCE: 61
agcgagcttg cagcctcacc gacgagtctc aactaaaagg gactcccgga gctaggggtg 60
gggactcggc ctcacacagt gagtgccggc tattggactt ttgtccagtg acagctgaga 120
caacaaggac cacgggagga ggtgtaggag agaagcgccg cgaacagcga tcgcccagca 180
ccaagtccgc ttccaggctt tcggtttctt tgcctccatc ttgggtgcgc cttcccggcg 240
tctaggggag cgaaggctga ggtggcagcg gcaggagagt ccggccgcga caggacgaac 300
tcccccactg gaaaggattc tgaaagaaat gaagtcagcc ctcagaaatg aagttgactg 360
cctgctggct ttctgttgac tggcccggag ctgtactgca agacccttgt gagcttccct 420
agtctaagag taggatgtct gctgaagtca tccatcaggt tgaagaagca cttgatacag 480
atgagaagga gatgctgctc tttttgtgcc gggatgttgc tatagatgtg gttccaccta 540
atgtcaggga ccttctggat attttacggg aaagaggtaa gctgtctgtc ggggacttgg 600
ctgaactgct ctacagagtg aggcgatttg acctgctcaa acgtatcttg aagatggaca 660
gaaaagctgt ggagacccac ctgctcagga accctcacct tgtttcggac tatagagtgc 720
tgatggcaga gattggtgag gatttggata aatctgatgt gtcctcatta attttcctca 780
tgaaggatta catgggccga ggcaagataa gcaaggagaa ggtttcttgg accttgtggt 840
tgagttggag aaactaaatc tggttgcccc agatcaactg gatttattag aaaaatgcct 900
aaagaacatc cacagaatag acctgaagac aaaaatccag aagtacaagc agtctgttca 960
aggagcaggg acaagttaca ggaatgttct ccaagcagca atccaaaaga gtctcaagga 1020
tccttcaaat aacttcaggc tccataatgg gagaagtaaa gaacaaagac ttaaggaaca 1080
gcttggcgct caacaagaac cagtgaagaa atccattcag gaatcagaag ctttttttgcc 1140 tcagagcata cctgaagaga gatacaagat gaagagcaag cccctaggaa tctgcctgat 1200
aatcgattgc attggcaatg agacagagct tcttcgagac accttcactt ccctgggcta 1260
tgaagtccag aaattcttgc atctcagtat gcatggtata tcccagattc ttggccaatt 1320
tgcctgtatg cccgagcacc gagactacga cagctttgtg tgtgtcctgg tgagccgagg 1380
aggctcccag agtgtgtatg gtgtggatca gactcactca gggctccccc tgcatcacat 1440
caggaggatg ttcatgggag attcatgccc ttatctagca gggaagccaa agatgttttt 1500
tattcagaac tatgtggtgt cagagggcca gctggaggac agcagcctct tggaggtgga 1560
tgggccagcg atgaagaatg tggaattcaa ggctcagaag cgagggctgt gcacagttca 1620
ccgagaagct gacttcttct ggagcctgtg tactgcggac atgtccctgc tggagcagtc 1680
tcacagctca ccatccctgt acctgcagtg cctctcccag aaactgagac aagaaagaaa 1740
acgcccactc ctggatcttc acattgaact caatggctac atgtatgatt ggaacagcag 1800
agtttctgcc aaggagaaat attatgtctg gctgcagcac actctgagaa agaaacttat 1860
cctctcctac acataagaaa ccaaaaggct gggcgtagtg gctcacacct gtaatcccag 1920
cactttggga ggccaaggag ggcagatcac ttcaggtcag gagttcgaga ccagcctggc 1980
caacatggta aacgctgtcc ctagtaaaaa tacaaaaatt a 2021

<210> SEQ ID NO 62
<211> LENGTH: 3254
<212> TYPE: DNA
<213> ORGANISM: Homo sapiens -continued

<400> SEQUENCE: 62

```
agagttgcac tgagtgtggc tgaagcagcg aggcgggagt ggaggtgcgc ggagtcaggc     60
agacagacag acacagccag ccagccaggt cggcagtata gtccgaactg caaatcttat    120
tttcttttca ccttctctct aactgcccag agctagcgcc tgtggctccc gggctggtgt    180
ttcgggagtg tccagagagc ctggtctcca gccgcccccg ggaggagagc cctgctgccc    240
aggcgctgtt gacagcggcg gaaagcagcg gtacccacgc gcccgccggg ggaagtcggc    300
gagcggctgc agcagcaaag aactttcccg gctgggagga ccggagacaa gtggcagagt    360
cccggagcca acttttgcaa gcctttcctg cgtcttaggc ttctccacgg cggtaaagac    420
cagaaggcgg cggagagcca cgcaagagaa gaaggacgtg cgctcagctt cgctcgcacc    480
ggttgttgaa cttgggcgag cgcgagccgc ggctgccggg cgccccctcc ccctagcagc    540
ggaggagggg acaagtcgtc ggagtccggg cggccaagac ccgccgccgg ccggccactg    600
cagggtccgc actgatccgc tccgcgggga gagccgctgc tctgggaagt gagttcgcct    660
gcggactccg aggaaccgct gcgcacgaag agcgctcagt gagtgaccgc gacttttcaa    720
agccgggtag cgcgcgcgag tcgacaagta agagtgcggg aggcatctta attaaccctg    780
cgctccctgg agcgagctgg tgaggagggc gcagcgggga cgacagccag cgggtgcgtg    840
cgctcttaga gaaactttcc ctgtcaaagg ctccgggggg cgcgggtgtc ccccgcttgc    900
cacagccctg ttgcggcccc gaaacttgtg cgcgcagccc aaactaacct cacgtgaagt    960
gacggactgt tctatgactg caaagatgga aacgaccttc tatgacgatg ccctcaacgc   1020
ctcgttcctc ccgtccgaga gcggacctta tggctacagt aaccccaaga tcctgaaaca   1080
gagcatgacc ctgaacctgg ccgacccagt ggggagcctg aagccgcacc tccgcgccaa   1140
gaactcggac ctcctcacct cgcccgacgt ggggctgctc aagctggcgt cgcccgagct   1200
ggagcgcctg ataatccagt ccagcaacgg gcacatcacc accacgccga cccccaccca   1260
gttcctgtgc cccaagaacg tgacagatga gcaggagggc ttcgccgagg gcttcgtgcg   1320
cgccctggcc gaactgcaca gccagaacac gctgcccagc gtcacgtcgg cggcgcagcc   1380
ggtcaacggg gcaggcatgg tggctcccgc ggtagcctcg gtggcagggg gcagcggcag   1440
cggcggcttc agcgccagcc tgcacagcga gccgccggtc tacgcaaacc tcagcaactt   1500
caacccaggc gcgctgagca gcggcggcgg ggcgccctcc tacggcgcgg ccggcctggc   1560
ctttcccgcg caaccccagc agcagcagca gccgccgcac cacctgcccc agcagatgcc   1620
cgtgcagcac ccgcggctgc aggccctgaa ggaggagcct cagacagtgc ccgagatgcc   1680
cggcgagaca ccgcccctgt cccccatcga catggagtcc caggagcgga tcaaggcgga   1740
gaggaagcgc atgaggaacc gcatcgctgc ctccaagtgc cgaaaaaagga agctggagag  1800
aatcgcccgg ctggaggaaa aagtgaaaac cttgaaagct cagaactcgg agctggcgtc   1860
cacggccaac atgctcaggg aacaggtggc acagcttaaa cagaaagtca tgaaccacgt   1920
taacagtggg tgccaactca tgctaacgca gcagttgcaa acattttgaa gagagaccgt   1980
cgggggctga ggggcaacga agaaaaaaaa taacacagag agacagactt gagaacttga   2040
caagttgcga cggagagaaa aaagaagtgt ccgagaacta aagccaaggg tatccaagtt   2100
ggactgggtt gcgtcctgac ggcgccccca gtgtgcacga gtgggaagga cttggcgcgc   2160
cctcccttgg cgtggagcca gggagcggcc gcctgcgggc tgccccgctt tgcggacggg   2220
ctgtccccgc gcgaacggaa cgttggactt ttcgttaaca ttgaccaaga actgcatgga   2280
cctaacattc gatctcattc agtattaaag gggggagggg gagggggtta caaactgcaa   2340
```

-continued

```
tagagactgt agattgcttc tgtagtactc cttaagaaca caaagcgggg ggagggttgg   2400

ggaggggcgg caggagggag gtttgtgaga gcgaggctga gcctacagat gaactctttc   2460

tggcctgcct tcgttaactg tgtatgtaca tatatatatt ttttaatttg atgaaagctg   2520

attactgtca ataaacagct tcatgccttt gtaagttatt tcttgtttgt ttgtttgggt   2580

atcctgccca gtgttgtttg taaataagag atttggagca ctctgagttt accatttgta   2640

ataaagtata taattttttt atgttttgtt tctgaaaatt ccagaaagga tatttaagaa   2700

aatacaataa actattggaa agtactcccc taacctcttt tctgcatcat ctgtagatac   2760

tagctatcta ggtggagttg aaagagttaa gaatgtcgat taaaatcact ctcagtgctt   2820

cttactatta agcagtaaaa actgttctct attagacttt agaaataaat gtacctgatg   2880

tacctgatgc tatggtcagg ttatactcct cctcccccag ctatctatat ggaattgctt   2940

accaaaggat agtgcgatgt ttcaggaggc tggaggaagg ggggttgcag tggagaggga   3000

cagcccactg agaagtcaaa catttcaaag tttggattgt atcaagtggc atgtgctgtg   3060

accatttata atgttagtag aaattttaca ataggtgctt attctcaaag caggaattgg   3120

tggcagattt tacaaaagat gtatccttcc aatttggaat cttctctttg acaattccta   3180

gataaaaaga tggcctttgc ttatgaatat ttataacagc attcttgtca caataaatgt   3240

attcaaatac caat                                                     3254
```

<210> SEQ ID NO 63
<211> LENGTH: 3254
<212> TYPE: DNA
<213> ORGANISM: Homo sapiens

<400> SEQUENCE: 63

```
agagttgcac tgagtgtggc tgaagcagcg aggcgggagt ggaggtgcgc ggagtcaggc     60

agacagacag acacagccag ccagccaggt cggcagtata gtccgaactg caaatcttat    120

tttcttttca ccttctctct aactgcccag agctagcgcc tgtggctccc gggctggtgt    180

ttcgggagtg tccagagagc ctggtctcca gccgcccccg ggaggagagc cctgctgccc    240

aggcgctgtt gacagcggcg gaaagcagcg gtacccacgc gcccgccggg ggaagtcggc    300

gagcggctgc agcagcaaag aactttcccg gctgggagga ccggagacaa gtggcagagt    360

cccggagcca acttttgcaa gcctttcctg cgtcttaggc ttctccacgg cggtaaagac    420

cagaaggcgg cggagagcca cgcaagagaa gaaggacgtg cgctcagctt cgctcgcacc    480

ggttgttgaa cttgggcgag cgcgagccgc ggctgccggg cgccccctcc ccctagcagc    540

ggaggagggg acaagtcgtc ggagtccggg cggccaagac ccgccgccgg ccggccactg    600

cagggtccgc actgatccgc tccgcgggga gagccgctgc tctgggaagt gagttcgcct    660

gcggactccg aggaaccgct gcgcacgaag agcgctcagt gagtgaccgc gacttttcaa    720

agccgggtag cgcgcgcgag tcgacaagta agagtgcggg aggcatctta attaaccctg    780

cgctccctgg agcgagctgg tgaggagggc gcagcgggga cgacagccag cgggtgcgtg    840

cgctcttaga gaaactttcc ctgtcaaagg ctccgggggg cgcgggtgtc ccccgcttgc    900

cacagccctg ttgcggcccc gaaacttgtg cgcgcagccc aaactaacct cacgtgaagt    960

gacggactgt tctatgactg caaagatgga aacgaccttc tatgacgatg ccctcaacgc   1020

ctcgttcctc ccgtccgaga gcggacctta tggctacagt aaccccaaga tcctgaaaca   1080

gagcatgacc ctgaacctgg ccgacccagt ggggagcctg aagccgcacc tccgcgccaa   1140
```

-continued

```
gaactcggac ctcctcacct cgcccgacgt ggggctgctc aagctggcgt cgcccgagct   1200
ggagcgcctg ataatccagt ccagcaacgg gcacatcacc accacgccga cccccaccca   1260
gttcctgtgc cccaagaacg tgacagatga gcaggagggc ttcgccgagg gcttcgtgcg   1320
cgccctggcc gaactgcaca gccagaacac gctgcccagc gtcacgtcgg cggcgcagcc   1380
ggtcaacggg gcaggcatgg tggctcccgc ggtagcctcg gtggcagggg gcagcggcag   1440
cggcggcttc agcgccagcc tgcacagcga gccgccggtc tacgcaaacc tcagcaactt   1500
caacccaggc gcgctgagca gcggcggcgg ggcgccctcc tacggcgcgg ccggcctggc   1560
ctttcccgcg caaccccagc agcagcagca gccgccgcac cacctgcccc agcagatgcc   1620
cgtgcagcac ccgcggctgc aggccctgaa ggaggagcct cagacagtgc ccgagatgcc   1680
cggcgagaca ccgcccctgt cccccatcga catggagtcc caggagcgga tcaaggcgga   1740
gaggaagcgc atgaggaacc gcatcgctgc ctccaagtgc cgaaaaagga agctggagag   1800
aatcgcccgg ctggaggaaa aagtgaaaac cttgaaagct cagaactcgg agctggcgtc   1860
cacggccaac atgctcaggg aacaggtggc acagcttaaa cagaaagtca tgaaccacgt   1920
taacagtggg tgccaactca tgctaacgca gcagttgcaa acattttgaa gagagaccgt   1980
cgggggctga ggggcaacga agaaaaaaaa taacacagag agacagactt gagaacttga   2040
caagttgcga cggagagaaa aaagaagtgt ccgagaacta aagccaaggg tatccaagtt   2100
ggactgggtt gcgtcctgac ggcgccccca gtgtgcacga gtgggaagga cttggcgcgc   2160
cctcccttgg cgtggagcca gggagcggcc gcctgcgggc tgccccgctt tgcggacggg   2220
ctgtccccgc gcgaacggaa cgttggactt ttcgttaaca ttgaccaaga actgcatgga   2280
cctaacattc gatctcattc agtattaaag gggggagggg gagggggtta caaactgcaa   2340
tagagactgt agattgcttc tgtagtactc cttaagaaca caaagcgggg ggagggttgg   2400
ggaggggcgg caggagggag gtttgtgaga gcgaggctga gcctacagat gaactctttc   2460
tggcctgcct tcgttaactg tgtatgtaca tatatatatt ttttaatttg atgaaagctg   2520
attactgtca ataaacagct tcatgccttt gtaagttatt tcttgtttgt ttgtttgggt   2580
atcctgccca gtgttgtttg taaataagag atttggagca ctctgagttt accatttgta   2640
ataaagtata taattttttt atgttttgtt tctgaaaatt ccagaaagga tatttaagaa   2700
aatacaataa actattggaa agtactcccc taacctcttt tctgcatcat ctgtagatac   2760
tagctatcta ggtggagttg aaagagttaa gaatgtcgat taaaatcact ctcagtgctt   2820
cttactatta agcagtaaaa actgttctct attagacttt agaaataaat gtacctgatg   2880
tacctgatgc tatggtcagg ttatactcct cctcccccag ctatctatat ggaattgctt   2940
accaaaggat agtgcgatgt ttcaggaggc tggaggaagg ggggttgcag tggagaggga   3000
cagcccactg agaagtcaaa catttcaaag tttggattgt atcaagtggc atgtgctgtg   3060
accatttata atgttagtag aaattttaca ataggtgctt attctcaaag caggaattgg   3120
tggcagattt tacaaaagat gtatccttcc aatttggaat cttctctttg acaattccta   3180
gataaaaaga tggcctttgc ttatgaatat ttataacagc attcttgtca caataaatgt   3240
attcaaatac caat                                                     3254
```

<210> SEQ ID NO 64
<211> LENGTH: 1832
<212> TYPE: DNA
<213> ORGANISM: Homo sapiens

<400> SEQUENCE: 64

-continued

```
gtgccgctcc ttggtggggg ctgttcatgg cggttccggg gtctccaaca tttttcccgg     60

ctgtggtcct aaatctgtcc aaagcagagg cagtggagct tgaggttctt gctggtgtga    120

aatgactgag tacaaactgg tggtggttgg agcaggtggt gttgggaaaa gcgcactgac    180

aatccagcta atccagaacc actttgtaga tgaatatgat cccaccatag aggattctta    240

cagaaaacaa gtggttatag atggtgaaac ctgtttgttg gacatactgg atacagctgg    300

acaagaagag tacagtgcca tgagagacca atacatgagg acaggcgaag gcttcctctg    360

tgtatttgcc atcaataata gcaagtcatt tgcggatatt aacctctaca gggagcagat    420

taagcgagta aaagactcgg atgatgtacc tatggtgcta gtgggaaaca agtgtgattt    480

gccaacaagg acagttgata caaaacaagc ccacgaactg gccaagagtt acgggattcc    540

attcattgaa acctcagcca agaccagaca gggtgttgaa gatgcttttt acacactggt    600

aagagaaata cgccagtacc gaatgaaaaa actcaacagc agtgatgatg ggactcaggg    660

ttgtatggga ttgccatgtg tggtgatgta acaagatact tttaaagttt tgtcagaaaa    720

gagccacttt caagctgcac tgacaccctg gtcctgactt ccctggagga gaagtattcc    780

tgttgctgtc ttcagtctca cagagaagct cctgctactt ccccagctct cagtagttta    840

gtacaataat ctctatttga gaagttctca gaataactac ctcctcactt ggctgtctga    900

ccagagaatg cacctcttgt tactccctgt tatttttctg ccctgggttc ttccacagca    960

caaacacacc tctgccaccc caggtttttc atctgaaaag cagttcatgt ctgaaacaga   1020

gaaccaaacc gcaaacgtga aattctattg aaaacagtgt cttgagctct aaagtagcaa   1080

ctgctggtga ttttttttt ctttttactg ttgaacttag aactatgcta atttttggag   1140

aaatgtcata aattactgtt ttgccaagaa tatagttatt attgctgttt ggtttgttta   1200

taatgttatc ggctctattc tctaaactgg catctgctct agattcataa atacaaaaat   1260

gaatactgaa ttttgagtct atcctagtct tcacaacttt gacgtaatta aatccaactt   1320

tcacagtgaa gtgccttttt cctagaagtg gtttgtagac ttcctttata atatttcagt   1380

ggaatagatg tctcaaaaat ccttatgcat gaaatgaatg tctgagatac gtctgtgact   1440

tatctaccat tgaaggaaag ctatatctat ttgagagcag atgccatttt gtacatgtat   1500

gaaattggtt ttccagaggc ctgttttggg gctttcccag gagaaagatg aaactgaaag   1560

cacatgaata atttcactta ataattttta cctaatctcc actttttca taggttacta    1620

cctatacaat gtatgtaatt tgtttcccct agcttactga taaacctaat attcaatgaa   1680

cttccatttg tattcaaatt tgtgtcatac cagaaagctc tacatttgca gatgttcaaa   1740

tattgtaaaa ctttggtgca ttgttattta atagctgtga tcagtgattt tcaaacctca   1800

aatatagtat attaacaaat tacattttca ct                                 1832
```

<210> SEQ ID NO 65
<211> LENGTH: 3890
<212> TYPE: DNA
<213> ORGANISM: Homo sapiens

<400> SEQUENCE: 65

```
atgaaggtga taagcttatt cattttggtg ggatttatag gagagttcca aagtttttca     60

agtgcctcct ctccagtcaa ctgccagtgg gacttctatg ccccttggtc agaatgcaat    120

ggctgtacca agactcagac tcgcaggcgg tcagttgctg tgtatgggca gtatggaggc    180

cagccttgtg ttggaaatgc ttttgaaaca cagtcctgtg aacctacaag aggatgtcca    240
```

-continued

```
acagaggagg gatgtggaga gcgtttcagg tgcttttcag gtcagtgcat cagcaaatca    300
ttggtttgca atggggattc tgactgtgat gaagacagtg ctgatgaaga cagatgtgag    360
gactcagaaa ggagaccttc ctgtgatatc gataaacctc ctcctaacat agaacttact    420
ggaaatggtt acaatgaact cactggccag tttaggaaca gagtcatcaa taccaaaagt    480
tttggtggtc aatgtagaaa ggtgtttagt ggggatggaa aagatttcta caggctgagt    540
ggaaatgtcc tgtcctatac attccaggtg aaaataaata atgattttaa ttatgaattt    600
tacaatagta cttggtctta tgtaaaacat acgtcgacag aacacacatc atctagtcgg    660
aagcgctcct tttttagatc ttcatcatct tcttcacgca gttatacttc acataccaat    720
gaaatccata aaggaaagag ttaccaactg ctggttgttg agaacactgt tgaagtggct    780
cagttcatta ataacaatcc agaattttta caacttgctg agccattctg gaaggagctt    840
tcccacctcc cctctctgta tgactacagt gcctaccgaa gattaatcga ccagtacggg    900
acacattatc tgcaatctgg gtcgttagga ggagaataca gagttctatt ttatgtggac    960
tcagaaaaat taaaacaaaa tgattttaat tcagtcgaag aaaagaaatg taaatcctca   1020
ggttggcatt ttgtcgttaa attttcaagt catggatgca aggaactgga aaacgcttta   1080
aaagctgctt caggaaccca gaacaatgta ttgcgaggag aaccgttcat cagaggggga   1140
ggtgcaggct tcatatctgg ccttagttac ctagagctgg acaatcctgc tggaaacaaa   1200
aggcgatatt ctgcctgggc agaatctgtg actaatcttc ctcaagtcat aaaacaaaag   1260
ctgacacctt tatatgagct ggtaaaggaa gtaccttgtg cctctgtgaa aaaactatac   1320
ctgaaatggg ctcttgaaga gtatctggat gaatttgacc cctgtcattg ccggccttgt   1380
caaaatggtg gtttggctac tgttgagggg acccattgtc tgtgccattg caaaccgtac   1440
acatttggtg cggcgtgtga gcaaggagtc ctcgtaggga atcaagcagg aggggttgat   1500
ggaggttgga gttgctggtc ctcttggagc ccctgtgtcc aagggaagaa aacaagaagc   1560
cgtgaatgca ataacccacc tcccagtggg ggtgggagat cctgcgttgg agaaacgaca   1620
gaaagcacac aatgcgaaga tgaggagctg gagcacttga ggttgcttga accacattgc   1680
tttcctttgt ctttggttcc aacagaattc tgtccatcac ctcctgcctt gaaagatgga   1740
tttgttcaag atgaaggtcc aatgtttcct gtggggaaaa atgtagtgta cacttgcaat   1800
gaaggatact ctcttattgg aaacccagtg gccagatgtg gagaagattt acggtggctt   1860
gttggggaaa tgcattgtca gaaaattgcc tgtgttctac ctgtactgat ggatggcata   1920
cagagtcacc cccaaaaacc tttctacaca gttggtgaga aggtgactgt ttcctgttca   1980
ggtggcatgt ccttagaagg tccttcagca tttctctgtg gctccagcct taagtggagt   2040
cctgagatga agaatgcccg ctgtgtacaa aaagaaaatc cgttaacaca ggcagtgcct   2100
aaatgtcagc gctgggagaa actgcagaat tcaagatgtg tttgtaaaat gccctacgaa   2160
tgtggacctt ccttggatgt atgtgctcaa gatgagagaa gcaaaaggat actgcctctg   2220
acagtttgca agatgcatgt tctccactgt cagggtagaa attacaccct tactggtagg   2280
gacagctgta ctctgcctgc ctcagctgag aaagcttgtg gtgcctgccc actgtgggga   2340
aaatgtgatg ctgagagcag caaatgtgtc tgccgagaag catcggagtg cgaggaagaa   2400
gggtttagca tttgtgtgga agtgaacggc aaggagcaga cgatgtctga gtgtgaggcg   2460
ggcgctctga gatgcagagg gcagagcatc tctgtcacca gcataaggcc ttgtgctgcg   2520
gaaacccagt aggctcctgg aggccatggt cagcttgctt ggaatccagc aggcagctgg   2580
ggctgagtga aaacatctgc acaactgggc actggacagc ttttccttct tctccagtgt   2640
```

-continued

```
ctaccttcct cctcaactcc cagccatctg tataaacaca atcctttgtt ctcccaaatc   2700

tgaatcgaat tactcttttg cctccttttt aatgtcagta aggatatgag cctttgcaca   2760

ggctggctgc gtgttcttga aataggtgtt accttctctg ggccttggtt ttttaaaatc   2820

tgtaaaatta gaggattgca ctagagaaac ttgaatgctc cattcaggcc tatcatttta   2880

ttaagtatga ttgacacagc ccatgggcca gaacacactc tacaaaatga ctaggataac   2940

agaaagaacg tgatctcctg attagagagg gtggttttcc tcaatggaac caaatataaa   3000

gaggacttga acaaaaatga cagatacaaa ctatttctat cctgagtagt aatctcacac   3060

ttcatcctat agagtcaacc accacagata ggaattcctt attctttttt taattttttt   3120

aagacagagt ctcactttgt tgcccaggct ggagcgcagt ggggtgatct catctccctg   3180

caacctccgc ctcctgggtt gaagcgattc ttgtgcctca gcttcccaag cagctgggat   3240

tacaggtgcc cgccaccacg cccagctaat ttttgcattt ttagtagaga tgggtttcac   3300

catgttggcc atgctcgtct ccaactcctg acctcaggta atccgtctgc cttggcctcc   3360

caaatgctgg gattacagac atgaaccacc acgcctggct ggaatactta ctcttgtcgg   3420

gagattgaac cactaaaatg ttagagcaga attcattatg ctgtggtcac aggggtgtct   3480

tgtctgagaa caaatacaat tcagtcttct ctttggggtt ttagtatgtg tcaaacatag   3540

gactggaagt ttgcccctgt tctttttttct tttgaaagaa catcagttca tgcctgaggc   3600

atgagtgact gtgcatttga gatagttttc cctattctgt ggatacagtc ccagagtttt   3660

cagggagtac acaggtagat tagtttgaag cattgacctt ttatttattc cttatttctc   3720

tttcatcaaa acaaaacagc agctgtggga ggagaaatga gagggcttaa atgaaattta   3780

aaataagcta tattatacaa atactatctc tgtattgttc tgaccctggt aaatatattt   3840

caaaacttca gatgacaagg attagaacac tcattaagat gctattcttc              3890
```

<210> SEQ ID NO 66
<211> LENGTH: 725
<212> TYPE: DNA
<213> ORGANISM: Homo sapiens

<400> SEQUENCE: 66

```
ctaacccaga aacatccaat tctcaaactg aagctcgcac tctcgcctcc agcatgaaag     60

tctctgccgc ccttctgtgc ctgctgctca tagcagccac cttcattccc caagggctcg    120

ctcagccaga tgcaatcaat gccccagtca cctgctgtta taacttcacc aataggaaga    180

tctcagtgca gaggctcgcg agctatagaa gaatcaccag cagcaagtgt cccaaagaag    240

ctgtgatctt caagaccatt gtggccaagg agatctgtgc tgaccccaag cagaagtggg    300

ttcaggattc catggaccac ctggacaagc aaacccaaac tccgaagact tgaacactca    360

ctccacaacc caagaatctg cagctaactt attttcccct agctttcccc agacaccctg    420

ttttatttta ttataatgaa ttttgtttgt tgatgtgaaa cattatgcct taagtaatgt    480

taattcttat ttaagttatt gatgttttaa gtttatcttt catggtacta gtgtttttta    540

gatacagaga cttggggaaa ttgcttttcc tcttgaacca cagttctacc cctgggatgt    600

tttgagggtc tttgcaagaa tcattaatac aaagaatttt ttttaacatt ccaatgcatt    660

gctaaaatat tattgtggaa atgaatattt tgtaactatt acaccaaata aatatatttt    720

tgtac                                                                725
```

<210> SEQ ID NO 67

-continued

<211> LENGTH: 3451
<212> TYPE: DNA
<213> ORGANISM: Homo sapiens
<220> FEATURE:
<221> NAME/KEY: misc_feature
<222> LOCATION: (841)..(1027)
<223> OTHER INFORMATION: n is a, c, g, or t
<220> FEATURE:
<221> NAME/KEY: misc_feature
<222> LOCATION: (1081)..(1225)
<223> OTHER INFORMATION: n is a, c, g, or t

<400> SEQUENCE: 67

```
ttcaatgttg atgtgaaaaa ttcaatgact ttcagcggcc cggtggaaga catgtttgga     60
tatactgttc aacaatatga aaatgaagaa ggaaaatggg tgcttattgg ttctccgtta    120
gttggccaac ccaaaaacag aactggagat gtctataagt gtccagttgg gagaggtgaa    180
tcattacctt gcgtaaagtt ggatctacca gttaatacat caattcccaa tgtcacagaa    240
gtaaaggaga acatgacatt tggatcaact ttagtcacca acccaaatgg aggatttctg    300
gcttgtgggc ccttatatgc ctatagatgt ggacatttgc attacacaac tggaatctgt    360
tctgacgtca gccccacatt tcaagtcgtg aattccattg cccctgtaca agaatgcagc    420
actcaactgg acatagtcat agtgctggat ggttccaaca gtatttaccc atgggacagt    480
gttacagctt ttttaaatga ccttcttgaa agaatggata ttggtcctaa acagacacag    540
gttggaattg tacagtatgg agaaaacgtg acccatgagt tcaacctcaa taagtattct    600
tccaccgaag aggtacttgt tgcagcaaag aaaatagtcc agagaggtgg ccgccagact    660
atgacagctc ttggaataga cacagcaaga aaggaggcat tcacggaagc ccggggtgcc    720
cgaagaggag ttaaaaaagt catggttatt gtgacagatg gagagtctca tgacaatcat    780
cgactgaaga aggtcatcca agactgtgaa gatgaaaaca ttcaacggtt ttccatagct    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnctt catatgaaat ggaaatgtct cagactggct tcagtgctca ttattcacag   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnngttac actgtaaact ctgctactgc ttcttctgga   1260
gatgtgctct atattgctgg acagcctcgg tacaatcata caggccaggt cattatctac   1320
aggatggaag atggaaacat caaaattctc cagacgctca gtggagaaca gattggttcc   1380
tactttggca gtattttaac aacaactgac attgacaagg attctaatac tgacattctt   1440
ctagtcggag cccctatgta catgggaaca gagaaggagg agcaaggaaa agtgtatgtg   1500
tatgctctca atcagacaag gtttgaatat caaatgagcc tggaacctat taagcagacg   1560
tgctgttcat ctcggcagca caattcatgc acaacagaaa acaaaaatga gccatgcggg   1620
gctcgttttg gaactgcaat tgctgctgta aaagacctca atcttgatgg atttaatgac   1680
atcgtgatag gagctccgct ggagatgatc acgggggagc tgtgtacatt tatcatggaa   1740
gtggcaagac tataaggaaa gagtatgcac aacgtattcc atcaggtggg gatggtaaga   1800
cactgaaatt ttttggccag tctatccacg gagaaatgga tttaaatggt gacggtctga   1860
cagatgtgac tattgggggc cttggtggtg ctgccctctt ctggtcccga gatgtggccg   1920
tagttaaagt gaccatgaat tttgagccaa ataaagtgaa tattcaaaag aaaaactgcc   1980
```

-continued atatggaggg aaaggaaaca gtatgcataa atgctacagt gtgttttgat gtgaaattaa 2040
agtctaaaga agacacgatt tatgaagctg atttgcagta ccgtgtcacc ctagattcac 2100
taagacaaat atcacgaagt tttttctctg gaactcaaga gagaaaggtt caaaggaaca 2160
tcacagttcg aaaatcagaa tgcactaagc actccttcta catgttgaca agcatgactt 2220
tcaggactct gtgagaataa cgttggactt taatcttacc gatccagaaa atgggcctgt 2280
tcttgatgat tctctaccaa actcagtaca tgaatatatt ccctttgcca aagattgtgg 2340
aaataaggaa aaatgtatct cagacctcag cctgcatgtc gccaccactg aaaaggacct 2400
gctgattgtc cgatcccaga atgataagtt caacgttagc ctcacagtca aaaatacaaa 2460
ggacagtgcc tataacacca ggacaatagt gcattattct ccaaatctag ttttttcagg 2520
aattgaggct atccaaaaag acagttgtga atctaatcat aatatcacat gtaaagttgg 2580
atatcccttc ctgagaagag gagagatggt aactttcaaa atattgtttc agtttaacac 2640
atcctatctc atggaaaatg tgaccattta tttaagtgca acaagtgaca gcgaagaacc 2700
tcctgaaacc ctttctgata atgtagtaaa catttctatc ccggtaaaat atgaagttgg 2760
actacagttt tacagctctg caagtgaata ccacatttca attgctgcca atgagacagt 2820
ccctgaagtt attaattcta ctgaggacat tggaaatgaa attaatatct tctacttgat 2880
tagaaaaagt ggatcttttc caatgccaga gcttaagctg tcaatttcat tccccaatat 2940
gacatcaaat ggttaccctg tgctgtaccc aactggattg tcatcttctg agaatgcaaa 3000
ctgcagaccc catatctttg aggatccttt cagtatcaac tctggaaaga aaatgactac 3060
atcaactgac catctcaaac gaggcacaat tctggactgc aatacatgta aatttgctac 3120
catcacatgt aatctcactt cttctgacat cagccaagtc aatgtttcgc ttatcttgtg 3180
gaaaccaact tttataaaat catatttttc cagcttaaat cttactataa ggggagaact 3240
tcggagtgaa aatgcatctc tggttttaag tagcagcaat caaaaaagag agcttgctat 3300
tcaaatatcc aaagatgggc taccgggcag agtgccatta tgggtcatcc tgctgagtgc 3360
ttttgccgga ttgttgctgt taatgctgct cattttagca ctgtggaaga ttggattctt 3420
caaaagacca ctgaaaaaga aaatggagaa a 3451

<210> SEQ ID NO 68
<211> LENGTH: 1772
<212> TYPE: DNA
<213> ORGANISM: Homo sapiens

<400> SEQUENCE: 68
gtatcactca gaatctggca gccagttccg tcctgacaga gttcacagca tatattggtg 60
gattcttgtc catagtgcat ctgctttaag aattaacgaa agcagtgtca agacagtaag 120
gattcaaacc atttgccaaa aatgagtcta agtgcattta ctctcttcct ggcattgatt 180
ggtggtacca gtggccagta ctatgattat gattttcccc tatcaattta tgggcaatca 240
tcaccaaact gtgcaccaga atgtaactgc cctgaaagct acccaagtgc catgtactgt 300
gatgagctga aattgaaaag tgtaccaatg gtgcctcctg gaatcaagta tcttttacctt 360 aggaataacc agattgacca tattgatgaa aaggcctttg agaatgtaac tgatctgcag 420
tggctcattc tagatcacaa ccttctagaa aactccaaga taaaagggag agttttctct 480
aaattgaaac aactgaagaa gctgcatata aaccacaaca acctgacaga gtctgtgggc 540
ccacttccca aatctctgga ggatctgcag cttactcata acaagatcac aaagctgggc 600

-continued

```
tcttttgaag gattggtaaa cctgaccttc atccatctcc agcacaatcg gctgaaagag     660

gatgctgttt cagctgcttt taaaggtctt aaatcactcg aatatacttga cttgagcttc    720

aatcagatag ccagactgcc ttctggtctc cctgtctctc ttctaactct ctacttagac     780

aacaataaga tcagcaacat ccctgatgag tatttcaagc gttttaatgc attgcagtat     840

ctgcgtttat ctcacaacga actggctgat agtggaatac ctggaaattc tttcaatgtg     900

tcatccctgg ttgagctgga tctgtcctat aacaagctta aaaacatacc aactgtcaat     960

gaaaaccttg aaaactatta cctggaggtc aatcaacttg agaagtttga cataaagagc    1020

ttctgcaaga tcctggggcc attatcctac tccaagatca agcatttgcg tttggatggc    1080

aatcgcatct cagaaaccag tcttccaccg gatatgtatg aatgtctacg tgttgctaac    1140

gaagtcactc ttaattaata tctgtatcct ggaacaatat tttatggtta tgtttttctg    1200

tgtgtcagtt ttcatagtat ccatatttta ttactgttta ttacttccat gaattttaaa    1260

atctgaggga aatgttttgt aaacatttat ttttttaaa gaaaagatga aaggcaggcc      1320

tatttcatca caagaacaca cacatataca cgaatagaca tcaaactcaa tgctttattt    1380

gtaaatttag tgttttttta tttctactgt caaatgatgt gcaaaacctt ttactggttg    1440

catggaaatc agccaagttt tataatcctt aaatcttaat gttcctcaaa gcttggatta    1500

aatacatatg gatgttactc tcttgcacca aattatcttg atacattcaa atttgtctgg    1560

ttaaaaaata ggtggtagat attgaggcca agaatattgc aaaatacatg aagcttcatg    1620

cacttaaaga agtattttta gaataagaat ttgcatactt acctagtgaa acttttctag    1680

aattattttt cactctaagt catgtatgtt tctctttgat tatttgcatg ttatgtttaa    1740

taagctacta gcaaaataaa acatagcaaa tg                                  1772
```

<210> SEQ ID NO 69
<211> LENGTH: 2198
<212> TYPE: DNA
<213> ORGANISM: Homo sapiens

<400> SEQUENCE: 69

```
tggacagagg agcagtaaca atccccactc tccaattgtg gaagagttcc aagtcccata      60

caacaaactc caggtgatct ttaagtcaga cttttccaat gaagagcgtt ttacggggtt     120

tgctgcatac tatgttgcca cagacataaa tgaatgcaca gattttgtag atgtcccttg     180

tagccacttc tgcaacaatt tcattggtgg ttacttctgc tcctgccccc cggaatattt     240

cctccatgat gacatgaaga attgcggagt taattgcagt ggggatgtat tcactgcact     300

gattggggag attgcaagtc ccaattatcc caaaccatat ccagagaact caaggtgtga     360

ataccagatc cggttggaga aagggttcca agtggtggtg accttgcgga gagaagattt     420

tgatgtggaa gcagctgact cagcgggaaa ctgccttgac agtttagttt ttgttgcagg     480

agatcggcaa tttggtcctt actgtggtca tggattccct gggcctctaa atattgaaac     540

caagagtaat gctcttgata tcatcttcca aactgatcta acagggcaaa aaaagggctg     600

gaaacttcgc tatcatggag atccaatgcc ctgccctaag gaagacactc ccaattctgt     660

ttgggagcct gcgaaggcaa aatatgtctt tagagatgtg gtgcagataa cctgtctgga     720

tgggtttgaa gttgtggagg gacgtgttgg tgcaacatct ttctattcga cttgtcaaag     780

caatggaaag tggagtaatt ccaaactgaa atgtcaacct gtggactgtg gcattcctga     840

atccattgag aatggtaaag ttgaagaccc agagagcact ttgtttggtt ctgtcatccg     900

ctacacttgt gaggagccat attactacat ggaaaatgga ggaggtgggg agtatcactg     960
```

-continued

```
tgctggtaac gggagctggg tgaatgaggt gctgggcccg gagctgccga aatgtgttcc   1020
aggtctgtgg agtccccaga gaacccctttg aagaaaaaca gaggataatt ggaggatccg   1080
atgcagatat taaaaacttc ccctggcaag tcttctttga caacccatgg gctggtggag   1140
cgctcattaa tgagtactgg gtgctgacgg ctgctcatgt tgtggaggga aacagggagc   1200
caacaatgta tgttgggtcc acctcagtgc agacctcacg gctggcaaaa tccaagatgc   1260
tcactcctga gcatgtgttt attcatccgg gatggaagct gctggaagtc ccagaaggac   1320
gaaccaattt tgataatgac attgcactgg tgcggctgaa agacccagtg aaaatgggac   1380
ccaccgtctc tcccatctgc ctaccaggca cctcttccga ctacaacctc atggatgggg   1440
acctgggact gatctcaggc tggggccgaa cagagaagag agatcgtgct gttcgcctca   1500
aggcggcaag gttacctgta gctcctttaa gaaaatgcaa agaagtgaaa gtggagaaac   1560
ccacagcaga tgcagaggcc tatgttttca ctcctaacat gatctgtgct ggaggagaga   1620
agggcatgga tagctgtaaa ggggacagtg gtggggcctt tgctgtacag gatcccaatg   1680
acaagaccaa attctacgca gctggcctgg tgtcctgggg gccccagtgt gggacctatg   1740
ggctctacac acgggtaaag aactatgttg actggataat gaagactatg caggaaaata   1800
gcaccccccg tgaggactaa tccagataca tcccaccagc ctctccaagg gtggtgacca   1860
atgcattacc ttctgttcct tatgatattc tcattatttc atcatgactg aaagaagaca   1920
cgagcgaatg atttaaatag aacttgattg ttgagacgcc ttgctagagg tagagtttga   1980
tcatagaatt gtgctggtca tacatttgtg gtctgactcc ttggggtcct ttccccggag   2040
tacctattgt agataacact atgggtgggg cactcctttc ttgcactatt ccacagggat   2100
accttaattc tttgtttcct ctttacctgt tcaaaattcc atttacttga tcattctcag   2160
tatccactgt ctatgtacaa taaaggatgt ttataagc                           2198

<210> SEQ ID NO 70
<211> LENGTH: 2177
<212> TYPE: DNA
<213> ORGANISM: Homo sapiens

<400> SEQUENCE: 70

aaactctgat ctggggagga accaggacta catagatcaa ggcagttttc ttctttgaga     60
aactatccca gatatcatca tagagtcttc tgctcttcct caactaccaa agaaaaacat    120
cagcgaagca gcaggccatg caccccccaa aaactccatc tggggctctt catagaaaaa    180
ggaaaatggc agcctggccc ttctccaggc tgtggaaagt ctctgatcca attctcttcc    240
aaatgacctt gatcgctgct ctgttgcctg ctgttcttgg caattgtggt cctccaccca    300
ctttatcatt tgctgccccg atggatatta cgttgactga gacacgcttc aaaactggaa    360
ctactctgaa atacacctgc ctccctggct acgtcagatc ccattcaact cagacgctta    420
cctgtaattc tgatggcgaa tgggtgtata acaccttctg tatctacaaa cgatgcagac    480
acccaggaga gttacgtaat gggcaagtag agattaagac agatttatct tttggatcac    540
aaatagaatt cagctgttca gaaggatttt tcttaattgg ctcaaccact agtcgttgtg    600
aagtccaaga tagaggagtt ggctggagtc atcctctccc acaatgtgaa attgtcaagt    660
gtaagcctcc tccagacatc aggaatggaa ggcacagcgg tgaagaaaat ttctacgcat    720
acggcttttc tgtcacctac agctgtgacc cccgcttctc actcttgggc catgcctcca    780
tttcttgcac tgtggagaat gaaacaatag gtgtttggag accaagccct cctacctgtg    840
```

-continued

```
aaaaaatcac ctgtcgcaag ccagatgttt cacatgggga aatggtctct ggatttggac    900

ccatctataa ttacaaagac actattgtgt ttaagtgcca aaaaggtttt gttctcagag    960

gcagcagtgt aattcattgt gatgctgata gcaaatggaa tccttctcct cctgcttgtg   1020

agcccaatag ttgtattaat ttaccagaca ttccacatgc ttcctgggaa acatatccta   1080

ggccgacaaa agaggatgtg tatgttgttg ggactgtgtt aaggtaccgc tgtcatcctg   1140

gctacaaacc cactacagat gagcctacga ctgtgatttg tcagaaaaat ttgagatgga   1200

ccccatacca aggatgtgag gcgttatgtt gccctgaacc aaagctaaat aatggtgaaa   1260

tcactcaaca caggaaaagt cgtcctgcca atcactgtgt ttatttctat ggagatgaga   1320

tttcattttc atgtcatgag accagtaggt tttcagctat atgccaagga gatggcacgt   1380

ggagtccccg aacaccatca tgtggagaca tttgcaattt tcctcctaaa attgcccatg   1440

ggcattataa acaatctagt tcatacagct ttttcaaaga agagattata tatgaatgtg   1500

ataaaggcta cattctggtc ggacaggcga aactctcctg cagttattca cactggtcag   1560

ctccagcccc tcaatgtaaa gctctgtgtc ggaaaccaga attagtgaat ggaaggttgt   1620

ctgtggataa ggatcagtat gttgagcctg aaaatgtcac catccaatgt gattctggct   1680

atggtgtggt tggtccccaa agtatcactt gctctgggaa cagaacctgg tacccagagg   1740

tgcccaagtg tgagtgggag acccccgaag gctgtgaaca agtgctcaca ggcaaaagac   1800

tcatgcagtg tctcccaaac ccagaggatg tgaaaatggc cctggaggta tataagctgt   1860

ctctggaaat tgaacaactg gaactacaga gagacagcgc aagacaatcc actttggata   1920

aagaactata atttttctca aaagaaggag gaaaaggtgt cttgctggct tgcctcttgc   1980

aattcaatac agatcagttt agcaaatcta ctgtcaattt ggcagtgata ttcatcataa   2040

taaatatcta gaaatgataa tttgctaaag tttagtgctt tgagattgtg aaattattaa   2100

tcatcctctg tgtggctcat gtttttgctt ttcaacacac aaagcacaaa tttttttttcg   2160

attaaaaatg tatgtat                                                  2177
```

<210> SEQ ID NO 71
<211> LENGTH: 387
<212> TYPE: DNA
<213> ORGANISM: Homo sapiens
<220> FEATURE:
<221> NAME/KEY: misc_feature
<222> LOCATION: (27)..(53)
<223> OTHER INFORMATION: n is a, c, g, or t

<400> SEQUENCE: 71

```
gccctgctgg ccctgctggt gctcccnnnn nnnnnnnnnn nnnnnnnnnn nnnggtcctc     60

aaggcccacg tggtgacaaa ggtgaaacag gtgaacgtgg agctgctggc atcaaaggac    120

atcgaggatt ccctggtaat ccaggtgccc caggttctcc agggccctgc tggtcagcag    180

ggtgcaatcg gcagtccagg acctgcaggc cccagaggac ctgttggacc cagtggacct    240

cctggcaaag atggaaccag tggacatcca ggtcccattg gaccaccagg gcctcgaggt    300

aacagaggtg aaagaggatc tgagggctcc ccaggccacc cagggcaacc aggccctcct    360

ggacctcctg gtgcccctgg tccttgc                                        387
```

<210> SEQ ID NO 72
<211> LENGTH: 14749
<212> TYPE: DNA
<213> ORGANISM: Homo sapiens
<220> FEATURE:
<221> NAME/KEY: misc_feature -continued
<222> LOCATION: (4989)..(4997)
<223> OTHER INFORMATION: n is a, c, g, or t
<220> FEATURE:
<221> NAME/KEY: misc_feature
<222> LOCATION: (10041)..(10537)
<223> OTHER INFORMATION: n is a, c, g, or t
<220> FEATURE:
<221> NAME/KEY: misc_feature
<222> LOCATION: (11852)..(11893)
<223> OTHER INFORMATION: n is a, c, g, or t

<400> SEQUENCE: 72
gggcgcgggg agagggcgcg ggagcggctc gcgcggcagg taccatgcgg acgcgcgagc 60
ccggcgaggg ccccggcagg cccggtccct gctcgggggc gcgctgagac ggcgggtgag 120
ctccacgaga gcgccgtcgc cacttcgggc caactttgcg attcccgaca gttaagcaat 180
ggggagacat ttggctttgc tcctgcttct gctccttctc ttccaacatt ttggagacag 240
tgatggcagc caacgacttg aacagactcc tctgcagttt acacacctcg agtacaacgt 300
caccgtgcag gagaactctg cagctaagac ttatgtgggg catcctgtca agatgggtgt 360
ttacattaca catccagcgt gggaagtaag gtacaaaatt gtttccggag acagtgaaaa 420
cctgttcaaa gctgaagagt acattctcgg agacttttgc tttctaagaa taaggaccaa 480
aggaggaaat acagctattc ttaatagaga agtgaaggat cactacacat tgatagtgaa 540
agcacttgaa aaaaatacta atgtggaggc gcgaacaaag gtcagggtgc aggtgctgga 600
tacaaatgac ttgagaccgt tattctcacc cacctcatac agcgtttctt tacctgaaaa 660
cacagctata aggaccagta tcgcaagagt cagcgccacg gatgcagaca taggaaccaa 720
cggggaattt tactacagtt ttaaagatcg aacagatatg tttgctattc acccaaccag 780
tggtgtgata gtgttaactg gtagacttga ttacctagag accaagctct atgagatgga 840
aatcctcgct gcggaccgtg gcatgaagtt gtatgggagc agtggcatca gcagcatggc 900
caagctaacg gtgcacatcg aacaggccaa tgaatgtgct ccggtgataa cagcagtgac 960
attgtcacca tcagaactgg acagggaccc agcatatgca attgtgacag tggatgactg 1020
cgatcagggt gccaatggtg acatagcatc tttaagcatc gtggcaggtg accttctcca 1080
gcagtttaga acagtgaggt cctttccagg gagtaaggag tataaagtca aagccatcgg 1140
tggcattgat tgggacagtc atcctttcgg ctacaatctc acactacagg ctaaagataa 1200
aggaactccg ccccagttct cttctgttaa agtcattcac gtgacttctc cacagttcaa 1260
agccgggcca gtcaagtttg aaaaggatgt ttacagagca gaaataagtg aatttgctcc 1320
tcccaacaca cctgtggtca tggtaaaggc cattcctgct tattcccatt tgaggtatgt 1380
ttttaaaagt acacctggaa aagctaaatt cagtttaaat tacaacactg gtctcatttc 1440
tattttagaa ccagttaaaa gacagcaggc agcccatttt gaacttgaag taacaacaag 1500
tgacagaaaa gcgtccacca aggtcttggt gaaagtctta ggtgcaaata gcaatccccc 1560
tgaatttacc cagacagcgt acaaagctgc ttttgatgag aacgtgccca ttggtactac 1620
tgtcatgagc ctgagtgccg tagaccctga tgagggtgag aacgggtacg tgacatacag 1680
tatcgcaaat ttaaatcatg tgccgtttgc gattgaccat ttcactggtg ccgtgagtac 1740
gtcagaaaac ctggactacg aactgatgcc tcgggtttat actctgagga ttcgtgcatc 1800
agactggggc ttgccgtacc gccgggaagt cgaagtcctt gctacaatta ctctcaataa 1860
cttgaatgac aacacacctt tgtttgagaa aataaattgt gaagggacaa ttcccagaga 1920
tctaggcgtg ggagagcaaa taaccactgt ttctgctatt gatgcagatg aacttcagtt 1980

-continued

```
ggtacagtat cagattgaag ctggaaatga actggatttc tttagtttaa accccaactc   2040
gggggtattg tcattaaagc gatcgctaat ggatggctta ggtgcaaagg tgtctttcac   2100
agtctgagaa tcacagctac agatggagaa aattttgcca caccattata tatcaacata   2160
acagtggctg ccagtcacaa gctggtaaac ttgcagtgtg aagagactgg tgttgccaaa   2220
atgctggcag agaagctcct gcaggcaaat aaattacaca accagggaga ggtggaggat   2280
attttcttcg attctcactc tgtcaatgct cacataccgc agtttagaag cactcttccg   2340
actggtattc aggtaaagga aaaccagcct gtgggttcca gtgtaatttt catgaactcc   2400
actgaccttg acactggctt caatggaaaa ctggtctatg ctgtttctgg aggaaatgag   2460
gatagttgct tcatgattga tatggaaaca ggaatgctga aaattttatc tcctcttgac   2520
cgtgaaacaa cagacaaata caccctgaat attaccgtct atgaccttgg gataccccag   2580
aaggctgcgt ggcgtcttct acatgtcgtg gttgtcgatg ccaatgataa tccacccgag   2640
tttttacagg agagctattt tgtggaagtg agtgaagaca aggaggtaca tagtgaaatc   2700
atccaggttg aagccacaga taaagacctg gggcccaacg gacacgtgac gtactcaatt   2760
gttacagaca cagacacatt ttcaattgac agcgtgacgg gtgttgttaa catcgcacgc   2820
cctctggatc gagagctgca gcatgagcac tccttaaaga ttgaggccag ggaccaagcc   2880
agagaagagc ctcagctgtt ctccactgtc gttgtgaaag tatcactaga agatgttaat   2940
gacaacccac ctacatttat tccacctaat tatcgtgtga aagtccgaga ggatcttcca   3000
gaaggaaccg tcatcatgtg gttagaagcc cacgatcctg atttaggtca gtctggtcag   3060
gtcagcacac agccttctgg accacggaga aggaaacttc gatgtggata aactcagtgg   3120
agcagttagg atcgtccagc agttggactt tgagaagaag caagtgtata atctcactgt   3180
gagggccaaa gacaagggaa agccagtttc tctgtcttct acttgctatg ttgaagttga   3240
ggtggttgat gtgaatgaga acctgcaccc acccgtgttt tccagctttg tggaaaaggg   3300
gacagtgaaa gaagatgcac ctgttggttc attggtaatg acggtgtcgg ctcatgatga   3360
ggacgccaga agagatgggg agatccgata ctccattaga gatggctctg gcgttggtgt   3420
tttcaaaata ggtgaagaga caggtgtcat agagacgtca gatcgactgg accgtgaatc   3480
gacctcccat tattggctaa cagtctttgc aaccgatcag ggtgtcgtgc ctctttcatc   3540
gttcatagag atctacatag aggttgagga tgtcaatgac aatgcaccac agacatcaga   3600
gcctgtttat tacccagaaa tcatggaaaa ttctcctaaa gatgtatctg tggtccagat   3660
cgaggcattt gatccagatt cgagctctaa tgacaagctc atgtacaaaa ttacaagtgg   3720
aaatccacaa ggattctttt caatacatcc taaaacaggt ctcatcacaa ctacgtcaag   3780
gaagctagac cgagaacagc aagatgaaca catattagag gttactgtga cagacaatgg   3840
tagtcccccc aaatcaacca ttgcaagagt cattgtgaaa atccttgatg aaaatgacaa   3900
caaacctcag tttctgcaaa agttctacaa aatcagactc cctgagcggg aaaagccaga   3960
ccgagaaaga aatgccagac gggagccgct ctatcgcgtc atagccaccg acaaggatga   4020
gggccccaat gcagaaatct cctacagcat cgaagacggg aatgagcatg gcaaattttt   4080
catcgaaccg aaaactggag tggtttcgtc caagaggttt tcagcagctg gagaatatga   4140
tattctttca attaaggcag ttgacaatgg tcgccctcaa aagtcatcaa ccaccagact   4200
ccatattgaa tggatctcca agcccaaacc gtccctggag cccatttcat ttgaagaatc   4260
attttttacc tttactgtga tggaaagtga ccccgttgct cacatgattg gagtaatatc   4320
tgtggagcct cctggcatac ccctttggtt tgacatcact ggtggcaact acgacagtca   4380
```

-continued

```
cttcgatgtg gacaagggaa ctggaaccat cattgttgcc aaacctcttg atgcagaaca   4440
gaagtcaaac tacaacctca cagtcgaggc tacagatgga accaccacta tcctcactca   4500
ggtattcatc aaagtaatag acacaaatga ccatcgtcct cagttttcta catcaaagta   4560
tgaagttgtt attcctgaag atacagcgcc agaaacagaa attttgcaaa tcagtgctgt   4620
ggatcaggat gagaaaaaca aactaatcta cactctgcag agcagtagag atccactgag   4680
tctcaagaaa tttcgtcttg atcctgcaac cggctctctc tatacttctg agaaactgga   4740
tcatgaagct gttcaccagc acaccctcac ggtcatggta cgagatcaag atgtgcctgt   4800
aaaacgcaac tttgcaagga ttgtggtcaa tgtcagcgac acgaatgacc acgccccgtg   4860
gttcaccgct tcctcctaca aagggcgggt ttatgaatcg gcagccgttg gctcagttgt   4920
gttgcaggtg acggctctgg acaaggacaa agggaaaaat gctgaagtgc tgtactcgat   4980
cgagtcagnn nnnnnnngaa atattggaaa ttcttttatg attgatcctg tcttgggctc   5040
tattaaaact gccaaagaat tagatcgaag taaccaagcg gagtatgatt taatggtaaa   5100
agctacagat aagggcagtc caccaatgag tgaaataact tctgtgcgta tctttgtcac   5160
aattgctgac aacgcctctc cgaagtttac atcaaaagaa tattctgttg aacttagtga   5220
aactgtcagc attgggagtt tcgttgggat ggttacagcc catagtcaat catcagtggt   5280
gtatgaaata aaagatggaa atacaggtga tgcttttgat attaatccac attctggaac   5340
tatcatcact cagaaagccc tggactttga aactttgccc atttacacat tgataataca   5400
aggaactaac atggctggtt tgtccactaa tacaacggtt ctagttcact tgcaggatga   5460
gaatgacaac gcgccagttt ttatgcaggc agaatataca ggactcatta gtgaatcagc   5520
ctcaattaac agcgtggtcc taacagacag gaatgtccca ctggtgattc gagcagctga   5580
tgctgataaa gactcaaatg ctttgcttgt atatcacatt gttgaaccat ctgtacacac   5640
atattttgct attgattcta gcactggtgc tattcataca gtactaagtc tggactatga   5700
agaaacaagt atttttcact ttaccgtcca agtgcatgac atgggaaccc cacgtttatt   5760
tgctgagtat gcagcgaatg taacagtaca tgtaattgac attaatgact gccccctgt    5820
gtttgccaag ccattatatg aagcatctct tttgttacca acatacaaag gagtaaaagt   5880
catcacagta aatgctacag atgctgattc aagtgcattc tcacagttga tttactccat   5940
caccgaaggc aacatcgggg agaagttttc tatggactac aagactggtg ctctcactgt   6000
ccaaaacaca actcagttaa gaagccgcta cgagctaacc gttagagctt ccgatggcag   6060
atttgccggc cttacctctg tcaaaattaa tgtgaaagaa agcaaagaaa gtcacctaaa   6120
gtttacccag gatgtctact ctgcggtagt gaaagagaat tccaccgagg ccgaaacatt   6180
agctgtcatt actgctattg ggaatccaat caatgagcct ttgttttatc acatcctcaa   6240
cccagatcgc agatttaaaa taagccgcac ttcaggagtt ctgtcaacca ctggcacgcc   6300
cttcgatcgt gagcagcagg aggcgtttga tgtggttgta gaagtgacag aggaacataa   6360
gccttctgca gtggcccacg ttgtcgtgaa ggtcattgta gaagaccaaa atgataatgc   6420
gccggtgttt gtcaaccttc cctactacgc cgttgttaaa gtggacactg aggtgggcca   6480
tgtcattcgc tatgtcactg ctgtagacag agacagtggc agaaacgggg aagtgcatta   6540
ctacctcaag gaacatcatg aacactttca aattggaccc ttgggtgaaa tttcactgaa   6600
aaagcaattt gagcttgaca ccttaaataa agaatatctt gttacagtgg ttgcaaaaga   6660
tggagggaac ccggcctttt cagcggaagt tatcgttccg atcactgtca tgaataaagc   6720
```

-continued

```
catgcctgtg tttgaaaaac ctttctacag tgcagagatt gcagagagca tccaggtgca   6780
cagccctgtg gtccacgtgc aggctaacag cccggaaggc ctgaaagtgt tctacagcat   6840
cacagacgga gaccctttca gccagttcac tattaacttc aatactggag ttatcaatgt   6900
catagctcct ctggactttg aggcccaccc ggcatataag ctgagcatac gcgcaactga   6960
ctccttgacg ggcgctcatg ctgaagtatt tgtggacatc atagtagacg acatcaatga   7020
taaccctcct gtgtttgctc agcagtctta tgcggtgacc ctgtctgagg catctgtaat   7080
tggaacgtct gttgttcaag ttagagccac cgattctgat tcagaaccaa atagaggaat   7140
ctcataccag atgtttggga atcacagcaa gagtcatgat cattttcatg tagacagcag   7200
cactggcctc atctcactac tcagaaccct ggattacgag cagtcccggc agcacacgat   7260
ttttgtgagg gcagttgatg gtggtatgcc cacgctgagc agtgatgtga ttgtcacggt   7320
ggacgttacc gacctcaatg ataatccacc actctttgaa caacagattt atgaagccag   7380
aattagcgag cacgcccctc atgggcattt cgtgacctgt gtaaaagcct atgatgcaga   7440
cagttcagac atagacaagt tgcagtattc cattctgtct ggcaatgatc ataaacattt   7500
tgtcattgac agtgcaacag ggattatcac cctctcaaac ctgcaccggc acgccctgaa   7560
gccattttac agtcttaacc tgtcagtgtc tgatggagtt tttagaagtt ccacccaggt   7620
tcatgtaact gtaattggag gcaatttgca cagtcctgct ttccttcaga acgaatatga   7680
agtggaacta gctgaaaacg ctcccctaca taccctggtg atggaggtga aaactacgga   7740
tggggattct ggtatttatg gtcacgttac ttaccatatt gtaaatgact ttgccaaaga   7800
cagattttac ataaatgaga gaggacagat atttactttg gaaaaacttg atcgagaaac   7860
cccggcggag aaagtgatct cagtccgttt aatggctaag gatgctggag gaaaagttgc   7920
tttctgcacc gtgaatgtca tccttacaga tgacaatgac aatgcaccac aatttcgagc   7980
aaccaaatac gaagtgaata tcgggtccag tgctgctaaa gggacttcag tcgttaaagt   8040
tcttgcaagt gatgccgatg agggctccaa tgccgacatc acctatgcca ttgaagcaga   8100
ctctgaaagt gtaaaagaga atttggaaat taacaaactg tccggcgtaa tcactacaaa   8160
ggagagcctc attggcttgg aaaatgaatt cttcactttc tttgttagag ctgtggataa   8220
tgggtctcca tcaaaagaat ctgttgttct tgtctatgtt aaaatccttc caccggaaat   8280
gcagcttcca aaattttcag aacctttcta tacctttaca gtgtcagagg acgtgcctat   8340
tggaacagag atagatctca tccgagcaga acatagtggg actgttcttt acagcctggt   8400
caaagggaat actccagaaa gcaataggga tgagtccttt gtgattgaca gacagagcgg   8460
gagactgaag ttggagaaga gtcttgatca tgagacaact aagtggtatc agttttccat   8520
actggccagg tgcactcaag atgaccatga gatggtggct tctgtagatg ttagtatcca   8580
agtgaaagat gcaaatgaca acagcccggt ctttgaatct agtccatatg aggcattcat   8640
tgttgaaaac ctgccagggg gaagtagagt aattcagatc agggcatctg atgctgactc   8700
aggaaccaac ggccaagtta tgtatagcct ggatcagtca caaagtgtgg aagtcattga   8760
atcctttgcc attaacatgg aaacaggctg gattacaact ttaaaggaac ttgaccatga   8820
aaagagagac aattaccaga ttaaagtggt tgcatcagat catggtgaaa agatccagct   8880
atcctccaca gccattgtgg atgttaccgt caccgatgtc aacgatagtc caccacgatt   8940
cacggccgag atctataaag ggactgtgag tgaggatgac ccccaaggtg ggggtgattgc  9000
catcttaagt accacggatg ctgattctga agagatcaac agacaagtta catatttcat   9060
aacaggaggg gatcctttag gacagtttgc cgttgaaact atacagaatg aatggaaggt   9120
```

-continued

```
atatgtgaag aaacctctag acagggaaaa aagggacaat taccttctta ctatcacggc   9180
aactgatggc accttctcat caaaagcgat agttgaagtg aaagttctgg atgcaaatga   9240
caacagtcca gtttgtgaaa agactttata ttcagacact attcctgaag acgtccttcc   9300
tggaaaattg atcatgcaga tctctgctac agacgcagac atccgctcta acgctgaaat   9360
tacttacacg ttattgggtt caggtgcaga aaaattcaaa ctaaatccag acacaggtga   9420
actgaaaacg tcaacccccc ttgatcgtga ggagcaagct gtttatcatc ttctcgtcag   9480
ggccacagat ggaggaggaa gattctgcca agccagtatt gtgctcacgc tagaagatgt   9540
gaacgataac gcccccgaat tctctgccga tccttatgcc atcaccgtgt ttgaaaacac   9600
agagccggga acgctgctga caagagtgca ggccacagat gccgacgcag gattaaatcg   9660
gaagatttta tactcactga ttgactctgc tgatgggcag ttctccatta acgaattatc   9720
tggaattatt cagttagaaa aacctttgga cagagaactc caggcagtat acaccctctc   9780
tttgaaagct gtggatcaag gcttgccaag gaggctgact gccactggca ctgtgattgt   9840
atcagttctt gacataaatg acaacccccc tgtgtttgag taccgtgaat atggtgccac   9900
cgtgtctgag gacattcttg ttggaactga agttcttcaa gtgtatgcag caagtcggga   9960
tattgaagca aatgcagaaa tcacctactc aataataagt ggaaatgaac atgggaaatt  10020
cagcatagat tctaaaacag nnnnnnnnnn nnnnnnnnnn nnnnnnnnnn nnnnnnnnnn  10080
nnnnnnnnnn nnnnnnnnnn nnnnnnnnnn nnnnnnnnnn nnnnnnnnnn nnnnnnnnnn  10140
nnnnnnnnnn nnnnnnnnnn nnnnnnnnnn nnnnnnnnnn nnnnnnnnnn nnnnnnnnnn  10200
nnnnnnnnnn nnnnnnnnnn nnnnnnnnnn nnnnnnnnnn nnnnnnnnnn nnnnnnnnnn  10260
nnnnnnnnnn nnnnnnnnnn nnnnnnnnnn nnnnnnnnnn nnnnnnnnnn nnnnnnnnnn  10320
nnnnnnnnnn nnnnnnnnnn nnnnnnnnnn nnnnnnnnnn nnnnnnnnnn nnnnnnnnnn  10380
nnnnnnnnnn nnnnnnnnnn nnnnnnnnnn nnnnnnnnnn nnnnnnnnnn nnnnnnnnnn  10440
nnnnnnnnnn nnnnnnnnnn nnnnnnnnnn nnnnnnnnnn nnnnnnnnnn nnnnnnnnnn  10500
nnnnnnnnnn nnnnnnnnnn nnnnnnnnnn nnnnnnngaa aataagccag tgggcttcag  10560
cgtgctgcag ctggtagtaa cagatgagga ttcttcccat aacggtccac ccttcttctt  10620
tactattgta actggaaatg atgagaaggc ttttgaagtt aacccgcaag gagtcctcct  10680
gacatcatct gccatcaaga ggaaggagaa agatcattac ttactgcagg tgaaggtggc  10740
agataatgga aagcctcagt tgtcatcttt gacatacatt gacattaggg taattgagga  10800
gagcatctat ccgcctgcga ttttgcccct ggagattttc atcacctctt ctggagaaga  10860
atactcaggt ggcgtcattg ggaagatcca tgccacagac caggacgtgt atgatactct  10920
aacctacagt ctcgaccctc agatggacaa cctgttctct gtttccagca caggggggcaa  10980
gctgatagca cacaaaaagc tagacatagg gcaatacctt ctcaatgtca gcgtaacaga  11040
tgggaagttc acgacggtgg ccgacatcac agtgcatatc agacaagtca cacaggagat  11100
gttgaaccac accatcgcga tccgctttgc caacctcact ccggaagaat tcgttggtga  11160
ctactggcgc aacttccagc gagctttacg gaacatcctg ggtgtgagga ggaacgacat  11220
acagattgtt agtttgcagt cctctgaacc tcacccacat ctggacgtct tactttttgt  11280
agagaaacca ggtagtgctc agatctcaac aaaacaactt ctgcacaaga ttaactcttc  11340
cgtgactgac attgaggaaa tcattggagt taggatactg aatgtattcc agaaactctg  11400
cgcgggactg gactgcccct ggaagttctg cgatgaaaag gtgtctgtgg atgaaagtgt  11460
```

-continued

```
gatgtcaaca cacagcacag ccagactgag ttttgtgact ccccgccacc acagggcagc  11520
ggtgtgtctc tgcaaagagg gaaggtgccc acctgtccac catggctgtg aagatgatcc  11580
gtgccctgag ggatccgaat gtgtgtctga tccctgggag gagaaacaca cctgtgtctg  11640
tcccagcggc aggtttggtc agtgcccagg gagttcatct atgacactga ctggaaacag  11700
ctacgtgaaa taccgtctga cggaaaatga aaacaaatta gagatgaaac tgaccatgag  11760
gctcagaaca tattccacgc atgcggttgt catgtatgct cgaggaactg actatagcat  11820
cttggagatt catcatggaa ggtgcagtca annnnnnnnn nnnnnnnnnn nnnnnnnnnn  11880
nnnnnnnnnn nnncattcag gtcaatgatg ggcagtggca cgcagtggcc ctggaagtga  11940
atggaaacta tgctcgcttg gttctagacc aagttcatac tgcatcgggc acagccccag  12000
ggactctgaa aaccctgaac ctggataact atgtgttttt tggtggccac atccgtcagc  12060
agggaacaag gcatggaaga agtcctcaag ttggtaatgg tttcaggggt tgtatggact  12120
ccatttattt gaatgggcag gagctccctt taaacagcaa acccagaagc tatgcacaca  12180
tcgaagagtc ggtggatgta tctccaggct gcttcctgac ggccacggaa gactgcgcca  12240
gcaacccttg ccagaatgga ggcgtttgca atccgtcacc tgctggaggt tattactgca  12300
aatgcagtgc cttgtacata gggacccact gtgagataag cgtcaatccg tgttcctcca  12360
agccatgcct ctatgggggc acgtgtgttg tcgacaacgg aggctttgtt tgccagtgta  12420
gaggattata tactggtcag aggtgtcagc ttagtccata ctgcaaagat gaaccctgta  12480
agaatggcgg aacatgcttt gacagtttgg atggcgccgt ttgtcagtgt gattcgggtt  12540
ttaggggaga aaggtgtcag agtgatatcg acgagtgctc tggaaaccct tgcctgcacg  12600
gggccctctg tgagaacacg cacggctcct atcactgcaa ctgcagccac gagtacaggg  12660
gacgtcactg cgaggatgct gcgcccaacc agtatgtgtc cacgccgtgg aacattgggt  12720
tggcggaagg aattggaatc gttgtgtttg ttgcagggat atttttactg gtggtggtgt  12780
ttgttctctg ccgtaagatg attagtcgga aaaagaagca tcaggctgaa cctaaagaca  12840
agcacctggg acccgctacg gctttcttgc aaagaccgta ttttgattcc aagctaaata  12900
agaacattta ctcagacata ccaccccagg tgcctgtccg gcctatttcc tacaccccga  12960
gtattccaag tgactcaaga aacaatctgg accgaaattc cttcgaagga tctgctatcc  13020
cagagcatcc cgaattcagc acttttaacc ccgagtctgt gcacgggcac cgaaaagcag  13080
tggcggtctg cagcgtggcg ccaaacctgc ctcccccacc cccttcaaac tccccttctg  13140
acagcgactc catccagaag cctagctggg actttgacta tgacacaaaa gtggtggatc  13200
ttgatccctg tctttccaag aagcctctag aggaaaagcc ttcccagcca tacagtgccc  13260
gggaaagcct gtctgaagtg cagtctctga gctccttcca gtccgaatcg tgcgatgaca  13320
atgggtatca ctgggataca tcagattgga tgccaagcgt tcctctgccg gacatacaag  13380
agttccccaa ctatgaggtg attgatgagc agacacccct gtactcagca gatccaaacg  13440
ccatcgatac ggactattac cctggaggct acgacatcga aagtgatttt cctccacccc  13500
cagaagactt ccccgcagct gatgagctac caccgttacc gcccgaattc agcaatcagt  13560
ttgaatccat ccaccctcct agagacatgc ctgccgcggg tagcttgggt tcttcatcaa  13620
gaaaccggca gaggttcaac ttgaatcagt atttgcccaa tttttatccc ctcgatatgt  13680
ctgaacctca aacaaaaggc actggtgaga atagtacttg tagagaaccc catgcccctt  13740
acccgccagg gtatcaaaga cacttcgagg cgcccgctgt cgagagcatg cccatgtctg  13800
tgtacgcctc caccgcctcc tgctctgacg tgtcagcctg ctgcgaagtg gagtccgagg  13860
```

-continued tcatgatgag tgactatgag agcggggacg acggccactt cgaagaggtg acgatcccgc 13920
ccctggattc ccagcagcac acggaagtct gactctcaac tccccccaaa gtgcctgact 13980
ttagtgaacc tagaggtgat gtgagtaatc cgcgctgttc tttgcagcag tgcttccaag 14040 cttttttgg tgagccgaat gggcatggct gcgctggatc ctgcgcctct ggacgtgcta 14100
gccatttcca gtgtcccaac tactgtcatc gtgaggtttt catcggctgt gccatttccc 14160
aacgtctttt gggatttaca tctgtctgtg ttaaaataat caaacgaaaa atcagtcctg 14220
tgttgtcagc atgattcatg tatttatata gatttgatta ttttaatttt cctgtctctt 14280 tttttgtaa attttatgta cagatttgat ttttcatagt tttaactaga tttccaagat 14340 atttgtgca tttgtttcaa ctgaattttg gtggtgtcag tgccattatc tagcaccctg 14400 atttttttt ttttactata accagggttt cattctgtct ttttccactg aagtgtgaca 14460
ttttgttagt acatttcagt gtagtcattc atttctagct gtacatagga tgaaggagag 14520
atcagataca tgaacatgtc ttacatgggt tgctgtattt agaattataa acatttttca 14580
ttattggaaa gtgtaacggg gaccttctgc atacctgttt agaaccaaaa ccaccatgac 14640
acagttttta tagtgtctgt atatttgtga tgcaatggtc ttgtaaaggt ttttaatgaa 14700
aactaccatt agccagtctt tcttactgac aataaattat taataaaat 14749

<210> SEQ ID NO 73
<211> LENGTH: 5508
<212> TYPE: DNA
<213> ORGANISM: Homo sapiens

<400> SEQUENCE: 73
gattttaggt gatgggcaag tcagaaagtc agatggatat aactgatatc aacactccaa 60
agccaaagaa gaaacagcga tggactccac tggagatcag cctctcggtc cttgtcctgc 120
tcctcaccat catagctgtg acaatgatcg cactctatgc aacctacgat gatggtattt 180
gcaagtcatc agactgcata aaatcagctg ctcgactgat ccaaaacatg gatgccacca 240
ctgagccttg tacagacttt ttcaaatatg cttgcggagg ctggttgaaa cgtaatgtca 300
ttcccgagac cagctcccgt tacggcaact ttgacatttt aagagatgaa ctagaagtcg 360
ttttgaaaga tgtccttcaa gaacccaaaa ctgaagatat agtagcagtg cagaaagcaa 420
aagcattgta caggtcttgt ataaatgaat ctgctattga tagcagaggt ggagaacctc 480
tactcaaact gttaccagac atatatgggt ggccagtagc aacagaaaac tgggagcaaa 540
aatatggtgc ttcttggaca gctgaaaaag ctattgcaca actgaattct aaatatggga 600
aaaaagtcct tattaatttg tttgttggca ctgatgataa gaattctgtg aatcatgtaa 660
ttcatattga ccaacctcga cttggcctcc cttctagaga ttactatgaa tgcactggaa 720
tctataaaga ggcttgtaca gcatatgtgg attttatgat ttctgtggcc agattgattc 780
gtcaggaaga aagattgccc atcgatgaaa accagcttgc tttggaaatg aataaagtta 840
tggaattgga aaaagaaatt gccaatgcta cggctaaacc tgaagatcga aatgatccaa 900
tgcttctgta taacaagatg acattggccc agatccaaaa taacttttca ctagagatca 960
atgggaagcc attcagctgg ttgaatttca caaatgaaat catgtcaact gtgaatatta 1020
gtattacaaa tgaggaagat gtggttgttt atgctccaga atatttaacc aaacttaagc 1080
ccattcttac caaatattct gccagagatc ttcaaaattt aatgtcctgg agattcataa 1140
tggatcttgt aagcagcctc agccgaacct acaaggagtc cagaaatgct ttccgcaagg 1200

-continued

```
ccctttatgg tacaacctca gaaacagcaa cttggagacg ttgtgcaaac tatgtcaatg   1260
ggaatatgga aaatgctgtg gggaggcttt atgtggaagc agcatttgct ggagagagta   1320
aacatgtggt cgaggatttg attgcacaga tccgagaagt tttattcag actttagatg    1380
acctcacttg gatggatgcc gagacaaaaa agagagctga agaaaaggcc ttagcaatta   1440
aagaaaggat cggctatcct gatgacattg tttcaaatga taacaaactg aataatgagt   1500
acctcgagtt gaactacaaa gaagatgaat acttcgagaa cataattcaa aatttgaaat   1560
tcagccaaag taaacaactg aagaagctcc gagaaaaggt ggacaaagat gagtggataa   1620
gtggagcagc tgtagtcaat gcattttact cttcaggaag aaatcagata gtcttcccag   1680
ccggcattct gcagcccccc ttctttagtg cccagcagtc caactcattg aactatgggg   1740
gcatcggcat ggtcatagga cacgaaatca cccatggctt cgatgacaat ggcagaaact   1800
ttaacaaaga tggagacctc gttgactggt ggactcaaca gtctgcaagt aactttaagg   1860
agcaatccca gtgcatggtg tatcagtatg gaaacttttc ctgggacctg gcaggtggac   1920
agcaccttaa tggaattaat acactgggag aaaacattgc tgataatgga ggtcttggtc   1980
aagcatacag agcctatcag aattatatta aaaagaatgg cgaagaaaaa ttacttcctg   2040
gacttgacct aaatcacaaa caactatttt tcttgaactt tgcacaggtg tggtgtggaa   2100
cctataggcc agagtatgcg gttaactcca ttaaaacaga tgtgcacagt ccaggcaatt   2160
tcaggattat tgggactttg cagaactctg cagagttttc agaagccttt cactgccgca   2220
agaattcata catgaatcca gaaaagaagt gccgggtttg gtgatcttca aaagaagcat   2280
tgcagccctt ggctagactt gccaacacca cagaaatggg gaattctcta atcgaaagaa   2340
aatgggccct aggggtcact gtactgactt gagggtgatt aacagagagg gcaccatcac   2400
aatacagata acattaggtt gtcctagaaa gggtgtggag ggaggaaggg ggtctaaggt   2460
ctatcaagtc aatcatttct cactgtgtac ataatgctta atttctaaag ataatattac   2520
tgtttatttc tgtttctcat atggtctacc agtttgctga tgtccctaga aaacaatgca   2580
aaacctttga ggtagaccag gatttctaat caaaagggaa aagaagatgt tgaagaatac   2640
agttaggcac cagaagaaca gtaggtgaca ctatagttta aaacacattg cctaactact   2700
agtttttact tttatttgca acatttacag tccttcaaaa tccttccaaa gaattcttat   2760
acacattggg gccttggagc ttacatagtt ttaaactcat ttttgccata catcagttat   2820
tcattctgtg atcatttatt ttaagcactc ttaaagcaaa aaatgaatgt ctaaaattgt   2880
tttttgttgt acctgctttg actgatgctg agattcttca ggcttcctgc aattttctaa   2940
gcaatttctt gctctatctc tcaaaacttg gtatttttca gagatttata taaatgtaaa   3000
aataataatt tttatattta attattaact acatttatga gtaactatta ttataggtaa   3060
tcaatgaata ttgaagtttc agcttaaaat aaacagttgt gaaccaagat ctataaagcg   3120
atatacagat gaaaatttga gactatttaa acttataaat catattgatg aaaagattta   3180
agcacaaact ttagggtaaa aattgccatt ggacagttgt ctagagatat atatacttgt   3240
ggttttcaaa ttggactttc aaaattaaat ctgtccctga gagtgtctct gataaaaggg   3300
caaatctgca cctatgtagc tctgcatctc ctgtcttttc aggtttgtca tcagatggaa   3360
atattttgat aataaattga aattgtgaac tcattgctcc ctaagactgt gacaactgtc   3420
taactttaga agtgcatttc tgaatagaaa tgggaggcct ctgatggacc ttctagaatt   3480
ataagtcaca aagagttctg gaaaagaact gtttactgct tgataggaat tcatcttttg   3540
aggcttctgt tcctctcttt tcctgttgta ttgactattt tcgttcatta cttgattaag   3600
```

-continued attttacaaa agaggagcac ttccaaaatt cttatttttc ctaacaaaag atgaaagcag 3660
ggaatttcta tctaaatgat gagtattagt tccctgtctc ttgaaaaatg cccatttgcc 3720
tttaaaaaaa aaagttacag aaatactata acatatgtac ataaattgca taaagcataa 3780
gtatacagtt caataaactt aactttaact gaacaatggc cctgtagcca gcacctgtaa 3840
gaaacagagc agtaccagcg ctctaaaagc acctccttgt cactttatta ctcccagaac 3900
aacaactatc ctgacttcta atatcattca ctagctttgc ctggttttgt cttttatgca 3960
gatagaatca atcagtatgt attcttttgt gcctggcttc tttctctcag ccttacattt 4020
gtgagattcc tctgtattgt gctgattgtg gatcttttca ttctcattgc agaataatgt 4080
tctattgtgg gacttattac aatttgttca tcctattgtt gatgggcact tgagaacttt 4140
ccattttggc gctattacaa atagtgcaac tatgaatgta ctgcatgtta ccatcttact 4200
tgagccttta atggacttat ttcttcaaat ccttccaaaa attattataa gcattgaaat 4260
tatagtttca agccaactgt ggataccctt accctttcct cctttatcac aaccaccgtt 4320
acaagtatac ttatatttcc ctaaaataca tttaaaactt acctaagtga catttgtagt 4380
tggagtaata ggagcttcca gctctaataa aacagctgtc tctaacttat tttatttcca 4440
tcatgtcaga gcaggtgaag agccagaagt gaagagtgac tagtacaaat tataaaaagc 4500
cactagactc ttcactgtta gctttttaaa acattaggct cccatcccta tggaggaaca 4560
actctccagt gcctggatcc cctctgtcta caaatataag attttctggg cctaaaggat 4620
agatcaaagt caaaaatagc aatgcctccc tatccctcac acatccagac atcatgaatt 4680
ttacatggta ctcttgttga gttctgtaga gccttctgat gtctctaaag cactaccgat 4740
tctttggagt tgtcacatca gataagacat atctctaatt ccatccataa atccagttct 4800
actatggctg agttctggtc aaagaaagaa agtttagaag ctgagacaca aagggttggg 4860
agctgatgaa actcacaaat gatggtagga agaagctctc gacaataccc gttggcaagg 4920
agtctgcctc catgctgcag tgttcgagtg gattgtaggt gcaagatgga aaggattgta 4980
ggtgcaagct gtccagagaa aagagtcctt gttccagccc tattctgcca ctcctgacag 5040
ggtgaccttg ggtatttgca atattccttt gggcctctgc ttctctcacc taaaaaaaga 5100
gaattagatt atattggtgg ttctcagcaa gagaaggagt atgtgtccaa tgctgccttc 5160
ccatgaatct gtctcccagt tatgaatcag tgggcaggat aaactgaaaa ctcccattta 5220
cgtgtctgaa tcgagtgaga caaaatttta gtccaaataa caagtaccaa agttttatca 5280
agtttgggtc tgtgctgctg ttactgttaa ccatttaagt ggggcaaaac cttgctaatt 5340
ttctcaaaag catttatcat tcttgttgcc acagctggag ctctcaaact aaaagacatt 5400
tgttattttg gaaagaagaa agactctatt ctcaaagttt cctaatcaga aatttttatc 5460
agtttccagt ctcaaaaata caaaataaaa acaaacgttt ttaatact 5508

<210> SEQ ID NO 74
<211> LENGTH: 1495
<212> TYPE: DNA
<213> ORGANISM: Homo sapiens

<400> SEQUENCE: 74
atgtccaatc agggaagtaa gtacgtcaat aaggaaattc aaaatgctgt caacggggtg 60
aaacagataa agactctcat agaaaaaaca aacgaagagc gcaagacact gctcagcaac 120
ctagaagaag ccaagaagaa gaaagaggat gccctaaatg agaccaggga atcagagaca 180

-continued

```
aagctgaagg agctcccagg agtgtgcaat gagaccatga tggccctctg ggaagagtgt    240

aagccctgcc tgaaacagac ctgcatgaag ttctacgcac gcgtctgcag aagtggctca    300

ggcctggttg gccgccagct tgaggagttc ctgaaccaga gctcgccctt ctacttctgg    360

atgaatggtg accgcatcga ctccctgctg gagaacgacc ggcagcagac gcacatgctg    420

gatgtcatgc aggaccactt cagccgcgcg tccagcatca tagacgagct cttccaggac    480

aggttcttca cccgggagcc ccaggatacc taccactacc tgcccttcag cctgccccac    540

cggaggcctc acttcttctt tcccaagtcc cgcatcgtcc gcagcttgat gcccttctct    600

ccgtacgagc ccctgaactt ccacgccatg ttccagccct tccttgagat gatacacgag    660

gctcagcagg ccatggacat ccacttccat agcccggcct tccagcaccc gccaacagaa    720

ttcatacgag aaggcgacga tgaccggact gtgtgccggg agatccgcca caactccacg    780

ggctgcctgc ggatgaagga ccagtgtgac aagtgccggg agatcttgtc tgtggactgt    840

tccaccaaca acccctccca ggctaagctg cggcgggagc tcgacgaatc cctccaggtc    900

gctgagaggt tgaccaggaa atacaacgag ctgctaaagt cctaccagtg gaagatgctc    960

aacacctcct ccttgctgga gcagctgaac gagcagttta actgggtgtc ccggctggca   1020

aacctcacgc aaggcgaaga ccagtactat ctgcgggtca ccacggtggc ttcccacact   1080

tctgactcgg acgttccttc cggtgtcact gaggtggtcg tgaagctctt tgactctgat   1140

cccatcactg tgacggtccc tgtagaagtc tccaggaaga accctaaatt tatggagacc   1200

gtggcggaga aagcgctgca ggaataccgc aaaaagcacc gggaggagtg agatgtggat   1260

gttgcttttg cacctacggg ggcatctgag tccagctccc cccaagatga gctgcagccc   1320

cccagagaga gctctgcacg tcaccaagta accaggcccc agcctccagg cccccaactc   1380

cgcccagcct ctccccgctc tggatcctgc actctaacac tcgactctgc tgctcatggg   1440

aagaacagaa ttgctcctgc atgcaactaa ttcaataaaa ctgtcttgtg agctg        1495
```

<210> SEQ ID NO 75
<211> LENGTH: 967
<212> TYPE: DNA
<213> ORGANISM: Homo sapiens

<400> SEQUENCE: 75

```
gaaggaaaaa gagcaacaga tccagggagc attcacctgc cctgtctcca aacagccttg     60

tgcctcacct acccccaacc tcccagaggg agcagctatt taaggggagc aggagtgcag    120

aacaaacaag acggcctggg gatacaactc tggagtcctc tgagagagcc accaaggagg    180

agcaggggag cgacggccgg ggcagaagtt gagaccaccc agcagaggag ctaggccagt    240

ccatctgcat ttgtcaccca agaactctta ccatgaagac cctcctactg ttggcagtga    300

tcatgatctt tggcctactg caggcccatg ggaatttggt gaatttccac agaatgatca    360

agttgacgac aggaaaggaa gccgcactca gttatggctt ctacggctgc cactgtggcg    420

tgggtggcag aggatccccc aaggatgcaa cggatcgctg ctgtgtcact catgactgtt    480

gctacaaacg tctggagaaa cgtggatgtg gcaccaaatt tctgagctac aagtttagca    540

actcggggag cagaatcacc tgtgcaaaac aggactcctg cagaagtcaa ctgtgtgagt    600

gtgataaggc tgctgccacc tgttttgcta gaaacaagac gacctacaat aaaaagtacc    660

agtactattc caataaacac tgcagaggga gcacccctcg ttgctgagtc ccctcttccc    720

tggaaacctt ccacccagtg ctgaatttcc ctctctcata ccctccctcc ctaccctaac    780

caagttcctt ggccatgcag aaagcatccc tcacccatcc tagaggccag gcaggagccc    840
```

-continued ttctataccc acccagaatg agacatccag cagatttcca gccttctact gctctcctcc 900
acctcaactc cgtgcttaac caaagaagct gtactccggg gggtctcttc tgaataaagc 960
aattagc 967

<210> SEQ ID NO 76
<211> LENGTH: 2515
<212> TYPE: DNA
<213> ORGANISM: Homo sapiens

<400> SEQUENCE: 76
gctccatcaa gtatgatggt gaaggatgaa tatgtgcatg actttgaggg acagccatcg 60
ttgtccactg aaggacattc aattcaaacc atccagcatc caccaagtaa tcgtgcatcg 120
acagagacat acagcacccc agctctgtta gccccatctg agtctaatgc taccagcact 180
gccaactttc ccaacattcc tgtggcttcc acaagtcagc ctgccagtat actgggggc 240 agccatagtg aaggactgtt gcagatagca tcagggcctc agccaggaca gcagcagaat 300
ggatttactg gtcagccagc tacttaccat cataacagca ctaccacctg gactggaagt 360
aggactgcac catacacacc taatttgcct caccaccaaa acggccatct tcagcaccac 420
ccgcctatgc cgccccatcc cggacattac tggcctgttc acaatgagct tgcattccag 480
cctcccattt ccaatcatcc tgctcctgag tattggtgtt ccattgctta ctttgaaatg 540
gatgttcagg taggagagac atttaaggtt ccttcaagct gccctattgt tactgttgat 600
ggatacgtgg acccttctgg aggagatcgc ttttgtttgg gtcaactctc caatgtccac 660
aggacagaag ccattgagag agcaaggttg cacataggca aaggtgtgca gttggaatgt 720
aaaggtgaag gtgatgtttg ggtcaggtgc cttagtgacc acgcggtctt tgtacagagt 780
tactacttag acagagaagc tgggcgtgca cctggagatg ctgttcataa gatctaccca 840
agtgcatata taaaggtctt tgatttgcgt cagtgtcatc gacagatgca gcagcaggcg 900
gctactgcac aagctgcagc agctgcccag gcagcagccg tggcaggaaa catccctggc 960
ccaggatcag taggtggaat agctccagct atcagtctgt cagctgctgc tggaattggt 1020
gttgatgacc ttcgtcgctt atgcatactc aggatgagtt ttgtgaaagg ctggggaccg 1080
gattacccaa gacagagcat caaagaaaca ccttgctgga ttgaaattca cttacaccgg 1140
gccctccagc tcctagacga agtacttcat accatgccga ttgcagaccc acaaccttta 1200
gactgaggtc ttttaccgtt ggggccctta accttatcag gatggtggac tacaaaatac 1260
aatcctgttt ataatctgaa gatatatttc acttttgttc tgctttatct tttcataaag 1320
ggttgaaaat gtgtttgctg ccttgctcct agcagacaga aactggatta aaacaatttt 1380
ttttttcctc ttcagaactt gtcaggcatg gctcagagct tgaagattag gagaaacaca 1440
ttcttattaa ttcttcacct gttatgtatg aaggaatcat tccagtgcta gaaaatttag 1500
ccctttaaaa cgtcttagag ccttttatct gcagaacatc gatatgtata tcattctaca 1560
gaataatcca gtattgctga ttttaaaggc agagaagttc tcaaagttaa ttcacctatg 1620
ttattttgtg tacaagttgt tattgttgaa catacttcaa aaataatgtg ccatgtgggt 1680
gagttaattt taccaagagt aactttactc tgtgtttaaa aagtaagtta ataatgtatt 1740
gtaatctttc atccaaaata ttttttgcaa gttatattag tgaagatggt ttcaattcag 1800
attgtcttgc aacttcagtt ttatttttgc caaggcaaaa aactcttaat ctgtgtgtat 1860
attgagaatc ccttaaaatt accagacaaa aaaatttaaa attacgtttg ttattcctag 1920

-continued

```
tggatgactg ttgatgaagt atacttttcc cctgttaaac agtagttgta ttcttctgta   1980

tttctaggca caaggttggt tgctaagaag cctataagag gaatttcttt tccttcattc   2040

atagggaaag gttttgtatt ttttaaaaca ctaaaagcag cgtcactcta cctaatgtct   2100

cactgttctg caaaggtggc aatgcttaaa ctaaataatg aataaactga atattttgga   2160

aactgctaaa ttctatgtta aatactgtgc agaataatgg aaacattaca gttcataata   2220

ggtagtttgg atatttttgt acttgatttg atgtgacttt ttttggtata atgtttaaat   2280

catgtatgtt atgatattgt ttaaaattca gtttttgtat cttggggcaa gactgcaaac   2340

tttttttatat cttttggtta ttctaagccc tttgccatca atgatcatat caattggcag   2400

tgactttgta tagagaattt aagtagaaaa gttgcagatg tattgactgt accacagaca   2460

caatatgtat gctttttacc tagctggtag cataaataaa actgaatctc aacat        2515
```

<210> SEQ ID NO 77
<211> LENGTH: 2017
<212> TYPE: DNA
<213> ORGANISM: Homo sapiens

<400> SEQUENCE: 77

```
gcaggcccgt tggaagtggt tgtgacaacc ccagcaatgt ggagaagcct ggggcttgcc     60

ctggctctct gtctcctccc atcgggagga acagagagcc aggaccaaag ctccttatgt    120

aagcaacccc cagcctggag cataagagat caagatccaa tgctaaactc caatggttca    180

gtgactgtgg ttgctcttct tcaagccagc tgatacctgt gcatactgca ggcatctaaa    240

ttagaagacc tgcgagtaaa actgaagaaa gaaggatatt ctaatatttc ttatattgtt    300

gttaatcatc aaggaatctc ttctcgatta aaatacacac atcttaagaa taaggtttca    360

gagcatattc ctgtttatca acaagaagaa aaccaaacag atgtctggac tcttttaaat    420

ggaagcaaag atgacttcct catatatgat agatgtggcc gtcttgtata tcatcttggt    480

ttgccttttt ccttcctaac tttcccatat gtagaagaag ccattaagat tgcttactgt    540

gaaaagaaat gtggaaactg ctctctcacg actctcaaag atgaagactt ttgtaaacgt    600

gtatctttgg ctactgtgga taaaacagtt gaaactccat cgcctcatta ccatcatgag    660

catcatcaca atcatggaca tcagcacctt ggcagcagtg agctttcaga gaatcagcaa    720

ccaggagcac caaatgctcc tactcatcct gctcctccag gccttcatca ccaccataag    780

cacaagggtc agcataggca gggtcaccca gagaaccgag atatgccagc aagtgaagat    840

ttacaagatt tacaaaagaa gctctgtcga aagagatgta taaatcaatt actctgtaaa    900

ttgcccacag attcagagtt ggctcctagg agctgatgct gccattgtcg acatctgata    960

tttgaaaaaa cagggtctgc aatcacctga cagtgtaaag aaaacctccc atctttatgt   1020

agctgacagg gacttcgggc agaggagaac ataactgaat cttgtcagtg acgtttgcct   1080

ccagctgcct gacaaataag tcagcagctt atacccacag aagccagtgc cagttgacgc   1140

tgaaagaatc aggcaaaaaa gtgagaatga ccttcaaact aaatatttaa aataggacat   1200

actccccaat ttagtctaga cacaatttca tttccagcat ttttataaac taccaaatta   1260

gtgaaccaaa aatagaaatt agatttgtgc aaacatggag aaatctactg aattggcttc   1320

cagattttaa attttatgtc atagaaatat tgactcaaac catatttttt atgatggagc   1380

aactgaaagg tgattgcagc ttttggttaa tatgtctttt tttttctttt tccagtgttc   1440

tatttgcttt aatgagaata gaaacgtaaa ctatgaccta ggggtttctg ttggataatt   1500

agcagtttag aatggaggaa gaacaacaaa gacatgcttt ccattttttt ctttacttat   1560
```

-continued

```
ctctcaaaac aatattactt tgtcttttca atcttctact tttaactaat aaaataagtg   1620

gattttgtat tttaagatcc agaaatactt aacacgtgaa tattttgcta aaaaagcata   1680

tataactatt ttaaatatcc atttatcttt tgtatatcta agactcatcc tgatttttac   1740

tatcacacat gaataaagcc tttgtatctt tctttctcta atgttgtatc atactcttct   1800

aaaacttgag tggctgtctt aaaagatata aggggaaaga taatattgtc tgtctctata   1860

ttgcttagta agtatttcca tagtcaatga tggtttaata ggtaaaccaa accctataaa   1920

cctgacctcc tttatggtta atactattaa gcaagaatgc agtacagaat tggatacagt   1980

acggatttgt ccaaataaat tcaataaaaa ccttaaa                            2017
```

<210> SEQ ID NO 78
<211> LENGTH: 1468
<212> TYPE: DNA
<213> ORGANISM: Homo sapiens

<400> SEQUENCE: 78

```
caaccacttg acaacctggt tagaagatgc ccgccagcat tccaattcca acatggtcat     60

tatgcttatt ggaaataaaa gtgatttaga atctagaaga gaagtaaaaa aagaagaagg    120

tgaagctttt gcacgagaac atggactcat cttcatggaa acgtctgcta agactgcttc    180

caatgtagaa gaggcattta ttaatacagc aaaagaaatt tatgaaaaaa ttcaagaagg    240

agtctttgac attaataatg aggcaaatgg cattaaaatt ggccctcagc atgctgctac    300

caatgcaaca catgcaggca atcagggagg acagcaggct gggggcggct gctgttgagt    360

ctgtttttac tgtctagctg cccaacgggg cctactcact tattctttca ccccctctcc    420

tcctgctcag ctgagacatg aaactatttg aaatggcttt atgtcacaga agactttaat    480

ccgtcaaatt cttgtataac tttgaataaa tggttaatgt tcacttaaaa gacagatttt    540

ggagattgta ttcatatcta tttgcatttg atttctaggt caattgatgt gattattttt    600

gttaaatgtt gtcttgtgcc cttaactacg aactgaattg tattaaacac tacaaagtca    660

tcttgagtat tttaaatcgg tttgtgtagt taggtttccc aacatctgtg gttacctaat    720

gtttaatatt atagaactgt cctcagaaac tttgtcaatt ttcacggcta taaggaaaca    780

gaaggactct tttaattctg tatttatcat ttactttctg tatatatagt ttaataacct    840

gcttgggtgt aatttgccaa gcttgaattc tttaatgcat ttgcataaat tctatactgt    900

ttagagctta aagctacaga agcattgtta ggaattgctt ggacactgaa ttttaaactt    960

tttgacattg ttaacaagca tgttcatctt ttcttgtcac tagtccaaga aaaatatgct   1020

taatgtatat tacaaaggct ttgtatatgt taacctgttt taatgccaaa agtttgcttt   1080

gtccacaatt tccttaagac ctcttcagaa agggatttgt ttgccttaat gaatactgtt   1140

gggaaaaaac acagtataat gagtgaaaag ggcagaagca agaaatttct acatcttagc   1200

gactccaaga agaatgagta tccacattta gatggcacat tatgaggact ttaatctttc   1260

cttaaacaca ataatgtttt ctttttcttt ttattcacat gatttctaag tatatttttc   1320

atgcaggaca gtttttcaac cttgatgtac agtgactgtg taaaattttt ctttcagtgg   1380

caacctctat aatctttaaa atatggtgag catcttgtct gttttgaagg ggatatgaca   1440

ataaatctat cagatggaaa atcctgtt                                      1468
```

<210> SEQ ID NO 79
<211> LENGTH: 3590
<212> TYPE: DNA

-continued

<213> ORGANISM: Homo sapiens

<400> SEQUENCE: 79

```
cctgggtctg acgcggccct gttcgagggg gcctctcttg tttatttatt tattttccgt     60
gggtgcctcc gagtgtgcgc gcgctctcgc tacccggcgg ggagggggtg gggggagggc    120
ccgggaaaag gggagttgg agccggggtc gaaacgccgc gtgacttgta ggtgagagaa    180
cgccgagccg tcgccgcagc ctccgccgcc gagaagccct tgttcccgct gctgggaagg    240
agagtctgtg ccgacaagat ggcggacggg gagctgaacg tggacagcct catcacccgg    300
ctgctggagg tacgaggatg tcgtccagga aagattgtgc agatgactga agcagaagtt    360
cgaggcttat gtatcaagtc tcgggagatc tttctcagcc agcctattct tttggaattg    420
gaagcaccgc tgaaaatttg tggagatatt catggacaat atacagattt actgagatta    480
tttgaatatg gaggtttccc accagaagcc aactatcttt tcttaggaga ttatgtggac    540
agaggaaagc agtctttgga aaccatttgt ttgctattgg cttataaaat caaatatcca    600
gagaacttct ttctcttaag aggaaaccat gagtgtgcta gcatcaatcg catttatgga    660
ttctatgatg aatgcaaacg aagatttaat attaaattgt ggaagacctt cactgattgt    720
tttaactgtc tgcctatagc agccattgtg gatgagaaga tcttctgttg tcatggagga    780
ttgtcaccag acctgcaatc tatggagcag attcggagaa ttatgagacc tactgatgtc    840
cctgatacag gtttgctctg tgatttgcta tggtctgatc cagataagga tgtgcaaggc    900
tggggagaaa atgatcgtgg tgtttccttt acttttggag ctgatgtagt cagtaaattt    960
ctgaatcgtc atgatttaga tttgatttgt cgagctcatc aggtggtgga agatggatat   1020
gaatttttg ctaaacgaca gttggtaacc ttattttcag ccccaaatta ctgtggcgag   1080
tttgataatg ctggtggaat gatgagtgtg gatgaaactt tgatgtgttc atttcagata   1140
ttgaaaccat ctgaaaagaa agctaaatac cagtatggtg gactgaattc tggacgtcct   1200
gtcactccac ctcgaacagc taatccgccg aagaaaaggt gaagaaagga attctgtaaa   1260
gaaaccatca gatttgttaa ggacatactt cataatatat aagtgtgcac tgtaaaacca   1320
tccagccatt tgacaccctt tatgatgtca cacctttaac ttaaggagac gggtaaagga   1380
tcttaaattt ttttctaata gaaagatgtg ctacactgta ttgtaataag tatactctgt   1440
tatagtcaac aaagttaaat ccaaattcaa aattatccat taaagttaca tcttcatgta   1500
tcacaatttt taaagttgaa aagcatccca gttaaactag atgtgatagt taaaccagat   1560
gaaagcatga tgatccatct gtgtaatgtg gttttagtgt tgcttggttg tttaattatt   1620
ttgagcttgt tttgttttg tttgttttca ctagaataat ggcaaatact tctaattttt   1680
ttccctaaac atttttaaaa gtgaaatatg ggaagagctt tacagacatt caccaactat   1740
tattttccct tgtttatcta cttagatatc tgtttaatct tactaagaaa actttcgcct   1800
cattacatta aaaaggaatt ttagagattg attgttttaa aaaaaaatac gcacattgtc   1860
caatccagtg attttaatca tacagtttga ctgggcaaac tttacagctg atagtgaata   1920
ttttgcttta tacaggaatt gacactgatt tggatttgtg cactctaatt tttaacttat   1980
tgatgctcta ttgtgcagta gcatttcatt taagataagg ctcatatagt attacccaac   2040
tagttggtaa tgtgattatg tggtaccttg gctttaggtt ttcattcgca cggaacacct   2100
tttggcatgc ttaacttcct ggtaacacct tcacctgcat tggttttctt tttcttttt   2160
ctttcttttt tttttttttt ttttttttga gttgttgttt gtttttagat ccacagtaca   2220
tgagaatcct tttttgacaa gccttggaaa gctgacactg tctcttttc ctccctctat    2280
```

-continued

```
acgaaggatg tatttaaatg aatgctggtc agtgggacat tttgtcaact atgggtattg   2340
ggtgcttaac tgtctaatat tgccatgtga atgttgtata cgattgtaag gcttatgtca   2400
ctaaagattt ttattctgat tttttcataa tcaaaggtca tatgatactg tatagacaag   2460
ctttgtagtg aagtatagta gcaataattt ctgtacctga tcaagtttat tgcagccttt   2520
cttttcctat ttcttttttt taagggttag tattaacaaa tggcaatgag tagaaaagtt   2580
aacatgaaga ttttagaagg agagaactta caggacacag atttgtgatt ctttgactgt   2640
gacactattg gatgtgattc taaaagcttt tattgagcat tgtcaaattt gtaagcttca   2700
tagggatgga catcatatct ataatgccct tctatatgtg ctaccataga tgtgacattt   2760
ttgaccttaa tatcgtcttt gaaaatgtta aattgagaaa cctgttaact tacattttat   2820
gaattggcac attgtattac ttactgcaag agatatttca ttttcagcac agtgcaaaag   2880
ttctttaaaa tgcatatgtc ttttttteta attccgtttt gttttaaagc acattttaaa   2940
tgtagttttc tcatttagta aaagttgtct aattgatatg aagcctgact gatttttttt   3000
ttccttacag tgagacattt aagcacacat tttattcaca tagatactat gtccttgaca   3060
tattgaaatg attcttttct gaaagtattc atgatctgca tatgatgtat taggttaggt   3120
cacaaaggtt ttatctgagg tgatttaaat aacttcctga ttggagtgtg taagctgagc   3180
gatttctaat aaaattttag ttgtacactt ttagtagtca tagtgaagca ggtctagaaa   3240
ataagccttt ggcagggaaa aagggcaatg ttgattaatc tcagtattaa accacattaa   3300
tctgtatccc attgtctggc ttttgtaaat tcatccaggt caagactaag tatgttggtt   3360
aataggaatc cttttttttt tttaaagact aaatgtgaaa aaataatcac tacttaagct   3420
aattaatatt ggtcattaaa tttaaaggat ggaaatttat catgtttaaa aattattcaa   3480
gcactcttaa aaccacttaa acagcctcca gtcataaaaa tgtgttcttt acaaatattt   3540
gcttggcaac acgacttgaa ataaataaaa ctttgtttct taggagaaaa              3590
```

<210> SEQ ID NO 80
<211> LENGTH: 1750
<212> TYPE: DNA
<213> ORGANISM: Homo sapiens

<400> SEQUENCE: 80

```
gcaacctgcc ccattatccc tggctgcgaa acaaccatcg agatttccaa agggcgaaca     60
gggctgggcc tgagcatcgt tgggggttca gacacgctgc tgggtgccat tattatccat    120
gaagtttatg aagaaggagc agcatgtaaa gatggaagac tctgggctgg agatcagatc    180
ttagaggtga atggaattga cttgagaaag gccacacatg atgaagcaat caatgtcctg    240
agacagacgc cacagagagt gcgcctgaca ctctacagag atgaggcccc atacaaagag    300
gaggaagtgt gtgacaccct cactattgag ctgcagaaga agccgggaaa aggcctagga    360
ttaagtattg ttggtaaaag aaacgatact ggagtatttg tgtcagacat tgtcaaagga    420
ggaattgcag atgccgatgg aagactgatg cagggagacc agatattaat ggtgaatggg    480
gaagacgttc gtaatgccac ccaagaagcg gttgccgctt tgctaaagtg ttccctaggc    540
acagtaacct tggaagttgg aagaatcaaa gctggtccat tccattcaga gaggaggcca    600
tctcaaagca gccaggtgag tgaaggcagc ctgtcatctt tcacttttcc actctctgga    660
tccagtacat ctgagtcact ggaaagtagc tcaaagaaga atgcattggc atctgaaata    720
cagggattaa gaacagtcga aatgaaaaag ggccctactg actcactggg aatcagcatt    780
```

-continued

```
gctggaggag taggcagccc acttggtgat gtgcctatat ttattgcaat gatgcaccca     840
actggagttg cagcacagac ccaaaaactc agagttgggg ataggattgt caccatctgt     900
ggcacatcca ctgagggcat gactcacacc caagcagtta acctactgaa aaatgcatct     960
ggctccattg aaatgcaggt ggttgctgga ggagacgtga gtgtggtcac aggtcatcag    1020
caggagcctg caagttccag tctttctttc actgggctga cgtcaagcag tatatttcag    1080
gatgatttag gacctcctca atgtaagtct attacactag agcgaggacc agatggctta    1140
ggcttcagta tagttggagg atatggcagc cctcatggag acttacccat ttatgttaaa    1200
acagtgtttg caaagggagc agcctctgaa gacggacgtc tgaaaagggg cgatcagatc    1260
attgctgtca atgggcagag tctagaagga gtcacccatg aagaagctgt tgccatcctt    1320
aaacggacaa aaggcactgt cactttgatg gttctctctt gaattggctg ccagaattga    1380
accaacccaa cccctagctc acctcctact gtaaagagaa tgcactggtc ctgacaattt    1440
ttatgctgtg ttcagccggg tcttcaaaac tgtagggggg aaataacact taagtttctt    1500
tttctcatct agaaatgctt tccttactga caacctaaca tcatttttct tttcttcttg    1560
cattttgtga acttaaagag aaggaatatt tgtgtaggtg aatctcgttt ttatttgtgg    1620
agatatctaa tgttttgtag tcacatgggc aagaattatt acatgctaag ctggttagta    1680
taaagaaaga taattctaaa gctaaccaaa gaaaatggct tcagtaaatt aggatgaaaa    1740
atgaaaatat                                                           1750
```

<210> SEQ ID NO 81
<211> LENGTH: 3254
<212> TYPE: DNA
<213> ORGANISM: Homo sapiens

<400> SEQUENCE: 81

```
ggagcgcaat ggcgtccaac cccgaacggg gggagattct gctcacggaa ctgcaggggg      60
attcccgaag tcttccgttt tctgagaatg tgagtgctgt tcaaaaatta gacttttcag     120
atacaatggt gcagcagaaa ttggatgata tcaaggatcg aattaagaga gaaataagga     180
aagaactgaa aatcaaagaa ggagctgaaa atctgaggaa agtcacaaca gataaaaaaa     240
gtttggctta tgtagacaac attttgaaaa aatcaaataa aaaattagaa gaactacatc     300
acaagctgca ggaattaaat gcacatattg ttgtatcaga tccagaagat attacagatt     360
gcccaaggac tccagatact ccaaataatg accctcgttg ttctactagc aacaatagat     420
tgaaggcctt acaaaaacaa ttggatatag aacttaaagt aaaacaaggt gcagagaata     480
tgatacagat gtattcaaat ggatcttcaa aggatcggaa actccatggt acagctcagc     540
aactgctcca ggacagcaag acaaaaatag aagtcatacg aatgcagatt cttcaggcag     600
tccagactaa tgaattggct tttgataatg caaaacctgt gataagtcct cttgaacttc     660
ggatggaaga attaaggcat cattttagga tagagtttgc agtagcagaa ggtgcaaaga     720
atgtaatgaa attacttggc tcaggaaaag taacagacag aaaagcactt tcagaagctc     780
aagcaagatt taatgaatca agtcagaagt tggacctttt aaagtattca ttagagcaaa     840
gattaaacga agtccccaag aatcatccca aaagcaggat tattattgaa gaactttcac     900
ttgttgctgc atcaccaaca ctaagtccac gtcaaagtat gatatctacg caaaatcaat     960
atagtacact atccaaacca gcagcactaa caggtacttt ggaagttcgt cttatgggct    1020
gccaagatat cctagagaat gtccctggac ggtcaaaagc aacatcagtt gcactgcctg    1080
gttggagtcc aagtgaaacc agatcatctt tcatgagcag aacgagtaaa agtaaaagcg    1140
```

-continued

```
gaagtagtcg aaatcttcta aaaaccgatg acttgtccaa tgatgtctgt gctgttttga   1200
agctcgataa tactgtggtt ggccaaacta gctggaaacc catttccaat cagtcatggg   1260
accagaagtt tacactggaa ctggacaggt cacgtgaact ggaaatttca gtttattggc   1320
gtgattggcg gtctctgtgt gctgtaaaat ttctgaggtt agaagatttt ttagacaacc   1380
aacggcatgg catgtgtctc tatttggaac cacagggtac tttatttgca gaggttacct   1440
tttttaatcc agttattgaa agaagaccaa aacttcaaag acaaaagaaa attttttcaa   1500
agcaacaagg caaaacattt ctcagagctc ctcaaatgaa tattaatatt gccacttggg   1560
gaaggctagt aagaagagct attcctacag taaatcattc tggcaccttc agccctcaag   1620
ctcctgtgcc tactacagtg ccagtggttg atgtacgcat ccctcaacta gcacctccag   1680
ctagtgattc tacagtaacc aaattggact ttgatcttga gcctgaacct cctccagccc   1740
caccacgagc ttcttctctt ggagaaatag atgaatcttc tgaattaaga gttttggata   1800
taccaggaca ggattcagag actgtttttg atattcagaa tgacagaaat agtatacttc   1860
caaaatctca atctgaatac aagcctgata ctcctcagtc aggcctagaa tatagtggta   1920
ttcaagaact tgaggacaga agatctcagc aaaggtttca gtttaatcta caagatttca   1980
ggtgttgtgc tgtcttggga agaggacatt ttggaaaggt gcttttagct gaatataaaa   2040
acacaaatga gatgtttgct ataaaagcct taaagaaagg agatattgtg gctcgagatg   2100
aagtagacag cctgatgtgt gaaaaaagaa tttttgaaac tgtgaatagt gtaaggcatc   2160
ccttttttggt gaaccttttt gcatgtttcc aaaccaaaga gcatgtttgc tttgtaatgg   2220
aatatgctgc cggtggggac ctaatgatgc acattcatac tgatgtcttt tctgaaccaa   2280
gagctgtatt ttatgctgct tgtgtagttc ttgggttgca gtatttacat gaacacaaaa   2340
ttgtttatag agatttgaaa ttggataact tattgctaga tacagagggc tttgtgaaaa   2400
ttgctgattt tggtctttgc aaagaaggaa tgggatatgg agatagaaca agcacatttt   2460
gtggcactcc tgaatttctt gccccagaag tattaacaga aacttcttat acaagggctg   2520
tagattggtg gggccttggc gtgcttatat atgaaatgct tgttggtgag tctccctttc   2580
ctggtgatga tgaagaggaa gtttttgaca gtattgtaaa tgatgaagta aggtatccaa   2640
ggttcttatc tacagaagcc atttctataa tgagaaggct gttaagaaga aatcctgaac   2700
ggcgccttgg ggctagcgag aaagatgcag aggatgtaaa aaagcaccca tttttccggc   2760
taattgattg gagcgctctg atggacaaaa aagtaaagcc accatttata cctaccataa   2820
gaggacgaga agatgttagt aattttgatg atgaatttac ctcagaagca cctattctga   2880
ctccacctcg agaaccaagg atactttcgg aagaggagca ggaaatgttc agagattttg   2940
actacattgc tgattggtgt taagttgcta gacactgcga aaccaagctg actcacaaga   3000
agacctctta aaaatagcaa cccttcattt gctctctgtg ccaccaatag cttctgagtt   3060
ttttgttgtt gttgttttta ttgaaacacg tgaagatttg tttaaaagta ccattctaat   3120
acttcttcaa aagtggctcc tcattgtact tcagcgtaaa tatgagcact ggaaacagtt   3180
tcatggagtt taagttgagt gaacatcggc catgaaaatc catcacgaat acttttggat   3240
caatagtcta tttt                                                      3254
```

<210> SEQ ID NO 82
<211> LENGTH: 509
<212> TYPE: DNA
<213> ORGANISM: Homo sapiens -continued

<400> SEQUENCE: 82
atgaaattca agttacatgt gaattctgcc aggcaataca aggacctgtg gaatatgagt 60
gatgacaaac cctttctatg tactgcgcct ggatgtggcc agagtgaagt caccctgctg 120
agaaatgaag tggcacagct gaaacagctt cttctggctc ataaagattg ccctgtaacc 180
gccatgcaga agaaatctgg ctatcatact gctgataaag atgatagttc agaagacatt 240
tcagtgccga gtagtccaca tacagaagct atacagcata gttcggtcag cacatccaat 300
ggagtcagtt caacctccaa ggcagaagct gtagccactt cagtcctcac ccagatggcg 360
gaccagagta cagagcctgc tctttcacag atcgttatgg ctccttcctc ccagtcacag 420
ccctcaggaa gttgattaaa aacctgcagt acaacagttt tagatactca ttagtgactt 480
caaagggaaa tcaaggaaag accagtttc 509

<210> SEQ ID NO 83
<211> LENGTH: 719
<212> TYPE: DNA
<213> ORGANISM: Homo sapiens

<400> SEQUENCE: 83
gaattctgga agttcattga agagtctgaa attagggact tatttcaaat ttggacatgg 60
ctagtcgagg cgcaacaaga cccaacggcc caaatactgg aaataaaata tgccagttca 120
aactagtact tctgggagag tccgctgttg gcaaatcaag cctagtgctt cgttttgtga 180
aaggccaatt tcatgaattt caagagagta ccattggggc tgcttttcta acccaaactg 240
tatgtcttga tgacactaca gtaaagtttg aaatctggga tacagctggt caagaaggat 300
accatagcct agcaccaatg tactacagag gagcacaagc agccatagtt gtatatgata 360
tcacaaatga ggagtccttt gcaagagcaa aaaattgggt taaagaactt cagaggcaag 420
caagtcctaa cattgtaata gctttatcgg gaaacaaggc cgacctagca aataaaagag 480
cagtagattt ccaggaagca cagtcctatg cagatgacaa tagtttatta ttcatggaga 540
catccgctaa aacatcaatg aatgtaaatg aaatattcat ggcaatagct aaaaaattgc 600
caaagaatga accacaaaat ccaggagcaa attctgccag aggaggagga gtagacctta 660
ccgaacccac acaaccaacc aggaatcagt gttgtagtaa ctaaacctct agtttgaac 719

<210> SEQ ID NO 84
<211> LENGTH: 1433
<212> TYPE: DNA
<213> ORGANISM: Homo sapiens

<400> SEQUENCE: 84
gacgctctgg gccgccacct ccgcggaccc tgagcgcaag agccaagccg ccagcgctgc 60
gatgtgggcc acgctgccgc tgctctgcgc cggggcctgg ctcctgggag tccccgtctg 120
cggtgccgcc gaactgtgcg tgaactcctt agagaagttt cacttcaagt catggatgtc 180
taagcaccgt aagacctaca gtacggagga gtaccaccac aggctgcaga cgtttgccag 240
caactggagg aagataaacg cccacaacaa tgggaaccac acatttaaaa tggcactgaa 300
ccaattttca gacatgagct ttgctgaaat aaaacacaag tatctctggt cagagcctca 360
gaattgctca gccaccaaaa gtaactacct tcgaggtact ggtccctacc caccttccgt 420
ggactggcgg aaaaaaggaa attttgtctc acctgtgaaa aatcagggtg cctgcggcag 480
ttgctggact ttctccacca ctggggccct ggagtctgcg atcgccatcg caaccggaaa 540
gatgctgtcc ttggcggaac agcagctggt ggactgcgcc caggacttca ataatcacgg 600

-continued ctgccaaggg ggtctcccca gccaggcttt cgagtatatc ctgtacaaca aggggatcat 660
gggtgaagac acctacccct accagggcaa ggatggttat tgcaagttcc aacctggaaa 720
ggccatcggc tttgtcaagg atgtagccaa catcacaatc tatgacgagg aagcgatggt 780
ggaggctgtg gccctctaca accctgtgag ctttgccttt gaggtgactc aggacttcat 840
gatgtataga accggcatct actccagtac ttcctgccat aaaactccag ataaagtaaa 900
ccatgcagta ctggctgttg ggtatggaga aaaaaatggg atcccttact ggatcgtgaa 960
aaactcttgg ggtccccagt ggggaatgaa cgggtacttc ctcatcgagc gcggaaagaa 1020
catgtgtggc ctggctgcct gcgcctccta ccccatccct ctggtgtgag ccgtggcagc 1080
cgcagcgcag actggcggag aaggagagga acgggcagcc tgggcctggg tggaaatcct 1140
gccctggagg aagttgtggg gagatccact gggaccccca acattctgcc ctcacctctg 1200
tgcccagcct ggaaacctac agacaaggag gagttccacc atgagctcac ccgtgtctat 1260
gacgcaaaga tcaccagcca tgtgccttag tgtccttctt aacagactca aaccacatgg 1320
accacgaata ttctttctgt ccagaagggc tactttccac atatagagct ccagggactg 1380
tcttttctgt attcgctgtt caataaacat tgagtgagca cctccccaga tgg 1433

<210> SEQ ID NO 85
<211> LENGTH: 2093
<212> TYPE: DNA
<213> ORGANISM: Homo sapiens

<400> SEQUENCE: 85
ggtcggggcc cgcggccgct cgcgcctctc gatgggcagc tcgcacttgc tcaacaaggg 60
cctgccgctt ggcgtccgac ctccgatcat gaacgggccc ctgcacccgc ggcccctggt 120
ggcattgctg gatggccggg actgcacagt ggagatgccc atcctgaagg acgtggccac 180
tgtggccttc tgcgacgcgc agtccacgca ggagatccat gagaaggtcc tgaacgaggc 240
tgtgggggcc ctgatgtacc acaccatcac tctcaccagg gaggacctgg agaagttcaa 300
agccctccgc atcatcgtcc ggattggcag tggttttgac aacatcgaca tcaagtcggc 360
cggggattta ggcattgccg tctgcaacgt gcccgcggcg tctgtggagg agacggccga 420
ctcgacgctg tgccacatcc tgaacctgta ccggcgggcc acctggctgc accaggcgct 480
gcgggagggc acacgagtcc agagcgtcga gcagatccgc gaggtggcgt ccggcgctgc 540
caggatccgc ggggagacct tggcatcat cggacttgtc gcgtggggca ggcagtggcg 600
ctgcgggcca aggccttcgg cttcaacgtg ctcttctacg acccttactt gtcggatggc 660
gtggagcggg cgctggggct gcagcgtgtc agcaccctgc aggacctgct cttccacagc 720
gactgcgtga ccctgcactg cggcctcaac gagcacaacc accacctcat caacgacttc 780
accgtcaagc agatgagaca aggggccttc ctggtgaaca cagcccgggg tggcctggtg 840
gatgagaagg cgctggccca ggccctgaag gagggccgga tccgcggcgc ggccctggat 900
gtgcacgagt cggaaccctt cagctttagc cagggccctc tgaaggatgc acccaacctc 960
atctgcaccc cccatgctgc atggtacagc gagcaggcat ccatcgagat gcgagaggag 1020
gcggcacggg agatccgcag agccatcaca ggccggatcc cagacagcct gaagaactgt 1080
gtcaacaagg accatctgac agccgccacc cactgggcca gcatggaccc cgccgtcgtg 1140
caccctgagc tcaatggggc tgcctatagg taccctccgg gcgtggtggg cgtggccccc 1200
actggcatcc cagctgctgt ggaaggtatc gtccccagcg ccatgtccct gtcccacggc 1260

-continued ctgccccctg tggcccaccc gccccacgcc ccttctcctg gccaaaccgt caagcccgag 1320
gcggatagag accacgccag tgaccagttg tagcccggga ggagctctcc agcctcggcg 1380
cctgggcaga gggcccggaa accctcggac cagagtgtgt ggaggaggca tctgtgtggt 1440
ggccctggca ctgcagagac tggtccgggc tgtcaggagg cgggaggggg cagcgctggg 1500
cctcgtgtcg cttgtcgtcg tccgtcctgt gggcgctctg ccctgtgtcc ttcgcgttcc 1560
tcgttaagca gaagaagtca gtagttattc tcccatgaac gttcttgtct gtgtacagtt 1620
tttagaacat tacaaaggat ctgtttgctt agctgtcaac aaaaagaaaa cctgaaggag 1680
catttggaag tcaatttgag gttttttttt ttgttttttt tttttttgta tgttggaacg 1740
tgccccagaa tgaggcagtt ggcaaacttc tcaggacaat gaatccttcc cgtttttctt 1800
tttatgccac acagtgcatt gttttttcta cctgcttgtc ttatttttag aataatttag 1860
aaaaacaaaa caaaggctgt ttttcctaat tttggcatga acccccccttt gttccaaatg 1920 aagacggcat cacgaagcag ctccaaaagg aaaagcttgg gcggtgccca gcgtgcccgc 1980
tgcccatcga cgtctgtcct ggggacgtgg agggtggcag cgtccccgcc tgcaccagtg 2040
ccgtcctgct gatgtggtag gctagcaata ttttggttaa aatcatgttt gtg 2093

<210> SEQ ID NO 86
<211> LENGTH: 3435
<212> TYPE: DNA
<213> ORGANISM: Homo sapiens

<400> SEQUENCE: 86
cgcgcggcca ggccctctta gccctctgcc gtttgggggg cacgggtgaa cctgccgccc 60
cactcccacc ccgccccgcc ccgcccgtac agccaaatcg gaagggacga gcctgccctt 120
tgaaagggtt ttttttcttg ctcctgcgga gggcgcccca gccatggccc tcaggagctc 180
cctagacccc gcagggactg ccctccatcc cggccgccgg ggcccgccct ctgcatcccg 240
cgggcagcct gtgtgaagcg gcctcccgca gcccccggcc cctcccccat ggaggaggag 300
gagggggcgg tggccaagga gtggggcacg acccccgcgg ggcccgtctg gaccgcggtg 360
ttcgactacg aggcggcggg cgacgaggag ctgaccctgc ggaggggcga tcgcgtccag 420
gtgctttccc aagactgtgc ggtgtccggc gacgagggct ggtggaccgg gcagctcccc 480
agcggccgcg tgggcgtctt ccccagcaac tacgtggccc ccggcgcccc cgctgcaccc 540
gcgggcctcc agctgcccca ggagatcccc ttccacgagc tgcagctaga ggagatcatc 600
ggtgtggggg gctttggcaa ggtctatcgg gccctgtggc gtggcgagga ggtggcagtc 660
aaggccgccc ggctggaccc tgagaaggac ccggcagtga cagcggagca ggtgtgccag 720
gaagcccggc tctttggagc cctgcagcac cccaacataa ttgcccttag gggcgcctgc 780
ctcaaccccc cacacctctg cctagtgatg gagtatgccc ggggtggtgc actgagcagg 840
gtgctggcag gtcgccgggt gccacctcac gtgctggtca actgggctgt gcaggtggcc 900
cggggcatga actacctaca caatgatgcc cctgtgccca tcatccaccg ggacctcaag 960
tccatcaaca tcctgatcct ggaggccatc gagaaccaca acctcgcaga cacggtgctc 1020
aagatcacgg acttcggcct cgcccgcgag tggcacaaga ccaccaagat gagcgctgcg 1080
gggacctacg cctggatggc gccggaggtt atccgtctct ccctcttctc caaaagcagt 1140
gatgtctgga gcttcggggt gctgctgtgg gagctgctga cgggggaggt cccctaccgt 1200
gagatcgacg ccttggccgt ggcgtatggc gtggctatga ataagctgac gctgcccatt 1260
ccctccacgt gccccgagcc ctttgcccgc ctcctggagg aatgctggga cccagacccc 1320

-continued

```
cacgggcggc cagatttcgg tagcatcttg aagcggcttg aagtcatcga acagtcagcc   1380
ctgttccaga tgccactgga gtccttccac tcgctgcagg aagactggaa gctggagatt   1440
cagcacatgt ttgatgacct tcggaccaag gagaaggagc ttcggagccg tgaggaggag   1500
ctgctgcggg cggcacagga gcagcgcttc caggaggagc agctgcggcg gcgggagcag   1560
gagctggcag aacgtgagat ggacatcgtg gaacgggagc tgcacctgct catgtgccag   1620
ctgagccagg agaagccccg ggtccgcaag cgcaagggca acttcaagcg cagccgcctg   1680
ctcaagctgc gggaaggcgg cagccacatc agcctgccct ctggctttga gcataagatc   1740
acagtccagg cctctccaac tctggataag cggaaaggat ccgatggggc cagcccccct   1800
gcaagcccca gcatcatccc ccggctgagg gccattcgcc tgactcccgt ggactgtggt   1860
ggcagcagca gtggcagcag cagtggagga agtgggacat ggagccgcgg tgggccccca   1920
aagaaggaag aactggtcgg gggcaagaag aagggacgaa cgtgggggcc cagctccacc   1980
ctgcagaagg agcgggtggg aggagaggag aggctgaagg ggctggggga aggaagcaaa   2040
cagtggtcat caagtgcccc caacctgggc aagtccccca aacacacacc cagtcgccgc   2100
tggcttcgcc agcctcaatg agatggagga gttcgcggag gcagaggatg gaggcagcag   2160
cgtgccccct tcccccctact cgaccccgtc ctacctctca gtgccactgc ctgccgagcc   2220
ctccccgggg gcgcgggcgc cgtgggagcc gacgccgtcc gcgccccccg ctcggtgggg   2280
acacggcgcc cggcggcgct gcgacctggc gctgctaggc tgcgccacgc tgctgggggc   2340
tgtgggcctg ggcgccgacg tggccgaggc gcgcgcggcc gacggtgagg agcagcggcg   2400
ctggctcgac ggcctcttct ttccccgcgc cggccgcttc ccgcggggcc tcagcccacc   2460
cgcgcgtccc cacggccgcc gcgaagacgt gggccccggc ctgggcctgg cgccctcggc   2520
caccctcgtg tcgctgtcgt ccgtgtccga ctgcaactcc acgcgttcac tgctgcgctc   2580
tgacagtgac gaggccgcac cggccgcgcc ctccccacca ccctccccgc ccgcgcccac   2640
acccacgccc tcgcccagca ccaacccccct ggtggacctg gagctggaga gcttcaagaa   2700
ggacccccgc cagtcgctca cgcccaccca cgtcacggct gcatgcgctg tgagccgcgg   2760
gcaccggcgg acgccatcgg atggggcgct ggggcagcgg gggccgcccg agcccgcggg   2820
ccatggccct ggccctcgtg accttctgga cttcccccgc ctgcccgacc cccaggccct   2880
gttcccagcc cgccgccggc cccctgagtt cccaggccgc cccaccaccc tgacctttgc   2940
cccgagacct cggccggctg ccagtcgccc ccgcttggac ccctggaaac tggtctcctt   3000
cggccggaca ctcaccatct cgcctcccag caggccagac actccggaga gccctgggcc   3060
ccccagcgtg cagcccacac tgctggacat ggacatggag ggcagaacc aagacagcac   3120
agtgccccctg tgcggggccc acggctccca ctaaggcctg cccaccaccg cccgcctggg   3180
cagccatgaa tgtagcgccc caggccctgc cccagcccgc catgccacaa ggtgggggag   3240
gccctgggca ggatgttcac tctatttatt ggggaaggag ggaggggggg gacacttaac   3300
ttattccttt gtaccccagg gggtggagcc ctgtgcccac cctgcactgg ggggagggtg   3360
ggcagggata ctcagggaca gggcatcatg gggatttgg cacaaaatgg agcattaaag   3420
gtaacccctg ccccc                                                     3435
```

<210> SEQ ID NO 87
<211> LENGTH: 2227
<212> TYPE: DNA
<213> ORGANISM: Homo sapiens -continued

<400> SEQUENCE: 87
gggcccgccc ctggtcacag ccagactgac tcagtttccc tgggaggtcc cgctcgagcc 60
cgtccttccc ctccctctgc ccgcccccag ccctcgcccc accctcggcg cccgcacatc 120
tgcctgctca gctccagacg gcgcccggac ccccgggcgc gggatccagc caggtgggag 180
ccccgcagat gaggtctctg aaggtgtgcc tgaaccagtg ccagcctgcc ctgtctgcag 240
catcggcctg atggggtggt gactgatccc tcagggctcc ggagccatgt ggcccaacgg 300
cagttccctg ggcccctgtt tccggcccac aaacattacc ctggaggaga gacggctgat 360
cgcctcgccc tggttcgccg cctccttctg cgtggtgggc ctggcctcca acctgctggc 420
cctgagcgtg ctggcgggcg cgcggcaggg gggttcgcac acgcgctcct ccttcctcac 480
cttcctctgc ggcctcgtcc tcaccgactt cctggggctg ctggtgaccg gtaccatcgt 540
ggtgtcccag cacgccgcgc tcttcgagtg gcacgccgtg gaccctggct gccgtctctg 600
tcgcttcatg ggcgtcgtca tgatcttctt cggcctgtcc ccgctgctgc tgggggccgc 660
catggcctca gagcgctacc tgggtatcac ccggcccttc tcgcgcccgg cggtcgcctc 720
gcagcgccgc gcctgggcca ccgtggggct ggtgtgggcg gccgcgctgg cgctgggcct 780
gctgcccctg ctgggcgtgg gtcgctacac cgtgcaatac ccggggtcct ggtgcttcct 840
gacgctgggc gccgagtccg gggacgtggc cttcgggctg ctcttctcca tgctgggcgg 900
cctctcggtc gggctgtcct tcctgctgaa cacggtcagc gtggccaccc tgtgccacgt 960
ctaccacggg caggaggcgg cccagcagcg tccccgggac tccgaggtgg agatgatggc 1020
tcagctcctg gggatcatgg tggtggccag cgtgtgttgg ctgcccctte tggtcttcat 1080
cgcccagaca gtgctgcgaa acccgcctgc catgagcccc gccgggcagc tgtcccgcac 1140
cacggagaag gagctgctca tctacttgcg cgtggccacc tggaaccaga tcctggaccc 1200
ctgggtgtat atcctgttcc gccgcgccgt gctccggcgt ctccagcctc gcctcagcac 1260
ccggcccagg tcgctgtccc tccagcccca gctcacgcag cgctccgggc tgcagtagga 1320
agtggacaga gcgcccctcc cgcgcctttc cgcggagccc ttggcccctc ggacagccca 1380
tctgcctgtt ctgaggattc aggggctggg ggtgctggat ggacagtggg catcagcagc 1440
agggttttgg gttgacccca atccaacccg gggaccccca actcctccct gatcctttta 1500
ccaagcactc tcccttcctc ggcccctttt tcccatccag agctcccacc ccttctctgc 1560
gtccctccca accccaggaa gggcatgcag acattggaag agggtcttgc attgctattt 1620
tttttttag acggagtctt gctctgtccc ccaggctgga gtgcagtggc gcaatctcag 1680
ctcactgcaa cctccacctc ccgggttcaa gcgattctcc tgcctcagcc tcctgagtag 1740
ctgggactat aggcgcgcgc caccacgccc ggctaatttt tgtatttta gtagagacgg 1800
ggtttcaccg tgttggccag gctggtcttg aactcctgac ctcaggtgat tcaccagcct 1860
cagcctccca aagtgctggg atcacaggca tgaaccacca cacctggcca tttttttttt 1920
tttttaga cggagtctca ctctgtggcc cagcctggag tacagtggca cgatctcggc 1980
tcactgcaac ctccgcctcc cgggttcaag cgattctcgt gcctcagcct cccgagcagc 2040
tgggattaca ggcgtaagcc actgcgcccg gccttgcatg ctctttgacc ctgaatttga 2100
cctacttgct ggggtacagt tgcttccttt tgaacctcca acagggaagg ctctgtccag 2160
aaaggattga atgtgaacgg gggcaccccc ttttcttgcc aaaatatatc tctgcctttg 2220
gttttat 2227

-continued

<210> SEQ ID NO 88
<211> LENGTH: 2662
<212> TYPE: DNA
<213> ORGANISM: Homo sapiens

<400> SEQUENCE: 88
cccggacatg gccgccaaca tgtacagggt cggagactac gtctactttg agaactcctc 60
cagcaaccca tacctgatcc ggagaatcga ggagctcaac aagacggcca atgggaacgt 120
ggaggccaaa gtggtgtgct tctaccggag gcgggacatc tccagcaccc tcatcgccct 180
ggccgacaag cacgcaaccc tgtcagtctg ctataaggcc ggaccggggg cggacaacgg 240
cgaggaaggg gaaatagaag aggaaatgga gaatccggaa atggtggacc tgcccgagaa 300
actaaagcac cagctgcggc atcgggagct gttcctctcc cggcagctgg agtctctgcc 360
cgccacgcac atcaggggca agtgcagcgt caccctgctc aacgagaccg agtcgctcaa 420
gtcctacctg gagcgggagg atttcttctt ctattctcta gtctacgacc cacagcagaa 480
gaccctgctg gcagataaag gagagattcg agtaggaaac cggtaccagg cagacatcac 540
cgacttgtta aaagaaggcg aggaggatgg ccgagaccag tccaggttgg agacccaggt 600
gtgggaggcg cacaacccac tcacagacaa gcagatcgac cagttcctgg tggtggcccg 660
ctctgtgggc accttcgcac gggccctgga ctgcagcagc tccgtccgac agcccagcct 720
gcacatgagc gccgcagctg cctcccgaga catcaccctg ttccacgcca tggatactct 780
ccacaagaac atctacgaca tctccaaggc catctcggcg ctggtgccgc agggcgggcc 840
cgtgctctgc agggacgaga tggaggagtg gtctgcatca gaggccaacc ttttcgagga 900
agccctggaa aaatatggga aggatttcac ggacattcag caagattttc tcccgtggaa 960
gtcgctgacc agcatcattg agtactacta catgtggaag accaccgaca gatacgtgca 1020
gcagaaacgc ttgaaagcag ctgaagctga gagcaagtta aagcaagttt atattcccaa 1080
ctataacaag ccaaatccga accaaatcag cgtcaacaac gtcaaggccg gtgtggtgaa 1140
cggcacgggg gcgccgggcc agagccctgg ggctggccgg gcctgcgaga gctgttacac 1200
cacacagtct taccagtggt attcttgggg tccccctaac atgcagtgtc gtctctgcgc 1260
atcttgttgg acatattgga agaaatatgg tggcttgaaa atgccaaccc ggttagatgg 1320
agagaggcca ggaccaaacc gcagtaacat gagtccccac ggcctcccag cccggagcag 1380
cgggagcccc aagtttgcca tgaagaccag gcaggctttc tatctgcaca cgacgaagct 1440
gacgcggatc gcccggcgcc tgtgccgtga gatcctgcgc ccgtggcacg ctgcgcggaa 1500
cccctacctg cccatcaaca gcgcggccat caaggccgag tgcacggcgc ggctgcccga 1560
agcctcccag agcccgctgg tgctgaagca ggcggtacgc aagccgctgg aagccgtgct 1620
tcggtatctt gagacccacc cccgcccccc caagcctgac cccgtgaaaa gcgtgtccag 1680
cgtgctcagc agcctgacgc ccgccaaggt ggcccccgtc atcaacaacg gctcccccac 1740
catcctgggc aagcgcagct acgagcagca caacggggtg gacggcaaca tgaagaagcg 1800
cctcttgatg cccagtaggg gtctggcaaa ccacggacag accaggcaca tgggaccaag 1860
ccggaacctc ctgctcaacg ggaagtccta ccccaccaaa gtgcgcctga tccggggggg 1920
ctccctgccc ccagtcaagc ggcggcggat gaactggatc gacgccccgg gtgacgtgtt 1980
ctacatgccc aaagaggaga ccaggaagat ccgcaagctg ctctcatcct cggaaaccaa 2040
gcgtgctgcc cgccggccct acaagcccat cgccctgcgc cagagccagg ccctgccgcc 2100
gcggccaccg ccacctgcgc ccgtcaacga cgagcccatc gtcatcgagg actaggggcc 2160

-continued

```
gcccccacct gcggccgccc cccgcccctc gcccgcccac acggcccctt cccagccagc   2220

ccgccgcccg cccctcagtt tggtagtgcc ccacctcccg ccctcacctg aagagaaacg   2280

cgctccttgg cggacactgg gggaggagag gaagaagcgc ggctaactta ttccgagaat   2340

gccgaggagt tgtcgttttt agctttgtgt ttactttttg gctggagcgg agatgagggg   2400

ccaccccgtg cccctgtgct gcggggcctt ttgcccggag gccgggccct aaggttttgt   2460

tgtgttctgt tgaaggtgcc attttaaatt ttatttttat tacttttttt gtagatgaac   2520

ttgagctctg taacttacac ctggaatgtt aggatcgtgc ggccgcggcc ggccgagctg   2580

cctggcgggg ttggcccttg tcttttcaag taattttcat attaaacaaa aacaaagaaa   2640

aaaaatctta taaaaaggaa aa                                            2662
```

<210> SEQ ID NO 89
<211> LENGTH: 552
<212> TYPE: DNA
<213> ORGANISM: Homo sapiens

<400> SEQUENCE: 89

```
atgagagagt acaaagtggt ggtgctgggc tcgggcggcg tgggcaagtc cgcgctcacc     60

gtgcagttcg tgacgggctc cttcatcgag aagtacgacc cgaccatcga agacttttac    120

cgcaaggaga ttgaggtgga ctcgtcgccg tcggtgctgg agatcctgga tacggcgggc    180

accgagcagt tcgcgtccat gcgggacctg tacatcaaga acggccaggg cttcatcctg    240

gtctacagcc tcgtcaacca gcagagcttc caggacatca agcccatgcg ggaccagatc    300

atccgcgtga agcggtacga gcgcgtgccc atgatcctgg tgggcaacaa ggtggacctg    360

gagggtgagc gcgaggtctc gtacggggag ggcaaggccc tggctgagga gtggagctgc    420

cccttcatgg agacgtcggc caaaaacaaa gcctcggtag acgagctatt tgccgagatc    480

gtgcggcaga tgaactacgc ggcgcagtcc aacggcgatg agggctgctg ctcggcctgc    540

gtgatcctct ga                                                        552
```

<210> SEQ ID NO 90
<211> LENGTH: 2198
<212> TYPE: DNA
<213> ORGANISM: Homo sapiens

<400> SEQUENCE: 90

```
gagctgcggg cgctgctgct gtggggccgc cgcctgcggc ctttgctgcg ggcgccggcg     60

ctggcggccg tgccgggagg aaaaccaatt ctgtgtcctc ggaggaccac agcccagttg    120

ggccccaggc gaaacccagc ctggagcttg caggcaggac gactgttcag cacgcagacc    180

gccgaggaca aggaggaacc cctgcactcg attatcagca gcacagagag cgtgcagggt    240

tccacttcca aacatgagtt ccaggccgag acaaagaagc ttttggacat tgttgcccgg    300

tccctgtact cagaaaaaga ggtgtttata cgggagctga tctccaatgc cagcgatgcc    360

ttggaaaaac tgcgtcacaa actggtgtct gacggccaag cactgccaga aatggagatt    420

cacttgcaga ccaatgccga gaaaggcacc atcaccatcc aggatactgg tatcgggatg    480

acacaggaag agctggtgtc caacctgggg acgattgcca gatcggggtc aaaggccttc    540

ctggatgctc tgcagaacca ggctgaggcc agcagcaaga tcatcggcca gtttggagtg    600

ggtttctact cagctttcat ggtggctgac agagtggagg tctattcccg ctcggcagcc    660

ccggggagcc tgggttacca gtggctttca gatggttctg gagtgtttga aatcgccgaa    720

gcttcgggag ttagaaccgg gacaaaaatc atcatccacc tgaaatccga ctgcaaggag    780
```

-continued

```
ttttccagcg aggcccgggt gcgagatgtg gtaacgaagt acagcaactt cgtcagcttc    840
cccttgtact tgaatggaag gcggatgaac accttgcagg ccatctggat gatggacccc    900
aaggatgtcc gtgagtggca acatgaggag ttctaccgct acgtcgcgca ggctcacgac    960
aagccccgct acaccctgca ctataagacg gacgcaccgc tcaacatccg cagcatcttc   1020
tacgtgcccg acatgaaacc gtccatgttt gatgtgagcc gggagctggg ctccagcgtt   1080
gcactgtaca gccgcaaagt cctcatccag accaaggcca cggacatcct gcccaagtgg   1140
ctgcgcttca tccgaggtgt ggtggacagt gaggacattc ccctgaacct cagccgggag   1200
ctgctgcagg agagcgcact catcaggaaa ctccgggacg ttttacagca gaggctgatc   1260
aaattcttca ttgaccagag taaaaaagat gctgagaagt atgcaaagtt ttttgaagat   1320
tacggcctgt tcatgcggga gggcattgtg accgccaccg agcaggaggt caaggaggac   1380
atagcaaagc tgctgcgcta cgagtcctcg gcgctgccct ccgggcagct aaccagcctc   1440
tcagaatacg ccagccgcat gcgggccggc acccgcaaca tctactacct gtgcgccccc   1500
aaccgtcacc tggcagagca ctcaccctac tatgaggcca tgaagaagaa agacacagag   1560
gttctcttct gctttgagca gtttgatgag ctcaccctgc tgcaccttcg tgagtttgac   1620
aagaagaagc tgatctctgt ggagacggac atagtcgtgg atcactacaa ggaggagaag   1680
tttgaggaca ggtccccagc cgccgagtgc ctatcagaga aggagacgga ggagctcatg   1740
gcctggatga gaaatgtgct ggggtcgcgt gtcaccaacg tgaaggtgac cctccgactg   1800
gacacccacc ctgccatggt caccgtgctg gagatggggg ctgcccgcca cttcctgcgc   1860
atgcagcagc tggccaagac ccaggaggag cgcgcacagc tcctgcagcc cacgctggag   1920
atcaacccca ggcacgcgct catcaagaag ctgaatcagc tgcgcgcaag cgagcctggc   1980
ctggctcagc tgctggtgga tcagatatac gagaacgcca tgattgctgc tggacttgtt   2040
gacgacccta gggccatggt gggccgcttg aatgagctgc ttgtcaaggc cctggagcga   2100
cactgacagc cagggggcca gaaggactga caccacagat gacagcccca cctccttgag   2160
ctttatttac ctaaatttaa aggtatttct taacccga                           2198
```

<210> SEQ ID NO 91
<211> LENGTH: 1790
<212> TYPE: DNA
<213> ORGANISM: Homo sapiens

<400> SEQUENCE: 91

```
agtgatgtcc ttgcattgcc catttttaag caagaagagt cgagtttgcc tcctgataat     60
gagaataaaa tcctgccttt tcaatatgtg ctttgtgctg ctacctctcc agcagtgaaa    120
ctccatgatg aaaccctaac gtatctcaat caaggacagt cttatgaaat tcgaatgcta    180
gacaatagga aacttggaga acttccagaa attaatggca aattggtgaa gagtatattc    240
cgtgtggtgt tccatgacag aaggcttcag tacactgagc atcagcagct agagggctgg    300
aggtggaacc gacctggaga cagaattctt gacatagata tcccgatgtc tgtgggtata    360
atcgatccta gggctaatcc aactcaacta aatacagtgg agttcctgtg ggaccctgca    420
aagaggacat ctgtgtttat tcaggtgcac tgtattagca cagagttcac tatgaggaaa    480
catggtggag aaaagggggt gccattccga gtacaaatag ataccttcaa ggagaatgaa    540
aacggggaat atactgagca cttacactcg gccagctgcc agatcaaagt tttcaagcca    600
aaggtgcaga cagaaagcaa aaaacggata gggaaaaaat ggagaaacga acacctcatg    660
```

-continued

```
aaaaggagaa atatcagcct tcctatgaga caaccatact cacagagtgt tctccatggc    720
ccgagatcac gtatgtcaat aactccccat cacctggctt caacagttcc catagcagtt    780
tttctcttgg ggaaggaaat ggttcaccaa accaccagcc agagccaccc cctccagtca    840
cagataacct cttaccaaca accacacctc aggaagctca gcagtggttg catcgaaatc    900
gtttttctac attcacaagg cttttcacaa acttctcagg ggcagattta ttgaaattaa    960
ctagagatga tgtgatccaa atctgtggcc ctgcagatgg aatcagactt tttaatgcat   1020
taaaaggccg gatggtgcgt ccaaggttaa ccatttatgt ttgtcaggaa tcactgcagt   1080
tgagggagca gcaacaacag cagcagcaac agcagcagaa gcatgaggat ggagactcaa   1140
atggtacttt cttcgtttac catgctatct atctagaaga actaacagct gttgaattga   1200
cagaaaaaat tgctcagctt ttcagcattt ccccttgcca gatcagccag atttacaagc   1260
aggggccaac aggaattcat gtgctcatca gtgatgagat gatacagaac tttcaggaag   1320
aagcatgttt tattctggac acaatgaaag cagaaaccaa tgatagctat catatcatac   1380
tgaagtagga gtgcggcgtt tcgtgcccag tggctgctcc ttccttcacc tctgaaaacg   1440
gccctcttga agggggatat gaatggagat ttgaaggtct gcaagaacct gactcgtctg   1500
actgtgtgtg gaggagtcca ggccatggag gcagaatcct ggccctctgt gttggcccaa   1560
gctcttgtgg tacacacaga ttactgccca atatgcagtt ctgcagctgt tttagttaaa   1620
tttctggacc ttgttgttgt taaatatcag tagaaactct acataattta gagtgtatgt   1680
agggcataat gatgatggga attgtgtgat gtttaacagg aagatcttaa attttgtgat   1740
atggagccct gtaatttttt tcttatataa aaatgggtat ctatattcat              1790

<210> SEQ ID NO 92
<211> LENGTH: 652
<212> TYPE: DNA
<213> ORGANISM: Homo sapiens

<400> SEQUENCE: 92

aggtctgttc cgcatgaaac tcctgctggg gaaggacttc cctgcctccc cacccaaggg     60
ctacttcctg accaagatct tccacccgaa cttgggcgcc aatggcgaga tgtgcgtcaa    120
cgtgctcaag agggactgga cggctgagct gggcatccga cacgtactgc tgaccatcaa    180
gtgcctgctg atccacccta accccgagtc tgcactcaac gaggaggcgg gccgcctgct    240
cttggagaac tacgaggagt atgcggctcg ggcccgtctg ctcacagaga tccacggggg    300
cgccggcggg cccagcggca gggccaaagc cgggcgggcc ctggccagtg gcactgcagc    360
ttcctccacc gactctgggg ccccaggggg cttgggaggg gctgagggtc ccatggccaa    420
gaagcatgct ggcgagcgcg ataagaagct ggcggccaag aaaaagacgg acaagaagcg    480
ggcgctacgg cggctgtagt gggctctctt cctccttcca ccgtgacccc aacctctcct    540
gtcccctccc tccaactctg tctctaagtt atttaaatta tggctggggt cggggagggt    600
acagggggca ctgagacctg gatttgtttt tttaaataaa gttggaaaag ca            652

<210> SEQ ID NO 93
<211> LENGTH: 771
<212> TYPE: DNA
<213> ORGANISM: Homo sapiens

<400> SEQUENCE: 93

gtcgtgttct ccgagttcct gtctctctgc caacgccgcc cggatggctt cccaaaaccg     60
cgacccagcc gccactagcg tcgccgccgc ccgtaaagga gctgagccga gcgggggcgc    120
```

-continued

```
cgcccggggt ccggtgggca aaaggctaca gcaggagctg atgaccctca tgatgtctgg    180
cgataaaggg atttctgcct tccctgaatc agacaacctt ttcaaatggg tagggaccat    240
ccatggagca gctggaacag tatatgaaga cctgaggtat aagctctcgc tagagttccc    300
cagtggctac ccttacaatg cgcccacagt gaagttcctc acgccctgct atcaccccaa    360
cgtggacacc cagggtaaca tatgcctgga catcctgaag gaaaagtggt ctgccctgta    420
tgatgtcagg accattctgc tctccatcca gagccttcta ggagaaccca acattgatag    480
tcccttgaac acacatgctg ccgagctctg gaaaaacccc acagctttta agaagtacct    540
gcaagaaacc tactcaaagc aggtcaccag ccaggagccc tgacccaggc tgcccagcct    600
gtccttgtgt cgtcttttta atttttcctt agatggtctg tcctttttgt gatttctgta    660
taggactctt tatcttgagc tgtggtattt ttgttttgtt tttgtctttt aaattaagcc    720
tcggttgagc ccttgtatat taaataaatg catttttgtc ctttttaga c              771
```

```
<210> SEQ ID NO 94
<211> LENGTH: 2527
<212> TYPE: DNA
<213> ORGANISM: Homo sapiens

<400> SEQUENCE: 94

ctccagcagc acccgagagg gtcaggagaa aagcggagga agctgggtag gccctgaggg     60
gcctcggtaa gccatcatga ccacccggca agccacgaag gatcccctcc tccggggtgt    120
atctcctacc cctagcaaga ttccggtacg ctctcagaaa cgcacgcctt tccccactgt    180
tacatcgtgc gccgtggacc aggagaacca agatccaagg agatgggtgc agaaaccacc    240
gctcaatatt caacgccccc tcgttgattc agcaggcccc aggccgaaag ccaggcacca    300
ggcagagaca tcacaaagat tggtggggat cagtcagcct cggaacccct tggaagagct    360
caggcctagc cctaggggtc aaaatgtggg gcctgggccc cctgcccaga cagaggctcc    420
agggaccata gagtttgtgg ctgaccctgc agccctggcc accatcctgt caggtgaggg    480
tgtgaagagc tgtcacctgg ggcgccagcc tagtctggct aaaagagtac tggttcgagg    540
aagtcaggga ggcaccaccc agagggtcca gggtgttcgg gcctctgcat atttggcccc    600
cagaaccccc acccaccgac tggaccctgc cagggcttcc tgcttctcta ggctggaggg    660
accaggacct cgaggccgga cattgtgtcc ccagaggcta caggctctga tttcaccttc    720
aggaccttcc tttcaccctt ccactcgccc cagtttccag gagctaagaa gggagacagc    780
tggcagcagc cggacttcag tgagccaggc ctcaggattg ctcctggaga ccccagtcca    840
gcctgctttc tctcttccta aaggagaacg cgaggttgtc actcactcag atgaaggagg    900
tgtggcctct cttggtctgg cccagcgagt accattaaga gaaaaccgag aaatgtcaca    960
taccagggac agccatgact cccacctgat gccctcccct gcccctgtgg cccagccctt   1020
gcctggccat gtggtgccat gtccatcacc ctttggacgg gctcagcgtg taccctcccc   1080
aggccctcca actctgacct catattcagt gttgcggcgt ctcaccgttc aacctaaaac   1140
ccggttcaca cccatgccat caacccccag agttcagcag gcccagtggc tgcgtggtgt   1200
ctcccctcag tcctgctctg aagatcctgc cctgccctgg gagcaggttg ccgtccggtt   1260
gtttgaccag gagagttgta taaggtcact ggagggttct gggaaaccac cggtggccac   1320
tccttctgga ccccactcta acagaacccc cagcctccag gaggtgaaga ttcaacgcat   1380
cggtatcctg caacagctgt tgagacagga agtagagggg ctggtagggg gccagtgtgt   1440
```

-continued

```
ccctcttaat ggaggctctt ctctggatat ggttgaactt cagcccctgc tgactgagat   1500

ttctagaact ctgaatgcca cagagcataa ctctgggact tcccaccttc ctggactgtt   1560

aaaacactca gggctgccaa agccctgtct tccagaggag tgcggggaac cacagccctg   1620

ccctccggca gagcctgggc ccccagaggc cttctgtagg agtgagcctg agataccaga   1680

gccctccctc caggaacagc ttgaagtacc agagccctac cctccagcag aacccaggcc   1740

cctagagtcc tgctgtagga gtgagcctga gataccggag tcctctcgcc aggaacagct   1800

tgaggtacct gagccctgcc ctccagcaga acccaggccc ctagagtcct actgtaggat   1860

tgagcctgag ataccggagt cctctcgcca ggaacagctt gaggtacctg agccctgccc   1920

tccagcagaa cccgggcccc ttcagcccag cacccagggg cagtctggac ccccagggcc   1980

ctgccctagg gtagagctgg gggcatcaga gccctgcacc ctggaacata gaagtctaga   2040

gtccagtcta ccaccctgct gcagtcagtg ggctccagca accaccagcc tgatcttctc   2100

ttcccaacac ccgctttgtg ccagcccccc tatctgctca ctccagtctt tgagaccccc   2160

agcaggccag gcaggcctca gcaatctggc ccctcgaacc ctagccctga gggagcgcct   2220

caaatcgtgt ttaaccgcca tccactgctt ccacgaggct cgtctggacg atgagtgtgc   2280

cttttacacc agccgagccc ctccctcagg ccccacccgg gtctgcacca accctgtggc   2340

tacattactc gaatggcagg atgccctgtg tttcattcca gttggttctg ctgcccccca   2400

gggctctcca tgatgagaca accactcctg ccctgccgta cttcttcctt ttagccctta   2460

tttattgtcg gtctgcccat gggactggga gccgcccact tttgtcctca ataaagtttc   2520

taaagta                                                             2527
```

<210> SEQ ID NO 95
<211> LENGTH: 2512
<212> TYPE: DNA
<213> ORGANISM: Homo sapiens

<400> SEQUENCE: 95

```
agaataatca tgggccagac tgggaagaaa tctgagaagg gaccagtttg ttggcggaag     60

cgtgtaaaat cagagtacat gcgactgaga cagctcaaga ggttcagacg agctgatgaa    120

gtaaaggtat gtttagttcc aatcgtcaga aaattttgga aagaacggaa atcttaaacc    180

aagaatggaa acagcgaagg atacagcctg tgcacatcct gacttctgtg agctcattgc    240

gcgggactag ggagtgttcg gtgaccagtg acttggattt tccaacacaa gtcatcccat    300

taaagactct gaatgcagtt gcttcagtac ccataatgta ttcttggtct cccctacagc    360

agaattttat ggtggaagat gaaactgttt tacataacat tccttatatg ggagatgaag    420

ttttagatca ggatggtact ttcattgaag aactaataaa aaattatgat gggaaagtac    480

acggggatag agaatgtggg tttataaatg atgaaatttt tgtggagttg gtgaatgccc    540

ttggtcaata taatgatgat gacgatgatg atgatggaga cgatcctgaa gaaagagaag    600

aaaagcagaa agatctggag gatcaccgag atgataaaga aagccgccca cctcggaaat    660

ttccttctga taaaattttt gaagccattt cctcaatgtt tccagataag ggcacagcag    720

aagaactaaa ggaaaaatat aaagaactca ccgaacagca gctcccaggc gcacttcctc    780

ctgaatgtac ccccaacata gatggaccaa atgctaaatc tgttcagaga gagcaaagct    840

tacactcctt tcatacgctt ttctgtaggc gatgttttaa atatgactgc ttcctacatc    900

cttttcatgc aacacccaac acttataagc ggaagaacac agaaacagct ctagacaaca    960

aaccttgtgg accacagtgt taccagcatt tggagggagc aaaggagttt gctgctgctc   1020
```

-continued tcaccgctga gcggataaag accccaccaa aacgtccagg aggccgcaga agaggacggc 1080
ttcccaataa cagtagcagg cccagcaccc ccaccattaa tgtgctggaa tcaaaggata 1140
cagacagtga tagggaagca gggactgaaa cgggggggaga gaacaatgat aaagaagaag 1200
aagagaagaa agatgaaact tcgagctcct ctgaagcaaa ttctcggtgt caaacaccaa 1260
taaagatgaa gccaaatatt gaacctcctg agaatgtgga gtggagtggt gctgaagcct 1320
caatgtttag agtcctcatt ggcacttact atgacaattt ctgtgccatt gctaggttaa 1380
ttgggaccaa aacatgtaga caggtgtatg agtttagagt caaagaatct agcatcatag 1440
ctccagctcc cgctgaggat gtggatactc ctccaaggaa aaagaagagg aaacaccggt 1500
tgtgggctgc acactgcaga aagatacagc tgaaaaagga cggctcctct aaccatgttt 1560
acaactatca accctgtgat catccacggc agccttgtga cagttcgtgc ccttgtgtga 1620
tagcacaaaa tttttgtgaa aagttttgtc aatgtagttc agagtgtcaa aaccgctttc 1680
cgggatgccg ctgcaaagca cagtgcaaca ccaagcagtg cccgtgctac ctggctgtcc 1740
gagagtgtga ccctgacctc tgtcttactt gtggagccgc tgaccattgg gacagtaaaa 1800
atgtgtcctg caagaactgc agtattcagc ggggctccaa aaagcatcta ttgctggcac 1860
catctgacgt ggcaggctgg gggattttta tcaaagatcc tgtgcagaaa aatgaattca 1920
tctcagaata ctgtggagag attatttctc aagatgaagc tgacagaaga gggaaagtgt 1980
atgataaata catgtgcagc tttctgttca acttgaacaa tgattttgtg gtggatgcaa 2040
cccgcaaggg taacaaaatt cgttttgcaa atcattcggt aaatccaaac tgctatgcaa 2100
aagttatgat ggttaacggt gatcacagga taggtatttt tgccaagaga gccatccaga 2160
ctggcgaaga gctgtttttt gattacagat acagccaggc tgatgccctg aagtatgtcg 2220
gcatcgaaag agaaatggaa atcccttgac atctgctacc tcctcccccc tcctctgaaa 2280
cagctgcctt agcttcagga acctcgagta ctgtgggcaa tttagaaaaa gaacatgcag 2340
tttgaaattc tgaatttgca aagtactgta agaataattt atagtaatga gtttaaaaat 2400 caactttta ttgccttctc accagctgca aagtgttttg taccagtgaa tttttgcaat 2460
aatgcagtat ggtacatttt tcaactttga ataaagaata cttgaacttg tc 2512

<210> SEQ ID NO 96
<211> LENGTH: 3403
<212> TYPE: DNA
<213> ORGANISM: Homo sapiens

<400> SEQUENCE: 96
caggtctgag gcgaagctag gtgagccgtg ggaagaaaag agggagcagc tagggcgcgg 60
gtctccctcc tcccggagtt tggaacggct gaagttcacc ttccagcccc tagcgccgtt 120
cgcgccgcta ggcctggctt ctgaggcggt tgcggtgctc ggtcgccgcc taagcggggc 180
agggtgcgaa caggggcttc gggccacgct tctcttggcg acaggatttt gctgtgaagt 240
ccgtccggga aacggaggaa aaaaagagtt gcgggaggct gtctgctaat aacggttctt 300
gatacatatt tgccagactt caagatttca gaaaaggggt gaaagagaag attgcaactt 360
tgagtcagac ctgtaggcct gatagactga ttaaaccaca gaaggtgacc tgctgagaaa 420
agtggtacaa atactgggaa aaacctgctc ttctgcgtta agtgggagac aatgtcacaa 480
gttaaaagct cttattccta tgatgccccc tcggatttca tcaatttttc atccttggat 540
gatgaaggag atactcaaaa catagattca tggtttgagg agaaggccaa tttggagaat 600

-continued

```
aagttactgg ggaagaatgg aactggaggg ctttttcagg gcaaaactcc tttgagaaag    660
gctaatcttc agcaagctat tgtcacacct ttgaaaccag ttgacaacac ttactacaaa    720
gaggcagaaa aagaaaatct tgtggaacaa tccattccgt caaatgcttg ttcttccctg    780
gaagttgagg cagccatatc aagaaaaact ccagcccagc ctcagagaag atctcttagg    840
ctttctgctc agaaggattt ggaacagaaa gaaaagcatc atgtaaaaat gaaagccaag    900
agatgtgcca ctcctgtaat catcgatgaa attctaccct ctaagaaaat gaaagtttct    960
aacaacaaaa agaagccaga ggaagaaggc agtgctcatc aagatactgc tgaaaacaat   1020
gcatcttccc cagagaaagc caagggtaga catactgtgc cttgtatgcc acctgcaaag   1080
cagaagtttc taaaaagtac tgaggagcaa gagctggaga agagtatgaa aatgcagcaa   1140
gaggtggtgg agatgcggaa aaagaatgaa gaattcaaga aacttgctct ggctggaata   1200
gggcaacctg tgaagaaatc agtgagccag gtcaccaaat cagttgactt ccacttccgc   1260
acagatgagc gaatcaaaca acatcctaag aaccaggagg aatataagga agtgaacttt   1320
acatctgaac tacgaaagca tccttcatct cctgcccgag tgactaaggg atgtaccatt   1380
gttaagcctt tcaacctgtc ccaaggaaag aaaagaacat ttgatgaaac agtttctaca   1440
tatgtgcccc ttgcacagca agttgaagac ttccataaac gaacccctaa cagatatcat   1500
ttgaggagca agaaggatga tattaacctg ttaccctcca aatcttctgt gaccaagatt   1560
tgcagagacc cacagactcc tgtactgcaa accaaacacc gtgcacgggc tgtgacctgc   1620
aaaagtacag cagagctgga ggctgaggag ctcgagaaat tgcaacaata caaattcaaa   1680
gcacgtgaac ttgatcccag aatacttgaa ggtgggccca tcttgcccaa gaaaccacct   1740
gtgaaaccac ccaccgagcc tattggcttt gatttggaaa ttgagaaaag aatccaggag   1800
cgagaatcaa agaagaaaac agaggatgaa cactttgaat ttcattccag accttgccct   1860
actaagattt tggaagatgt tgtgggtgtt cctgaaaaga aggtacttcc aatcaccgtc   1920
cccaagtcac cagcctttgc attgaagaac agaattcgaa tgcccaccaa agaagatgag   1980
gaagaggacg aaccggtagt gataaaagct caacctgtgc cacattatgg ggtgcctttt   2040
aagccccaaa tcccagaggc aagaactgtg gaaatatgcc ctttctcgtt tgattctcga   2100
gacaaagaac gtcagttaca gaaggagaag aaaataaaag aactgcagaa aggggaggtg   2160
cccaagttca aggcacttcc cttgcctcat tttgacacca ttaacctgcc agagaagaag   2220
gtaaagaatg tgacccagat tgaacctttc tgcttggaga ctgacagaag aggtgctctg   2280
aaggcacaga cttggaagca ccagctggaa gaagaactga gacagcagaa agaagcagct   2340
tgtttcaagg ctcgtccaaa caccgtcatc tctcaggagc cctttgttcc caagaaagag   2400
aagaaatcag ttgctgaggg cctttctggt tctctagttc aggaaccttt tcagctggct   2460
actgagaaga gagccaaaga gcggcaggag ctggagaaga gaatggctga ggtagaagcc   2520
cagaaagccc agcagttgga ggaggccaga ctacaggagg aagagcagaa aaaagaggag   2580
ctggccaggc tacggagaga actggtgcat aaggcaaatc caatacgcaa gtaccagggt   2640
ctggagataa agtcaagtga ccagcctctg actgtgcctg tatctcccaa attctccact   2700
cgattccact gctaaactca gctgtgagct gcggataccg cccggcaatg ggacctgctc   2760
ttaacctcaa acctaggacc gtcttgcttt gtcattgggc atggagagaa cccatttctc   2820
cagactttta cctacccgtg cctgagaaag catacttgac aactgtggac tccagttttg   2880
ttgagaattg ttttcttaca ttactaaggc taataatgag atgtaactca tgaatgtctc   2940
gattagactc catgtagtta cttcctttaa accatcagcc ggccttttat atgggtcttc   3000
```

-continued

```
actctgacta gaatttagtc tctgtgtcag cacagtgtaa tctctattgc tattgcccct   3060

tacgactctc accctctccc cacttttttt aaaaatttta accagaaaat aaagatagtt   3120

aaatcctaag atagagatta agtcatggtt taaatgagga acaatcagta aatcagattc   3180

tgtcctcttc tctgcatacc gtgaatttat agttaaggat ccctttgctg tgagggtaga   3240

aaacctcacc aactgcacca gtgaggaaga agactgcgtg gattcatggg gagcctcaca   3300

gcagccacgc agcaggctct gggtggggct gccgttaagg cacagttctt tccttactgg   3360

tgctgataac aacagggaac cgtgcagtgt gcattttaag acc                     3403
```

<210> SEQ ID NO 97
<211> LENGTH: 2688
<212> TYPE: DNA
<213> ORGANISM: Homo sapiens

<400> SEQUENCE: 97

```
cttcaacccg cgccggcggc gactgcagtt cctgcgagcg aggagcgcgg gacctgctga     60

cacgctgacg ccttcgagcg cggcccgggg cccggagcgg ccggagcagc ccgggtcctg    120

accccggccc ggctcccgct ccgggctctg ccggcgggcg ggcgagcgcg gcgcggtccg    180

ggccgggggg atgtctcggc ggacgcgctg cgaggatctg gatgagctgc actaccagga    240

cacagattca gatgtgccgg agcagaggga tagcaagtgc aaggtcaaat ggacccatga    300

ggaggacgag cagctgaggg ccctggtgag gcagtttgga cagcaggact ggaagttcct    360

ggccagccac ttccctaacc gcactgacca gcaatgccag tacaggtggc tgagagtttt    420

gaatccagac cttgtcaagg ggccatggac caaagaggaa gaccaaaaag tcatcgagct    480

ggttaagaag tatggcacaa agcagtggac actgattgcc aagcacctga agggccggct    540

ggggaagcag tgccgtgaac gctggcacaa ccacctcaac cctgaggtga agaagtcttg    600

ctggaccgag gaggaggacc gcatcatctg cgaggcccac aaggtgctgg gcaaccgctg    660

ggccgagatc gccaagatgt tgccagggag gacagacaat gctgtgaaga atcactggaa    720

ctctaccatc aaaaggaagg tggacacagg aggcttcttg agcgagtcca aagactgcaa    780

gcccccagtg tacttgctgc tggagctcga ggacaaggac ggcctccaga gtgcccagcc    840

cacggaaggc cagggaagtc ttctgaccaa ctggccctcc gtccctccta ccataaagga    900

ggaggaaaac agtgaggagg aacttgcagc agccaccaca tcgaaggaac aggagcccat    960

cggtacagat ctggacgcag tgcgaacacc agagcccttg gaggaattcc cgaagcgtga   1020

ggaccaggaa ggctccccac cagaaacgag cctgccttac aagtgggtgg tggaggcagc   1080

taacctcctc atccctgctg tgggttctag cctctctgaa gccctggact tgatcgagtc   1140

ggaccctgat gcttggtgtg acctgagtaa atttgacctc cctgaggaac catctgcaga   1200

ggacagtatc aacaacagcc tagtgcagct gcaagcgtca catcagcagc aagtcctgcc   1260

accccgccag ccttccgccc tggtgcccag tgtgaccgag taccgcctgg atggccacac   1320

catctcagac ctgagccgga gcagccgggg cgagctgatc cccatctccc ccagcactga   1380

agtcgggggc tctggcattg gcacaccgcc ctctgtgctc aagcggcaga ggaagaggcg   1440

tgtggctctg tcccctgtca ctgagaatag caccagtctg tccttcctgg attcctgtaa   1500

cagcctcacg cccaagagca cacctgttaa gaccctgccc ttctcgccct cccagtttct   1560

gaacttctgg aacaaacagg acacattgga gctggagagc cctcgctga catccacccc    1620

agtgtgcagc cagaaggtgg tggtcaccac accactgcac cgggacaaga cacccctgca   1680
```

-continued

```
ccagaaacat gctgcgtttg taaccccaga tcagaagtac tccatggaca acactcccca   1740

cacgccaacc ccgttcaaga acgccctgga gaagtacgga cccctgaagc ccctgccaca   1800

gaccccgcac ctggaggagg acttgaagga ggtgctgcgt tctgaggctg gcatcgaact   1860

catcatcgag gacgacatca ggcccgagaa gcagaagagg aagcctgggc tgcggcggag   1920

ccccatcaag aaagtccgga agtctctggc tcttgacatt gtggatgagg atgtgaagct   1980

gatgatgtcc acactgccca agtctctatc cttgccgaca actgcccctt caaactcttc   2040

cagcctcacc ctgtcaggta tcaaagaaga caacagcttg ctcaaccagg gcttcttgca   2100

ggccaagccc gagaaggcag cagtggccca gaagccccga agccacttca cgacacctgc   2160

ccctatgtcc agtgcctgga agacggtggc ctgcgggggg accagggacc agcttttcat   2220

gcaggagaaa gcccggcagc tcctgggccg cctgaagccc agccacacat ctcggaccct   2280

catcttgtcc tgaggtgttg agggtgtcac gagcccattc tcatgtttac aggggttgtg   2340

ggggcagagg gggtctgtga atctgagagt cattcaggtg acctcctgca gggagccttc   2400

tgccaccagc ccctccccag actctcaggt ggaggcaaca gggccatgtg ctgccctgtt   2460

gccgagccca gctgtgggcg gctcctggtg ctaacaacaa agttccactt ccaggtctgc   2520

ctggttccct ccccaaggcc acagggagct ccgtcagctt ctcccaagcc cacgtcaggc   2580

ctggcctcat ctcagaccct gcttaggatg ggggatgtgg ccaggggtgc tcctgtgctc   2640

accctctctt ggtgcatttt tttggaagaa taaaattgcc tctctctt                2688
```

<210> SEQ ID NO 98
<211> LENGTH: 1883
<212> TYPE: DNA
<213> ORGANISM: Homo sapiens

<400> SEQUENCE: 98

```
atgaggttga cgctactttg ttgcacctgg agggaagaac gtatgggaga ggaaggaagc     60

gagttgcccg tgtgtgcaag ctgcggccag aggatctatg atggccagta cctccaggcc    120

ctgaacgcgg actggcacgc agactgcttc aggtgttgtg actgcagtgc ctccctgtcg    180

caccagtact atgagaagga tgggcagctc ttctgcaaga aggactactg ggcccgctat    240

ggcgagtcct gccatgggtg ctctgagcaa atcaccaagg gactggttat ggtggctggg    300

gagctgaagt accaccccga gtgtttcatc tgcctcacgt gtgggacctt tatcggtgac    360

ggggacacct acacgctggt ggagcactcc aagctgtact gcgggcactg ctactaccag    420

actgtggtga cccccgtcat cgagcagatc ctgcctgact cccctggctc ccacctgccc    480

cacaccgtca ccctggtgtc catcccagcc tcatctcatg gcaagcgtgg actttcagtc    540

tccattgacc ccccgcacgg cccaccgggc tgtggcaccg agcactcaca caccgtccgc    600

gtccagggag tggatccggg ctgcatgagc ccagatgtga agaattccat ccacgtcgga    660

gaccggatct tggaaatcaa tggcacgccc atccgaaatg tgcccctgga cgagattgac    720

ctgctgattc aggaaaccag ccgcctgctc cagctgaccc tcgagcatga ccctcacgat    780

acactgggcc acgggctggg gcctgagacc agccccctga gctctccggc ttatactccc    840

agcggggagg cgggcagctc tgcccggcag aaacctgtct tcgcaaggac ctgggtcgct    900

ctgagtccct ccgcgtagtc tgccggccac accgcatctt ccggccgtcg gacctcatcc    960

acggggaggt gctgggcaag ggctgcttcg gccaggctat caaggtgaca caccgtgaga   1020

caggtgaggt gatggtgatg aaggagctga tccggttcga cgaggagacc cagaggacgt   1080

tcctcaagga ggtgaaggtc atgcgatgcc tggaacaccc caacgtgctc aagttcatcg   1140
```

-continued

```
gggtgctcta caaggacaag aggctcaact tcatcactga gtacatcaag ggcggcacgc   1200

tccggggcat catcaagagc atggacagcc agtacccatg gagccagaga gtgagctttg   1260

ccaaggacat cgcatcaggg atggcctacc tccactccat gaacatcatc caccgagacc   1320

tcaactccca caactgcctg gtccgcgaga acaagaatgt ggtggtggct gacttcgggc   1380

tggcgcgtct catggtggac gagaagactc agcctgaggg cctgcggagc ctcaagaagc   1440

cagaccgcaa gaagcgctac accgtggtgg gcaaccccta ctggatggca cctgagatga   1500

tcaacggccg cagctatgat gagaaggtgg atgtgttctc ctttgggatc gtcctgtgcg   1560

agatcatcgg gcgggtgaac gcagaccctg actacctgcc ccgcaccatg gactttggcc   1620

tcaacgtgcg aggattcctg gaccgctact gccccccaaa ctgccccccg agcttcttcc   1680

ccatcaccgt gcgctgttgc gatctggacc ccgagaagag gccatccttt gtgaagctgg   1740

aacactggct ggagaccctc cgcatgcacc tggccggcca cctgccactg ggcccacagc   1800

tggagcagct ggacagaggt ttctgggaga cctaccggcg cggcgagagc ggactgcctg   1860

cccaccctga ggtccccgac tga                                           1883
```

<210> SEQ ID NO 99
<211> LENGTH: 597
<212> TYPE: DNA
<213> ORGANISM: Homo sapiens

<400> SEQUENCE: 99

```
atgcctggct tcgactacaa gttcctggag aagcccaagc gacggctgct gtgcccactg     60

tgcgggaagc ccatgcgcga gcctgtgcag gtttccacct gcggccaccg tttctgcgat    120

acctgcctgc aggagttcct cagtgaagga gtcttcaagt gccctgagga ccagcttcct    180

ctggactatg ccaagatcta cccagacccg gagctggaag tacaagtatt gggcctgcct    240

atccgctgca tccacagtga ggagggctgc cgctggagtg ggccactacg tcatctacag    300

ggccacctga atacctgcag cttcaatgtc attccctgcc ctaatcgctg ccccatgaag    360

ctgagccgcc gtgatctacc tgcacacttg cagcatgact gccccaagcg gcgcctcaag    420

tgcgagtttt gtggctgtga cttcagtggg gaggcctatg aggtggatga gagttctctg    480

ggctttggtt atcccaagtt catctcccac caggacattc gaaagcgaaa ctatgtgcgg    540

gatgatgcag tcttcatccg tgctgctgtt gaactgcccc ggaagatcct cagctga       597
```

<210> SEQ ID NO 100
<211> LENGTH: 23
<212> TYPE: DNA
<213> ORGANISM: Artificial
<220> FEATURE:
<223> OTHER INFORMATION: Synthetic

<400> SEQUENCE: 100

```
cgtatgcccc gctgaatctc gtg                                             23
```

<210> SEQ ID NO 101
<211> LENGTH: 24
<212> TYPE: DNA
<213> ORGANISM: Artificial
<220> FEATURE:
<223> OTHER INFORMATION: Synthetic

<400> SEQUENCE: 101

```
tggccaatca tccgtgctca tctg                                            24
```

-continued

<210> SEQ ID NO 102
<211> LENGTH: 24
<212> TYPE: DNA
<213> ORGANISM: Artificial
<220> FEATURE:
<223> OTHER INFORMATION: Synthetic

<400> SEQUENCE: 102
cggagtcaac ggatttggtc gtat 24

<210> SEQ ID NO 103
<211> LENGTH: 24
<212> TYPE: DNA
<213> ORGANISM: Artificial
<220> FEATURE:
<223> OTHER INFORMATION: Synthetic

<400> SEQUENCE: 103
agccttctcc atggtggtga agac 24

<210> SEQ ID NO 104
<211> LENGTH: 2005
<212> TYPE: DNA
<213> ORGANISM: Homo sapiens

<400> SEQUENCE: 104
ttgcaggctg ctgggctggg gctaagggct gctcagtttc cttcagcggg gcactgggaa 60
gcgccatggc actgcagggc atctcggtcg tggagctgtc cggcctggcc ccgggcccgt 120
tctgtgctat ggtcctggct gacttcgggg cgcgtgtggt acgcgtggac cggcccggct 180
cccgctacga cgtgagccgc ttgggccggg gcaagcgctc gctagtgctg gacctgaagc 240
agccgcgggg agccgccgtg ctgcggcgtc tgtgcaagcg gtcggatgtg ctgctggagc 300
ccttccgccg cggtgtcatg gagaaactcc agctgggccc agagattctg cagcgggaaa 360
atccaaggct tatttatgcc aggctgagtg gatttggcca gtcaggaagc ttctgccggt 420
tagctggcca cgatatcaac tatttggctt tgtcaggtgt tctctcaaaa attggcagaa 480
gtggtgagaa tccgtatgcc ccgctgaatc tcctggctga ctttgctggt ggtggcctta 540
tgtgtgcact gggcattata atggctcttt ttgaccgcac acgcactggc aagggtcagg 600
tcattgatgc aaatatggtg gaaggaacag catatttaag ttcttttctg tggaaaactc 660
agaaatcgag tctgtgggaa gcacctcgag gacagaacat gttggatggt ggagcacctt 720
tctatacgac ttacaggaca gcagatgggg aattcatggc tgttggagca atagaacccc 780
agttctacga gctgctgatc aaaggacttg gactaaagtc tgatgaactt cccaatcaga 840
tgagcatgga tgattggcca gaaatgaaga agaagtttgc agatgtattt gcaaagaaga 900
cgaaggcaga gtggtgtcaa atctttgacg gcacagatgc ctgtgtgact ccggttctga 960
cttttgagga ggttgttcat catgatcaca acaaggaacg gggctcgttt atcaccagtg 1020
aggagcagga cgtgagcccc cgccctgcac ctctgctgtt aaacacccca gccatccctt 1080
ctttcaaaag ggatcctttc ataggagaac acactgagga gatacttgaa gaatttggat 1140
tcagccgcga agagatttat cagcttaact cagataaaat cattgaaagt aataaggtaa 1200
aagctagtct ctaacttcca ggcccacggc tcaagtgaat ttgaatactg catttacagt 1260
gtagagtaac acataacatt gtatgcatgg aaacatggag gaacagtatt acagtgtcct 1320
accactctaa tcaagaaaag aattacagac tctgattcta cagtgatgat tgaattctaa 1380
aaatggttat cattagggct tttgatttat aaaactttgg gtacttatac taaattatgg 1440
tagttattct gccttccagt ttgcttgata tatttgttga tattaagatt cttgacttat 1500
attttgaatg ggttctagtg aaaaaggaat gatatattct tgaagacatc gatatacatt 1560
tatttacact cttgattcta caatgtagaa aatgaggaaa tgccacaaat tgtatggtga 1620
taaaagtcac gtgaaacaga gtgattggtt gcatccaggc cttttgtctt ggtgttcatg 1680
atctccctct aagcacattc caaactttag caacagttat cacactttgt aatttgcaaa 1740
gaaaagtttc acctgtattg aatcagaatg ccttcaactg aaaaaaacat atccaaaata 1800
atgaggaaat gtgttggctc actacgtaga gtccagaggg acagtcagtt ttagggttgc 1860
ctgtatccag taactcgggg cctgtttccc cgtgggtctc tgggctgtca gctttccttt 1920
ctccatgtgt ttgatttctc ctcaggctgg tagcaagttc tggatcttat acccaacaca 1980
cagcaacatc cagaaataaa gatct 2005

<210> SEQ ID NO 105
<211> LENGTH: 24
<212> TYPE: DNA
<213> ORGANISM: Artificial
<220> FEATURE:
<223> OTHER INFORMATION: Synthetic

<400> SEQUENCE: 105
tggccaatca tccgtgctca tctg 24

<210> SEQ ID NO 106
<211> LENGTH: 24
<212> TYPE: DNA
<213> ORGANISM: Artificial
<220> FEATURE:
<223> OTHER INFORMATION: Synthetic

<400> SEQUENCE: 106
agccttctcc atggtggtga agac 24

<210> SEQ ID NO 107
<211> LENGTH: 24
<212> TYPE: DNA
<213> ORGANISM: Artificial
<220> FEATURE:
<223> OTHER INFORMATION: Synthetic

<400> SEQUENCE: 107
agccttctcc atggtggtga agac 24

<210> SEQ ID NO 108
<211> LENGTH: 21
<212> TYPE: DNA
<213> ORGANISM: Artificial
<220> FEATURE:
<223> OTHER INFORMATION: Synthetic

<400> SEQUENCE: 108
gccagactgg gaagaaatct g 21

<210> SEQ ID NO 109
<211> LENGTH: 21
<212> TYPE: DNA
<213> ORGANISM: Artificial
<220> FEATURE:
<223> OTHER INFORMATION: Synthetic

<400> SEQUENCE: 109

-continued

```
tgtgctggaa aatccaagtc a                                              21


<210> SEQ ID NO 110
<211> LENGTH: 24
<212> TYPE: DNA
<213> ORGANISM: Artificial
<220> FEATURE:
<223> OTHER INFORMATION: Synthetic

<400> SEQUENCE: 110

cggagtcaac ggatttggtc gtat                                           24


<210> SEQ ID NO 111
<211> LENGTH: 24
<212> TYPE: DNA
<213> ORGANISM: Artificial
<220> FEATURE:
<223> OTHER INFORMATION: Synthetic

<400> SEQUENCE: 111

agccttctcc atggtggtga agac                                           24


<210> SEQ ID NO 112
<211> LENGTH: 35
<212> TYPE: DNA
<213> ORGANISM: Artificial
<220> FEATURE:
<223> OTHER INFORMATION: Synthetic

<400> SEQUENCE: 112

ggggtaccat gggcggccgc gaacaaaagt tgatt                               35


<210> SEQ ID NO 113
<211> LENGTH: 33
<212> TYPE: DNA
<213> ORGANISM: Artificial
<220> FEATURE:
<223> OTHER INFORMATION: Synthetic

<400> SEQUENCE: 113

ggggaattct catgccagca atagatgctt ttt                                 33


<210> SEQ ID NO 114
<211> LENGTH: 3042
<212> TYPE: DNA
<213> ORGANISM: Homo sapiens

<400> SEQUENCE: 114

cggaggcgct gggcgcacgg cgcggagccg gccggagctc gaggccggcg gcggcgggag     60

agcgacccgg gcggcctcgt agcggggccc cggatccccg agtggcggcc ggagcctcga    120

aaagagattc tcagcgctga ttttgagatg atgggcttgg gaaacgggcg tcgcagcatg    180

aagtcgccgc ccctcgtgct ggccgccctg gtggcctgca tcatcgtctt gggcttcaac    240

tactggattg cgagctcccg gagcgtggac ctccagacac ggatcatgga gctggaaggc    300

agggtccgca gggcggctgc agagagaggc gccgtggagc tgaagaagaa cgagttccag    360

ggagagctgg agaagcagcg ggagcagctt gacaaaatcc agtccagcca caacttccag    420

ctggagagcg tcaacaagct gtaccaggac gaaaaggcgg ttttggtgaa taacatcacc    480

acaggtgaga ggctcatccg agtgctgcaa gaccagttaa agaccctgca gaggaattac    540

ggcaggctgc agcaggatgt cctccagttt cagaagaacc agaccaacct ggagaggaag    600

ttctcctacg acctgagcca gtgcatcaat cagatgaagg aggtgaagga acagtgtgag    660
```

-continued

```
gagcgaatag aagaggtcac caaaaagggg aatgaagctg tagcttccag agacctgagt    720
gaaaacaacg accagagaca gcagctccaa gccctcagtg agcctcagcc caggctgcag    780
gcagcaggcc tgccacacac agaggtgcca caagggaagg gaaacgtgct tggtaacagc    840
aagtcccaga caccagcccc cagttccgaa gtggttttgg attcaaagag acaagttgag    900
aaagaggaaa ccaatgagat ccaggtggtg aatgaggagc ctcagaggga caggctgccg    960
caggagccag gccgggagca ggtggtggaa gacagacctg taggtggaag aggcttcggg   1020
ggagccggag aactgggcca gaccccacag gtgcaggctg ccctgtcagt gagccaggaa   1080
aatccagaga tggagggccc tgagcgagac cagcttgtca tccccgacgg acaggaggag   1140
gagcaggaag ctgccgggga agggagaaac cagcagaaac tgagaggaga agatgactac   1200
aacatggatg aaaatgaagc agaatctgag acagacaagc aagcagccct ggcagggaat   1260
gacagaaaca tagatgtttt taatgttgaa gatcagaaaa gagacaccat aaatttactt   1320
gatcagcgtg aaaagcggaa tcatacactc tgaattgaac tggaatcaca tatttcacaa   1380
cagggccgaa gagatgacta taaaatgttc atgagggact gaatactgaa aactgtgaaa   1440
tgtactaaat aaaatgtaca tctgaagatg attattgtga aattttagta tgcactttgt   1500
gtaggaaaaa atggaatggt cttttaaaca gcttttgggg gggtactttg gaagtgtcta   1560
ataaggtgtc acaatttttg gtagtaggta tttcgtgaga agttcaacac caaaactgga   1620
acatagttct ccttcaagtg ttggcgacag cggggcttcc tgattctgga atataacttt   1680
gtgtaaatta acagccacct atagaagagt ccatctgctg tgaaggagag acagagaact   1740
ctgggttccg tcgtcctgtc cacgtgctgt accaagtgct ggtgccagcc tgttacctgt   1800
tctcactgaa aagtctggct aatgctcttg tgtagtcact tctgattctg acaatcaatc   1860
aatcaatggc ctagagcact gactgttaac acaaacgtca ctagcaaagt agcaacagct   1920
ttaagtctaa atacaaagct gttctgtgtg agaatttttt aaaaggctac ttgtataata   1980
acccttgtca tttttaatgt acaaaacgct attaagtggc ttagaatttg aacatttgtg   2040
gtctttattt actttgcttc gtgtgtgggc aaagcaacat cttccctaaa tatatattac   2100
caagaaaagc aagaagcaga ttaggttttt gacaaaacaa acaggccaaa agggggctga   2160
cctggagcag agcatggtga gaggcaaggc atgagagggc aagtttgttg tggacagatc   2220
tgtgcctact ttattactgg agtaaaagaa aacaaagttc attgatgtcg aaggatatat   2280
acagtgttag aaattaggac tgtttagaaa aacaggaata caatggttgt ttttatcata   2340
gtgtacacat ttagcttgtg gtaaatgact cacaaaactg attttaaaat caagttaatg   2400
tgaattttga aaattactac ttaatcctaa ttcacaataa caatggcatt aaggtttgac   2460
ttgagttggt tcttagtatt atttatggta aataggctct taccacttgc aaataactgg   2520
ccacatcatt aatgactgac ttcccagtaa ggctctctaa ggggtaagta ggaggatcca   2580
caggatttga gatgctaagg ccccagagat cgtttgatcc aaccctctta ttttcagagg   2640
ggaaaatggg gcctagaagt tacagagcat ctagctggtg cgctggcacc cctggcctca   2700
cacagactcc cgagtagctg ggactacagg cacacagtca ctgaagcagg ccctgtttgc   2760
aattcacgtt gccacctcca acttaaacat tcttcatatg tgatgtcctt agtcactaag   2820
gttaaacttt cccacccaga aaaggcaact tagataaaat cttagagtac tttcatactc   2880
ttctaagtcc tcttccagcc tcactttgag tcctccttgg ggttgatagg aattttctct   2940
tgctttctca ataaagtctc tattcatctc atgtttaatt tgtacgcata gaattgctga   3000
```

-continued gaaataaaat gttctgttca acttaaaaaa aaaaaaaaaa aa 3042

<210> SEQ ID NO 115
<211> LENGTH: 2368
<212> TYPE: DNA
<213> ORGANISM: Homo sapiens

<400> SEQUENCE: 115
cgggcgatgc cgcgctgcgg gggggccgca cagccgccgc caccgccacc gccgccgggt 60
ggggtgggag gggcgggaac gcgcgccgcc gcctccaggg tgggcgcctt tcgccgtgga 120
cgccgaccgt ccgggacgag ggtttcatca ccttaaatgg ttttgaacca atgaaggtgt 180
attcccttaa aaagacggac agcccatcgt gtgaactata gagtttgtgg acagatttat 240
attgggttca tagtggcgtc atgcacgcag actcctgcaa gttcccctaa gttcttagag 300
gactgctttg ccttttgatc tgagagttgc aaagttccat aaagaatggc ccttgtggat 360
aagcacaaag tcaagagaca gcgattggac agaatttgtg aaggtatccg cccccagatc 420
atgaacggcc ccctgcaccc ccgccccctg gtggcgctgc tggacggccg cgactgcact 480
gtggagatgc ccatcctgaa ggacctggcc actgtggcct tctgtgacgc gcagtcgacg 540
caggaaatcc acgagaaggt tctaaacgaa gccgtgggcg ccatgatgta ccacaccatc 600
accctcacca gggaggacct ggagaagttc aaggccctga gagtgatcgt gcggataggc 660
agtggctatg acaacgtgga catcaaggct gccggcgagc tcggaattgc cgtgtgcaac 720
atcccgtctg cagccgtgga agagacagcg gactctacca tctgccacat cctcaacctg 780
taccggagga acacgtggct gtaccaggca ctgcgggaag gcacgcgggt tcagagcgtg 840
gagcagatcc gcgaggtggc ctcgggagcg gcccgcatcc gtggggagac gctgggcctc 900
attggctttg gtcgcacggg gcaggcggtt gcagttcgag ccaaggcctt tggattcagc 960
gtcatatttt atgaccccta cttgcaggat gggatcgagc ggtccctggg cgtgcagagg 1020
gtctacaccc tgcaggattt gctgtatcag agcgactgcg tctccttgca ctgcaatctc 1080
aacgaacata accaccacct catcaatgac tttaccataa agcagatgag gcagggagca 1140
ttccttgtga acgcagcccg tggcggcctg gtggacgaga aagccttagc acaagccctc 1200
aaggagggca ggatacgagg ggcagccctc gacgtgcatg agtcagagcc cttcagcttt 1260
gctcagggtc cgttgaaaga tgccccgaat ctcatctgca ctcctcacac tgcctggtac 1320
agtgagcagg cgtcactgga gatgagggag gcagctgcca ccgagatccg ccgagccatc 1380
acaggtcgca tcccagaaag cttaagaaat tgtgtgaaca aggaattctt tgtcacatca 1440
gcgccttggt cagtaataga ccagcaagca attcatcctg agctcaatgg tgccacatac 1500
agatatccgc caggcatcgt gggtgtggct ccaggaggac ttcctgcagc catggaaggg 1560
atcatccctg gaggcatccc agtgactcac aacctcccga cagtggcaca tccttcccaa 1620
gcgccctctc ccaaccagcc cacaaaacac ggggacaatc gagagcaccc caacgagcaa 1680
tagcagagaa tgccagaagg taatcactca gatacacttg ggaccaagag acagtgaaaa 1740
atagatgaac taagagaaaa agaatcggat ggtctttgta actgattctg gacatatgca 1800
tcattgatgt tgcagtgttg aaactacaag agctagaaaa ctgaagatgt cgtctgctta 1860
cggaagcgct gaaagactag gatgtgattt attaacgacc aacttctgtt attgtgtgtt 1920
aagtttttca tctgtgcatc aaatcacaaa aagaataaat agagcttttt cctttatcag 1980
tcccttgggc acagcaggtc ctgaacaccc tgctctacaa tgttgcatca agagttcaaa 2040
caacaaaata aaaaatatta agaggaaatc cccatcctgt gacttgagtc ccttaagtct 2100

-continued

```
acaggggctg gtgacctctt tttgctaata ggaaaatcac attactacaa aatggggaga   2160
aaactgtttg cctgtggtag acacctgcac gcataggatt gaagacagta caggctgctg   2220
tacagagaag cgcctctcac atctgaactg catactgagc gggcaagtcg gttgtaagtt   2280
cagtaaaacc ctctgatgat gcaaaaaaaa aaaaaaagta ttaagtttca caagctgttt   2340
gtactcaaat atattttctc agtttcag                                      2368
```

<210> SEQ ID NO 116
<211> LENGTH: 1362
<212> TYPE: DNA
<213> ORGANISM: Homo sapiens

<400> SEQUENCE: 116

```
catttgggga cgctctcagc tctcggcgca cggcccagct tccttcaaaa tgtctactgt     60
tcacgaaatc ctgtgcaagc tcagcttgga gggtgatcac tctacacccc caagtgcata    120
tgggtctgtc aaagcctata ctaactttga tgctgagcgg gatgctttga acattgaaac    180
agccatcaag accaaaggtg tggatgaggt caccattgtc aacattttga ccaaccgcag    240
caatgcacag agacaggata ttgccttcgc ctaccagaga aggaccaaaa aggaacttgc    300
atcagcactg aagtcagcct tatctggcca cctggagacg gtgattttgg gcctattgaa    360
gacacctgct cagtatgacg cttctgagct aaaagcttcc atgaaggggc tgggaaccga    420
cgaggactct ctcattgaga tcatctgctc cagaaccaac caggagctgc aggaaattaa    480
cagagtctac aaggaaatgt acaagactga tctggagaag gacattattt cggacacatc    540
tggtgacttc cgcaagctga tggttgccct ggcaaagggt agaagagcag aggatggctc    600
tgtcattgat tatgaactga ttgaccaaga tgctcgggat ctctatgacg ctggagtgaa    660
gaggaaagga actgatgttc ccaagtggat cagcatcatg accgagcgga gcgtgcccca    720
cctccagaaa gtatttgata ggtacaagag ttacagccct tatgacatgt tggaaagcat    780
caggaaagag gttaaaggag acctggaaaa tgctttcctg aacctggttc agtgcattca    840
gaacaagccc ctgtattttg ctgatcggct gtatgactcc atgaagggca aggggacgcg    900
agataaggtc ctgatcagaa tcatggtctc ccgcagtgaa gtggacatgt tgaaaattag    960
gtctgaattc aagagaaagt acggcaagtc cctgtactat tatatccagc aagacactaa   1020
gggcgactac cagaaagcgc tgctgtacct gtgtggtgga gatgactgaa gcccgacacg   1080
gcctgagcgt ccagaaatgg tgctcaccat gcttccagct aacaggtcta gaaaaccagc   1140
ttgcgaataa cagtccccgt ggccatccct gtgagggtga cgttagcatt acccccaacc   1200
tcattttagt tgcctaagca ttgcctggcc ttcctgtcta gtctctcctg taagccaaag   1260
aaatgaacat tccaaggagt tggaagtgaa gtctatgatg tgaaacactt tgcctcctgt   1320
gtactgtgtc ataaacagat gaataaactg aatttgtact tt                      1362
```

<210> SEQ ID NO 117
<211> LENGTH: 2137
<212> TYPE: DNA
<213> ORGANISM: Homo sapiens

<400> SEQUENCE: 117

```
gccccaggtg cgcttcccct agagagggat tttccggtct cgtgggcaga ggaacaacca     60
ggaacttggg ctcagtctcc accccacagt ggggcggatc cgtcccggat aagacccgct    120
gtctggccct gagtagggtg tgacctccgc agccgcagag gaggagcgca gcccggcctc    180
```

-continued

```
gaagaacttc tgcttgggtg gctgaactct gatcttgacc tagagtcatg gccatggcaa    240

ccaaaggagg tactgtcaaa gctgcttcag gattcaatgc catggaagat gcccagaccc    300

tgaggaaggc catgaaaggg ctcggcaccg atgaagacgc cattattagc gtccttgcct    360

accgcaacac cgcccagcgc caggagatca ggacagccta caagagcacc atcggcaggg    420

acttgataga cgacctgaag tcagaactga gtggcaactt cgagcaggtg attgtgggga    480

tgatgacgcc cacggtgctg tatgacgtgc aagagctgcg aagggccatg aagggagccg    540

gcactgatga gggctgccta attgagatcc tggcctcccg gacccctgag gagatccggc    600

gcataagcca aacctaccag cagcaatatg gacggagcct tgaagatgac attcgctctg    660

acacatcgtt catgttccag cgagtgctgg tgtctctgtc agctggtggg agggatgaag    720

gaaattatct ggacgatgct ctcgtgagac aggatgccca ggacctgtat gaggctggag    780

agaagaaatg gggacagat gaggtgaaat ttctaactgt tctctgttcc cggaaccgaa    840

atcacctgtt gcatgtgttt gatgaataca aaaggatatc acagaaggat attgaacaga    900

gtattaaatc tgaaacatct ggtagctttg aagatgctct gctggctata gtaaagtgca    960

tgaggaacaa atctgcatat tttgctgaaa agctctataa atcgatgaag ggcttgggca   1020

ccgatgataa caccctcatc agagtgatgg tttctcgagc agaaattgac atgttggata   1080

tccgggcaca cttcaagaga ctctatggaa agtctctgta ctcgttcatc aagggtgaca   1140

catctggaga ctacaggaaa gtactgcttg ttctctgtgg aggagatgat taaaataaaa   1200

atcccagaag gacaggagga ttctcaacac tttgaatttt tttaacttca tttttctaca   1260

ctgctattat cattatctca gaatgcttat ttccaattaa aacgcctaca gctgcctcct   1320

agaatataga ctgtctgtat tattattcac ctataattag tcattatgat gctttaaagc   1380

tgtacttgca tttcaaagct tataagatat aaatggagat tttaaagtag aaataaatat   1440

gtattccatg tttttaaaag attactttct actttgtgtt tcacagacat tgaatatatt   1500

aaattattcc atattttctt ttcagtgaaa aattttttaa atggaagact gttctaaaat   1560

cactttttc cctaatccaa tttttagagt ggctagtagt ttcttcattt gaaattgtaa   1620

gcatccggtc agtaagaatg cccatccagt tttctatatt tcatagtcaa agccttgaaa   1680

gcatctacaa atctcttttt ttaggttttg tccatagcat cagttgatcc ttactaagtt   1740

tttcatggga gacttccttc atcacatctt atgttgaaat cactttctgt agtcaaagta   1800

taccaaaacc aatttatctg aactaaattc taaagtatgg ttatacaaac catatacatc   1860

tggttaccaa acataaatgc tgaacattcc atattattat agttaatgtc ttaatccagc   1920

ttgcaagtga atggaaaaaa aaataagctt caaactaggt attctgggaa tgatgtaatg   1980

ctctgaattt agtatgatat aaagaaaact tttttgtgct aaaaatactt tttaaaatca   2040

attttgttga ttgtagtaat ttctatttgc actgtgcctt tcaactccag aaacattctg   2100

aagatgtact tggatttaat taaaaagttc actttgt                            2137
```

<210> SEQ ID NO 118
<211> LENGTH: 1958
<212> TYPE: DNA
<213> ORGANISM: Homo sapiens

<400> SEQUENCE: 118

```
gctgctgcgc ccgcggctcc ccagtgcccc gagtgccccg cgggccccgc gagcgggagt     60

gggacccagc cctaggcaga acccaggcgc cgcgcccggg acgcccgcgg agagagccac    120

tcccgcccac gtcccatttc gcccctcgcg tccggagtcc ccgtggccag atctaaccat    180
```

-continued gagctaccct ggctatcccc cgcccccagg tggctaccca ccagctgcac caggtggtgg 240
tccctgggga ggtgctgcct accctcctcc gcccagcatg ccccccatcg ggctggataa 300
cgtggccacc tatgcggggc agttcaacca ggactatctc tcgggaatgg cggccaacat 360
gtctgggaca tttggaggag ccaacatgcc caacctgtac cctggggccc ctggggctgg 420
ctacccacca gtgccccctg gcggctttgg gcagcccccc tctgcccagc agcctgttcc 480
tccctatggg atgtatccac ccccaggagg aaacccaccc tccaggatgc cctcatatcc 540
gccataccca ggggcccctg tgccgggcca gcccatgcca cccccggac agcagccccc 600 aggggcctac cctgggcagc caccagtgac ctaccctggt cagcctccag tgccactccc 660
tgggcagcag cagccagtgc cgagctaccc aggataccgg gggtctggga ctgtcacccc 720
cgctgtgccc ccaacccagt ttggaagccg aggcaccatc actgatgctc ccggctttga 780 cccccctgcga gatgccgagg tcctgcggaa ggccatgaaa ggcttcggga cggatgagca 840
ggccatcatt gactgcctgg ggagtcgctc caacaagcag cggcagcaga tcctactttc 900
cttcaagacg gcttacggca aggatttgat caaagatctg aaatctgaac tgtcaggaaa 960
ctttgagaag acaatcttgg ctctgatgaa gaccccagtc ctctttgaca tttatgagat 1020
aaaggaagcc atcaaggggg ttggcactga tgaagcctgc ctgattgaga tcctcgcttc 1080
ccgcagcaat gagcacatcc gagaattaaa cagagcctac aaagcagaat tcaaaaagac 1140
cctggaagag gccattcgaa gcgacacatc agggcacttc cagcggctcc tcatctctct 1200
ctctcaggga aaccgtgatg aaagcacaaa cgtggacatg tcactcgccc agagagatgc 1260
ccaggagctg tatgcggccg gggagaaccg cctgggaaca gacgagtcca agttcaatgc 1320
ggttctgtgc tcccggagcc gggcccacct ggtagcagtt ttcaatgagt accagagaat 1380
gacaggccgg gacattgaga agagcatctg ccgggagatg tccggggacc tggaggaggg 1440
catgctggcc gtggtgaaat gtctcaagaa taccccagcc ttctttgcgg agaggctcaa 1500
caaggccatg aggggggcag gaacaaagga ccggaccctg attcgcatca tggtgtctcg 1560
cagcgagacc gacctcctgg acatcagatc agagtataag cggatgtacg gcaagtcgct 1620
gtaccacgac atctcgggag atacttcagg ggattaccgg aagattctgc tgaagatctg 1680
tggtggcaat gactgaacag tgactggtgg ctcacttctg cccacctgcc ggcaacacca 1740
gtgccaggaa aaggccaaaa gaatgtctgt ttctaacaaa tccacaaata gccccgagat 1800
tcaccgtcct agagcttagg cctgtcttcc accccctcctg acccgtatag tgtgccacag 1860
gacctgggtc ggtctagaac tctctcagga tgccttttct accccatccc tcacagcctc 1920
ttgctgctaa aatagatgtt tcatttttct gaaaaaaa 1958

<210> SEQ ID NO 119
<211> LENGTH: 5791
<212> TYPE: DNA
<213> ORGANISM: Homo sapiens

<400> SEQUENCE: 119
ggctcatgct cgggagcgtg gttgagcggc tggcgcggtt gtcctggagc aggggcgcag 60
gaattctgat gtgaaactaa cagtctgtga gccctggaac ctccactcag agaagatgaa 120
ggatatcgac ataggaaaag agtatatcat ccccagtcct gggtatagaa gtgtgaggga 180
gagaaccagc acttctggga cgcacagaga ccgtgaagat tccaagttca ggagaactcg 240
accgttggaa tgccaagatg ccttggaaac agcagcccga gccgagggcc tctctcttga 300

-continued

```
tgcctccatg cattctcagc tcagaatcct ggatgaggag catcccaagg gaaagtacca    360
tcatggcttg agtgctctga agcccatccg gactacttcc aaacaccagc acccagtgga    420
caatgctggg ctttttcct gtatgacttt ttcgtggctt tcttctctgg cccgtgtggc     480
ccacaagaag gggagctct caatggaaga cgtgtggtct ctgtccaagc acgagtcttc     540
tgacgtgaac tgcagaagac tagagagact gtggcaagaa gagctgaatg aagttgggcc    600
agacgctgct tccctgcgaa gggttgtgtg gatcttctgc cgcaccaggc tcatcctgtc    660
catcgtgtgc ctgatgatca cgcagctggc tggcttcagt ggaccagcct tcatggtgaa    720
acacctcttg gagtataccc aggcaacaga gtctaacctg cagtacagct tgttgttagt    780
gctgggcctc ctcctgacgg aaatcgtgcg gtcttggtcg cttgcactga cttgggcatt    840
gaattaccga accggtgtcc gcttgcgggg ggccatccta accatggcat ttaagaagat    900
ccttaagtta aagaacatta aagagaaatc cctgggtgag ctcatcaaca tttgctccaa    960
cgatgggcag agaatgtttg aggcagcagc cgttggcagc ctgctggctg gaggacccgt   1020
tgttgccatc ttaggcatga tttataatgt aattattctg ggaccaacag gcttcctggg   1080
atcagctgtt tttatcctct tttacccagc aatgatgttt gcatcacggc tcacagcata   1140
tttcaggaga aaatgcgtgg ccgccacgga tgaacgtgtc cagaagatga atgaagttct   1200
tacttacatt aaatttatca aaatgtatgc ctgggtcaaa gcattttctc agagtgttca   1260
aaaaatccgc gaggaggagc gtcggatatt ggaaaaagct gggtacttcc agagcatcac   1320
tgtgggtgtg gctcccattg tggtggtgat tgccagcgtg gtgaccttct ctgttcatat   1380
gaccctgggc ttcgatctga cagcagcaca ggctttcaca gtggtgacag tcttcaattc   1440
catgactttt gctttgaaag taacaccgtt ttcagtaaag tccctctcag aagcctcagt   1500
ggctgttgac agatttaaga gtttgtttct aatggaagag gttcacatga taaagaacaa   1560
accagccagt cctcacatca agatagagat gaaaaatgcc accttggcat gggactcctc   1620
ccactccagt atccagaact cgcccaagct gacccccaaa atgaaaaaag acaagagggc   1680
ttccaggggc aagaaagaga aggtgaggca gctgcagcgc actgagcatc aggcggtgct   1740
ggcagagcag aaaggccacc tcctcctgga cagtgacgag cggcccagtc ccgaagagga   1800
agaaggcaag cacatccacc tgggccacct gcgcttacag aggacactgc acagcatcga   1860
tctggagatc caagagggta aactggttgg aatctgtggc agtgtgggaa gtggaaaaac   1920
ctctctcatt tcagccattt taggccagat gacgcttcta gagggcagca ttgcaatcag   1980
tggaaccttc gcttatgtgg cccagcaggc ctggatcctc aatgctactc tgagagacaa   2040
catcctgttt gggaaggaat atgatgaaga aagatacaac tctgtgctga acagctgctg   2100
cctgaggcct gacctggcca ttcttcccag cagcgacctg acggagattg gagagcgagg   2160
agccaacctg agcggtgggc agcgccagag gatcagcctt gcccgggcct tgtatagtga   2220
caggagcatc tacatcctgg acgacccccct cagtgcctta gatgcccatg tgggcaacca  2280
catcttcaat agtgctatcc ggaaacatct caagtccaag acagttctgt ttgttaccca   2340
ccagttacag tacctggttg actgtgatga agtgatcttc atgaaagagg gctgtattac   2400
ggaaagaggc acccatgagg aactgatgaa tttaaatggt gactatgcta ccatttttaa   2460
taacctgttg ctgggagaga caccgccagt tgagatcaat tcaaaaaagg aaaccagtgg   2520
ttcacagaag aagtcacaag acaagggtcc taaaacagga tcagtaaaga aggaaaaagc   2580
agtaaagcca gaggaagggc agcttgtgca gctggaagag aaagggcagg gttcagtgcc   2640
ctggtcagta tatggtgtct acatccaggc tgctgggggc cccttggcat tcctggttat   2700
```

-continued

```
tatggccctt ttcatgctga atgtaggcag caccgccttc agcacctggt ggttgagtta   2760
ctggatcaag caaggaagcg ggaacaccac tgtgactcga gggaacgaga cctcggtgag   2820
tgacagcatg aaggacaatc ctcatatgca gtactatgcc agcatctacg ccctctccat   2880
ggcagtcatg ctgatcctga aagccattcg aggagttgtc tttgtcaagg gcacgctgcg   2940
agcttcctcc cggctgcatg acgagctttt ccgaaggatc cttcgaagcc ctatgaagtt   3000
ttttgacacg acccccacag ggaggattct caacaggttt tccaaagaca tggatgaagt   3060
tgacgtgcgg ctgccgttcc aggccgagat gttcatccag aacgttatcc tggtgttctt   3120
ctgtgtggga atgatcgcag gagtcttccc gtggttcctt gtggcagtgg ggccccttgt   3180
catcctcttt tcagtcctgc acattgtctc cagggtcctg attcgggagc tgaagcgtct   3240
ggacaatatc acgcagtcac ctttcctctc ccacatcacg tccagcatac agggccttgc   3300
caccatccac gcctacaata aagggcagga gtttctgcac agataccagg agctgctgga   3360
tgacaaccaa gctccttttt ttttgtttac gtgtgcgatg cggtggctgg ctgtgcggct   3420
ggacctcatc agcatcgccc tcatcaccac cacggggctg atgatcgttc ttatgcacgg   3480
gcagattccc ccagcctatg cgggtctcgc catctcttat gctgtccagt taacggggct   3540
gttccagttt acggtcagac tggcatctga gacagaagct cgattcacct cggtggagag   3600
gatcaatcac tacattaaga ctctgtcctt ggaagcacct gccagaatta agaacaaggc   3660
tccctcccct gactggcccc aggagggaga ggtgaccttt gagaacgcag agatgaggta   3720
ccgagaaaac ctccctctcg tcctaaagaa agtatccttc acgatcaaac ctaaagagaa   3780
gattggcatt gtggggcgga caggatcagg gaagtcctcg ctggggatgg ccctcttccg   3840
tctggtggag ttatctggag gctgcatcaa gattgatgga gtgagaatca gtgatattgg   3900
ccttgccgac ctccgaagca aactctctat cattcctcaa gagccggtgc tgttcagtgg   3960
cactgtcaga tcaaatttgg accccttcaa ccagtacact gaagaccaga tttgggatgc   4020
cctggagagg acacacatga aagaatgtat tgctcagcta cctctgaaac ttgaatctga   4080
agtgatggag aatggggata acttctcagt gggggaacgg cagctcttgt gcatagctag   4140
agccctgctc cgccactgta agattctgat tttagatgaa gccacagctg ccatggacac   4200
agagacagac ttattgattc aagagaccat ccgagaagca tttgcagact gtaccatgct   4260
gaccattgcc catcgcctgc acacggttct aggctccgat aggattatgg tgctggccca   4320
gggacaggtg gtggagtttg acaccccatc ggtccttctg tccaacgaca gttcccgatt   4380
ctatgccatg tttgctgctg cagagaacaa ggtcgctgtc aagggctgac tcctccctgt   4440
tgacgaagtc tcttttcttt agagcattgc cattccctgc ctggggcggg cccctcatcg   4500
cgtcctccta ccgaaacctt gcctttctcg attttatctt tcgcacagca gttccggatt   4560
ggcttgtgtg tttcactttt agggagagtc atattttgat tattgtattt attccatatt   4620
catgtaaaca aaatttagtt tttgttctta attgcactct aaaaggttca gggaaccgtt   4680
attataattg tatcagaggc ctataatgaa gctttatacg tgtagctata tctatatata   4740
attctgtaca tagcctatat ttacagtgaa aatgtaagct gtttatttta tattaaaata   4800
agcactgtgc taataacagt gcatattcct ttctatcatt tttgtacagt ttgctgtact   4860
agagatctgg ttttgctatt agactgtagg aagagtagca tttcattctt ctctagctgg   4920
tggtttcacg gtgccaggtt ttctgggtgt ccaaaggaag acgtgtggca atagtgggcc   4980
ctccgacagc cccctctgcc gcctccccac ggccgctcca ggggtggctg gagacgggtg   5040
```

-continued

```
ggcggctgga gaccatgcag agcgccgtga gttctcaggg ctcctgcctt ctgtcctggt   5100

gtcacttact gtttctgtca ggagagcagc ggggcgaagc ccaggcccct tttcactccc   5160

tccatcaaga atggggatca cagagacatt cctccgagcc ggggagtttc tttcctgcct   5220

tcttcttttt gctgttgttt ctaaacaaga atcagtctat ccacagagag tcccactgcc   5280

tcaggttcct atggctggcc actgcacaga gctctccagc tccaagacct gttggttcca   5340

agccctggag ccaactgctg ctttttgagg tggcactttt tcatttgcct attcccacac   5400

ctccacagtt cagtggcagg gctcaggatt tcgtgggtct gttttccttt ctcaccgcag   5460

tcgtcgcaca gtctctctct ctctctcccc tcaaagtctg caactttaag cagctcttgc   5520

taatcagtgt ctcacactgg cgtagaagtt tttgtactgt aaagagacct acctcaggtt   5580

gctggttgct gtgtggtttg gtgtgttccc gcaaaccccc tttgtgctgt ggggctggta   5640

gctcaggtgg gcgtggtcac tgctgtcatc aattgaatgg tcagcgttgc atgtcgtgac   5700

caactagaca ttctgtcgcc ttagcatgtt tgctgaacac cttgtggaag caaaaatctg   5760

aaaatgtgaa taaaattatt ttggattttg t                                  5791
```

<210> SEQ ID NO 120
<211> LENGTH: 1992
<212> TYPE: DNA
<213> ORGANISM: Homo sapiens

<400> SEQUENCE: 120

```
aaacttcccg cacgcgttac aggagccagg tcggtataag cgccacgcct cgccgcccgt     60

caagctgtcc acatccctgg cctcagcccg ccacatcacc ctgacctgct tacgcccaga    120

ttttcttcaa tcacatctga ataaatcact tgaagaaagc ttatagcttc attgcaccat    180

gtgtggcatt tgggcgctgt ttggcagtga tgattgcctt tctgttcagt gtctgagtgc    240

tatgaagatt gcacacagag gtccagatgc attccgtttt gagaatgtca atggatacac    300

caactgctgc tttggatttc accggttggc ggtagttgac ccgctgtttg gaatgcagcc    360

aattcgagtg aagaaatatc cgtatttgtg gctctgttac aatggtgaaa tctacaacca    420

taagaagatg caacagcatt ttgaatttga ataccagacc aaagtggatg gtgagataat    480

ccttcatctt tatgacaaag gaggaattga gcaaacaatt tgtatgttgg atggtgtgtt    540

tgcatttgtt ttactggata ctgccaataa gaaagtgttc ctgggtagag atacatatgg    600

agtcagacct ttgtttaaag caatgacaga agatggattt ttggctgtat gttcagaagc    660

taaaggtctt gttacattga agcactccgc gactcccttt ttaaaagtgg agccttttct    720

tcctggacac tatgaagttt tggatttaaa gccaaatggc aaagttgcat ccgtggaaat    780

ggttaaatat catcactgtc gggatgtacc cctgcacgcc ctctatgaca atgtggagaa    840

actctttcca ggttttgaga tagaaactgt gaagaacaac ctcaggatcc tttttaataa    900

tgctgtaaag aaacgtttga tgacagacag aaggattggc tgccttttat caggggggctt    960

ggactccagc ttggttgctg ccactctgtt gaagcagctg aaagaagccc aagtacagta   1020

tcctctccag acatttgcaa ttggcatgga agacagcccc gatttactgg ctgctagaaa   1080

ggtggcagat catattggaa gtgaacatta tgaagtcctt tttaactctg aggaaggcat   1140

tcaggctctg gatgaagtca tattttcctt ggaaacttat gacattacaa cagttcgtgc   1200

ttcagtaggt atgtatttaa tttccaagta tattcggaag aacacagata gcgtggtgat   1260

cttctctgga gaaggatcag atgaacttac gcagggttac atatattttc acaaggctcc   1320

ttctcctgaa aaagccgagg aggagagtga gaggcttctg agggaactct atttgtttga   1380
```

-continued tgttctccgc gcagatcgaa ctactgctgc ccatggtctt gaactgagag tcccatttct 1440
agatcatcga tttttttcct attacttgtc tctgccacca gaaatgagaa ttccaaagaa 1500
tgggatagaa aaacatctcc tgagagagac gtttgaggat tccaatctga tacccaaaga 1560
gattctctgg cgaccaaaag aagccttcag tgatggaata acttcagtta agaattcctg 1620
gtttaagatt ttacaggaat acgttgaaca tcaggttgat gatgcaatga tggcaaatgc 1680
agcccagaaa tttcccttca atactcctaa aaccaaagaa ggatattact accgtcaagt 1740
ctttgaacgc cattacccag gccgggctga ctggctgagc cattactgga tgcccaagtg 1800
gatcaatgcc actgaccctt ctgcccgcac gctgacccac tacaagtcag ctgtcaaagc 1860
ttaggtggtc tttatgctgt aatgtgaaag caaatatttc ttcgtgttgg atggggactg 1920
tgggtagata ggggaacaat gagagtcaac tcaggctaac ttgggtttga aaaaaataaa 1980
attcctaaat tt 1992

<210> SEQ ID NO 121
<211> LENGTH: 5698
<212> TYPE: DNA
<213> ORGANISM: Homo sapiens

<400> SEQUENCE: 121
aggttcaagt ggagctctcc taaccgacgc gcgtctgtgg agaagcggct tggtcggggg 60
tggtctcgtg gggtcctgcc tgtttagtcg ctttcagggt tcttgagccc cttcacgacc 120
gtcaccatgg aagtgtcacc attgcagcct gtaaatgaaa atatgcaagt caacaaaata 180
aagaaaaatg aagatgctaa gaaaagactg tctgttgaaa gaatctatca aaagaaaaca 240
caattggaac atattttgct ccgcccagac acctacattg gttctgtgga attagtgacc 300
cagcaaatgt gggtttacga tgaagatgtt ggcattaact atagggaagt cacttttgtt 360
cctggtttgt acaaaatctt tgatgagatt ctagttaatg ctgcggacaa caaacaaagg 420
gacccaaaaa tgtcttgtat tagagtcaca attgatccgg aaaacaattt aattagtata 480
tggaataatg gaaaaggtat tcctgttgtt gaacacaaag ttgaaaagat gtatgtccca 540
gctctcatat ttggacagct cctaacttct agtaactatg atgatgatga aaagaaagtg 600
acaggtggtc gaaatggcta tggagccaaa ttgtgtaaca tattcagtac caaatttact 660
gtggaaacag ccagtagaga atacaagaaa atgttcaaac agacatggat ggataatatg 720
ggaagagctg gtgagatgga actcaagccc ttcaatggag aagattatac atgtatcacc 780
tttcagcctg atttgtctaa gtttaaaatg caaagcctgg acaaagatat tgttgcacta 840
atggtcagaa gagcatatga tattgctgga tccaccaaag atgtcaaagt ctttcttaat 900
ggaaataaac tgccagtaaa aggatttcgt agttatgtgg acatgtattt gaaggacaag 960
ttggatgaaa ctggtaactc cttgaaagta atacatgaac aagtaaacca caggtgggaa 1020
gtgtgtttaa ctatgagtga aaaaggcttt cagcaaatta gctttgtcaa cagcattgct 1080
acatccaagg gtggcagaca tgttgattat gtagctgatc agattgtgac taaacttgtt 1140
gatgttgtga agaagaagaa caagggtggt gttgcagtaa aagcacatca ggtgaaaaat 1200
cacatgtgga tttttgtaaa tgccttaatt gaaaacccaa cctttgactc tcagacaaaa 1260
gaaaacatga ctttacaacc caagagcttt ggatcaacat gccaattgag tgaaaaattt 1320
atcaaagctg ccattggctg tggtattgta gaaagcatac taaactgggt gaagtttaag 1380
gcccaagtcc agttaaacaa gaagtgttca gctgtaaaac ataatagaat caagggaatt 1440

-continued

```
cccaaactcg atgatgccaa tgatgcaggg ggccgaaact ccactgagtg tacgcttatc   1500
ctgactgagg gagattcagc caaaactttg gctgtttcag gccttggtgt ggttgggaga   1560
gacaaatatg ggttttccc tcttagagga aaaatactca atgttcgaga agcttctcat   1620
aagcagatca tggaaaatgc tgagattaac aatatcatca agattgtggg tcttcagtac   1680
aagaaaaact atgaagatga agattcattg aagacgcttc gttatgggaa gataatgatt   1740
atgacagatc aggaccaaga tggttcccac atcaaaggct tgctgattaa ttttatccat   1800
cacaactggc cctctcttct gcgacatcgt tttctggagg aatttatcac tcccattgta   1860
aaggtatcta aaaacaagca agaaatggca ttttacagcc ttcctgaatt tgaagagtgg   1920
aagagttcta ctccaaatca taaaaaatgg aaagtcaaat attacaaagg tttgggcacc   1980
agcacatcaa aggaagctaa agaatacttt gcagatatga aaagacatcg tatccagttc   2040
aaatattctg gtcctgaaga tgatgctgct atcagcctgg cctttagcaa aaaacagata   2100
gatgatcgaa aggaatggtt aactaatttc atggaggata gaagacaacg aaagttactt   2160
gggcttcctg aggattactt gtatggacaa actaccacat atctgacata taatgacttc   2220
atcaacaagg aacttatctt gttctcaaat tctgataacg agagatctat cccttctatg   2280
gtggatggtt tgaaaccagg tcagagaaag gttttgttta cttgcttcaa acggaatgac   2340
aagcgagaag taaaggttgc ccaattagct ggatcagtgg ctgaaatgtc ttcttatcat   2400
catggtgaga tgtcactaat gatgaccatt atcaatttgg ctcagaattt tgtgggtagc   2460
aataatctaa acctcttgca gcccattggt cagtttggta ccaggctaca tggtggcaag   2520
gattctgcta gtccacgata catctttaca atgctcagct ctttggctcg attgttattt   2580
ccaccaaaag atgatcacac gttgaagttt ttatatgatg acaaccagcg tgttgagcct   2640
gaatggtaca ttcctattat tcccatggtg ctgataaatg gtgctgaagg aatcggtact   2700
gggtggtcct gcaaaatccc caactttgat gtgcgtgaaa ttgtaaataa catcaggcgt   2760
ttgatggatg gagaagaacc tttgccaatg cttccaagtt acaagaactt caagggtact   2820
attgaagaac tggctccaaa tcaatatgtg attagtggtg aagtagctat tcttaattct   2880
acaaccattg aaatctcaga gcttcccgtc agaacatgga cccagacata caaagaacaa   2940
gttctagaac ccatgttgaa tggcaccgag aagacacctc ctctcataac agactatagg   3000
gaataccata cagataccac tgtgaaattt gttgtgaaga tgactgaaga aaaactggca   3060
gaggcagaga gagttggact acacaaagtc ttcaaactcc aaactagtct cacatgcaac   3120
tctatggtgc tttttgacca cgtaggctgt ttaaagaaat atgacacggt gttggatatt   3180
ctaagagact tttttgaact cagacttaaa tattatggat taagaaaaga atggctccta   3240
ggaatgcttg gtgctgaatc tgctaaactg aataatcagg ctcgctttat cttagagaaa   3300
atagatggca aaataatcat tgaaaataag cctaagaaag aattaattaa agttctgatt   3360
cagaggggat atgattcgga tcctgtgaag gcctggaaag aagcccagca aaaggttcca   3420
gatgaagaag aaaatgaaga gagtgacaac gaaaaggaaa ctgaaaagag tgactccgta   3480
acagattctg gaccaacctt caactatctt cttgatatgc ccctttggta tttaaccaag   3540
gaaaagaaag atgaactctg caggctaaga aatgaaaaag aacaagagct ggacacatta   3600
aaaagaaaga gtccatcaga tttgtggaaa gaagacttgg ctacatttat tgaagaattg   3660
gaggctgttg aagccaagga aaaacaagat gaacaagtcg gacttcctgg gaaagggggg   3720
aaggccaagg ggaaaaaaac acaaatggct gaagttttgc cttctccgcg tggtcaaaga   3780
gtcattccac gaataaccat agaaatgaaa gcagaggcag aaaagaaaaa taaaaagaaa   3840
```

-continued

```
attaagaatg aaaatactga aggaagccct caagaagatg gtgtggaact agaaggccta   3900

aaacaaagat tagaaaagaa acagaaaaga gaaccaggta caaagacaaa gaaacaaact   3960

acattggcat ttaagccaat caaaaaagga aagaagagaa atccctggtc tgattcagaa   4020

tcagatagga gcagtgacga aagtaatttt gatgtccctc cacgagaaac agagccacgg   4080

agagcagcaa caaaaacaaa attcacaatg gatttggatt cagatgaaga tttctcagat   4140

tttgatgaaa aaactgatga tgaagatttt gtcccatcag atgctagtcc acctaagacc   4200

aaaacttccc caaaacttag taacaaagaa ctgaaaccac agaaaagtgt cgtgtcagac   4260

cttgaagctg atgatgttaa gggcagtgta ccactgtctt caagccctcc tgctacacat   4320

ttcccagatg aaactgaaat tacaaaccca gttcctaaaa agaatgtgac agtgaagaag   4380

acagcagcaa aaagtcagtc ttccacctcc actaccggtg ccaaaaaaag ggctgcccca   4440

aaaggaacta aaagggatcc agctttgaat tctggtgtct ctcaaaagcc tgatcctgcc   4500

aaaaccaaga atcgccgcaa aaggaagcca tccacttctg atgattctga ctctaatttt   4560

gagaaaattg tttcgaaagc agtcacaagc aagaaatcca agggggagag tgatgacttc   4620

catatggact ttgactcagc tgtggctcct cgggcaaaat ctgtacgggc aaagaaacct   4680

ataaagtacc tggaagagtc agatgaagat gatctgtttt aaaatgtgag gcgattattt   4740

taagtaatta tcttaccaag cccaagactg gttttaaagt tacctgaagc tcttaacttc   4800

ctcccctctg aatttagttt ggggaaggtg tttttagtac aagacatcaa agtgaagtaa   4860

agcccaagtg ttctttagct ttttataata ctgtctaaat agtgaccatc tcatgggcat   4920

tgttttcttc tctgctttgt ctgtgttttg agtctgcttt cttttgtctt taaaacctga   4980

tttttaagtt cttctgaact gtagaaatag ctatctgatc acttcagcgt aaagcagtgt   5040

gtttattaac catccactaa gctaaaacta gagcagtttg atttaaaagt gtcactcttc   5100

ctccttttct actttcagta gatatgagat agagcataat tatctgtttt atcttagttt   5160

tatacataat ttaccatcag atagaacttt atggttctag tacagatact ctactacact   5220

cagcctctta tgtgccaagt ttttctttaa gcaatgagaa attgctcatg ttcttcatct   5280

tctcaaatca tcagaggcca aagaaaaaca ctttggctgt gtctataact tgacacagtc   5340

aatagaatga agaaaattag agtagttatg tgattatttc agctcttgac ctgtcccctc   5400

tggctgcctc tgagtctgaa tctcccaaag agagaaacca atttctaaga ggactggatt   5460

gcagaagact cggggacaac atttgatcca agatcttaaa tgttatattg ataaccatgc   5520

tcagcaatga gctattagat tcattttggg aaatctccat aatttcaatt tgtaaacttt   5580

gttaagacct gtctacattg ttatatgtgt gtgacttgag taatgttatc aacgtttttg   5640

taaatattta ctatgttttt ctattagcta aattccaaca attttgtact ttaataaa     5698
```

<210> SEQ ID NO 122
<211> LENGTH: 2753
<212> TYPE: DNA
<213> ORGANISM: Homo sapiens

<400> SEQUENCE: 122

```
gcgccatgga gcagtggcgg cagtgcggcc gctggctcat cgattgcaag gtcctgccgc     60

ccaaccaccg ggtggtgtgg ccctcggccg tggtcttcga cctggcgcag gcgctgcgcg    120

acggggtcct tctgtgccag ctgctgcaca acctctcccc cggctccatc gacctcaagg    180

acatcaactt ccggccgcag atgtcccagt ttctgtgttt gaagaacata cgcaccttcc    240
```

-continued

```
tgaaagtctg ccacgataaa tttggattaa ggaacagcga gctgtttgac ccctttgacc    300
tcttcgatgt gcgagacttt ggaaaggtca tctccgcggt gtcgaggctc tccctgcaca    360
gcatcgcgca gaacaaaggg atcaggcctt ttccctcaga ggagaccaca gagaatgacg    420
atgacgtcta ccgcagcctg gaggagctgg ccgacgagca tgacctgggg gaggacatct    480
acgactgcgt cccgtgtgag gatggagggg acgacatcta cgaggacatc atcaaggtgg    540
aggtgcagca gcccatgatt agatacatgc agaaaatggg catgactgaa gatgacaaga    600
ggaactgctg cctgctggag atccaggaga ccgaggccaa gtactaccgc accctggagg    660
acattgagaa gaactacatg agccccctgc ggctggtgct gagcccggcg gacatggcag    720
ctgtcttcat taacctggag gacctgatca aggtgcatca cagcttcctg agggccatcg    780
acgtgtccgt gatggtgggg ggcagcacgc tggccaaggt cttcctcgat ttcaaggaaa    840
ggcttctgat ctacggggag tactgcagcc acatggagca cgcccagaac acactgaacc    900
agctcctggc cagccgggag gacttcaggc agaaagtcga ggagtgcaca ctgaaggtcc    960
aggatggaaa atttaagctg caagacctgc tggtggtccc catgcagagg gtgctcaaat   1020
accacctgct cttgaaggag cttctgagcc attctgcgga acggcctgag aggcagcagc   1080
tcaaagaagc actggaagcc atgcaggact tggcgatgta catcaatgaa gttaaacggg   1140
acaaggagac cttgaggaaa atcagcgaat ttcagagttc tatagaaaat ttgcaagtga   1200
aactggagga atttggaaga ccaaagattg acggggaact gaaagtccgg tccatagtca   1260
accacaccaa gcaggacagg tacttgttcc tgtttgacaa ggtggtcatc gtctgcaagc   1320
ggaagggcta cagctacgag ctcaaggaga tcatcgagct gctgttccac aagatgaccg   1380
acgaccccat gaacaacaag gacgtcaaga agtctcacgg gaaaatgtgg tcctacggct   1440
tctacctaat tcaccttcaa ggaaagcagg gcttccagtt tttctgcaaa acagaagata   1500
tgaagaggaa gtggatggag cagtttgaga tggccatgtc aaacatcaag ccagacaaag   1560
ccaatgccaa ccaccacagt ttccagatgt acacgtttga caagaccacc aactgcaaag   1620
cctgcaaaat gttcctcagg ggcaccttct accagggata catgtgtacc aagtgtggcg   1680
tcggggcaca caaggagtgc ctggaagtga tacctccctg caagttcact tctcctgcag   1740
atctggacgc ctccggagcg ggaccaggtc ccaagatggt ggccatgcag aattaccatg   1800
gcaacccagc ccctcccggg aagcctgtgc tgaccttcca gacgggcgac gtgcttgagc   1860
tgctgagggg cgaccctgag tctccgtggt gggagggtcg tctggtacaa accaggaagt   1920
cagggtattt ccccagctca tctgtgaagc cctgccctgt ggatggaagg ccgcccatca   1980
gccggccgcc atcccgggag atcgactaca ctgcataccc ctggtttgca ggtaacatgg   2040
agaggcagca gacggacaac ctgctcaagt cccacgccag cgggacctac ctgatcaggg   2100
agcggcctgc cgaggctgag cgctttgcaa taagcatcaa gttcaatgat gaggtgaagc   2160
acatcaaggt ggtggagaag gacaactgga tccacatcac agaggccaag aaattcgaca   2220
gcctcctgga gttggtggag tactaccagt gccactcact gaaggagagc ttcaagcagc   2280
tggacaccac actcaagtac ccctacaagt cccgggaacg ttcggcctcc agggcctcca   2340
gccggtcccc agcttcctgt gcttcctaca actttttcttt tctcagtcct cagggcctca  2400
gctttgcttc tcagggcccc tccgctccct tctggtcagt gttcacgccc cgcgtcatcg   2460
gcacagctgt ggccaggtat aactttgccg cccgagatat gagggagctt tcgctgcggg   2520
agggtgacgt ggtgaggatc tacagccgca tcggcggaga ccagggctgg tggaagggcg   2580
agaccaacgg acggattggc tggtttcctt caacgtacgt agaagaggag ggcatccagt   2640
```

-continued

```
gacggcagga acgtggacaa gactcgcaga ttttcttggg agagtcactc cagccctgaa    2700

gtctgtctct agctcctctg tgactcagag gggaaatacc aacctcccag tct           2753


<210> SEQ ID NO 123
<211> LENGTH: 23
<212> TYPE: DNA
<213> ORGANISM: Artificial
<220> FEATURE:
<223> OTHER INFORMATION: Synthetic

<400> SEQUENCE: 123

cgtatgcccc gctgaatctc gtg                                              23
```